(12) United States Patent
Mueller et al.

(10) Patent No.: US 7,858,622 B2
(45) Date of Patent: Dec. 28, 2010

(54) SELECTED CGRP ANTAGONISTS, PROCESSES FOR PREPARING THEM AND THEIR USE AS PHARMACEUTICAL COMPOSITIONS

(75) Inventors: Stephan Georg Mueller, Warthausen (DE); Klaus Rudolf, Warthausen (DE); Philipp Lustenberger, Basel (CH); Gerhard Schaenzle, Biberach (DE); Marco Santagostino, Mittelbiberach (DE); Dirk Stenkamp, Biberach (DE); Kirsten Arndt, Biberach (DE); Henri Doods, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/486,026

(22) Filed: Jun. 17, 2009

(65) Prior Publication Data
US 2010/0004228 A1    Jan. 7, 2010

Related U.S. Application Data

(62) Division of application No. 11/462,511, filed on Aug. 4, 2006, now Pat. No. 7,579,341.

(30) Foreign Application Priority Data

Aug. 17, 2005 (DE) .......................... 10 2005 038 831
Oct. 25, 2005 (DE) .......................... 10 2005 050 953

(51) Int. Cl.
C07D 401/14 (2006.01)
A61K 31/4545 (2006.01)
A61P 25/06 (2006.01)

(52) U.S. Cl. .................. 514/236.2; 514/318; 544/129; 546/187

(58) Field of Classification Search ............... 514/236.2, 514/318; 544/129; 546/187
See application file for complete search history.

(56) References Cited

U.S. PATENT DOCUMENTS

| | | | |
|---|---|---|---|
| 6,344,449 B1 | 2/2002 | Rudolf et al. | |
| 7,696,209 B2 * | 4/2010 | Mueller et al. ......... | 514/253.09 |
| 2004/0132716 A1 | 7/2004 | Rudolf et al. | |
| 2004/0214819 A1 | 10/2004 | Rudolf et al. | |
| 2005/0234067 A1 | 10/2005 | Mueller et al. | |
| 2005/0250763 A1 | 11/2005 | Mueller et al. | |
| 2005/0282857 A1 | 12/2005 | Rudolf et al. | |
| 2006/0079504 A1 | 4/2006 | Rudolf et al. | |
| 2006/0142273 A1 | 6/2006 | Rudolf et al. | |
| 2006/0142274 A1 | 6/2006 | Rudolf et al. | |
| 2006/0154921 A1 | 7/2006 | Rudolf et al. | |
| 2006/0252750 A1 | 11/2006 | Mueller et al. | |
| 2006/0252931 A1 | 11/2006 | Mueller et al. | |
| 2007/0072847 A1 | 3/2007 | Mueller et al. | |
| 2007/0238715 A1 | 10/2007 | Rudolf et al. | |
| 2007/0244099 A1 | 10/2007 | Rudolf et al. | |
| 2007/0249592 A1 | 10/2007 | Rudolf et al. | |
| 2008/0103134 A1 | 5/2008 | Rudolf et al. | |
| 2008/0176836 A1 | 7/2008 | Rudolf et al. | |

FOREIGN PATENT DOCUMENTS

| | | |
|---|---|---|
| CA | 2503455 A1 | 5/2004 |
| CA | 2503462 A1 | 5/2004 |
| CA | 2513132 A1 | 7/2004 |
| CA | 2558889 A1 | 10/2005 |
| CA | 2562526 A1 | 10/2005 |
| WO | 2004037810 A1 | 5/2004 |
| WO | 2004037811 A1 | 5/2004 |
| WO | 2004063171 A1 | 7/2004 |
| WO | 2005092880 A1 | 10/2005 |
| WO | 2005100343 A1 | 10/2005 |
| WO | 2005100352 A1 | 10/2005 |
| WO | 2006069754 A1 | 7/2006 |
| WO | 2006072413 A1 | 7/2006 |
| WO | 2006072415 A1 | 7/2006 |

OTHER PUBLICATIONS

Rudolf et al. "preparation of modified amino acids . . . " CA 128:257695 (1998).

John J. Mallee et al; Receptor Activity-modifying Protein 1 Determines the Species Selectivity of Non-peptide CGRP Receptor Antagonists: The Journal of Biological Chemistry (Apr. 19, 2002) vol. 277, No. 16, p. 14294-14928; The American Society for Biochemistry and Molecular Biology, Inc.

* cited by examiner

Primary Examiner—Bruck Kifle
(74) Attorney, Agent, or Firm—Michael P. Morris; Alan R. Stempel

(57) ABSTRACT

The present invention relates to the CGRP antagonists of general formula I

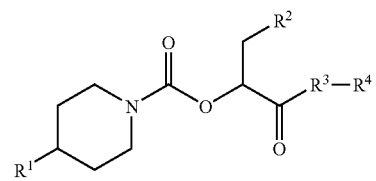

wherein $R^1$, $R^2$, $R^3$ and $R^4$ are as defined in claim 1, the tautomers, the isomers, the diastereomers, the enantiomers, the hydrates thereof, the mixtures thereof and the salts thereof and the hydrates of the salts thereof, particularly the physiologically acceptable salts thereof with inorganic or organic acids or bases, as well as those compounds of general formula I wherein one or more hydrogen atoms are replaced by deuterium, pharmaceutical compositions containing these compounds, their use and processes for preparing them.

15 Claims, No Drawings

SELECTED CGRP ANTAGONISTS, PROCESSES FOR PREPARING THEM AND THEIR USE AS PHARMACEUTICAL COMPOSITIONS

RELATED APPLICATIONS

This application is a division of U.S. application Ser. No. 11/462,511, filed Aug. 4, 2006 now U.S. Pat. No. 7,579,341.

The present invention relates to the CGRP antagonists of general formula I

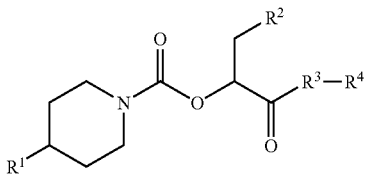

wherein $R^1$, $R^2$, $R^3$ and $R^4$ are as defined herein, the tautomers, the isomers, the diastereomers, the enantiomers, the hydrates thereof, the mixtures thereof and the salts thereof and the hydrates of the salts thereof, particularly the physiologically acceptable salts thereof with inorganic or organic acids or bases, as well as those compounds of general formula I wherein one or more hydrogen atoms are replaced by deuterium, pharmaceutical compositions containing these compounds, their use and processes for preparing them.

PRIOR ART

CGRP antagonists for the treatment of migraine have already been described in International Patent Applications PCT/EP97/04862 and PCT/EP03/11762.

DETAILED DESCRIPTION OF THE INVENTION

In the above general formula I in a first embodiment $R^1$ denotes a group selected from

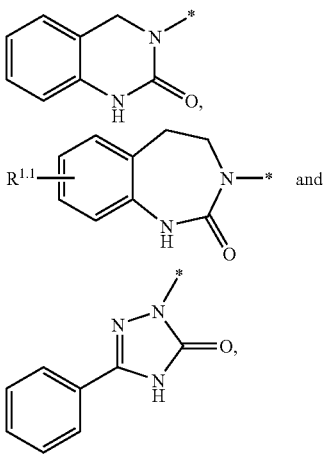

wherein
$R^{1.1}$ denotes H or $H_3C$—O, $R^2$ denotes a group selected from

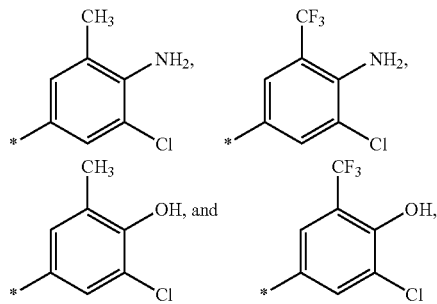

$R^3$ denotes a group of general formula II

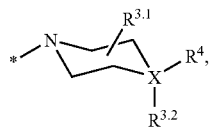

wherein
X denotes N or C,
$R^{3.1}$ denotes H, $C_{1-3}$-alkyl or $R^{3.1.1}$—O—C(O),
$R^{3.1.1}$ denotes H, $C_{1-6}$-alkyl, $H_2N$—$C_{2-4}$-alkylene, ($C_{1-3}$-alkyl)-NH—$C_{2-4}$-alkylene, ($C_{1-3}$-alkyl)$_2$N—$C_{2-4}$-alkylene, $H_2N$—C(O)—$C_{1-3}$-alkylene, ($C_{1-3}$-alkyl)-NH—C(O)—$C_{1-3}$-alkylene, ($C_{1-3}$-alkyl)$_2$N—C(O)—$C_{1-3}$-alkylene or $R^{3.1.1.1}$—$C_{2-4}$-alkylene,
$R^{3.1.1.1}$ denotes a group selected from

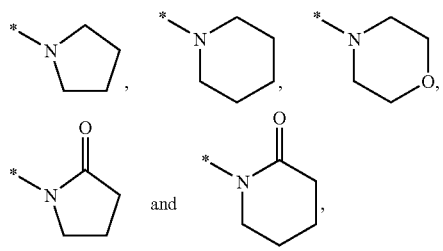

$R^{3.2}$ denotes a pair of free electrons, if X=N, or
$R^{3.2}$ denotes H, $C_{1-3}$-alkyl or $R^{3.2.1}$—O—C(O), if X=C,
$R^{3.2.1}$ denotes H, $C_{1-6}$-alkyl, $H_2N$—$C_{2-4}$-alkylene, ($C_{1-3}$-alkyl)-NH—$C_{2-4}$-alkylene, ($C_{1-3}$-alkyl)$_2$N—$C_{2-4}$-alkylene, $H_2N$—C(O)-$C_{1-3}$-alkylene, ($C_{1-3}$-alkyl)-NH—C(O)—$C_{1-3}$-alkylene, ($C_{1-3}$-alkyl)$_2$N—C(O)—$C_{1-3}$-alkylene or $R^{3.2.1.1}$—$C_{2-4}$-alkylene,
$R^{3.2.1.1}$ denotes a group selected from

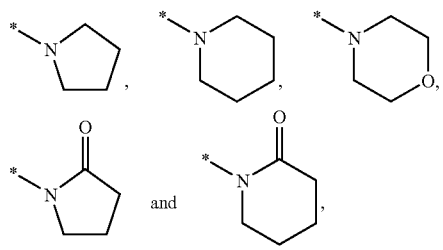

R⁴ denotes a group of general formulae III

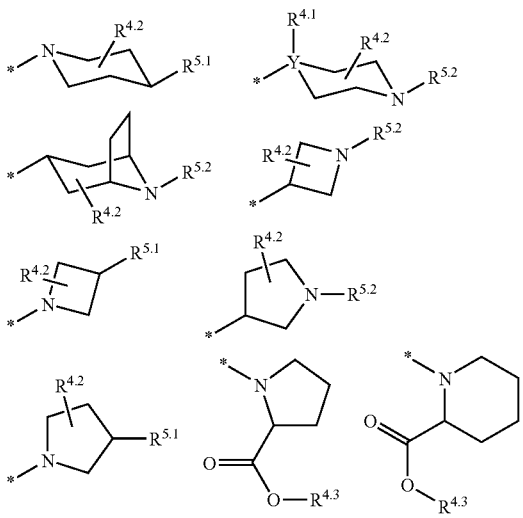

wherein
Y denotes C and
R⁴·¹ denotes H or C₁₋₃-alkyl, or
Y denotes N and
R⁴·¹ denotes a pair of free electrons,
with the proviso that X and Y do not simultaneously represent N,
R⁴·² denotes H, C₁₋₃-alkyl or R⁴·²·¹—O—C(O),
R⁴·²·¹ denotes H, C₁₋₆-alkyl, H₂N—C₂₋₄-alkylene, (C₁₋₃-alkyl)-NH—C₂₋₄-alkylene, (C₁₋₃-alkyl)₂N—C₂₋₄-alkylene, H₂N—C(O)—C₁₋₃-alkylene, (C₁₋₃-alkyl)-NH—C(O)—C₁₋₃-alkylene, (C₁₋₃-alkyl)₂N—C(O)—C₁₋₃-alkylene or R⁴·²·¹·¹—C₂₋₄-alkylene,
R⁴·²·¹·¹ denotes a group selected from

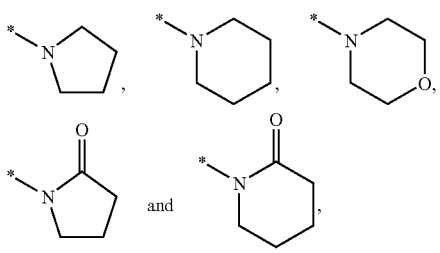

and
R⁴·³ denotes H, C₁₋₆-alkyl, H₂N—C₂₋₄-alkylene, (C₁₋₃-alkyl)-NH—C₂₋₄-alkylene, (C₁₋₃-alkyl)₂N—C₂₋₄-alkylene, H₂N—C(O)—C₁₋₃-alkylene, (C₁₋₃-alkyl)-NH—C(O)—C₁₋₃-alkylene, (C₁₋₃-alkyl)₂N—C(O)—C₁₋₃-alkylene or R⁴·³·¹—C₂₋₄-alkylene,
R⁴·³·¹ denotes a group selected from

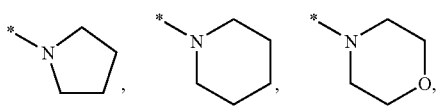

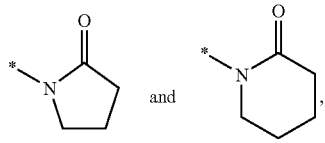

R⁵·¹ denotes H, C₁₋₃-alkyl, R⁵·¹·¹—O—C(O), R⁵·¹·¹—O—C(O)—C₁₋₃-alkylene-NH, R⁵·¹·¹—O—C(O)—C₁₋₃-alkylene-N(C₁₋₃-alkyl), R⁵·¹·¹—O—C(O)—C₁₋₃-alkylene-O, R⁵·¹·¹—O—C(O)—C₁₋₃-alkylene, R⁵·¹·¹—O—C(O)—C(O), R⁵·¹·¹—O—C(O)—C(O)—O, R⁵·¹·¹—O—C(O)—C₁₋₃-alkylene-C(O) or R⁵·¹·¹—O—C(O)—C₁₋₃-alkylene-C(O)—O, R⁵·¹·¹ denotes H, C₁₋₈-alkyl, phenyl, indanyl, pyridyl-C₁₋₃-alkylene, HO—C₂₋₄-alkylene, C₁₋₆-alkyl-O—C₂₋₄-alkylene, H₂N—C₂₋₄-alkylene, (C₁₋₆-alkyl)-NH—C₂₋₄-alkylene, (C₁₋₆-alkyl)₂N—C₂₋₄-alkylene, H₂N—C(O)—C₁₋₃-alkylene, (C₁₋₆-alkyl)-NH—C(O)—C₁₋₃-alkylene, (C₁₋₆-alkyl)₂N—C(O)—C₁₋₃-alkylene, C₁₋₆-alkyl-C(O)—O—C₁₋₃-alkylene, C₁₋₆-alkyl-O—C(O)—O—C₁₋₃-alkylene, R⁵·¹·¹—C(O)—C₁₋₃-alkylene or R⁵·¹·¹·²—C₂₋₄-alkylene, R⁵·¹·¹·¹ denotes a group selected from

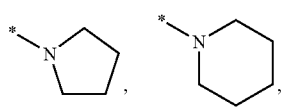

R⁵·¹·¹·² denotes a group selected from

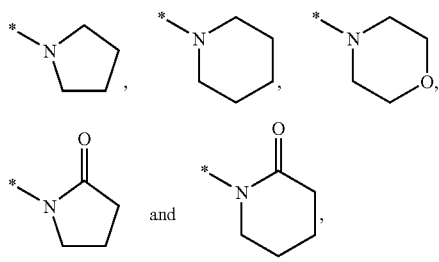

R⁵·² denotes H, C₁₋₃-alkyl, R⁵·²·¹—O—C(O)—C₁₋₃-alkylene-NH, R⁵·²·¹—O—C(O)—C₁₋₃-alkylene-O, R⁵·²·¹—O—C(O)—C₁₋₃-alkylene, R⁵·²·¹—O—C(O)—C(O) or R⁵·²·¹—O—C(O)—C₁₋₃-alkylene-C(O), R⁵·²·¹ denotes H, C₁₋₈-alkyl, phenyl, indanyl, pyridyl-C₁₋₃-alkylene, HO—C₂₋₄-alkylene, C₁₋₆-alkyl-O—C₂₋₄-alkylene, C₁₋₆-alkyl-O—C₂₋₄-alkylene-O—C₂₋₄-alkylene, H₂N—C₂₋₄-alkylene, (C₁₋₆-alkyl)-NH—C₂₋₄-alkylene, (C₁₋₆-alkyl)₂N—C₂₋₄-alkylene, H₂N—C(O)—C₁₋₃-alkylene, (C₁₋₆-alkyl)-NH—C(O)—C₁₋₃-alkylene, (C₁₋₆-alkyl)₂N—C(O)—C₁₋₃-alkylene, C₁₋₆-alkyl-C(O)—O—C₁₋₃-alkylene, C₁₋₆-alkyl-O—C(O)—O—C₁₋₃-alkylene, R⁵·²·¹·¹—C(O)—C₁₋₃-alkylene or R⁵·²·¹·²—C₂₋₄-alkylene, $R^{5.2.1.1}$ denotes a group selected from

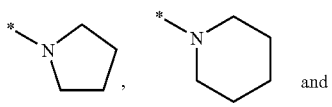

$R^{5.2.1.2}$ denotes a group selected from

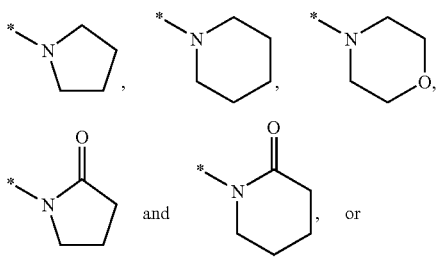

$R^{5.2.1}$ denotes a group of formula

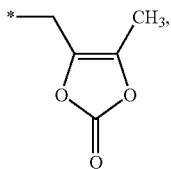

with the proviso that at least one of the groups $R^{3.1}$, $R^{3.2}$, $R^{4.2}$, $R^{5.1}$ or $R^{5.2}$ denotes a group other than H or $C_{1-3}$-alkyl, the tautomers, the diastereomers, the enantiomers, the hydrates, the mixtures thereof and the salts thereof as well as the hydrates of the salts thereof, particularly the physiologically acceptable salts thereof with inorganic or organic acids or bases.

A preferred first embodiment of the present invention consists of the compounds of the above general formula I, wherein
$R^1$ denotes a group selected from

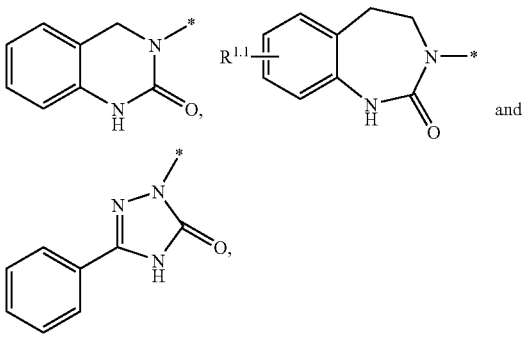

wherein
$R^{1.1}$ denotes H or $H_3C$—O, $R^2$ denotes a group selected from

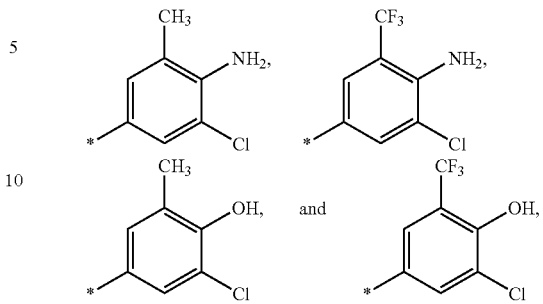

$R^3$ denotes a group of general formula II

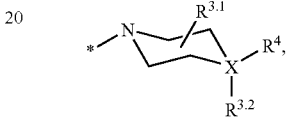

wherein
X denotes N or C,
$R^{3.1}$ denotes H, $C_{1-3}$-alkyl or HO—C(O),
$R^{3.2}$ denotes a pair of free electrons, if X=N, or
$R^{3.2}$ denotes H, $C_{1-3}$-alkyl or HO—C(O), if X=C,
$R^4$ denotes a group of general formulae III

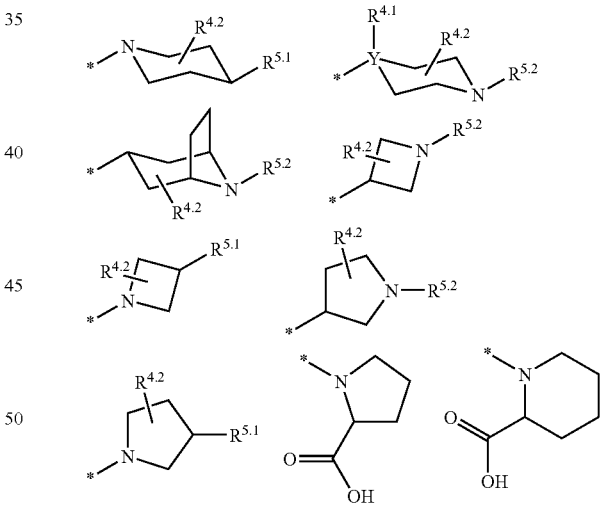

wherein
Y denotes C and
$R^{4.1}$ denotes H or $C_{1-3}$-alkyl, or
Y denotes N and
$R^{4.1}$ denotes a pair of free electrons,
with the proviso that X and Y do not simultaneously represent N,
$R^{4.2}$ denotes H, $C_{1-3}$-alkyl or HO—C(O),
$R^{5.1}$ denotes H, $C_{1-3}$-alkyl, HO—C(O), HO—C(O)—$C_{1-3}$-alkylene-NH, HO—C(O)—$C_{1-3}$-alkylene-N($C_{1-3}$-alkyl), HO—C(O)—$C_{1-3}$-alkylene-O, HO—C(O)—$C_{1-3}$-alkylene, HO—C(O)—C(O), HO—C(O)—C(O)—O, HO—C(O)—C$_{1-3}$-alkylene-C(O) or HO—C(O)—C$_{1-3}$-alkylene-C(O)—O, R$^{5.2}$ denotes H, C$_{1-3}$-alkyl, HO—C(O)—C$_{1-3}$-alkylene-NH, HO—C(O)—C$_{1-3}$-alkylene-O, HO—C(O)—C$_{1-3}$-alkylene, HO—C(O)—C(O) or HO—C(O)—C$_{1-3}$-alkylene-C(O), with the proviso that at least one of the groups R$^{3.1}$, R$^{3.2}$, R$^{4.2}$, R$^{5.1}$ or R$^{5.2}$ denotes a group other than H or C$_{1-3}$-alkyl, the tautomers, the diastereomers, the enantiomers, the hydrates, the mixtures thereof and the salts thereof as well as the hydrates of the salts thereof, particularly the physiologically acceptable salts thereof with inorganic or organic acids or bases.

A second embodiment of the present invention consists of the compounds of the above general formula I, wherein R$^1$ denotes a group selected from

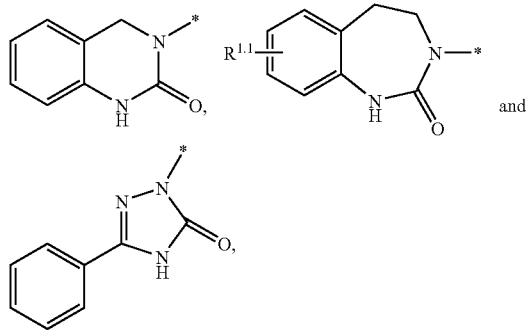

wherein
R$^{1.1}$ denotes H or H$_3$C—O,
R$^2$ denotes a group selected from

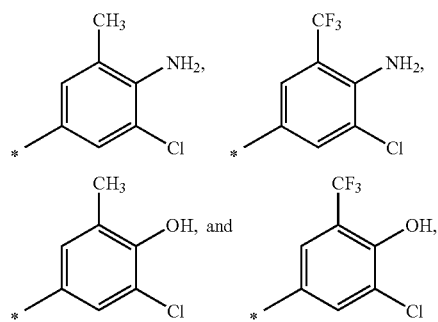

R$^3$ denotes a group of general formula II

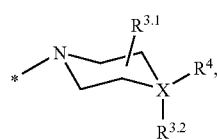

wherein
x denotes N or C,
R$^{3.1}$ denotes H, C$_{1-3}$-alkyl or R$^{3.1.1}$—(O)C,
R$^{3.1.1}$ denotes HO, C$_{1-6}$-alkyl-O, R$^{3.2}$ denotes a pair of free electrons, if X=N, or
R$^{3.2}$ denotes H or C$_{1-3}$-alkyl, if X=C,
R$^4$ denotes a group of general formulae III

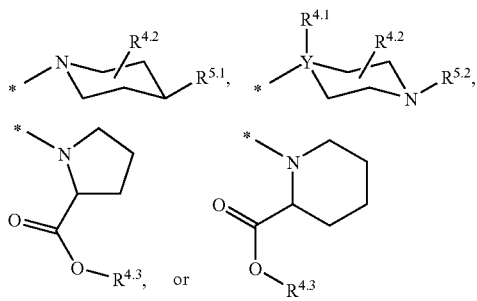

wherein
Y denotes C and
R$^{4.1}$ denotes H or C$_{1-3}$-alkyl, or
Y denotes N and
R$^{4.1}$ denotes a pair of free electrons,
with the proviso that X and Y do not simultaneously represent N,
R$^{4.2}$ denotes H, C$_{1-3}$-alkyl or R$^{4.2.1}$—(O)C,
R$^{4.2.1}$ denotes HO, C$_{1-6}$-alkyl-O, and
R$^{4.3}$ denotes H, C$_{1-6}$-alkyl, H$_2$N—C$_{2-4}$-alkylene, (C$_{1-3}$-alkyl)-NH—C$_{2-4}$-alkylene, (C$_{1-3}$-alkyl)$_2$N—C$_{2-4}$-alkylene, H$_2$N—C(O)—C$_{1-3}$-alkylene, (C$_{1-3}$-alkyl)-NH—C(O)—C$_{1-3}$-alkylene, (C$_{1-3}$-alkyl)$_2$N—C(O)—C$_{1-3}$-alkylene or R$^{4.3.1}$—C$_{2-4}$-alkylene,
R$^{4.3.1}$ denotes a group selected from

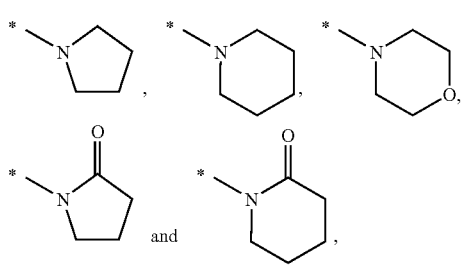

R$^{5.1}$ denotes R$^{5.1.1}$—O—C(O), R$^{5.1.1}$—O—C(O)—C$_{1-3}$-alkylene-NH, R$^{5.1.1}$—O—C(O)—C$_{1-3}$-alkylene-O, R$^{5.1.1}$—O—C(O)—C$_{1-3}$-alkylene, R$^{5.1.1}$—O—C(O)—C(O) or R$^{5.1.1}$—O—C(O)—C$_{1-3}$-alkylene-C(O),
R$^{5.1.1}$ denotes H, C$_{1-8}$-alkyl, phenyl, indanyl, pyridyl-C$_{1-3}$-alkylene, HO—C$_{2-4}$-alkylene, C$_{1-6}$-alkyl-O—C$_{2-4}$-alkylene, H$_2$N—C$_{2-4}$-alkylene, (C$_{1-6}$-alkyl)-NH—C$_{2-4}$-alkylene, (C$_{1-6}$-alkyl)$_2$N—C$_{2-4}$-alkylene, H$_2$N—C(O)—C$_{1-3}$-alkylene, (C$_{1-6}$-alkyl)-NH—C(O)—C$_{1-3}$-alkylene, (C$_{1-6}$-alkyl)$_2$N—C(O)—C$_{1-3}$-alkylene, C$_{1-6}$-alkyl-C(O)—O—C$_{1-3}$-alkylene, C$_{1-6}$-alkyl-O—C(O)—O—C$_{1-3}$-alkylene, R$^{5.1.1.1}$—C(O)—C$_{1-3}$-alkylene or R$^{5.1.1.2}$—C$_{2-4}$-alkylene, $R^{5.1.1.1}$ denotes a group selected from

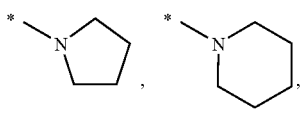

$R^{5.1.1.2}$ denotes a group selected from

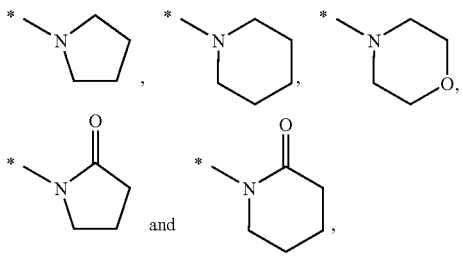

$R^{5.2}$ denotes $R^{5.2.1}$—O—C(O)—$C_{1-3}$-alkylene-NH, $R^{5.2.1}$—O—C(O)—$C_{1-3}$-alkylene-O, $R^{5.2.1}$—O—C(O)—$C_{1-3}$-alkylene, $R^{5.2.1}$—O—C(O)—C(O) or $R^{5.2.1}$—O—C(O)—$C_{1-3}$-alkylene-C(O), $R^{5.2.1}$ denotes H, $C_{1-8}$-alkyl, phenyl, indanyl, pyridyl-$C_{1-3}$-alkylene, HO—$C_{2-4}$-alkylene, $C_{1-6}$-alkyl-O—$C_{2-4}$-alkylene, $H_2N$—$C_{2-4}$-alkylene, $(C_{1-6}$-alkyl)-NH—$C_{2-4}$-alkylene, $(C_{1-6}$-alkyl$)_2$N—$C_{2-4}$-alkylene, $H_2N$—C(O)—$C_{1-3}$-alkylene, $(C_{1-6}$-alkyl)-NH—C(O)—$C_{1-3}$-alkylene, $(C_{1-6}$-alkyl$)_2$N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.2.1.1}$—C(O)—$C_{1-3}$-alkylene or $R^{5.2.1.2}$—$C_{2-4}$-alkylene, $R^{5.2.1.1}$ denotes a group selected from

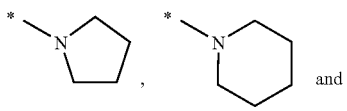

$R^{5.2.1.2}$ denotes a group selected from

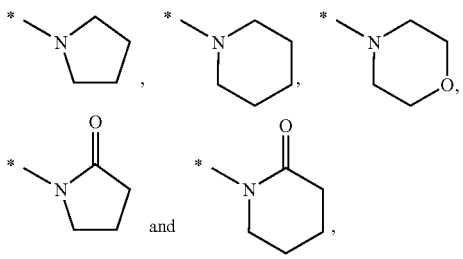

the tautomers, the diastereomers, the enantiomers, the hydrates, the mixtures thereof and the salts thereof as well as the hydrates of the salts thereof, particularly the physiologically acceptable salts thereof with inorganic or organic acids or bases.

A preferred second embodiment of the present invention consists of the compounds of the above general formula I, wherein
$R^1$ denotes a group selected from

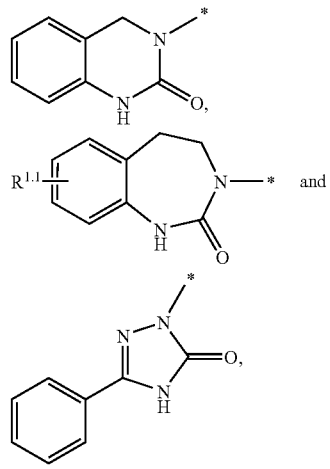

wherein
$R^{1.1}$ denotes H or $H_3C$—O,
$R^2$ denotes a group selected from

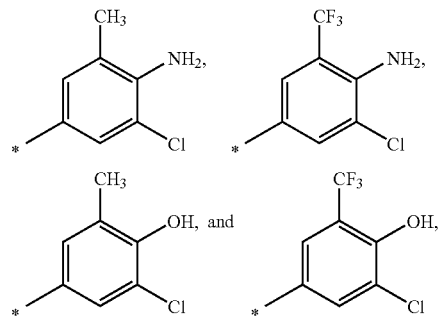

$R^3$ denotes a group of general formula II

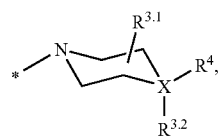

wherein
X denotes N or C,
$R^{3.1}$ denotes H, $C_{1-3}$-alkyl or HO—C(O),
$R^{3.2}$ denotes a pair of free electrons, if X=N, or
$R^{3.2}$ denotes H or $C_{1-3}$-alkyl, if X=C,
$R^4$ denotes a group of general formulae III

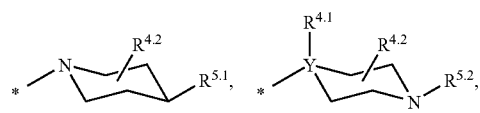

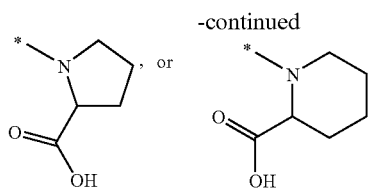

wherein
Y denotes C and
R[4.1] denotes H or $C_{1-3}$-alkyl, or
Y denotes N and
R[4.1] denotes a pair of free electrons,
with the proviso that X and Y do not simultaneously represent N,
R[4.2] denotes H, $C_{1-3}$-alkyl or HO—C(O),
R[5.1] denotes HO—C(O), HO—C(O)—$C_{1-3}$-alkylene-NH, HO—C(O)—$C_{1-3}$-alkylene-O, HO—C(O)—$C_{1-3}$-alkylene, HO—C(O)—$C_{1-3}$-alkylene-C(O),
R[5.2] denotes HO—C(O)—$C_{1-3}$-alkylene-NH, HO—C(O)—$C_{1-3}$-alkylene-O, HO—C(O)—$C_{1-3}$-alkylene, HO—C(O)—C(O) or HO—C(O)—$C_{1-3}$-alkylene-(O), the tautomers, the diastereomers, the enantiomers, the hydrates, the mixtures thereof and the salts thereof as well as the hydrates of the salts thereof, particularly the physiologically acceptable salts thereof with inorganic or organic acids or bases.

A third embodiment of the present invention consists of the compounds of the above general formula I, wherein
R[1] denotes a group selected from

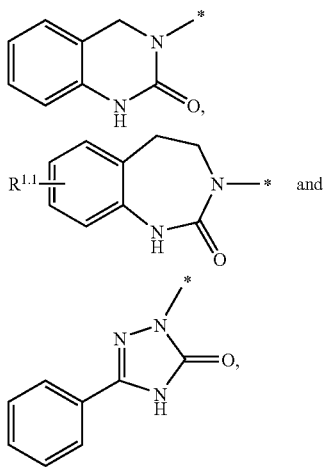

wherein
R[1.1] denotes H or $H_3C$—O,
R[2] denotes a group selected from

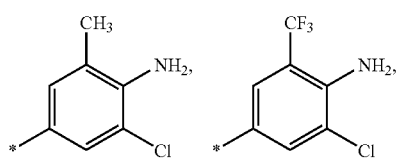

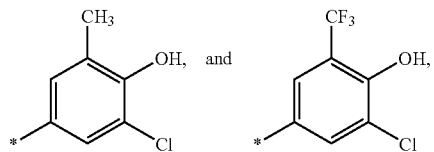

R[3]-R[4] together denote a group of general formulae IV

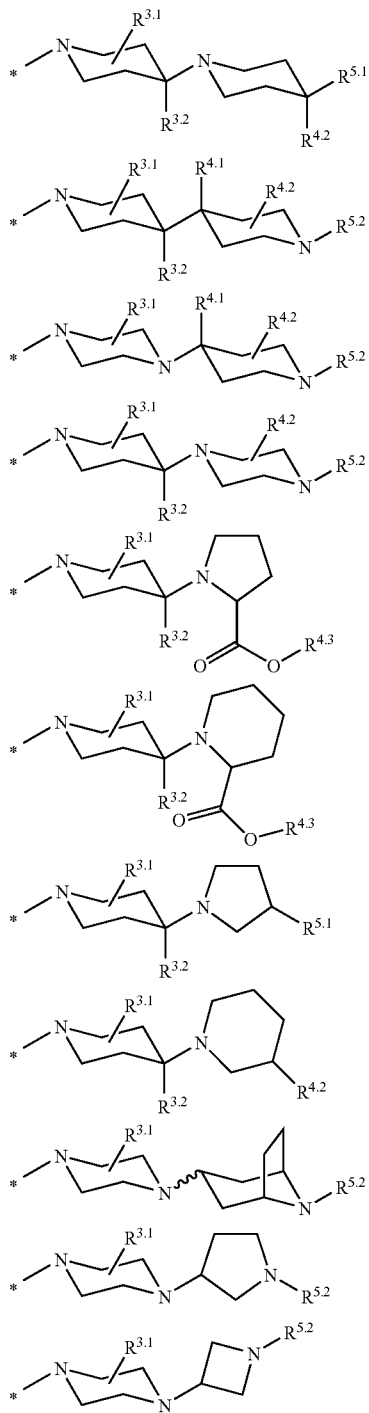

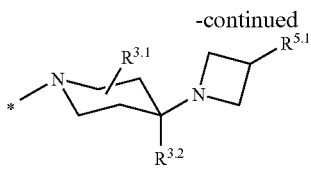

wherein
R³·¹ denotes H, H₃C or R³·¹·¹—O—C(O),
R³·¹·¹ denotes H, C₁₋₆-alkyl, (C₁₋₃-alkyl)₂N—C₂₋₄-alkylene, (C₁₋₃-alkyl)₂N—C(O)—C₁₋₃-alkylene or R³·¹·¹·¹—C₂₋₄-alkylene,
R³·¹·¹·¹ denotes a group selected from

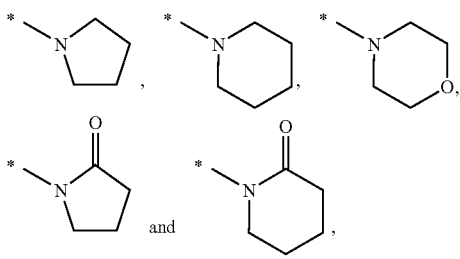

R³·² denotes H, C₁₋₃-alkyl or R³·²·¹—O—C(O),
R³·²·¹ denotes H, C₁₋₆-alkyl, (C₁₋₃-alkyl)₂N—C₂₋₄-alkylene, (C₁₋₃-alkyl)₂N—C(O)—C₁₋₃-alkylene or R³·²·¹·¹—C₂₋₄-alkylene,
R³·²·¹·¹ denotes a group selected from

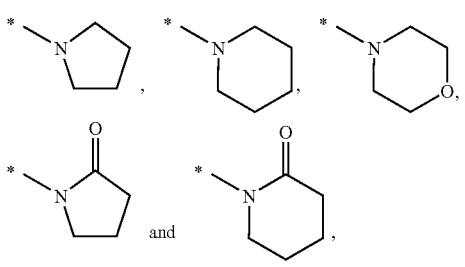

R⁴·¹ denotes H or C₁₋₃-alkyl,
R⁴·² denotes H, C₁₋₃-alkyl or R⁴·²·¹—O—C(O),
R⁴·²·¹ denotes H, C₁₋₆-alkyl, (C₁₋₃-alkyl)₂N—C₂₋₄-alkylene, (C₁₋₃-alkyl)₂N—C(O)—C₁₋₃-alkylene or R⁴·²·¹·¹—C₂₋₄-alkylene,
R⁴·²·¹·¹ denotes a group selected from

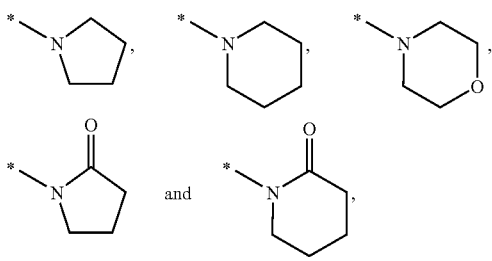

R⁴·³ denotes H, C₁₋₆-alkyl, H₂N—C₂₋₄-alkylene, (C₁₋₃-alkyl)-NH—C₂₋₄-alkylene, (C₁₋₃-alkyl)₂N—C₂₋₄-alkylene, H₂N—C(O)—C₁₋₃-alkylene, (C₁₋₃-alkyl)-NH—C(O)—C₁₋₃-alkylene, (C₁₋₃-alkyl)₂N—C(O)—C₁₋₃-alkylene or R⁴·³·¹—C₂₋₄-alkylene,
R⁴·³·¹ denotes a group selected from

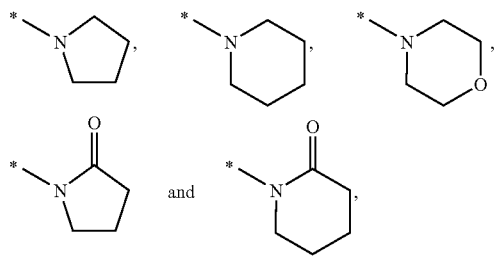

R⁵·¹ denotes H, H₃C, R⁵·¹·¹—O—C(O), R⁵·¹·¹—O—C(O)—C₁₋₃-alkylene-NH, R⁵·¹·¹—O—C(O)—C₁₋₃-alkylene-N(C₁₋₃-alkyl), R⁵·¹·¹—O—C(O)—C₁₋₃-alkylene-O, R⁵·¹·¹—O—C(O)—C₁₋₃-alkylene, R⁵·¹·¹—O—C(O)—C(O), R⁵·¹·¹—O—C(O)—C(O)—O, R⁵·¹·¹—O—C(O)—C₁₋₃-alkylene-C(O) or R⁵·¹·¹—O—C(O)—C₁₋₃-alkylene-C(O)—O,
R⁵·¹·¹ denotes H, C₁₋₈-alkyl, phenyl, indanyl, pyridyl-C₁₋₃-alkylene, HO—C₂₋₄-alkylene, C₁₋₆-alkyl-O—C₂₋₄-alkylene, H₂N—C₂₋₄-alkylene, (C₁₋₆-alkyl)-NH—C₂₋₄-alkylene, (C₁₋₆-alkyl)₂N—C₂₋₄-alkylene, H₂N—C(O)—C₁₋₃-alkylene, (C₁₋₆-alkyl)-NH—C(O)—C₁₋₃-alkylene, (C₁₋₆-alkyl)₂N—C(O)—C₁₋₃-alkylene, C₁₋₆-alkyl-C(O)—O—C₁₋₃-alkylene, C₁₋₆-alkyl-O—C(O)—O—C₁₋₃-alkylene, R⁵·¹·¹·¹—C(O)—C₁₋₃-alkylene or R⁵·¹·¹·²—C₂₋₄-alkylene,
R⁵·¹·¹·¹ denotes a group selected from

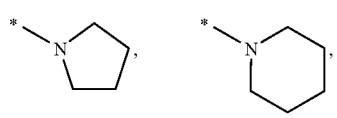

R⁵·¹·¹·² denotes a group selected from

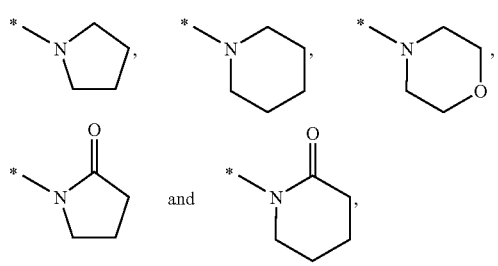

R⁵·² denotes H, H₃C, R⁵·²·¹—O—C(O)—C₁₋₃-alkylene-NH, R⁵·²·¹—O—C(O)—C₁₋₃-alkylene-O, R⁵·²·¹—O—C(O)—C₁₋₃-alkylene, R⁵·²·¹—O—C(O)—C(O) or R⁵·²·¹—O—C(O)—C₁₋₃-alkylene-C(O),
R⁵·²·²·¹ denotes H, C₁₋₈-alkyl, phenyl, indanyl, pyridyl-C₁₋₃-alkylene, HO—C₂₋₄-alkylene, C₁₋₆-alkyl-O—C₂₋₄-alkylene, C₁₋₆-alkyl-O—C₂₋₄-alkylene-O—C₂₋₄-alkylene, H₂N—C₂₋₄-alkylene, (C₁₋₆-alkyl)-NH—C₂₋₄-alkylene, (C₁₋₆-alkyl)₂N—C₂₋₄-alkylene, H₂N—C(O)—C₁₋₃-alkylene, (C₁₋₆-alkyl)-NH—C(O)—C₁₋₃-alkylene, (C₁₋₆-alkyl)₂N—C(O)—C₁₋₃-alkylene, C₁₋₆- alkyl-C(O)—O—$C_{1-3}$-alkylene, $C_{1-6}$-alkyl-O—C(O)—O—$C_{1-3}$-alkylene, $R^{5.2.1.1}$—C(O)—$C_{1-3}$-alkylene or $R^{5.2.1.2}$—$C_{2-4}$-alkylene, $R^{5.2.1.1}$ denotes a group selected from

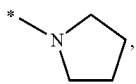 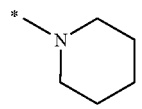 and $R^{5.2.1.2}$ denotes a group selected from

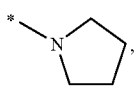 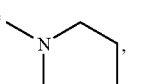 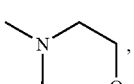

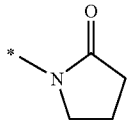 and 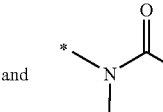 or $R^{5.2.1}$ denotes a group of formula

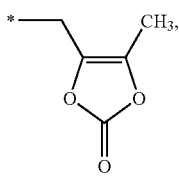

with the proviso that at least one of the groups $R^{3.1}$, $R^{3.2}$, $R^{4.2}$, $R^{5.1}$ or $R^{5.2}$ denotes a group other than H or $C_{1-3}$-alkyl, the tautomers, the diastereomers, the enantiomers, the hydrates, the mixtures thereof and the salts thereof as well as the hydrates of the salts thereof, particularly the physiologically acceptable salts thereof with inorganic or organic acids or bases.

A preferred third embodiment of the present invention consists of the compounds of the above general formula I, wherein $R^1$ denotes a group selected from

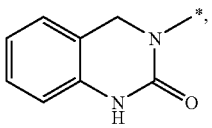

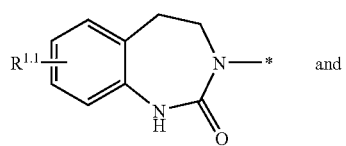 and

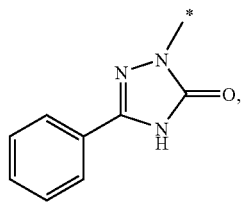

wherein
$R^{1.1}$ denotes H or $H_3C$—O,
$R^2$ denotes a group selected from

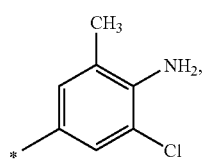 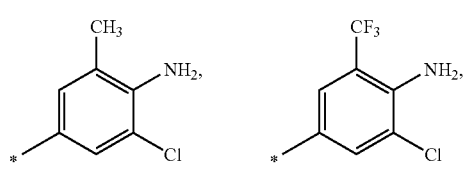

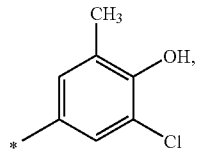 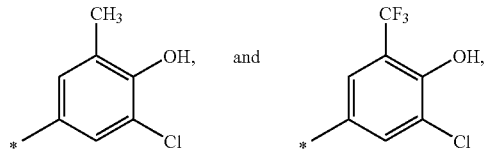

$R^3$-$R^4$ together denote a group of general formulae IV

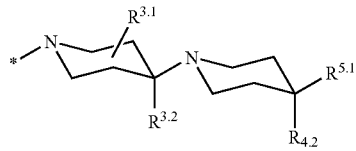

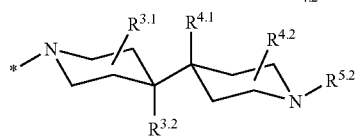

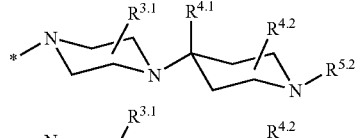

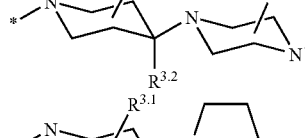

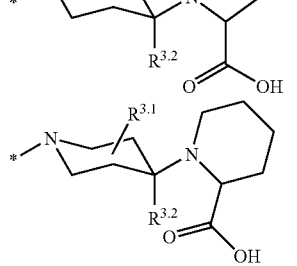

-continued

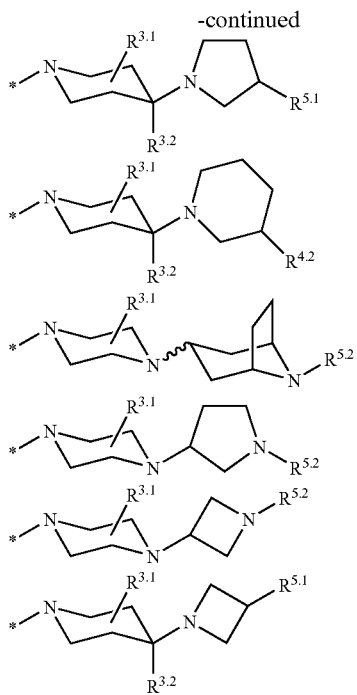

wherein
R[3.1] denotes H, H₃C or HO—C(O),
R[3.2] denotes H, $C_{1-3}$-alkyl or HO—C(O),
R[4.1] denotes H or $C_{1-3}$-alkyl,
R[4.2] denotes H, $C_{1-3}$-alkyl or HO—C(O),
R[5.1] denotes H, H₃C, HO—C(O), HO—C(O)—$C_{1-3}$-alkylene-NH, HO—C(O)—$C_{1-3}$-alkylene-N($C_{1-3}$-alkyl), HO—C(O)—$C_{1-3}$-alkylene-O, HO—C(O)—$C_{1-3}$-alkylene, HO—C(O)—C(O), HO—C(O)—C(O)—O—HO—C(O)—$C_{1-3}$-alkylene-C(O) or HO—C(O)—$C_{1-3}$-alkylene-C(O)—O,
R[5.2] denotes H, H₃C, HO—C(O)—$C_{1-3}$-alkylene-NH, HO—C(O)—$C_{1-3}$-alkylene-O, HO—C(O)—$C_{1-3}$-alkylene, HO—C(O)—C(O) or HO—C(O)—$C_{1-3}$-alkylene-C(O), with the proviso that at least one of the groups R[3.1], R[3.2], R[4.2], R[5.1] or R[5.2] denotes a group other than H, H₃C or $C_{1-3}$-alkyl, the tautomers, the diastereomers, the enantiomers, the hydrates, the mixtures thereof and the salts thereof as well as the hydrates of the salts thereof, particularly the physiologically acceptable salts thereof with inorganic or organic acids or bases.

A fourth embodiment of the present invention consists of the compounds of the above general formula I, wherein
R¹ denotes a group selected from

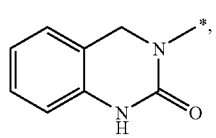

-continued

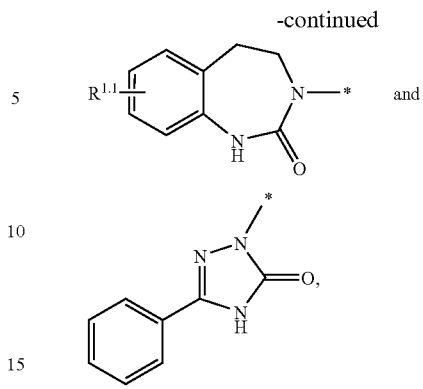

wherein
R[1.1] denotes H or H₃C—O,
R² denotes a group selected from

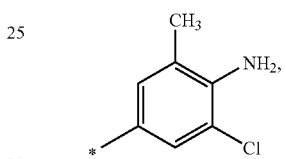

and

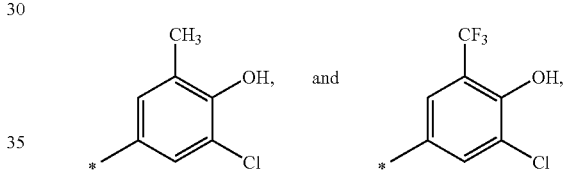

R³-R⁴ together denote a group of general formulae IV

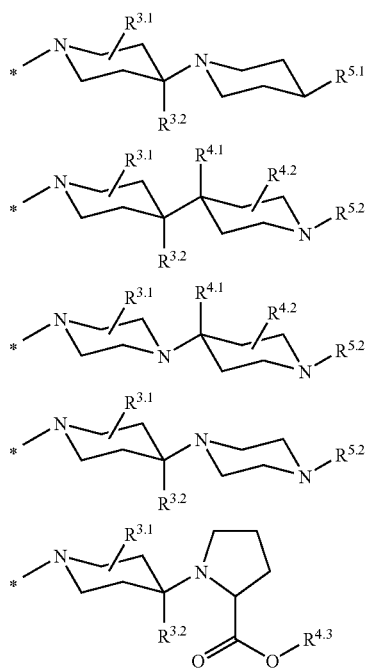

-continued

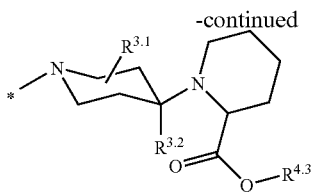

wherein $R^{3.1}$ denotes H, $R^{3.2}$ denotes H or $C_{1-3}$-alkyl, $R^{4.1}$ denotes H or $C_{1-3}$-alkyl, $R^{4.2}$ denotes H, $R^{4.3}$ denotes H, $C_{1-6}$-alkyl, $H_2N$—$C_{2-4}$-alkylene, $(C_{1-3}$-alkyl)-NH—$C_{2-4}$-alkylene, $(C_{1-3}$-alkyl)$_2$N—$C_{2-4}$-alkylene, $H_2N$—C(O)—$C_{1-3}$-alkylene, $(C_{1-3}$-alkyl)-NH—C(O)—$C_{1-3}$-alkylene, $(C_{1-3}$-alkyl)$_2$N—C(O)—$C_{1-3}$-alkylene or $R^{4.3.1}$—$C_{2-4}$-alkylene, $R^{4.3.1}$ denotes a group selected from

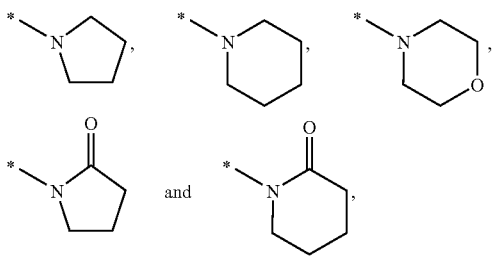

$R^{5.1}$ denotes $R^{5.1.1}$—O—C(O), $R^{5.1.1}$—O—C(O)—$C_{1-3}$-alkylene-NH, $R^{5.1.1}$—O—C(O)—$C_{1-3}$-alkylene-O, $R^{5.1.1}$—O—C(O)—$C_{1-3}$-alkylene, $R^{5.1.1}$—O—C(O)—C(O) or $R^{5.1.1}$—O—C(O)—$C_{1-3}$-alkylene-C(O), $R^{5.1.1}$ denotes H, $C_{1-8}$-alkyl, phenyl, indanyl, pyridyl-$C_{1-3}$-alkylene, HO—$C_{2-4}$-alkylene, $C_{1-6}$-alkyl-O—$C_{2-4}$-alkylene, $H_2N$—$C_{2-4}$-alkylene, $(C_{1-6}$-alkyl)-NH—$C_{2-4}$-alkylene, $(C_{1-6}$-alkyl)$_2$N—$C_{2-4}$-alkylene, $H_2N$—C(O)—$C_{1-3}$-alkylene, $(C_{1-6}$-alkyl)-NH—C(O)—$C_{1-3}$-alkylene, $(C_{1-6}$-alkyl)$_2$N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.1.1.1}$—C(O)—$C_{1-3}$-alkylene or $R^{5.1.1.2}$—$C_{2-4}$-alkylene, $R^{5.1.1.1}$ denotes a group selected from

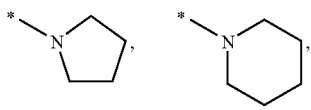

$R^{5.1.1.2}$ denotes a group selected from

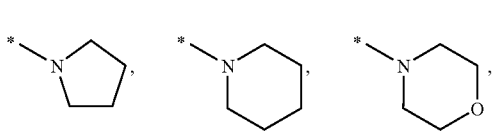

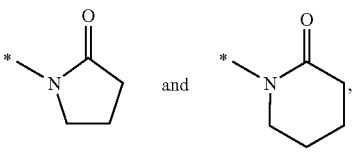

$R^{5.2}$ denotes $R^{5.2.1}$—O—C(O)—$C_{1-3}$-alkylene-NH, $R^{5.2.1}$—O—C(O)—$C_{1-3}$-alkylene-O, $R^{5.2.1}$—O—C(O)—$C_{1-3}$-alkylene, $R^{5.2.1}$—O—C(O)—C(O) or $R^{5.2.1}$—O—C(O)—$C_{1-3}$-alkylene-C(O), $R^{5.2.1}$ denotes H, $C_{1-8}$-alkyl, phenyl, indanyl, pyridyl-$C_{1-3}$-alkylene, HO—$C_{2-4}$-alkylene, $C_{1-6}$-alkyl-O—$C_{2-4}$-alkylene, $H_2N$—$C_{2-4}$-alkylene, $(C_{1-6}$-alkyl)-NH—$C_{2-4}$-alkylene, $(C_{1-6}$-alkyl)$_2$N—$C_{2-4}$-alkylene, $H_2N$—C(O)—$C_{1-3}$-alkylene, $(C_{1-6}$-alkyl)-NH—C(O)—$C_{1-3}$-alkylene, $(C_{1-6}$-alkyl)$_2$N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.2.1.1}$—C(O)—$C_{1-3}$-alkylene or $R^{5.2.1.2}$—$C_{2-4}$-alkylene, $R^{5.2.1.1}$ denotes a group selected from

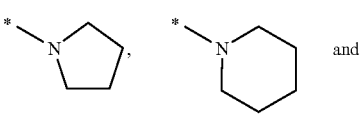

$R^{5.2.1.2}$ denotes a group selected from

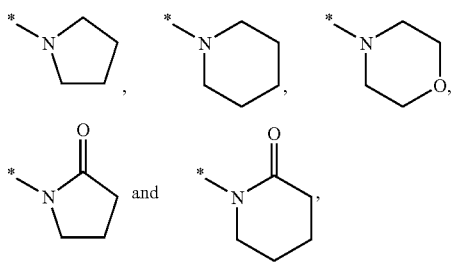

the tautomers, the diastereomers, the enantiomers, the hydrates, the mixtures thereof and the salts thereof as well as the hydrates of the salts thereof, particularly the physiologically acceptable salts thereof with inorganic or organic acids or bases.

A preferred fourth embodiment of the present invention consists of the compounds of the above general formula I, wherein $R^1$ denotes a group selected from

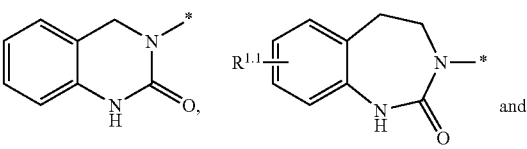

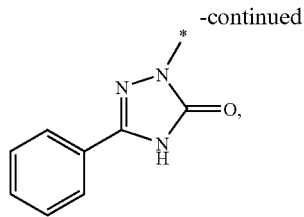

wherein
$R^{1.1}$ denotes H or $H_3C—O$,
$R^2$ denotes a group selected from

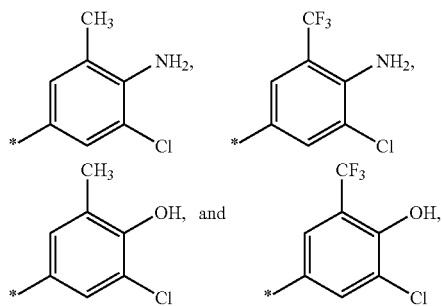

$R^3$-$R^4$ together denote a group of general formulae IV

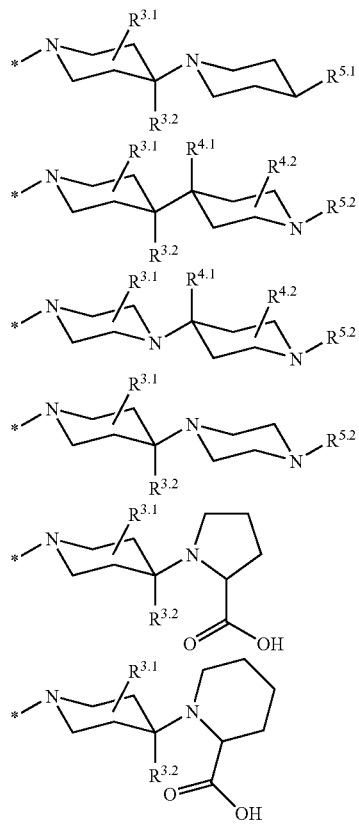

wherein
$R^{3.1}$ denotes H,
$R^{3.2}$ denotes H or $C_{1-3}$-alkyl,
$R^{4.1}$ denotes H or $C_{1-3}$-alkyl,
$R^{4.2}$ denotes H,
$R^{5.1}$ denotes HO—C(O), HO—C(O)—$C_{1-3}$-alkylene-NH, HO—C(O)—$C_{1-3}$-alkylene-O, HO—C(O)—$C_{1-3}$-alkylene, HO—C(O)—C(O) or HO—C(O)—$C_{1-3}$-alkylene-C(O),
$R^{5.2}$ denotes HO—C(O)—$C_{1-3}$-alkylene-NH, HO—C(O)—$C_{1-3}$-alkylene-O, HO—C(O)—$C_{1-3}$-alkylene, HO—C(O)—C(O) or HO—C(O)—$C_{1-3}$-alkylene-C(O), the tautomers, the diastereomers, the enantiomers, the hydrates, the mixtures thereof and the salts thereof as well as the hydrates of the salts thereof, particularly the physiologically acceptable salts thereof with inorganic or organic acids or bases.

A fifth embodiment of the present invention consists of the compounds of the above general formula I, wherein
$R^1$ denotes a group selected from

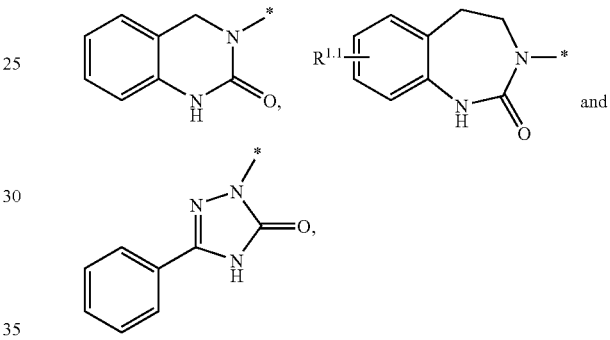

wherein
$R^{1.1}$ denotes H or $H_3C—O$,
$R^2$ denotes a group selected from

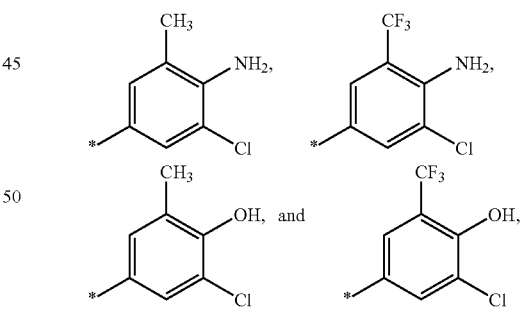

$R^3$-$R^4$ together denote a group of general formulae IV

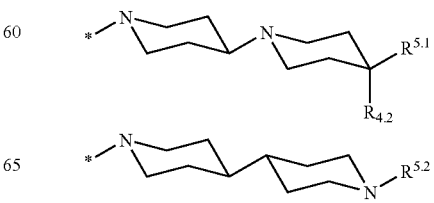

-continued

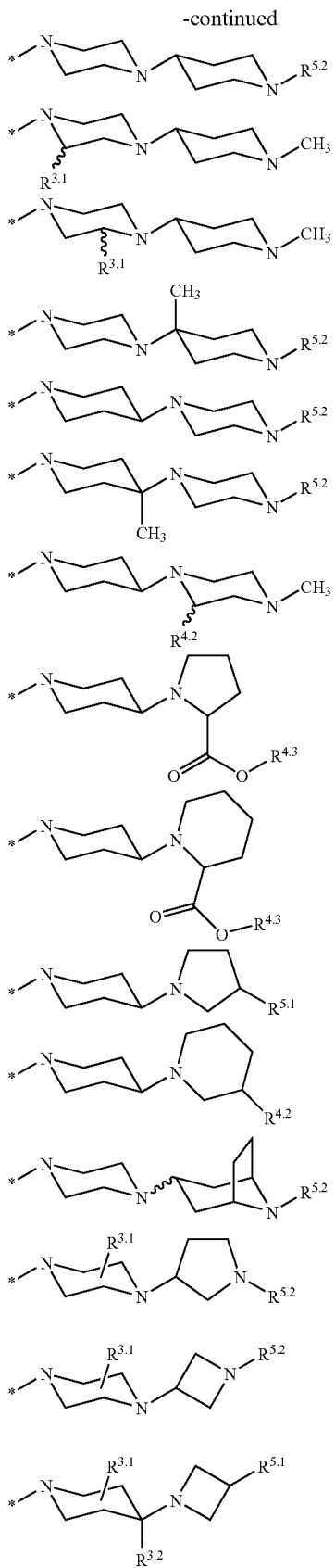

wherein
R[3.1] denotes H or R[3.1.1]—O—C(O),
R[3.1.1] denotes H, $C_{1-6}$-alkyl, $(C_{1-3}$-alkyl$)_2$N—$C_{2-4}$-alkylene, $(C_{1-3}$-alkyl$)_2$N—C(O)—$C_{1-3}$-alkylene or R[3.1.1.1]—$C_{2-4}$-alkylene,
R[3.1.1.1] denotes a group

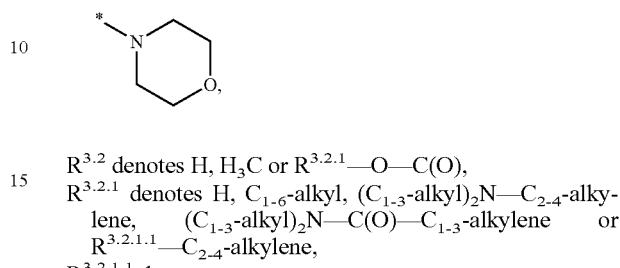

R[3.2] denotes H, $H_3C$ or R[3.2.1]—O—C(O),
R[3.2.1] denotes H, $C_{1-6}$-alkyl, $(C_{1-3}$-alkyl$)_2$N—$C_{2-4}$-alkylene, $(C_{1-3}$-alkyl$)_2$N—C(O)—$C_{1-3}$-alkylene or R[3.2.1.1]—$C_{2-4}$-alkylene,
R[3.2.1.1] denotes a group

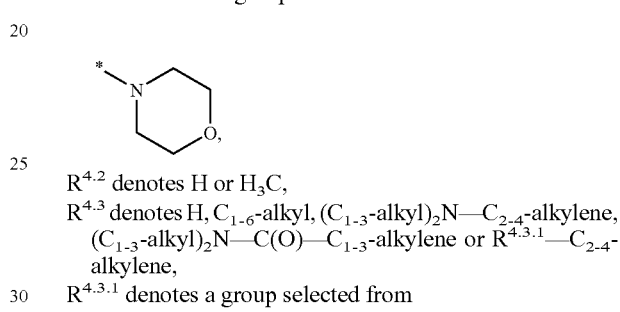

R[4.2] denotes H or $H_3C$,
R[4.3] denotes H, $C_{1-6}$-alkyl, $(C_{1-3}$-alkyl$)_2$N—$C_{2-4}$-alkylene, $(C_{1-3}$-alkyl$)_2$N—C(O)—$C_{1-3}$-alkylene or R[4.3.1]—$C_{2-4}$-alkylene,
R[4.3.1] denotes a group selected from

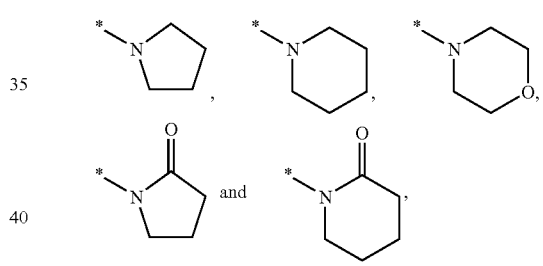

R[5.1] denotes H, $H_3C$, R[5.1.1]—O—C(O), R[5.1.1]—O—C(O)—$C_{1-3}$-alkylene-NH, R[5.1.1]—O—C(O)—$C_{1-3}$-alkylene-N($C_{1-3}$-alkyl), R[5.1.1]—O—C(O)—$C_{1-3}$-alkylene-O, R[5.1.1]—O—C(O)—$C_{1-3}$-alkylene, R[5.1.1]—O—C(O)—C(O), R[5.1.1]—O—C(O)—C(O)—O—R[5.1.1]—O—C(O)—$C_{1-3}$-alkylene-C(O) or R[5.1.1]—O—C(O)—$C_{1-3}$-alkylene-C(O)—O,
R[5.1.1] denotes H, $C_{1-8}$-alkyl, phenyl, indanyl, pyridyl-$CH_2$, HO—$C_{2-4}$-alkylene, $C_{1-6}$-alkyl-O—$C_{2-4}$-alkylene, $H_2N$—$C_{2-4}$-alkylene, $(C_{1-6}$-alkyl)-NH—$C_{2-4}$-alkylene, $(C_{1-6}$-alkyl$)_2$N—$C_{2-4}$-alkylene, $H_2N$—C(O)—$C_{1-3}$-alkylene, $(C_{1-6}$-alkyl)-NH—C(O)—$C_{1-3}$-alkylene, $(C_{1-6}$-alkyl$)_2$N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, R[5.1.1.1]—C(O)—$C_{1-3}$-alkylene or R[5.1.1.2]—$C_{2-4}$-alkylene,
R[5.1.1.1] denotes a group selected from

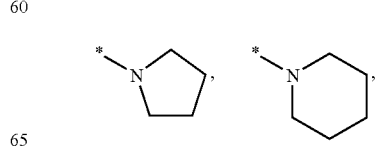

$R^{5.1.1.2}$ denotes a group selected from

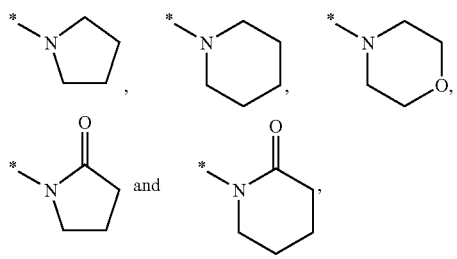

$R^{5.2}$ denotes H, $H_3C$, $R^{5.2.1}$—O—C(O)—$C_{1-3}$-alkylene, $R^{5.2.1}$—O—C(O)—C(O) or $R^{5.2.1}$—O—C(O)—$C_{1-3}$-alkylene-C(O), $R^{5.2.1}$ denotes H, $C_{1-8}$-alkyl, phenyl, indanyl, pyridyl-$CH_2$, HO—$C_{2-4}$-alkylene, $C_{1-6}$-alkyl-O—$C_{2-4}$-alkylene, $C_{1-6}$-alkyl-O—$C_{2-4}$-alkylene-O—$C_{2-4}$-alkylene, $H_2N$—$C_{2-4}$-alkylene, ($C_{1-6}$-alkyl)-NH—$C_{2-4}$-alkylene, ($C_{1-6}$-alkyl)$_2$N—$C_{2-4}$-alkylene, $H_2N$—C(O)—$C_{1-3}$-alkylene, ($C_{1-6}$-alkyl)-NH—C(O)—$C_{1-3}$-alkylene, ($C_{1-6}$-alkyl)$_2$N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.2.1.1}$—C(O)—$C_{1-3}$-alkylene or $R^{5.2.1.2}$—$C_{2-4}$-alkylene, $R^{5.2.1.1}$ denotes a group selected from

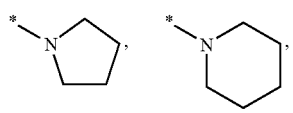

$R^{5.2.1.2}$ denotes a group selected from

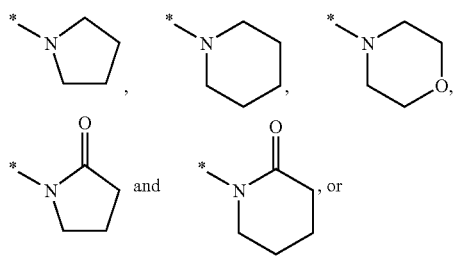

$R^{5.2.1}$ denotes a group of formula

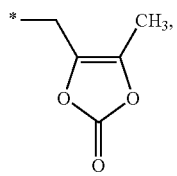

with the proviso that at least one of the groups $R^{3.1}$, $R^{3.2}$, $R^{5.1}$ or $R^{5.2}$ denotes a group other than H, $H_3C$ or $C_{1-3}$-alkyl, the tautomers, the diastereomers, the enantiomers, the hydrates, the mixtures thereof and the salts thereof as well as the hydrates of the salts thereof, particularly the physiologically acceptable salts thereof with inorganic or organic acids or bases.

A preferred fifth embodiment of the present invention consists of the compounds of the above general formula I, wherein $R^1$ denotes a group selected from

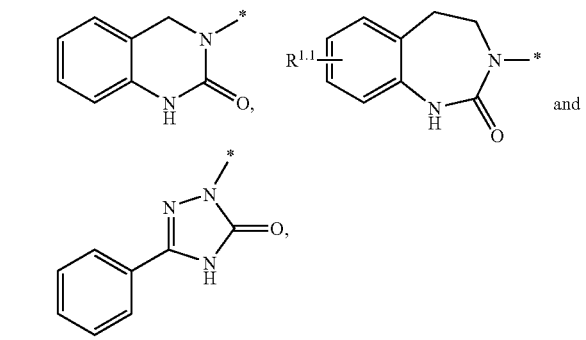

wherein
$R^{1.1}$ denotes H or $H_3C$—O,
$R^2$ denotes a group selected from

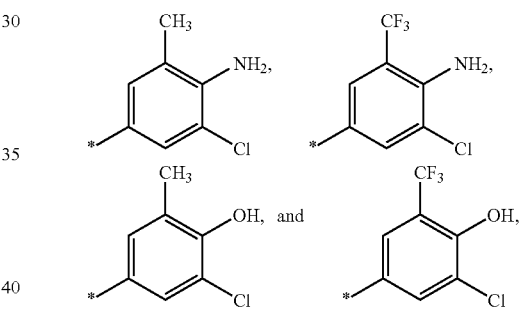

$R^3$-$R^4$ together denote a group of general formulae IV

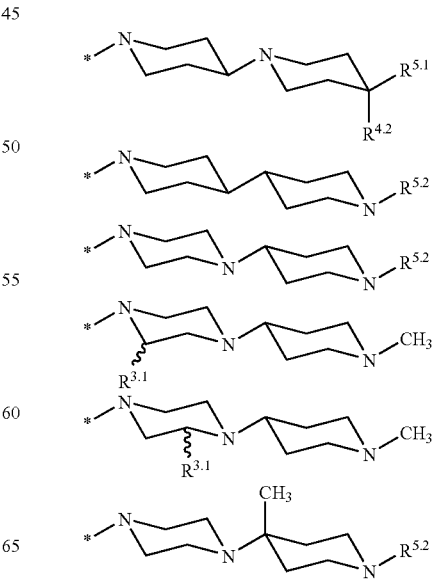

27

-continued

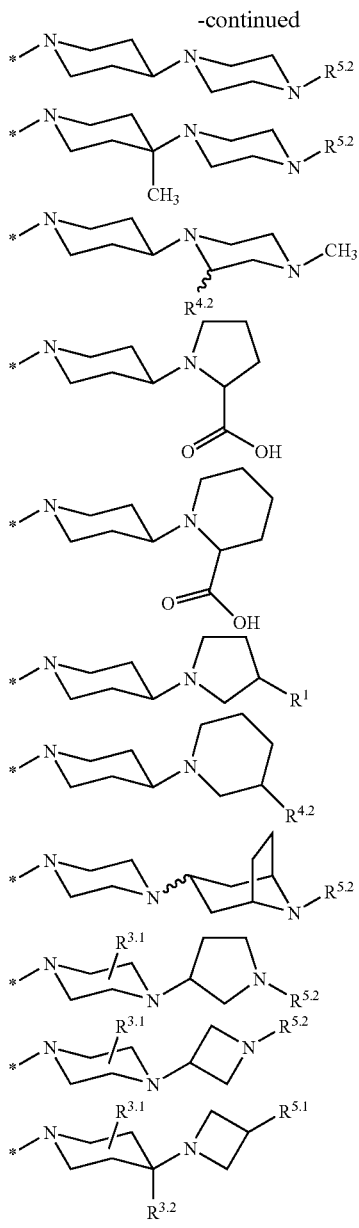

wherein
R$^{3.1}$ denotes H or HO—C(O),
R$^{3.2}$ denotes H, H$_3$C or HO—C(O),
R$^{4.2}$ denotes H or H$_3$C,
R$^{5.1}$ denotes HO—C(O), HO—C(O)—C$_{1-3}$-alkylene-NH, HO—C(O)—C$_{1-3}$-alkylene-N(C$_{1-3}$-alkyl), HO—C(O)—C$_{1-3}$-alkylene-O, HO—C(O)—C$_{1-3}$-alkylene, HO—C(O)—C(O), HO—C(O)—C(O)—O, HO—C(O)—C$_{1-3}$-alkylene-C(O) or HO—C(O)—C$_{1-3}$-alkylene-C(O)—O,
R$^{5.2}$ denotes HO—C(O)—C$_{1-3}$-alkylene, HO—C(O)—C(O) or HO—C(O)—C$_{1-3}$-alkylene-C(O), with the proviso that at least one of the groups R$^{3.1}$, R$^{3.2}$, R$^{4.2}$, R$^{5.1}$ or R$^{5.2}$ denotes a group other than H, H$_3$C or C$_{1-3}$-alkyl, the tautomers, the diastereomers, the enantiomers, the hydrates, the mixtures thereof and the salts thereof as well as the hydrates of the salts thereof, particularly the physiologically acceptable salts thereof with inorganic or organic acids or bases.

A sixth embodiment of the present invention consists of the compounds of the above general formula I, wherein R$^1$ denotes a group selected from

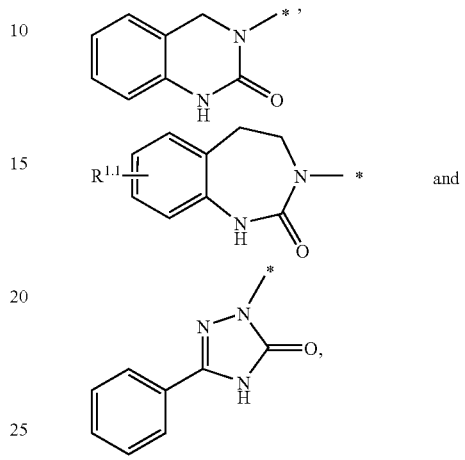

wherein
R$^{1.1}$ denotes H or H$_3$C—O,
R$^2$ denotes a group selected from

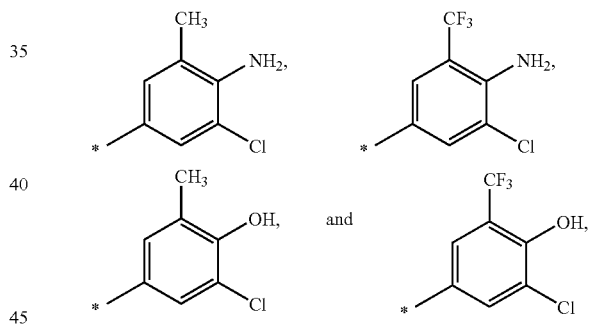

R$^3$-R$^4$ together denote a group of general formulae IV

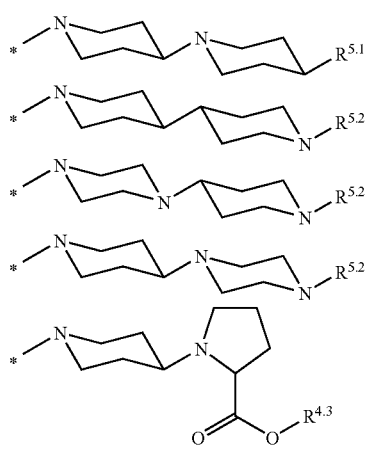

-continued

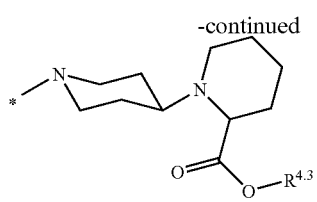

wherein
R$^{4.3}$ denotes H, C$_{1-6}$-alkyl, (C$_{1-3}$-alkyl)$_2$N—C$_{2-4}$-alkylene, (C$_{1-3}$-alkyl)$_2$N—C(O)—C$_{1-3}$-alkylene or R$^{4.3.1}$—C$_{2-4}$-alkylene,
R$^{4.3.1}$ denotes a group selected from

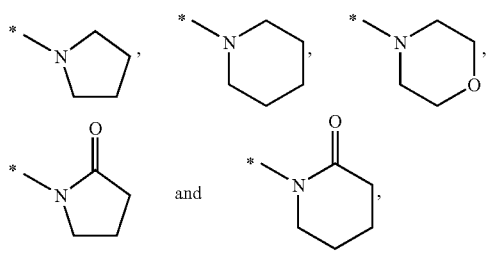

R$^{5.1}$ denotes R$^{5.1.1}$—O—C(O), R$^{5.1.1}$—O—C(O)—C$_{1-3}$-alkylene-NH, R$^{5.1.1}$—O—C(O)—C$_{1-3}$-alkylene-O, R$^{5.1.1}$—O—C(O)—C$_{1-3}$-alkylene, R$^{5.1.1}$—O—C(O)—C(O) or R$^{5.1.1}$—O—C(O)—C$_{1-3}$-alkylene-C(O),
R$^{5.1.1}$ denotes H, C$_{1-8}$-alkyl, phenyl, indanyl, pyridyl-CH$_2$, HO—C$_{2-4}$-alkylene, C$_{1-6}$-alkyl-O—C$_{2-4}$-alkylene, H$_2$N—C$_{2-4}$-alkylene, (C$_{1-6}$-alkyl)-NH—C$_{2-4}$-alkylene, (C$_{1-6}$-alkyl)$_2$N—C$_{2-4}$-alkylene, H$_2$N—C(O)—C$_{1-3}$-alkylene, (C$_{1-6}$-alkyl)-NH—C(O)—C$_{1-3}$-alkylene, (C$_{1-6}$-alkyl)$_2$N—C(O)—C$_{1-3}$-alkylene, C$_{1-6}$-alkyl-C(O)—O—C$_{1-3}$-alkylene, C$_{1-6}$-alkyl-O—C(O)—O—C$_{1-3}$-alkylene, R$^{5.1.1.1}$—C(O)—C$_{1-3}$-alkylene or R$^{5.1.1.2}$—C$_{2-4}$-alkylene,
R$^{5.1.1.1}$ denotes a group selected from

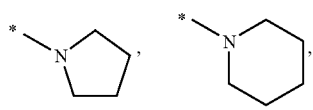

R$^{5.1.1.2}$ denotes a group selected from

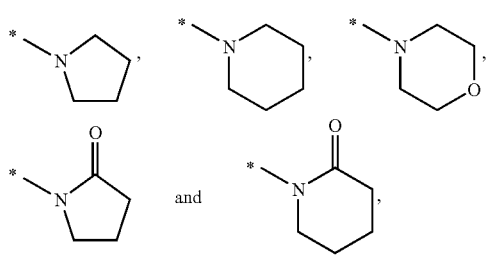

R$^{5.2}$ denotes R$^{5.2.1}$—O—C(O)—C$_{1-3}$-alkylene, R$^{5.2.1}$—O—C(O)—C(O) or R$^{5.2.1}$—O—C(O)—C$_{1-3}$-alkylene-C(O),
R$^{5.2.1}$ denotes H, C$_{1-8}$-alkyl, phenyl, indanyl, pyridyl-CH$_2$, HO—C$_{2-4}$-alkylene, C$_{1-6}$-alkyl-O—C$_{2-4}$-alkylene, H$_2$N—C$_{2-4}$-alkylene, (C$_{1-6}$-alkyl)-NH—C$_{2-4}$-alkylene, (C$_{1-6}$-alkyl)$_2$N—C$_{2-4}$-alkylene, H$_2$N—C(O)—C$_{1-3}$-alkylene, (C$_{1-6}$-alkyl)-NH—C(O)—C$_{1-3}$-alkylene, (C$_{1-6}$-alkyl)$_2$N—C(O)—C$_{1-3}$-alkylene, C$_{1-6}$-alkyl-C(O)—O—C$_{1-3}$-alkylene, C$_{1-6}$-alkyl-O—C(O)—O—C$_{1-3}$-alkylene, R$^{5.2.1.1}$—C(O)—C$_{1-3}$-alkylene or R$^{5.2.1.2}$—C$_{2-4}$-alkylene,
R$^{5.2.1.1}$ denotes a group selected from

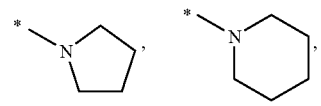

R$^{5.2.1.2}$ denotes a group selected from

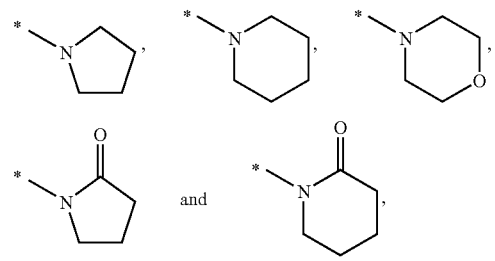

the tautomers, the diastereomers, the enantiomers, the hydrates, the mixtures thereof and the salts thereof as well as the hydrates of the salts thereof, particularly the physiologically acceptable salts thereof with inorganic or organic acids or bases.

A preferred sixth embodiment of the present invention consists of the compounds of the above general formula I, wherein
R$^1$ denotes a group selected from

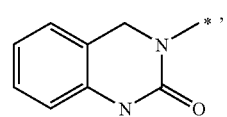
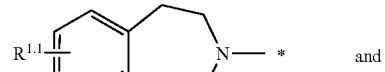
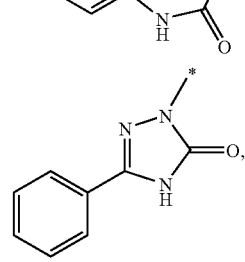

wherein
R$^{1.1}$ denotes H or H$_3$C—O, $R^2$ denotes a group selected from

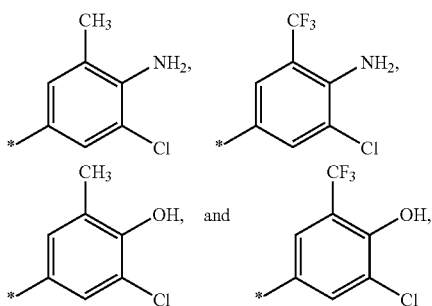

$R^3$-$R^4$ together denote a group of general formulae IV

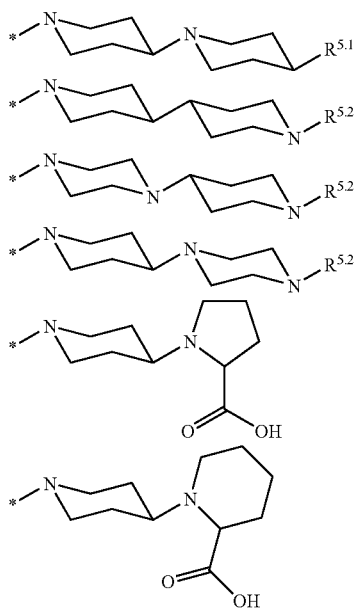

$R^{5.1}$ denotes HO—C(O), HO—C(O)—$C_{1-3}$-alkylene-NH, HO—C(O)—$C_{1-3}$-alkylene-O, HO—C(O)—$C_{1-3}$-alkylene, HO—C(O)—C(O) or HO—C(O)—$C_{1-3}$-alkylene-C(O), $R^{5.2}$ denotes HO—C(O)—$C_{1-3}$-alkylene, HO—C(O)—C(O) or HO—C(O)—$C_{1-3}$-alkylene-C(O), the tautomers, the diastereomers, the enantiomers, the hydrates, the mixtures thereof and the salts thereof as well as the hydrates of the salts thereof, particularly the physiologically acceptable salts thereof with inorganic or organic acids or bases.

A seventh embodiment of the present invention consists of the compounds of the above general formula I, wherein $R^1$ denotes a group selected from

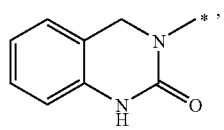

-continued

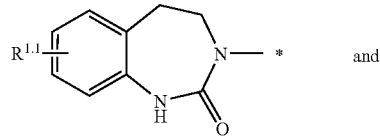

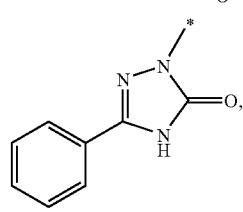

wherein
$R^{1.1}$ denotes H or $H_3C$—O,
$R^2$ denotes a group selected from

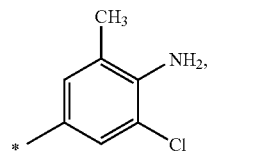

$R^3$-$R^4$ together denote a group of formulae IV

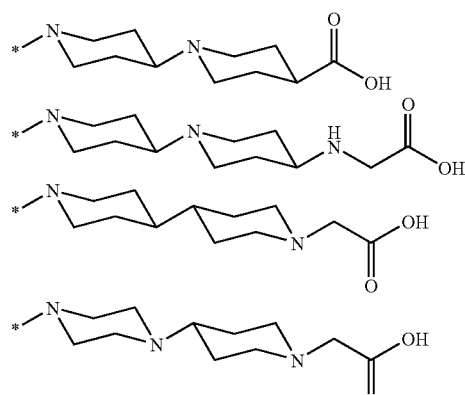

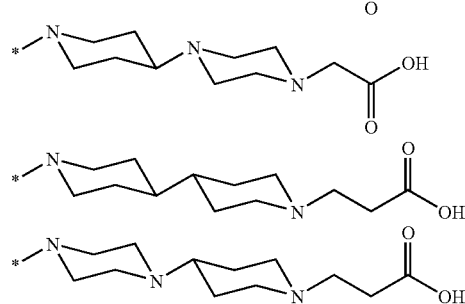

-continued
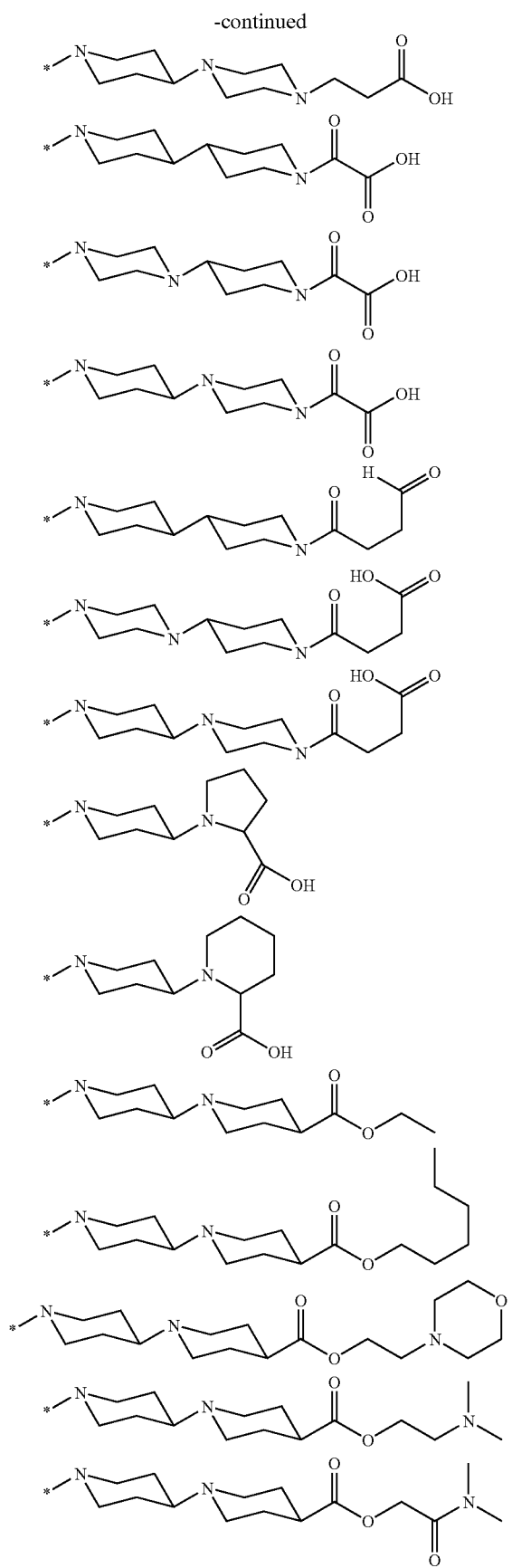
-continued
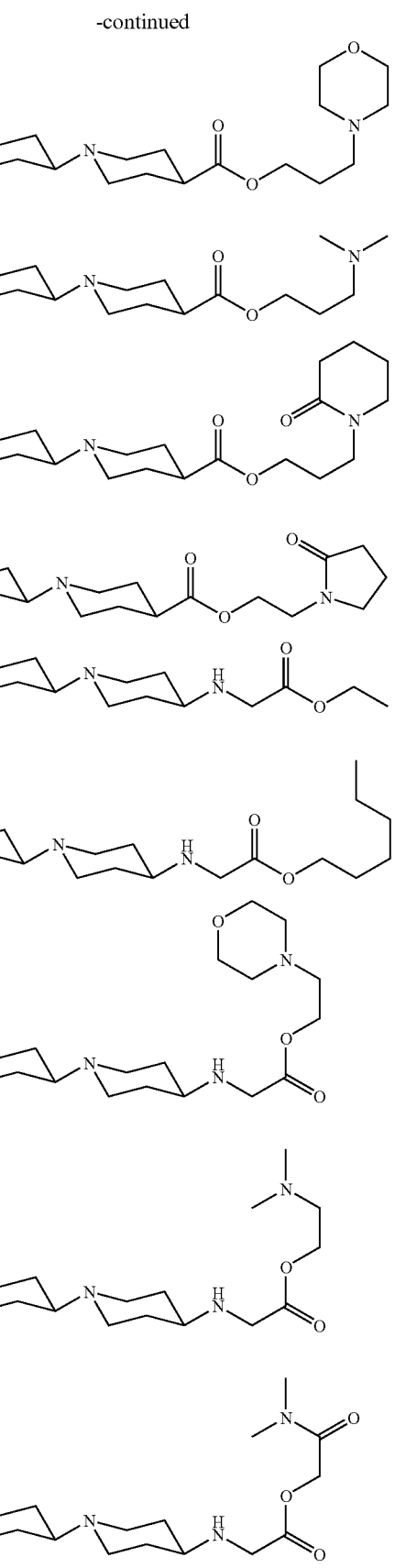

-continued
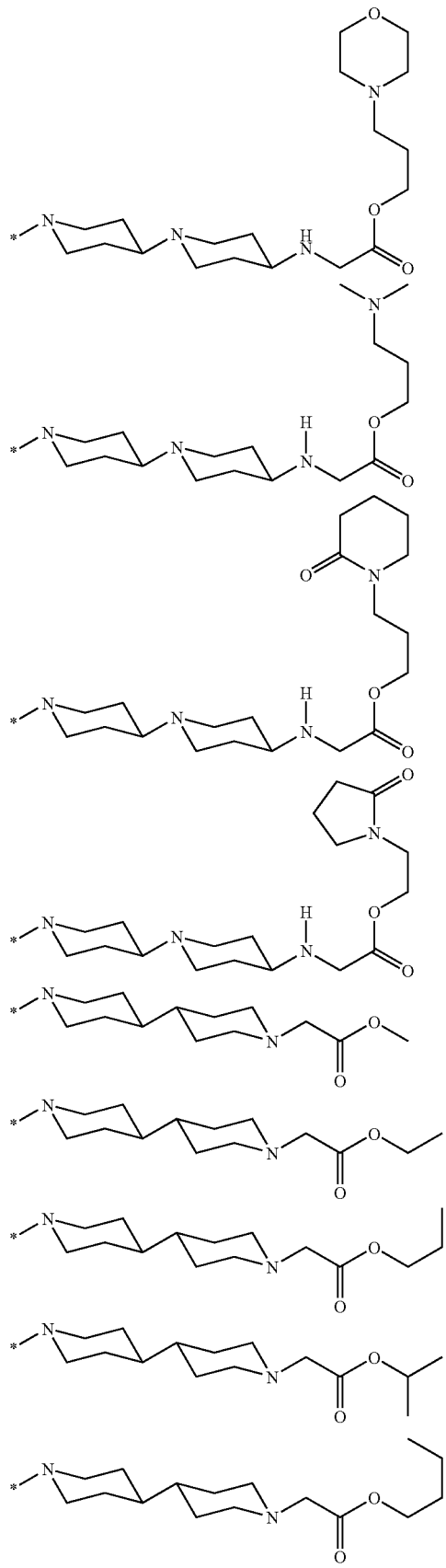
-continued
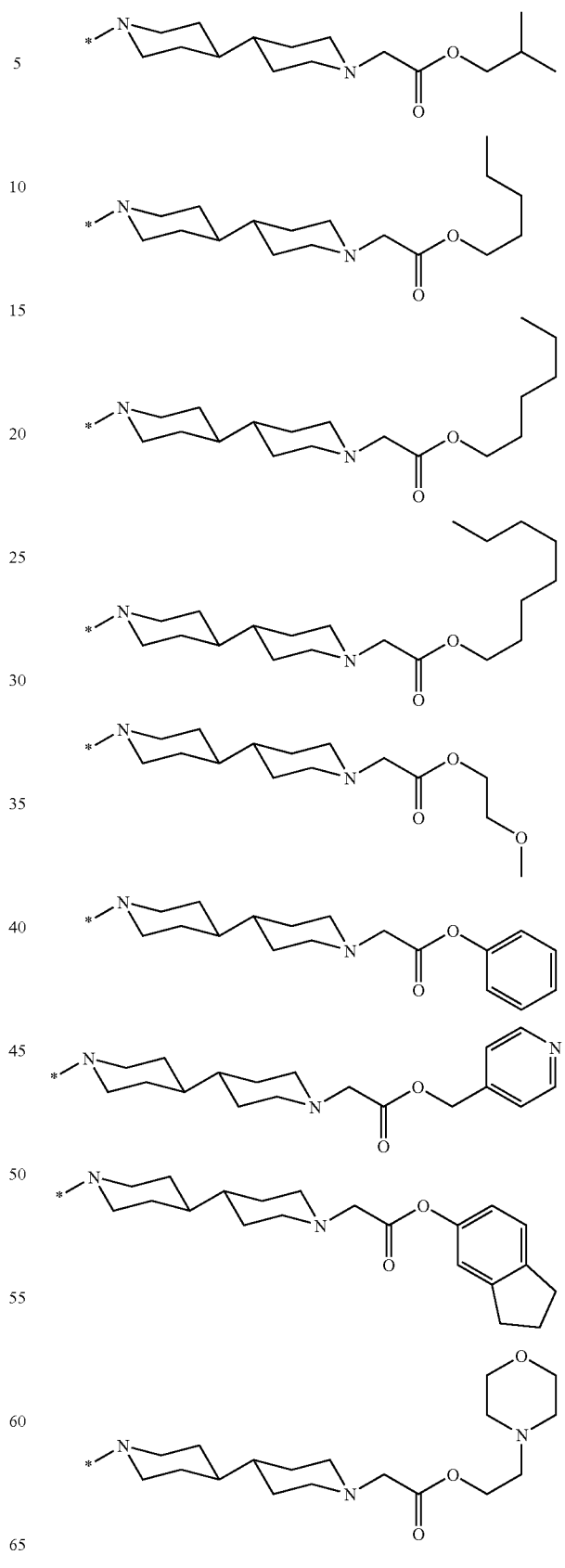

-continued
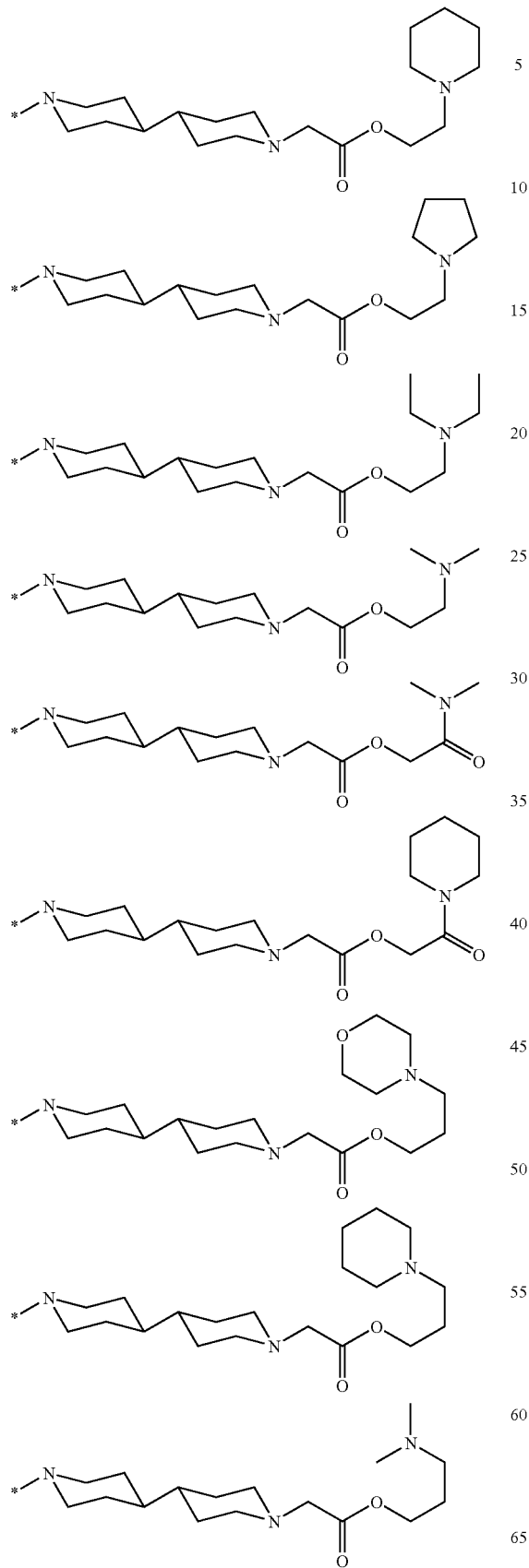
-continued
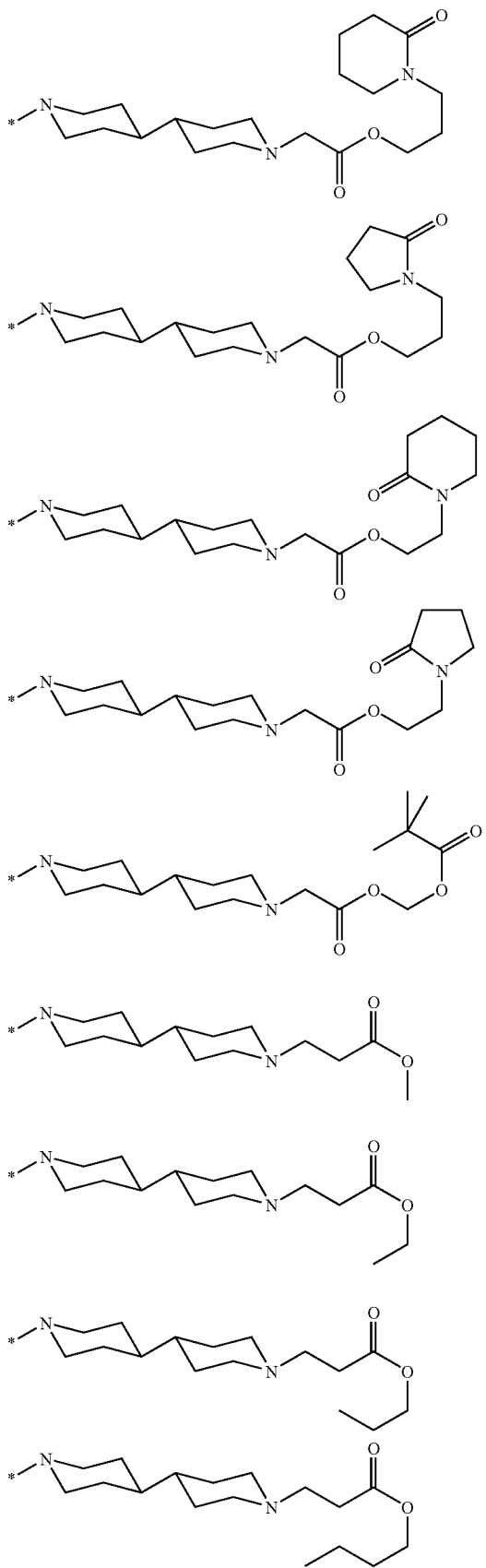

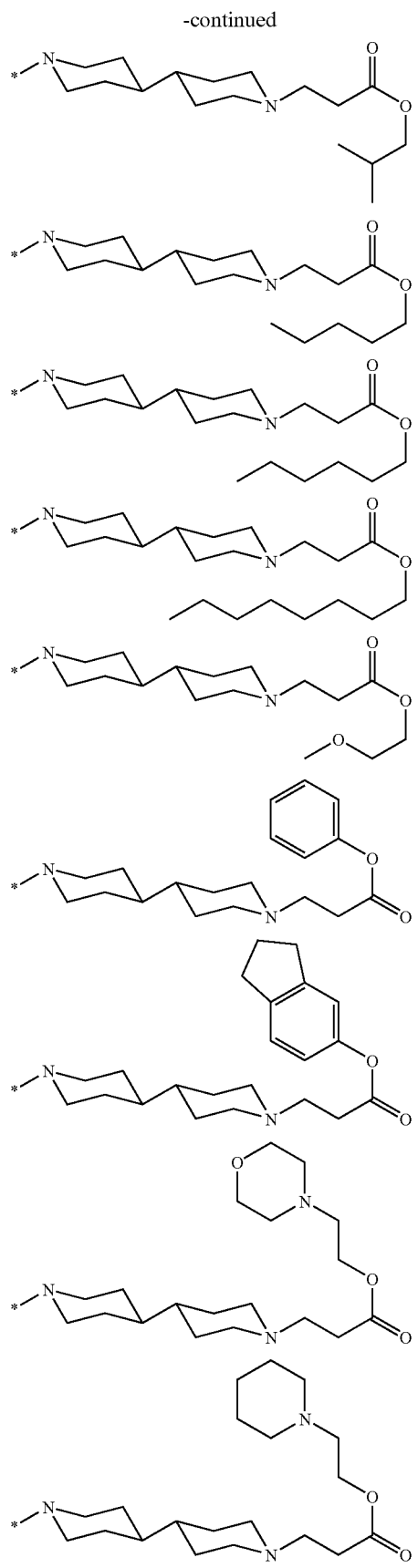

41
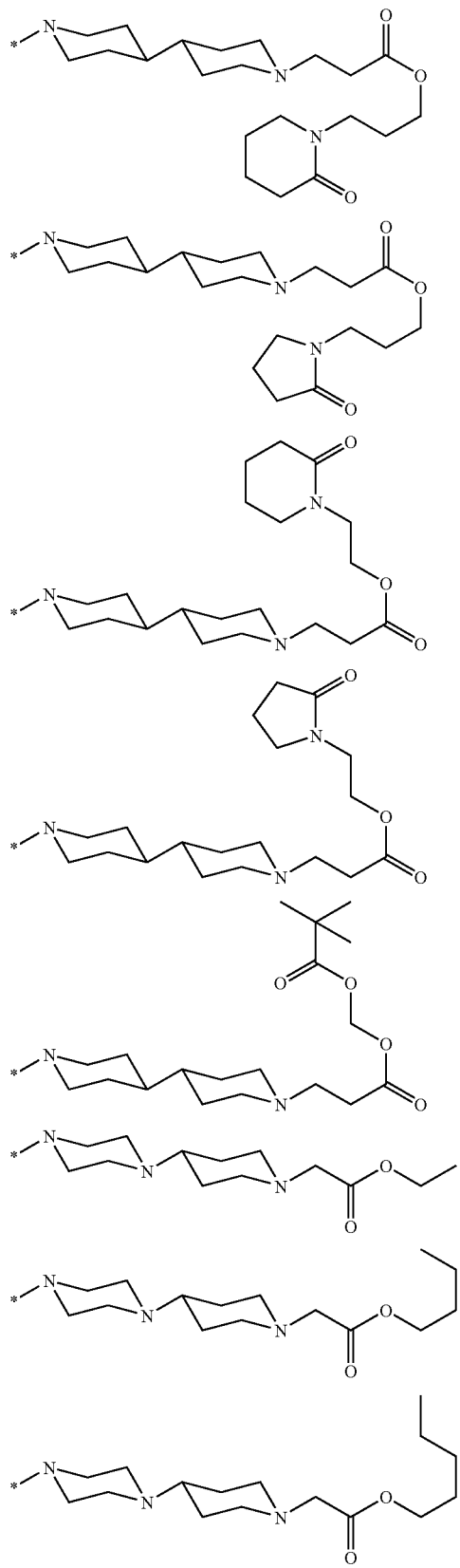
42
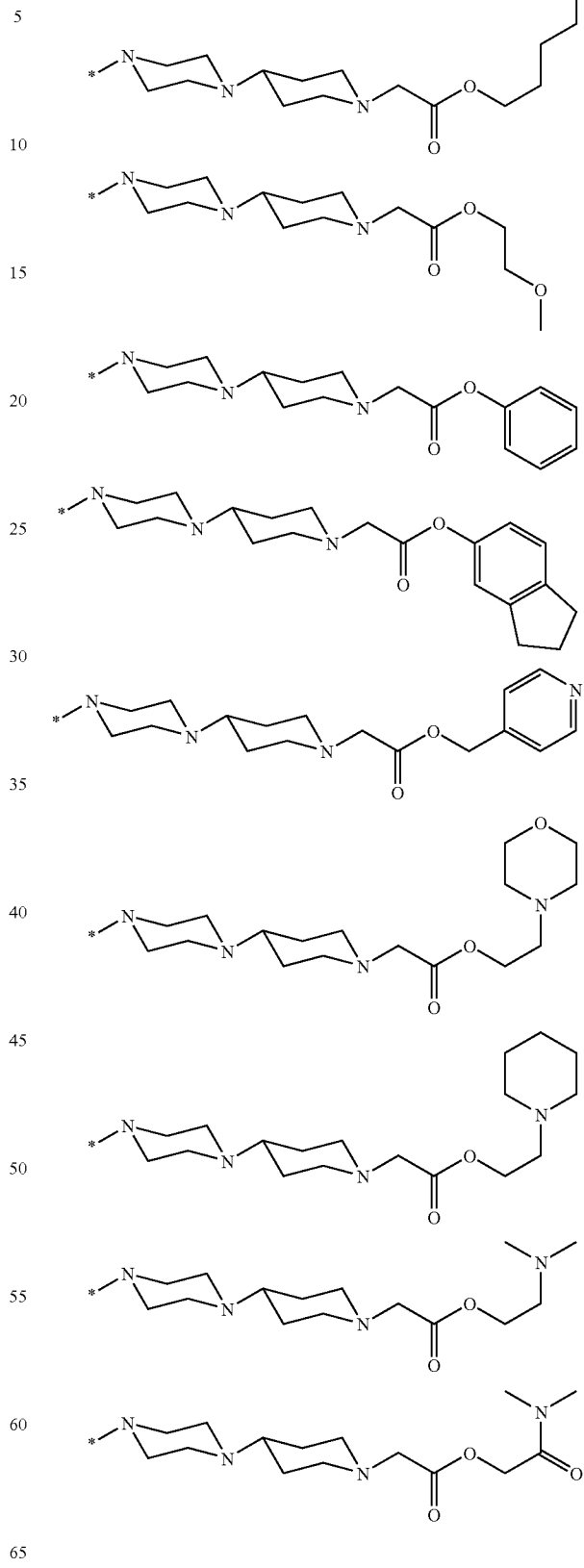

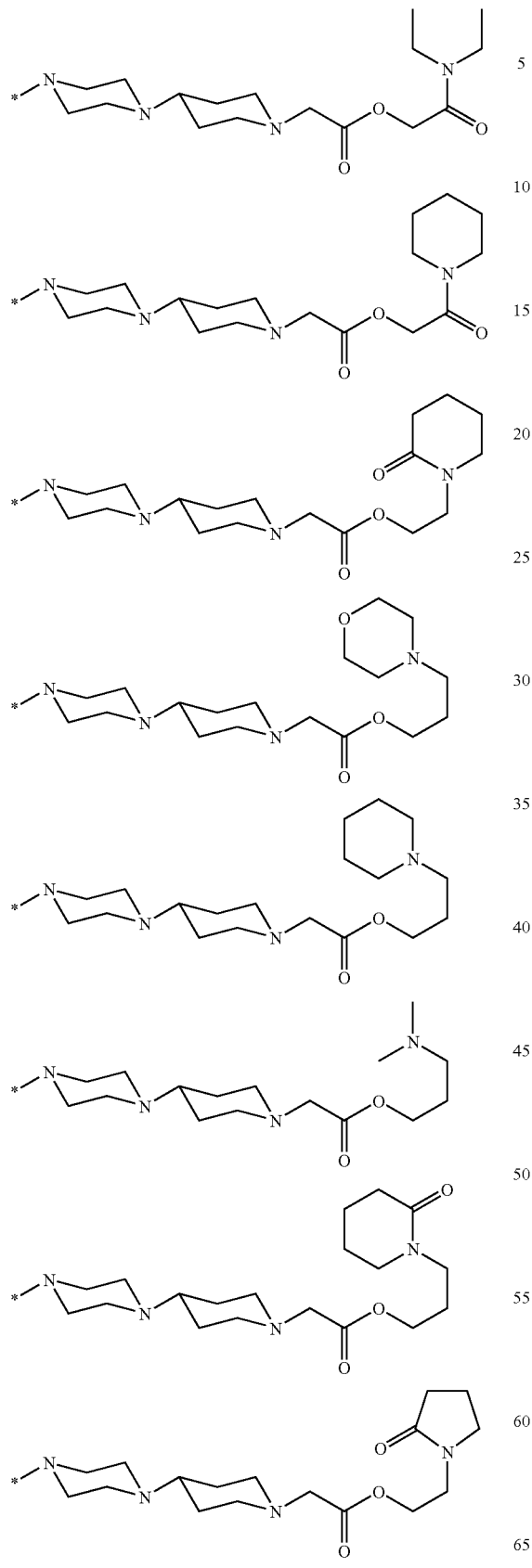
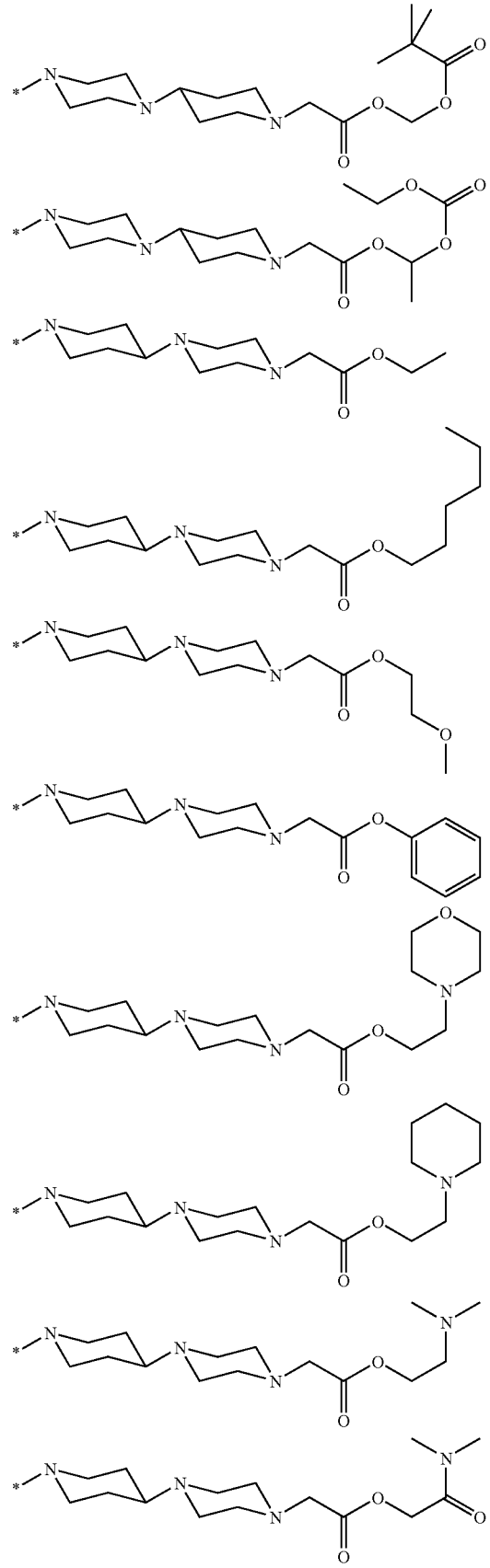

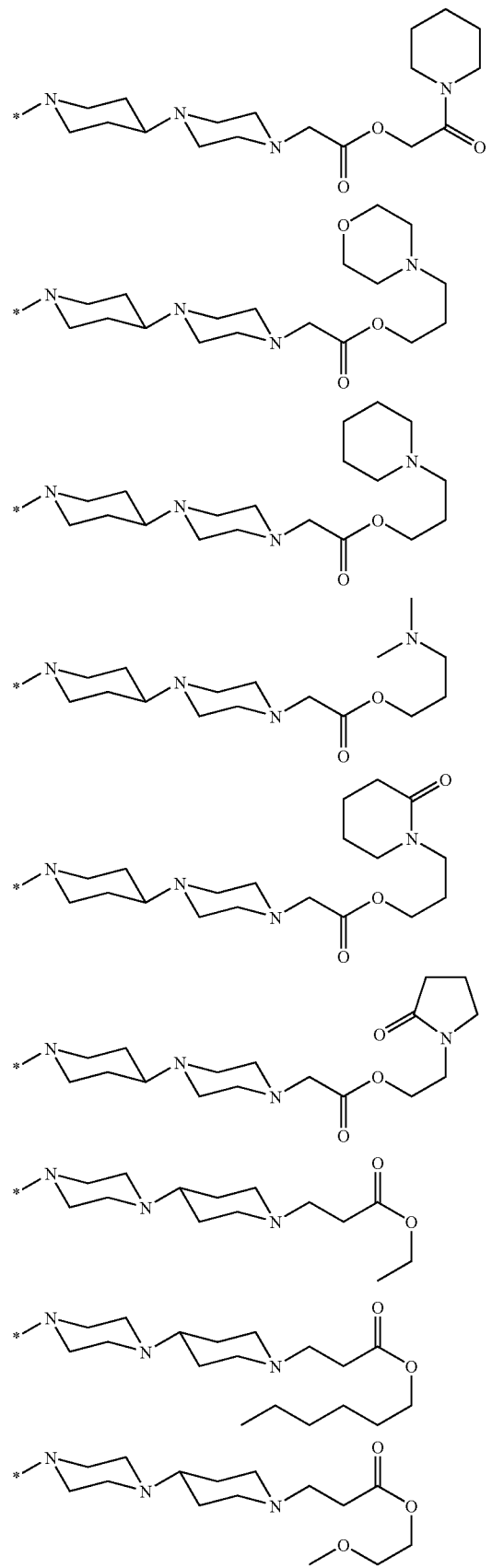
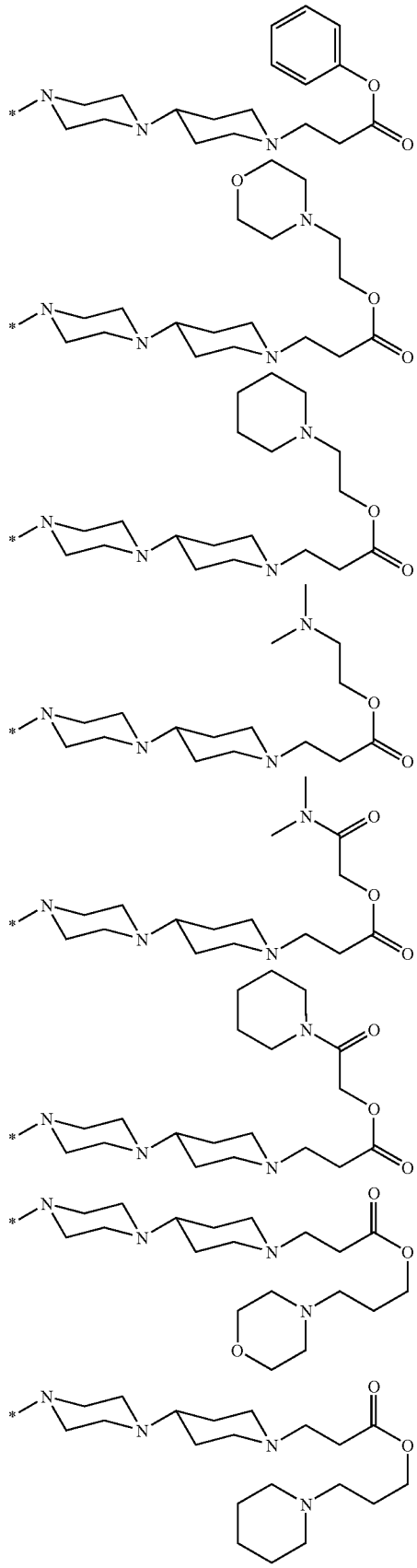

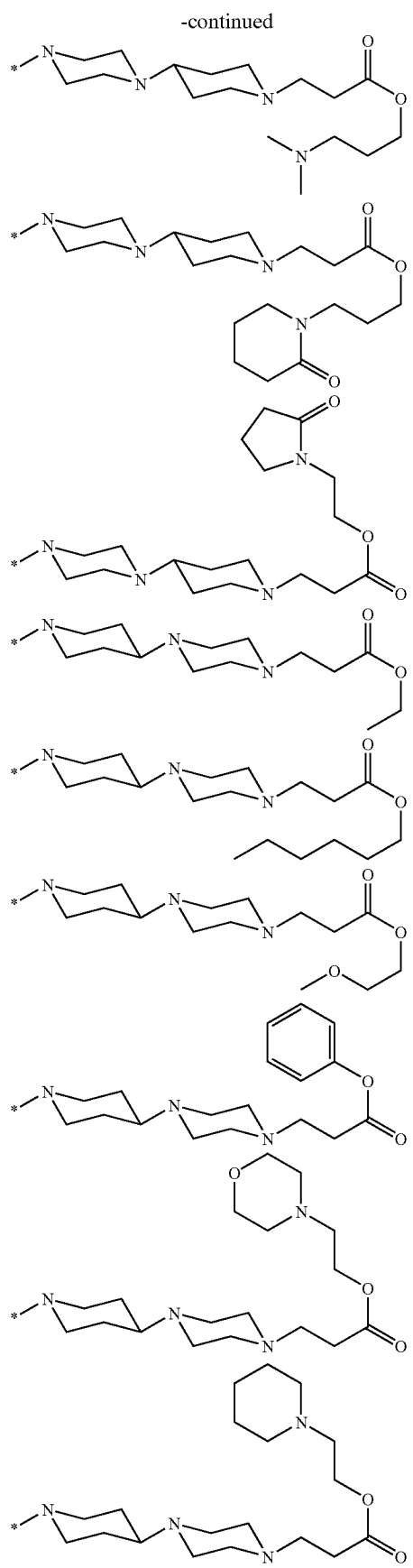

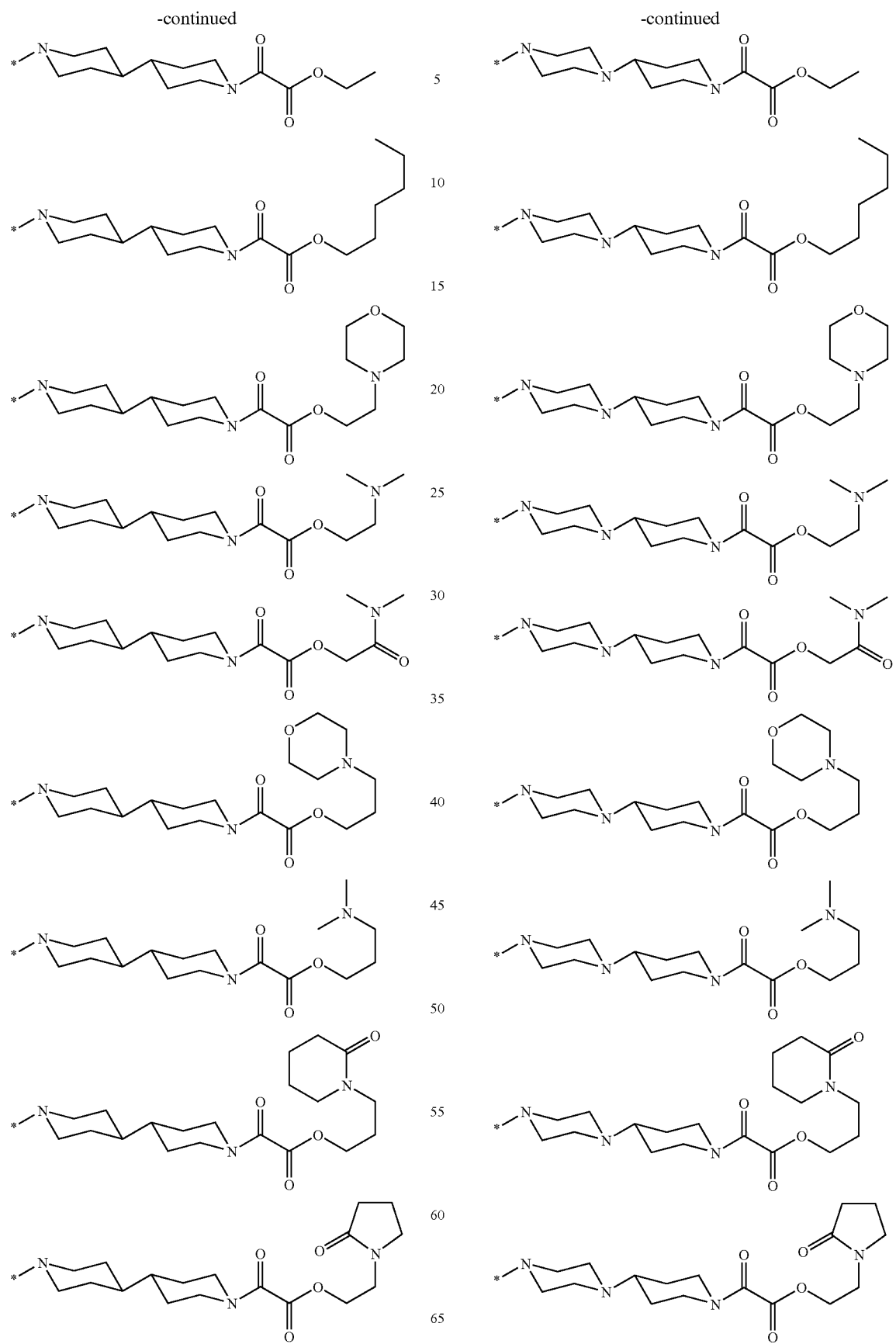

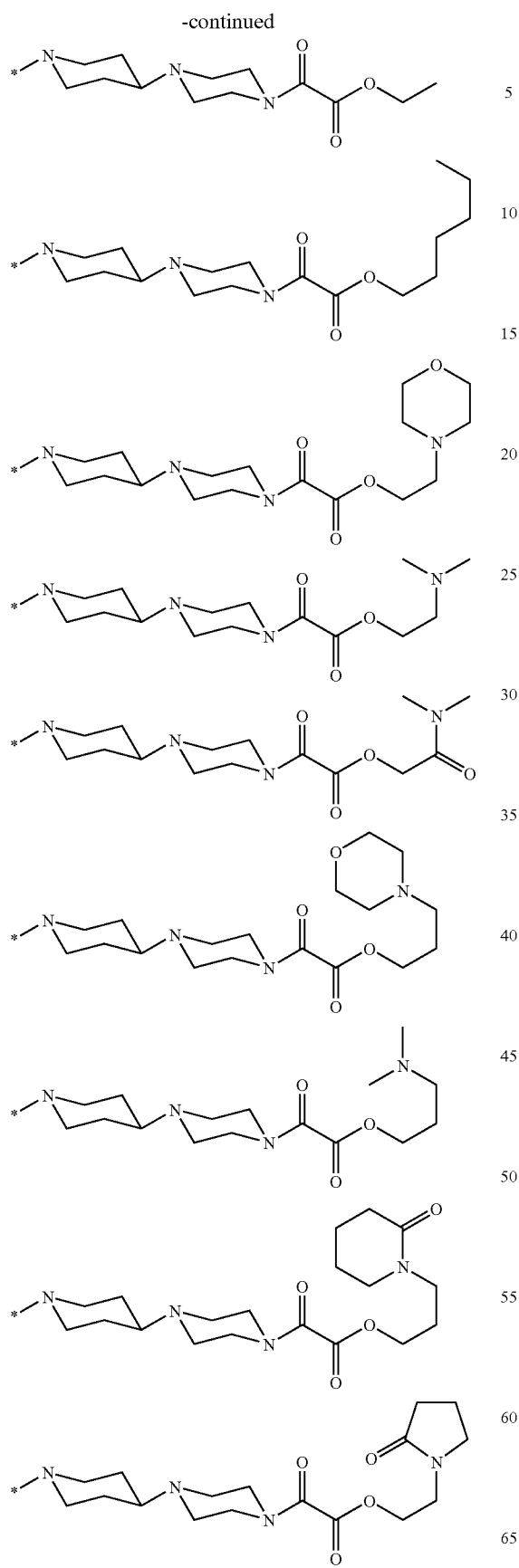
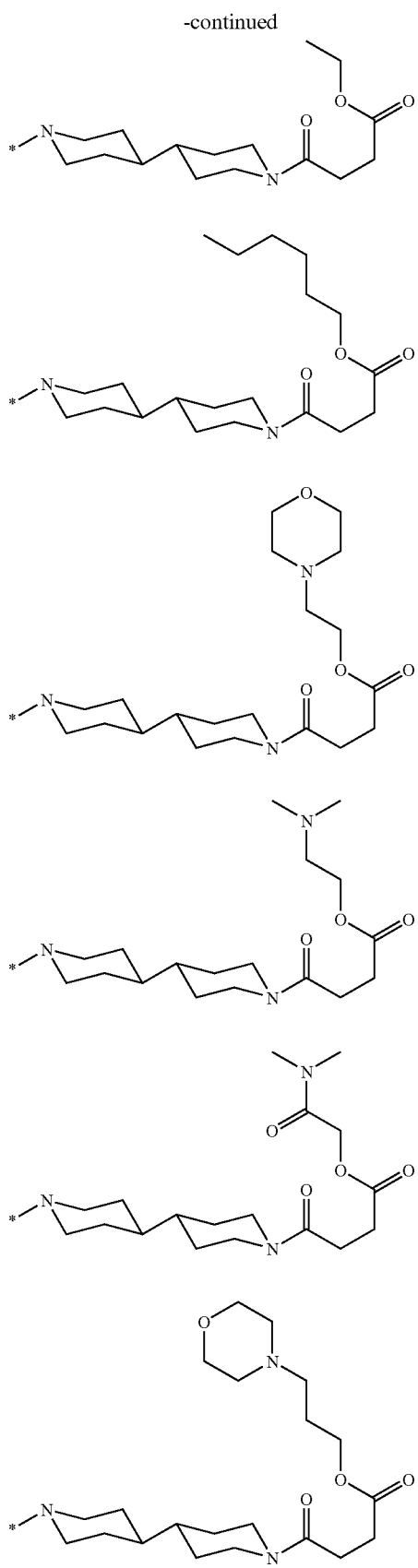

-continued
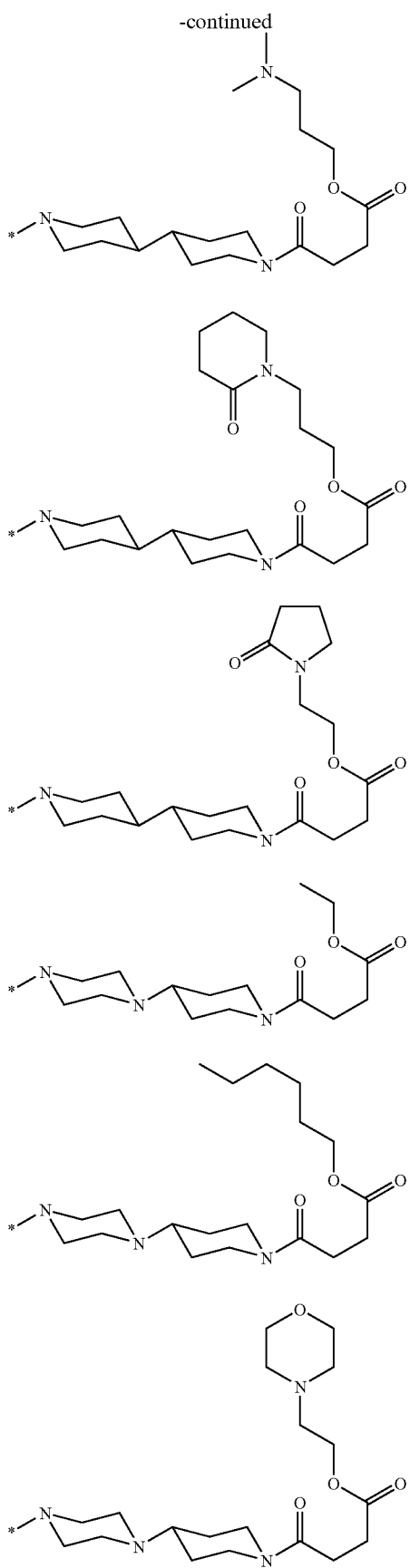
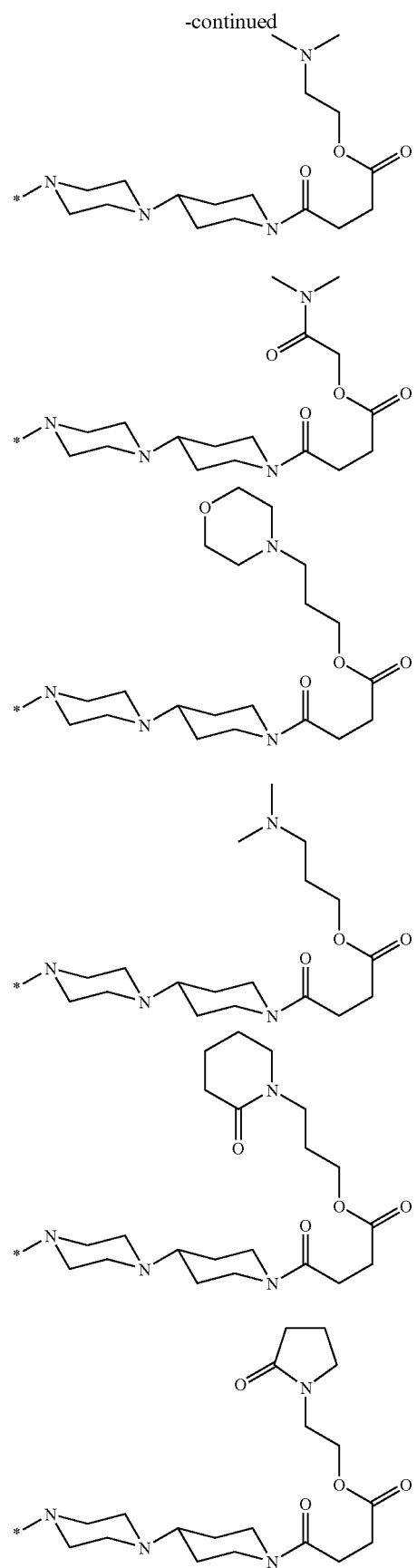

55
-continued
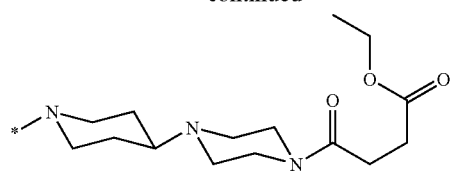
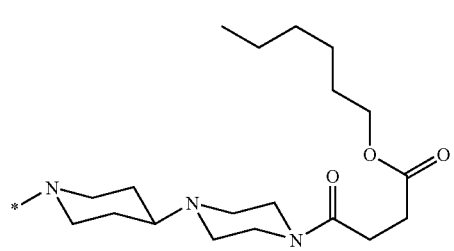
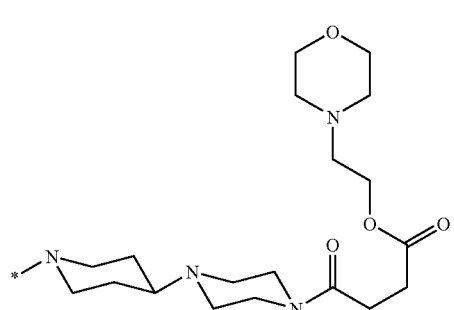
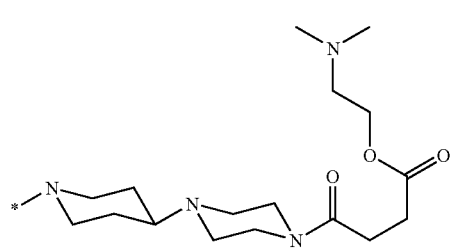
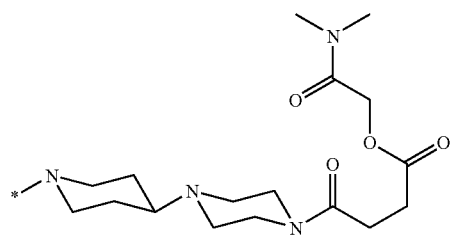
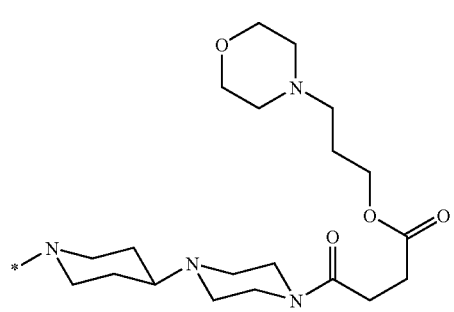
56
-continued
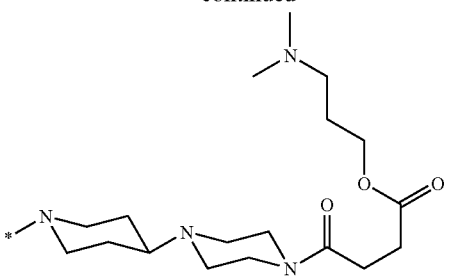
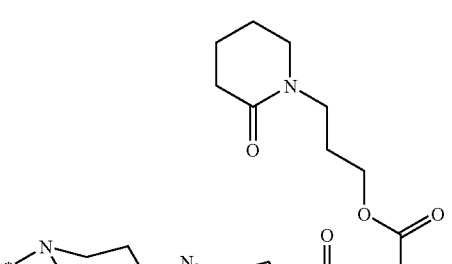
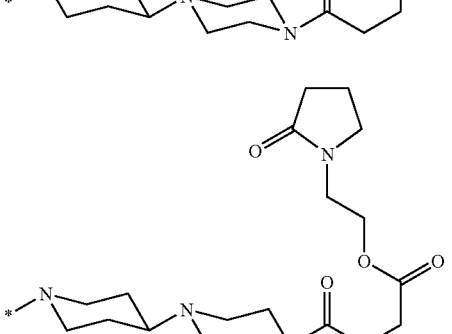
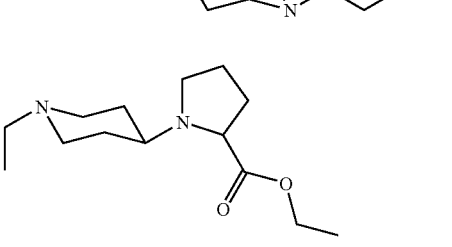
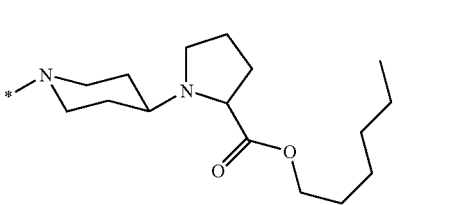
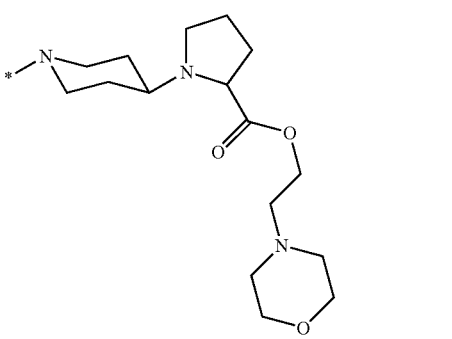

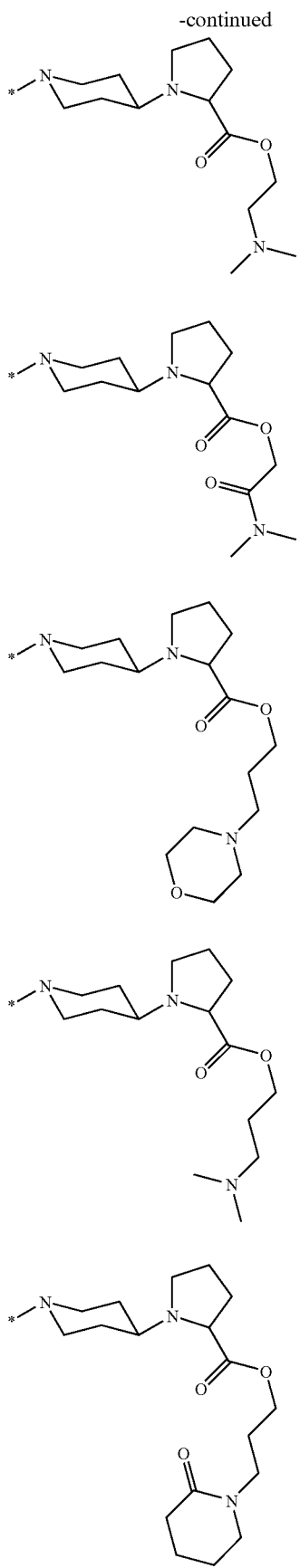
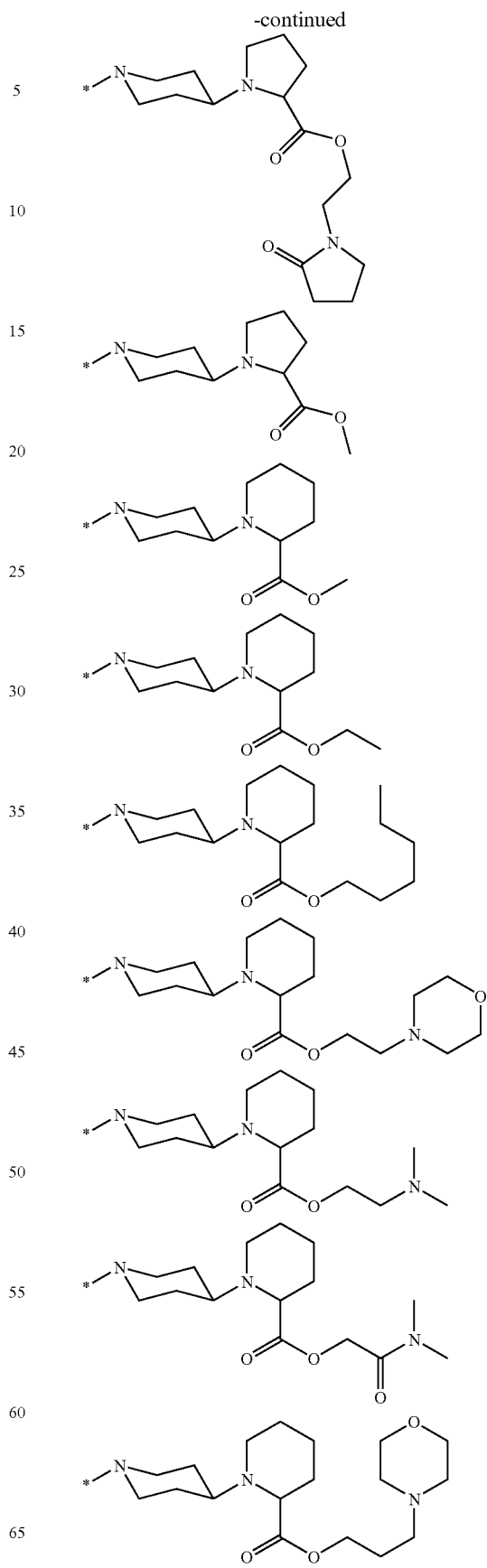

-continued
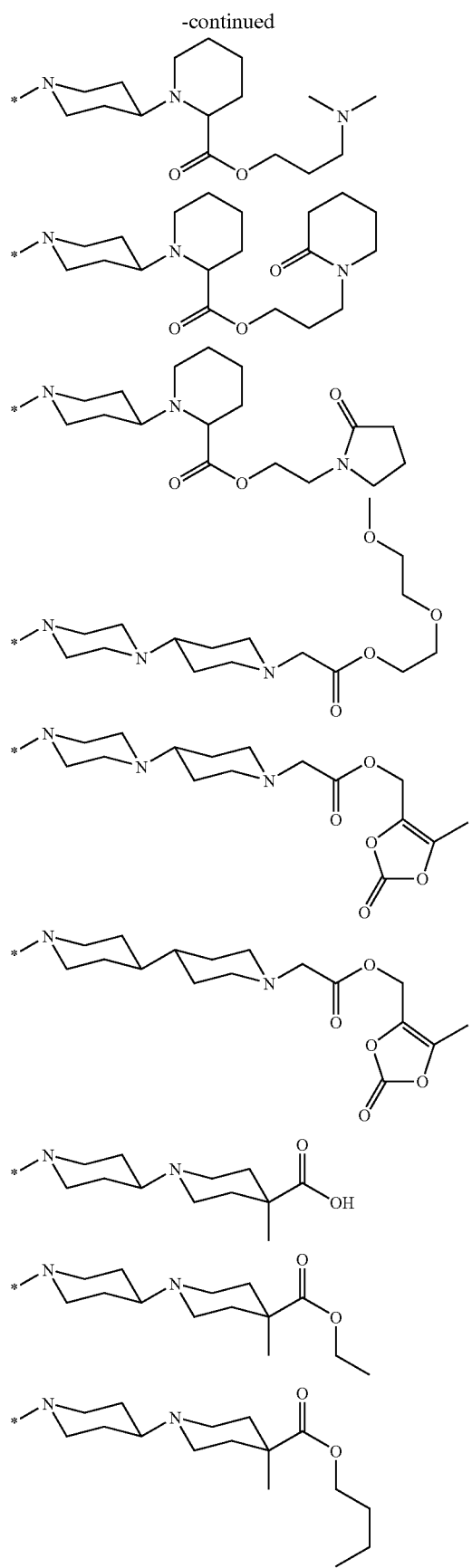
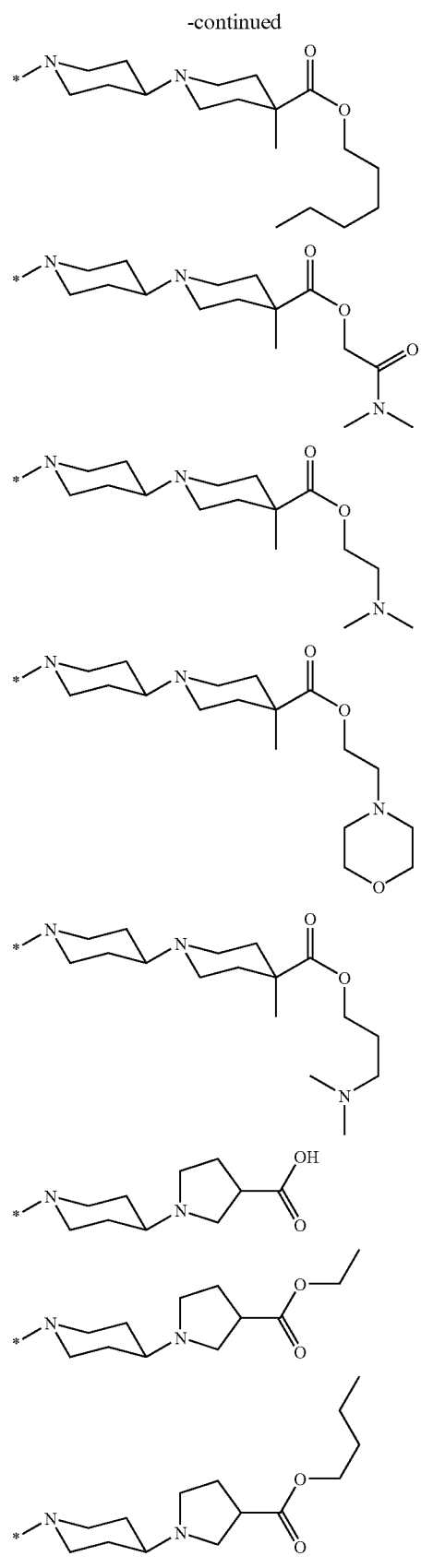

-continued
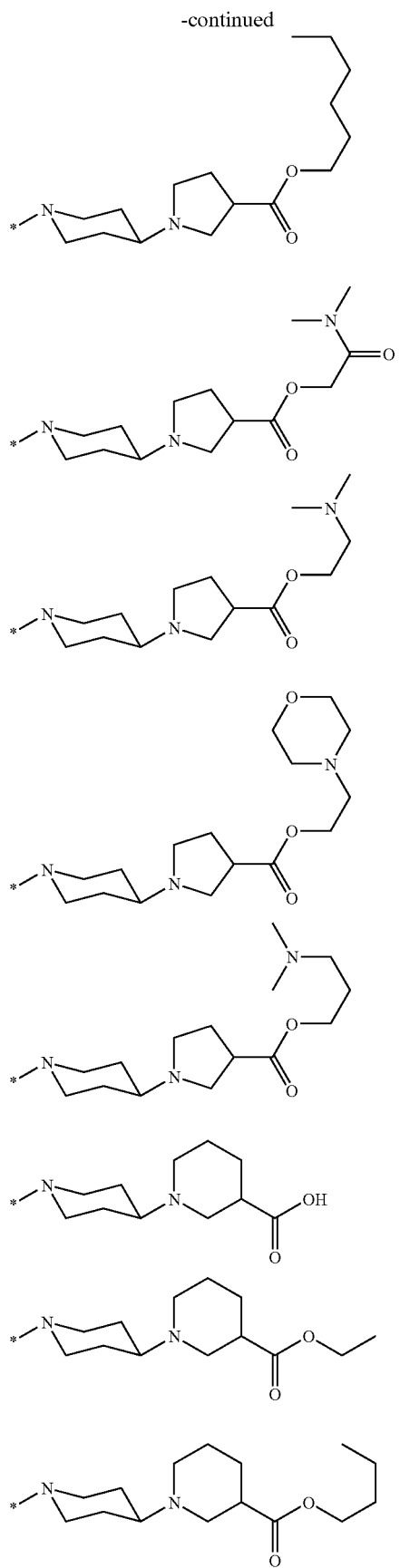
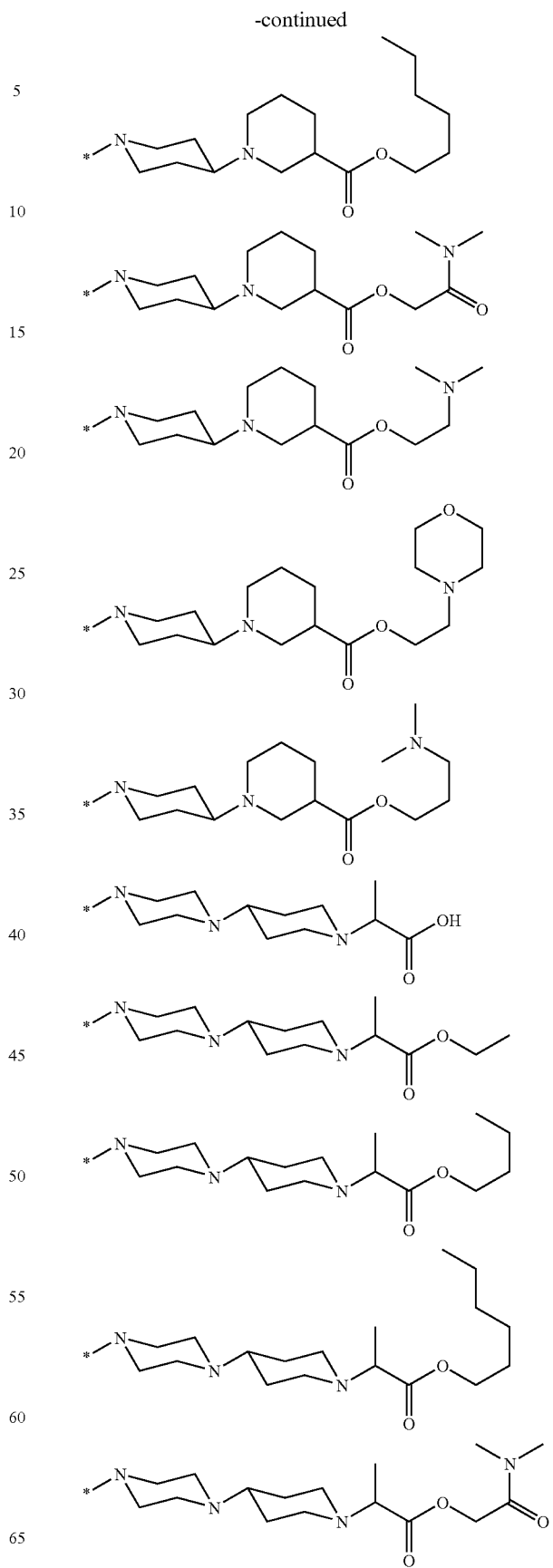

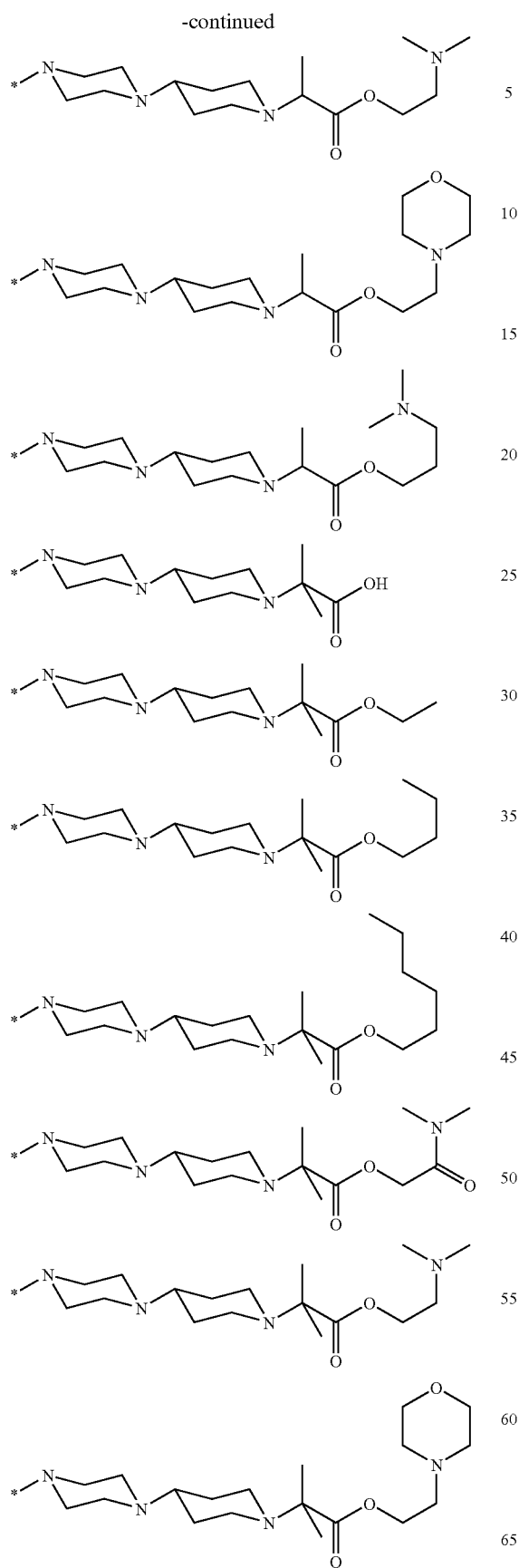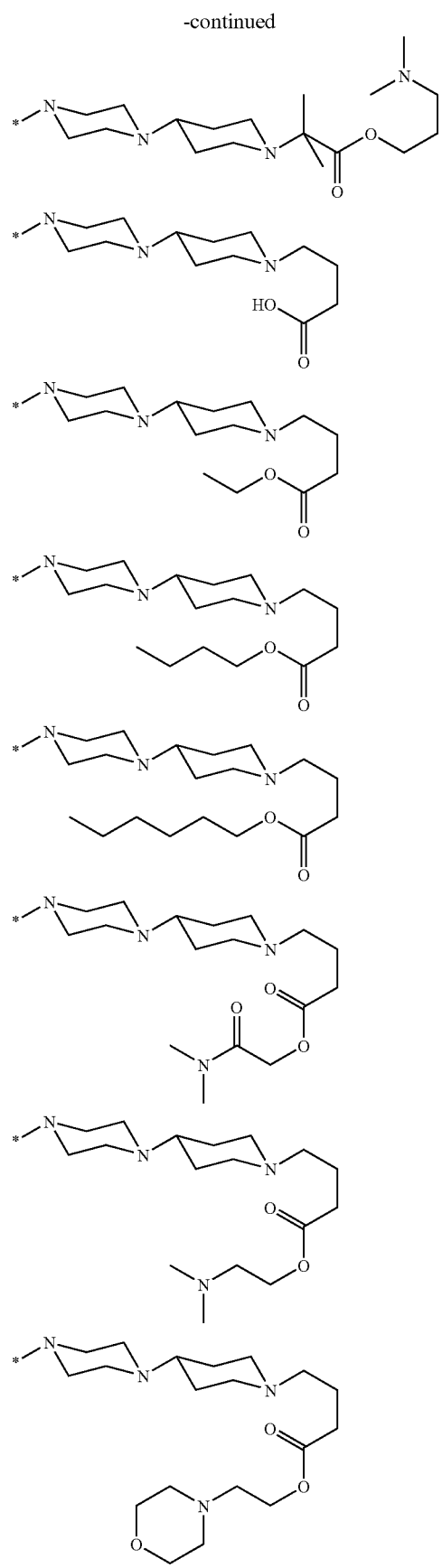

-continued
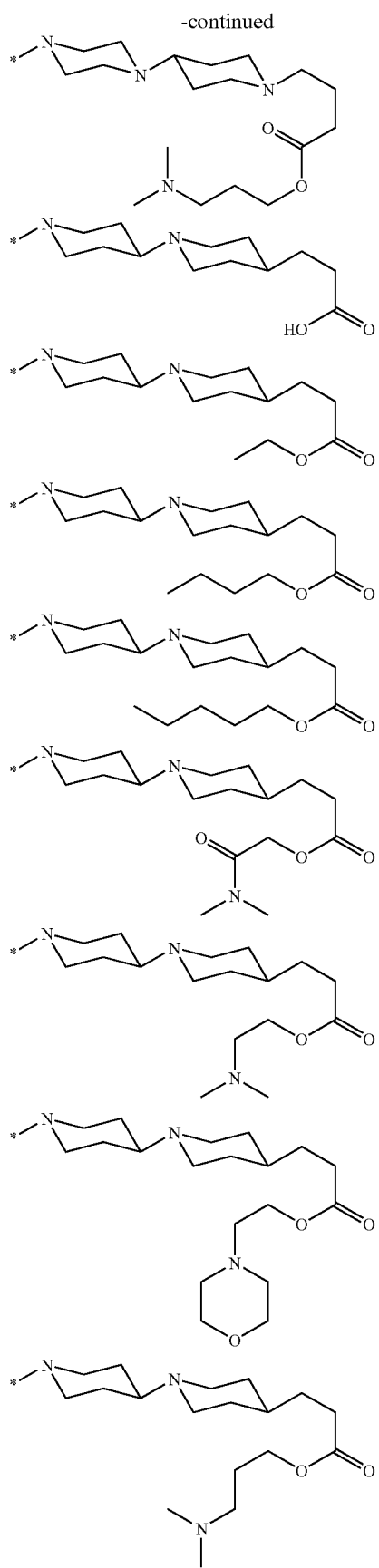
-continued
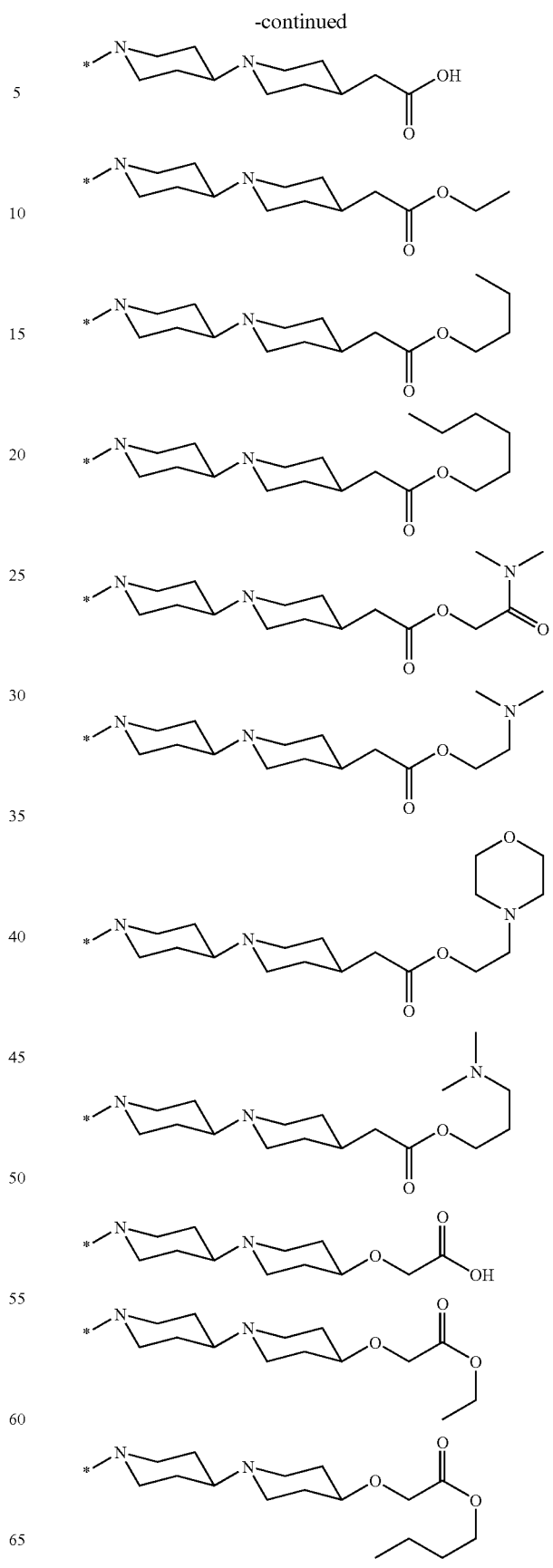

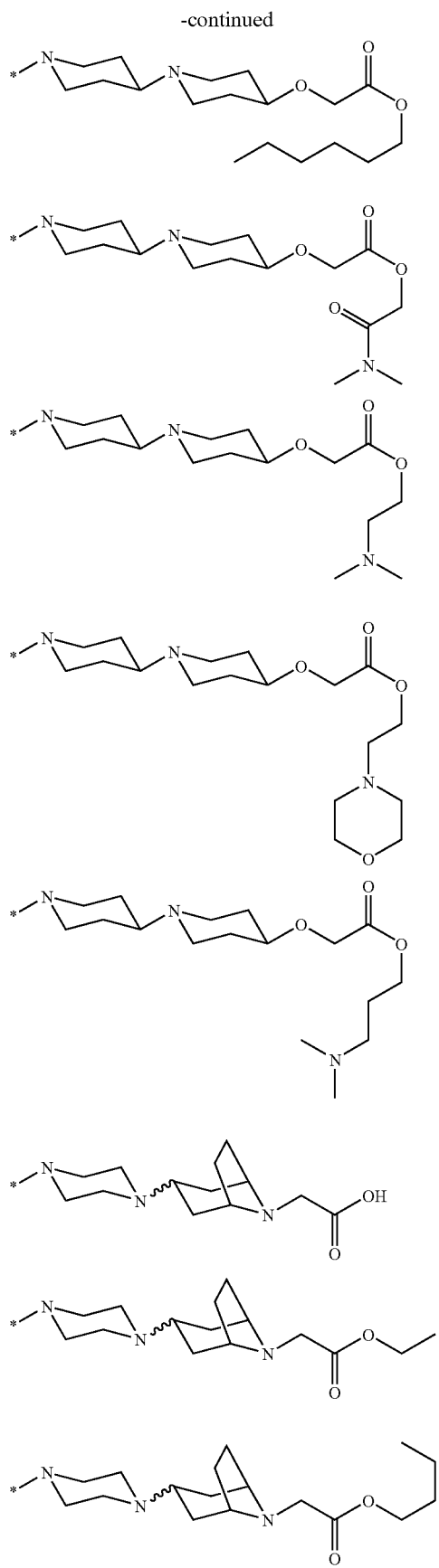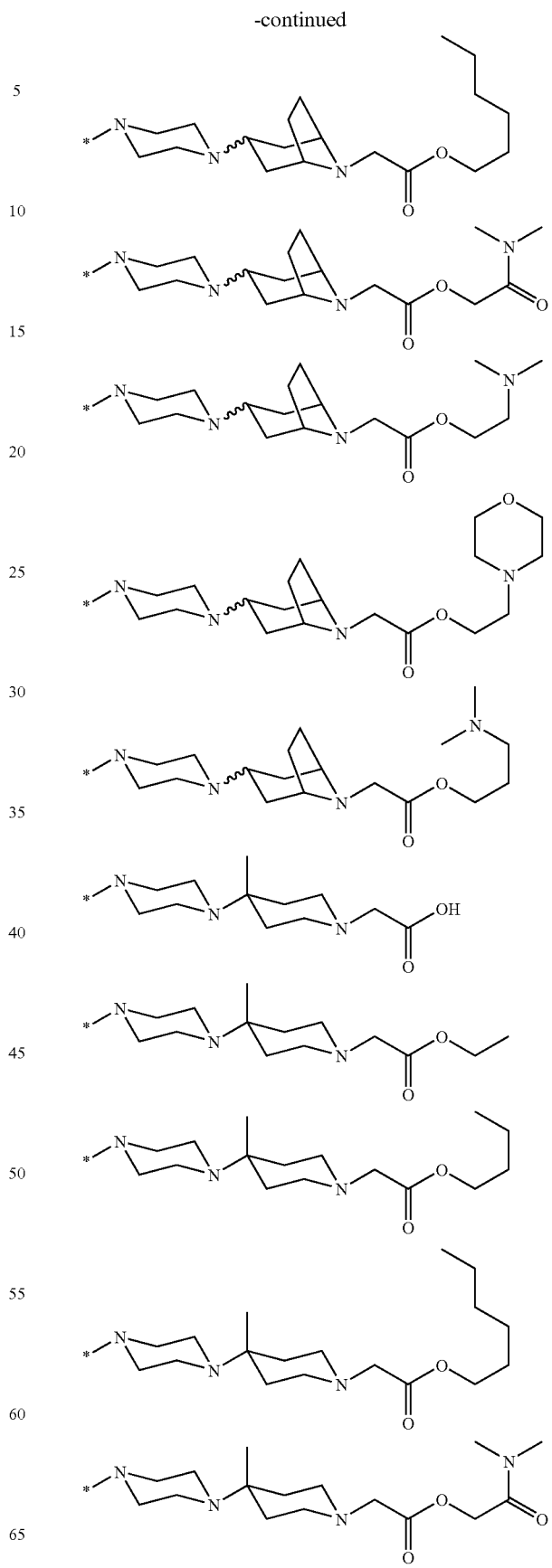

-continued
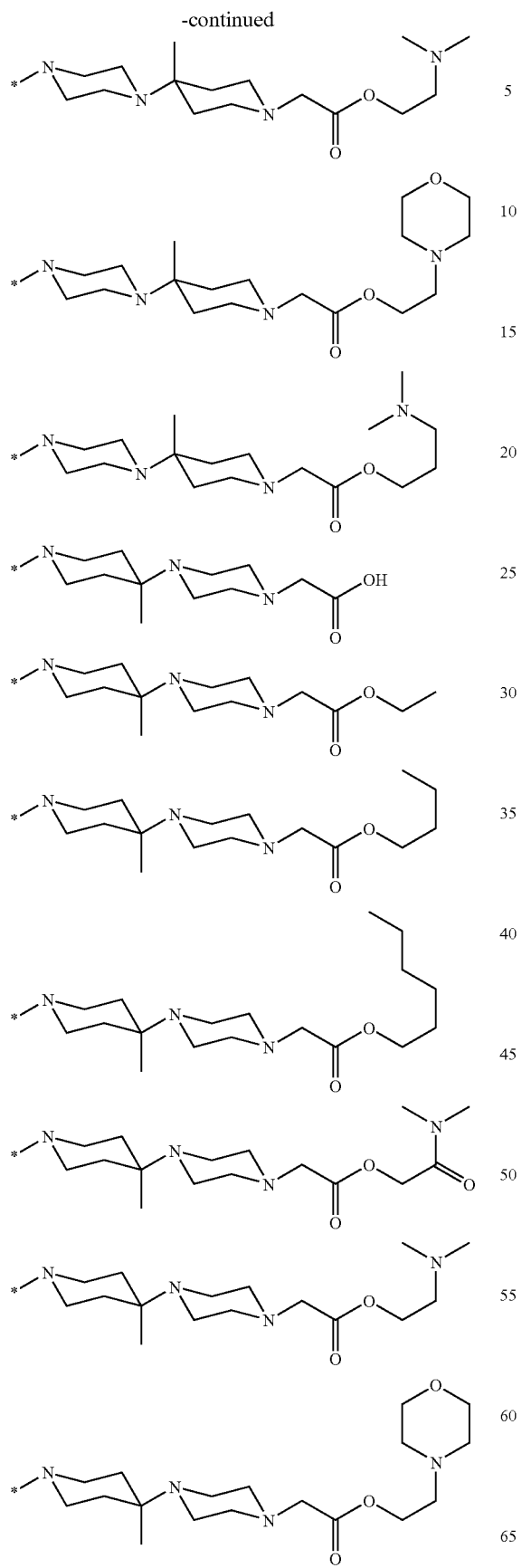
-continued
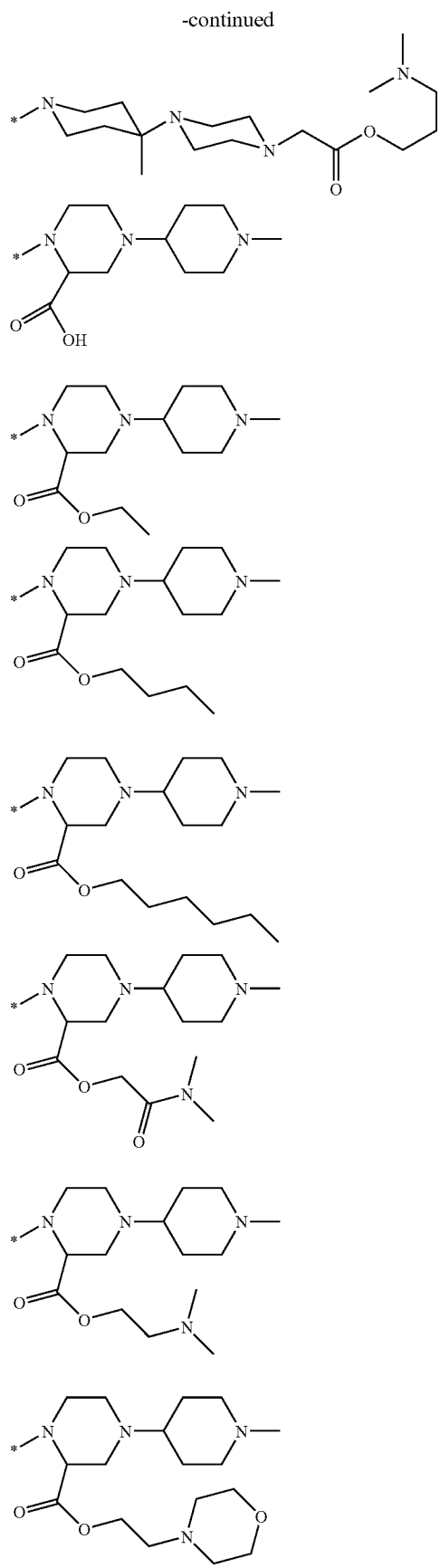

71
-continued
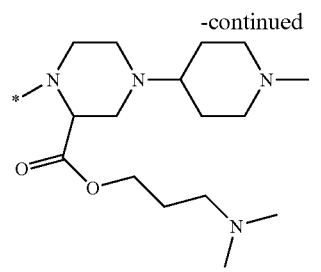
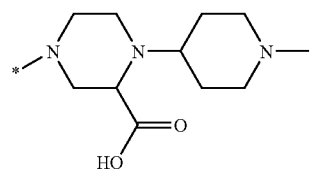
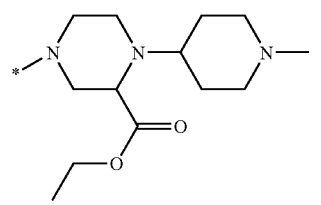
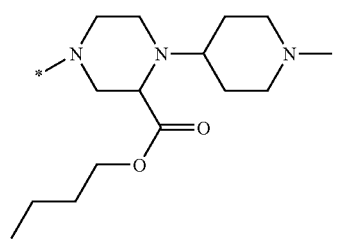
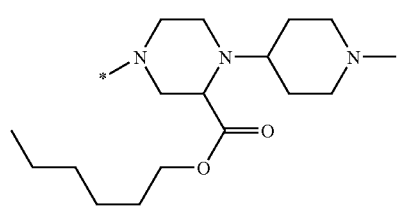
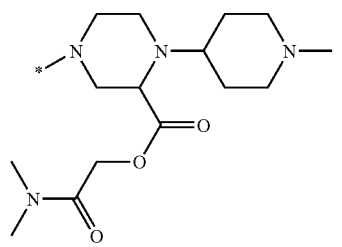
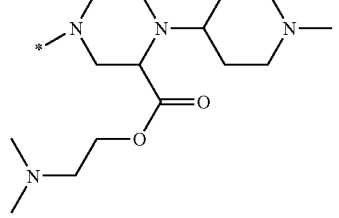
72
-continued
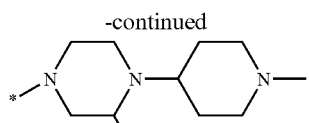
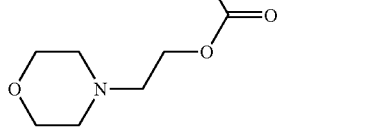
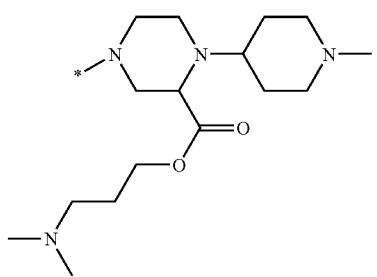
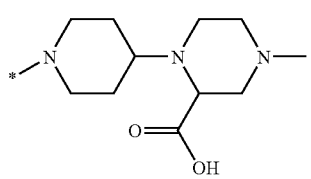
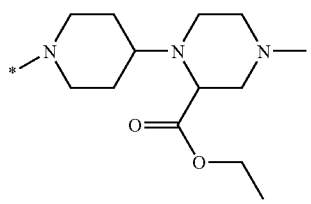
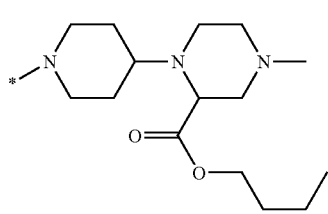
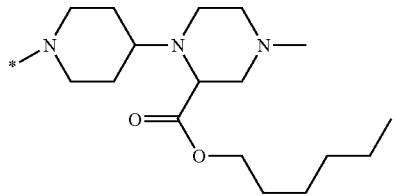
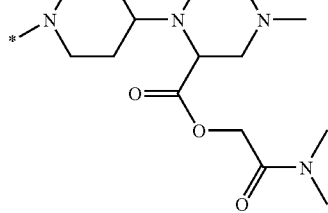

-continued
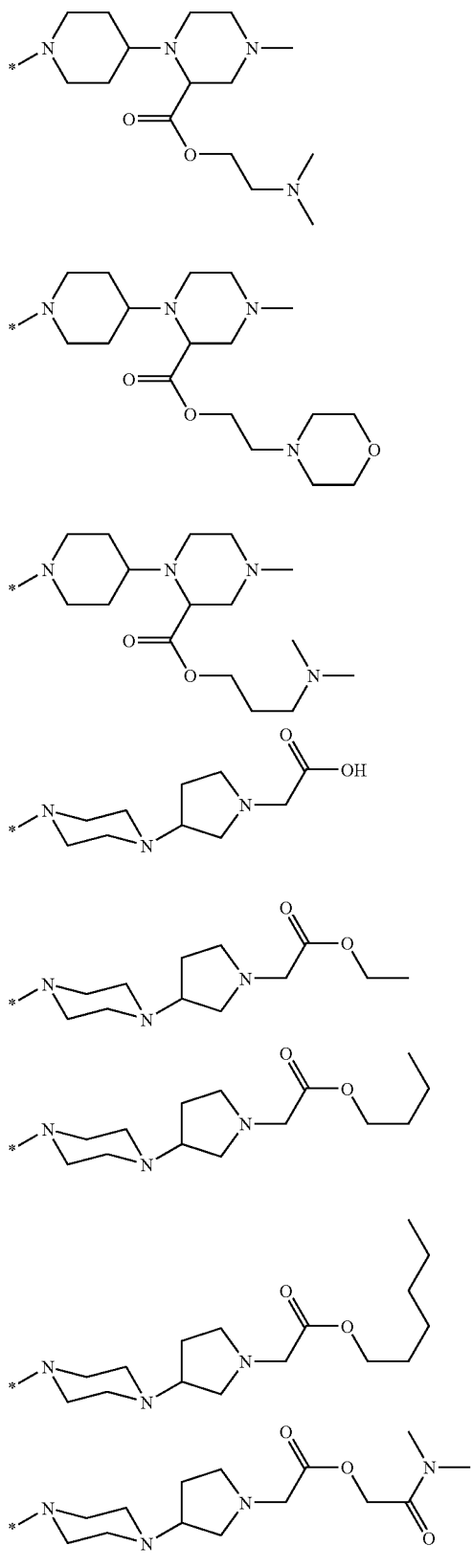
-continued
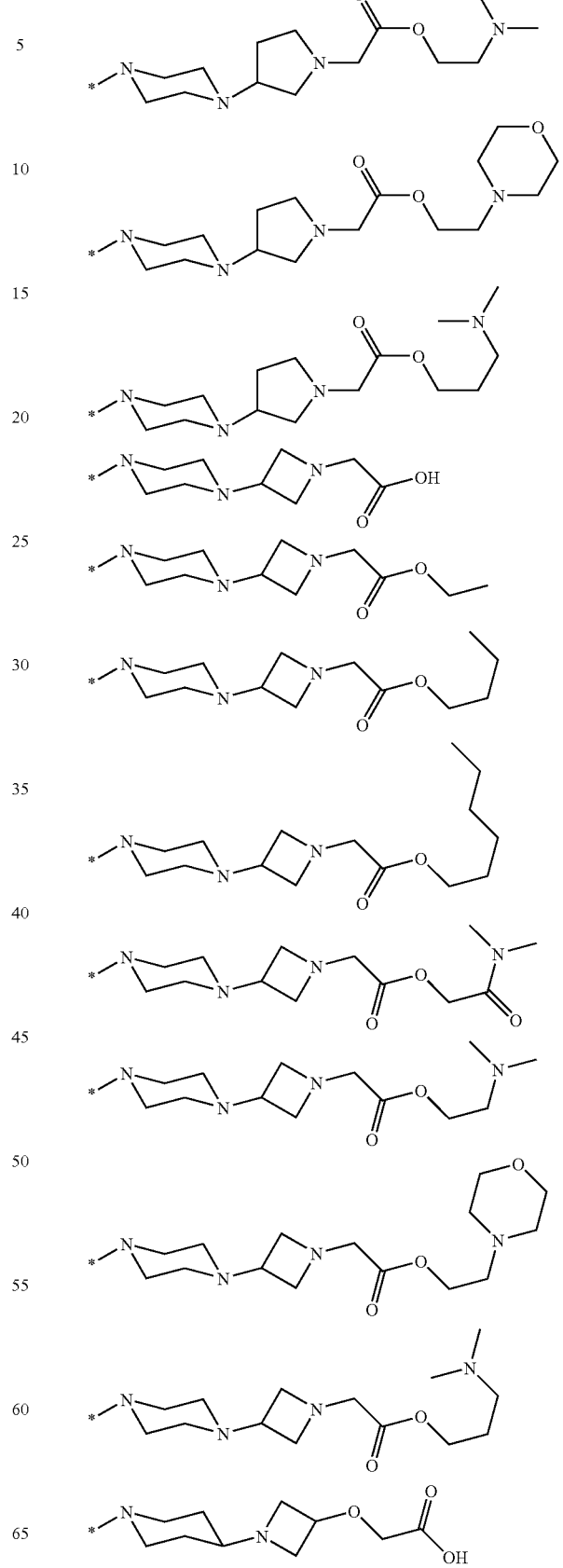

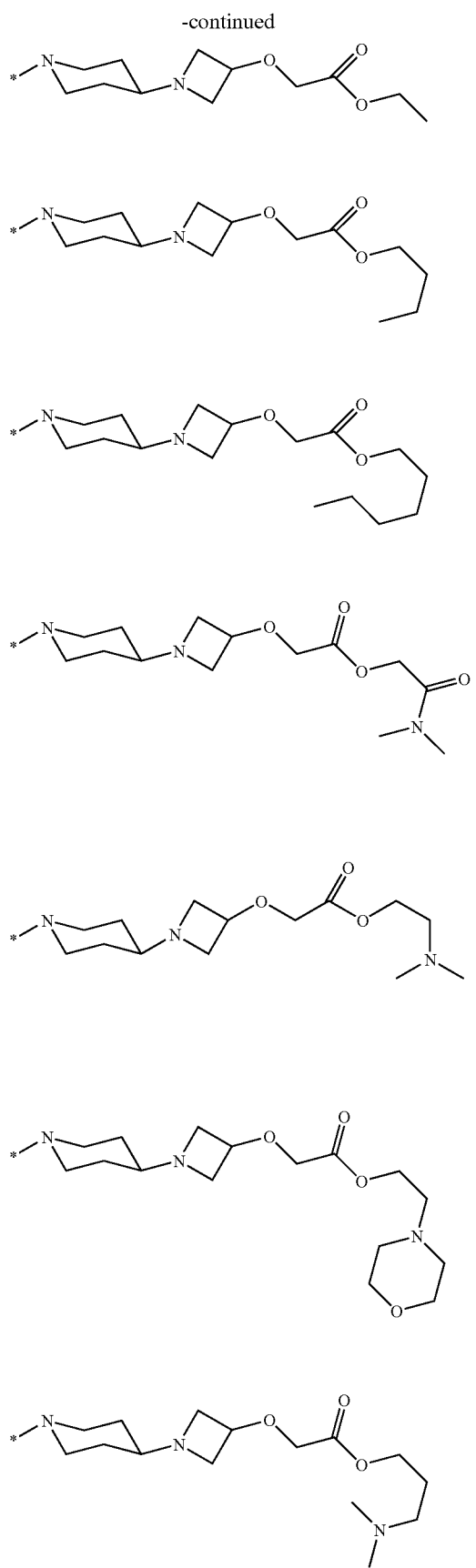
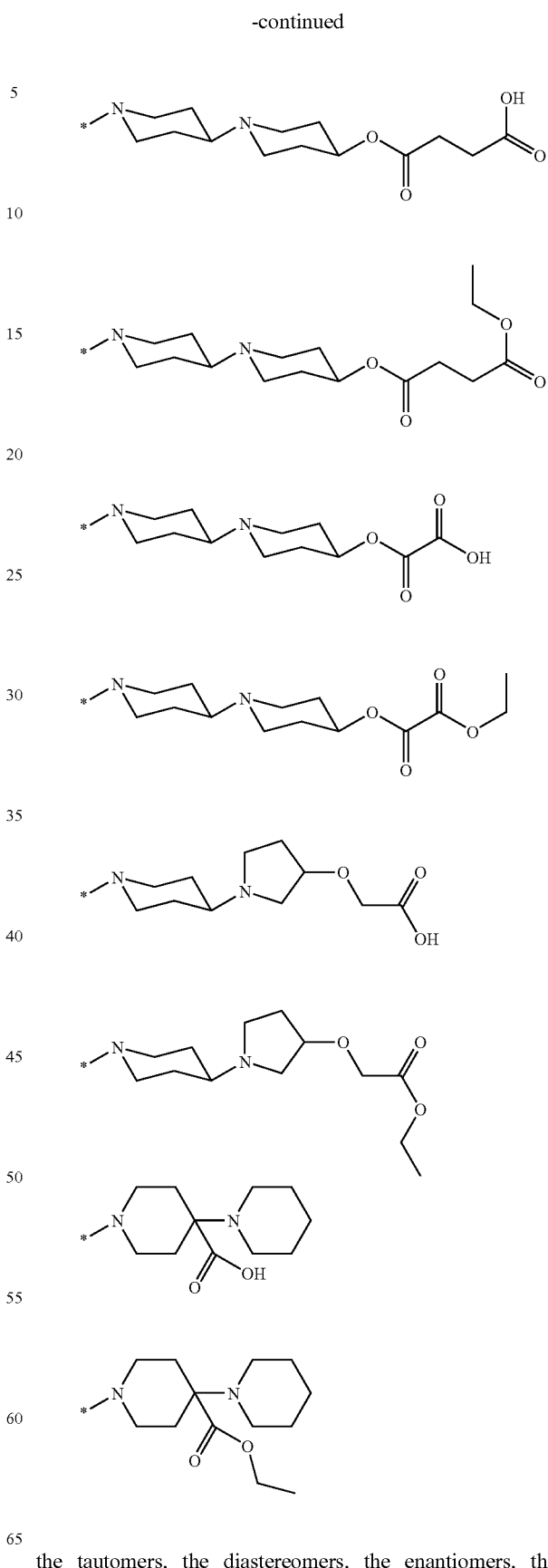
the tautomers, the diastereomers, the enantiomers, the hydrates, the mixtures thereof and the salts thereof as well as the hydrates of the salts thereof, particularly the physiologically acceptable salts thereof with inorganic or organic acids or bases.

The following compounds are also mentioned as examples of most particularly preferred compounds of the above general formula I:

| No. | Structure |
|---|---|
| (1) | 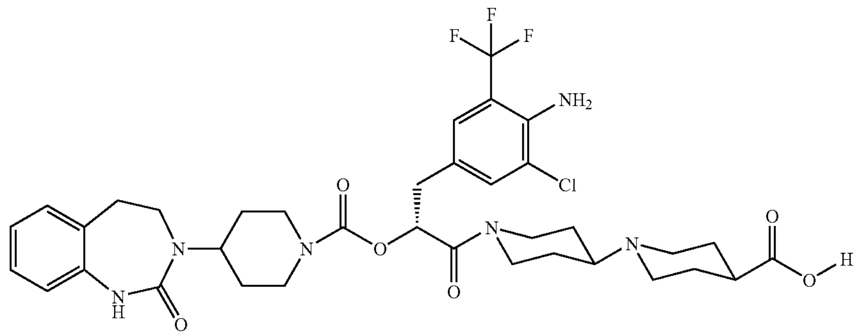 |
| (2) | 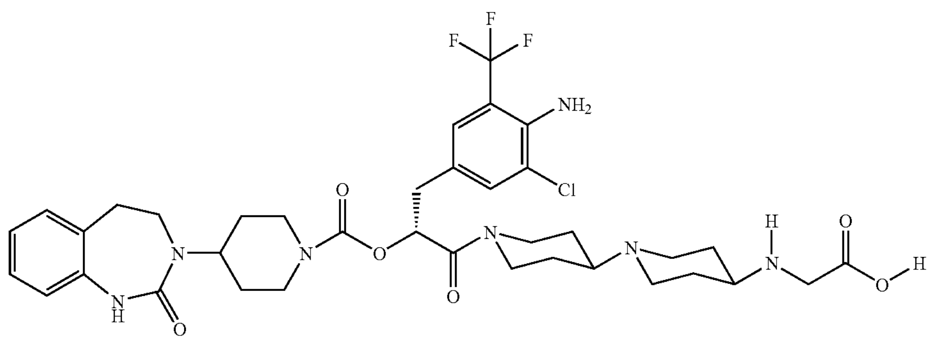 |
| (3) | 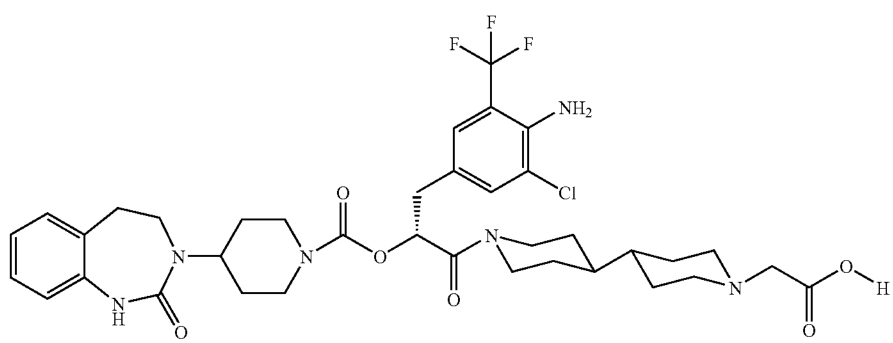 |

-continued

| No. | Structure |
|---|---|
| (4) | 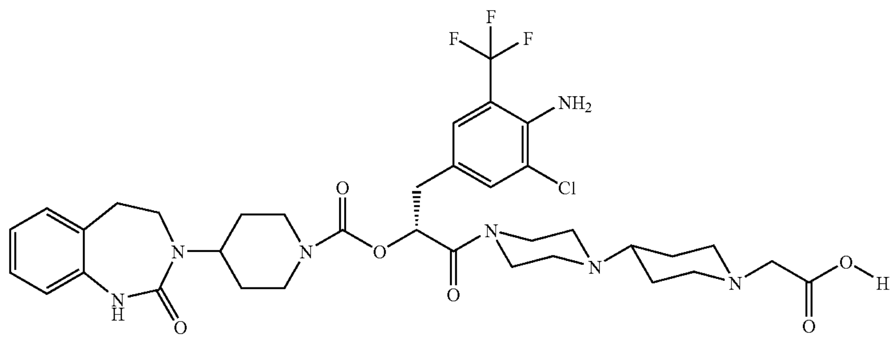 |
| (5) | 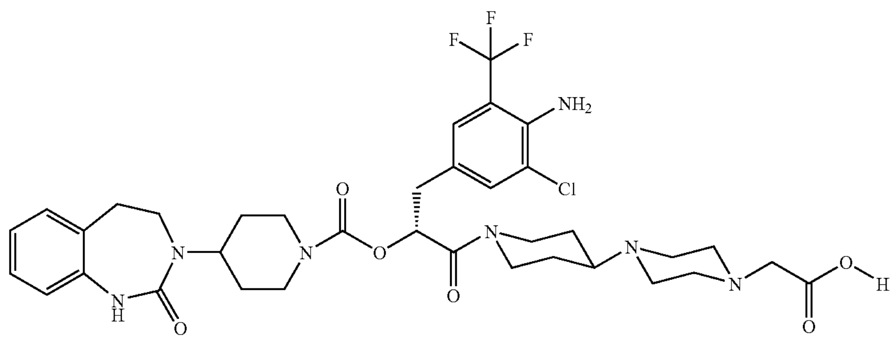 |
| (6) | 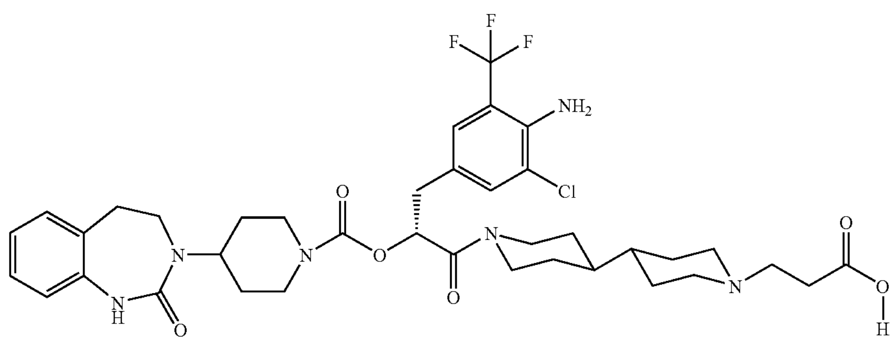 |
| (7) | 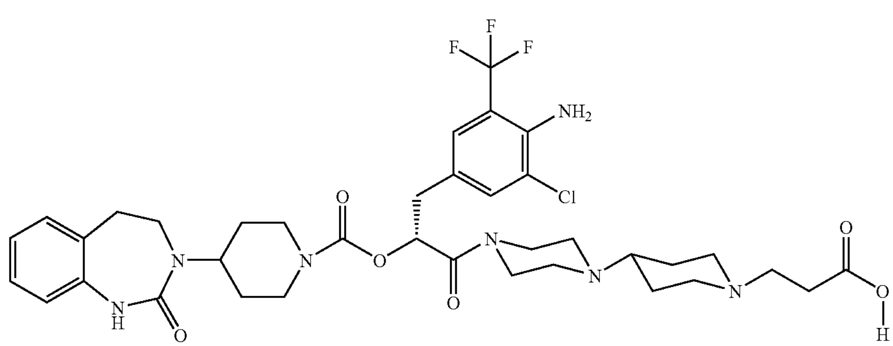 |

| No. | Structure |
|---|---|
| (8) | 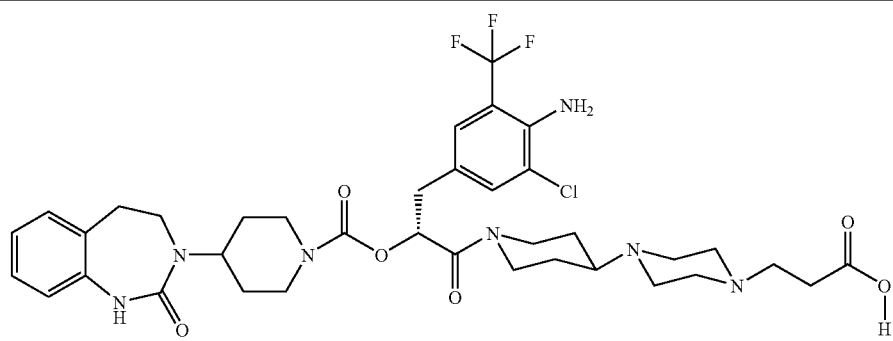 |
| (9) | 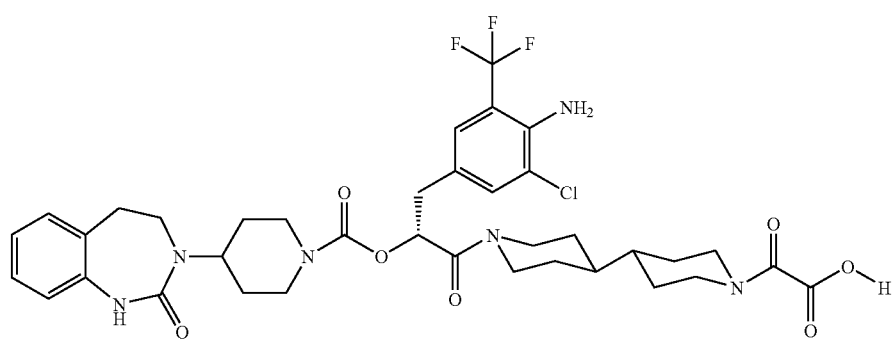 |
| (10) | 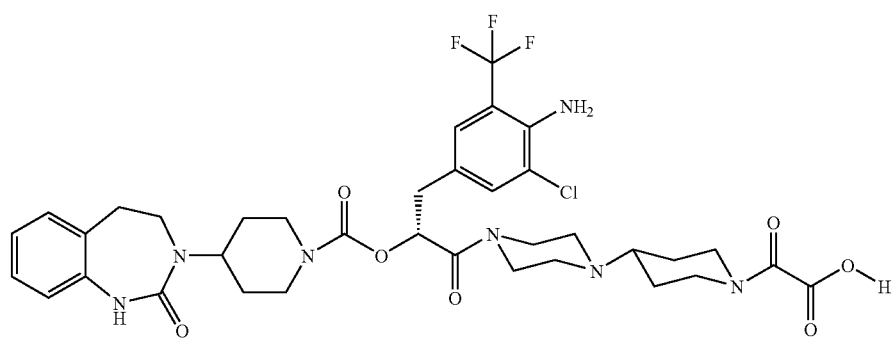 |
| (11) | 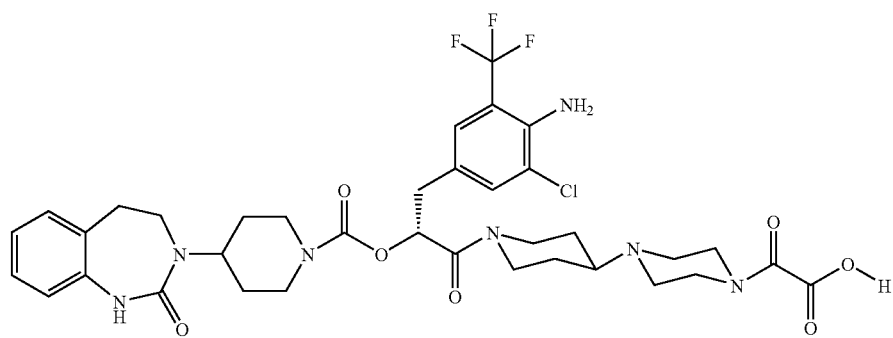 |

| No. | Structure |
|---|---|
| (12) | 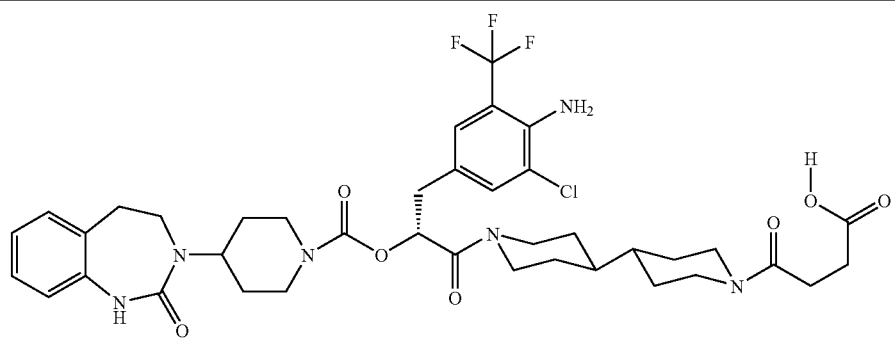 |
| (13) | 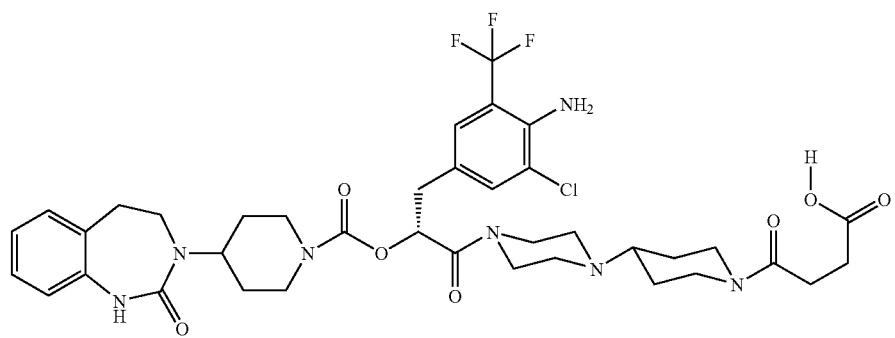 |
| (14) | 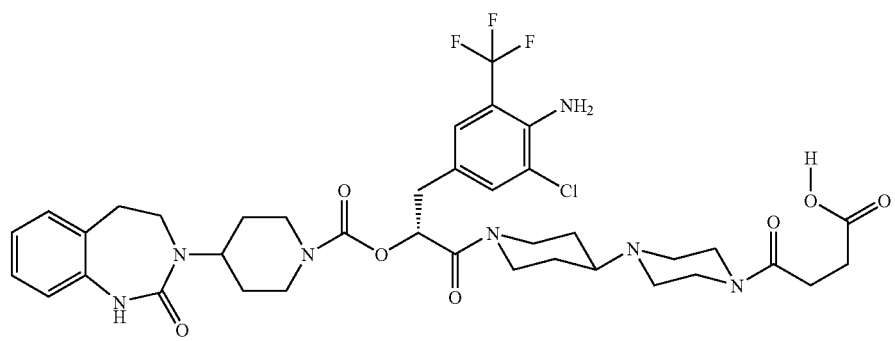 |
| (15) | 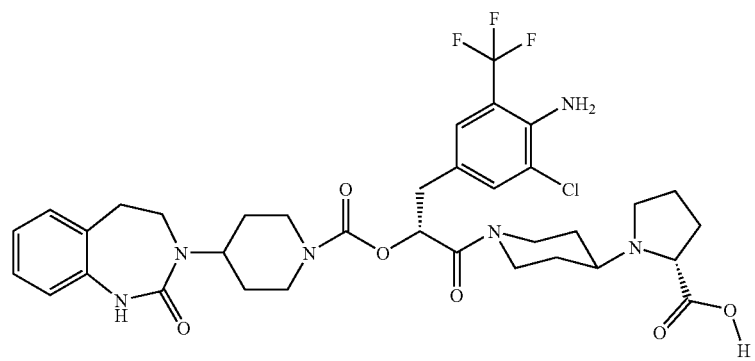 |

| No. | Structure |
|---|---|
| (16) | 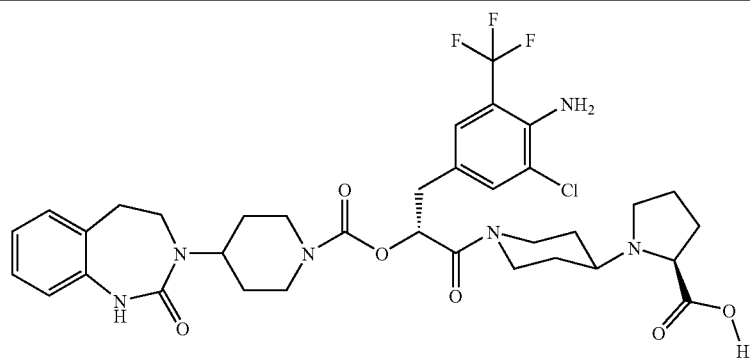 |
| (17) | 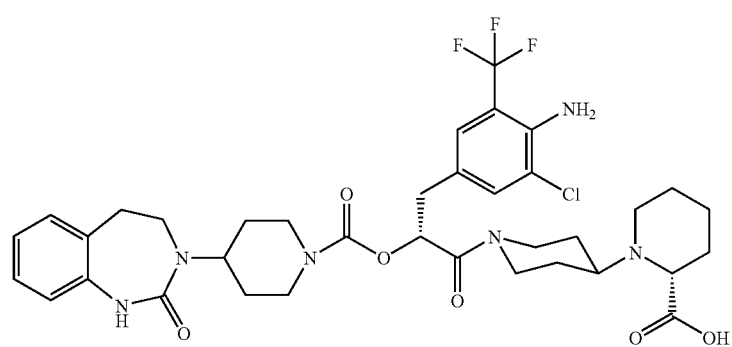 |
| (18) | 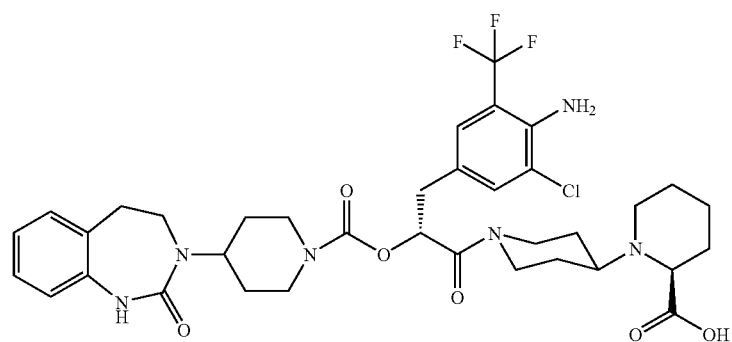 |
| (19) | 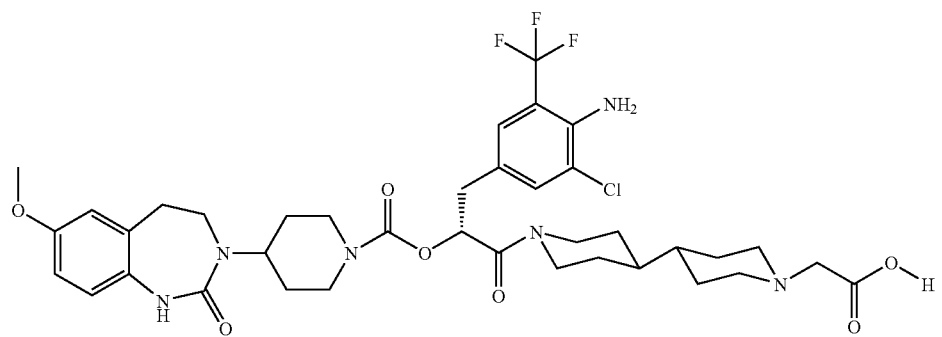 |

-continued
| No. | Structure |
|---|---|
| (20) | 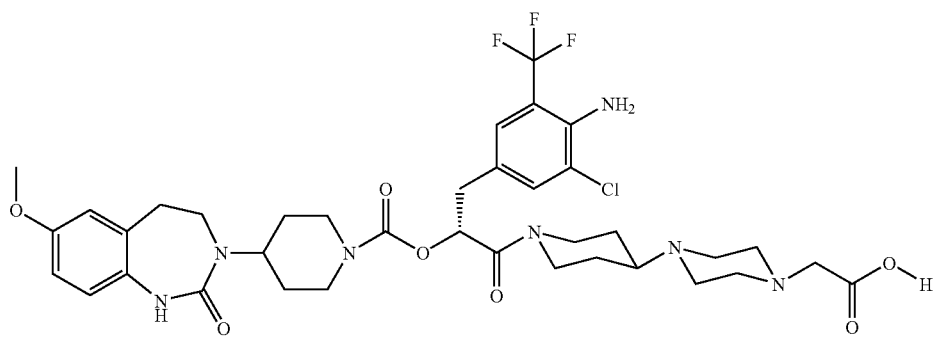 |
| (21) | 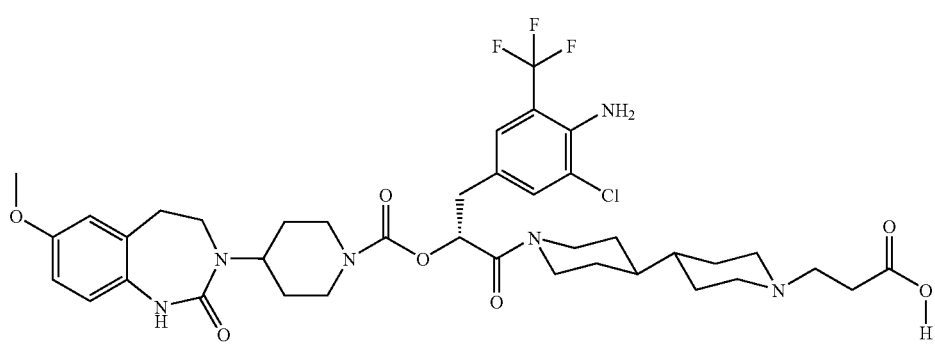 |
| (22) | 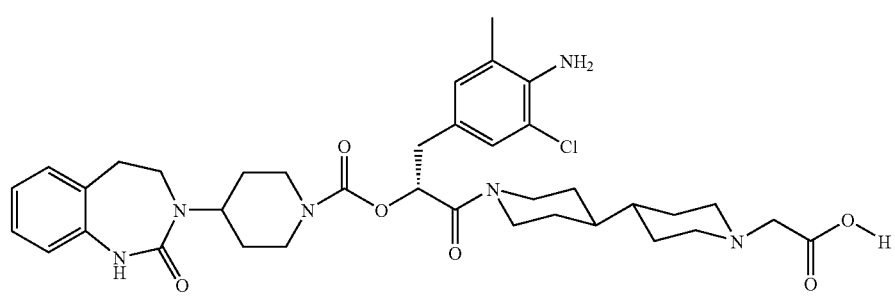 |
| (23) | 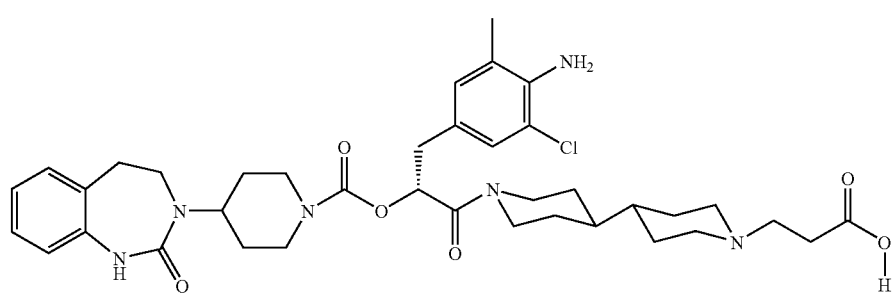 |
| (24) | 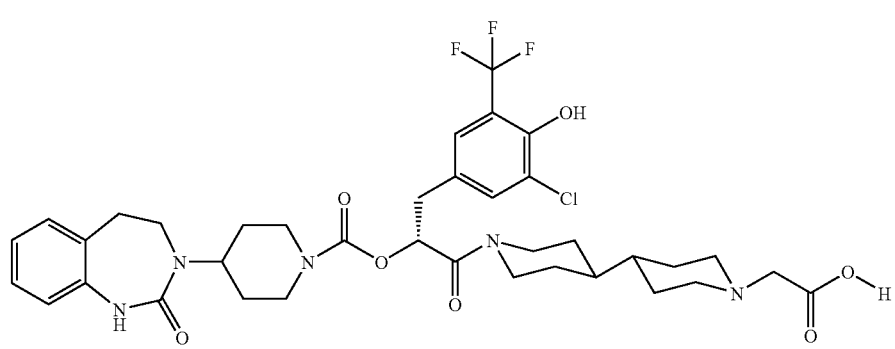 |

| No. | Structure |
|---|---|
| (25) | 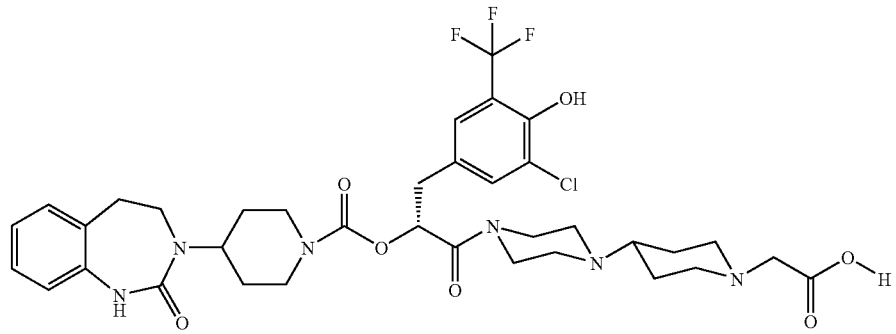 |
| (26) | 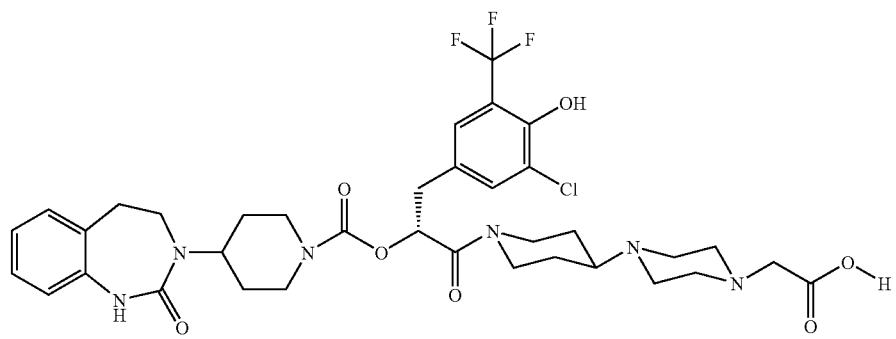 |
| (27) | 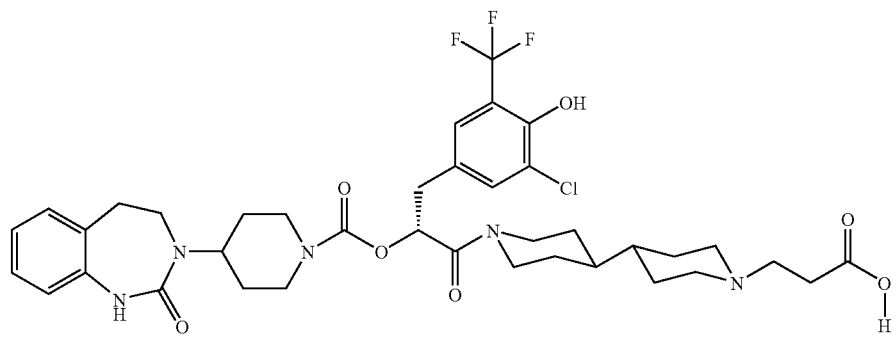 |
| (28) | 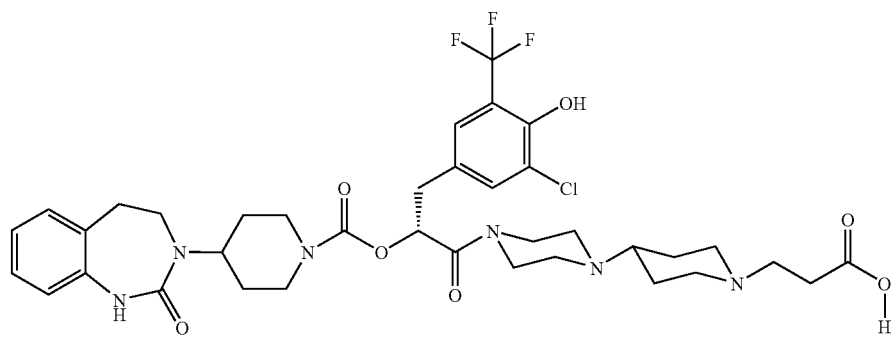 |

-continued
| No. | Structure |
|---|---|
| (29) | 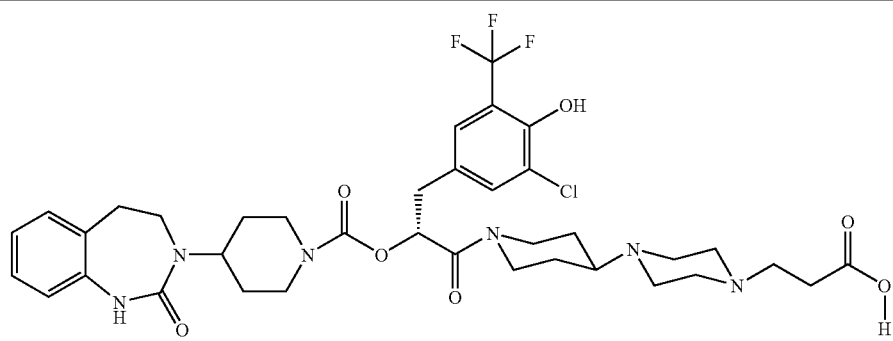 |
| (30) | 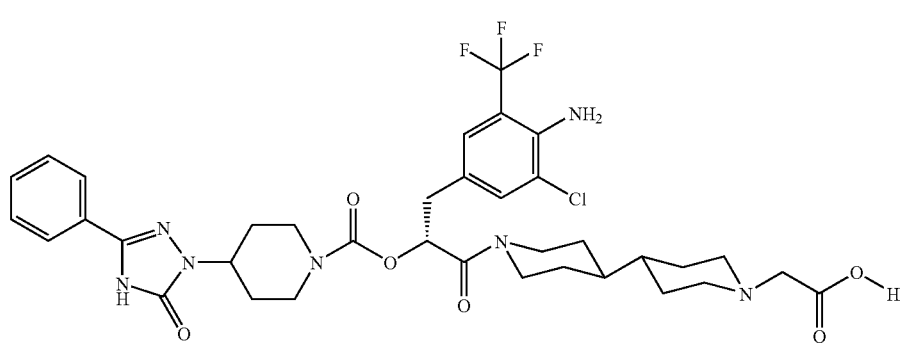 |
| (31) | 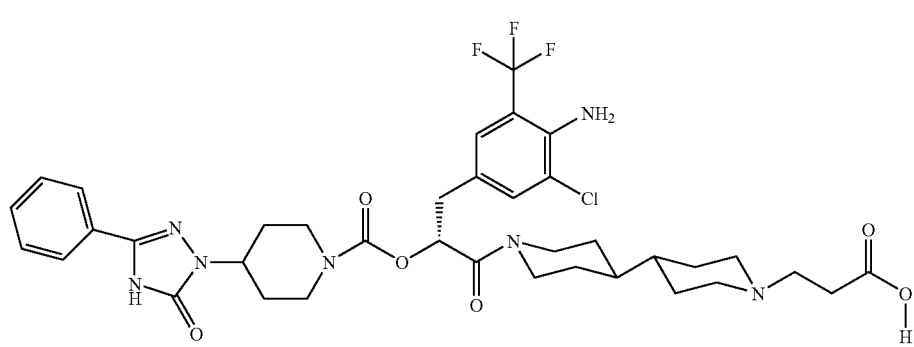 |
| (32) | 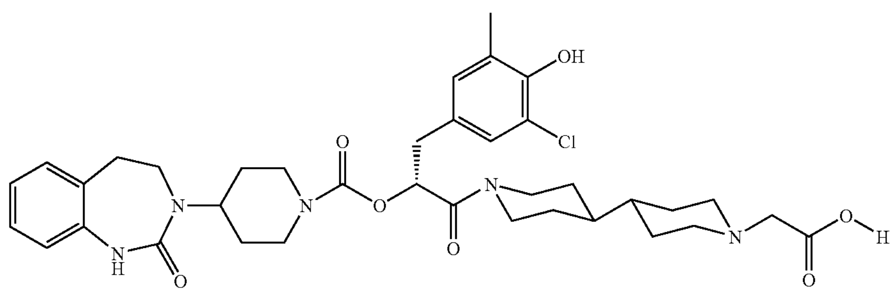 |
| (33) | 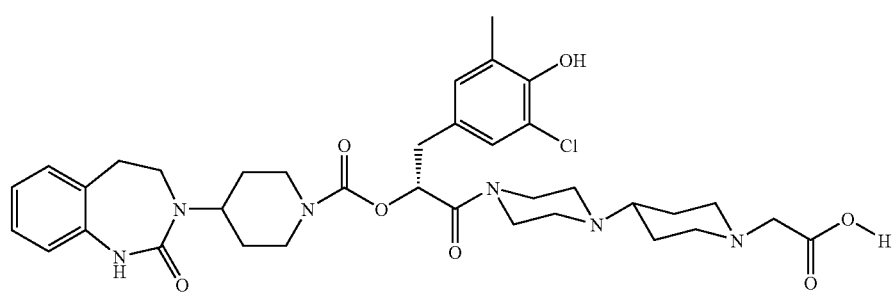 |

| No. | Structure |
|---|---|
| (34) | 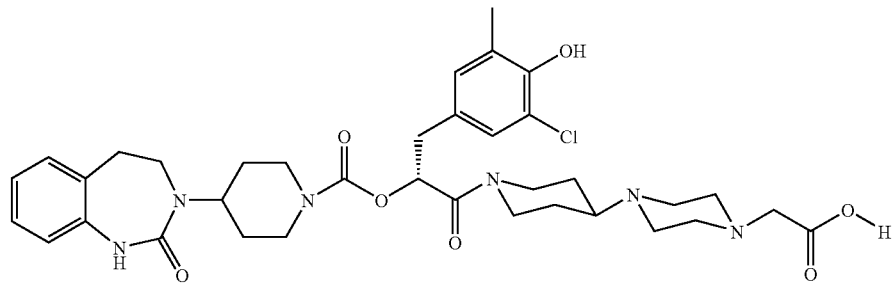 |
| (35) | 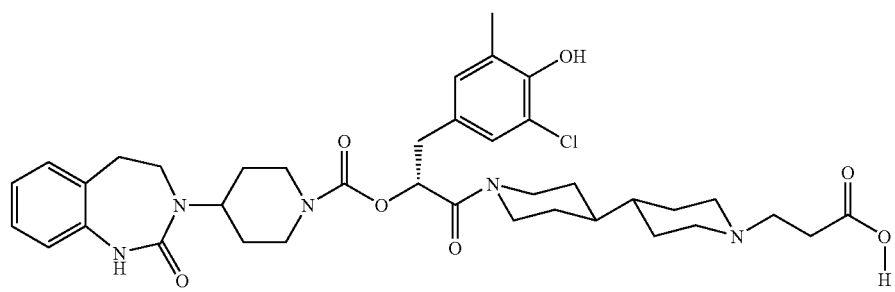 |
| (36) | 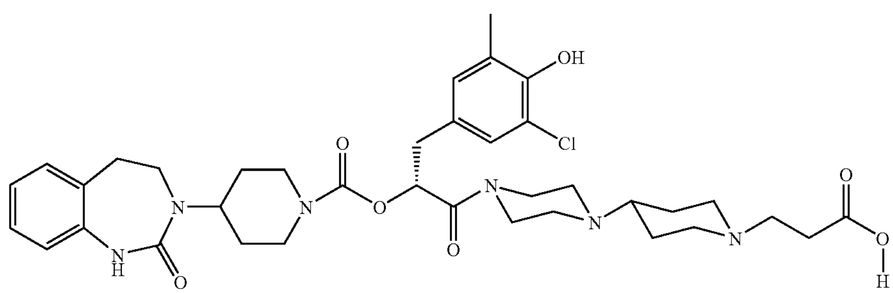 |
| (37) | 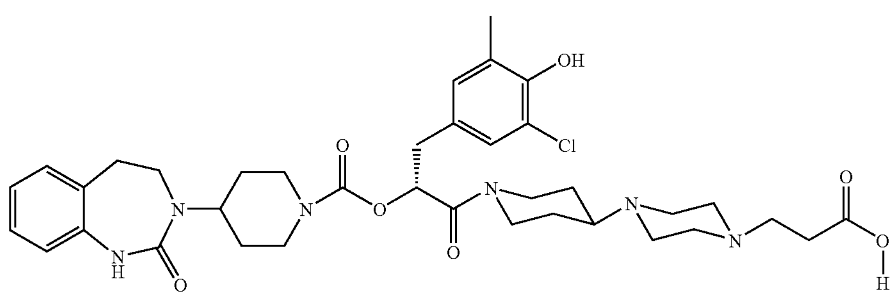 |
| (38) | 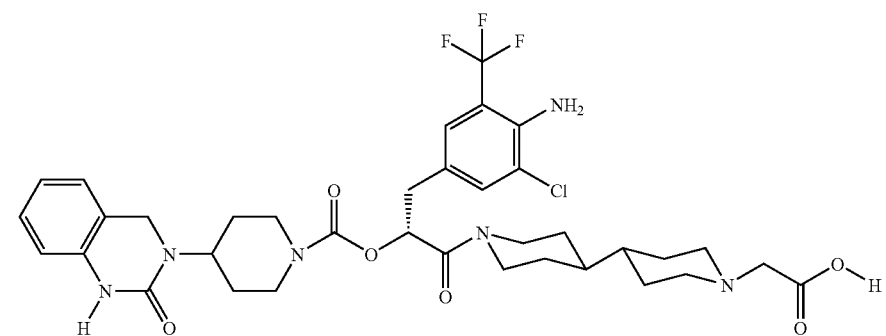 |

| No. | Structure |
|---|---|
| (39) | 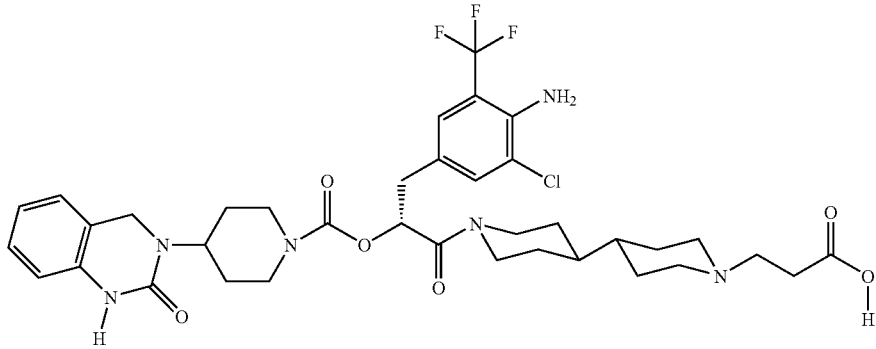 |
| (40) | 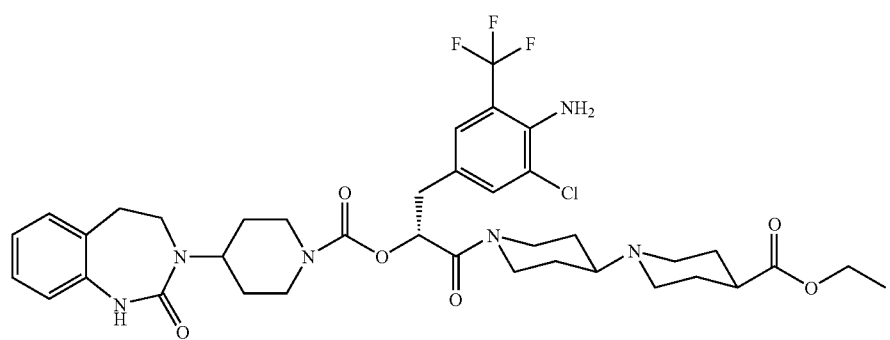 |
| (41) | 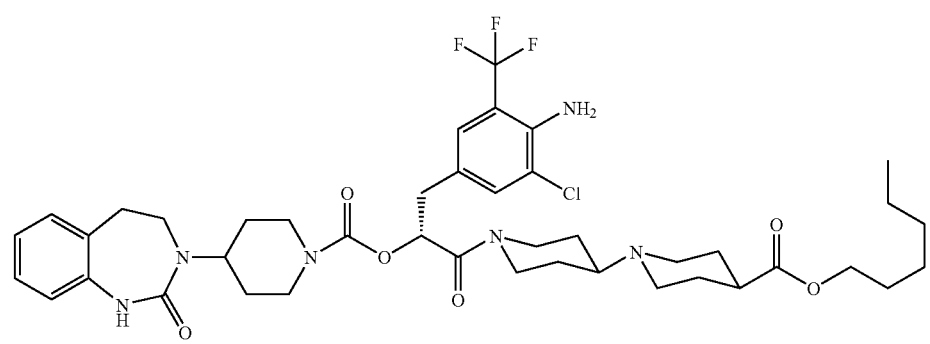 |
| (42) | 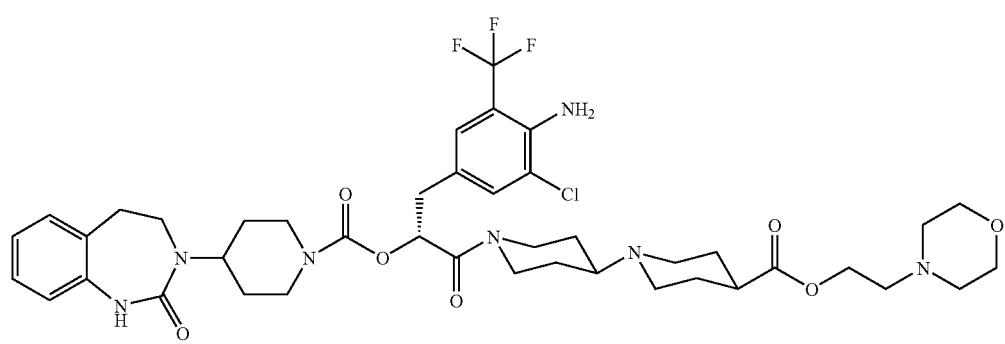 |

| No. | Structure |
|---|---|
| (43) | 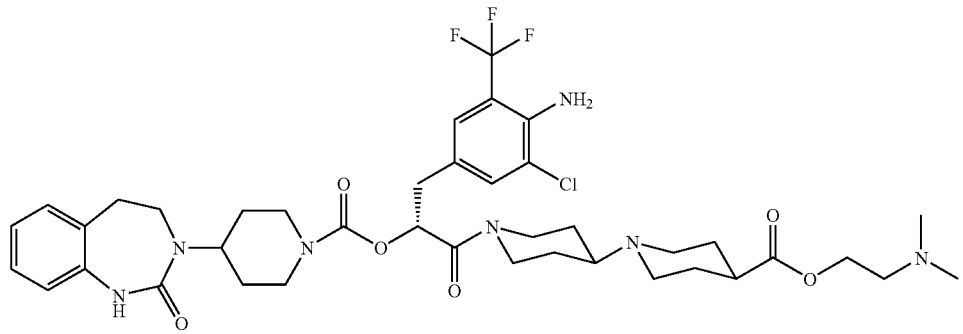 |
| (44) | 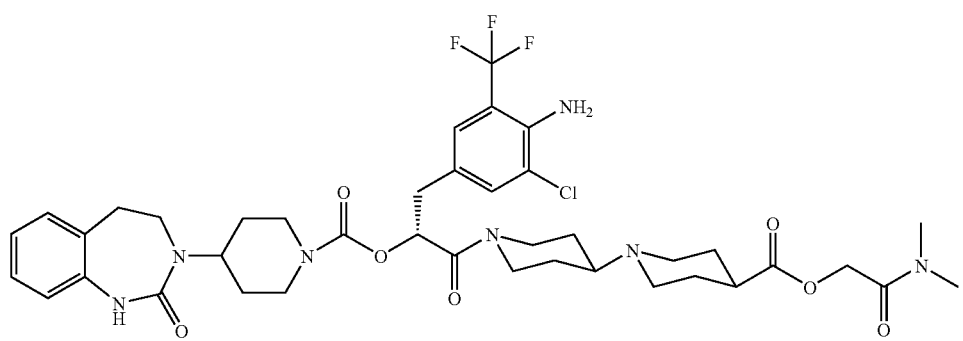 |
| (45) | 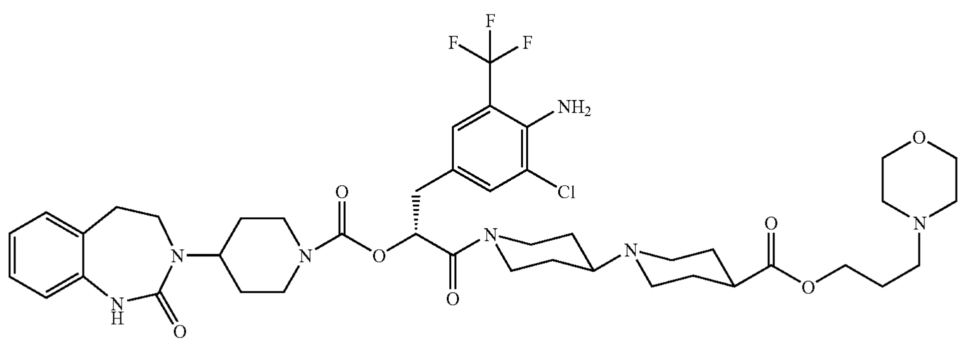 |
| (46) | 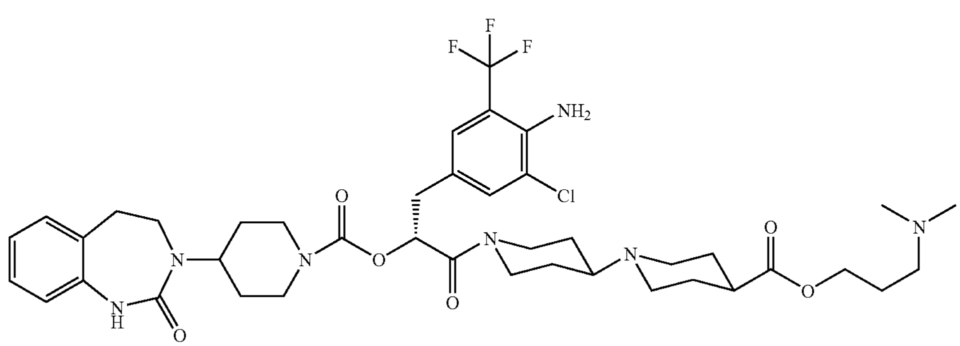 |

| No. | Structure |
|---|---|
| (47) | 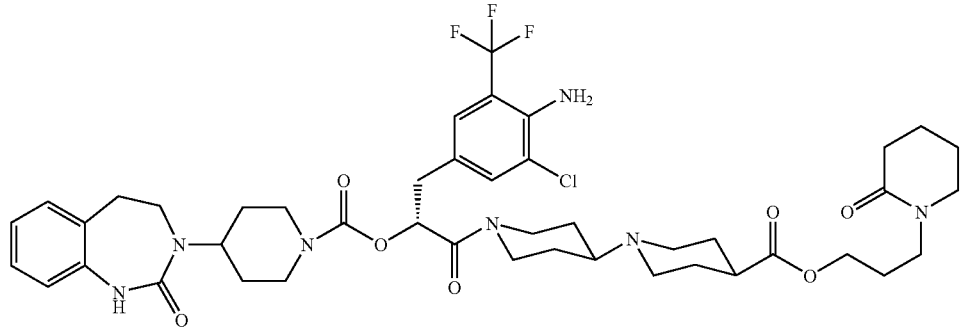 |
| (48) | 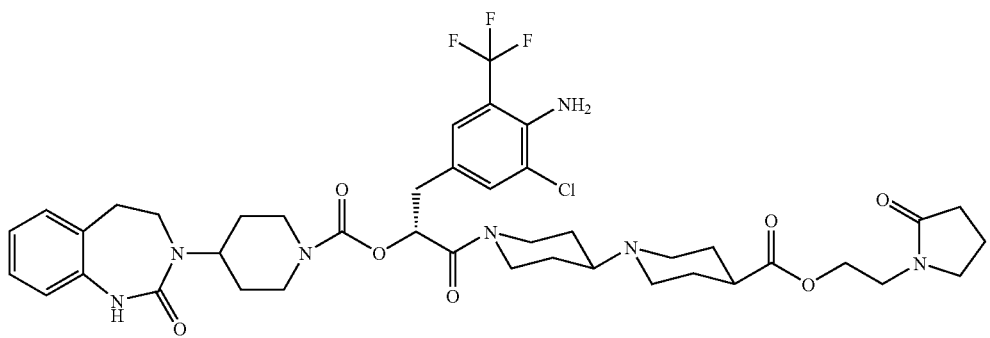 |
| (49) | 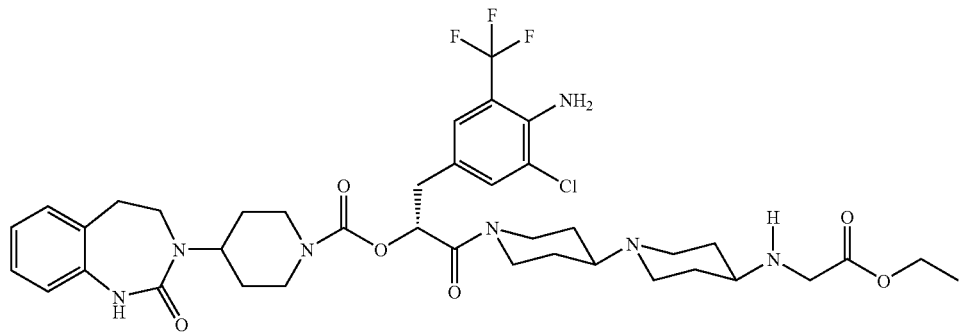 |
| (50) | 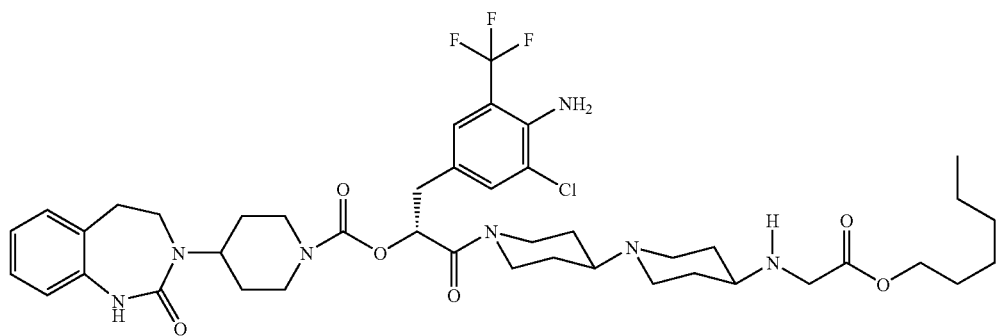 |

-continued
| No. | Structure |
|---|---|
| (51) | 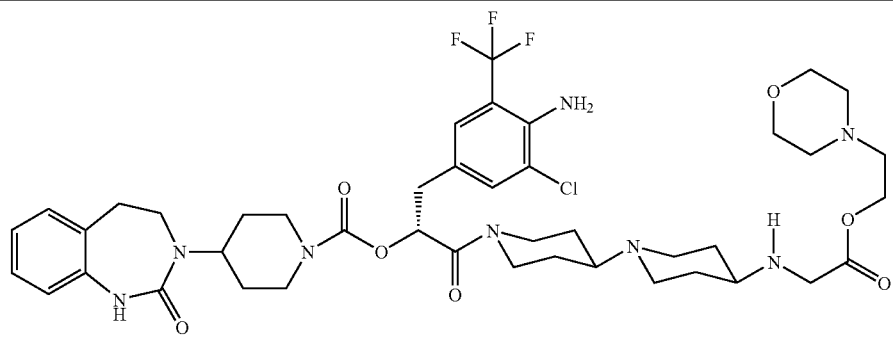 |
| (52) | 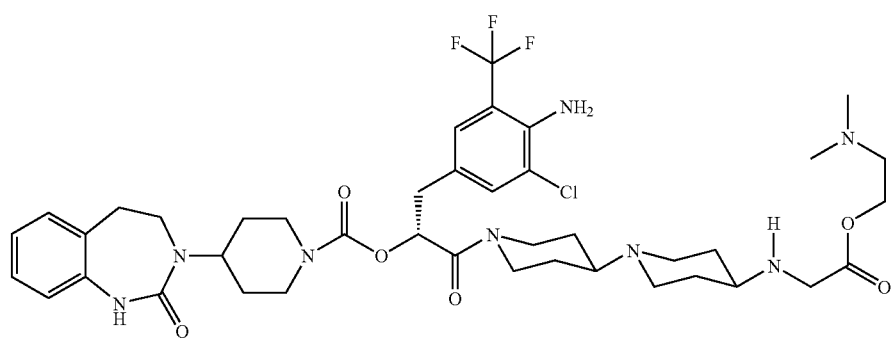 |
| (53) | 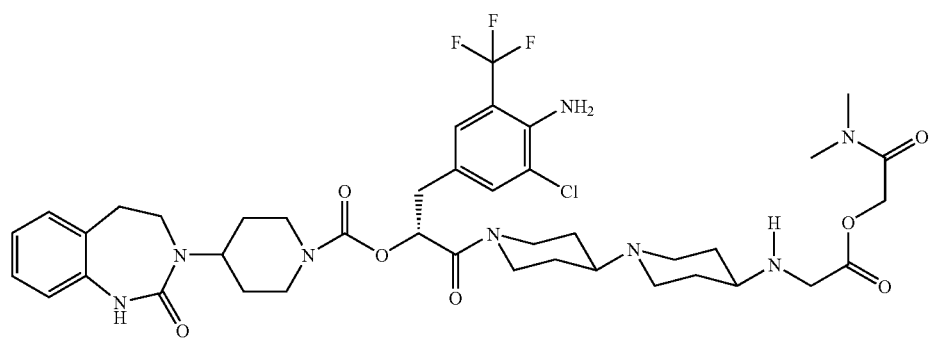 |
| (54) | 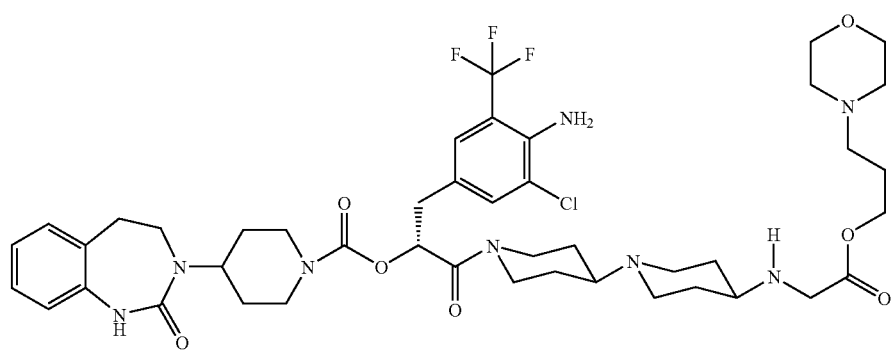 |

| No. | Structure |
|---|---|
| (55) | 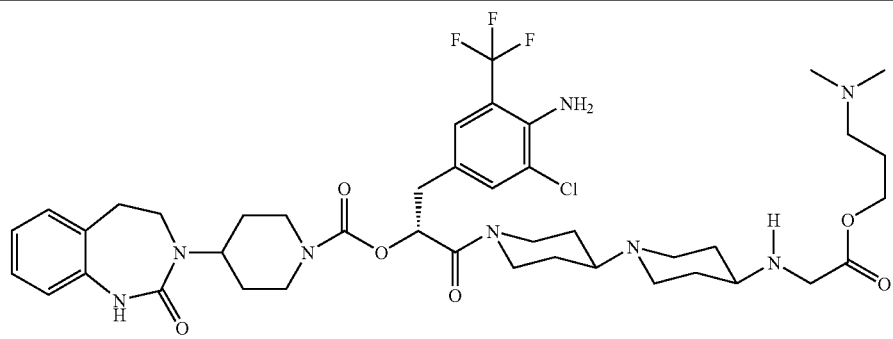 |
| (56) | 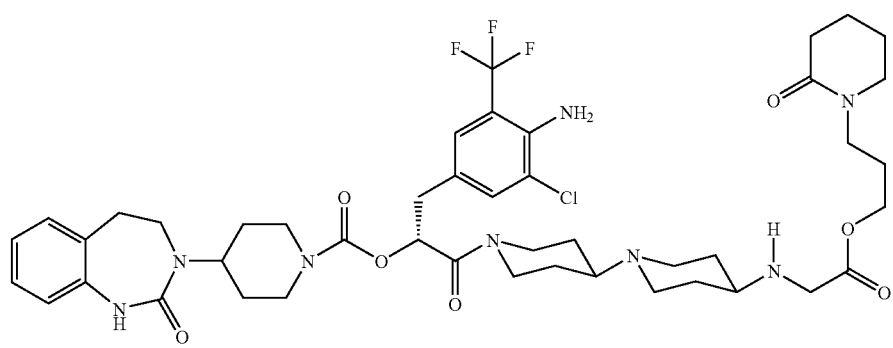 |
| (57) | 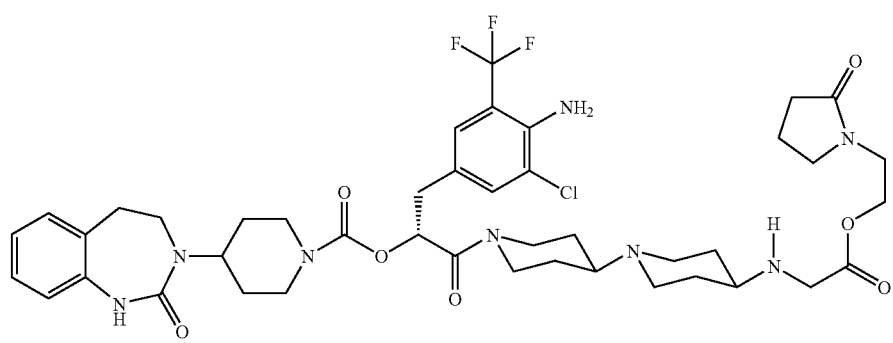 |
| (58) | 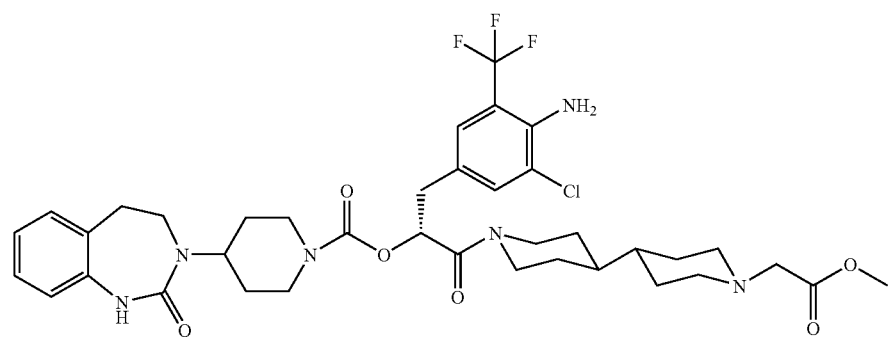 |

| No. | Structure |
|---|---|
| (59) | 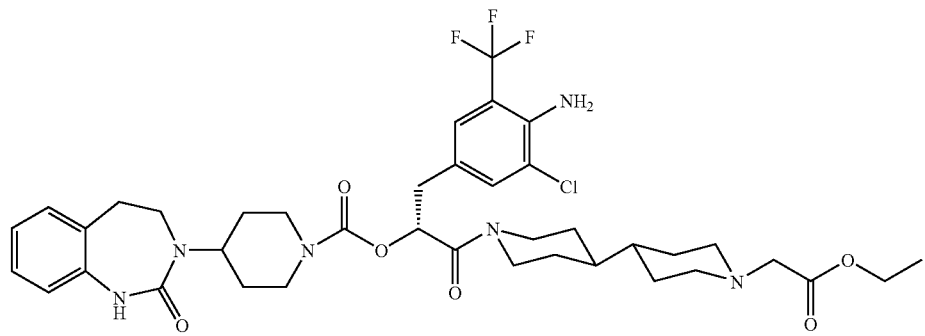 |
| (60) | 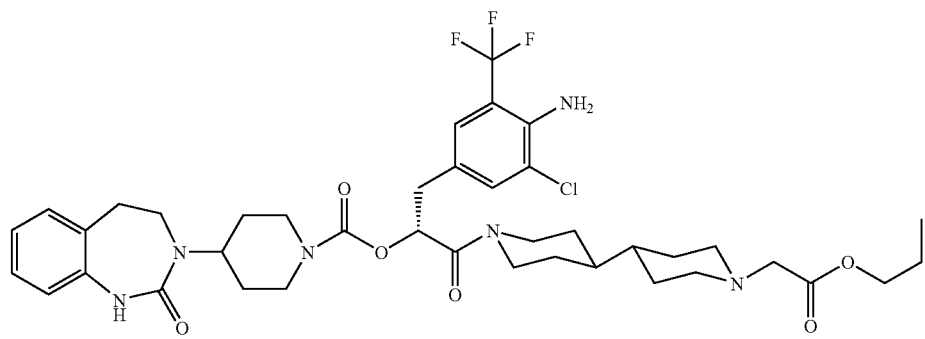 |
| (61) | 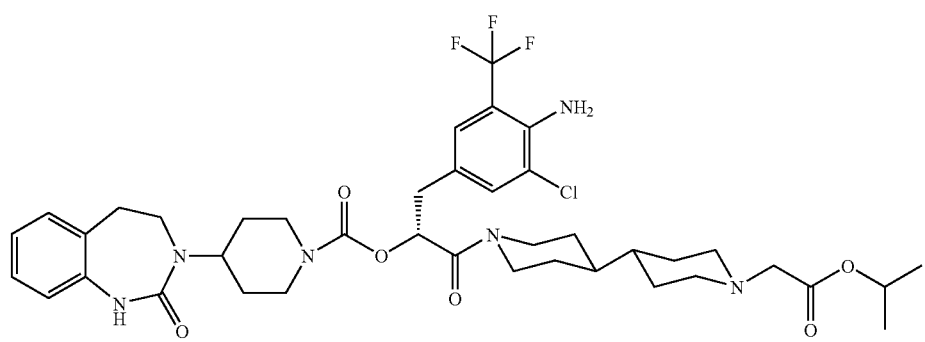 |
| (62) | 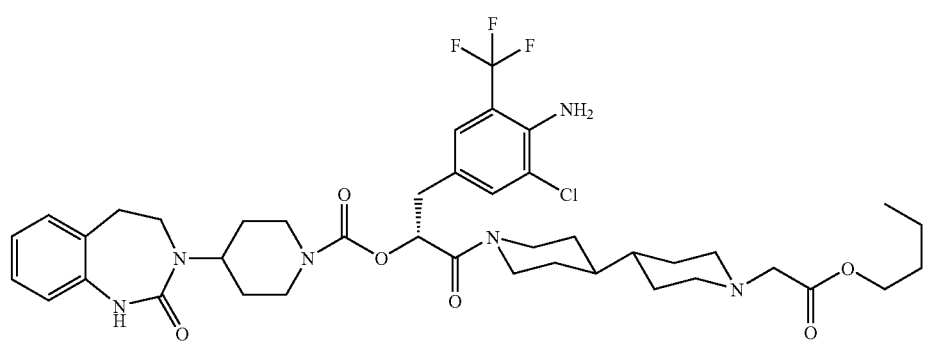 |

| No. | Structure |
|---|---|
| (63) | 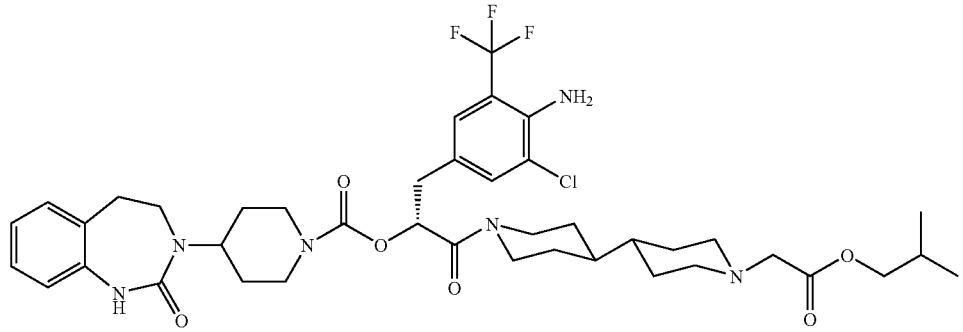 |
| (64) | 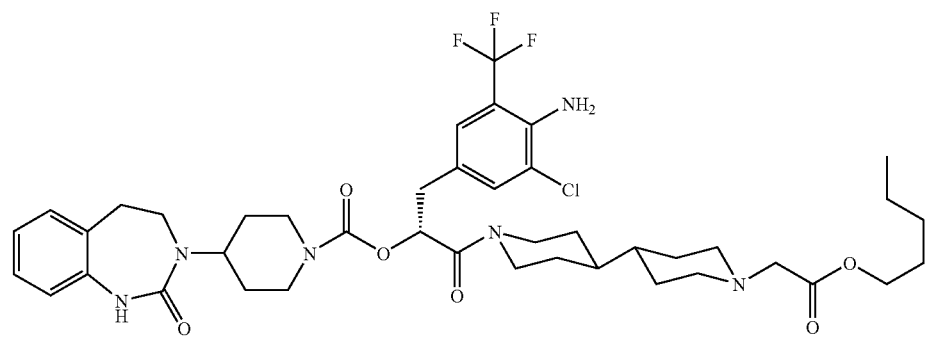 |
| (65) | 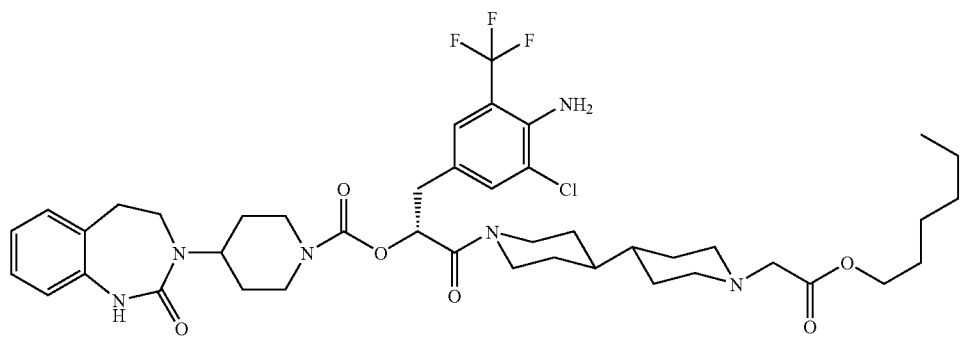 |
| (66) | 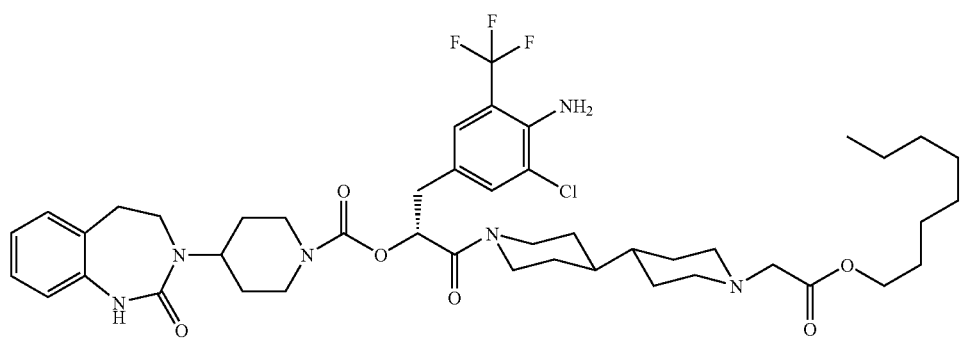 |

| No. | Structure |
|---|---|
| (67) | 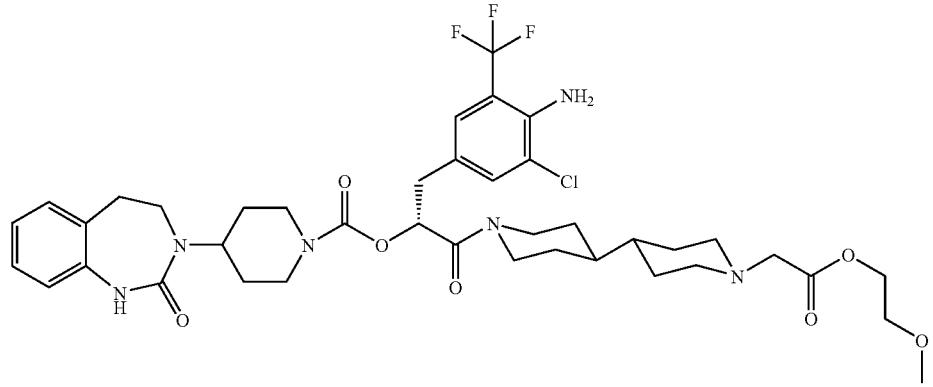 |
| (68) | 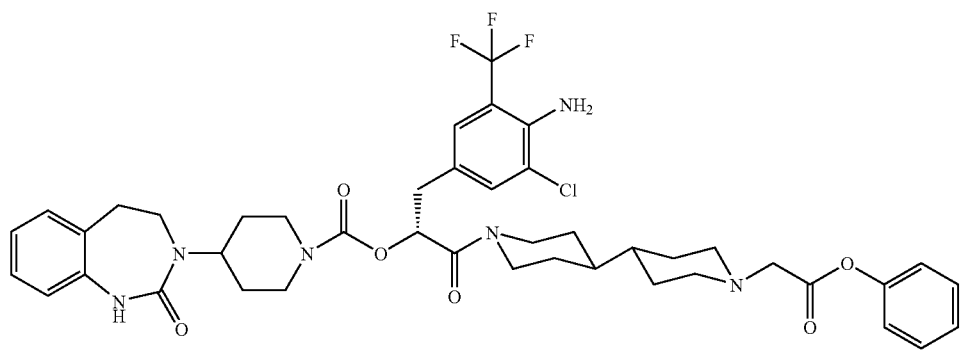 |
| (69) | 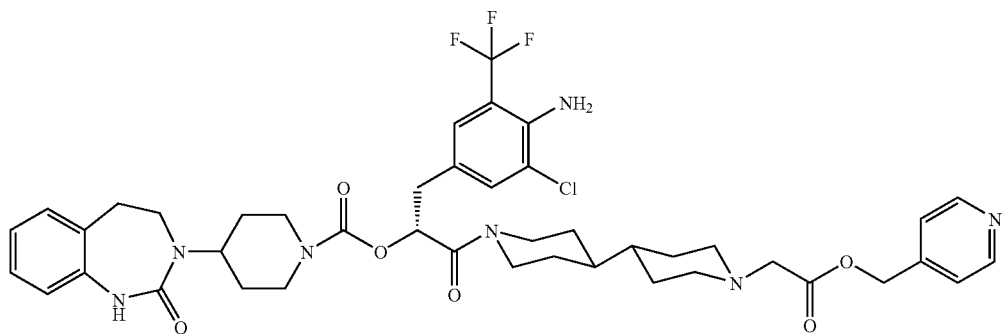 |
| (70) | 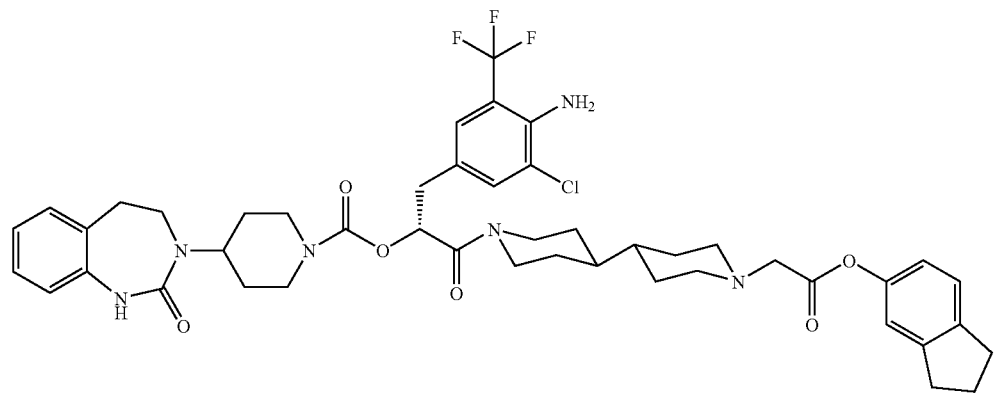 |

| No. | Structure |
|---|---|
| (71) | 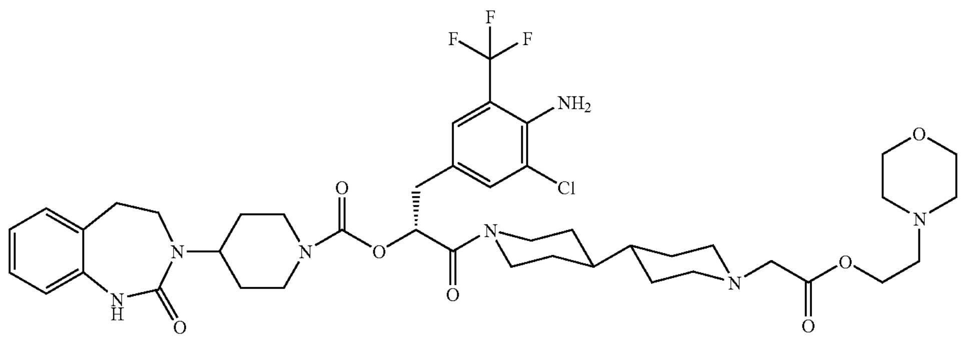 |
| (72) | 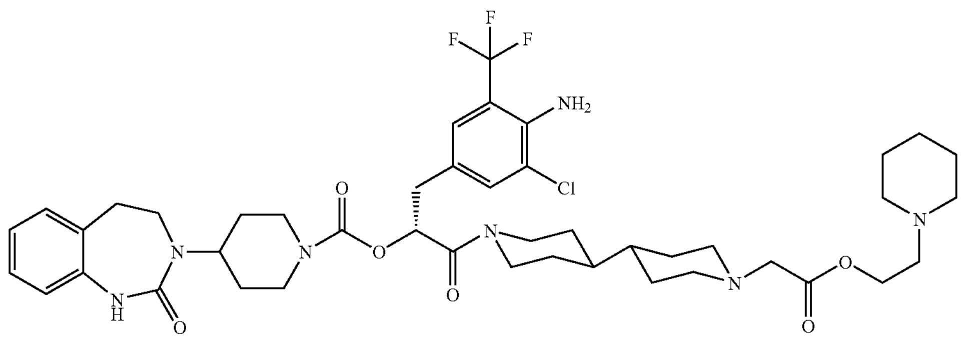 |
| (73) | 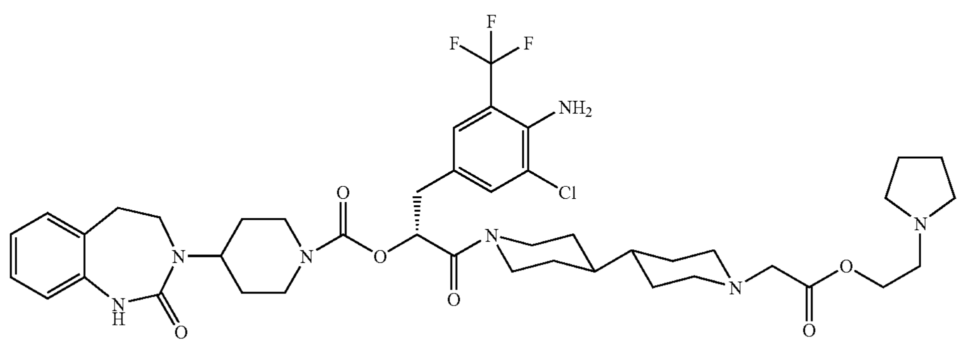 |
| (74) | 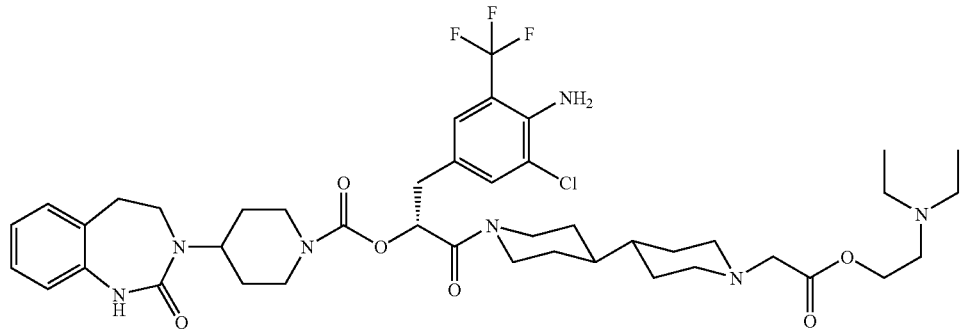 |

| No. | Structure |
|---|---|
| (75) | 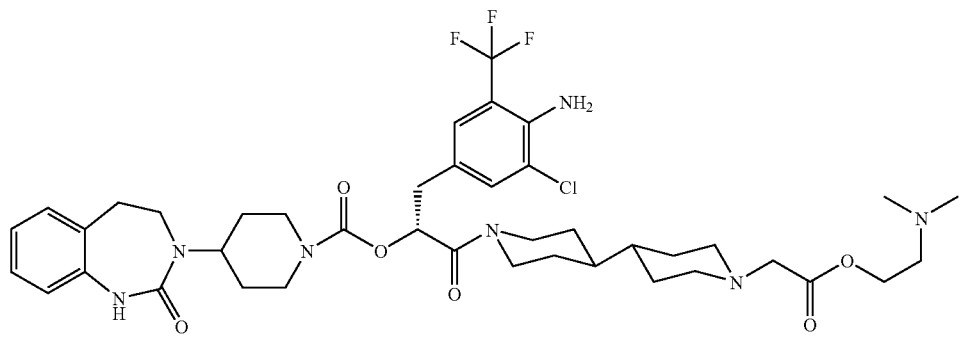 |
| (76) | 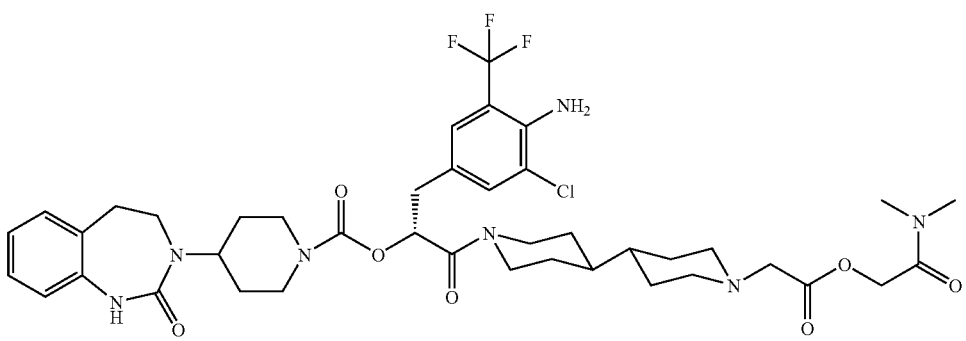 |
| (77) | 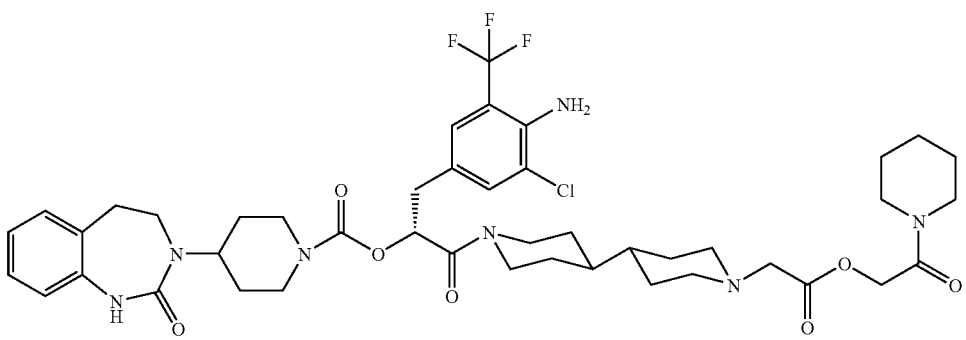 |
| (78) | 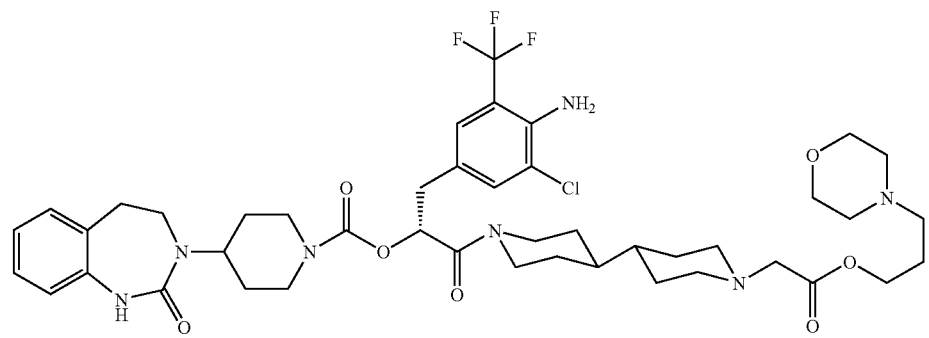 |

| No. | Structure |
|---|---|
| (79) | 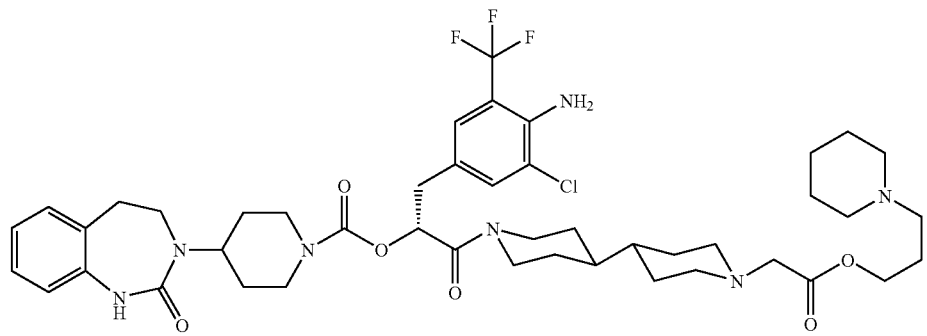 |
| (80) | 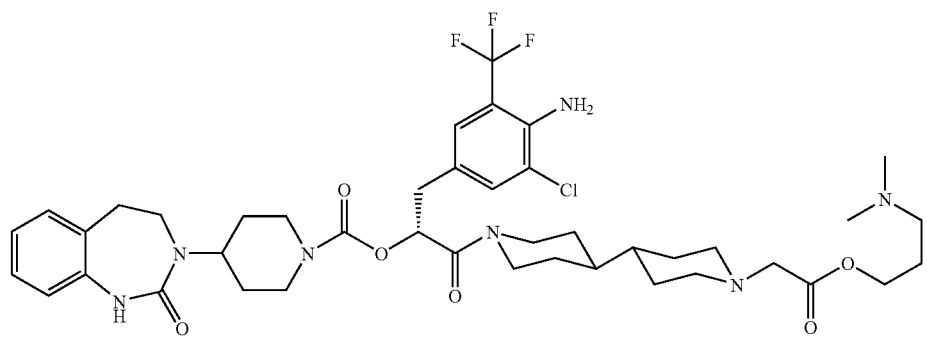 |
| (81) | 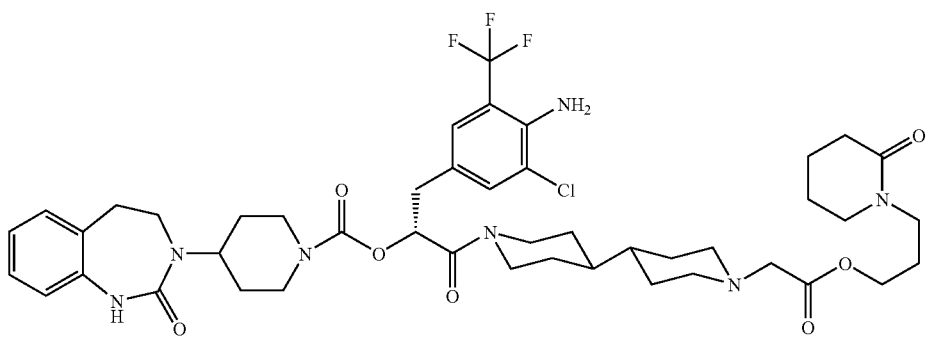 |
| (82) | 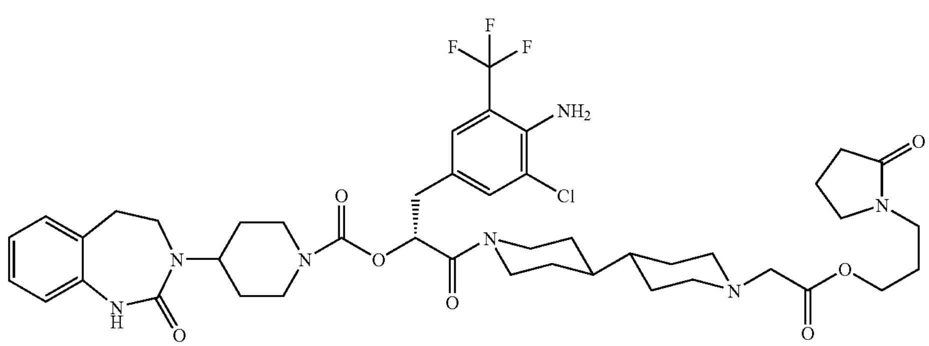 |

| No. | Structure |
|---|---|
| (83) | 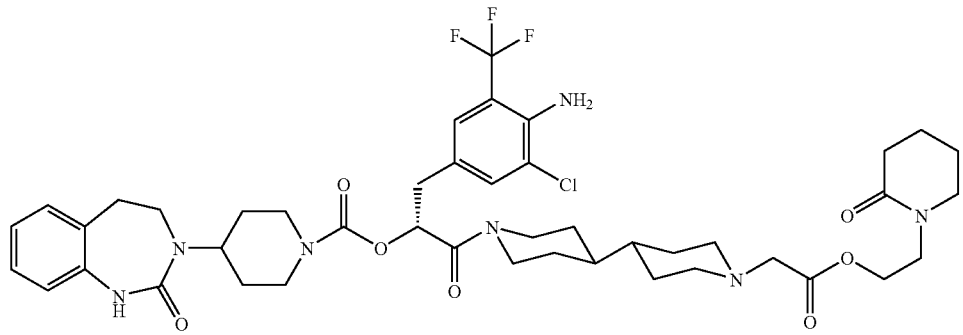 |
| (84) | 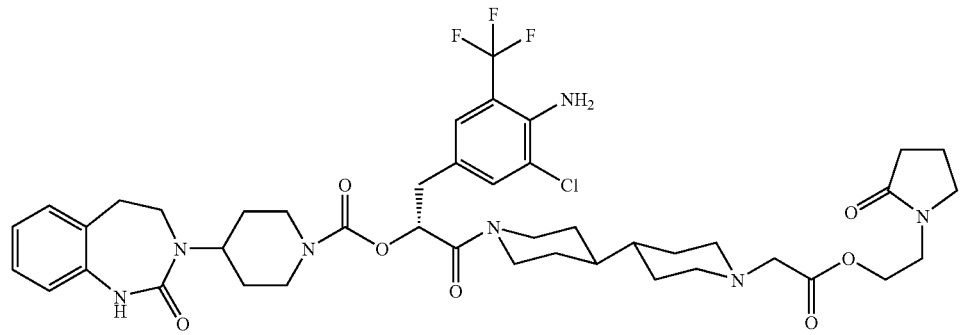 |
| (85) | 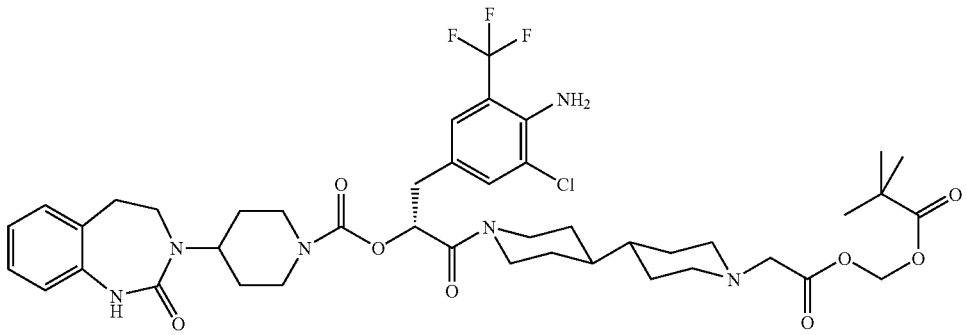 |
| (86) | 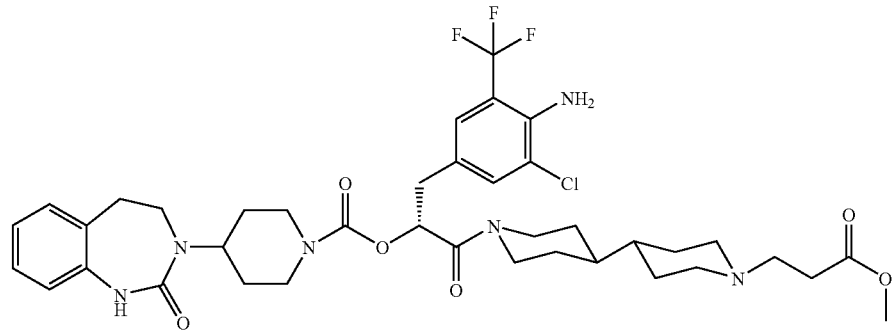 |

| No. | Structure |
|---|---|
| (87) | 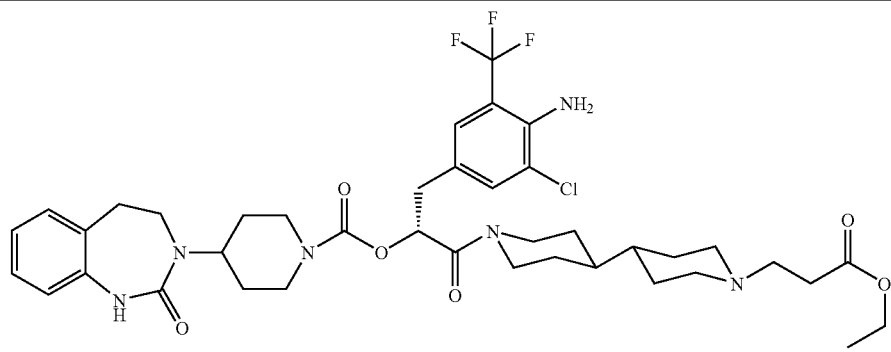 |
| (88) | 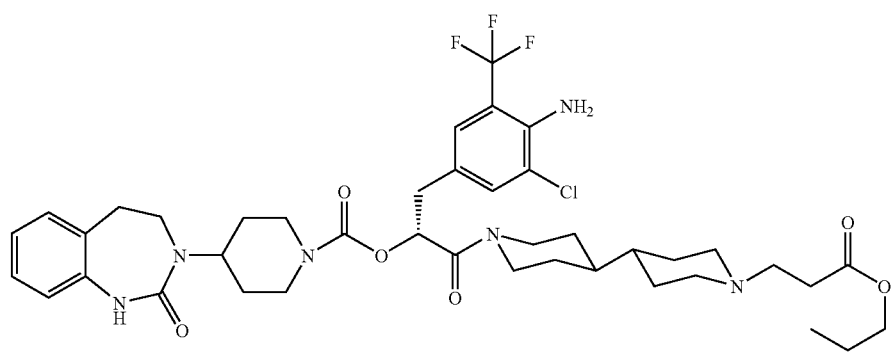 |
| (89) | 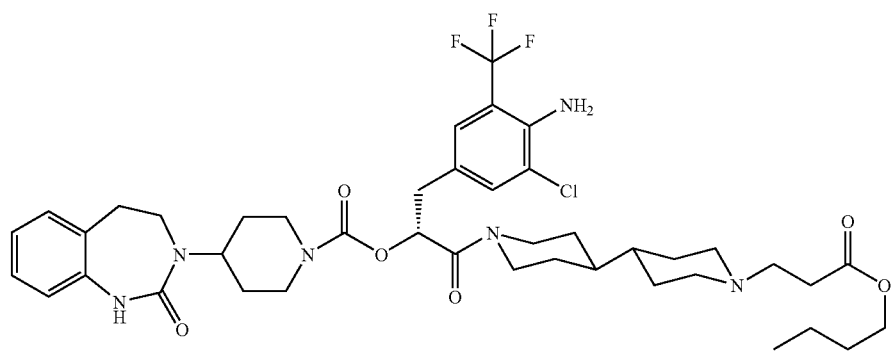 |
| (90) | 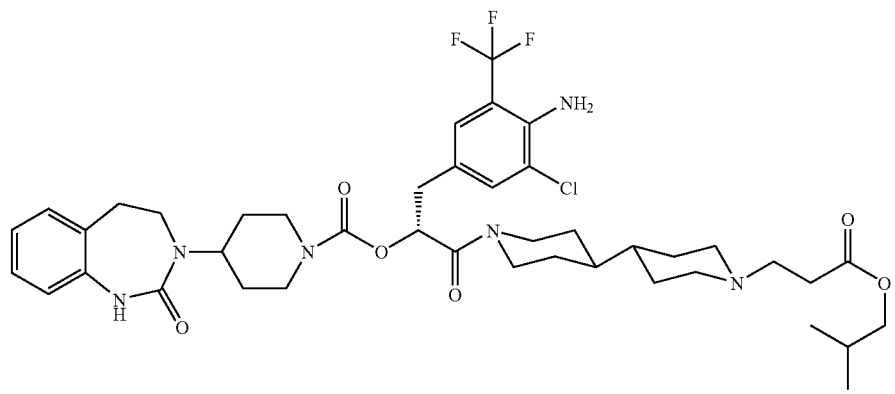 |

| No. | Structure |
|---|---|
| (91) | 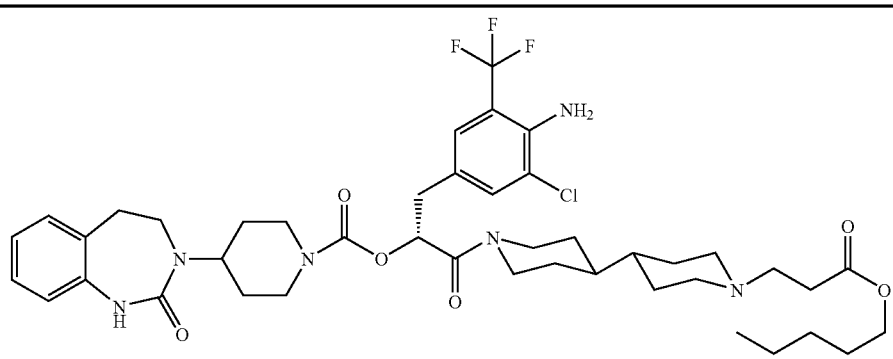 |
| (92) | 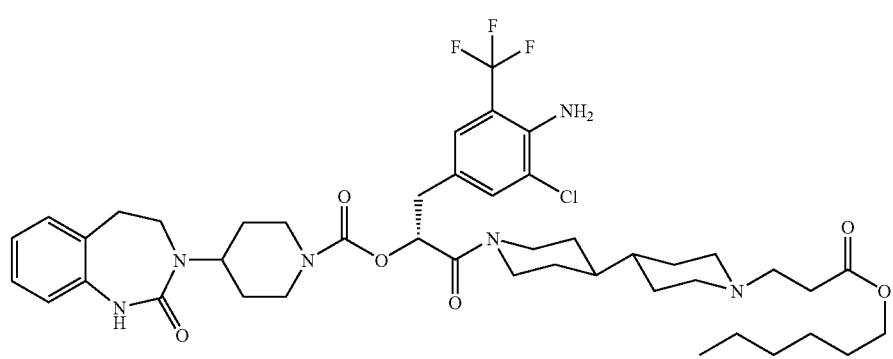 |
| (93) | 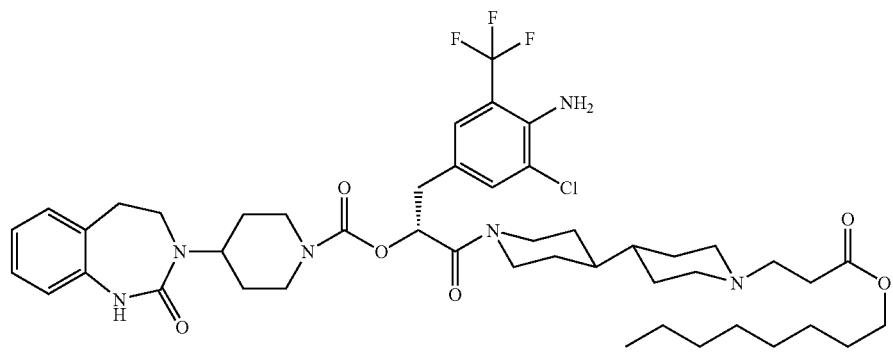 |
| (94) | 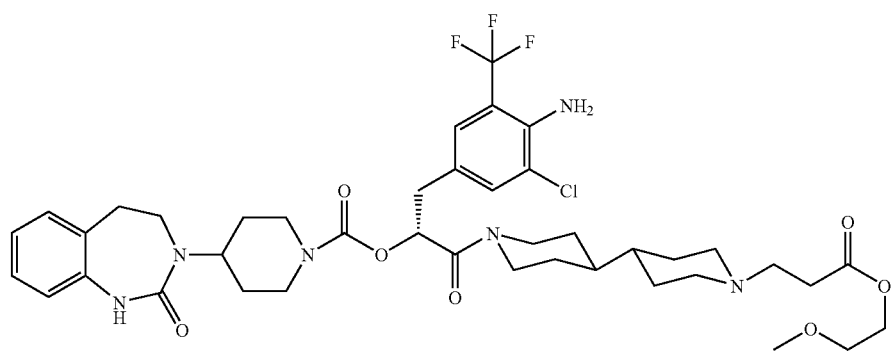 |

| No. | Structure |
|---|---|
| (95) | 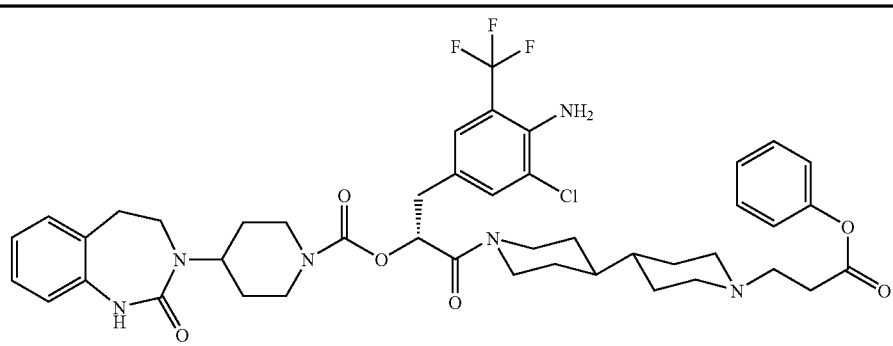 |
| (96) | 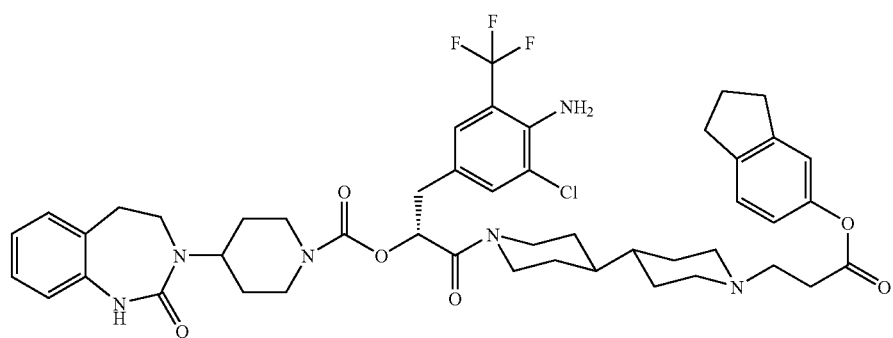 |
| (97) | 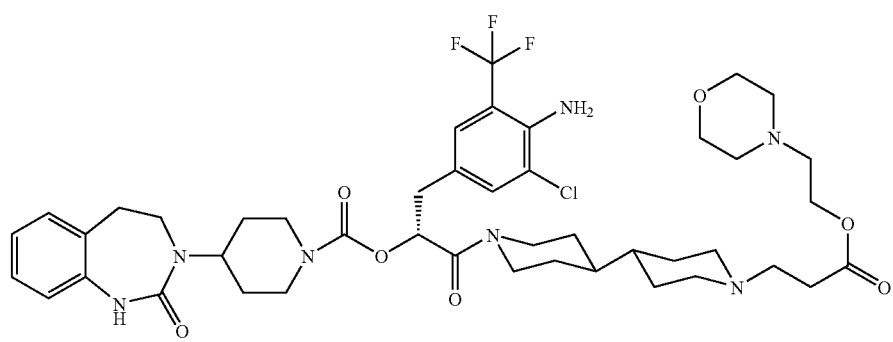 |
| (98) | 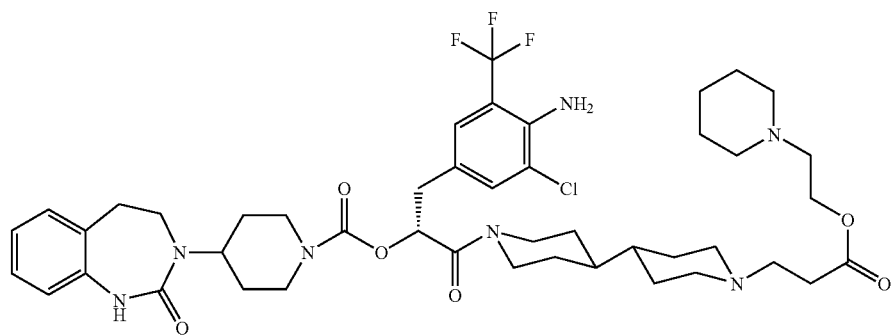 |

| No. | Structure |
|---|---|
| (99) | 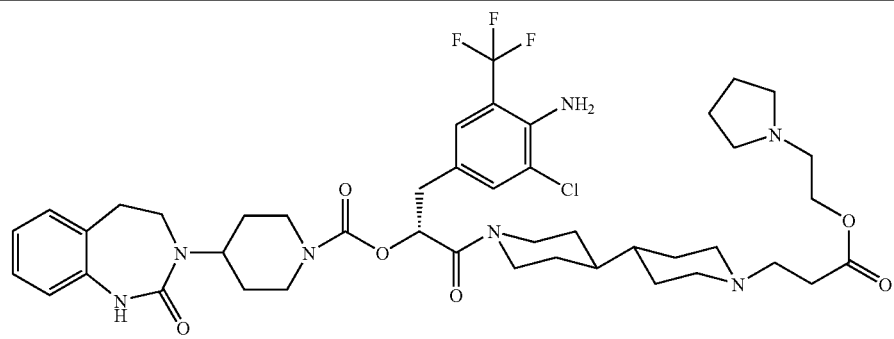 |
| (100) | 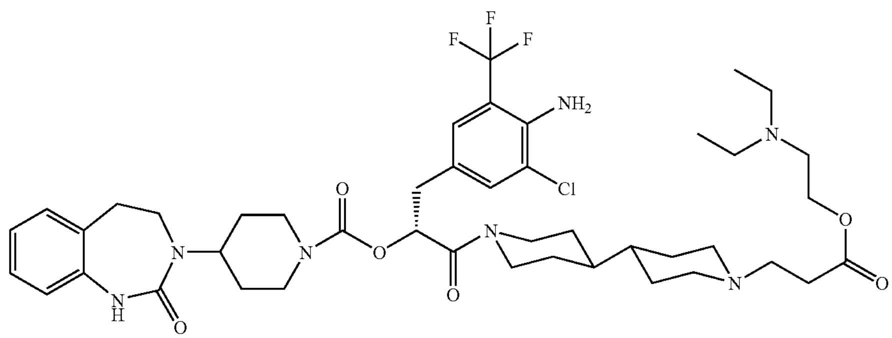 |
| (101) | 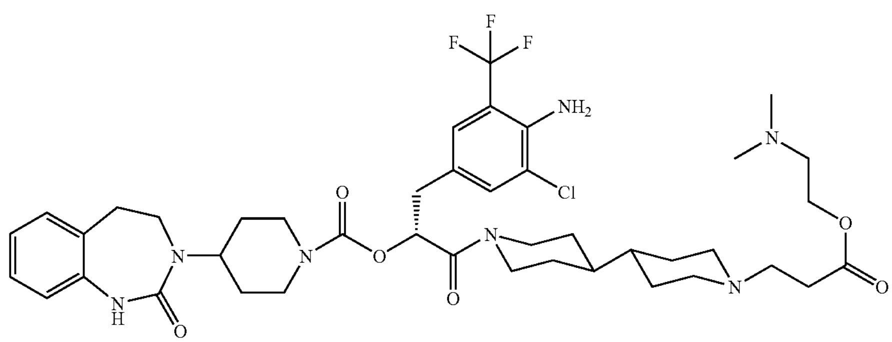 |
| (102) | 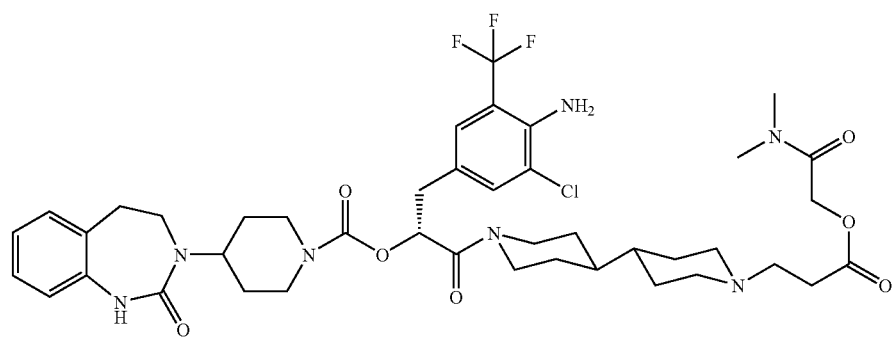 |

-continued
| No. | Structure |
|---|---|
| (103) | 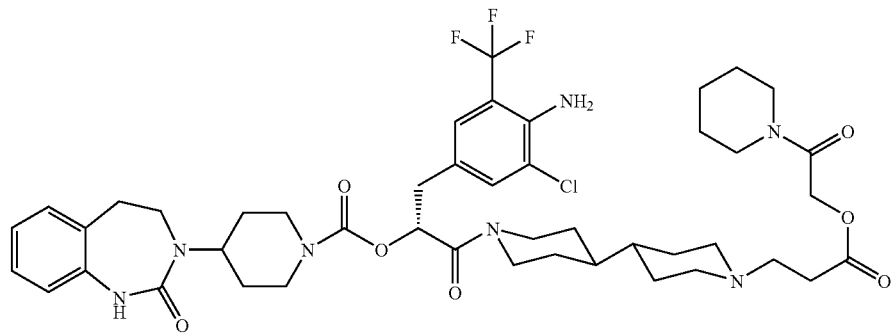 |
| (104) | 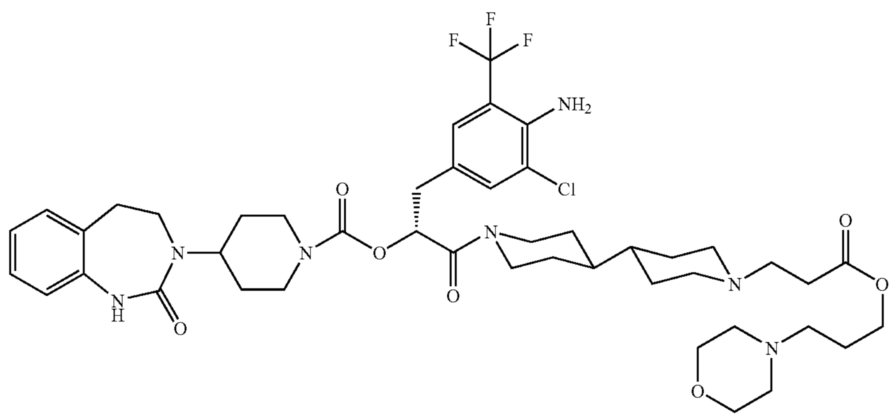 |
| (105) | 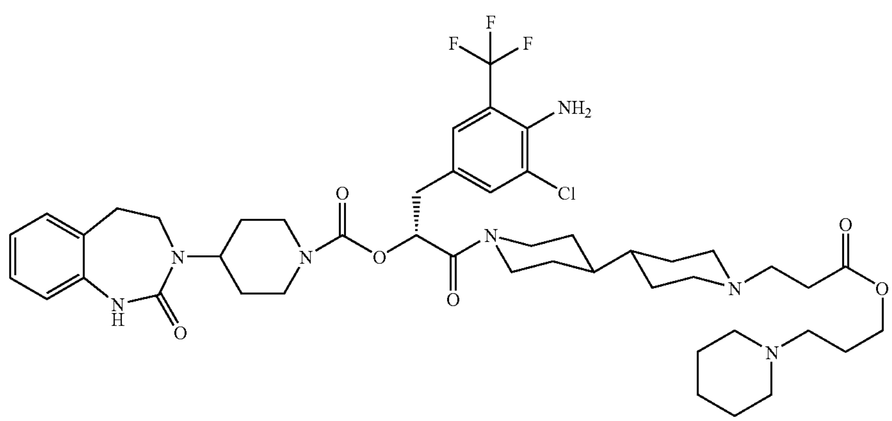 |

| No. | Structure |
|---|---|
| (106) | 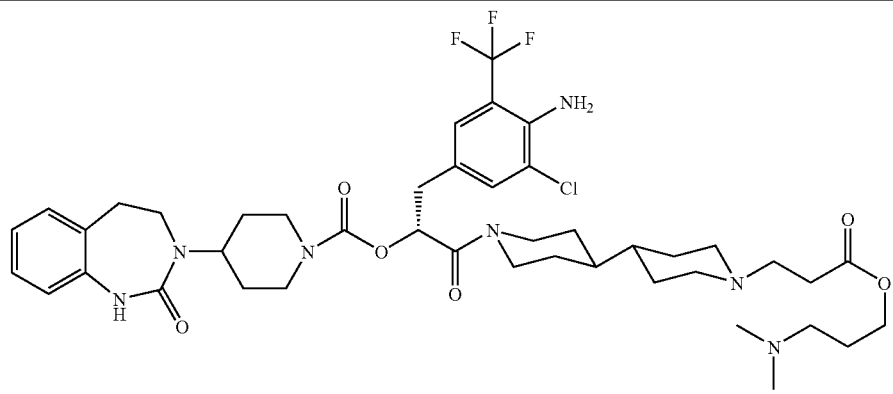 |
| (107) | 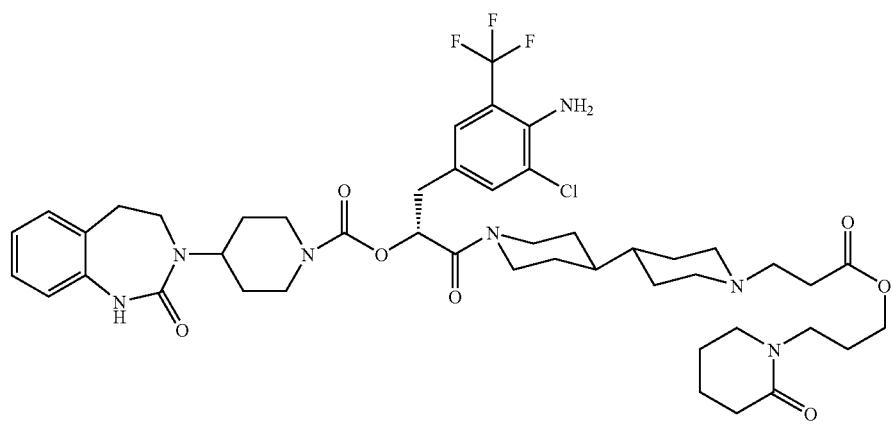 |
| (108) | 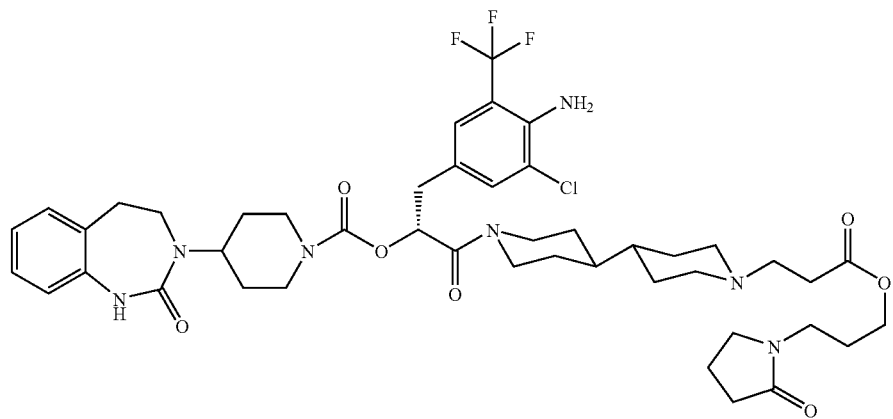 |
| (109) | 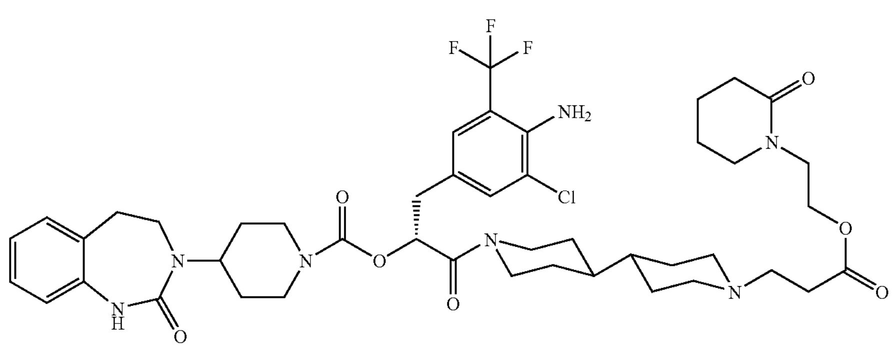 |

| No. | Structure |
|---|---|
| (110) | 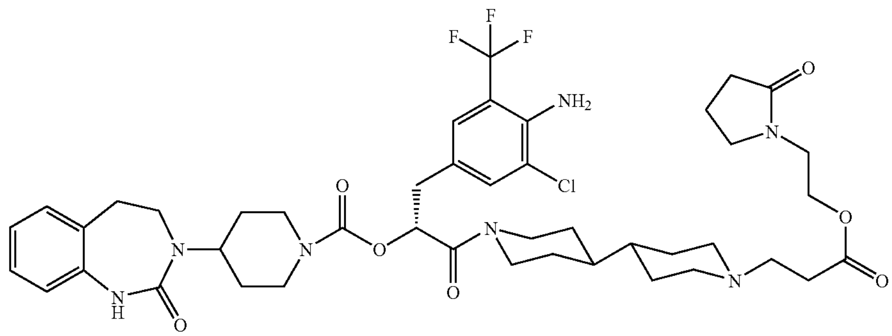 |
| (111) | 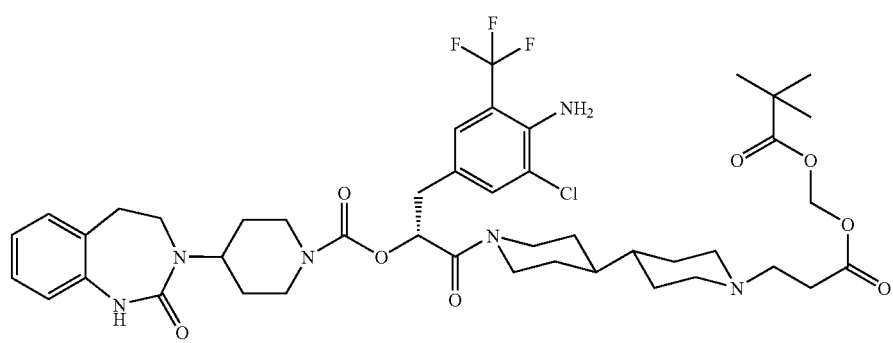 |
| (112) | 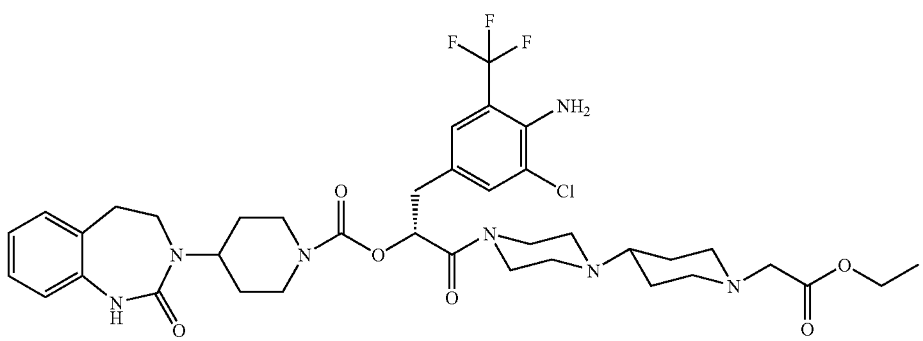 |
| (113) | 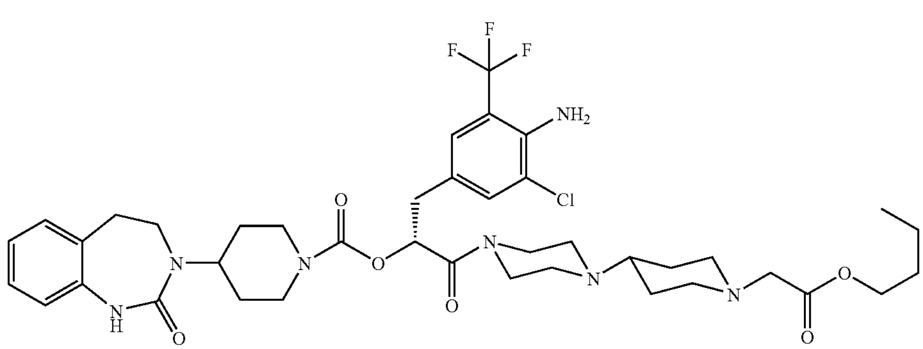 |

| No. | Structure |
|---|---|
| (114) | 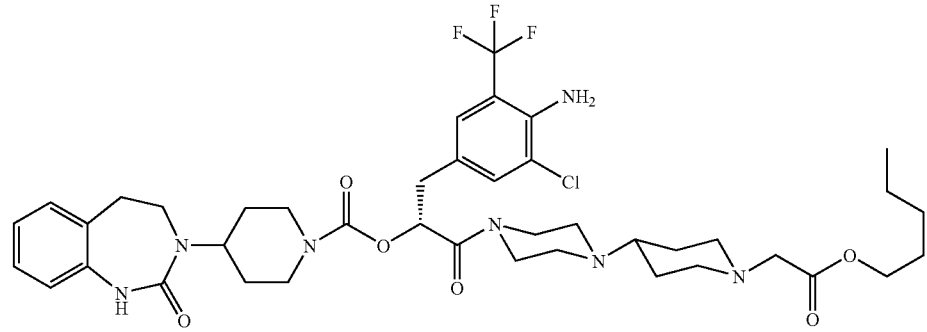 |
| (115) | 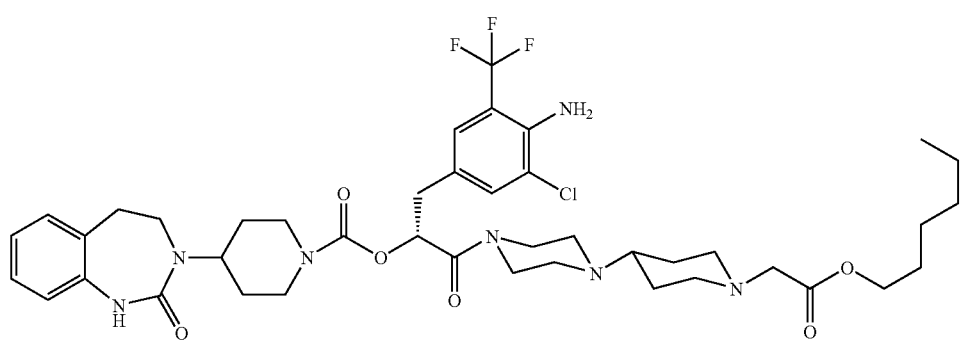 |
| (116) | 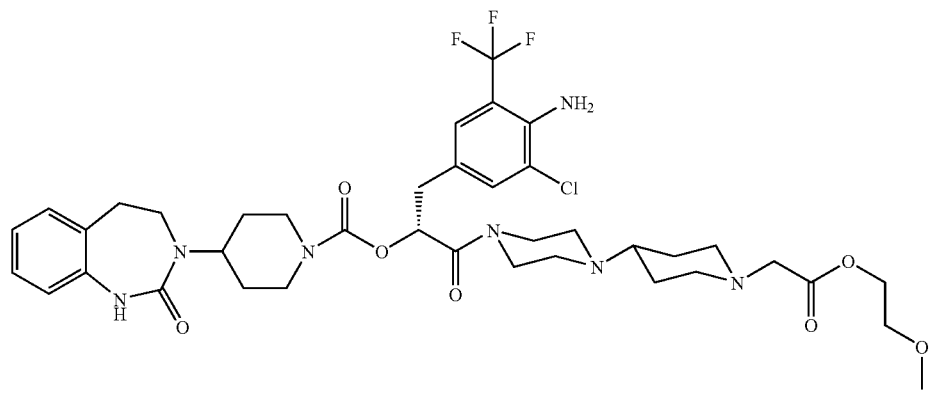 |
| (117) | 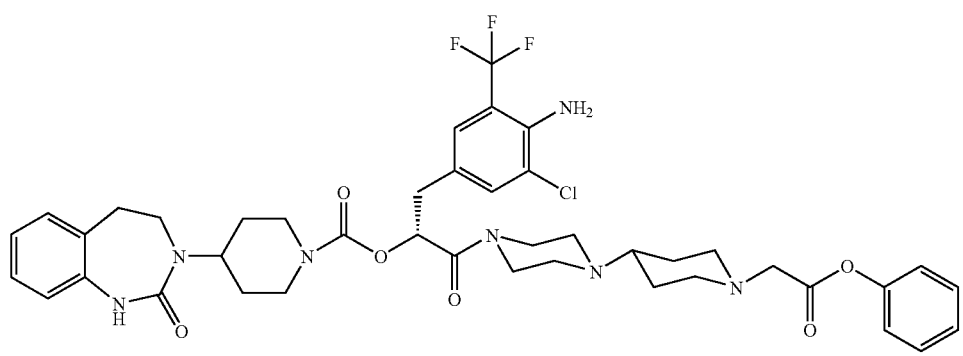 |

| No. | Structure |
|---|---|
| (118) | 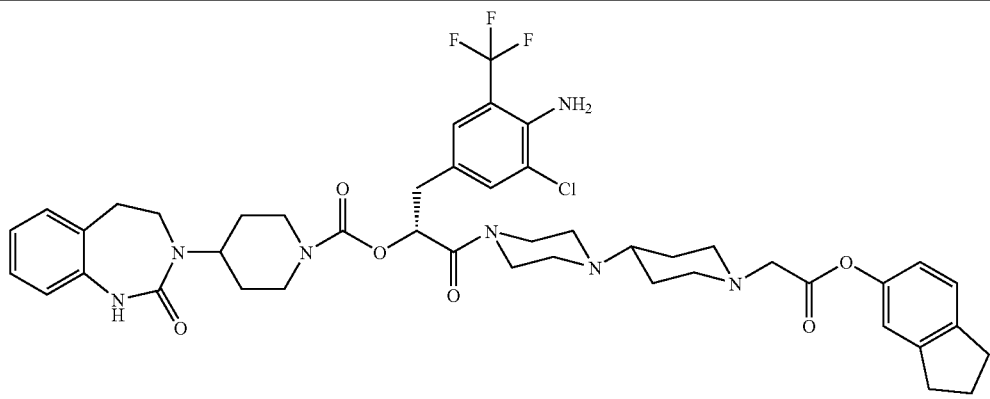 |
| (119) | 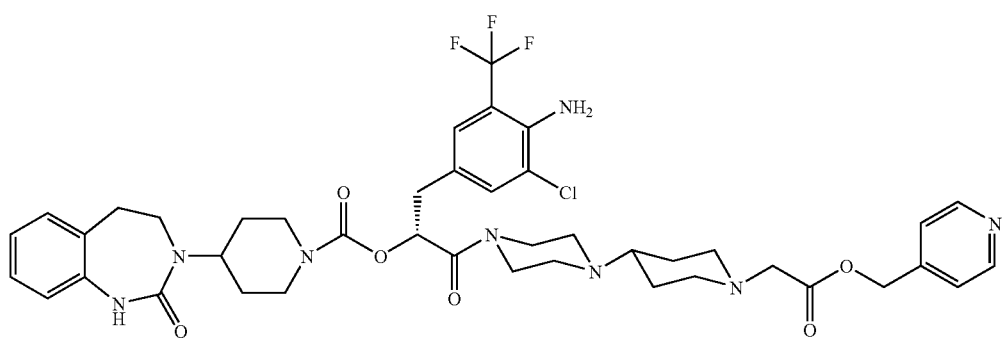 |
| (120) | 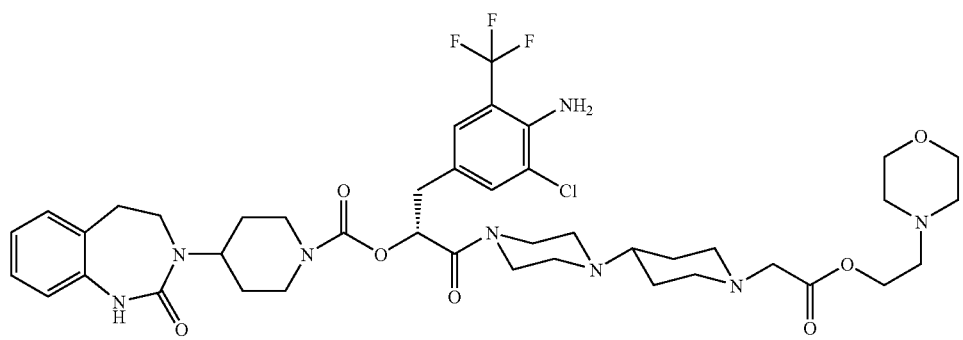 |
| (121) | 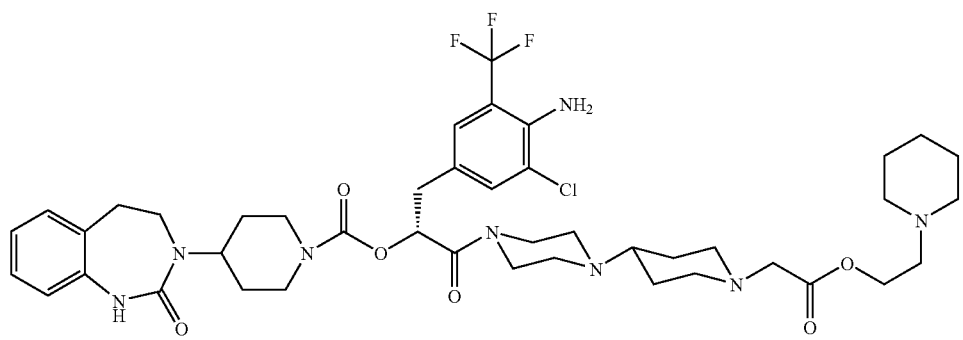 |

| No. | Structure |
|---|---|
| (122) | 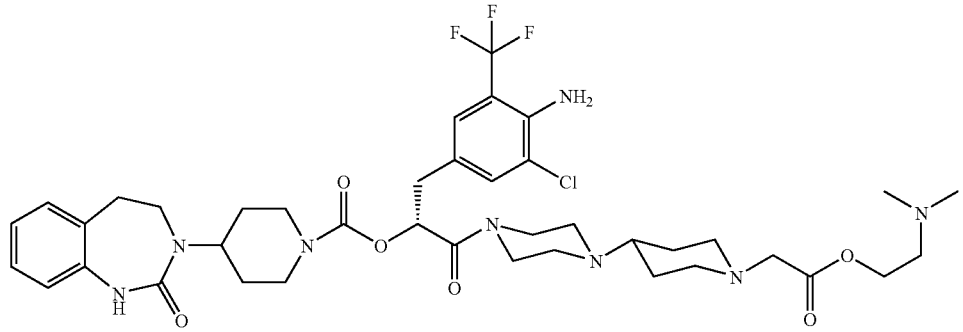 |
| (123) | 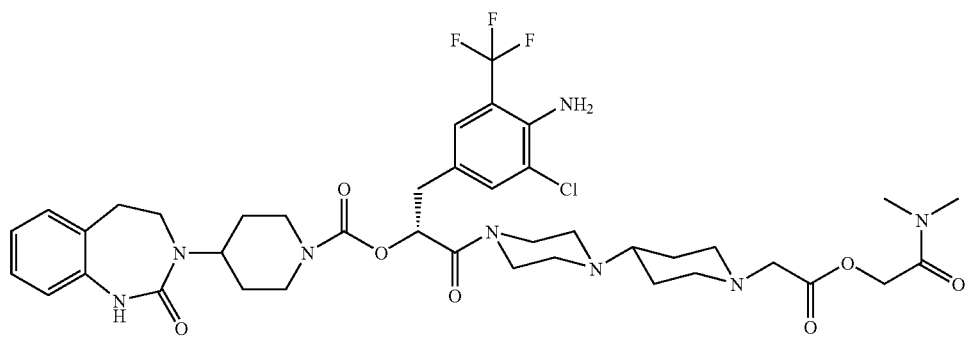 |
| (124) | 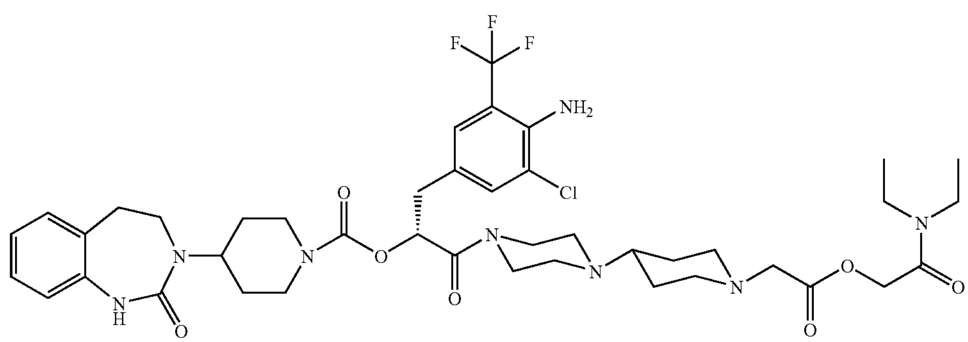 |
| (125) | 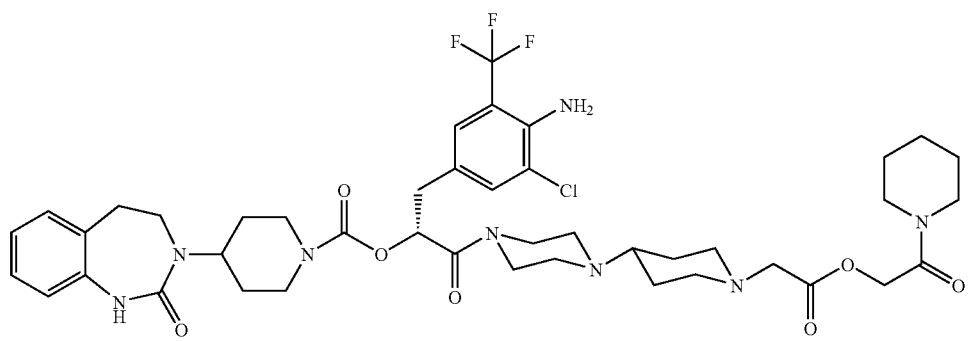 |

| No. | Structure |
|---|---|
| (126) | 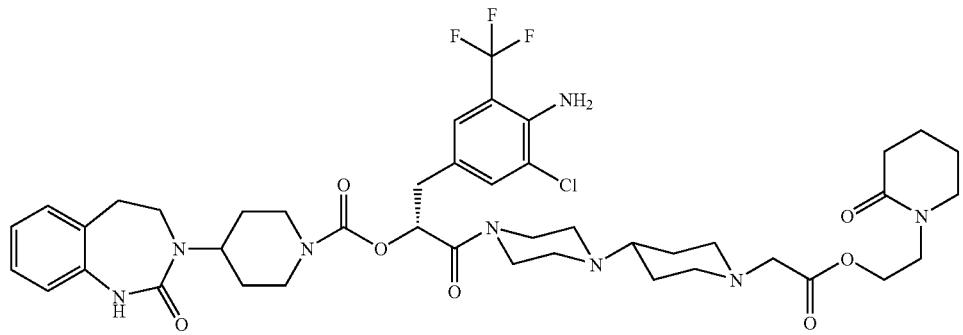 |
| (127) | 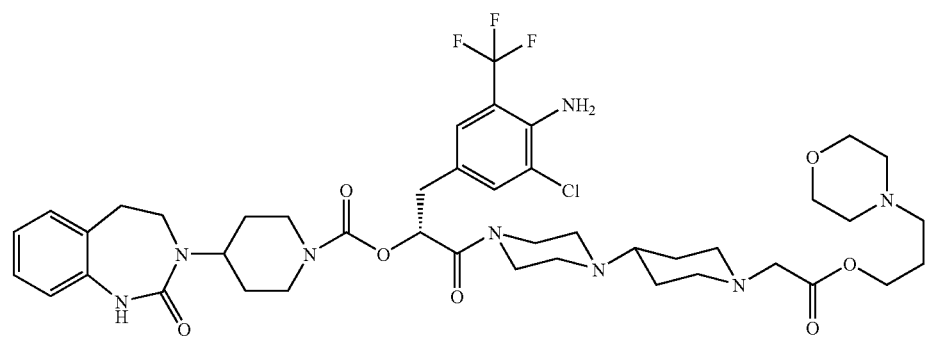 |
| (128) | 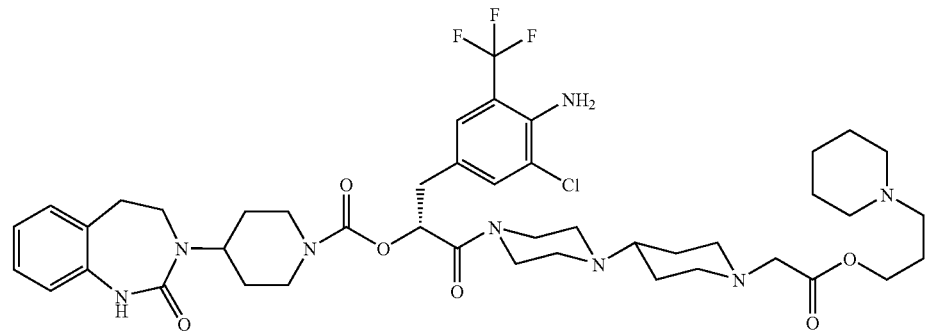 |
| (129) | 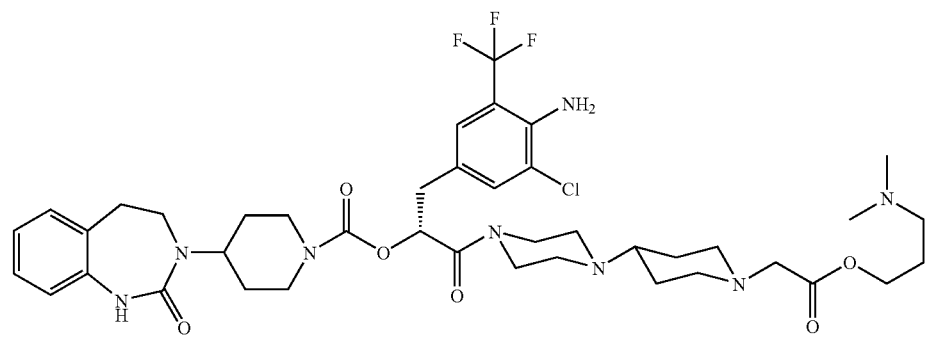 |

-continued

| No. | Structure |
|---|---|
| (130) | 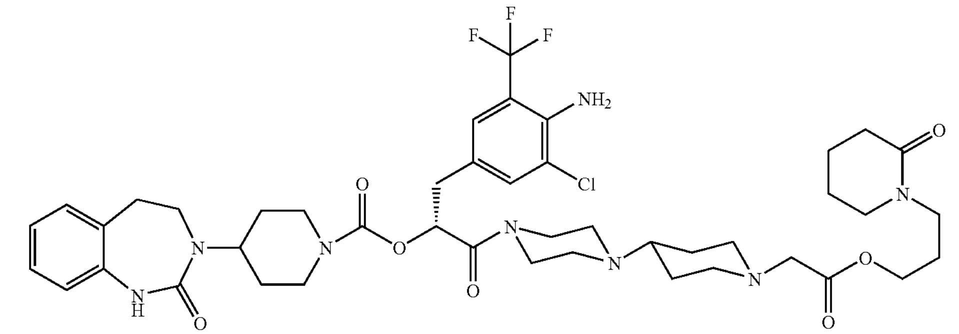 |
| (131) | 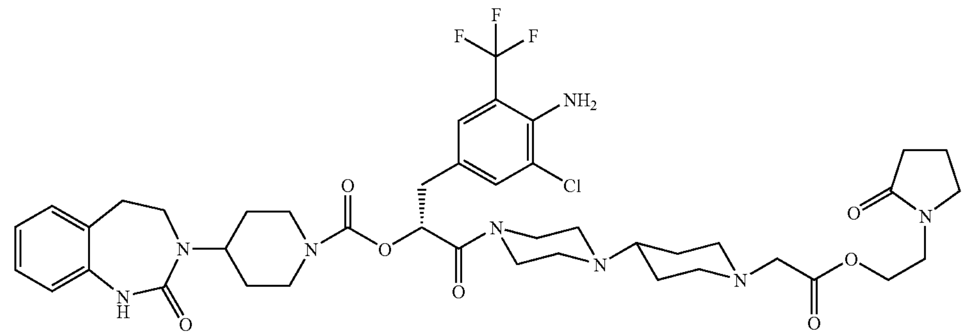 |
| (132) | 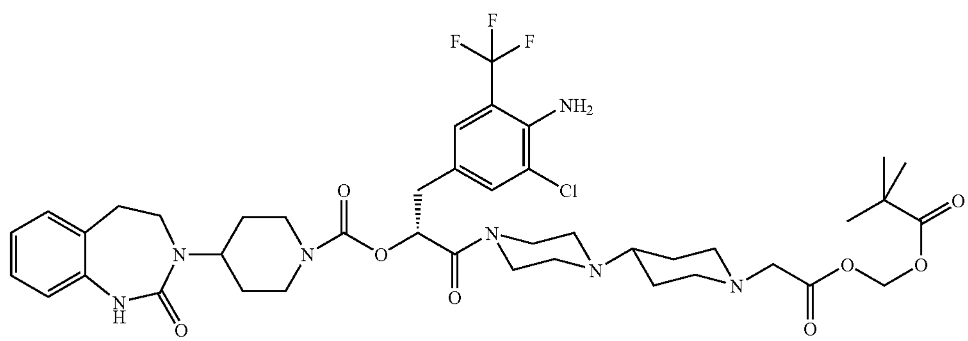 |
| (133) | 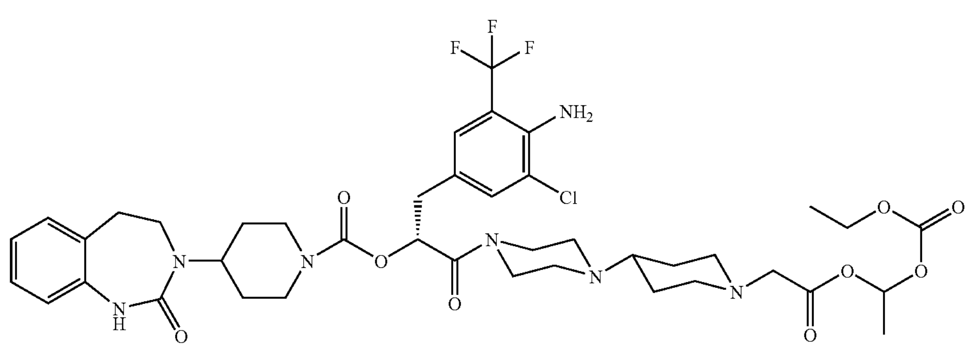 |

| No. | Structure |
|---|---|
| (134) | 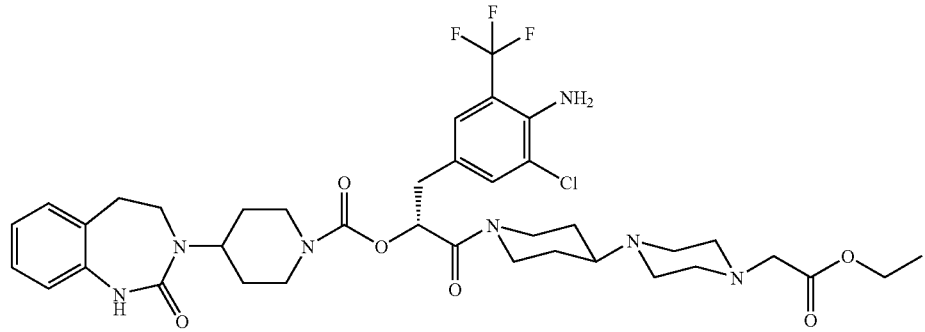 |
| (135) | 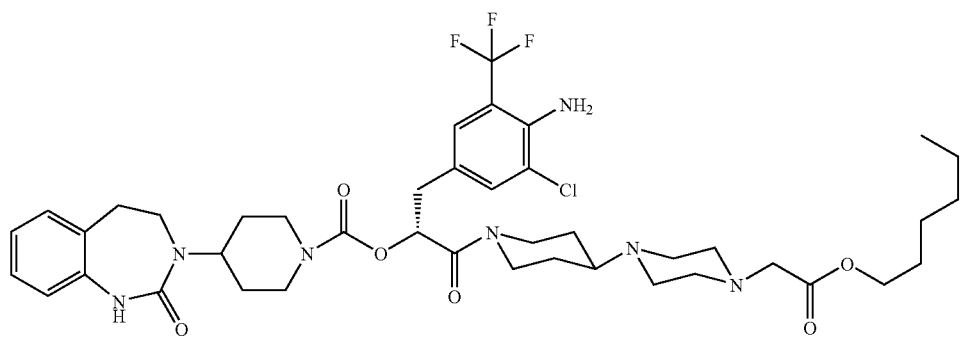 |
| (136) | 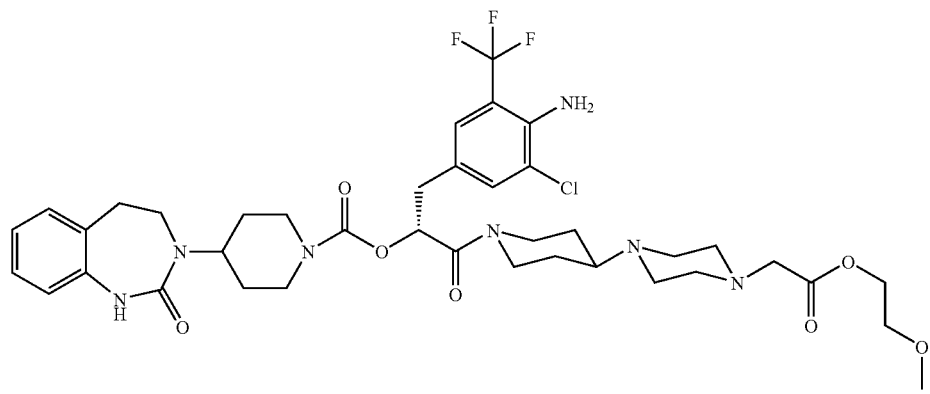 |
| (137) | 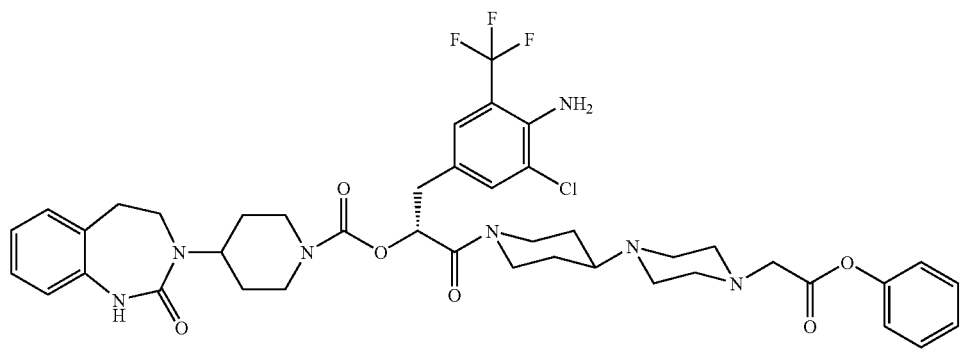 |

| No. | Structure |
|---|---|
| (138) | 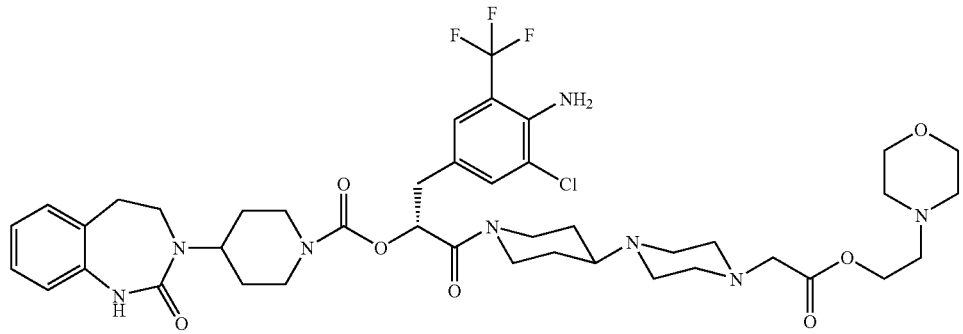 |
| (139) | 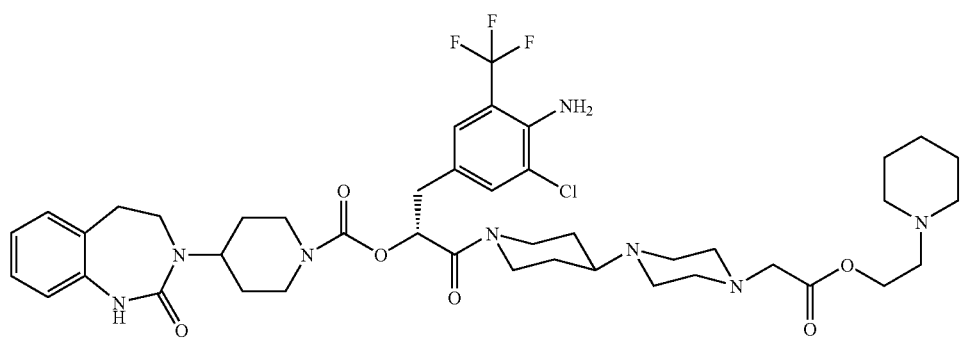 |
| (140) | 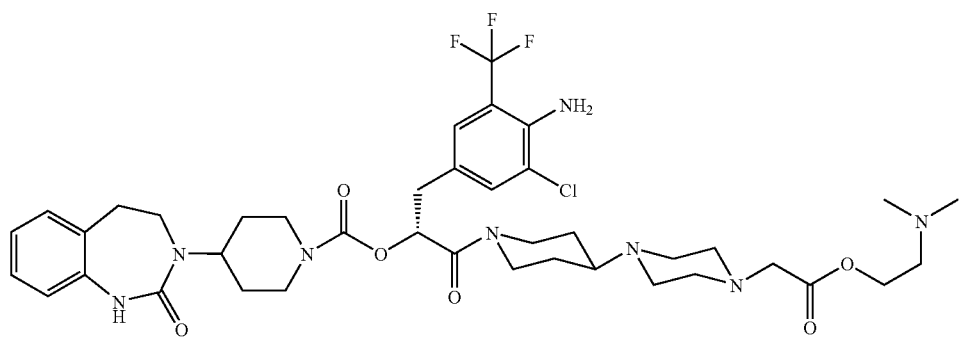 |
| (141) | 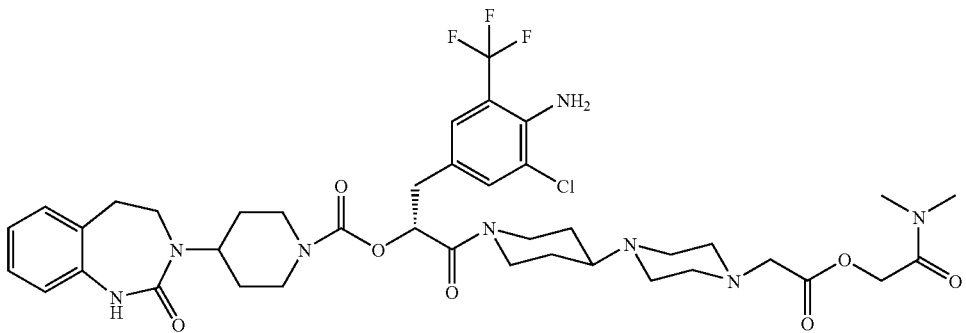 |

| No. | Structure |
|---|---|
| (142) | 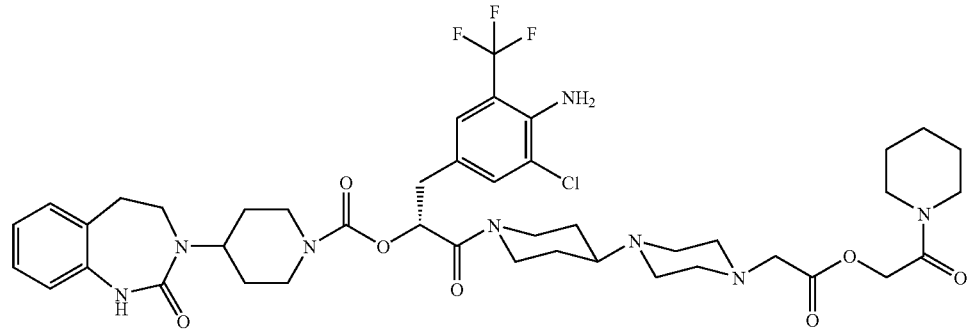 |
| (143) | 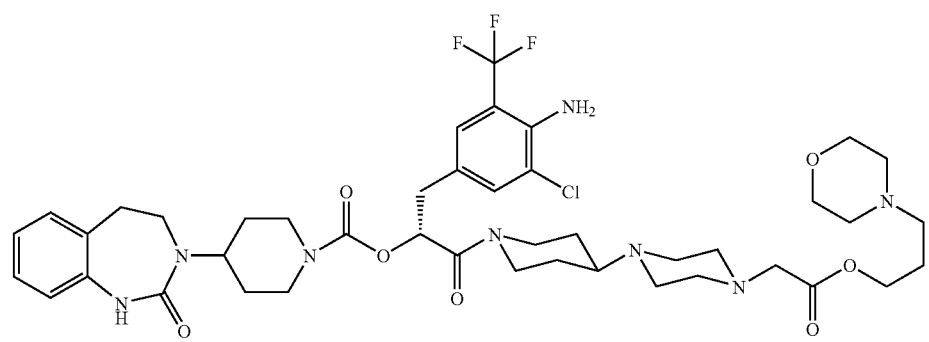 |
| (144) | 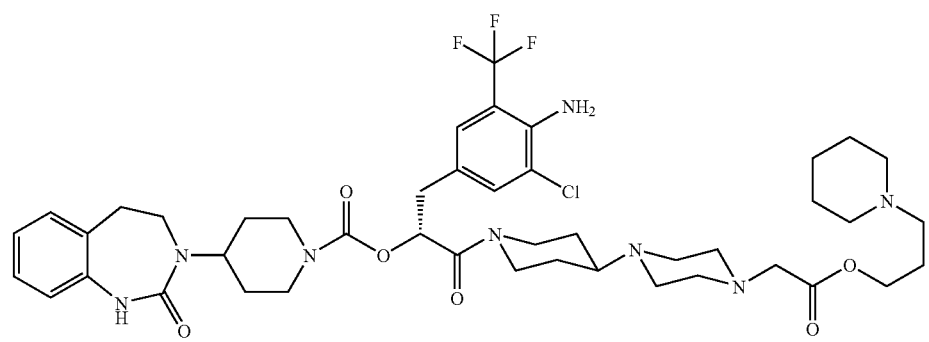 |
| (145) | 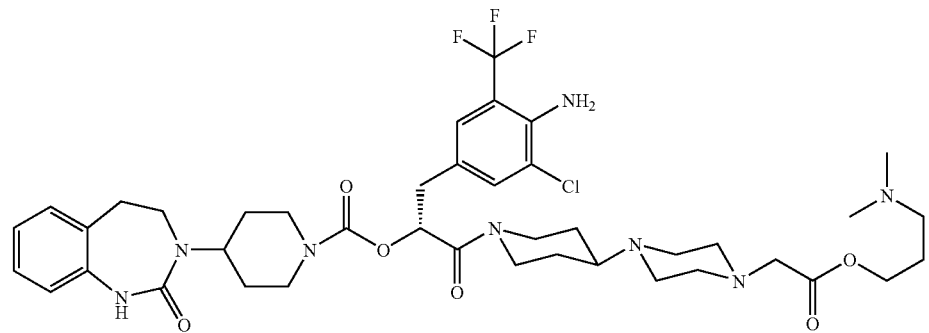 |

| No. | Structure |
|---|---|
| (146) | 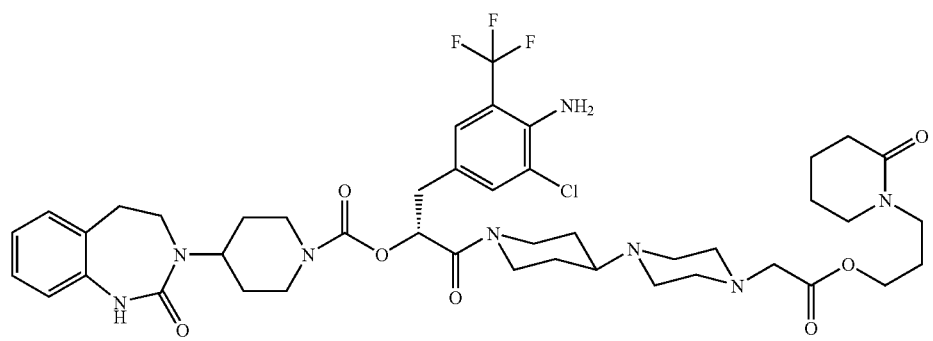 |
| (147) | 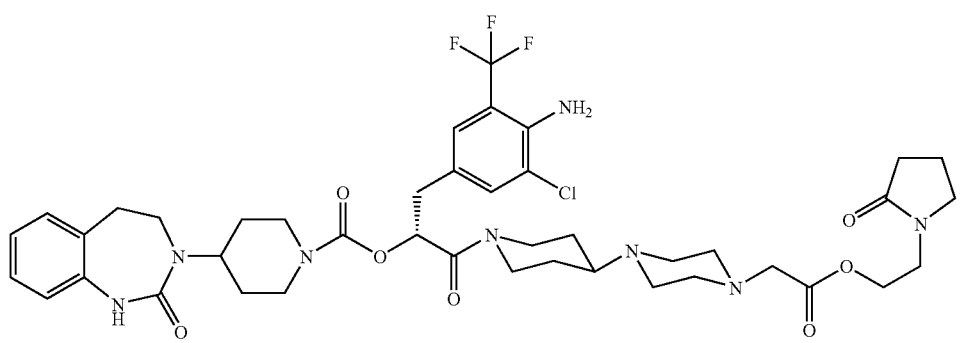 |
| (148) | 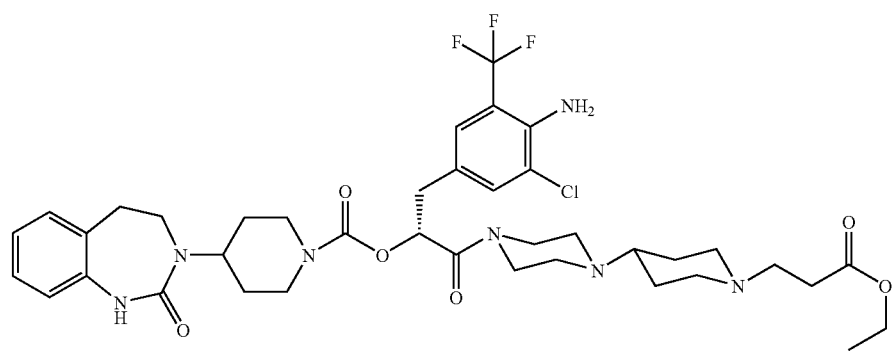 |
| (149) | 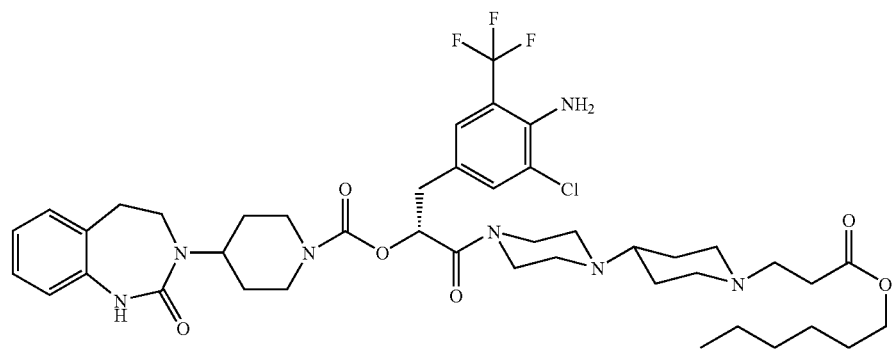 |

| No. | Structure |
|---|---|
| (150) | 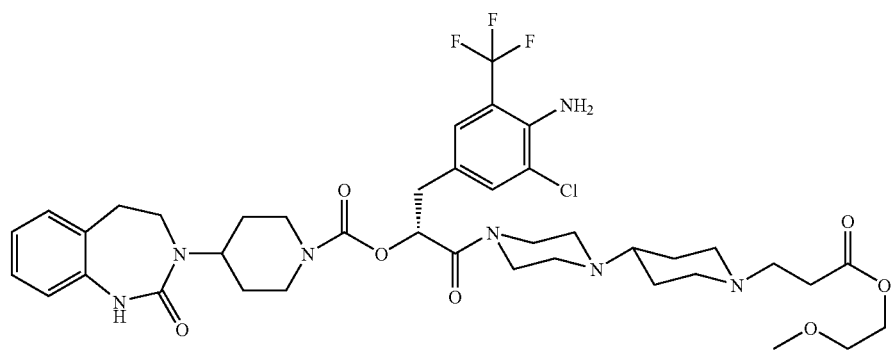 |
| (151) | 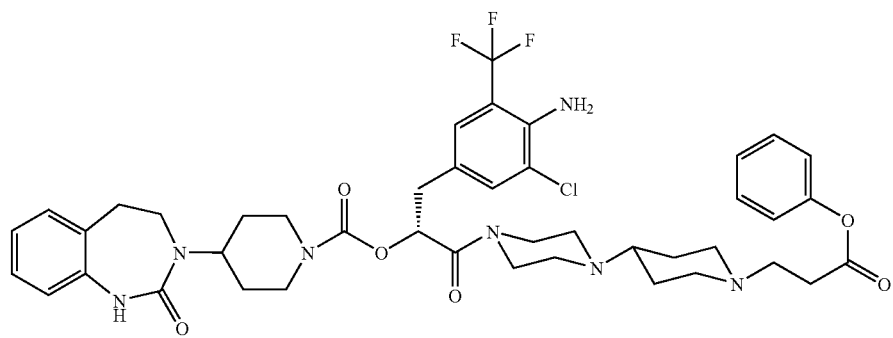 |
| (152) | 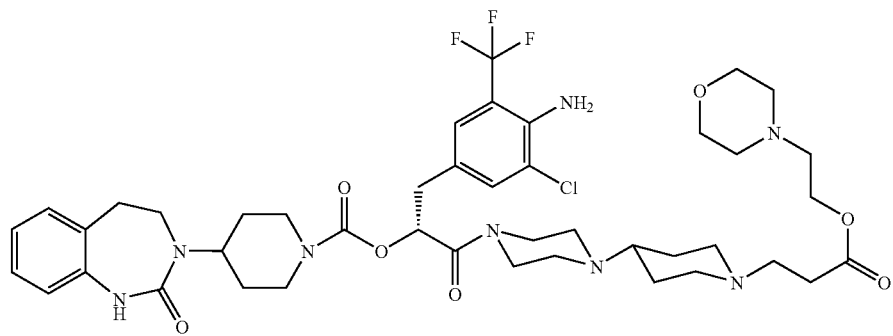 |
| (153) | 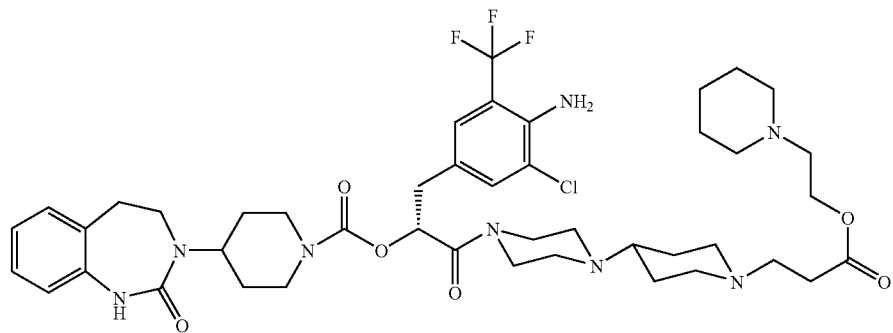 |

| No. | Structure |
|---|---|
| (154) | 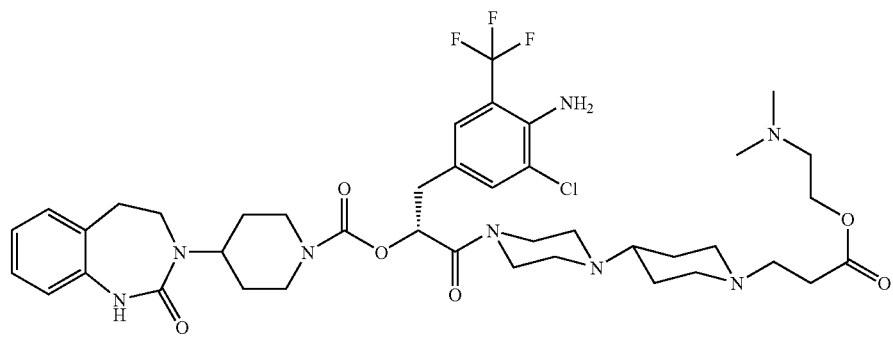 |
| (155) | 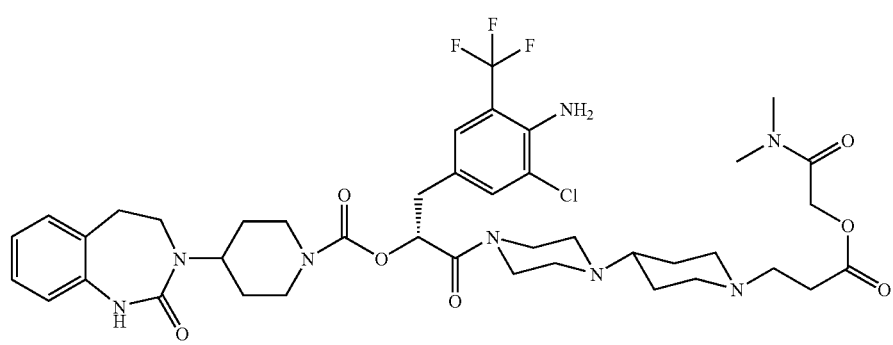 |
| (156) | 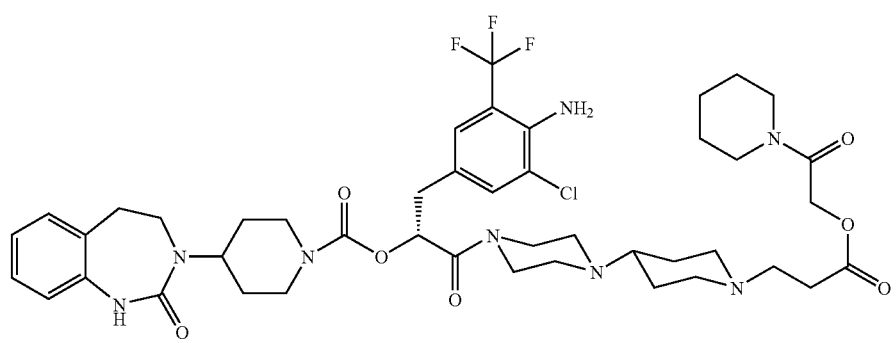 |
| (157) | 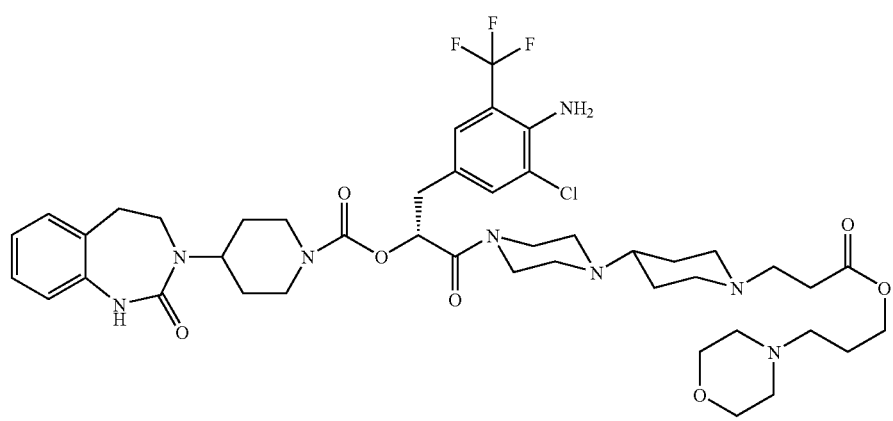 |

-continued

| No. | Structure |
|---|---|
| (158) | 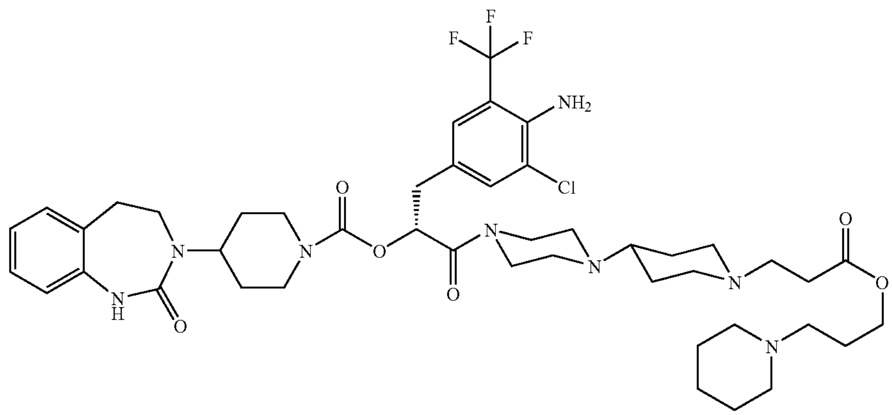 |
| (159) | 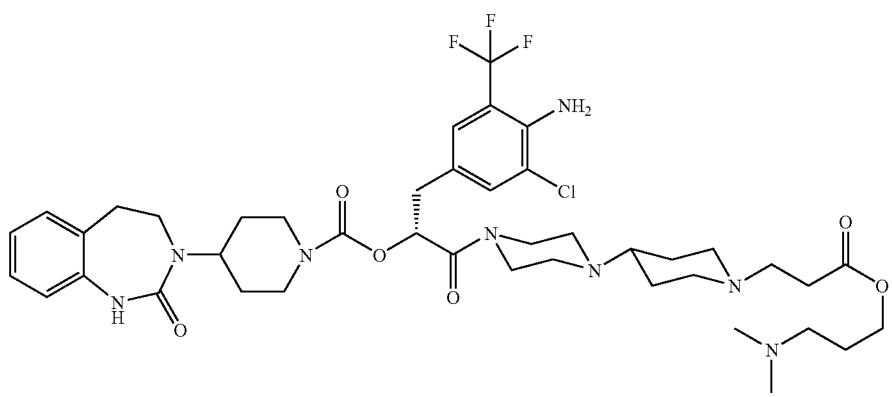 |
| (160) | 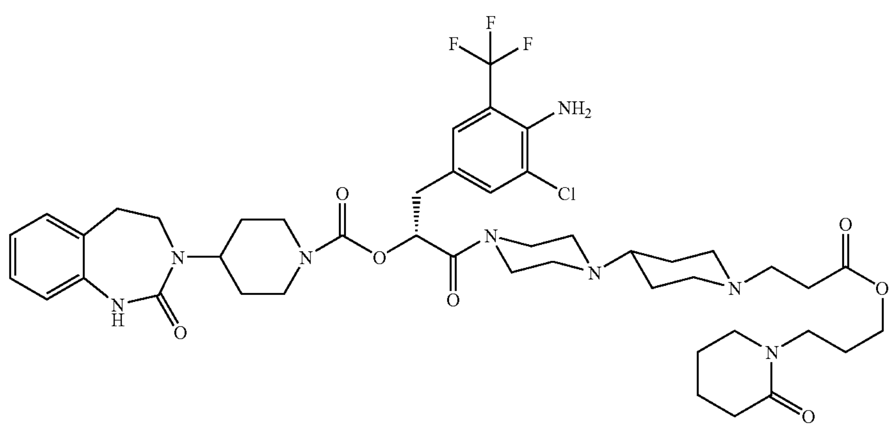 |
| (161) | 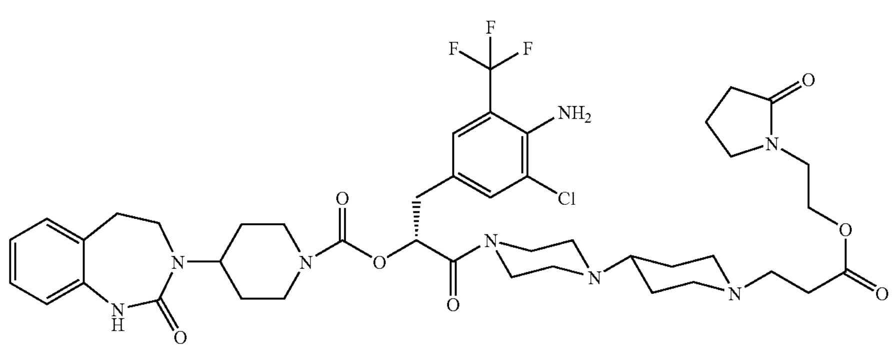 |

| No. | Structure |
|---|---|
| (162) | 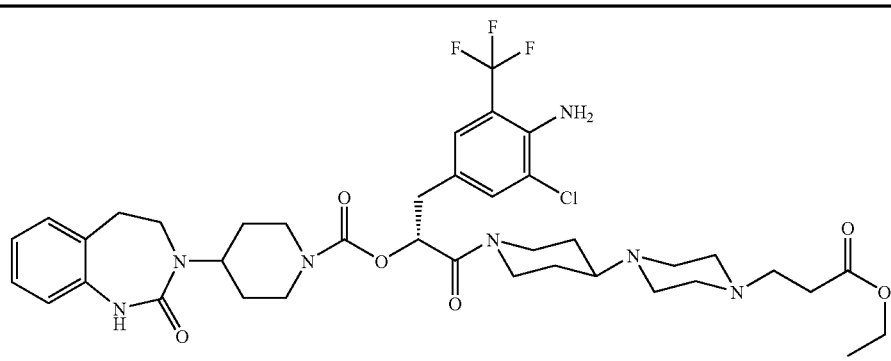 |
| (163) | 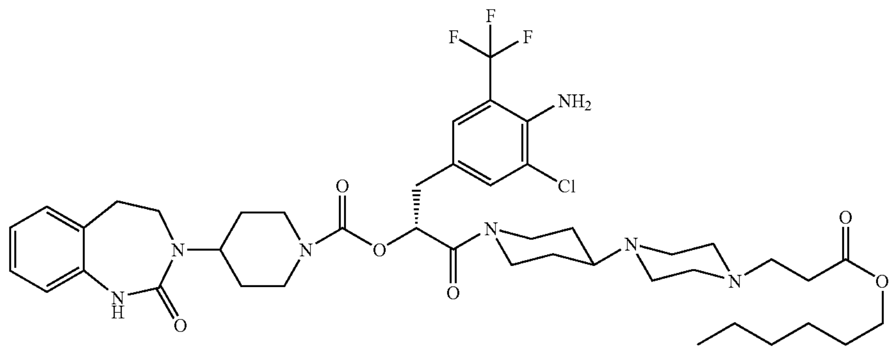 |
| (164) | 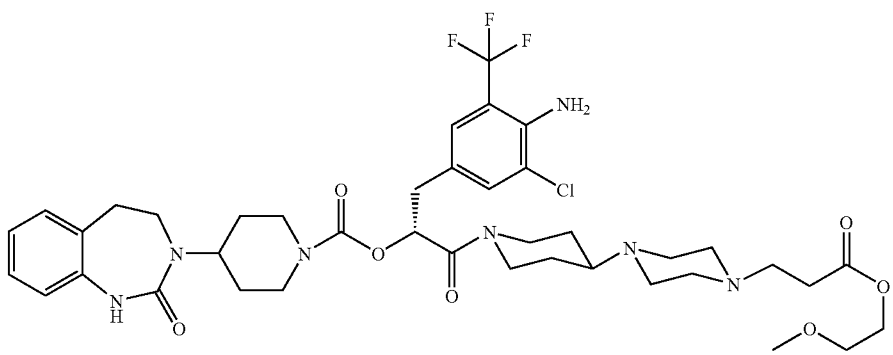 |
| (165) | 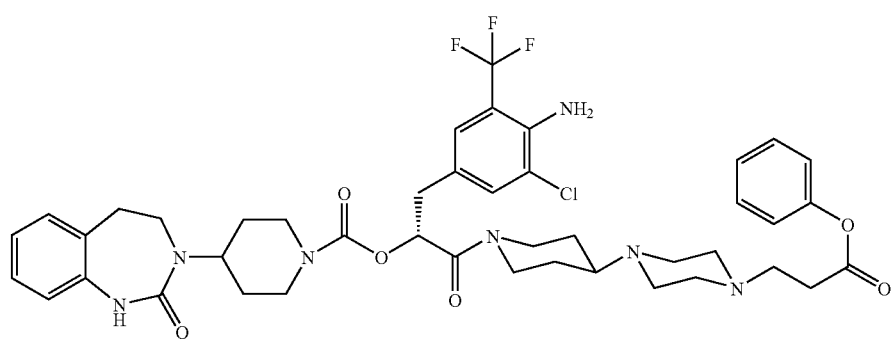 |

-continued
| No. | Structure |
|---|---|
| (166) | 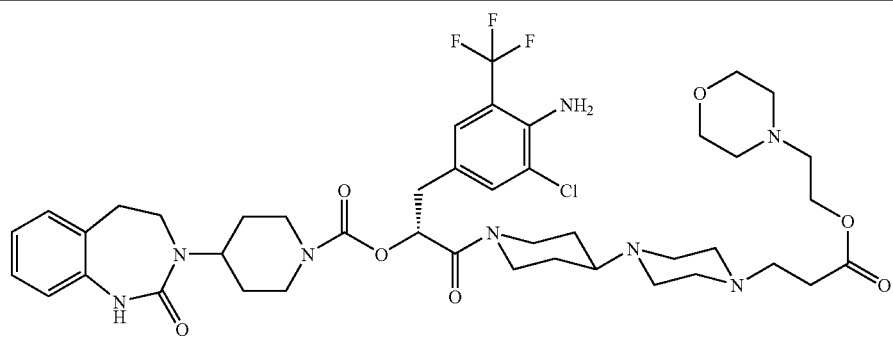 |
| (167) | 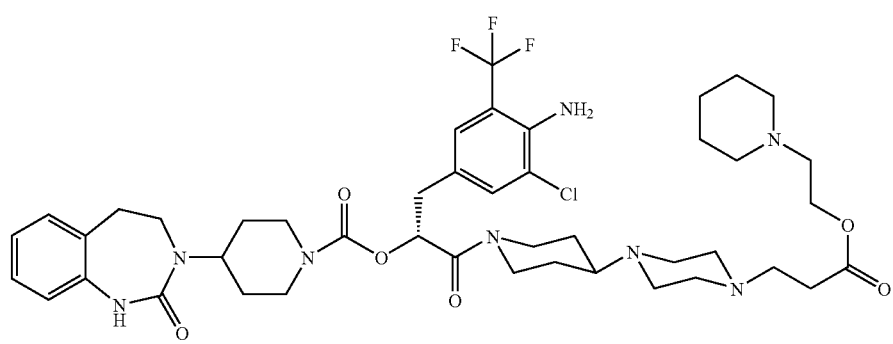 |
| (168) | 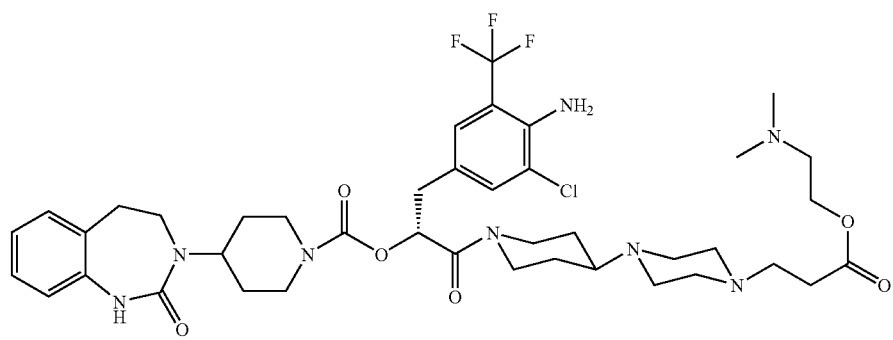 |
| (169) | 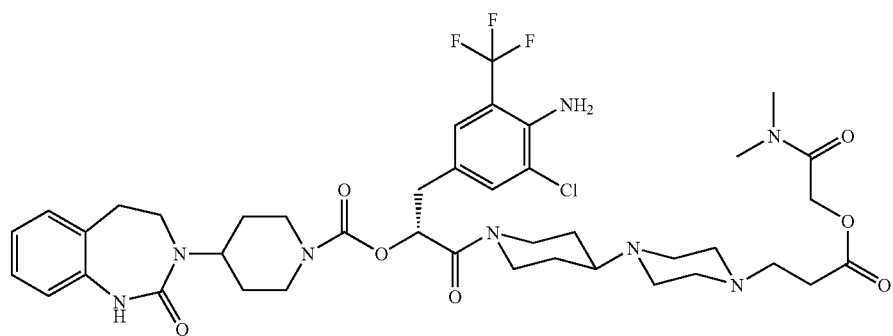 |

| No. | Structure |
|---|---|
| (170) | 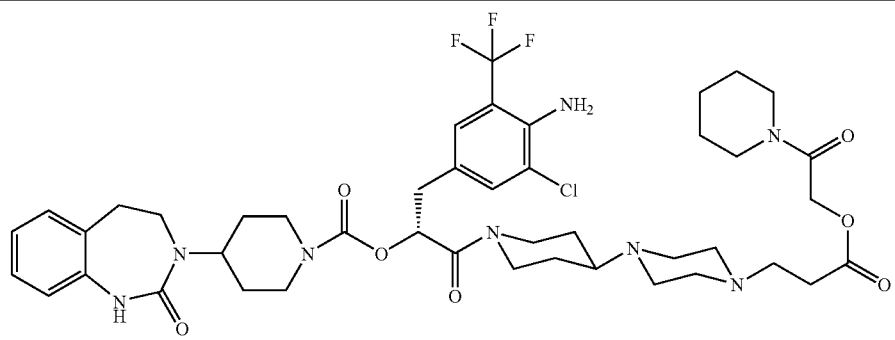 |
| (171) | 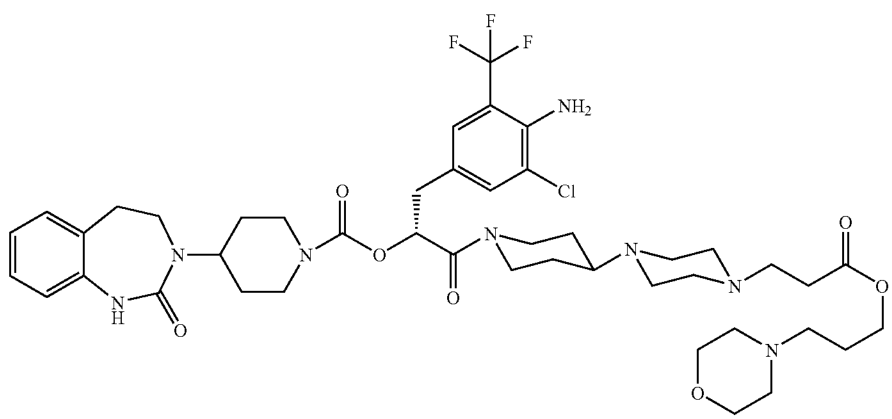 |
| (172) | 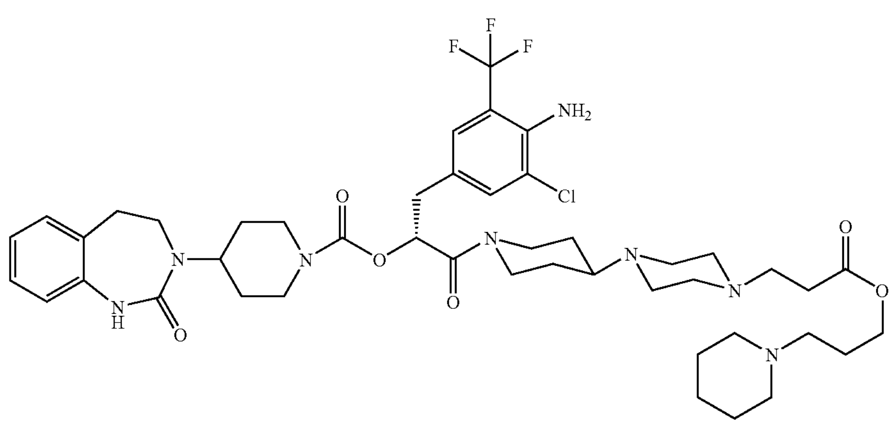 |

| No. | Structure |
|---|---|
| (173) | 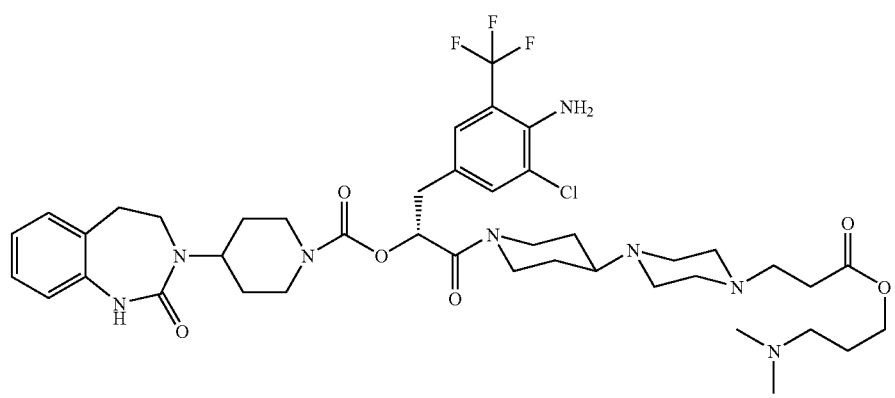 |
| (174) | 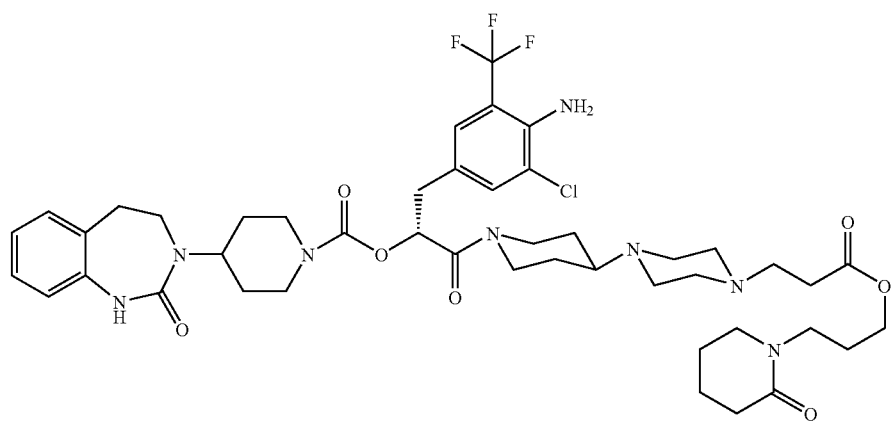 |
| (175) | 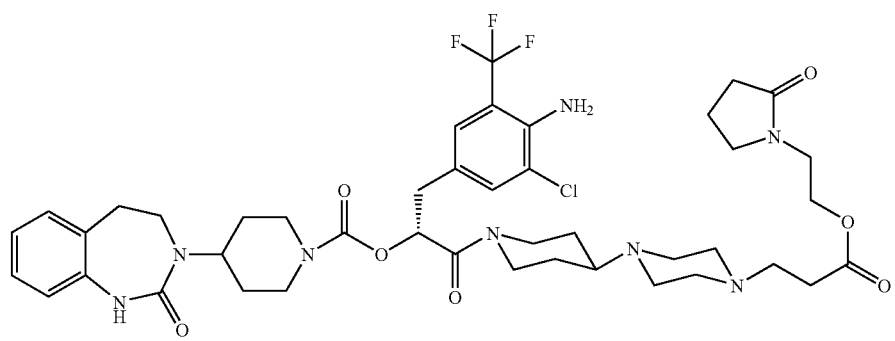 |
| (176) | 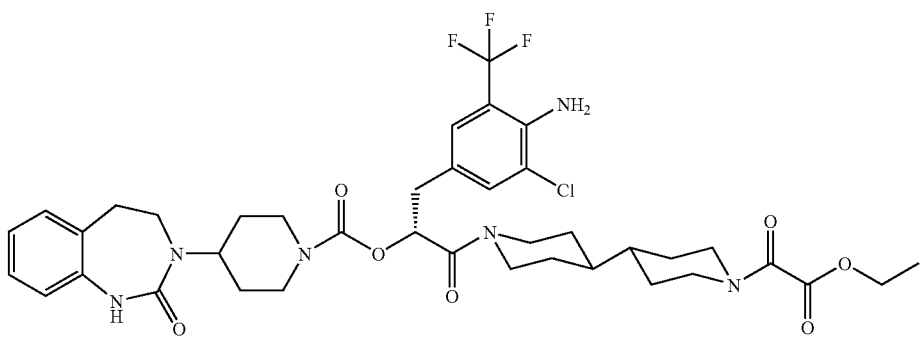 |

| No. | Structure |
|---|---|
| (177) | 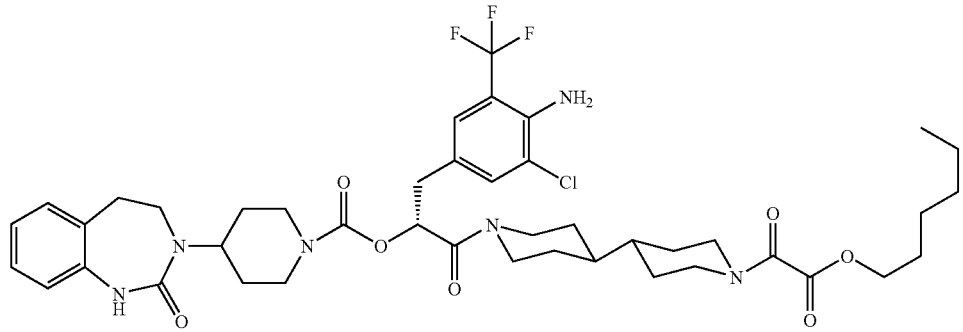 |
| (178) | 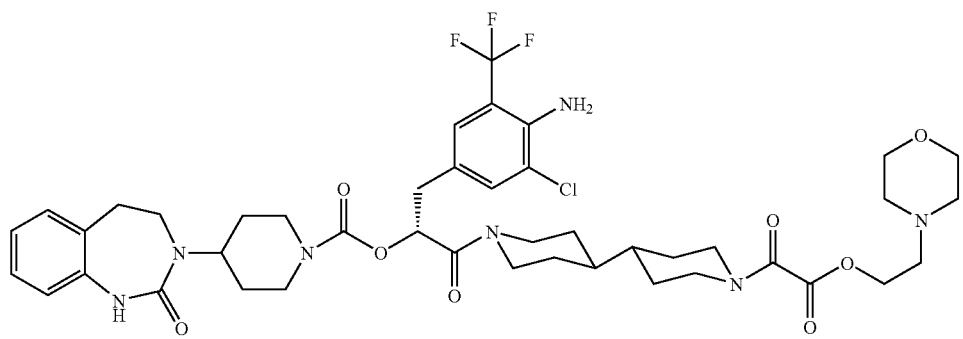 |
| (179) | 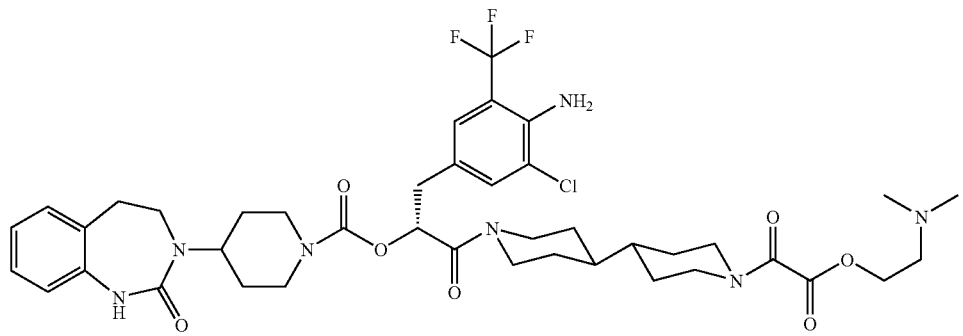 |
| (180) | 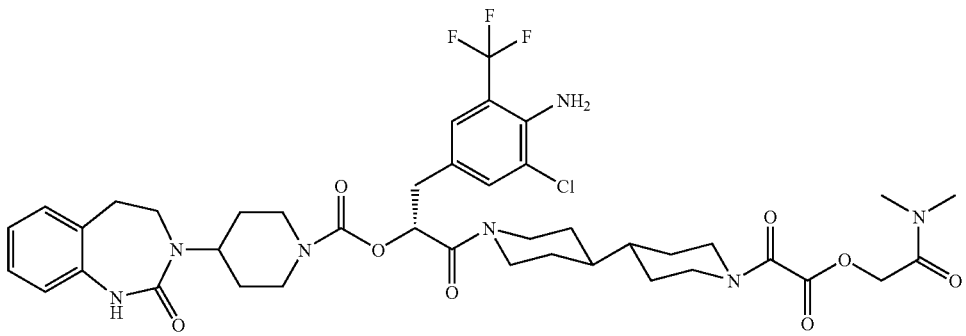 |

| No. | Structure |
|---|---|
| (181) | 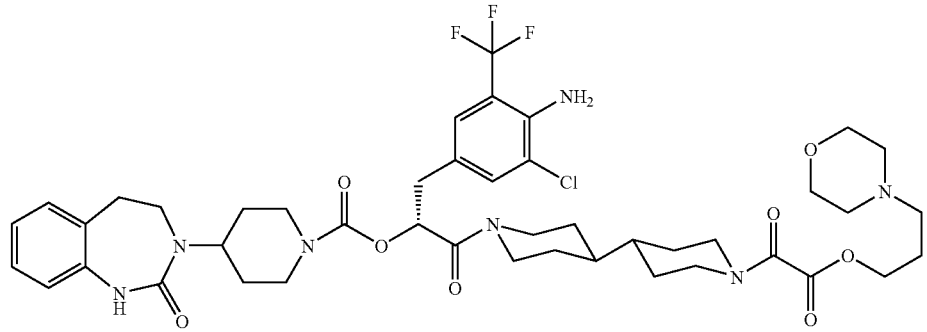 |
| (182) | 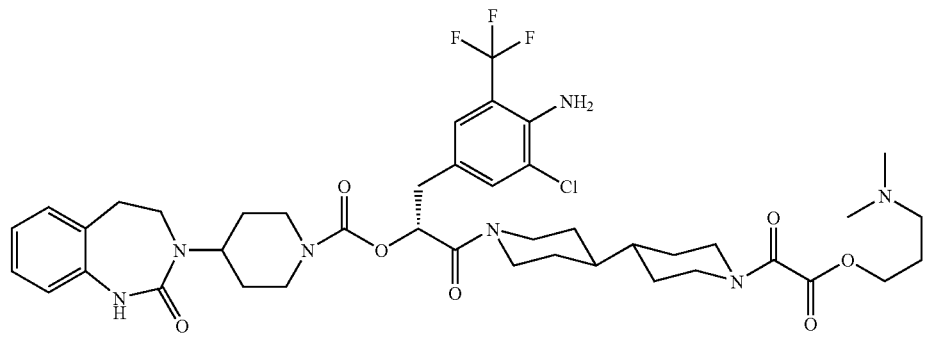 |
| (183) | 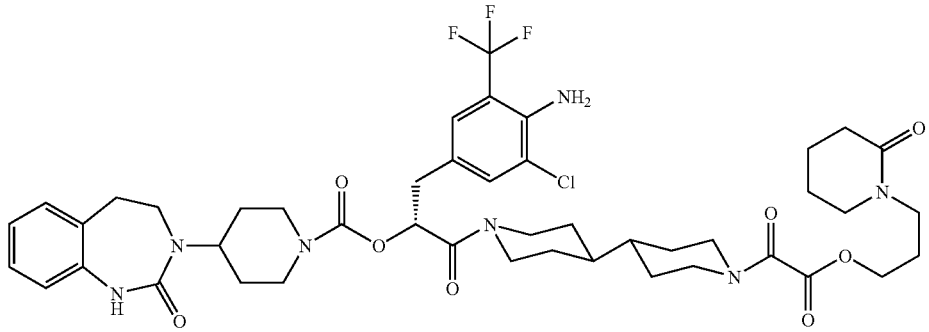 |
| (184) | 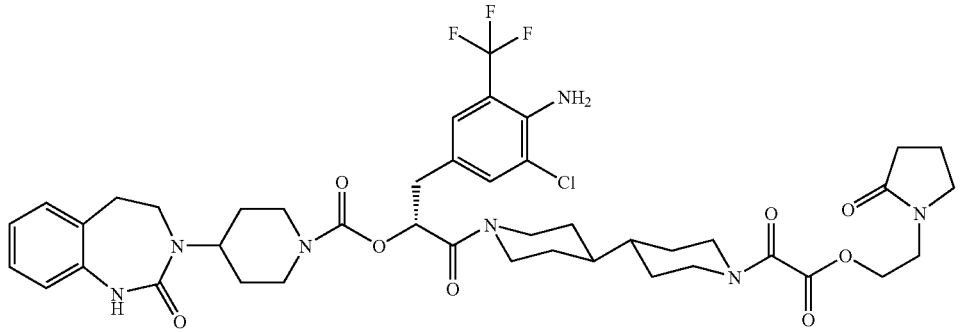 |

| No. | Structure |
|---|---|
| (185) | 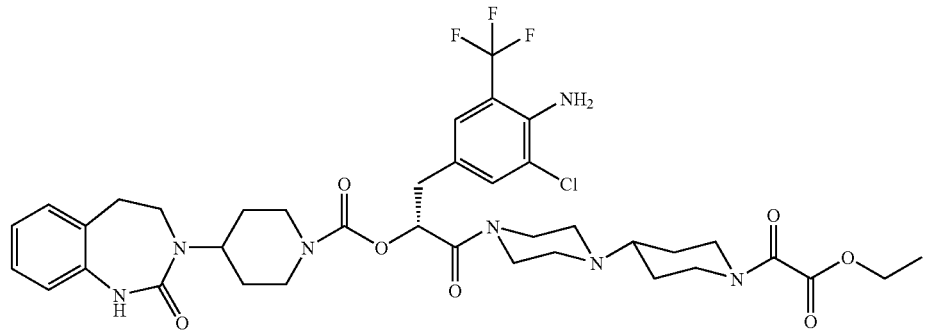 |
| (186) | 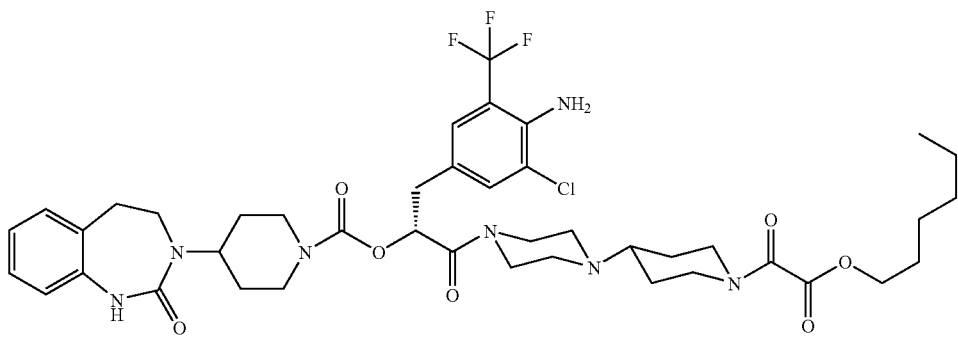 |
| (187) | 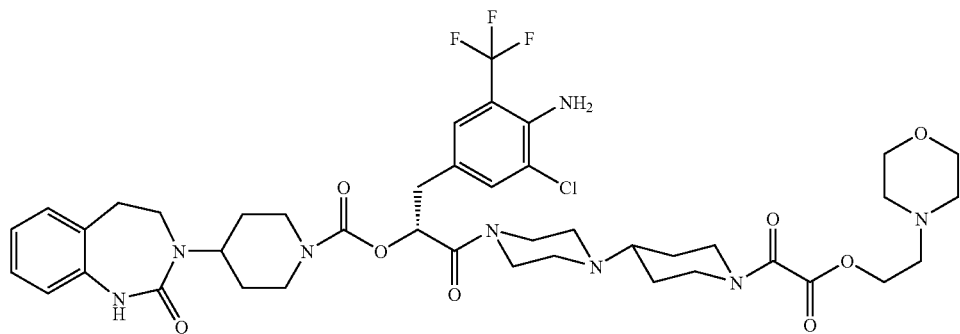 |
| (188) | 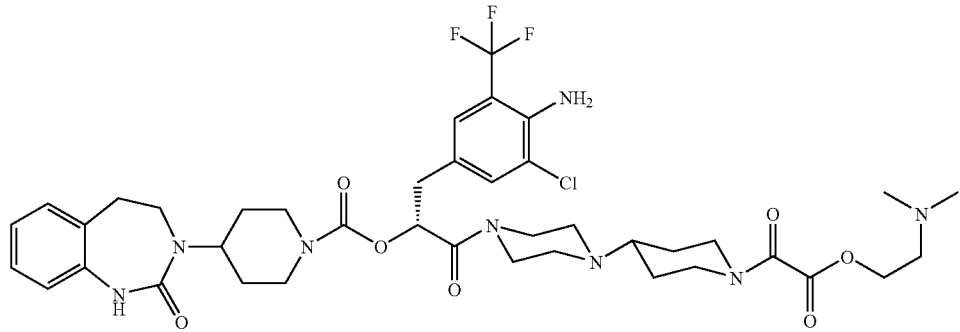 |

-continued
| No. | Structure |
|---|---|
| (189) | 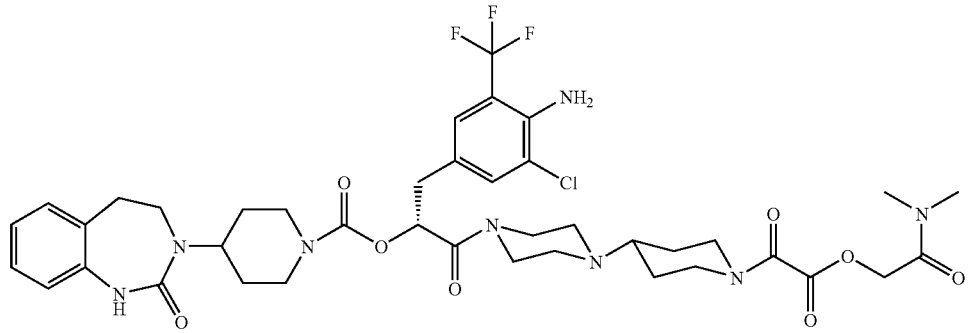 |
| (190) | 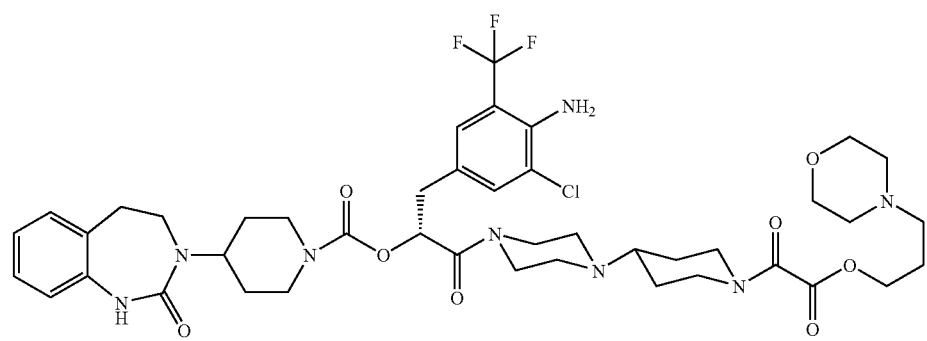 |
| (191) | 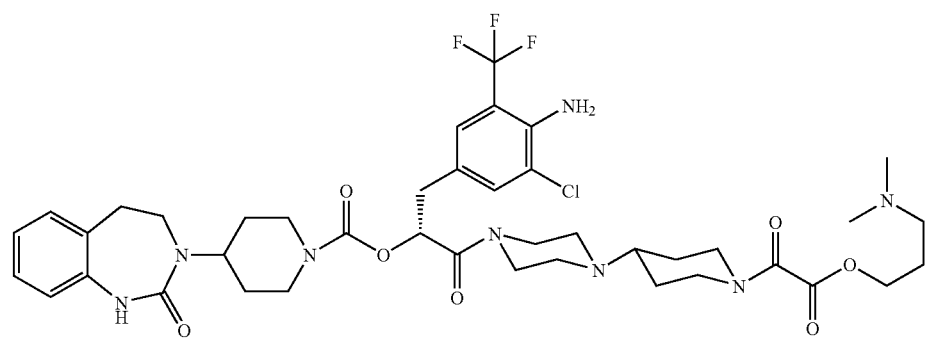 |
| (192) | 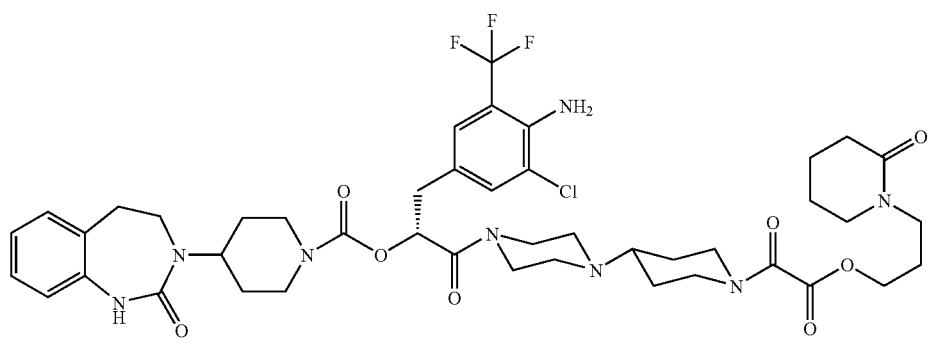 |

-continued
| No. | Structure |
|---|---|
| (193) | 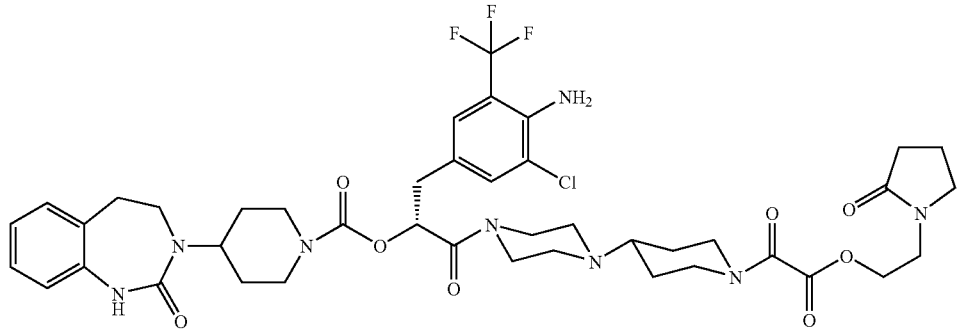 |
| (194) | 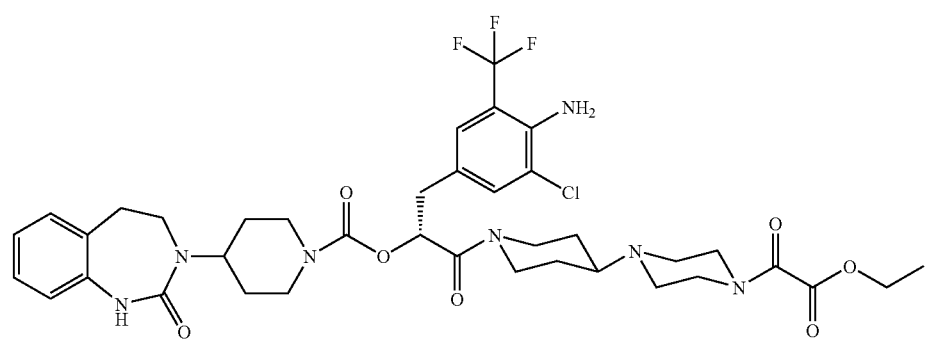 |
| (195) | 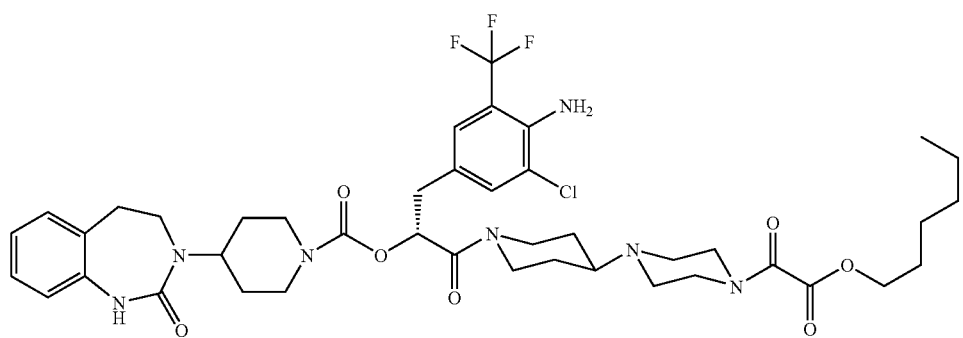 |
| (196) | 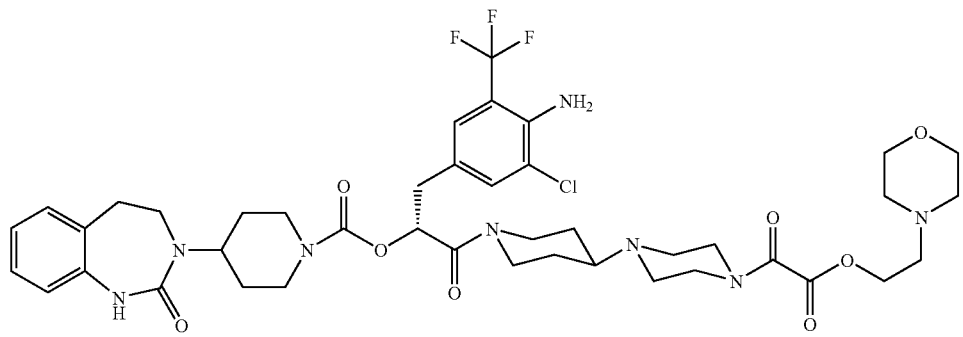 |

| No. | Structure |
|---|---|
| (197) | 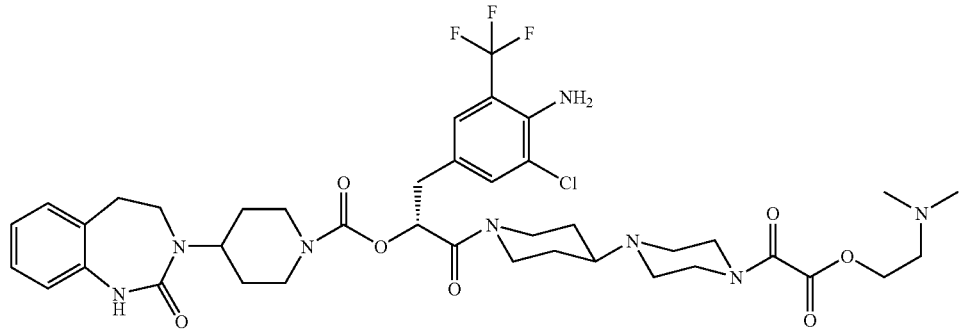 |
| (198) | 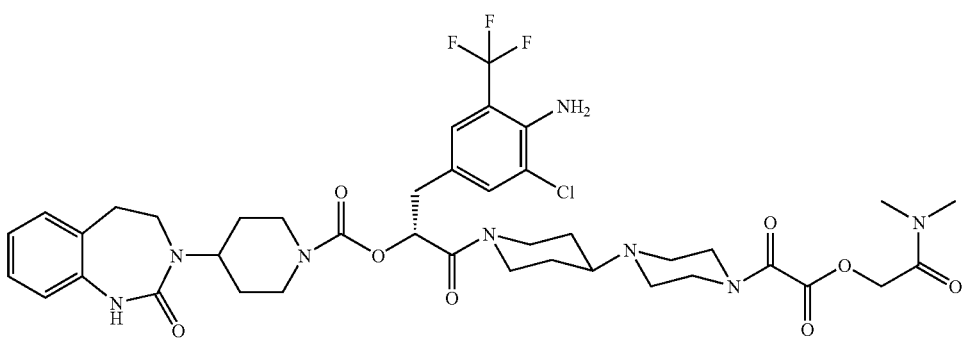 |
| (199) | 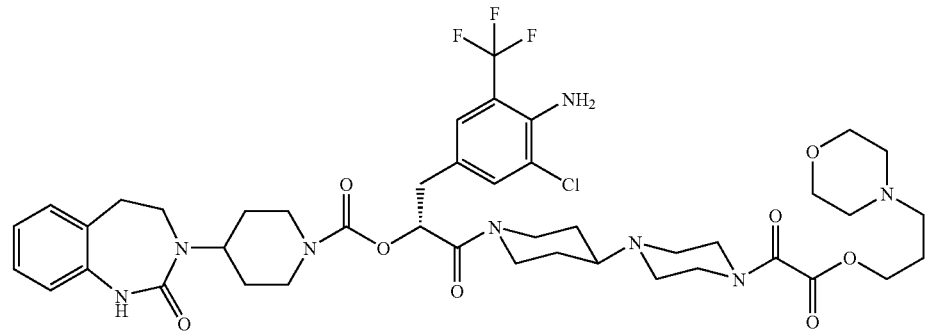 |
| (200) | 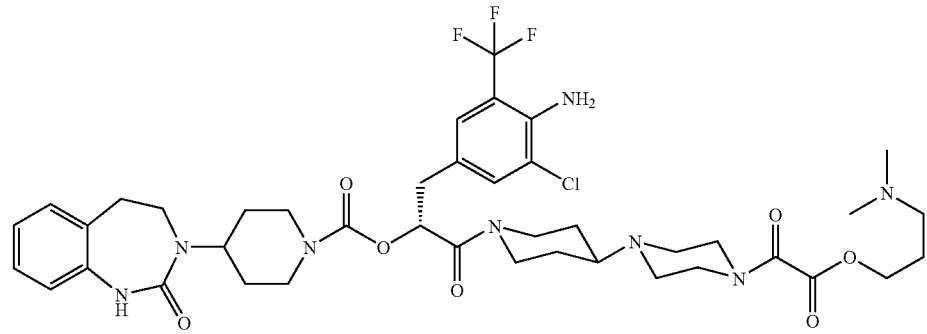 |

| No. | Structure |
|---|---|
| (201) | 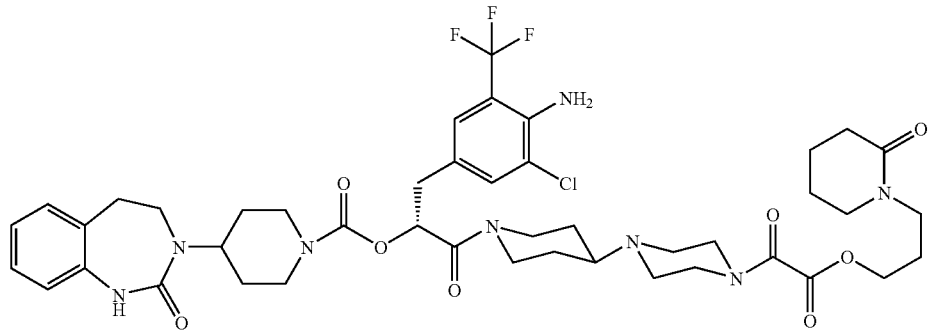 |
| (202) | 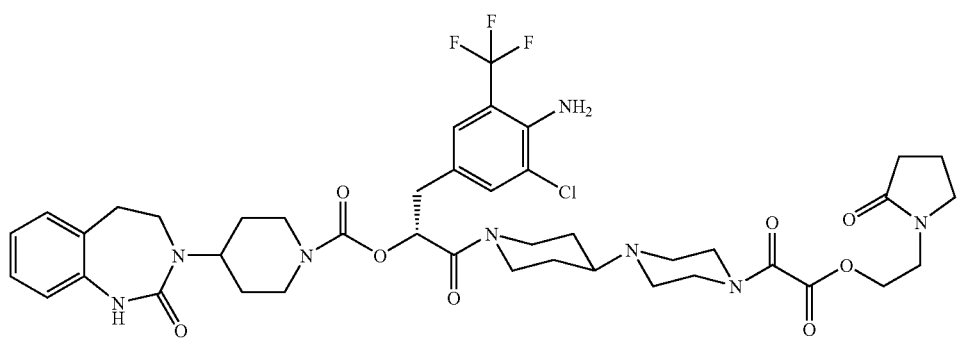 |
| (203) | 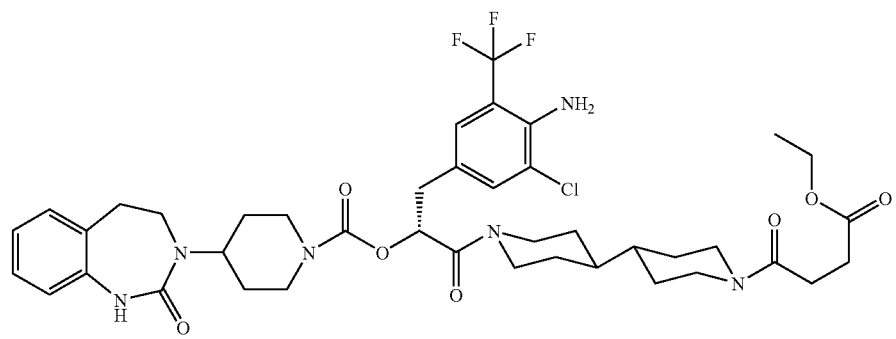 |
| (204) | 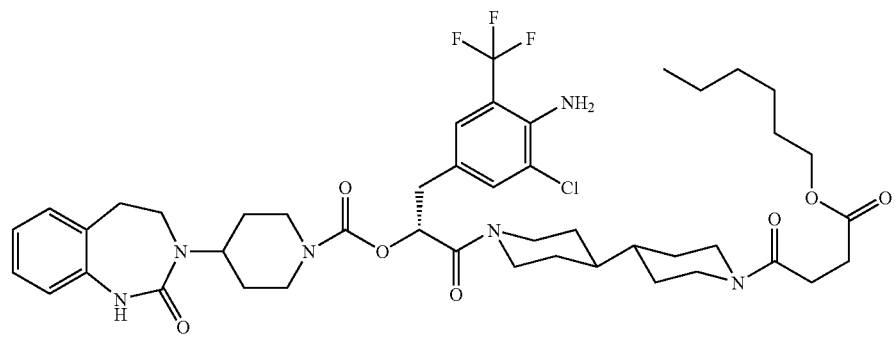 |

| No. | Structure |
|---|---|
| (205) | 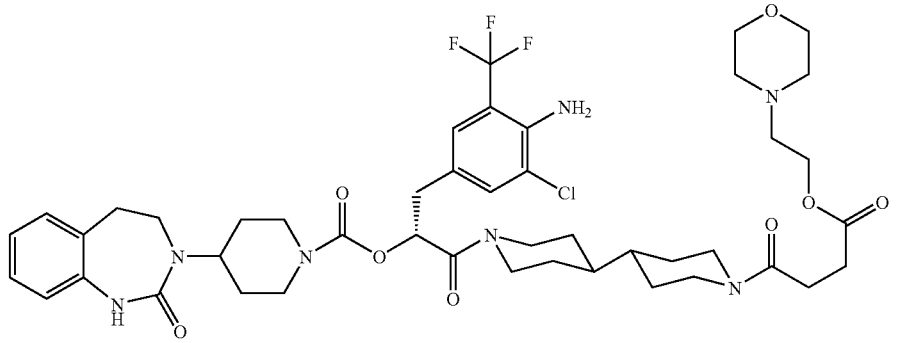 |
| (206) | 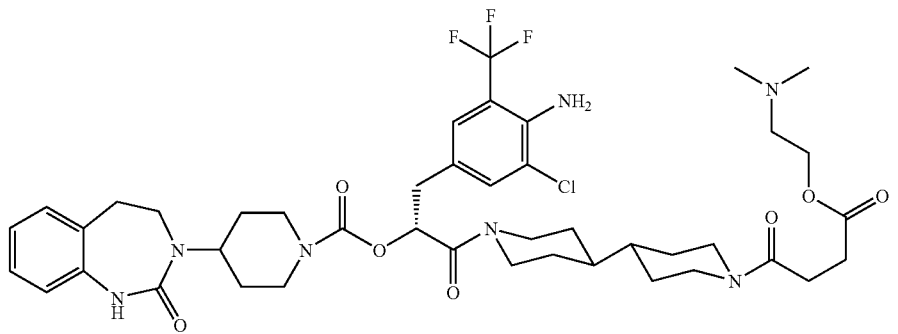 |
| (207) | 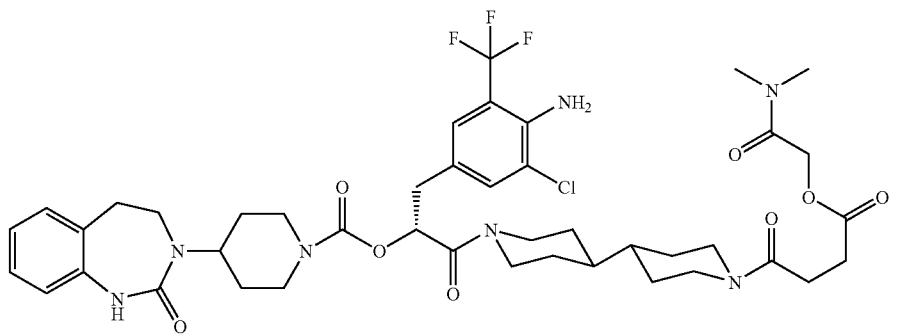 |
| (208) | 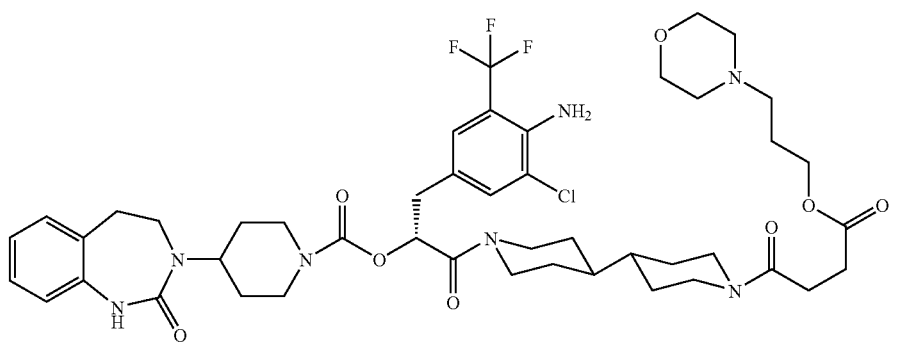 |

| No. | Structure |
|---|---|
| (209) | 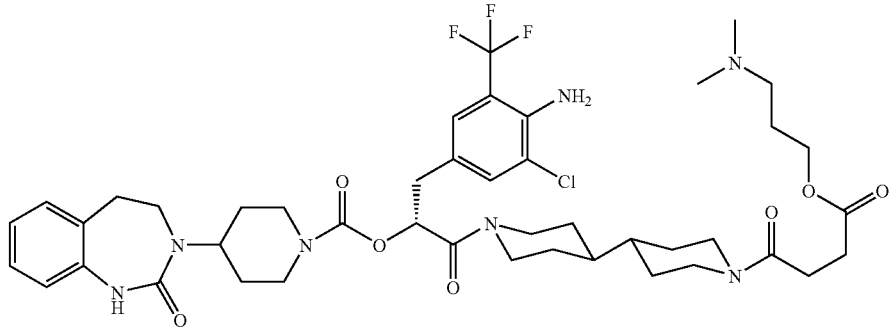 |
| (210) | 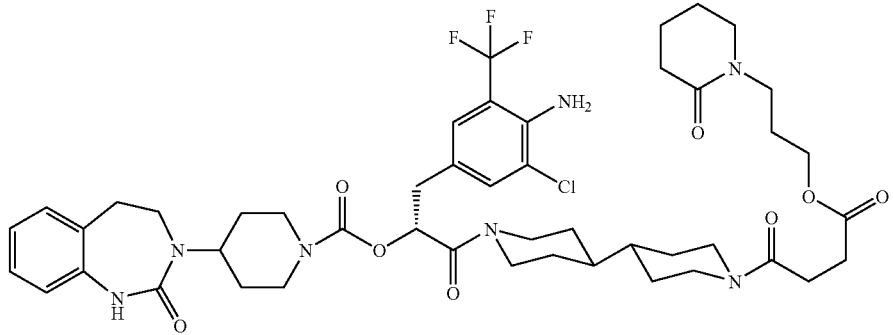 |
| (211) | 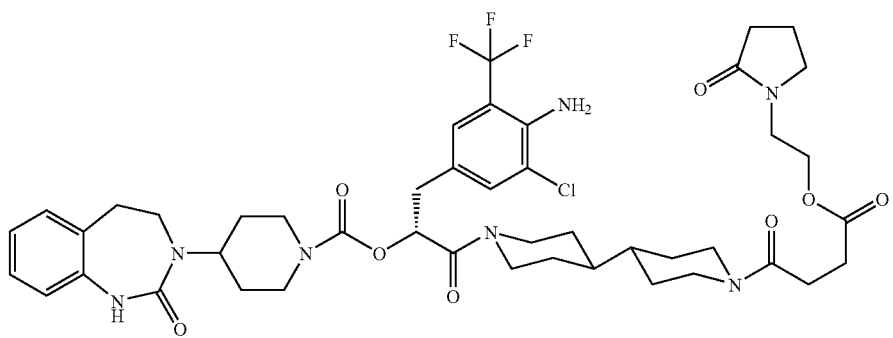 |
| (212) | 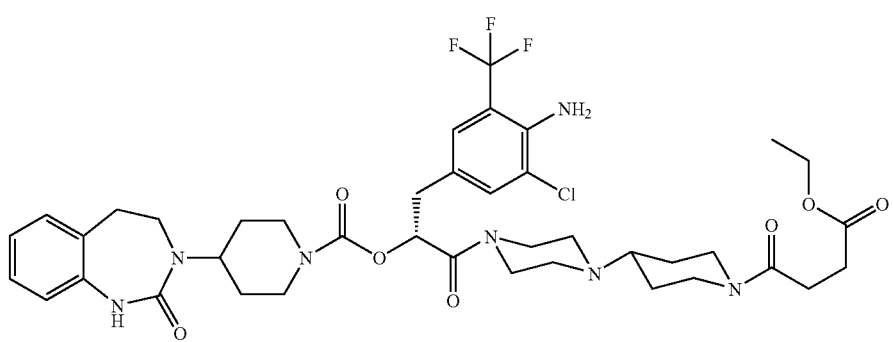 |

| No. | Structure |
|---|---|
| (213) | 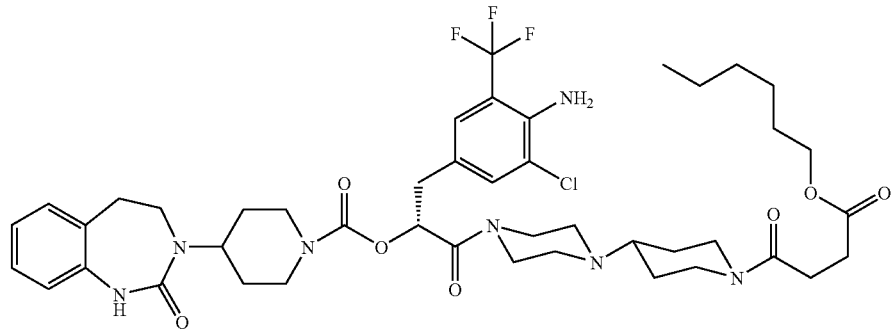 |
| (214) | 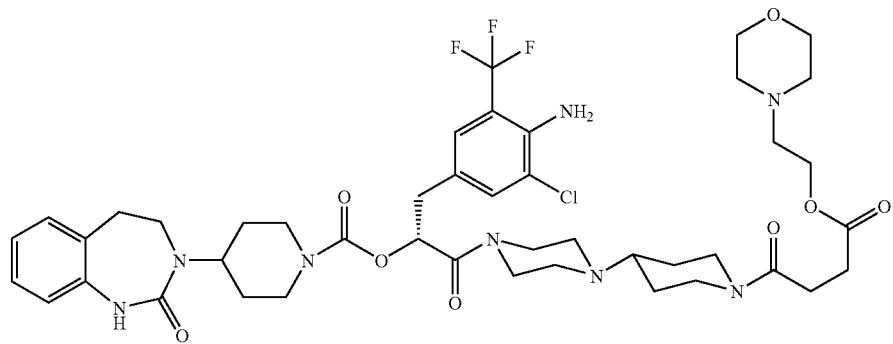 |
| (215) | 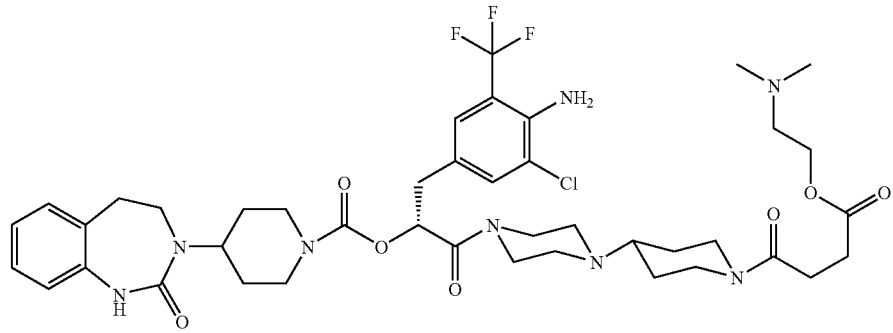 |
| (216) | 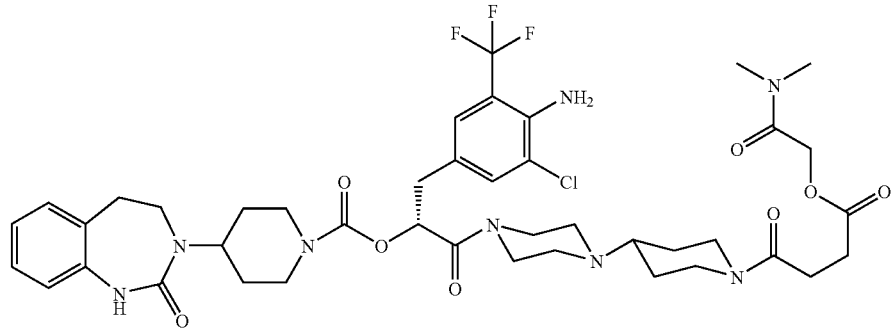 |

| No. | Structure |
|---|---|
| (217) | 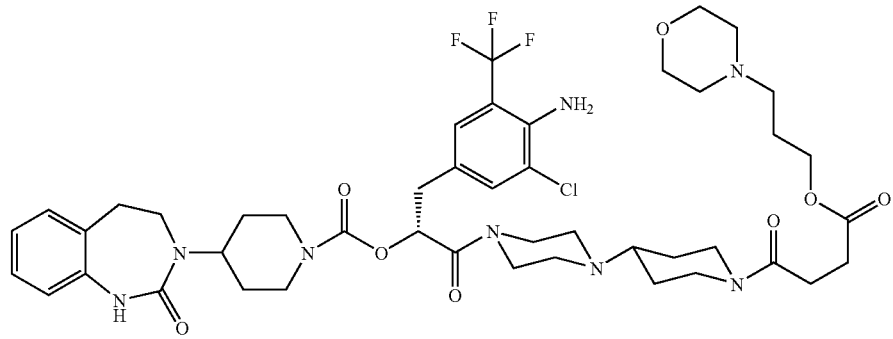 |
| (218) | 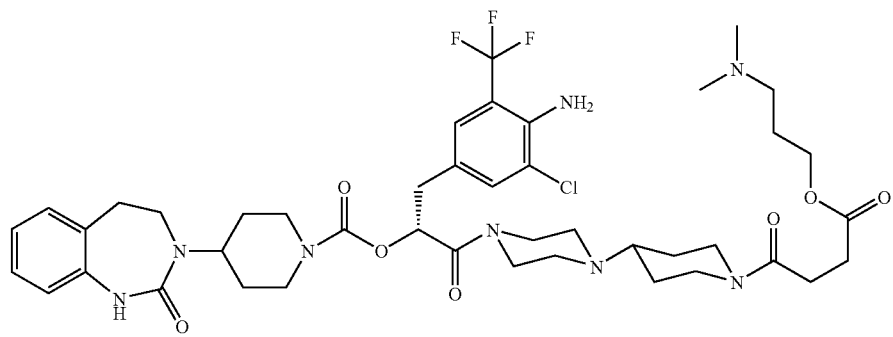 |
| (219) | 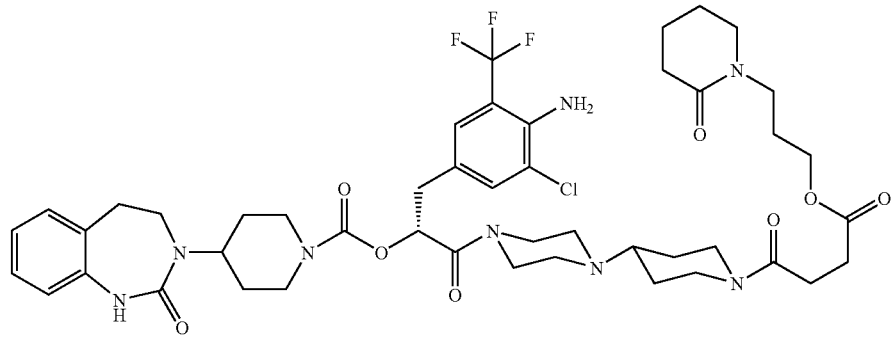 |
| (220) | 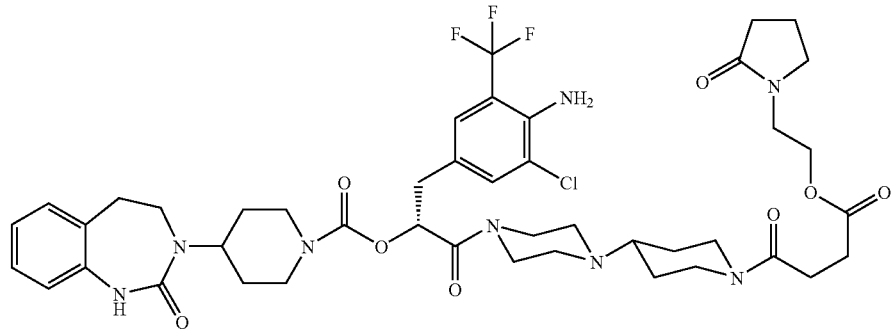 |

| No. | Structure |
|---|---|
| (221) | 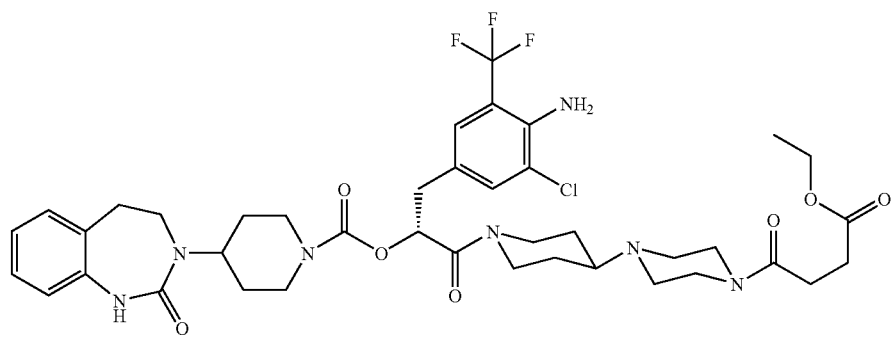 |
| (222) | 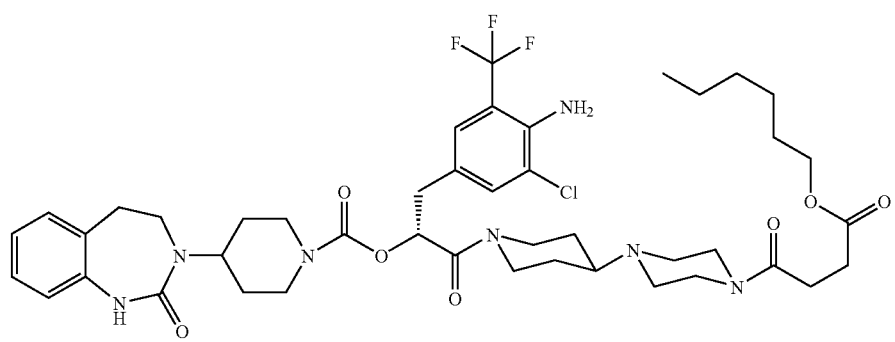 |
| (223) | 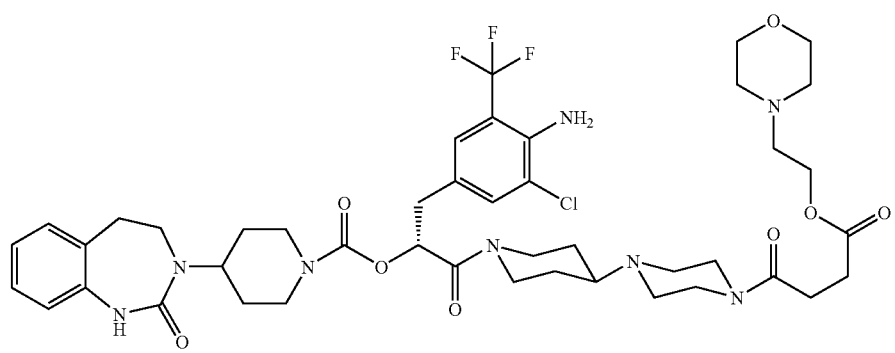 |
| (224) | 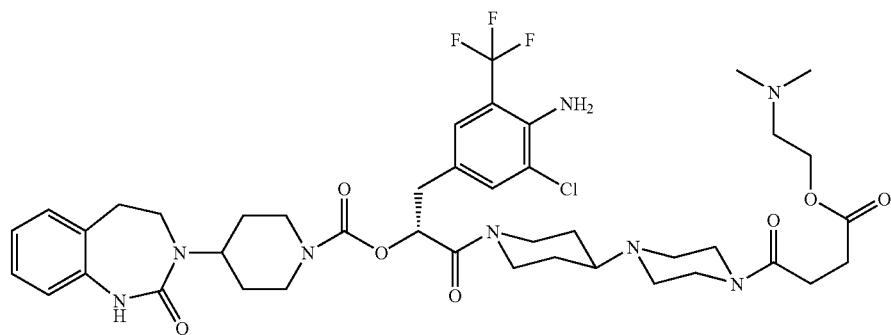 |

| No. | Structure |
|---|---|
| (225) | 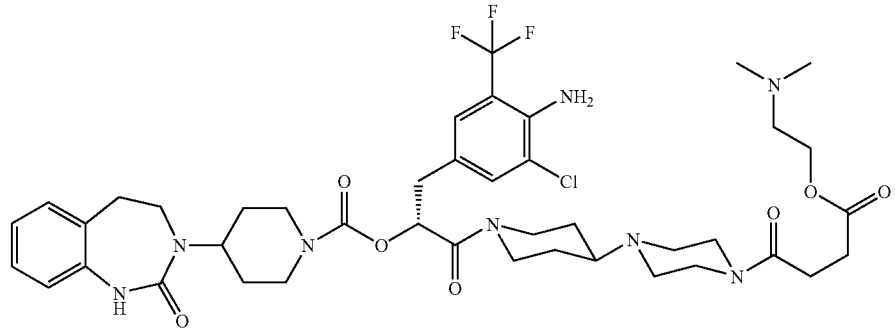 |
| (226) | 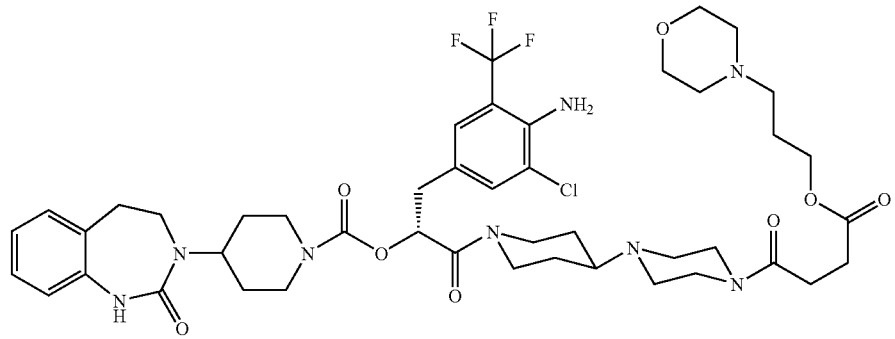 |
| (227) | 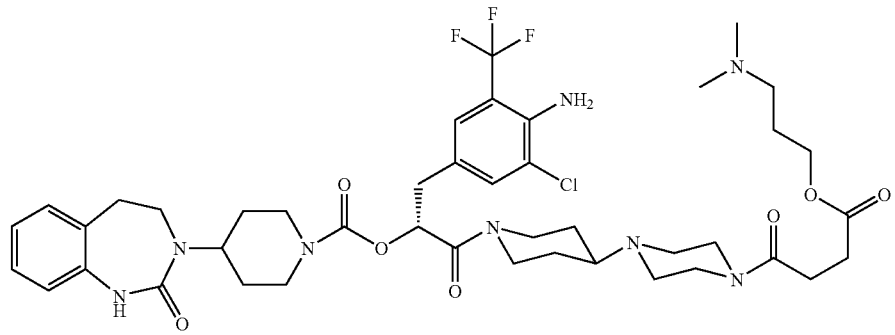 |
| (228) | 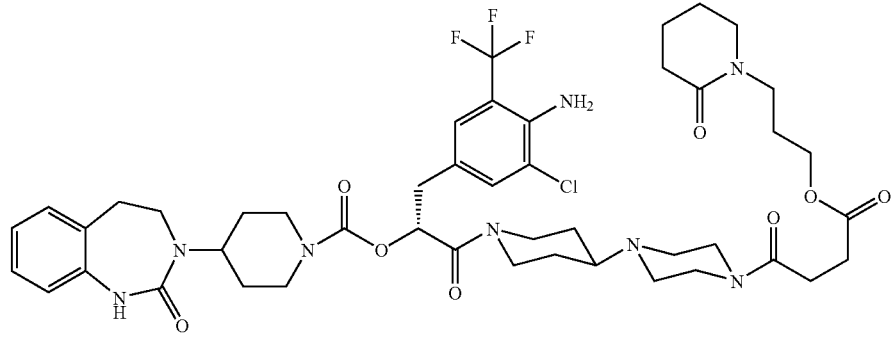 |

| No. | Structure |
|---|---|
| (229) | 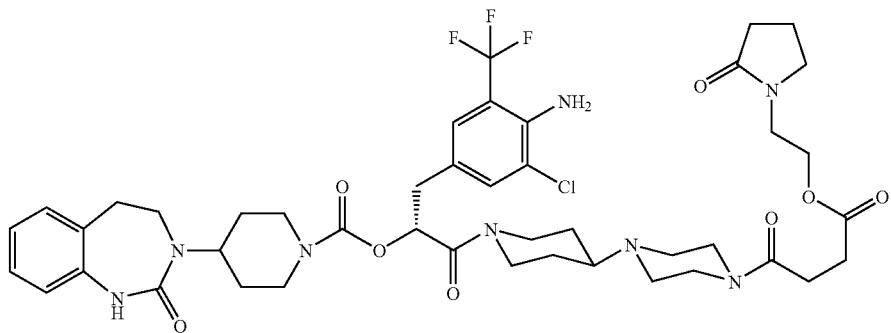 |
| (230) | 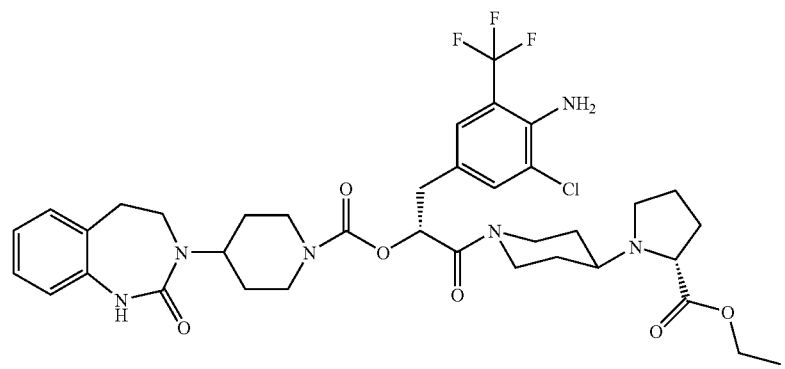 |
| (231) | 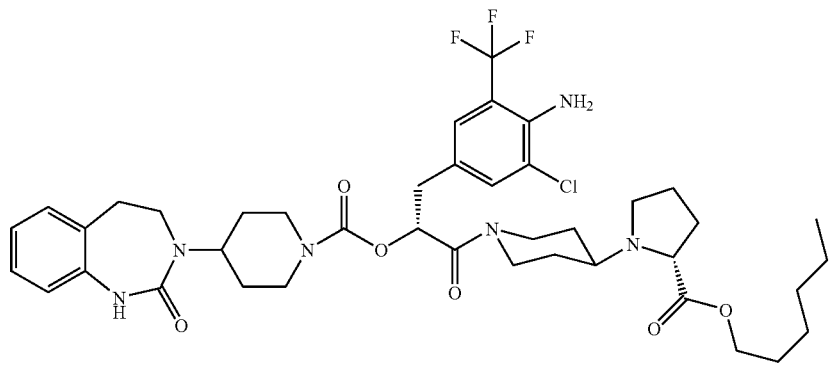 |

| No. | Structure |
|---|---|
| (232) | 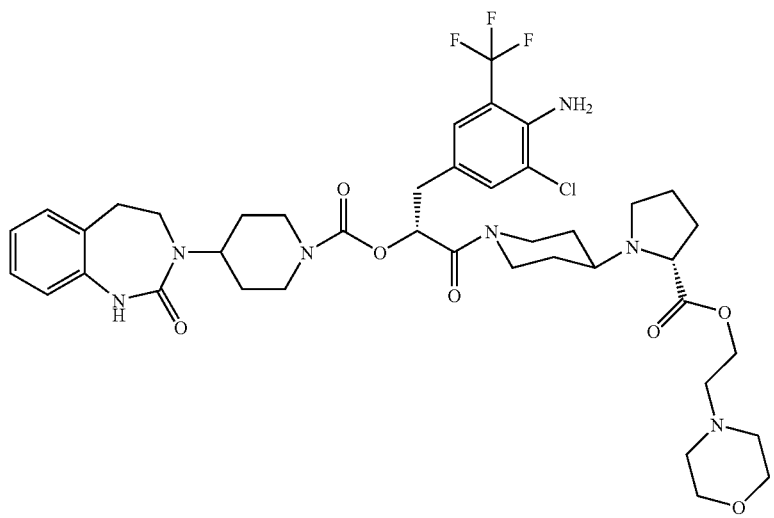 |
| (233) | 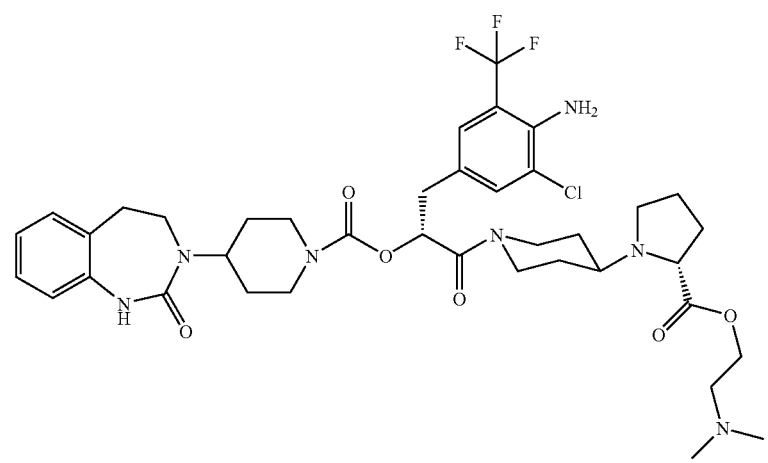 |
| (234) | 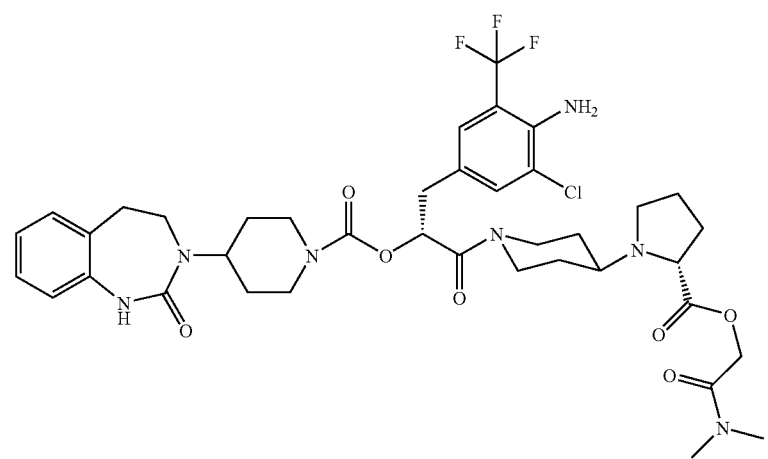 |

| No. | Structure |
|---|---|
| (235) | 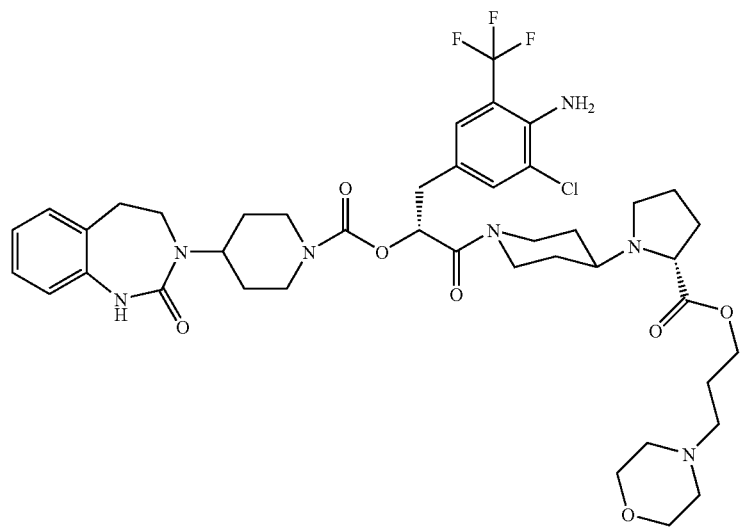 |
| (236) | 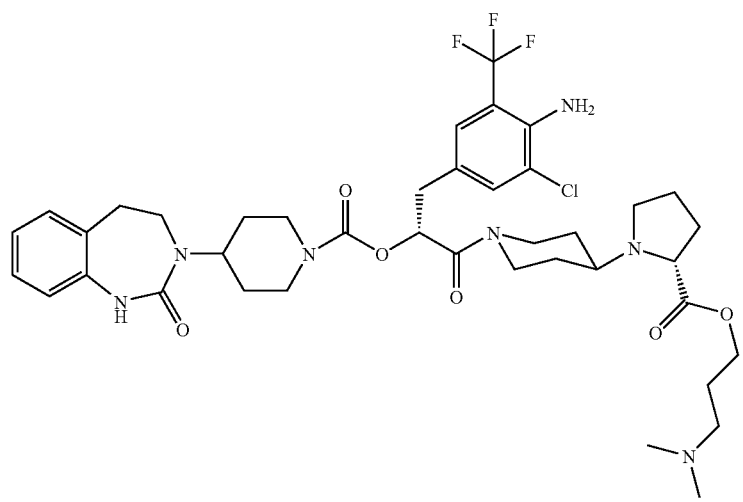 |
| (237) | 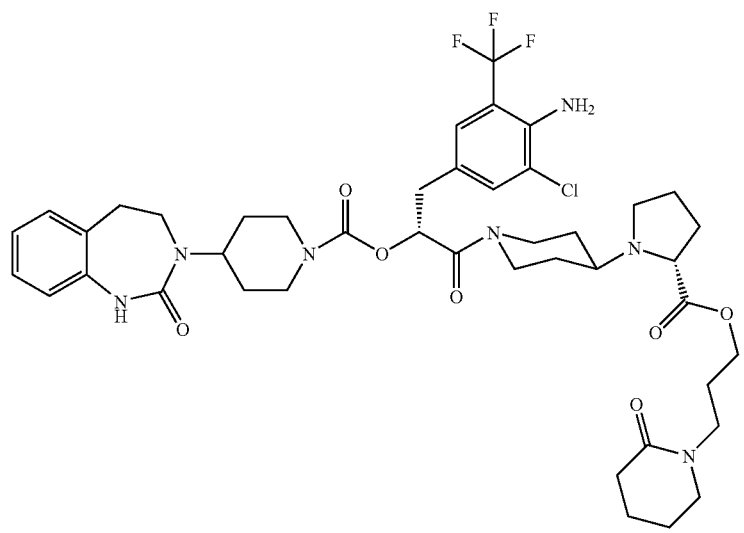 |

| No. | Structure |
|---|---|
| (238) | 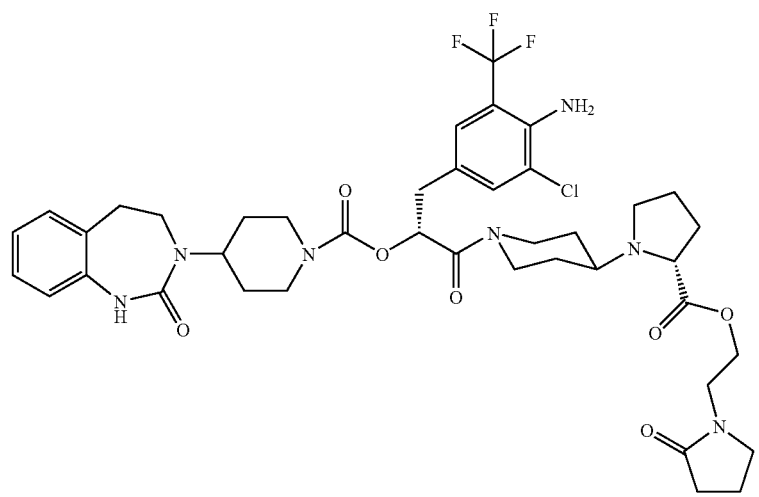 |
| (239) | 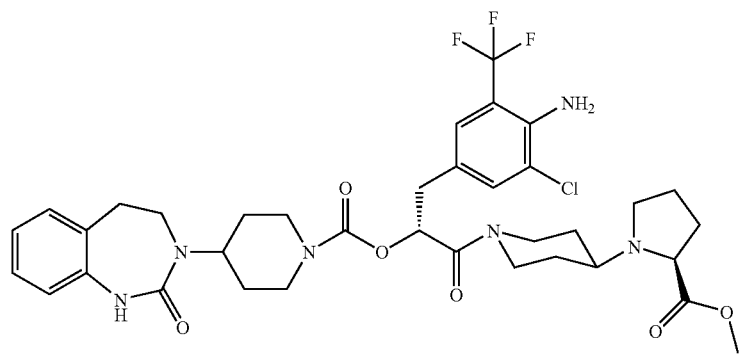 |
| (240) | 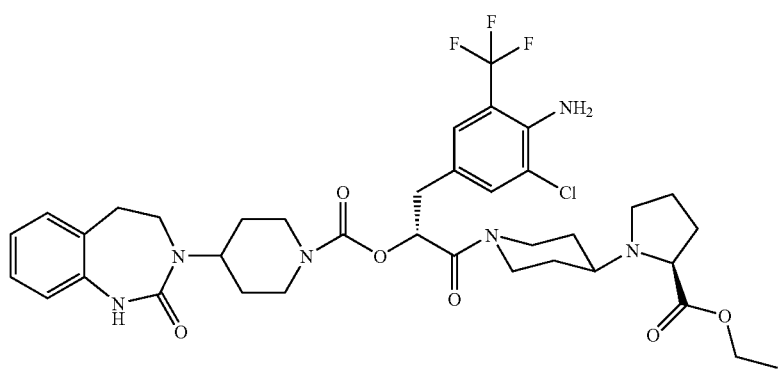 |
| (241) | 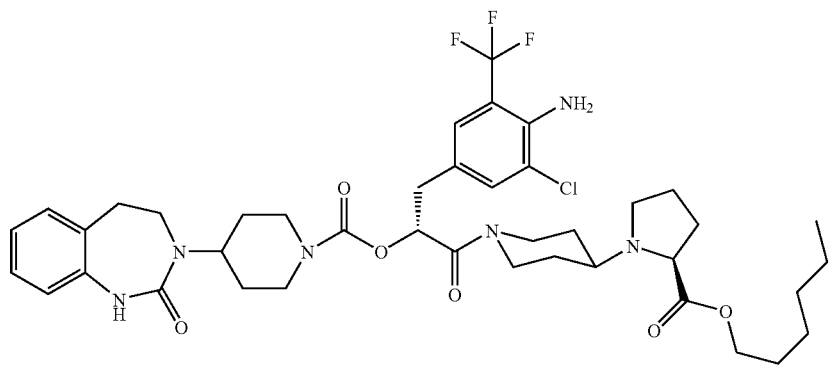 |

| No. | Structure |
|---|---|
| (242) | 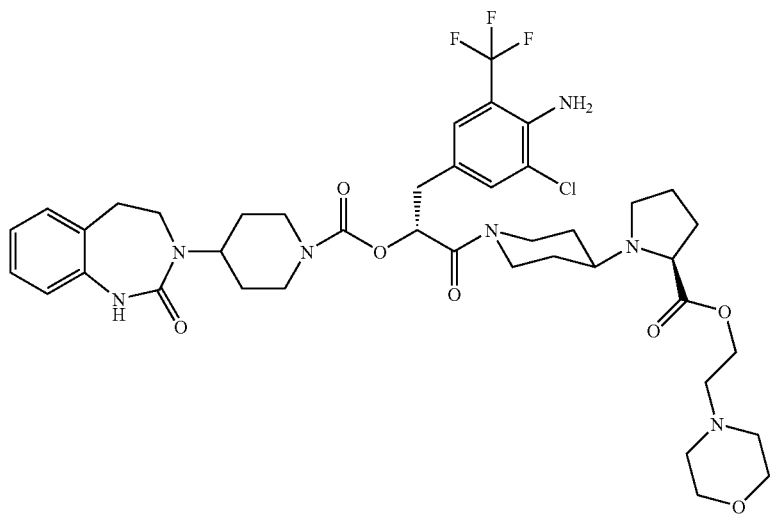 |
| (243) | 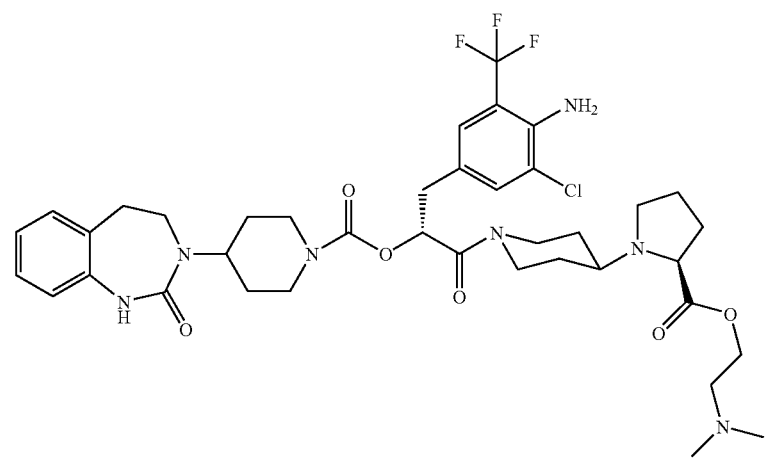 |
| (244) | 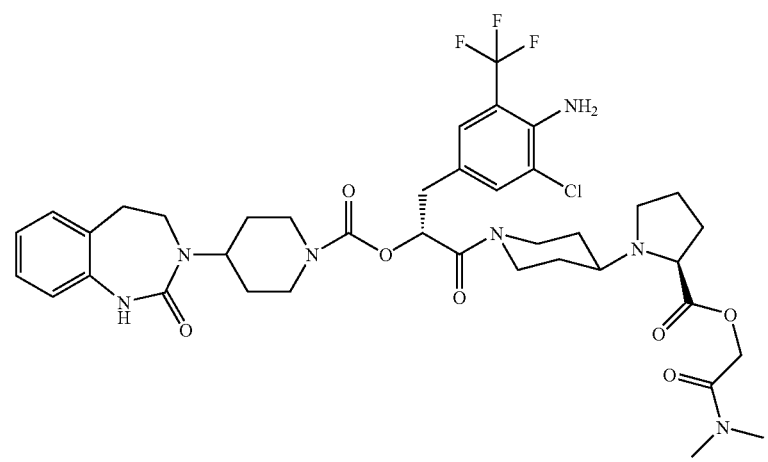 |

| No. | Structure |
|---|---|
| (245) | 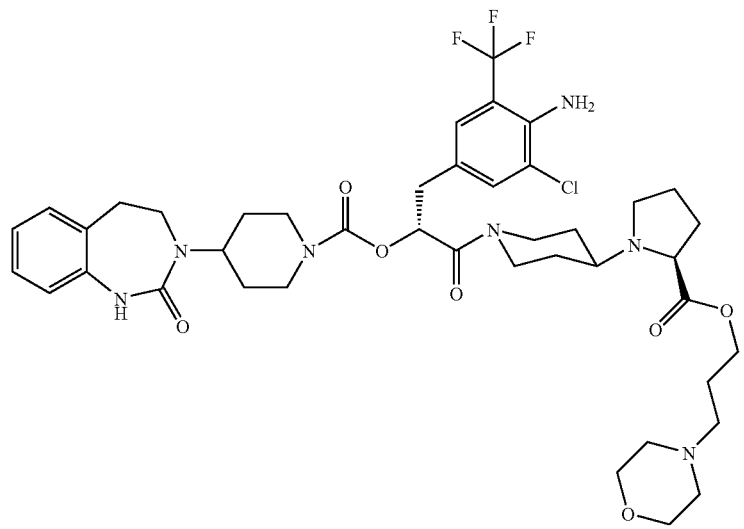 |
| (246) | 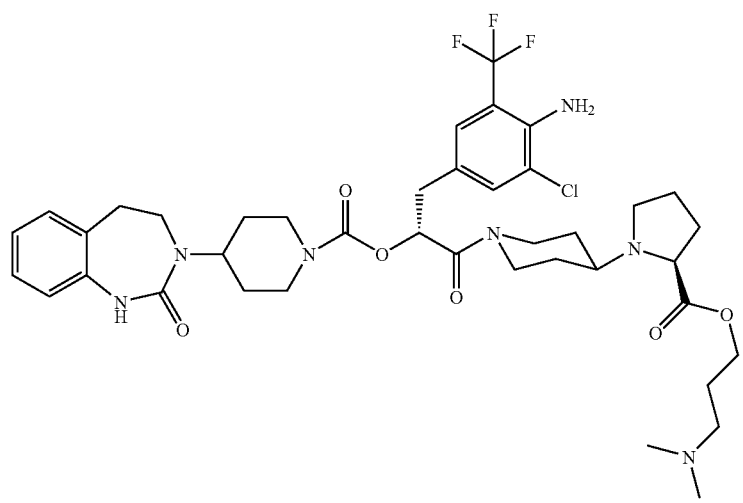 |
| (247) | 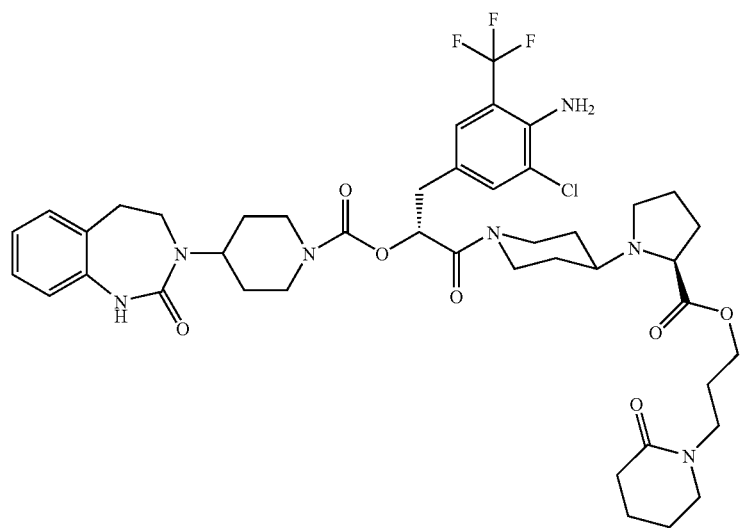 |

| No. | Structure |
|---|---|
| (248) | 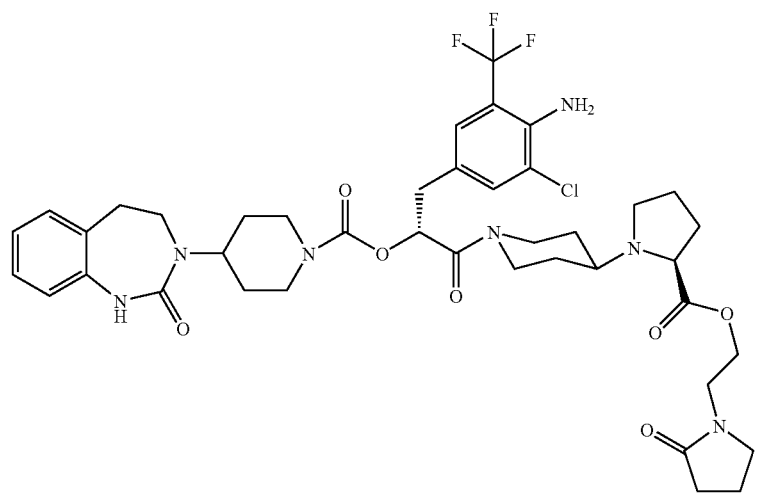 |
| (249) | 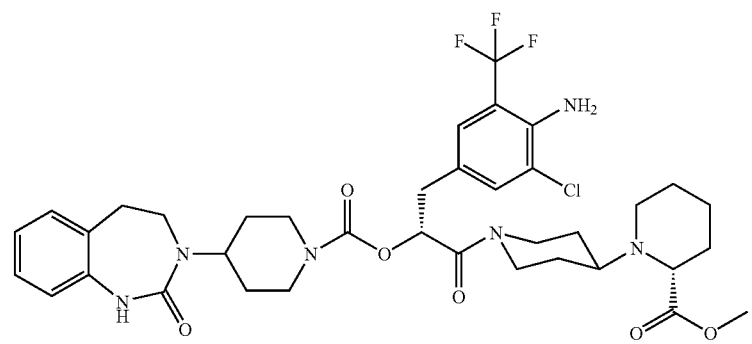 |
| (250) | 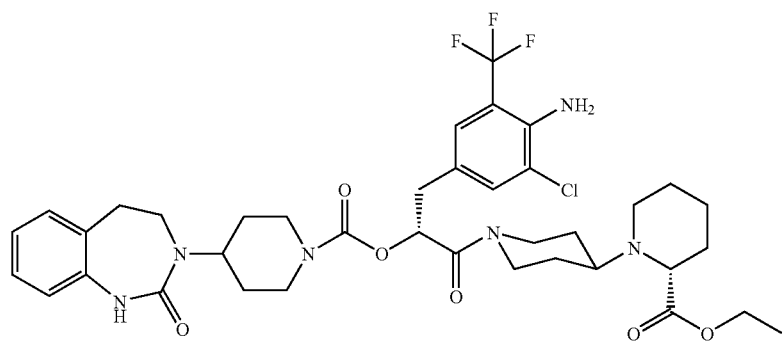 |

| No. | Structure |
|---|---|
| (251) | 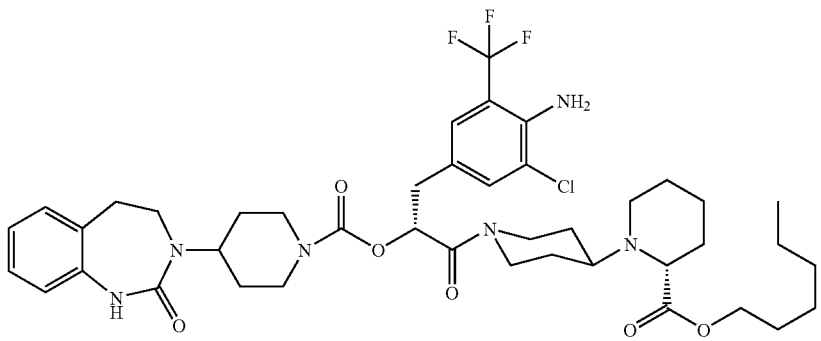 |
| (252) | 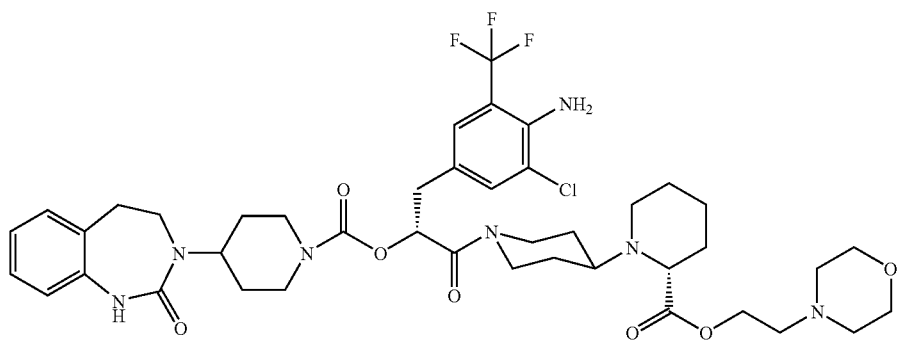 |
| (253) | 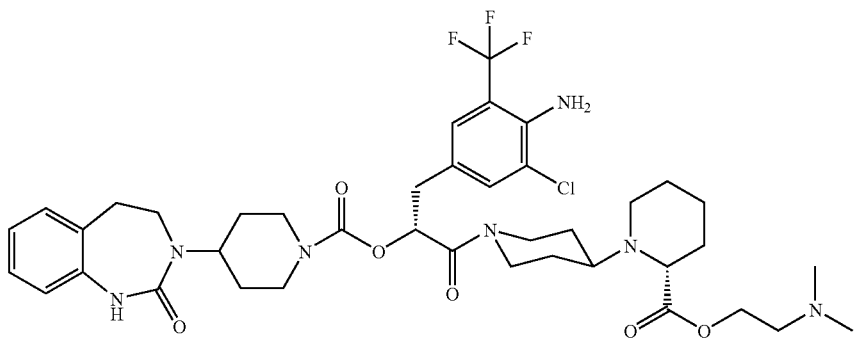 |
| (254) | 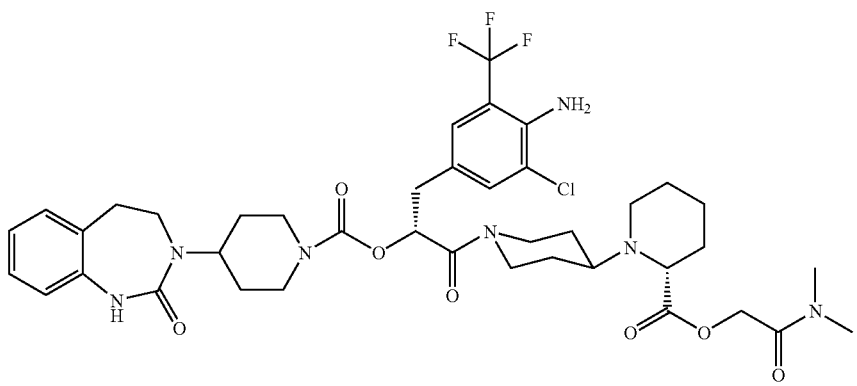 |

| No. | Structure |
|---|---|
| (255) | 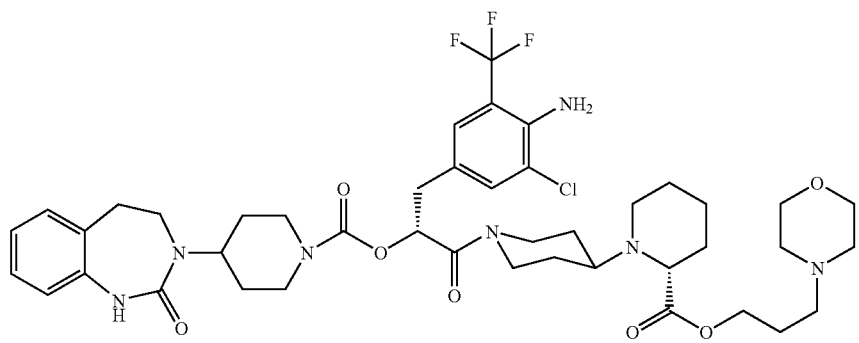 |
| (256) | 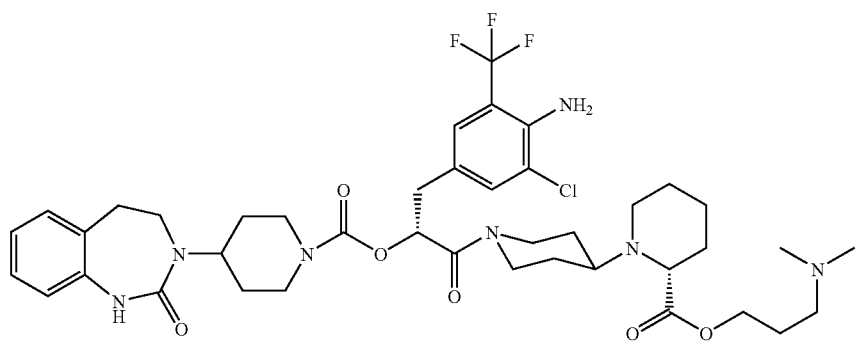 |
| (257) | 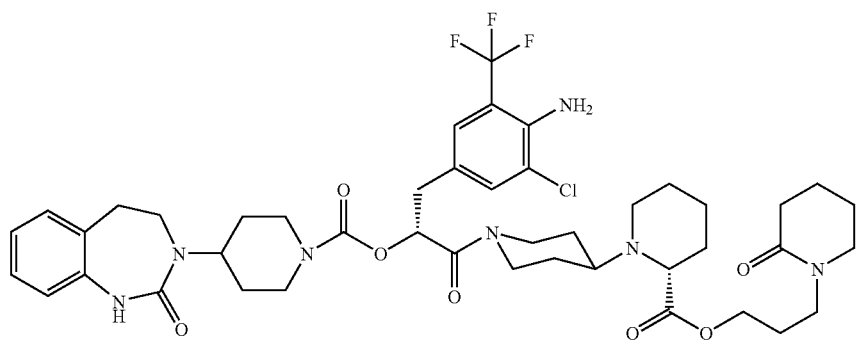 |
| (258) | 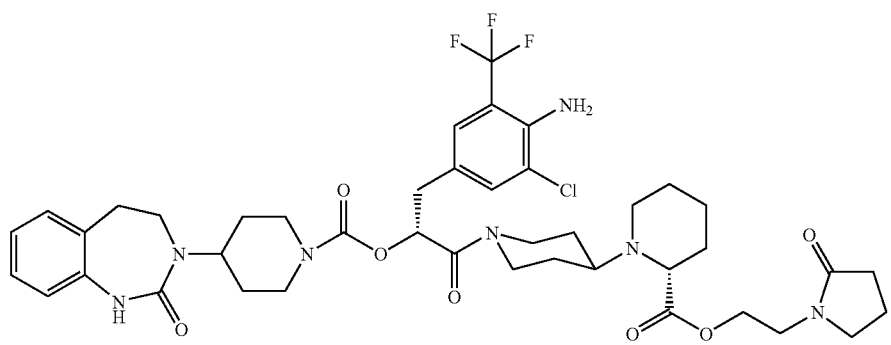 |

| No. | Structure |
|---|---|
| (259) | 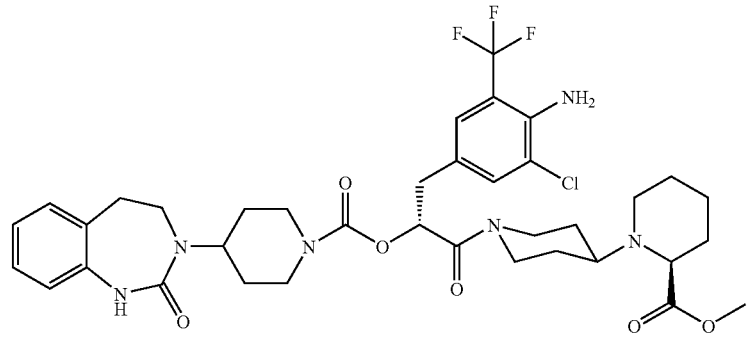 |
| (260) | 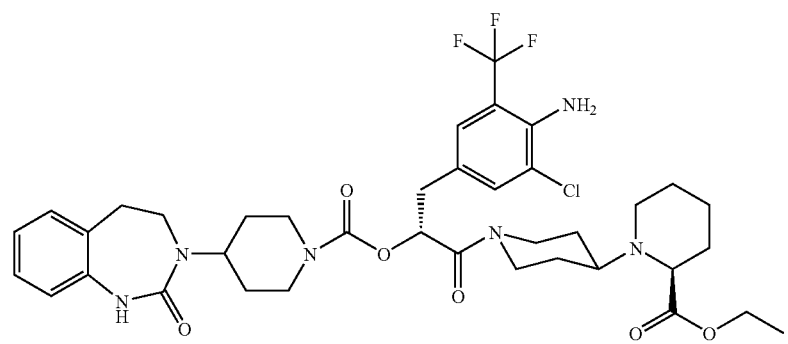 |
| (261) | 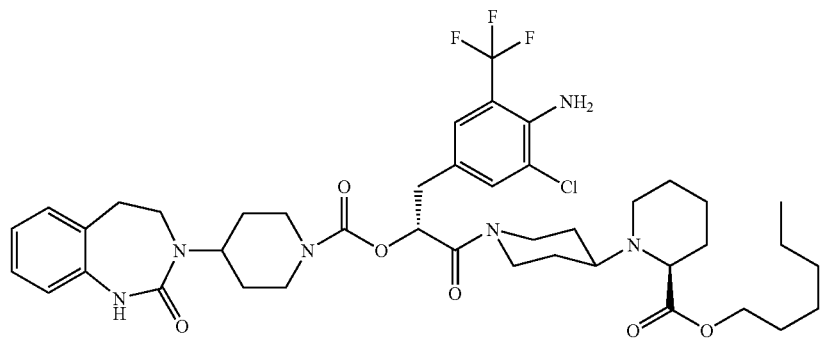 |
| (262) | 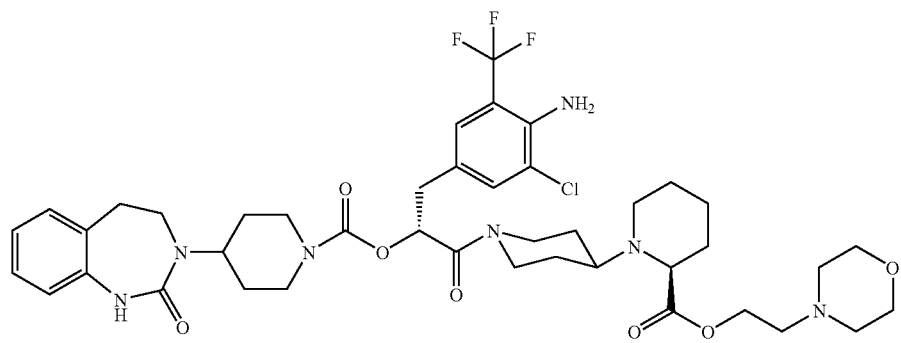 |

| No. | Structure |
|---|---|
| (263) | 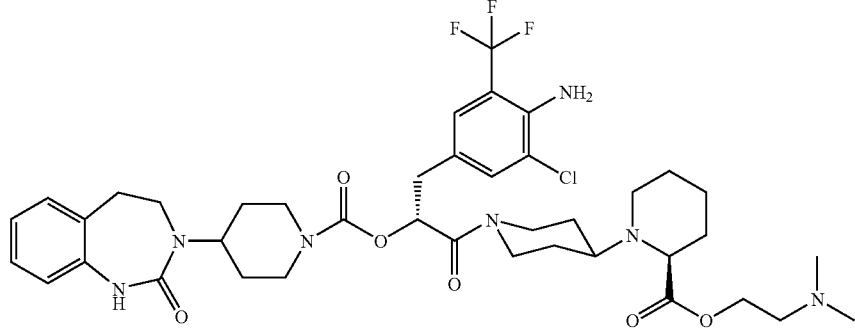 |
| (264) | 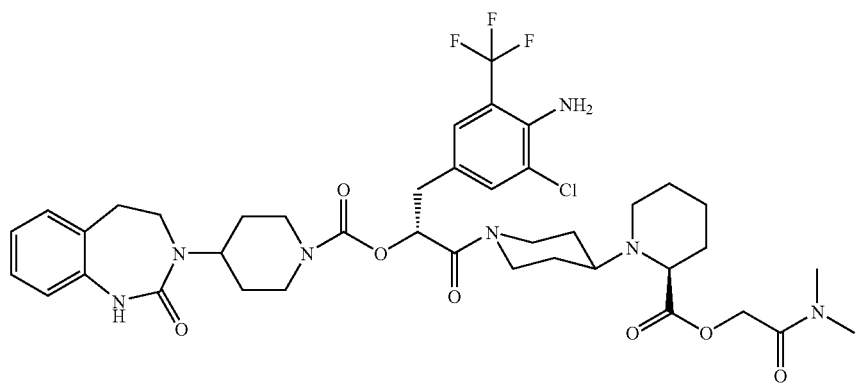 |
| (265) | 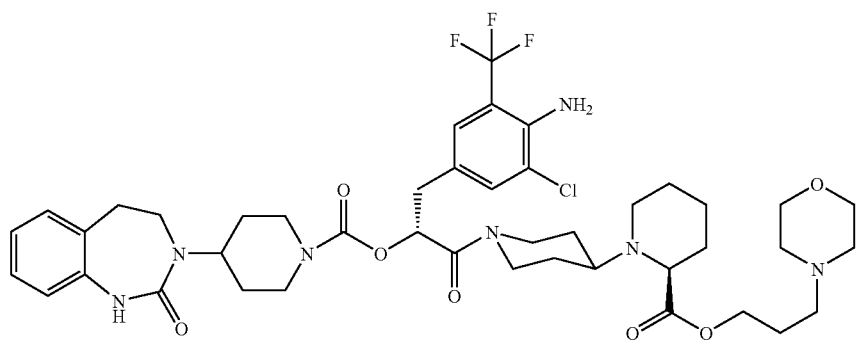 |
| (266) | 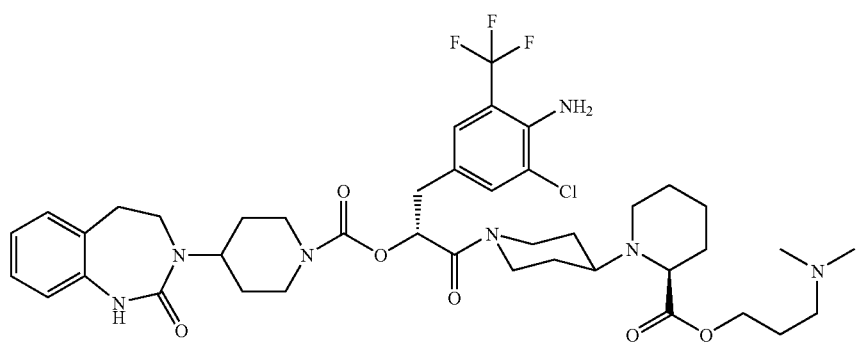 |

| No. | Structure |
|---|---|
| (267) | 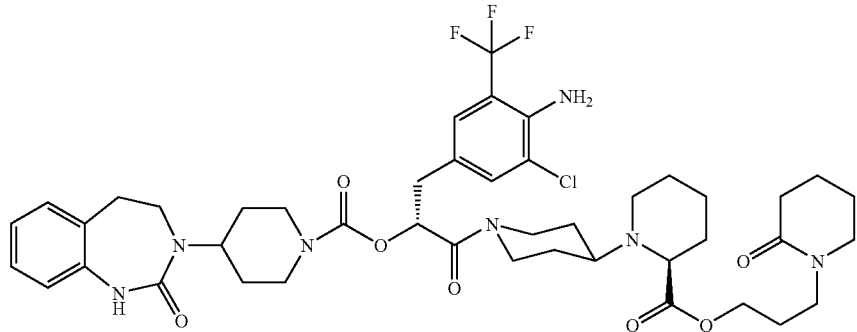 |
| (268) | 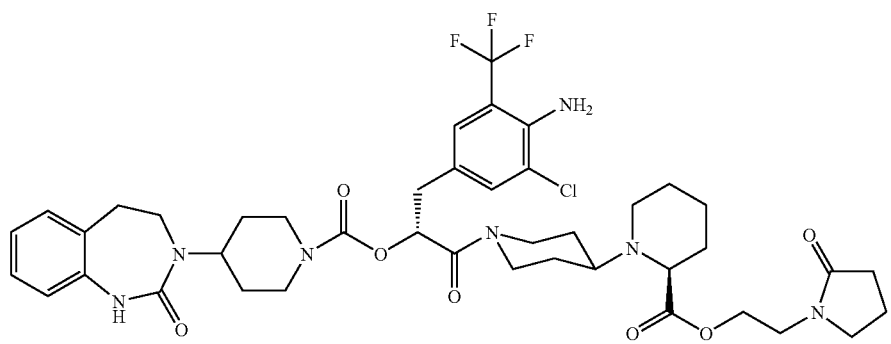 |
| (269) | 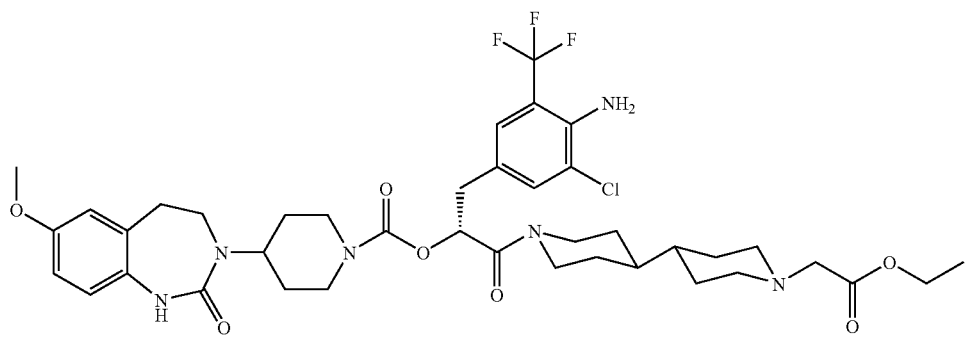 |
| (270) | 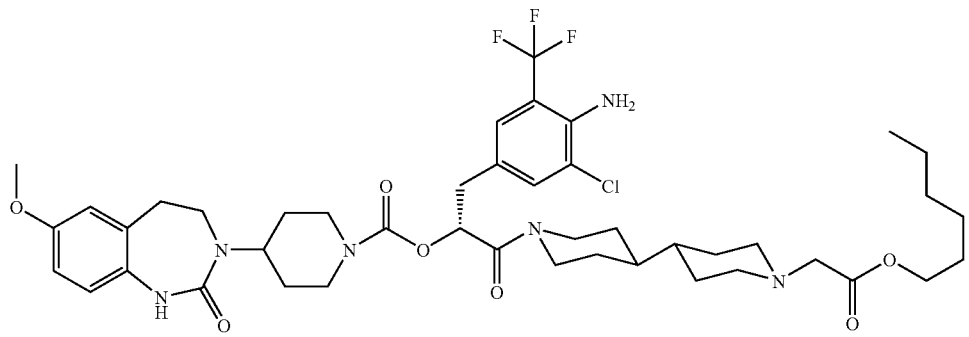 |

| No. | Structure |
|---|---|
| (271) | 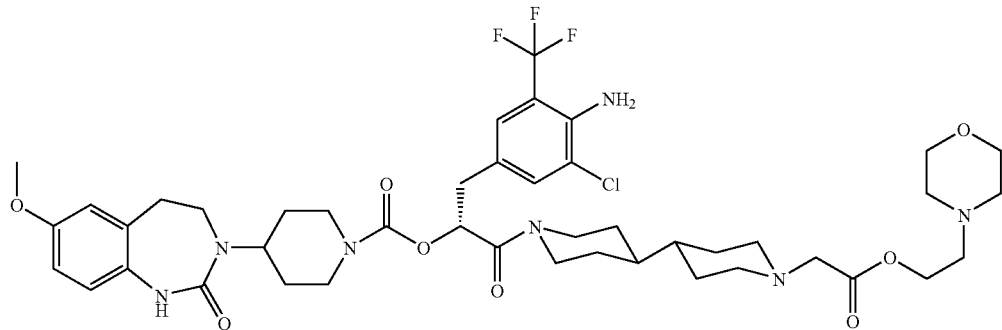 |
| (272) | 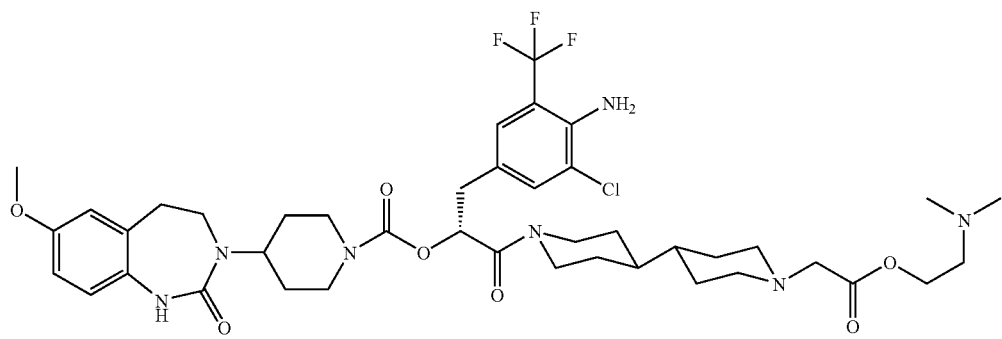 |
| (273) | 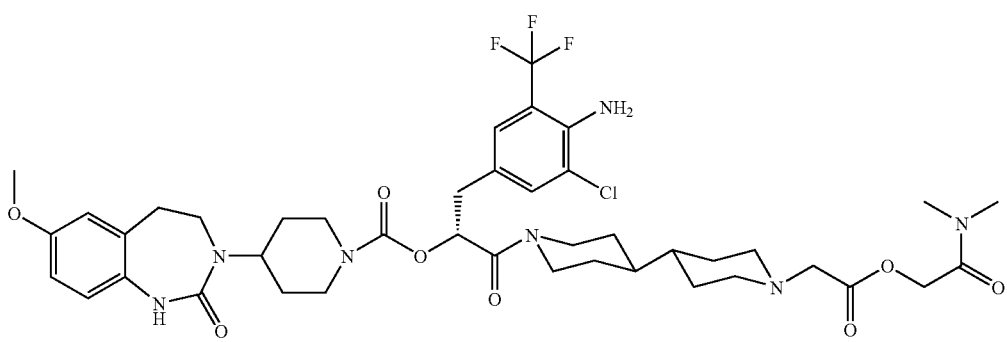 |
| (274) | 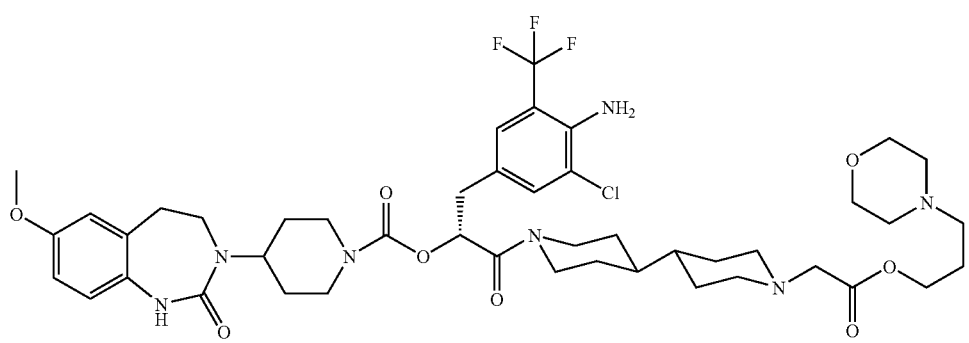 |

| No. | Structure |
|---|---|
| (275) | 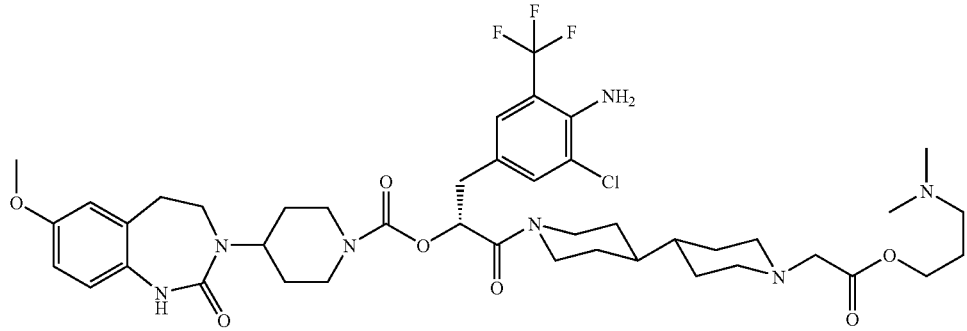 |
| (276) | 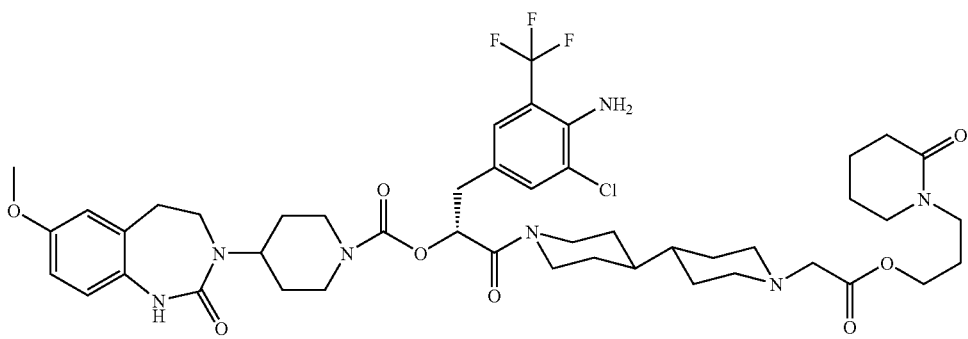 |
| (277) | 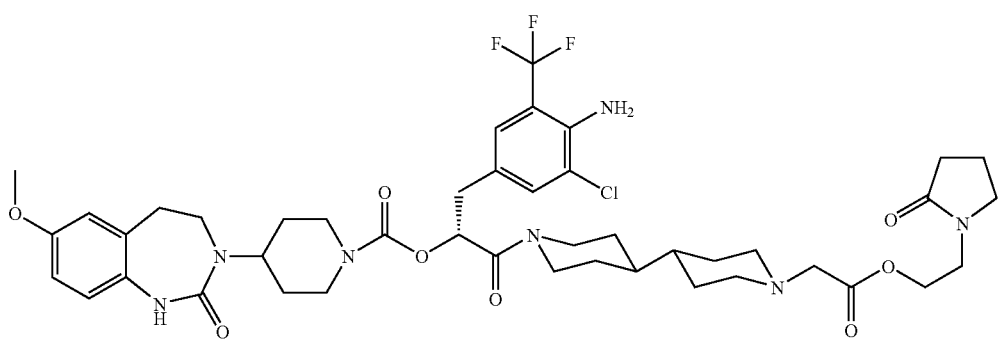 |
| (278) | 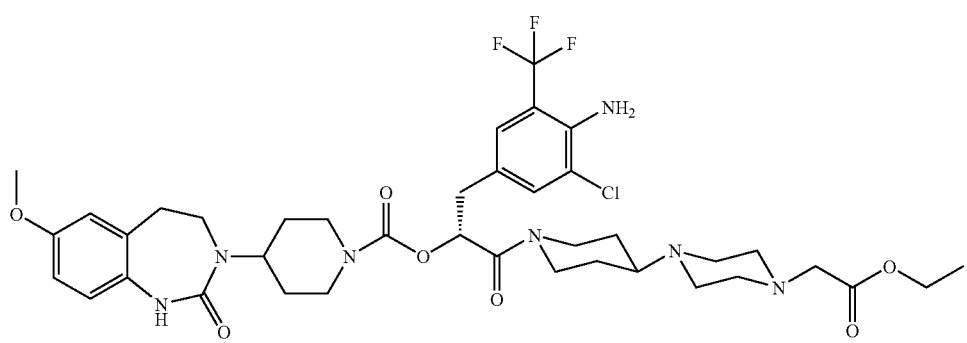 |

| No. | Structure |
|---|---|
| (279) | 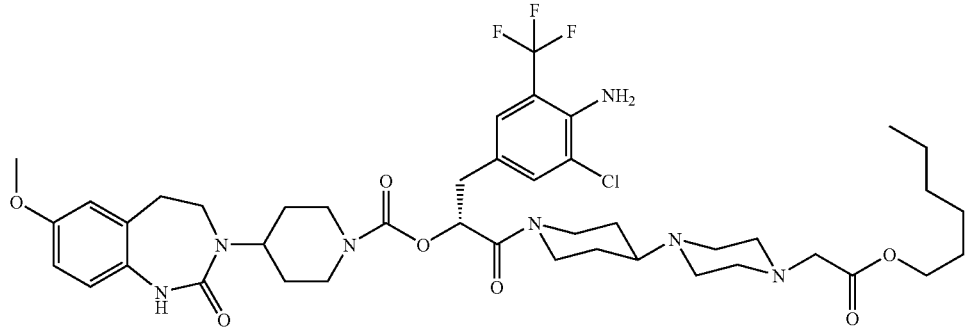 |
| (280) | 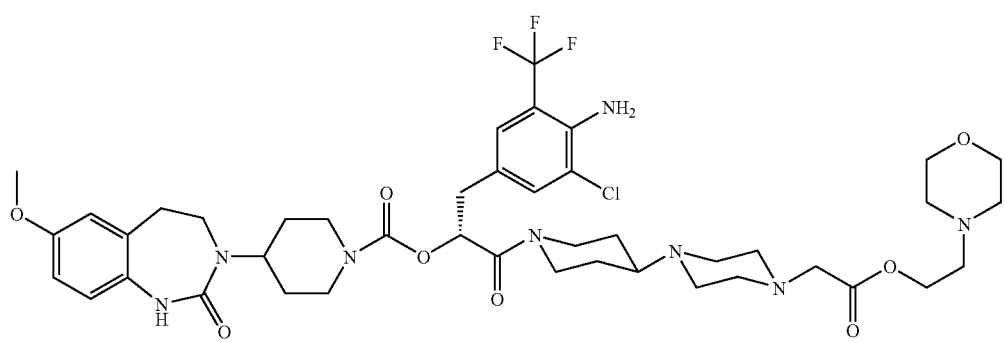 |
| (281) | 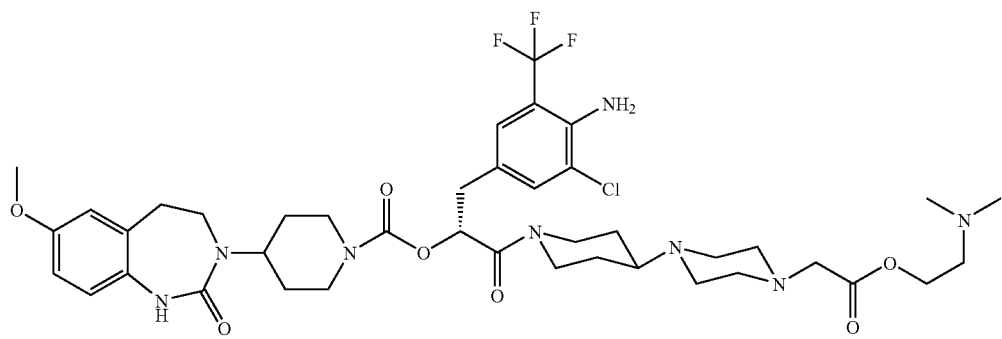 |
| (282) | 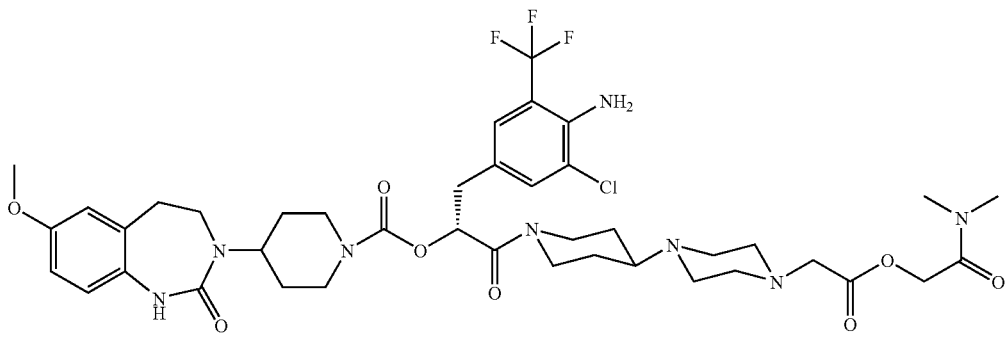 |

| No. | Structure |
|---|---|
| (283) | 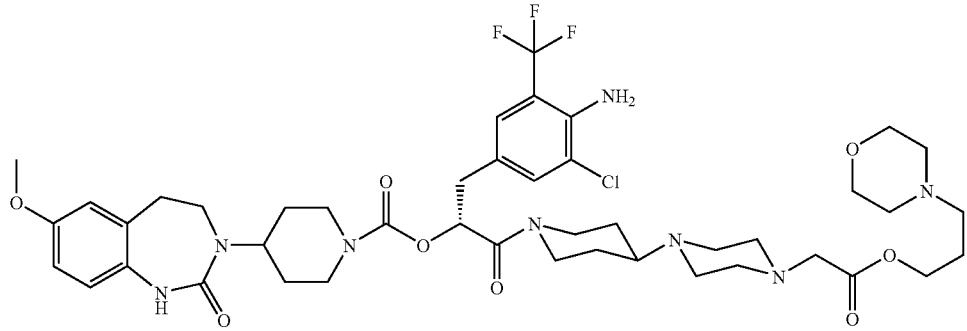 |
| (284) | 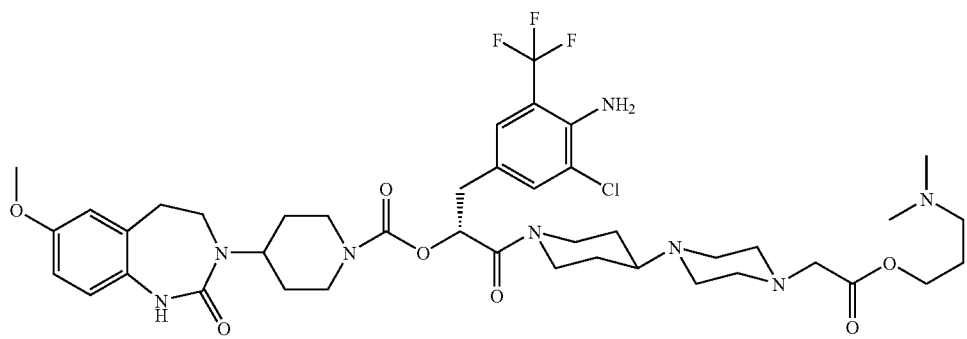 |
| (285) | 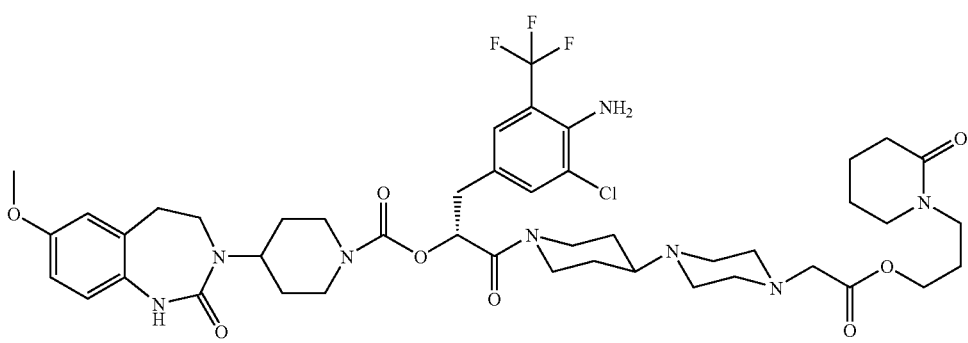 |
| (286) | 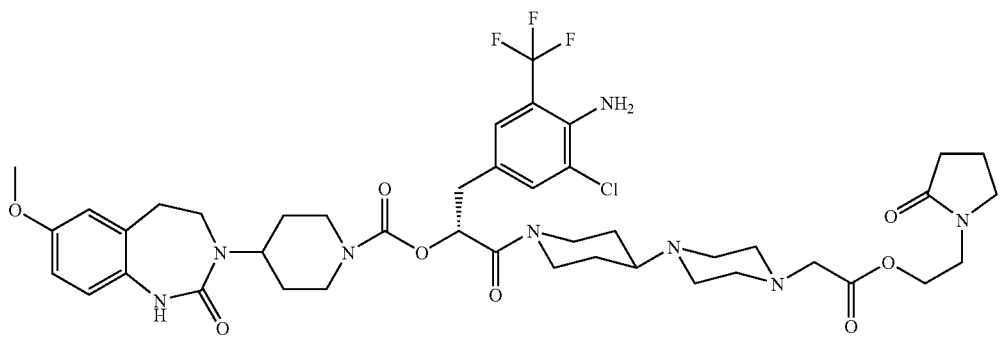 |

| No. | Structure |
|---|---|
| (287) | 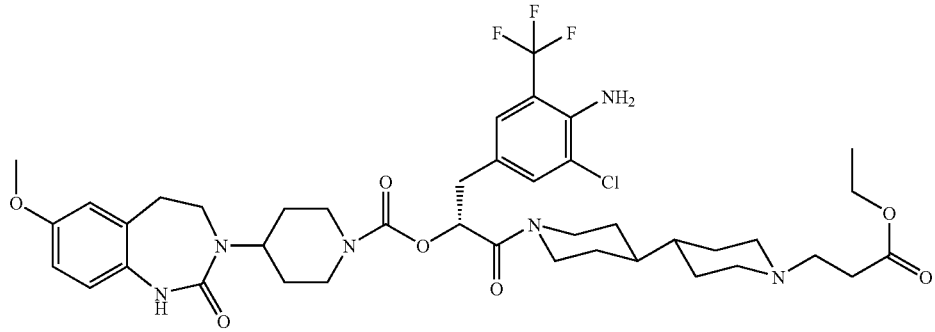 |
| (288) | 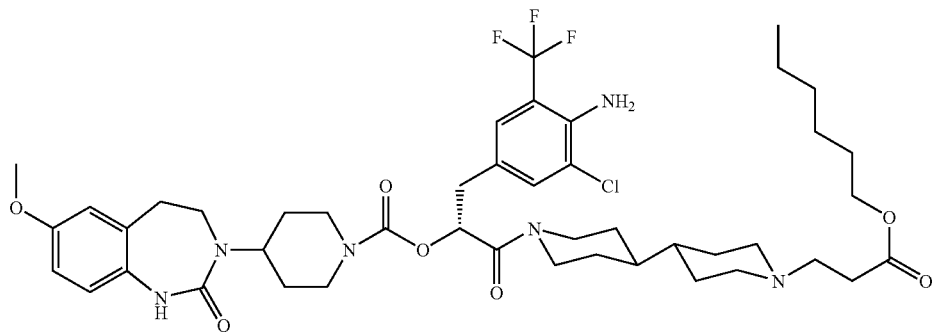 |
| (289) | 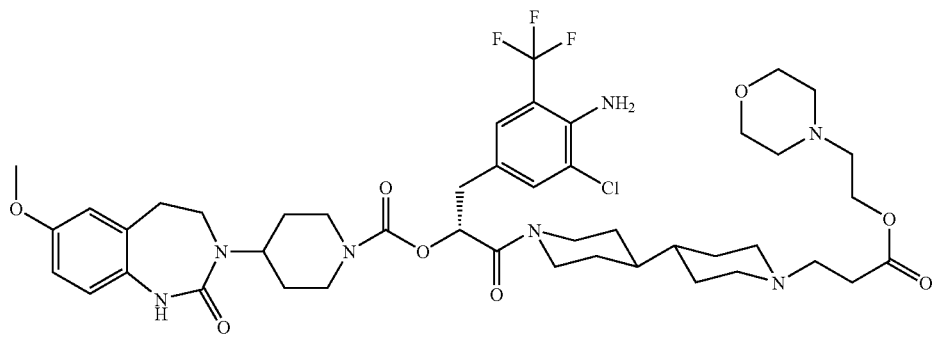 |
| (290) | 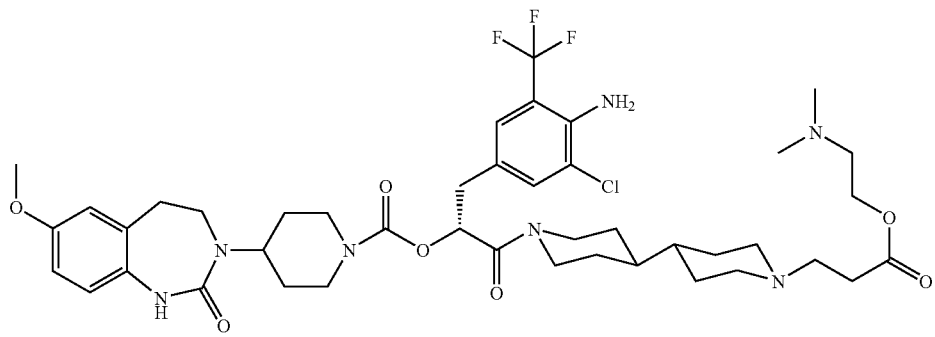 |

| No. | Structure |
|---|---|
| (291) | 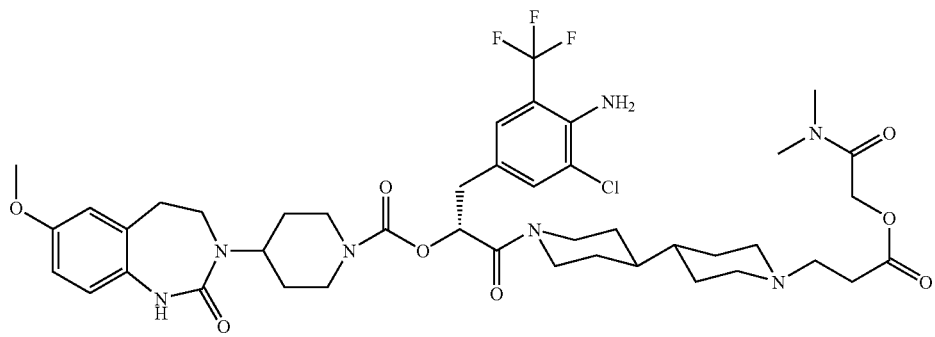 |
| (292) | 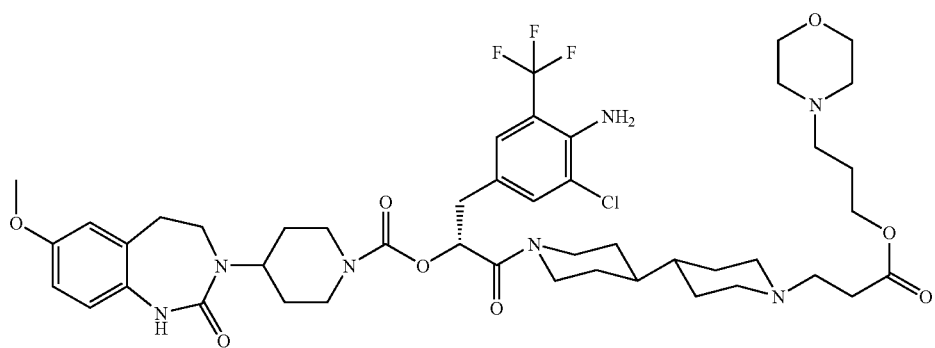 |
| (293) | 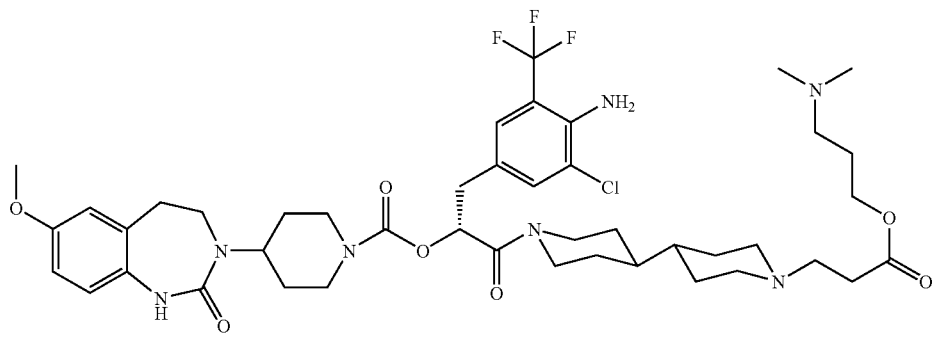 |
| (294) | 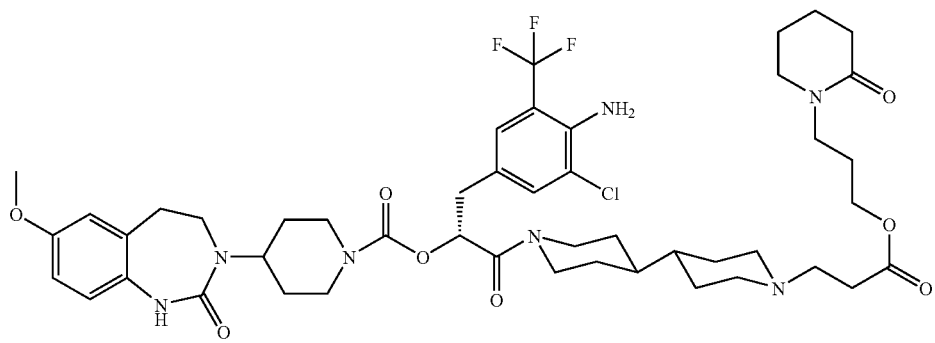 |

| No. | Structure |
|---|---|
| (295) | 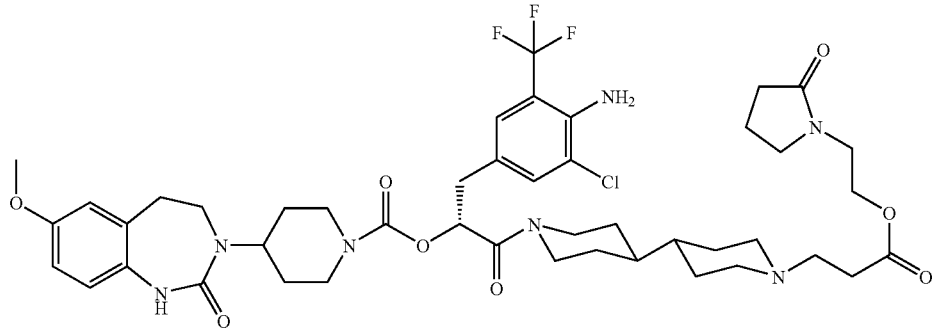 |
| (296) | 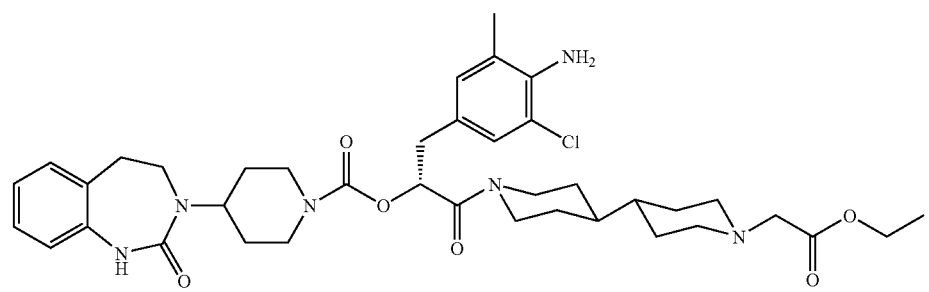 |
| (297) | 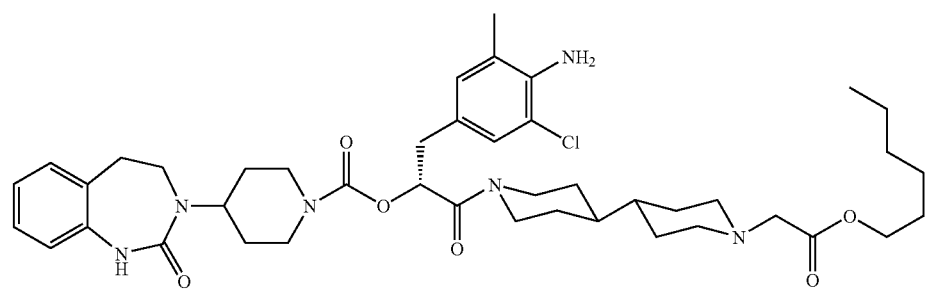 |
| (298) | 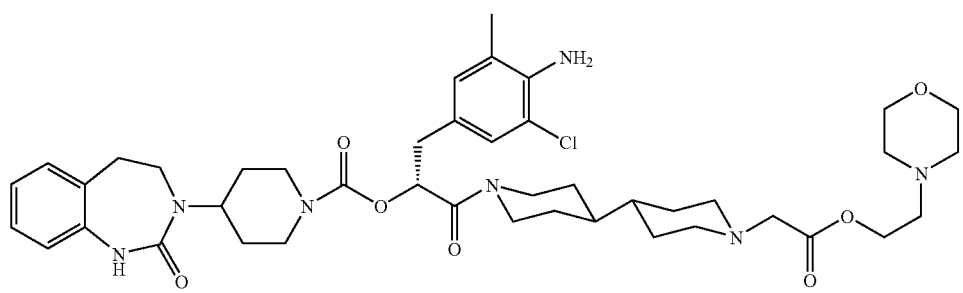 |
| (299) | 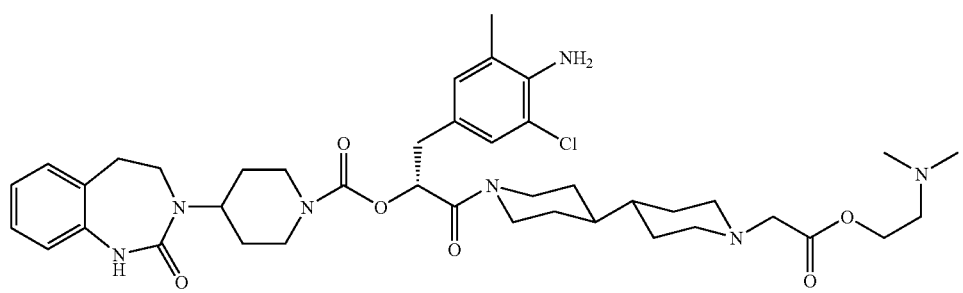 |

| No. | Structure |
|---|---|
| (300) | 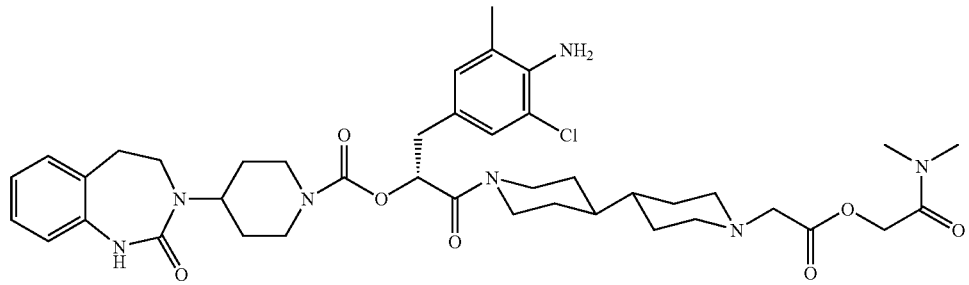 |
| (301) | 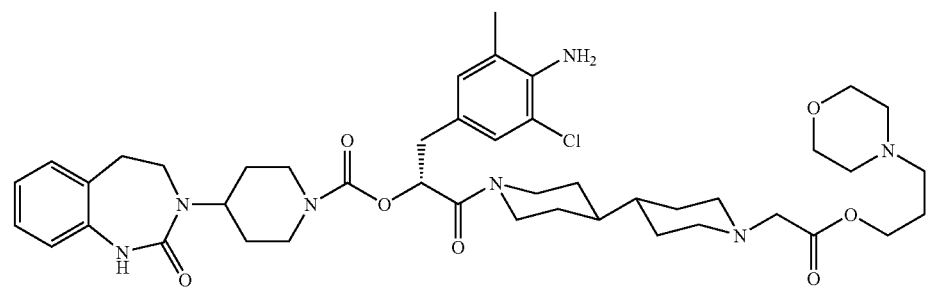 |
| (302) | 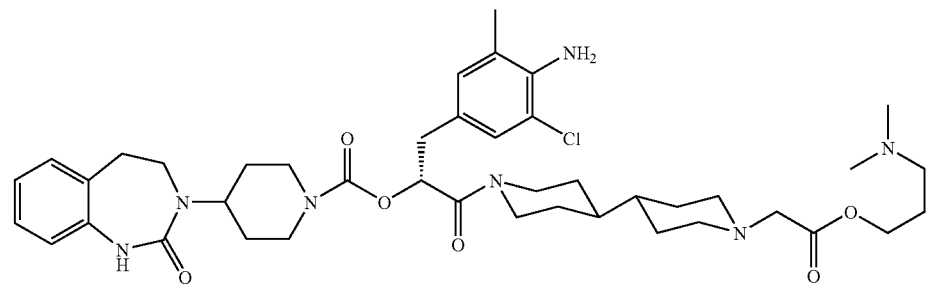 |
| (303) | 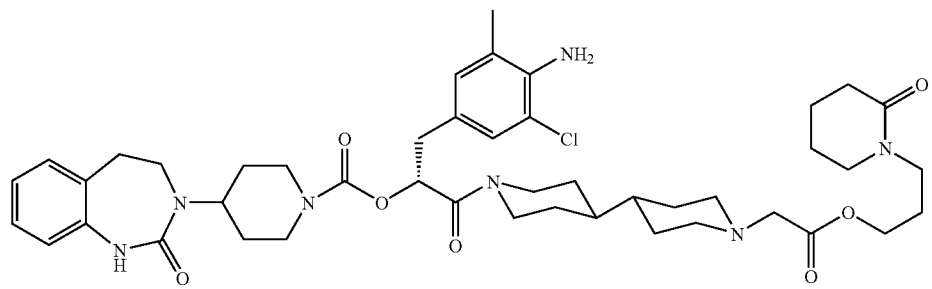 |
| (304) | 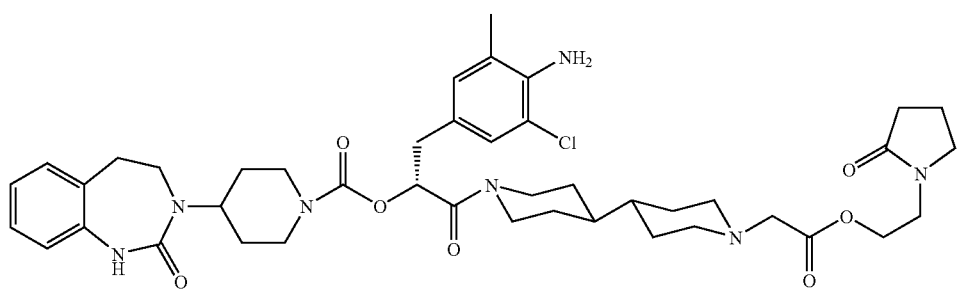 |

| No. | Structure |
|---|---|
| (305) | 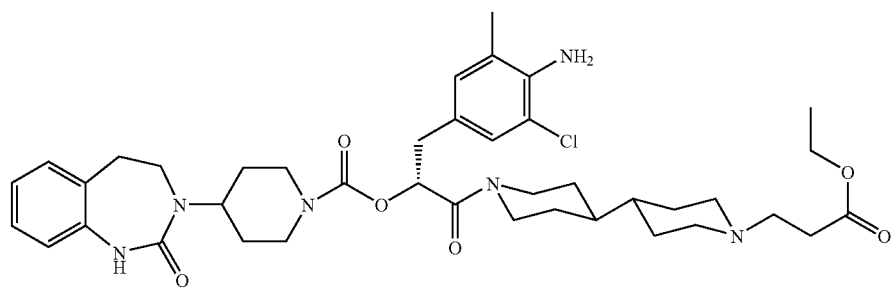 |
| (306) | 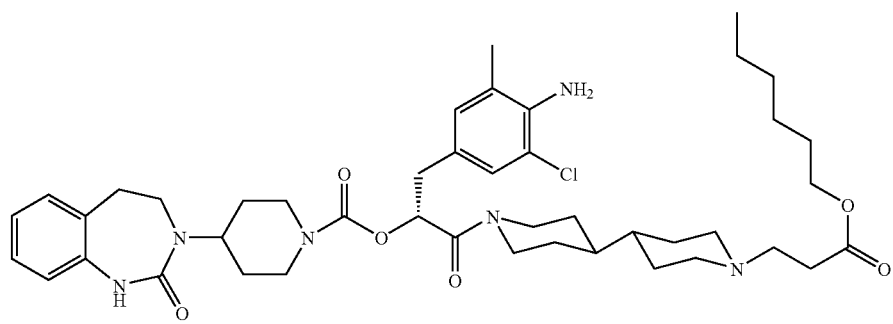 |
| (307) | 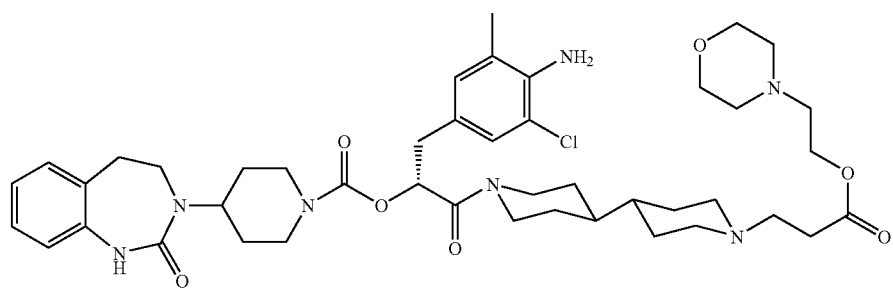 |
| (308) | 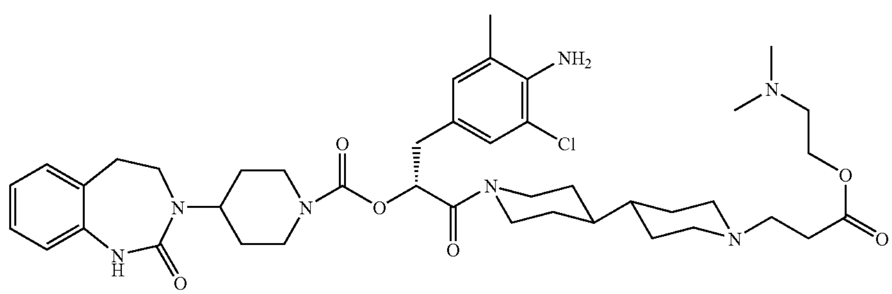 |
| (309) | 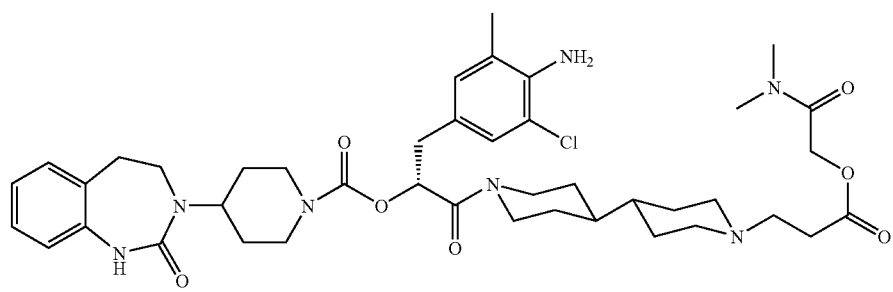 |

| No. | Structure |
|---|---|
| (310) | 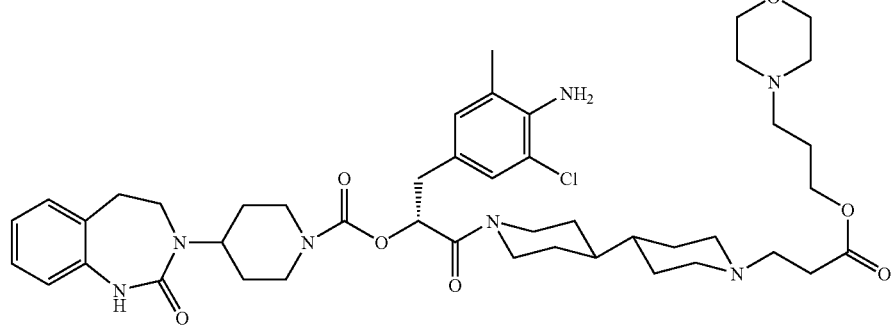 |
| (311) | 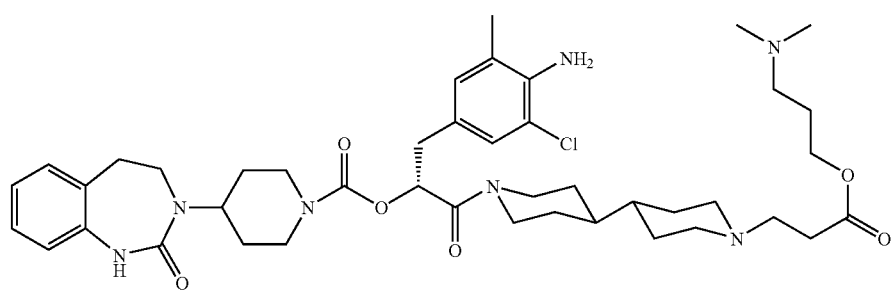 |
| (312) | 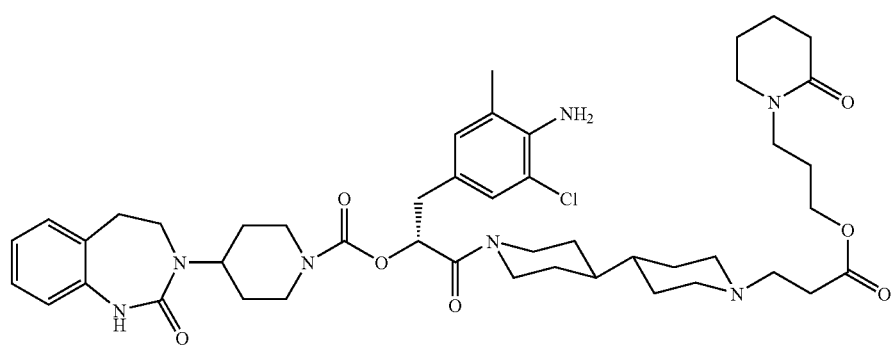 |
| (313) | 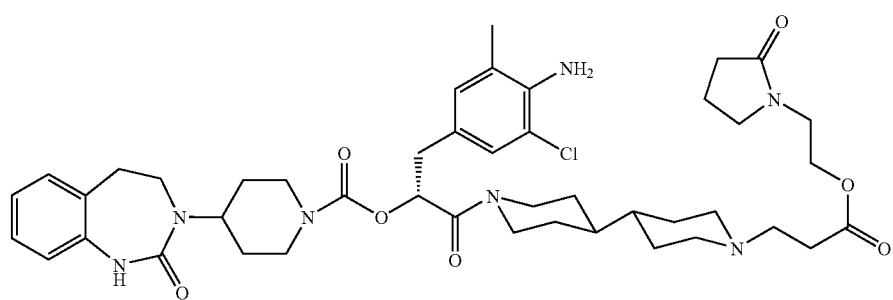 |

| No. | Structure |
|---|---|
| (314) | 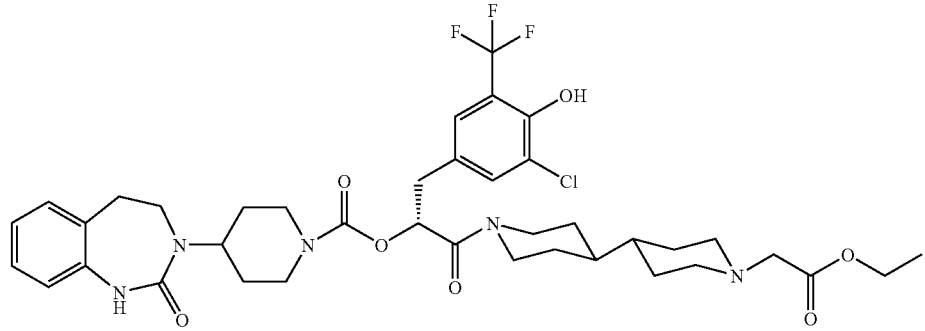 |
| (315) | 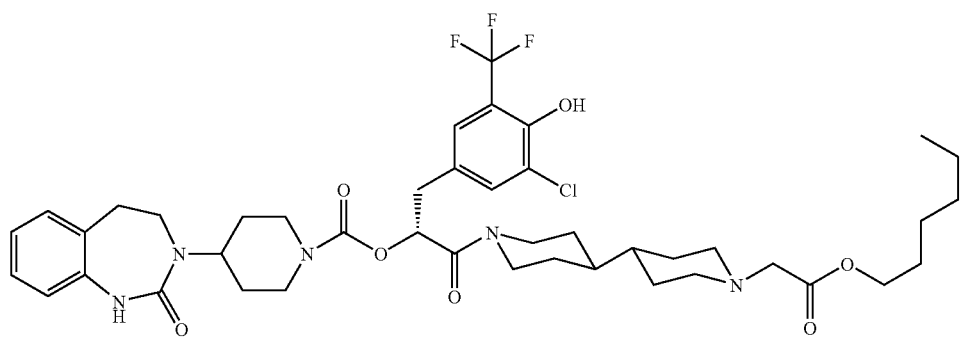 |
| (316) | 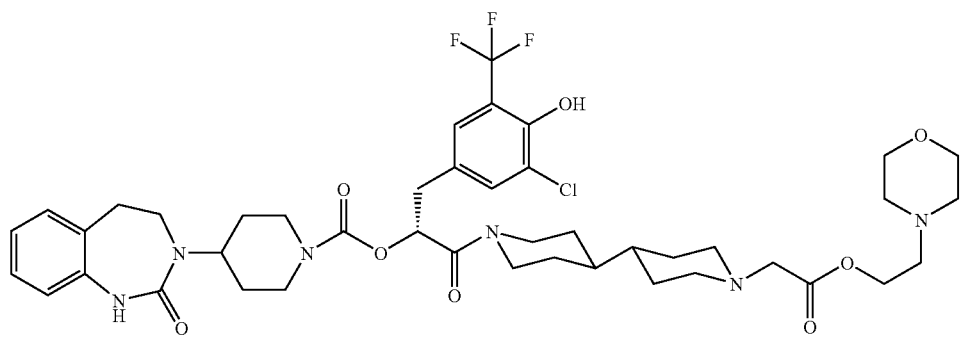 |
| (317) | 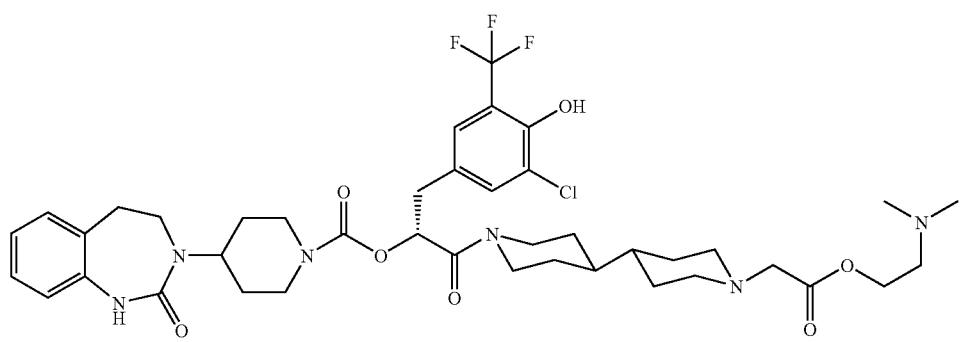 |

| No. | Structure |
|---|---|
| (318) | 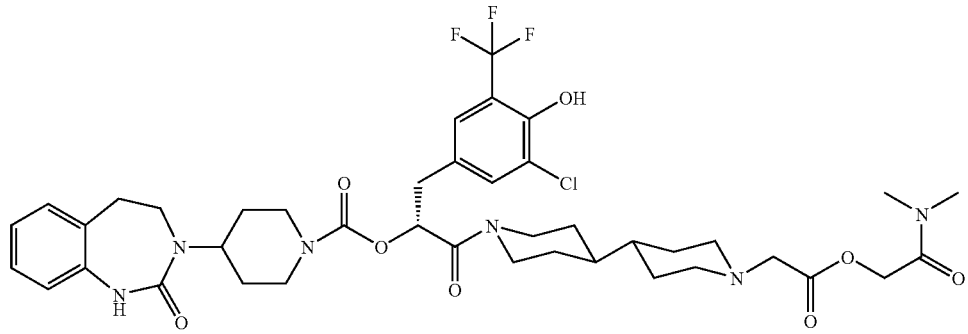 |
| (319) | 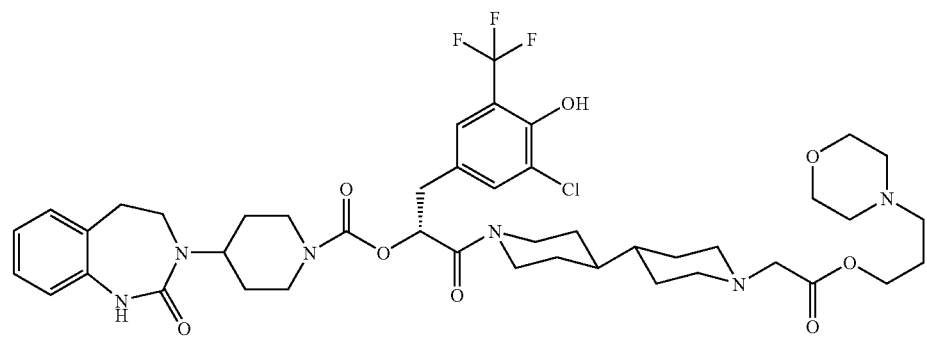 |
| (320) | 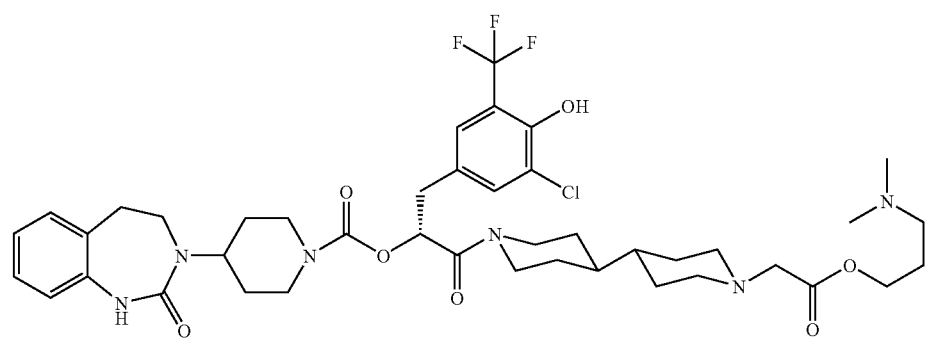 |
| (321) | 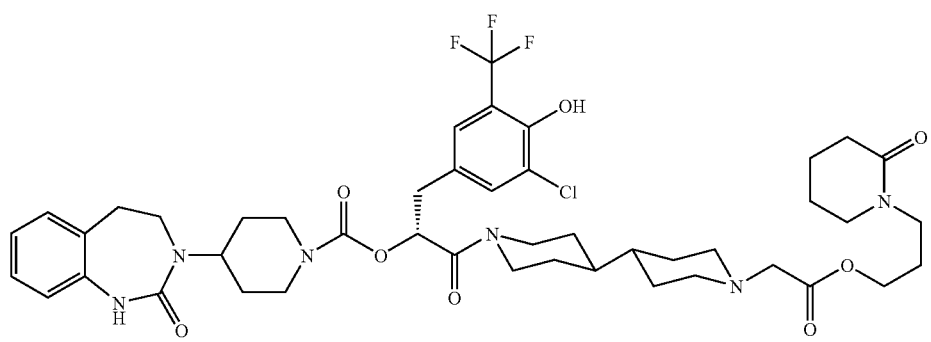 |

| No. | Structure |
|---|---|
| (322) | 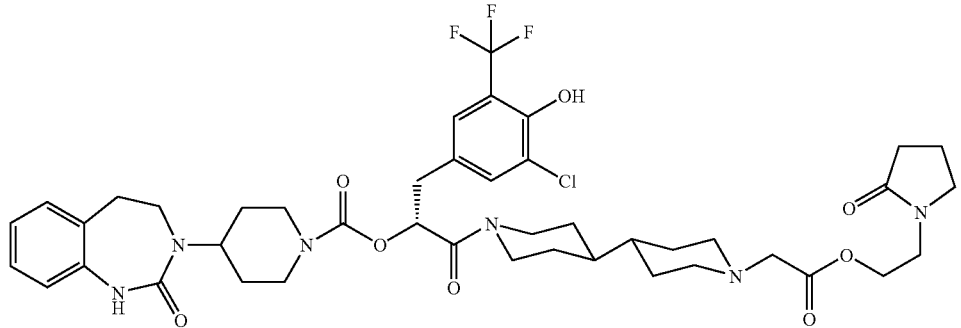 |
| (323) | 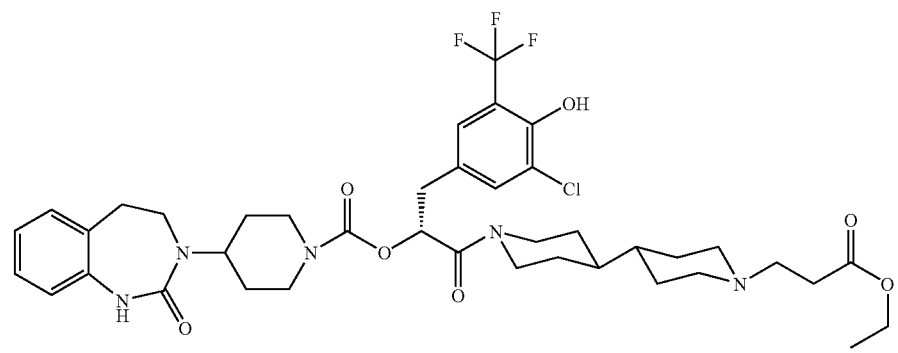 |
| (324) | 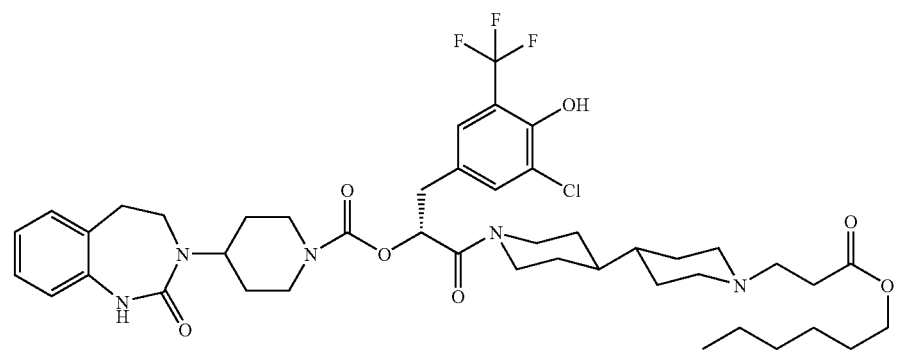 |

| No. | Structure |
|---|---|
| (325) | 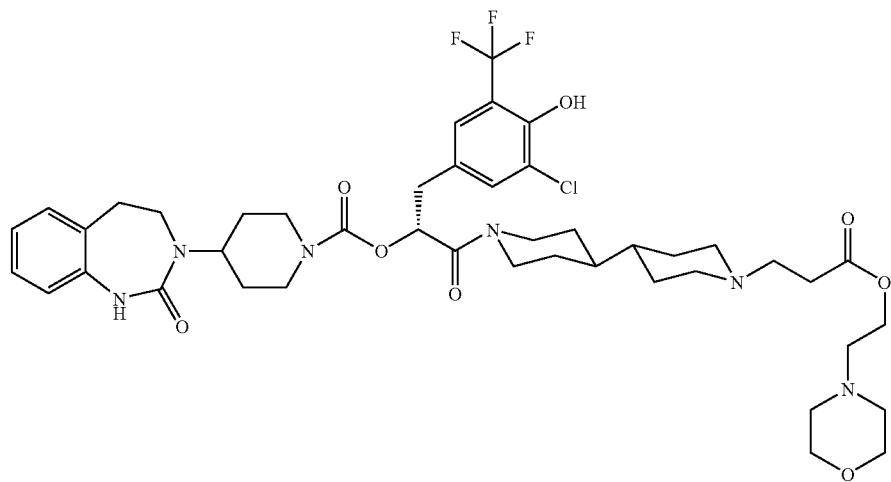 |
| (326) | 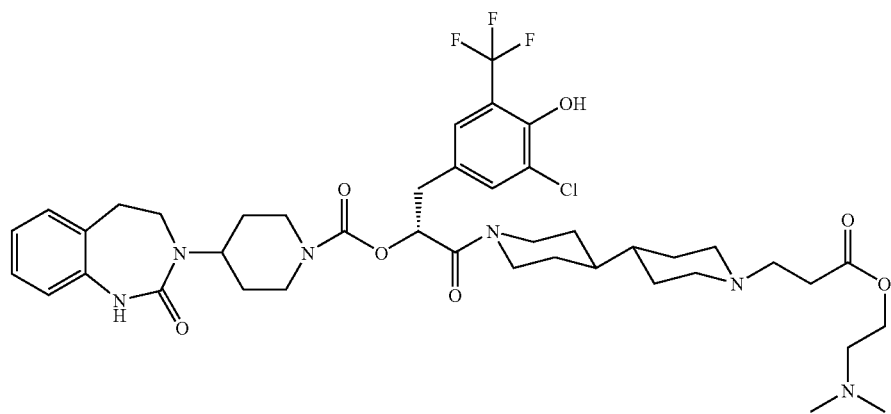 |
| (327) | 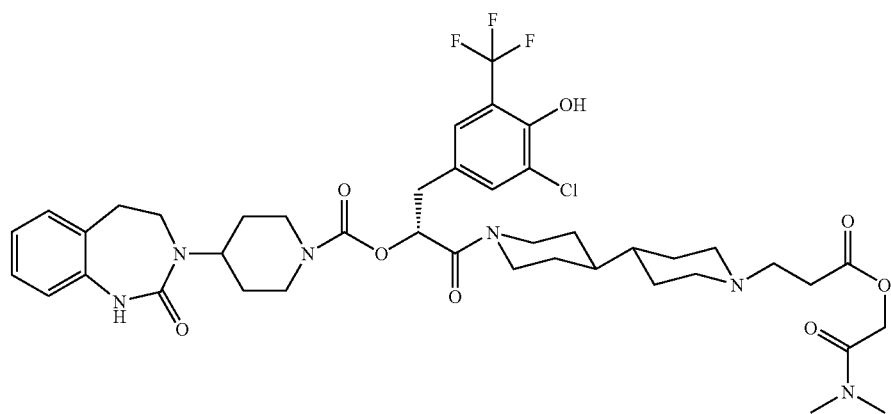 |

| No. | Structure |
|---|---|
| (328) | 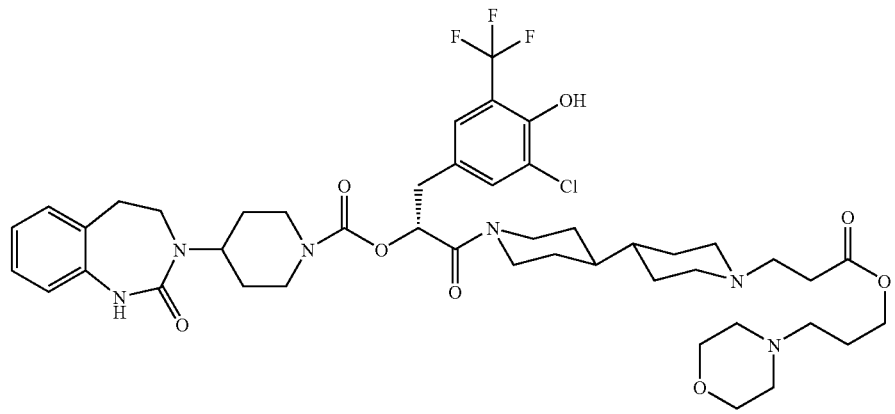 |
| (329) | 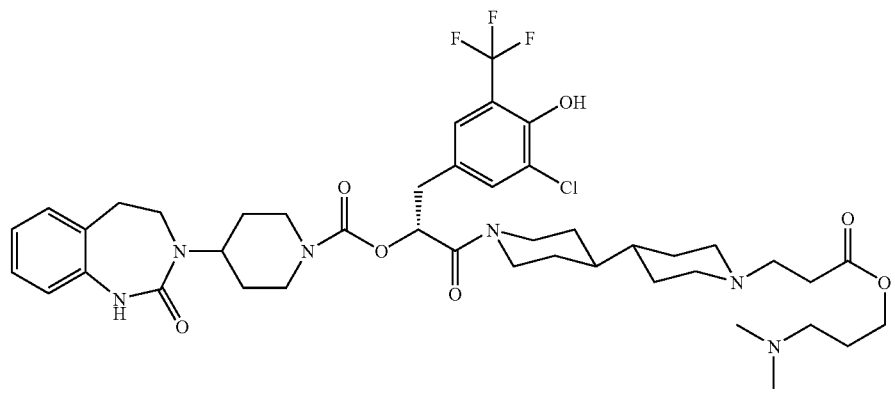 |
| (330) | 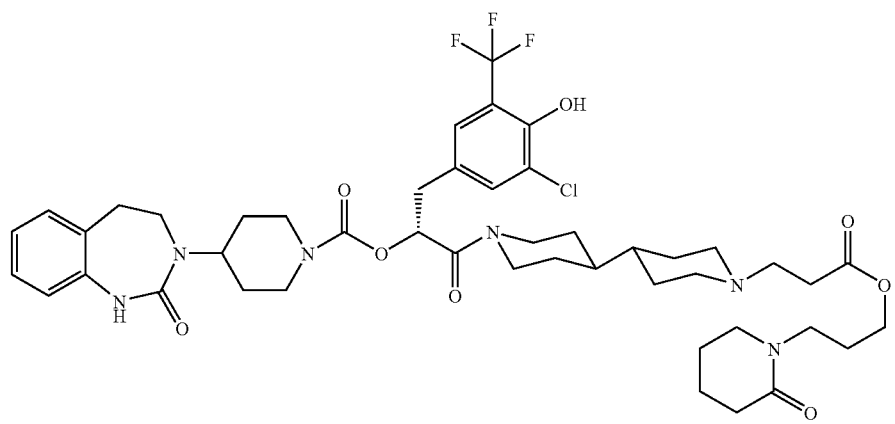 |

| No. | Structure |
|---|---|
| (331) | 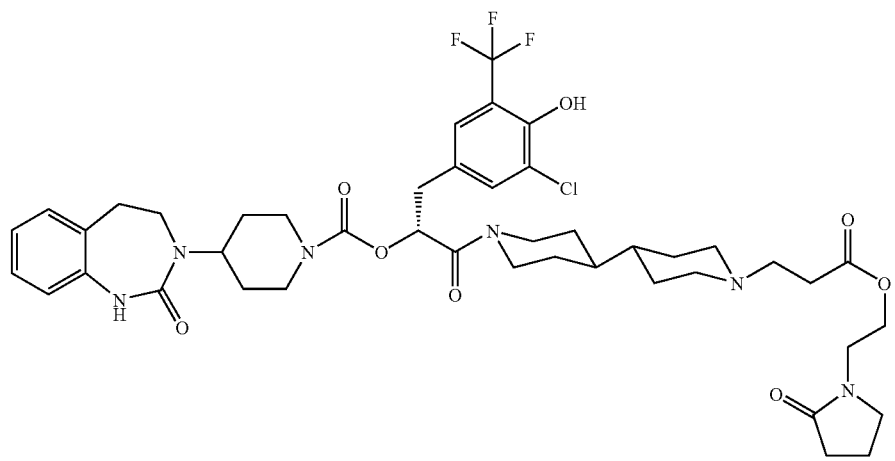 |
| (332) | 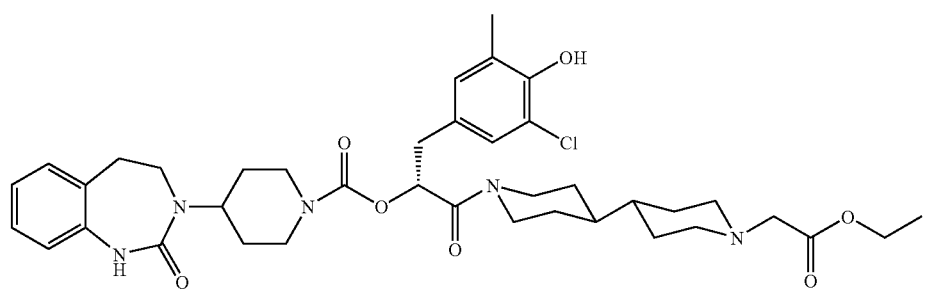 |
| (333) | 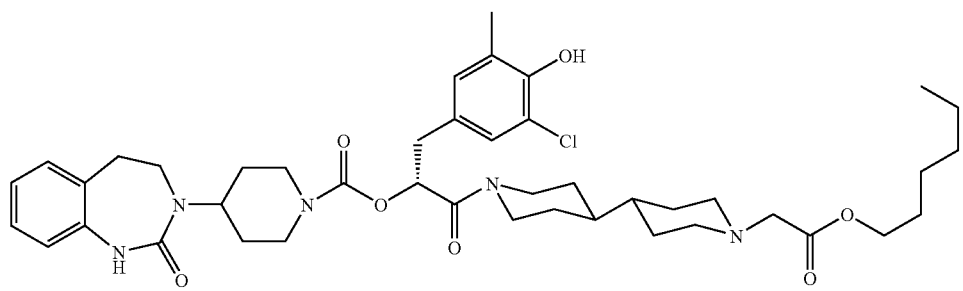 |
| (334) | 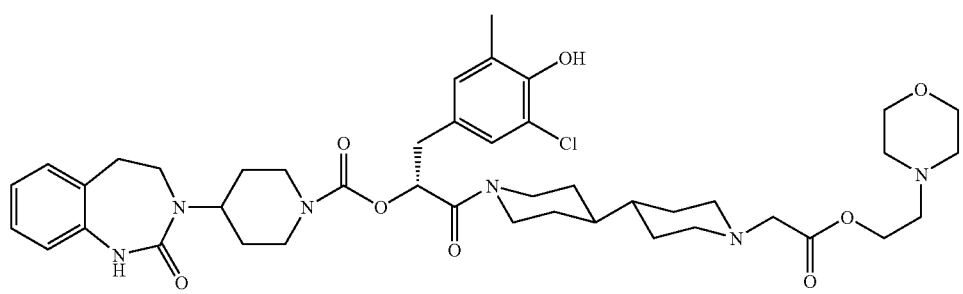 |

| No. | Structure |
|---|---|
| (335) | 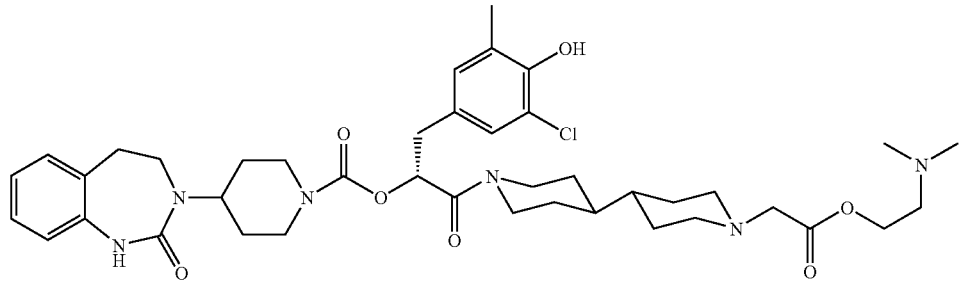 |
| (336) | 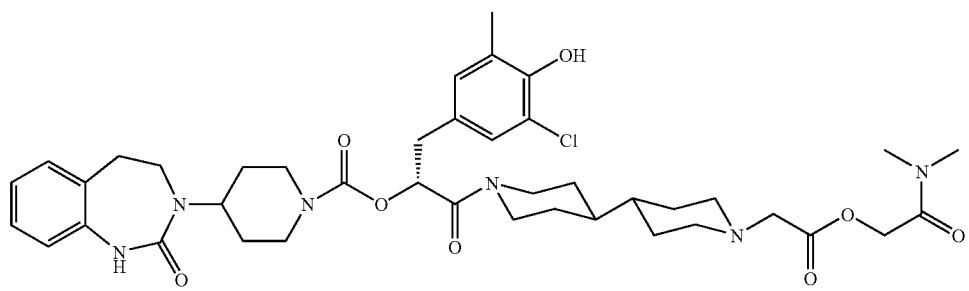 |
| (337) | 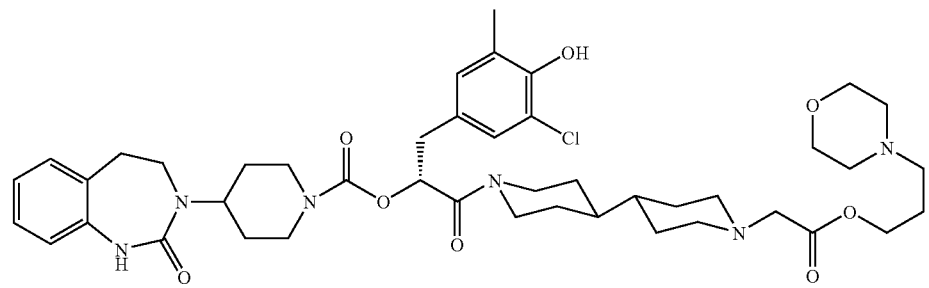 |
| (338) | 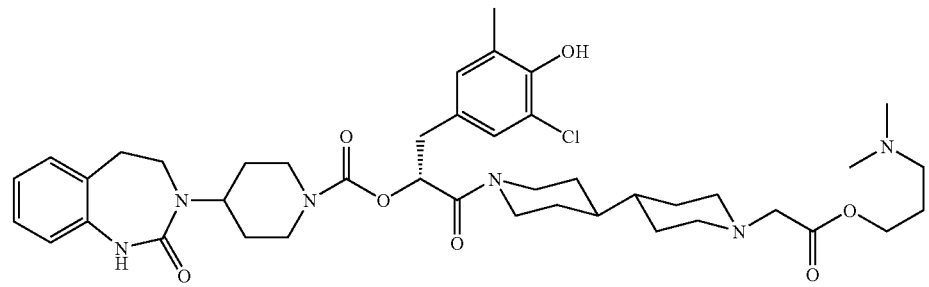 |
| (339) | 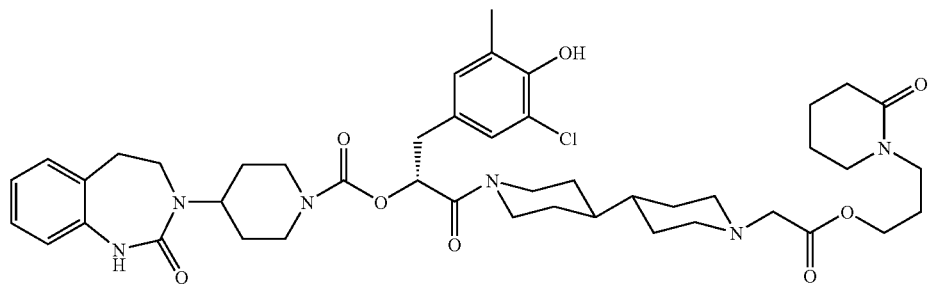 |

| No. | Structure |
|---|---|
| (340) | 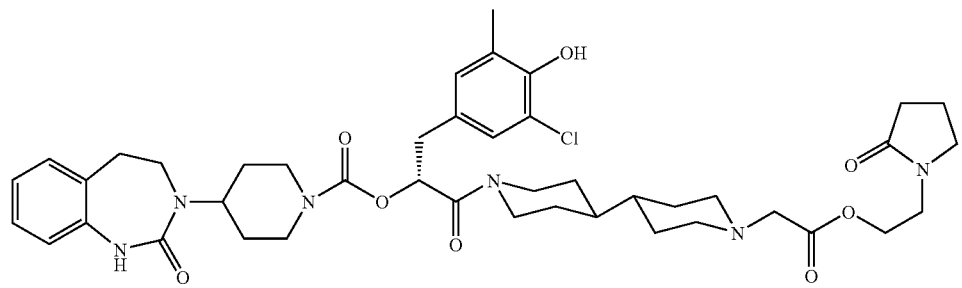 |
| (341) | 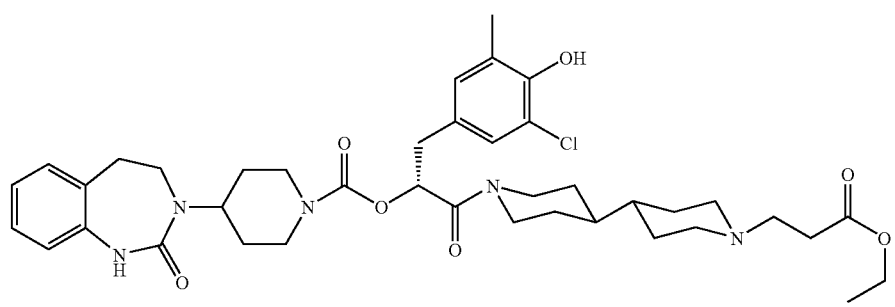 |
| (342) | 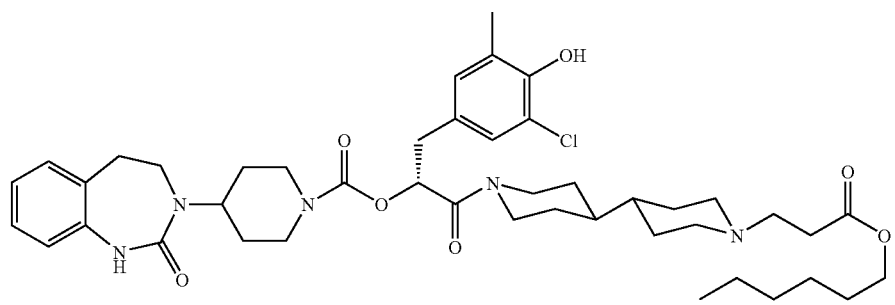 |
| (343) | 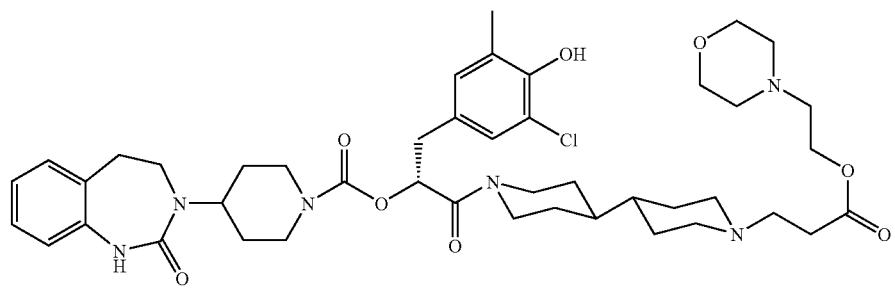 |
| (344) | 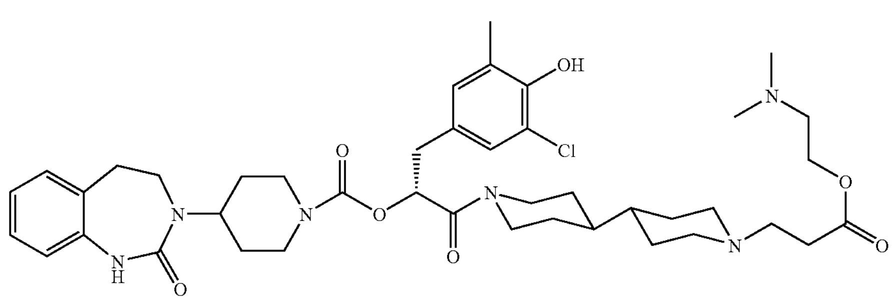 |

| No. | Structure |
|---|---|
| (345) | 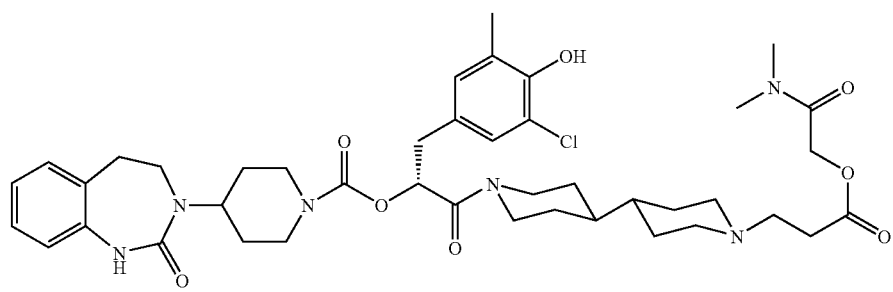 |
| (346) | 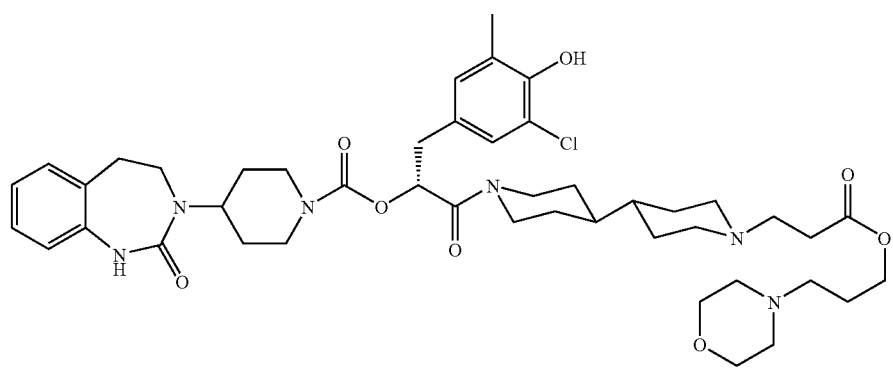 |
| (347) | 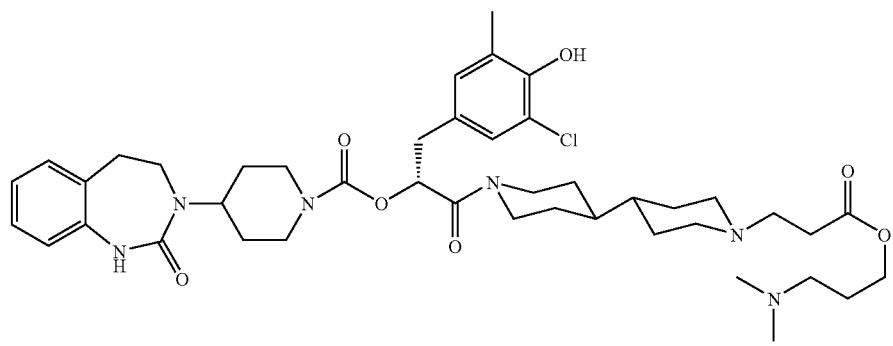 |
| (348) | 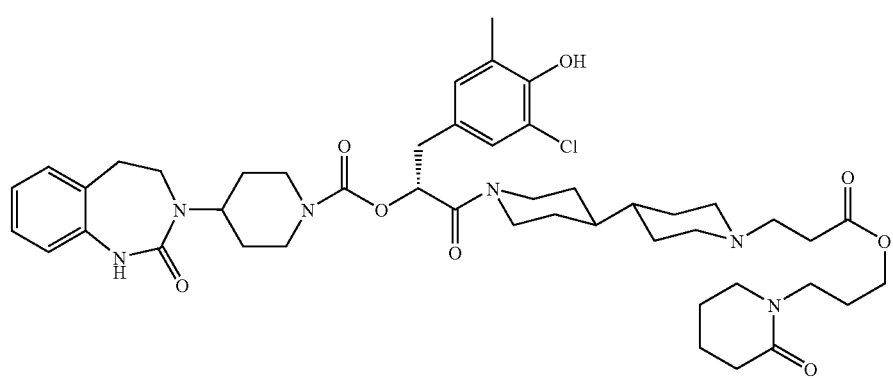 |

| No. | Structure |
|---|---|
| (349) | 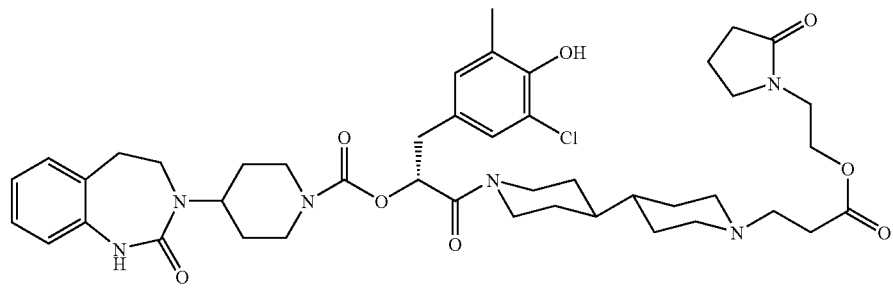 |
| (350) | 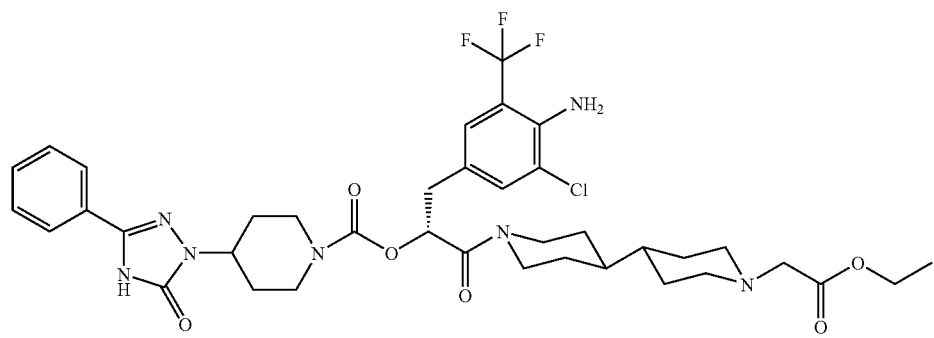 |
| (351) | 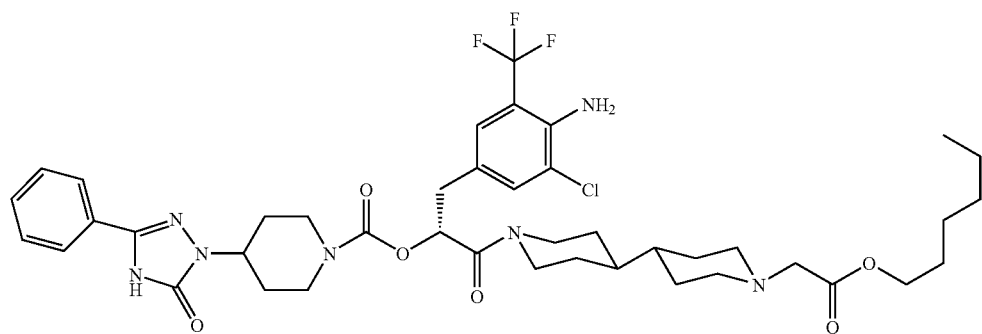 |
| (352) | 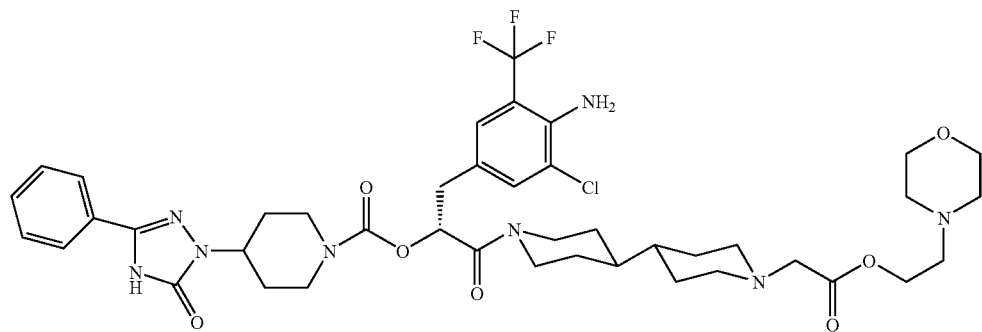 |

| No. | Structure |
|---|---|
| (353) | 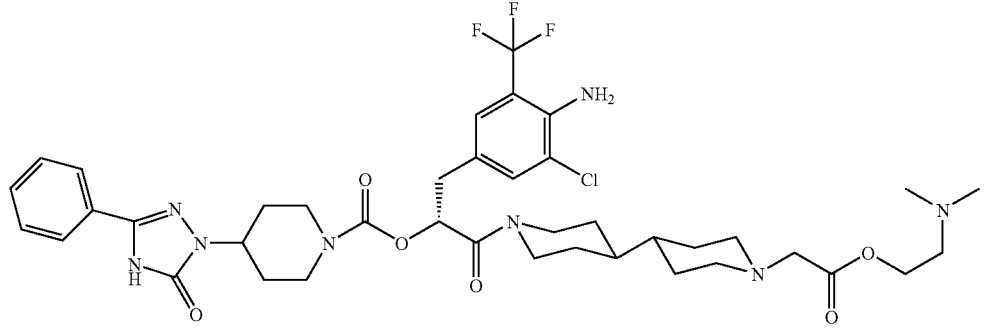 |
| (354) | 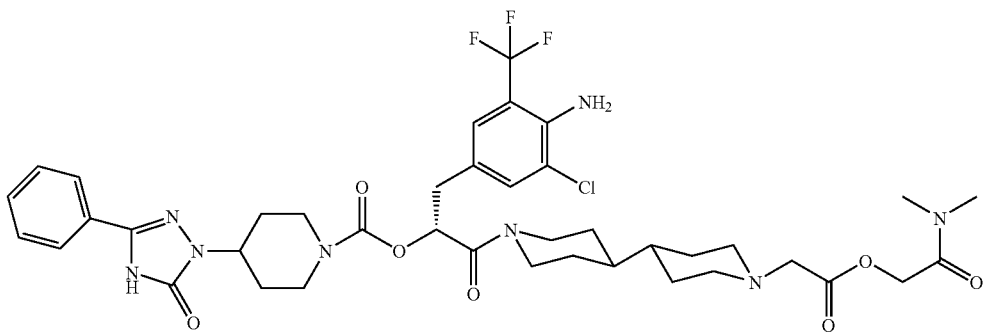 |
| (355) | 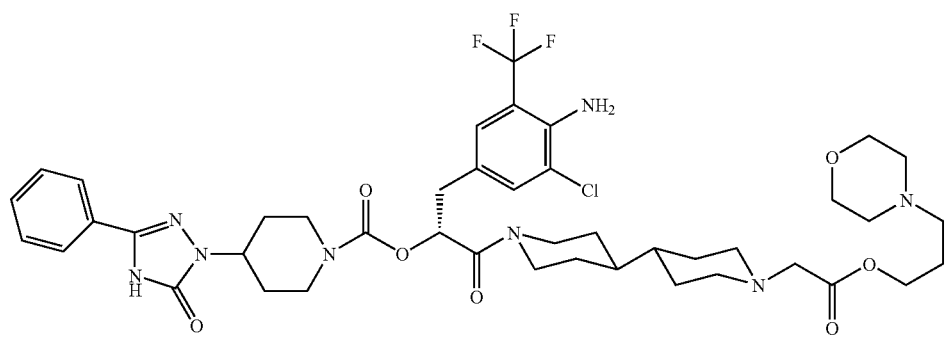 |
| (356) | 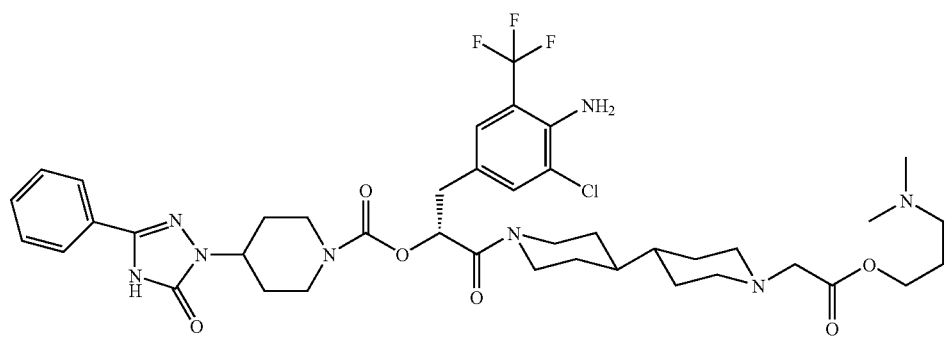 |

| No. | Structure |
|---|---|
| (357) | 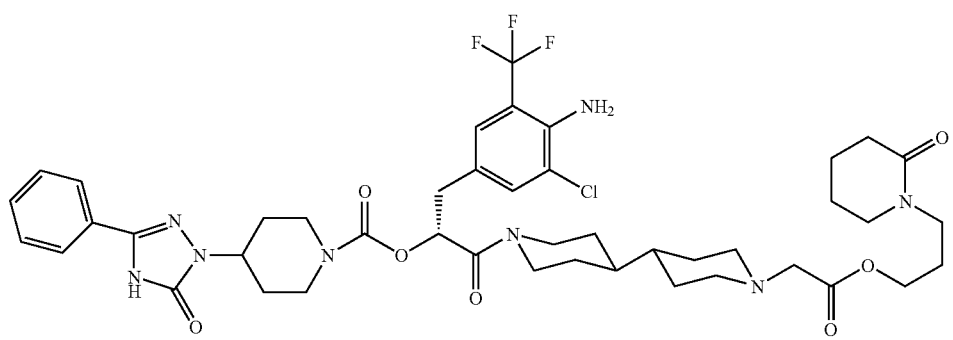 |
| (358) | 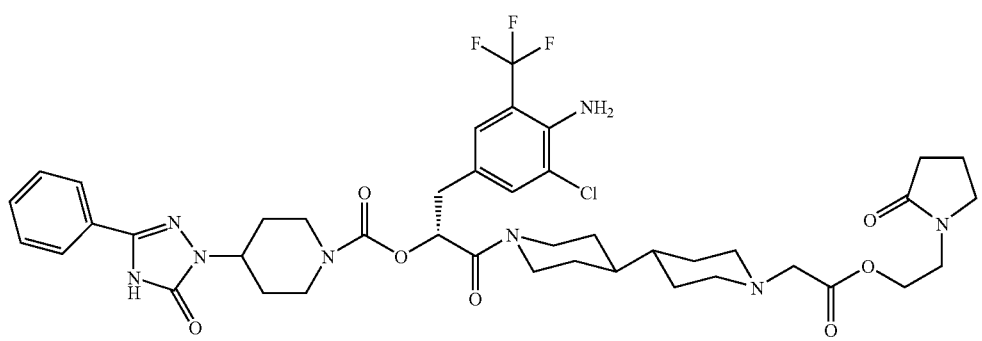 |
| (359) | 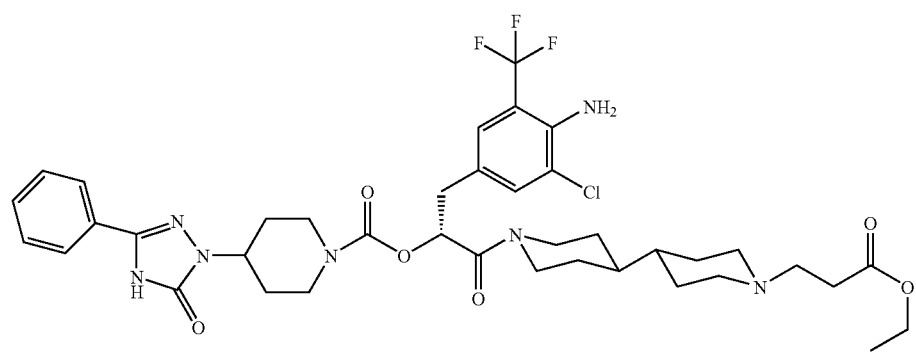 |
| (360) | 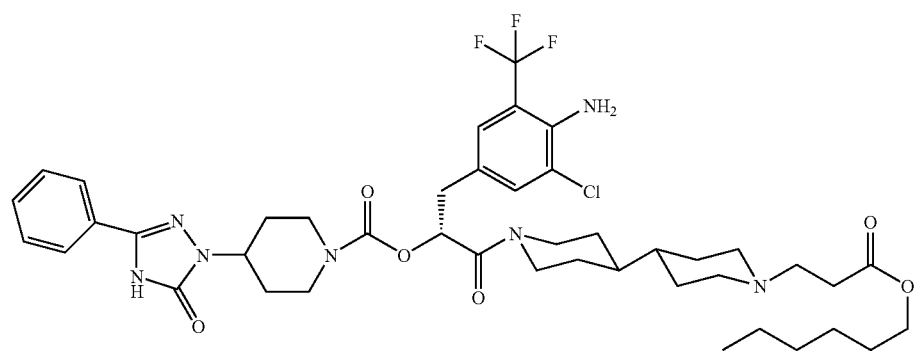 |

| No. | Structure |
|---|---|
| (361) | 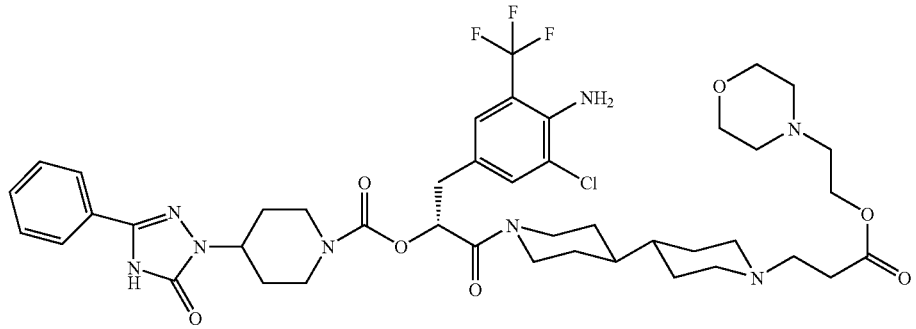 |
| (362) | 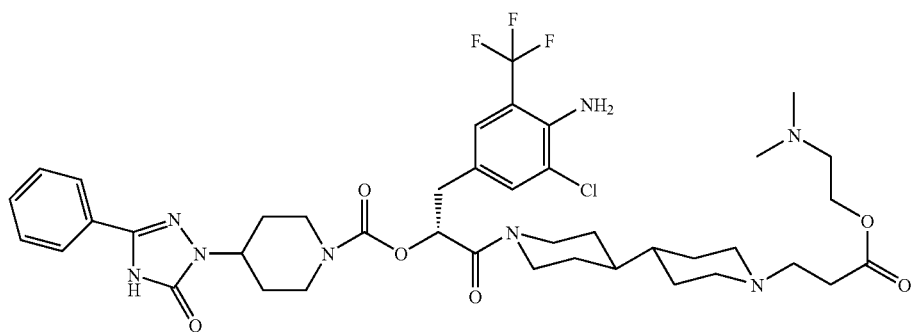 |
| (363) | 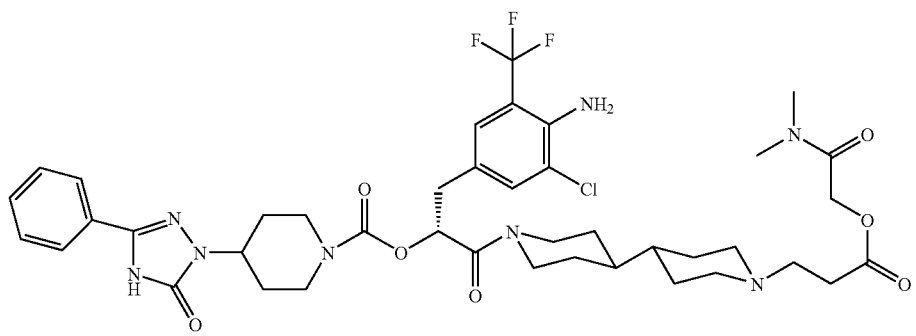 |
| (364) | 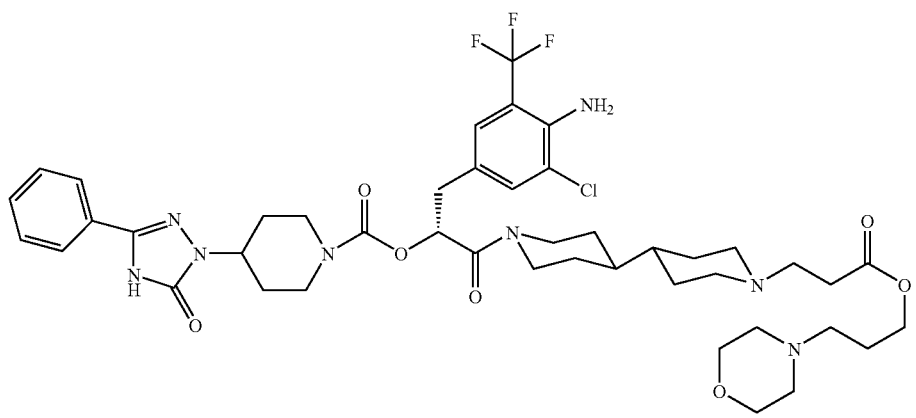 |

| No. | Structure |
|---|---|
| (365) | 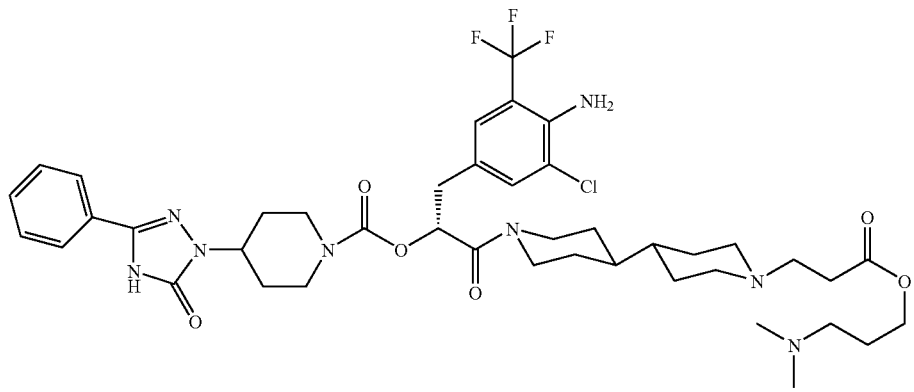 |
| (366) | 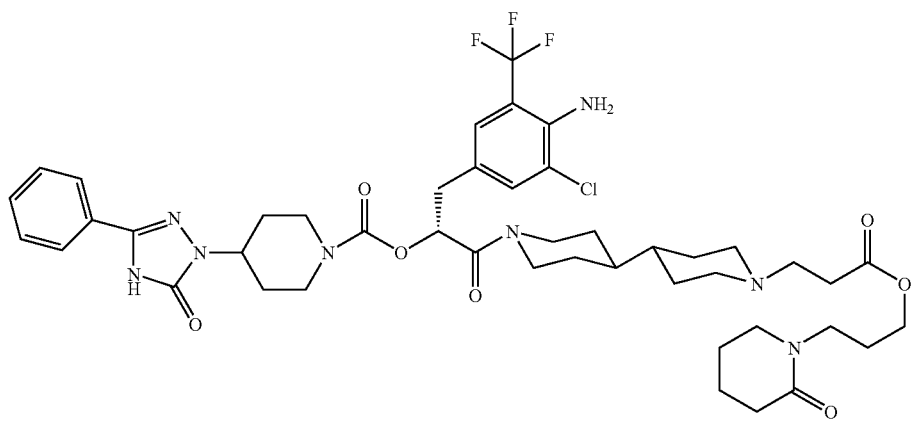 |
| (367) | 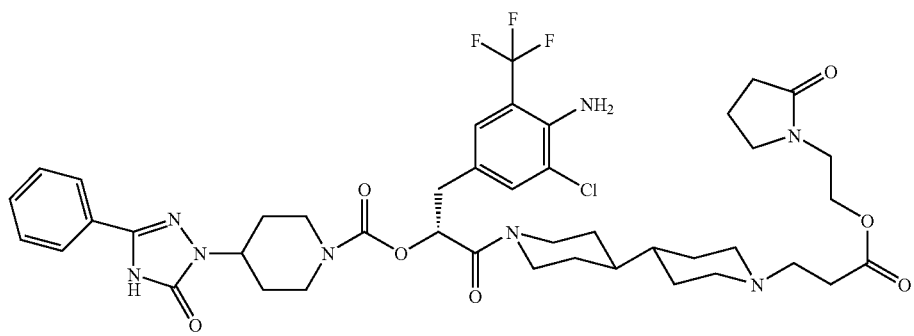 |
| (368) | 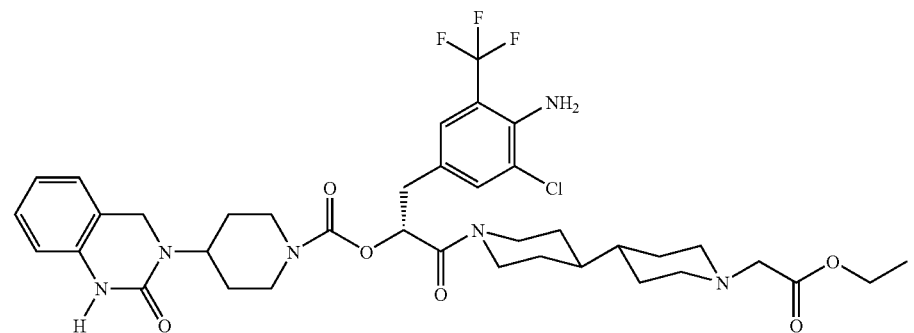 |

| No. | Structure |
|---|---|
| (369) | 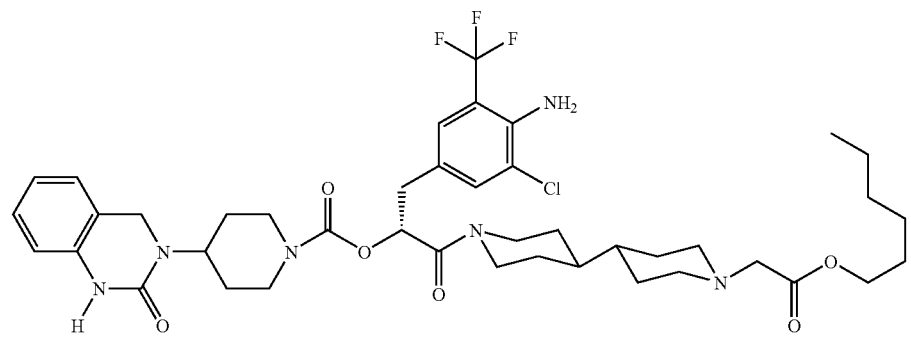 |
| (370) | 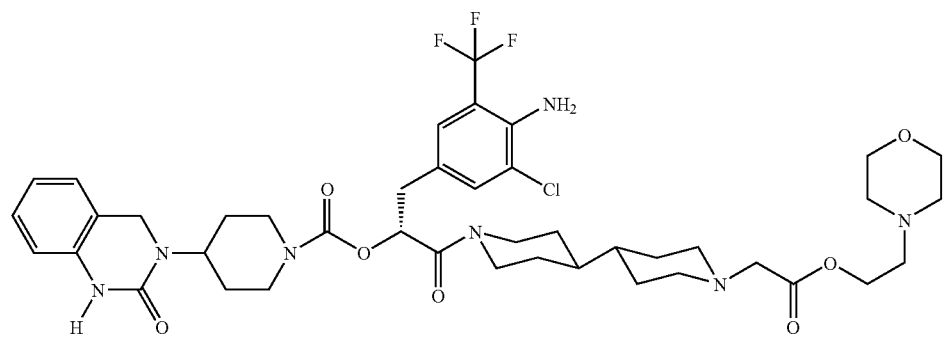 |
| (371) | 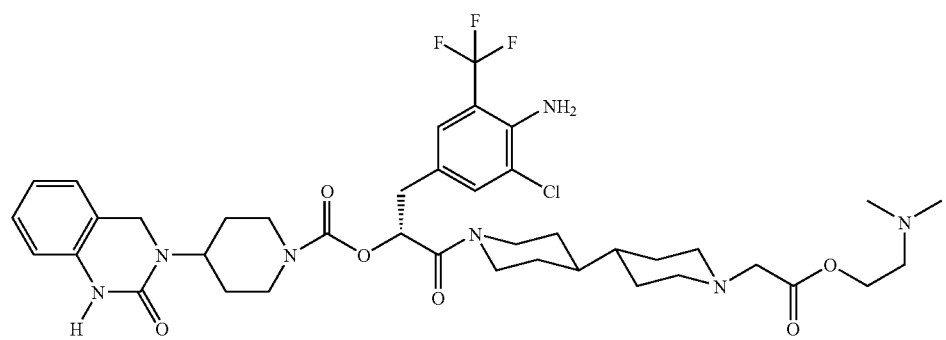 |
| (372) | 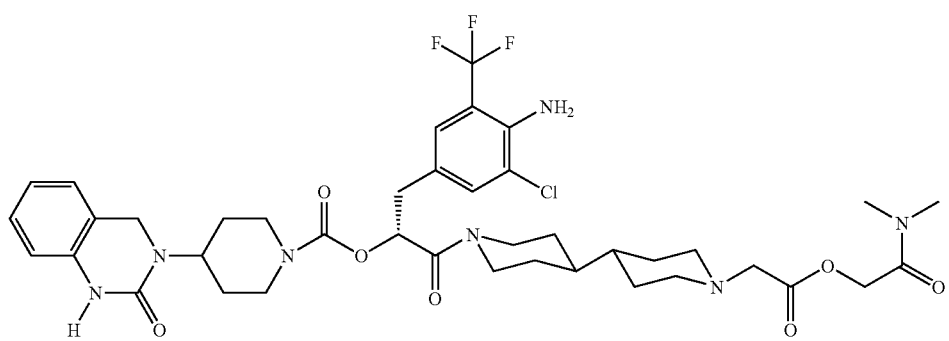 |

US 7,858,622 B2
265 266
-continued
| No. | Structure |
|---|---|
| (373) | 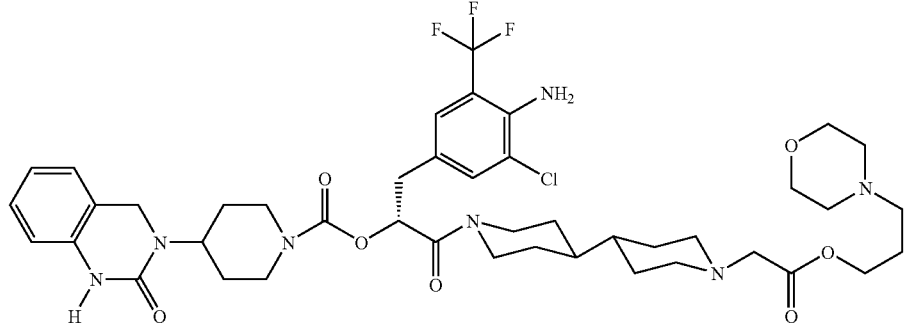 |
| (374) | 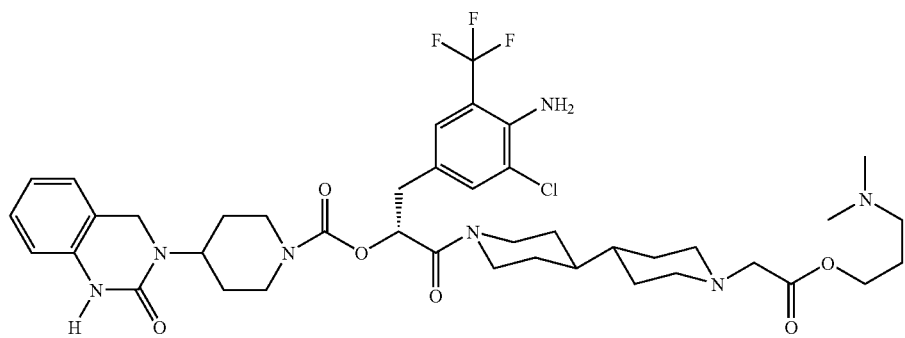 |
| (375) | 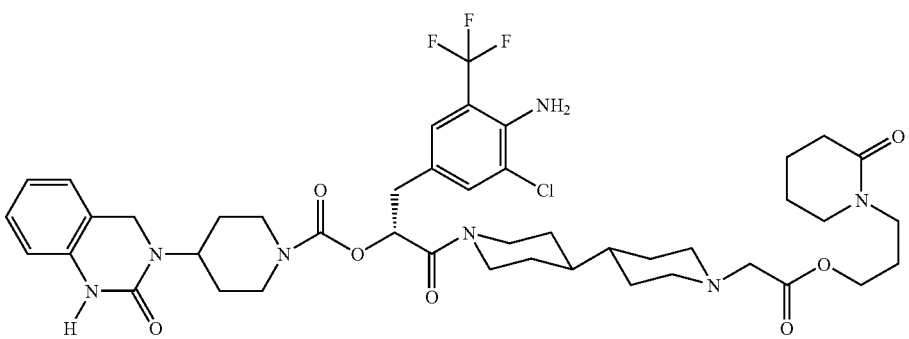 |
| (376) | 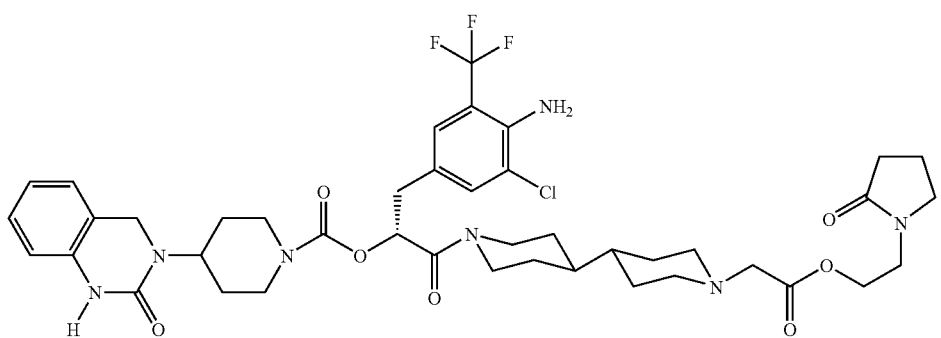 |

| No. | Structure |
|---|---|
| (377) | 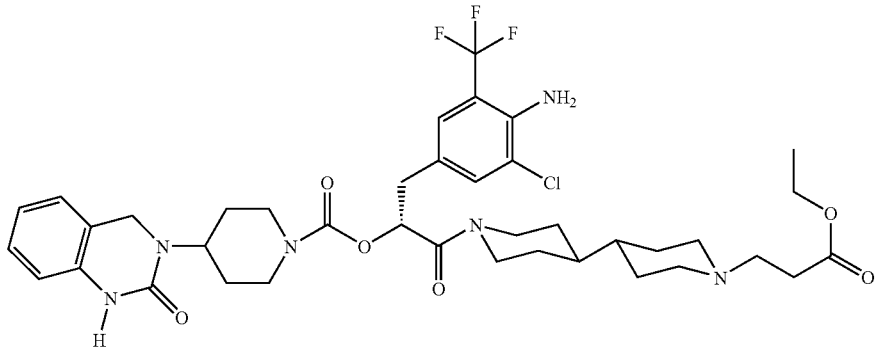 |
| (378) | 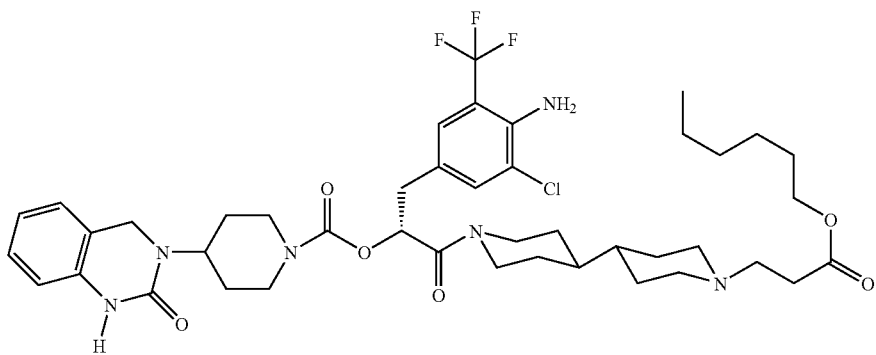 |
| (379) | 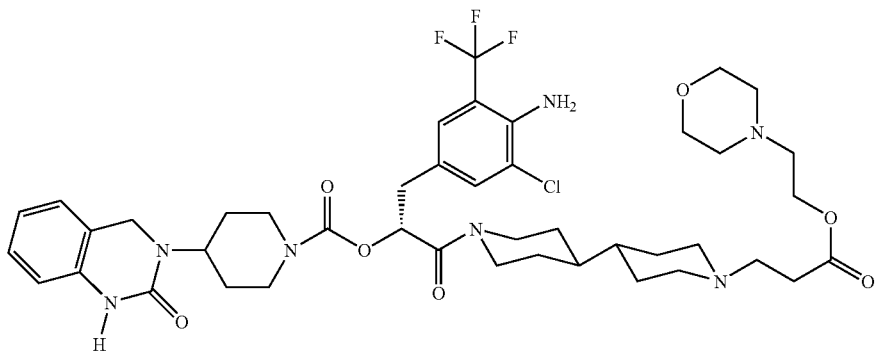 |
| (380) | 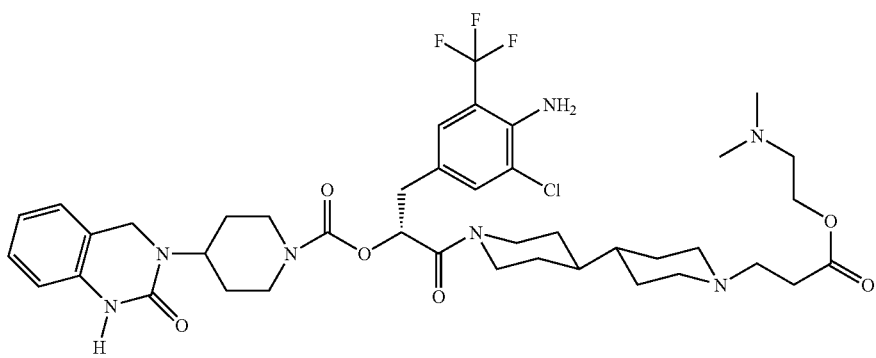 |

| No. | Structure |
|---|---|
| (381) | 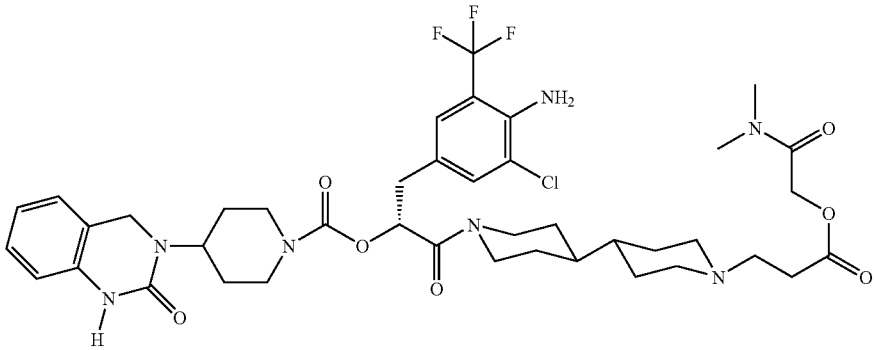 |
| (382) | 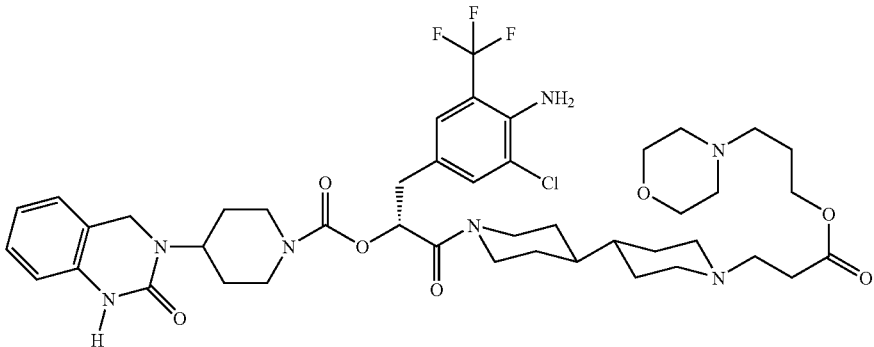 |
| (383) | 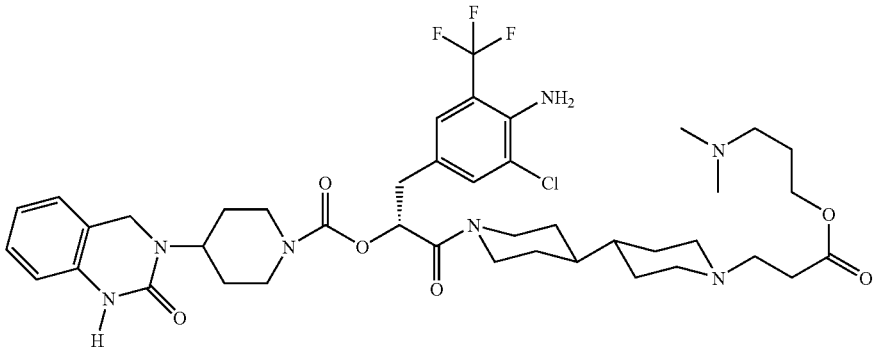 |
| (384) | 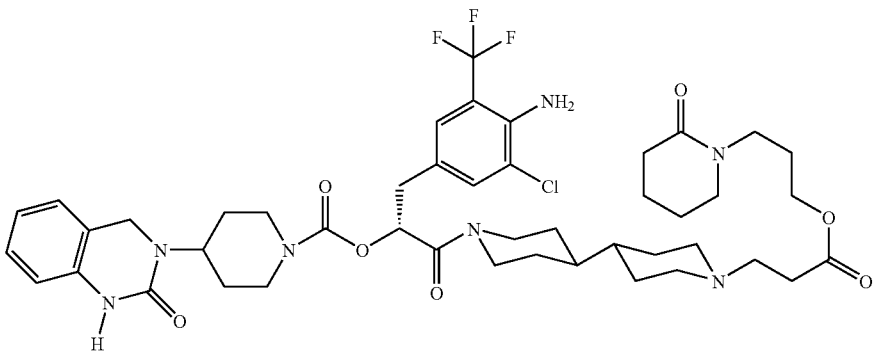 |

-continued

| No. | Structure |
|---|---|
| (385) | 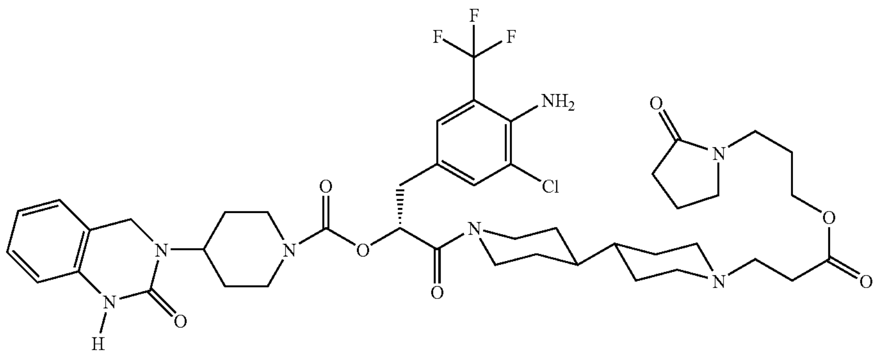 |
| (386) | 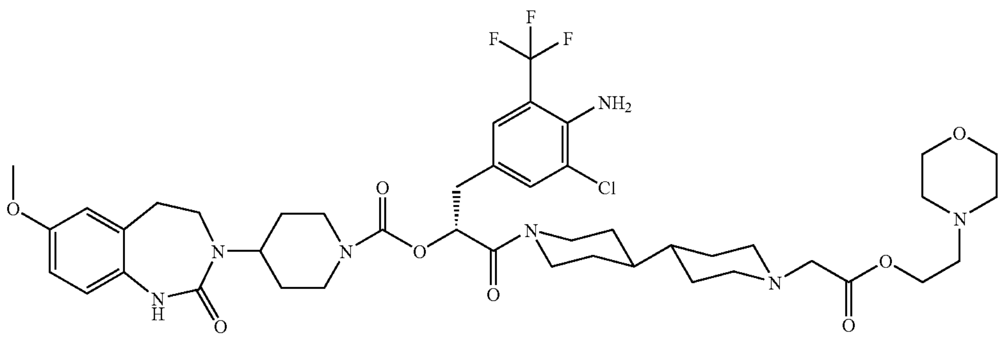 |
| (387) | 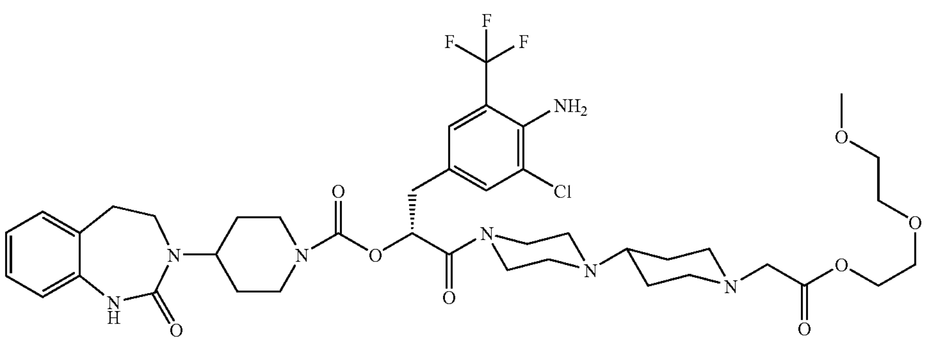 |
| (388) | 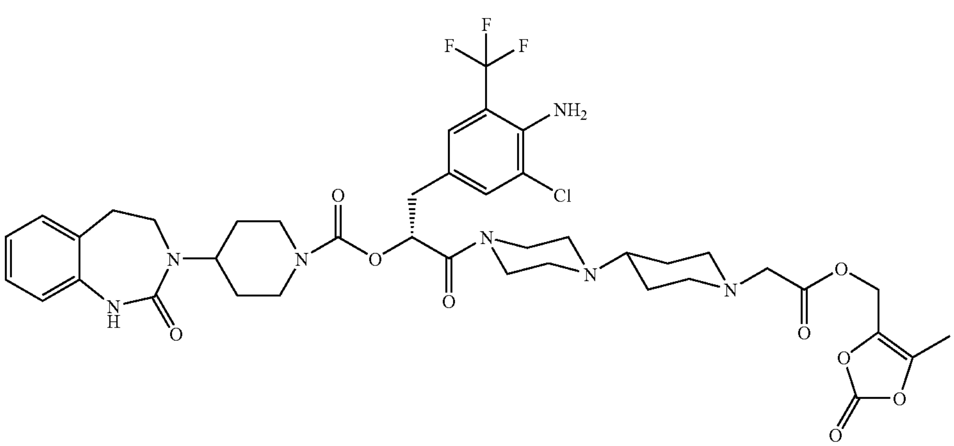 |

| No. | Structure |
|---|---|
| (389) | 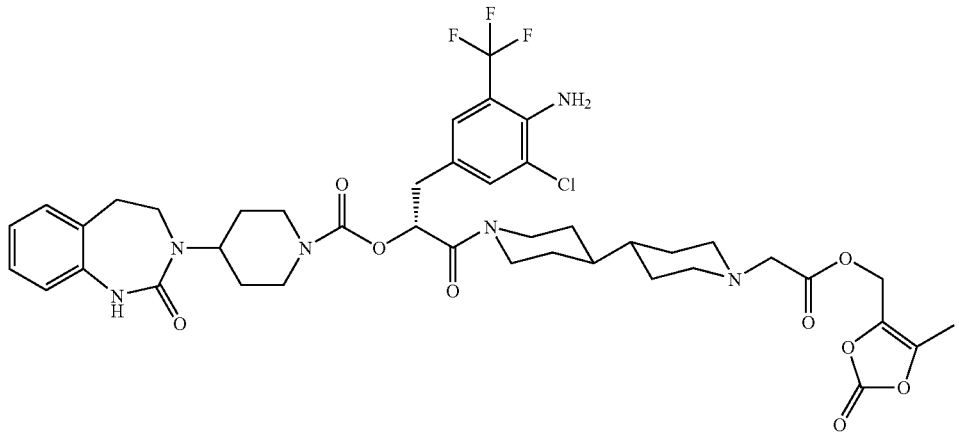 |
| (390) | 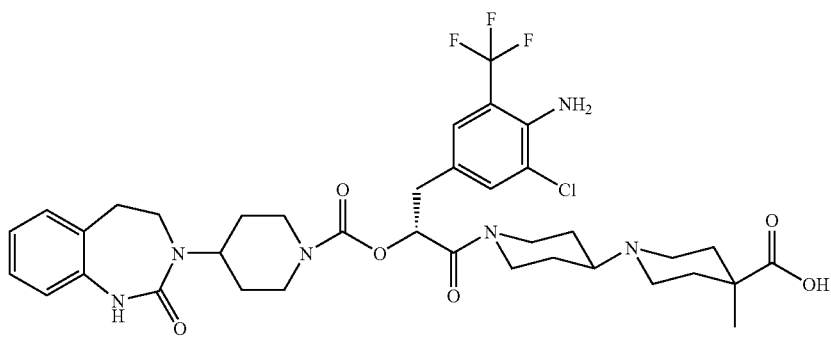 |
| (391) | 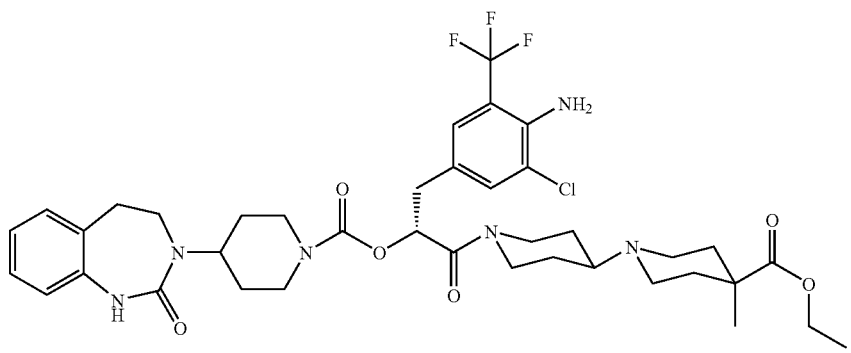 |
| (392) | 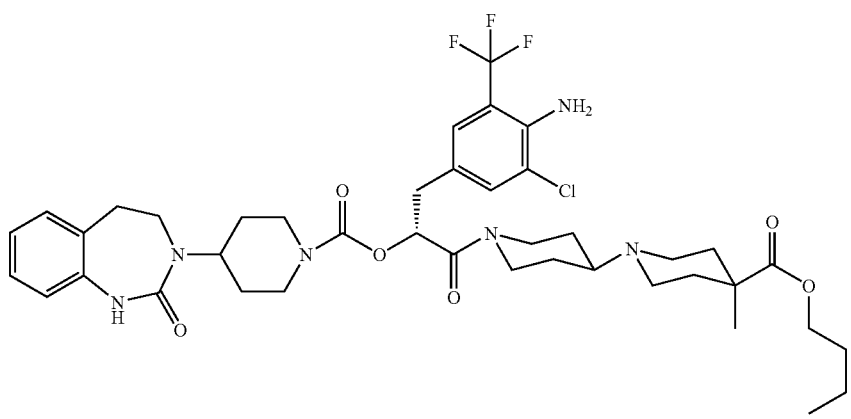 |

| No. | Structure |
|---|---|
| (393) | 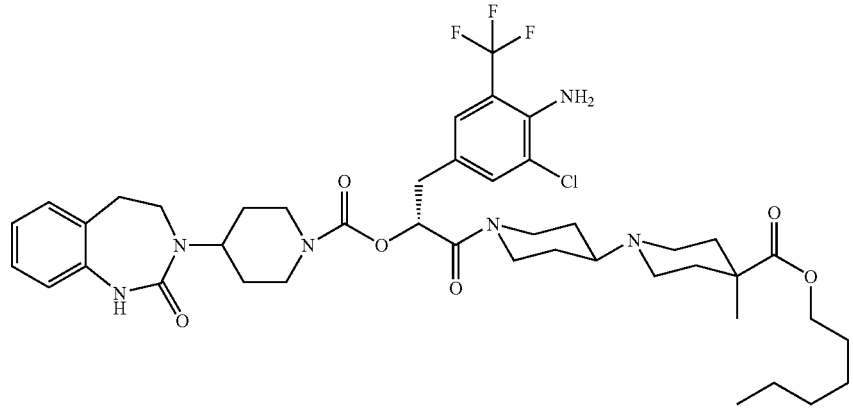 |
| (394) | 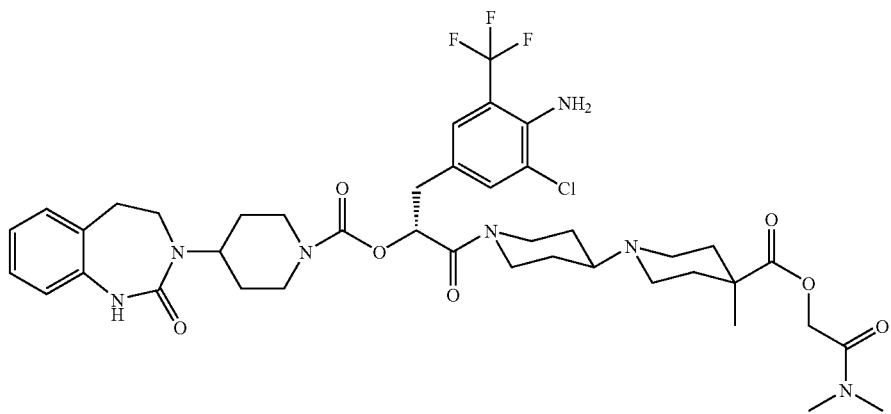 |
| (395) | 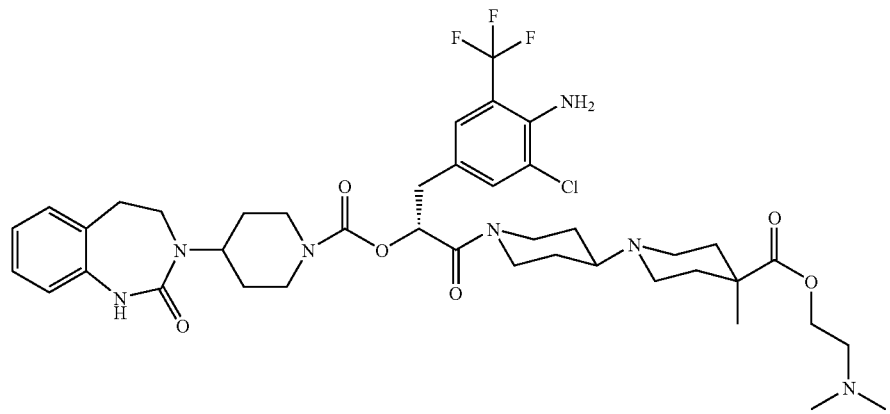 |

| No. | Structure |
|---|---|
| (396) | 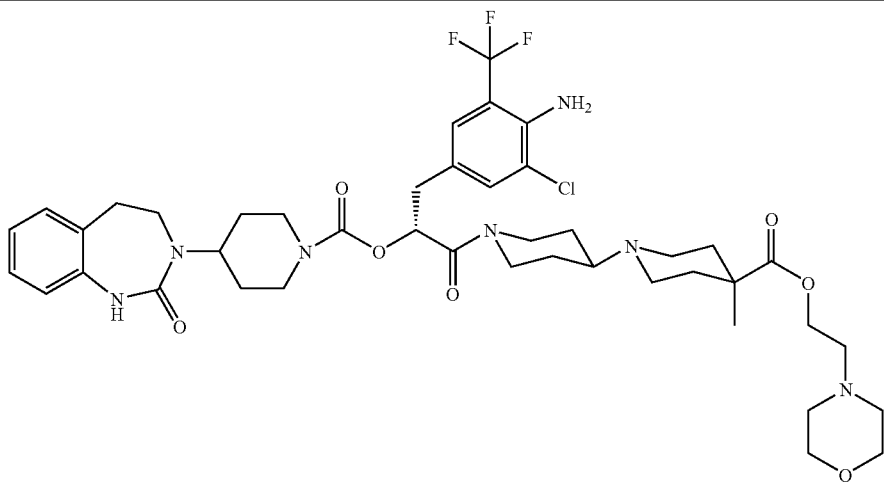 |
| (397) | 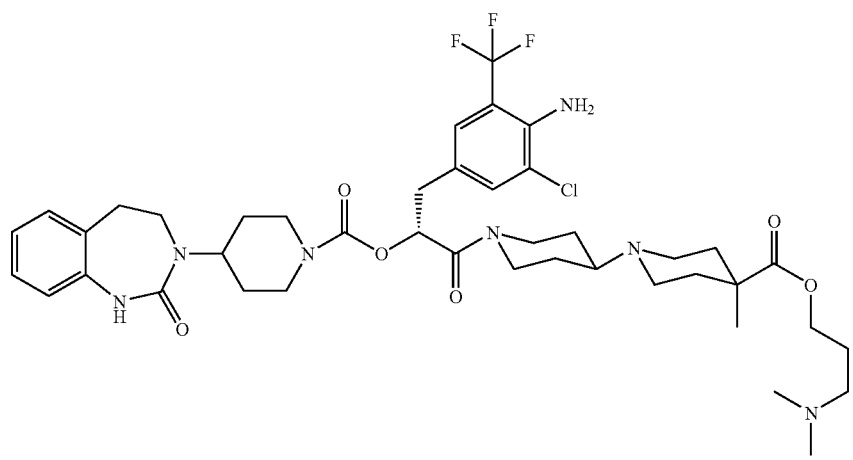 |
| (398) | 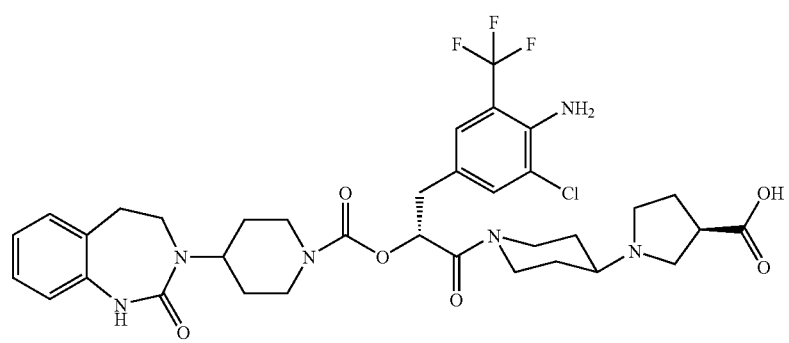 |
| (399) | 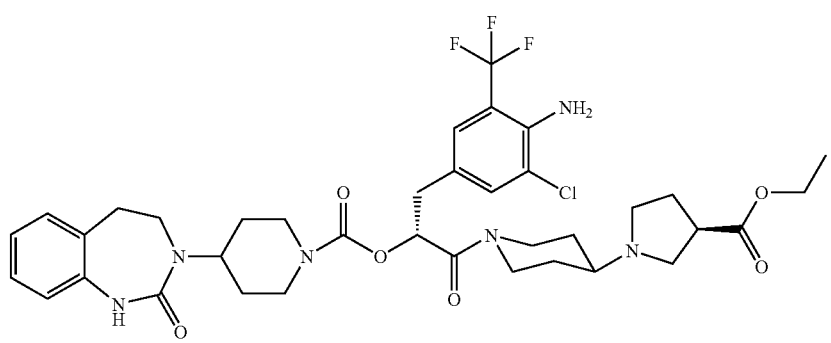 |

| No. | Structure |
|---|---|
| (400) | 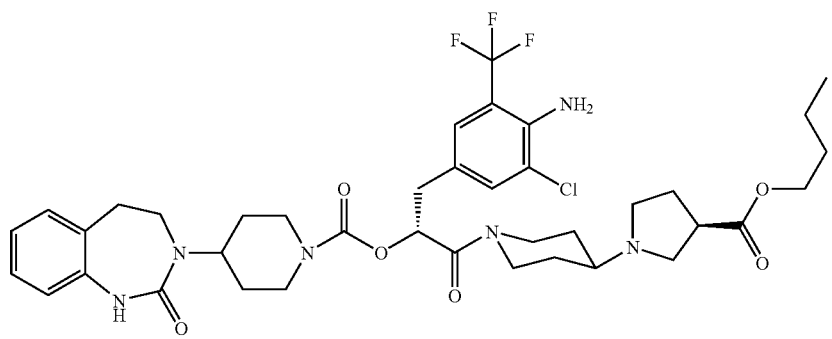 |
| (401) | 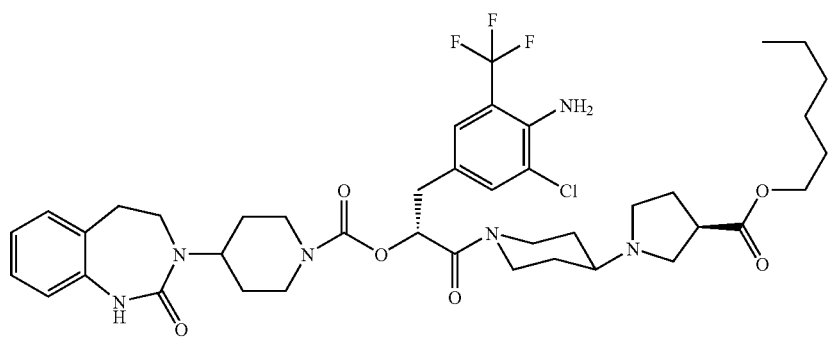 |
| (402) | 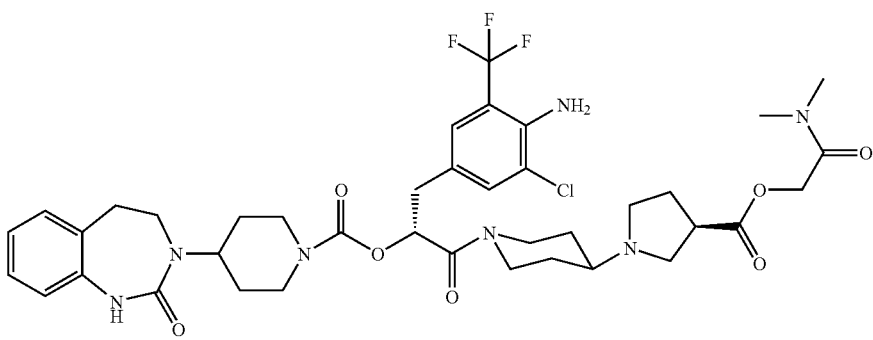 |
| (403) | 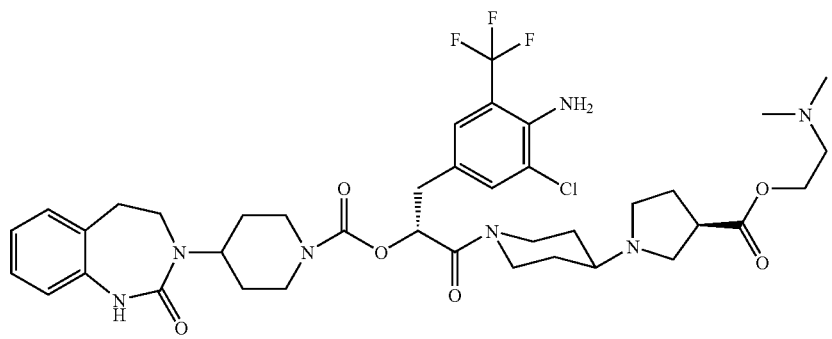 |

| No. | Structure |
|---|---|
| (404) | 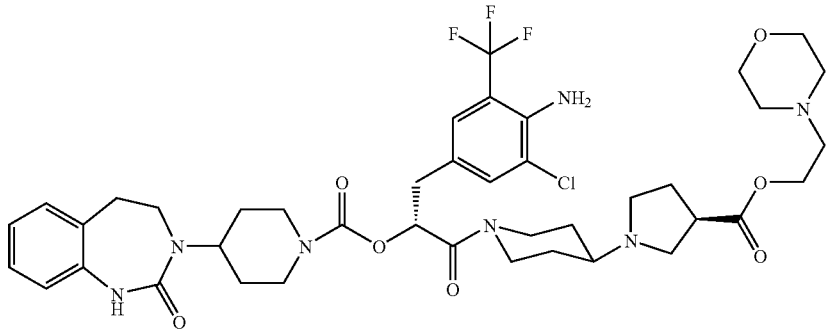 |
| (405) | 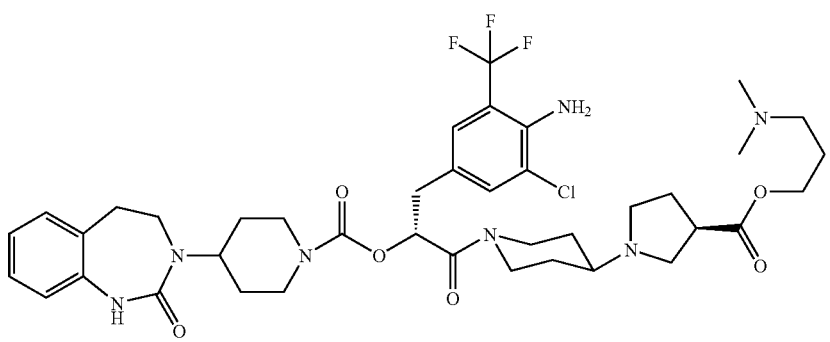 |
| (406) | 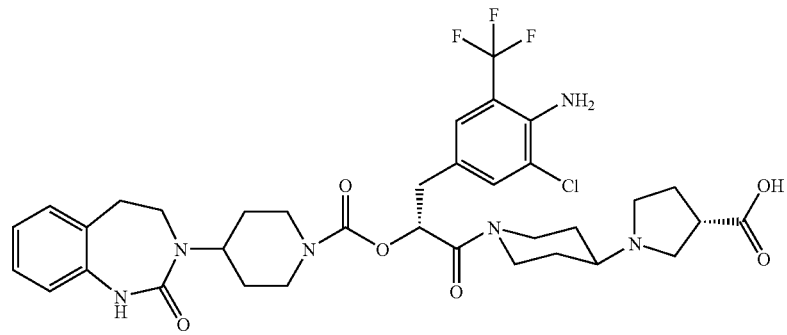 |
| (407) | 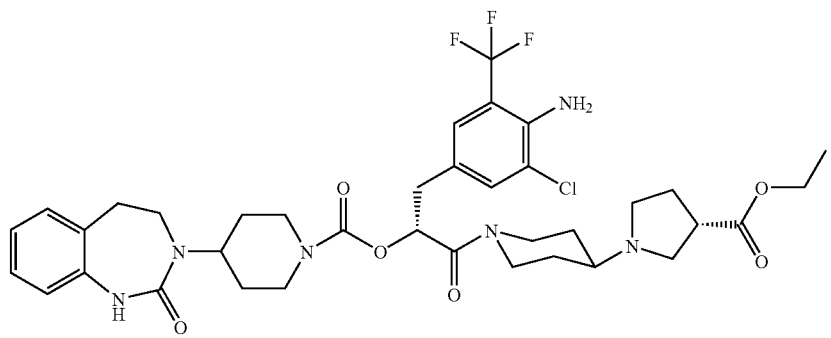 |

| No. | Structure |
|---|---|
| (408) | 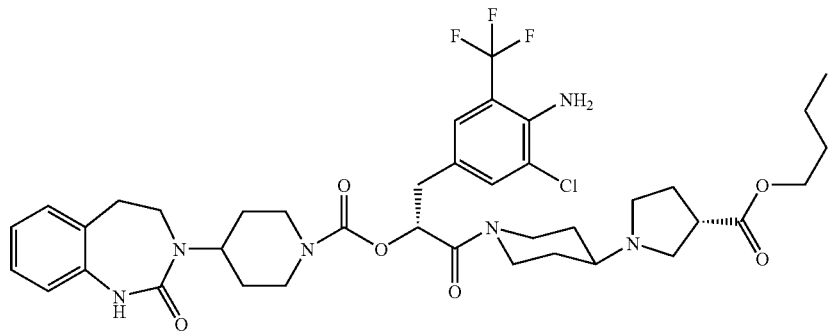 |
| (409) | 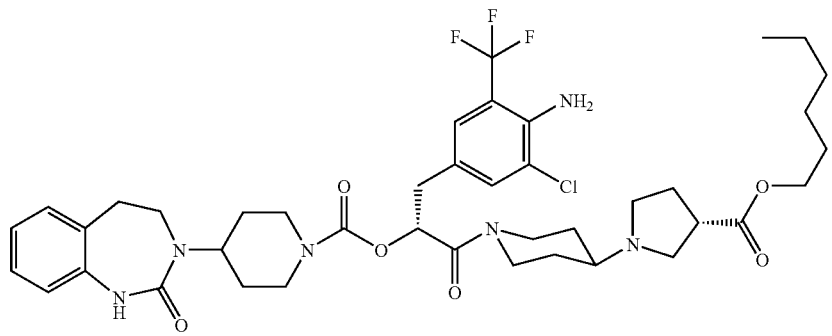 |
| (410) | 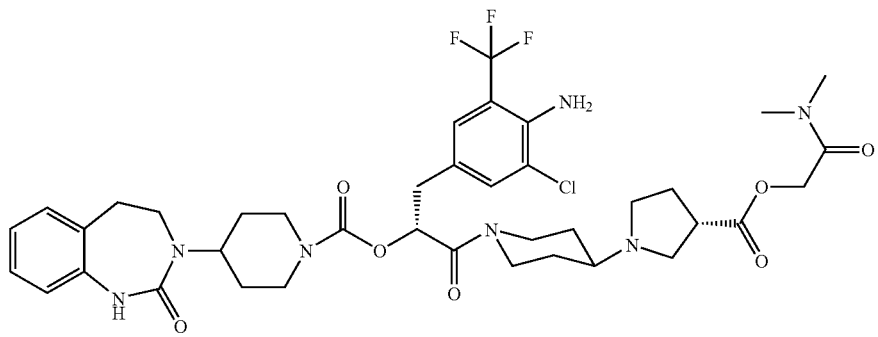 |
| (411) | 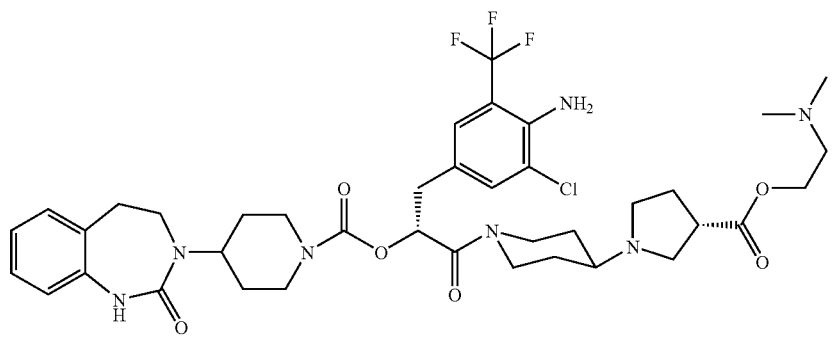 |

| No. | Structure |
|---|---|
| (412) | 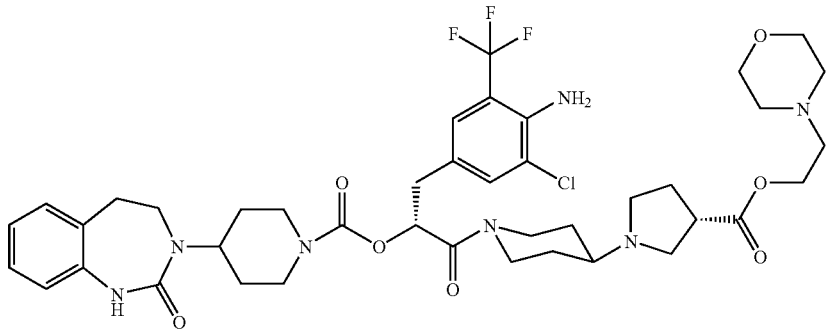 |
| (413) | 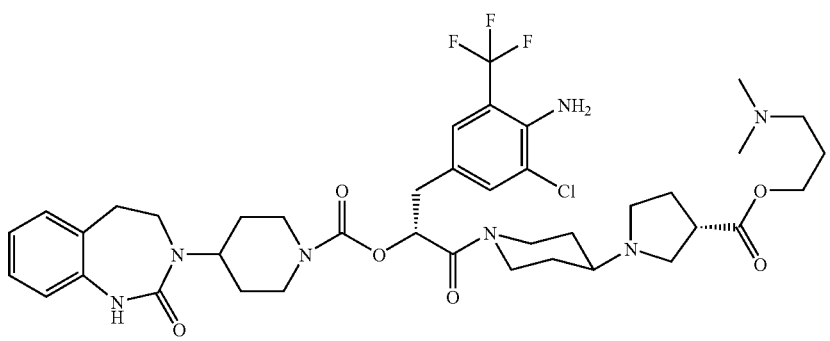 |
| (414) | 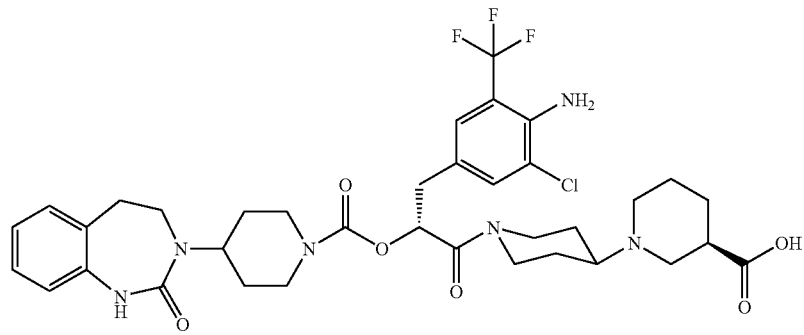 |
| (415) | 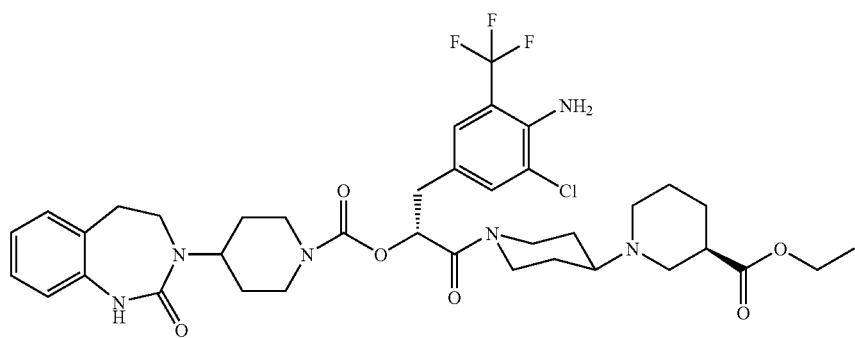 |

| No. | Structure |
|---|---|
| (416) | 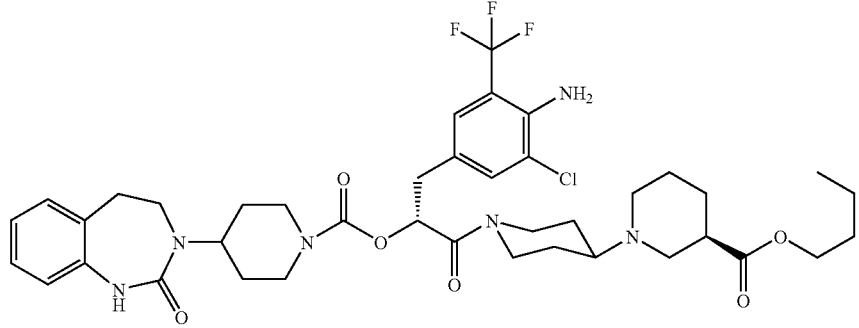 |
| (417) | 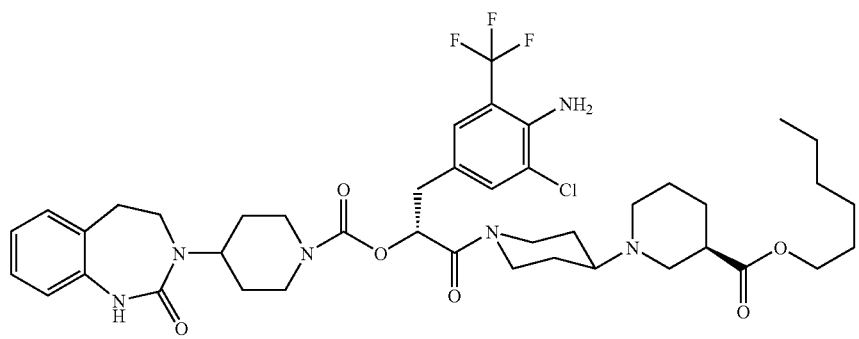 |
| (418) | 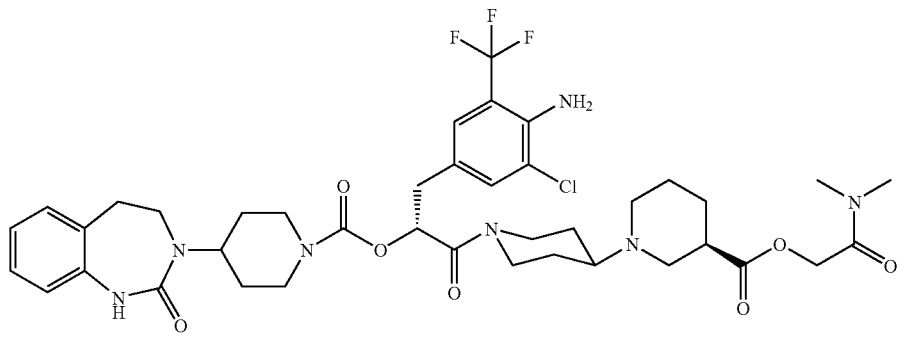 |
| (419) | 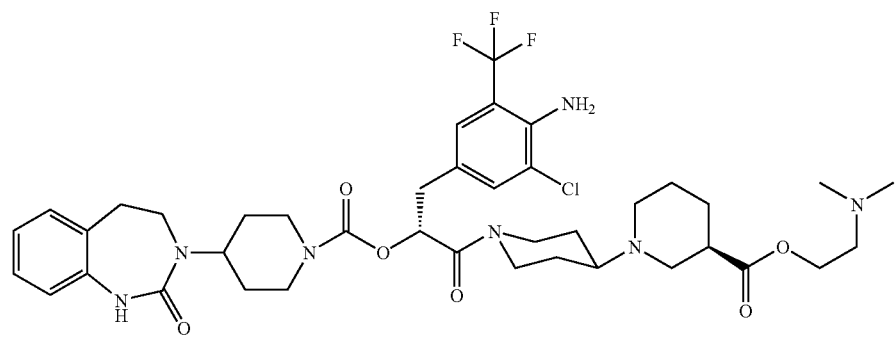 |

| No. | Structure |
|---|---|
| (420) | 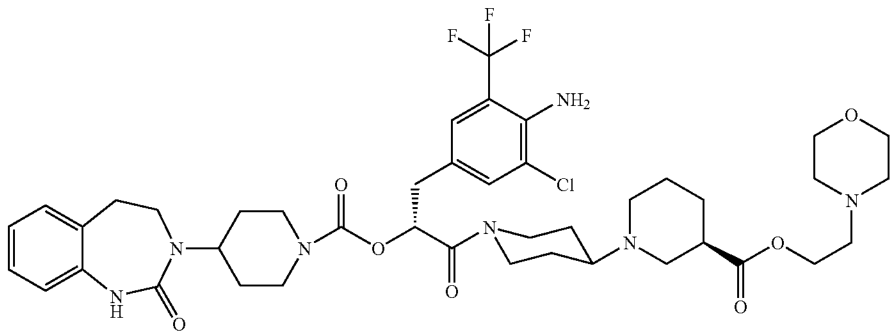 |
| (421) | 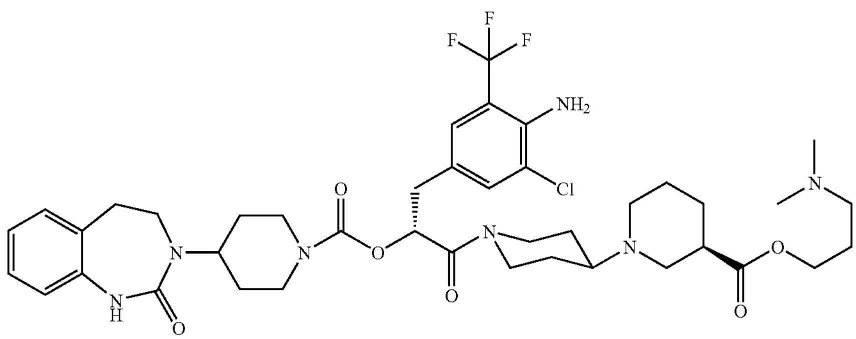 |
| (422) | 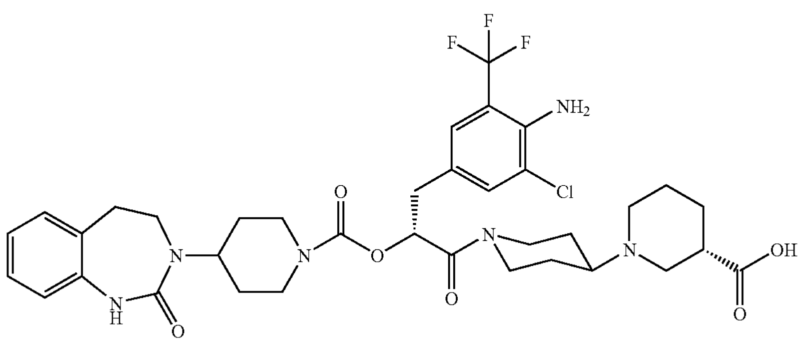 |
| (423) | 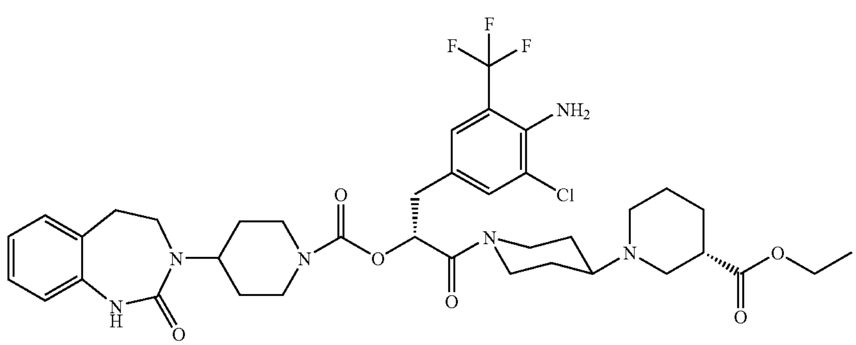 |

| No. | Structure |
|---|---|
| (424) | 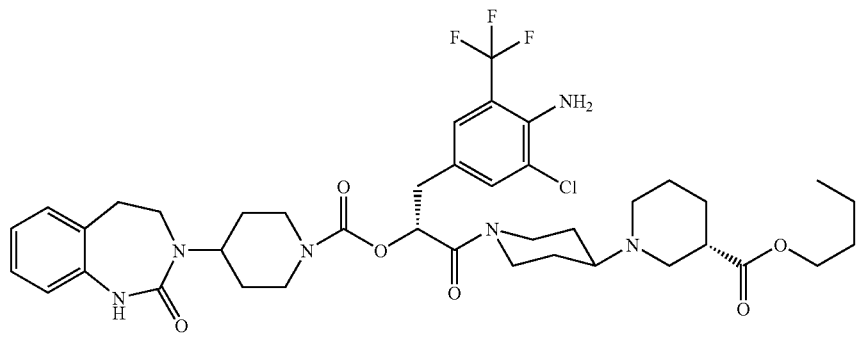 |
| (425) | 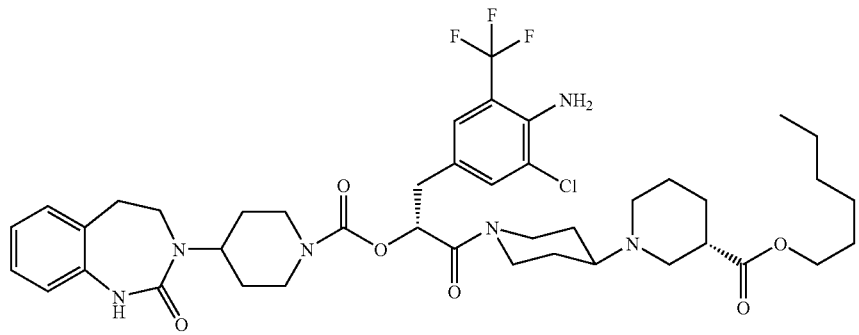 |
| (426) | 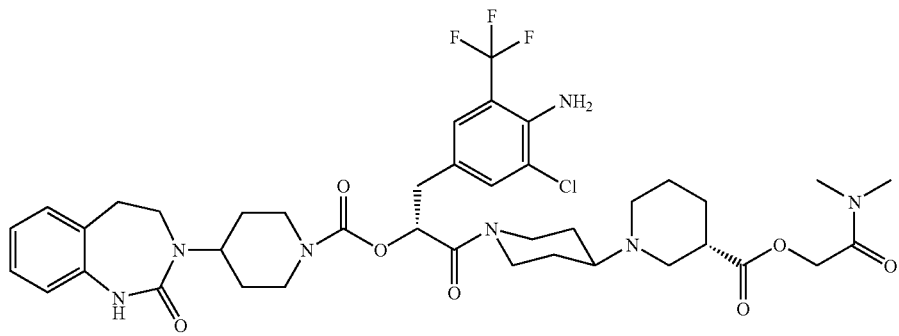 |
| (427) | 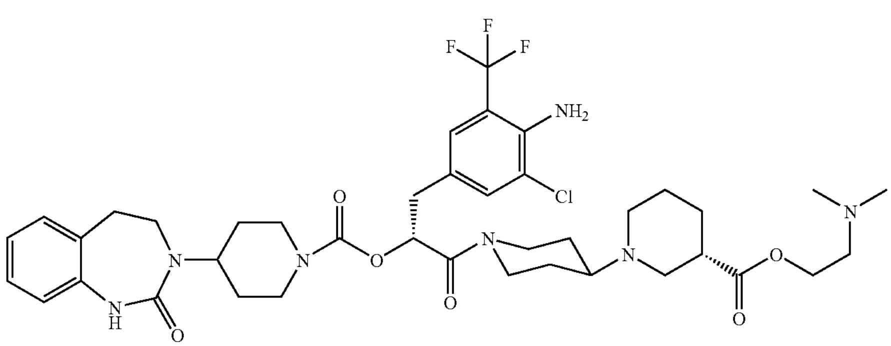 |

| No. | Structure |
|---|---|
| (428) | 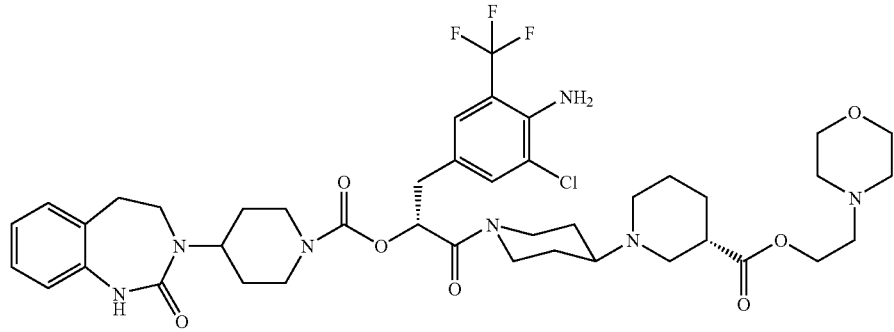 |
| (429) | 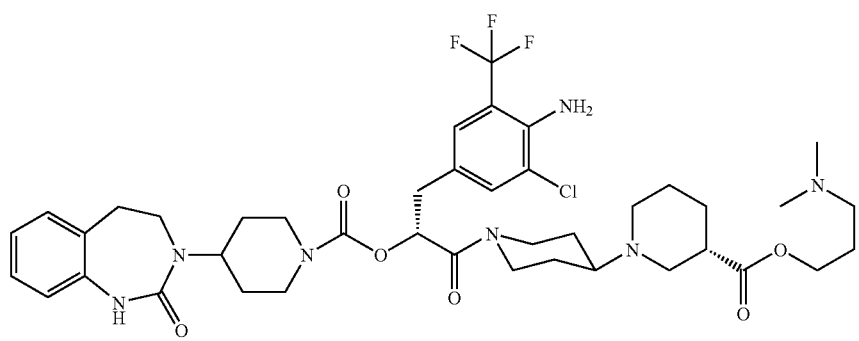 |
| (430) | 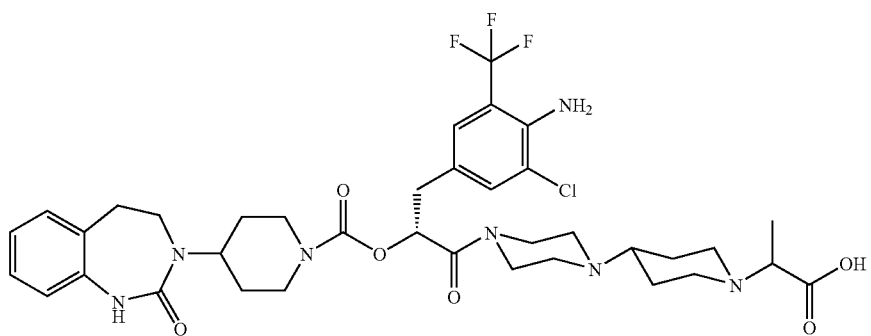 |
| (431) | 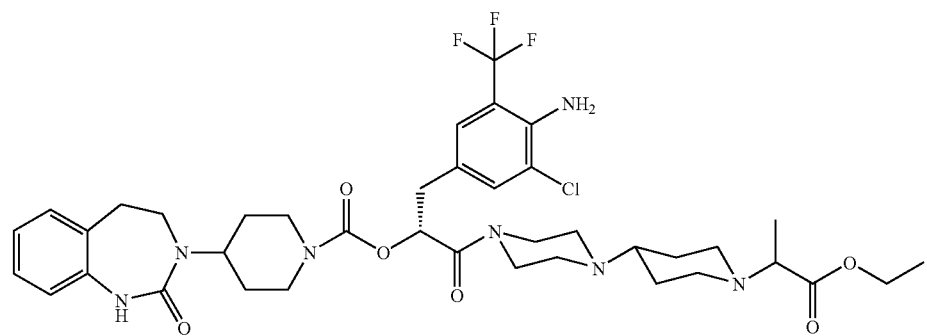 |

| No. | Structure |
|---|---|
| (432) | 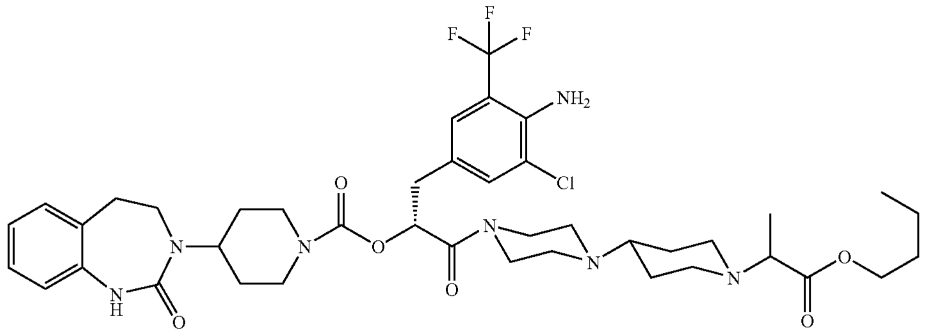 |
| (433) | 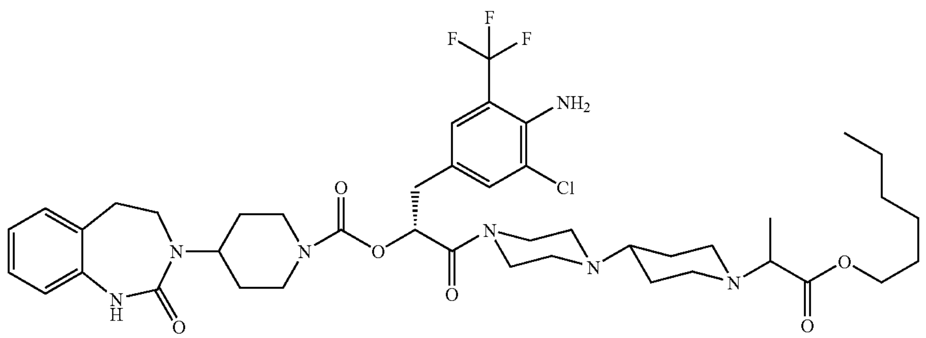 |
| (434) | 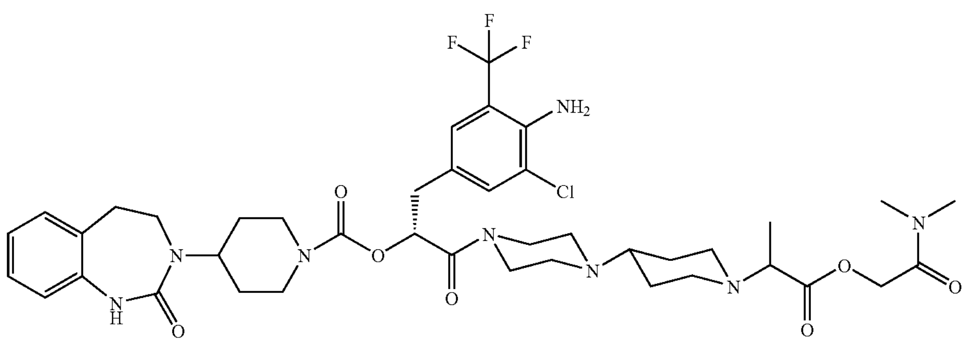 |
| (435) | 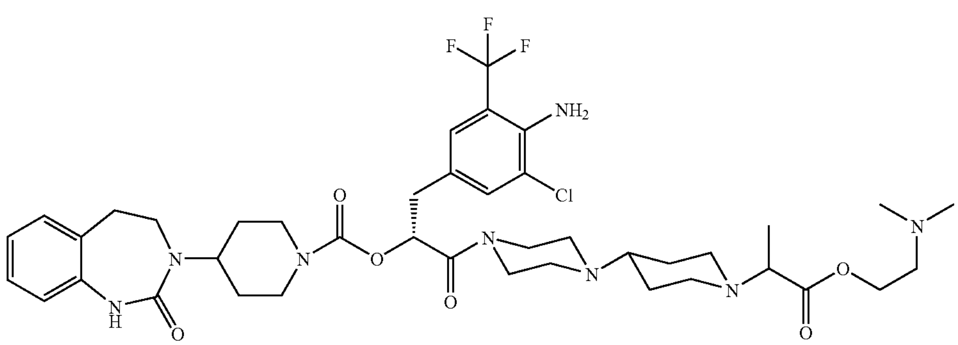 |

| No. | Structure |
|---|---|
| (436) | 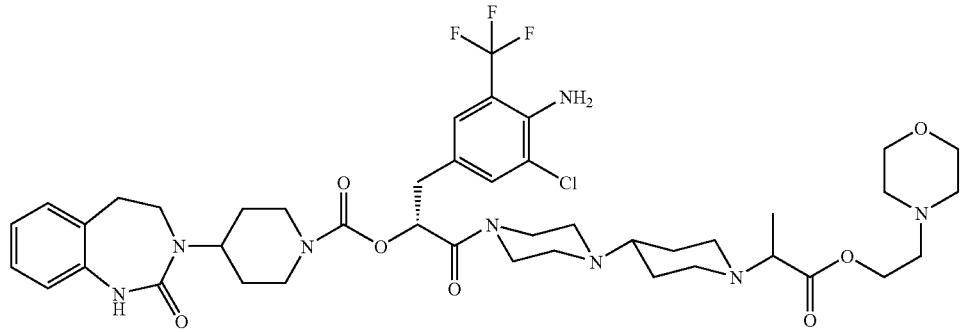 |
| (437) | 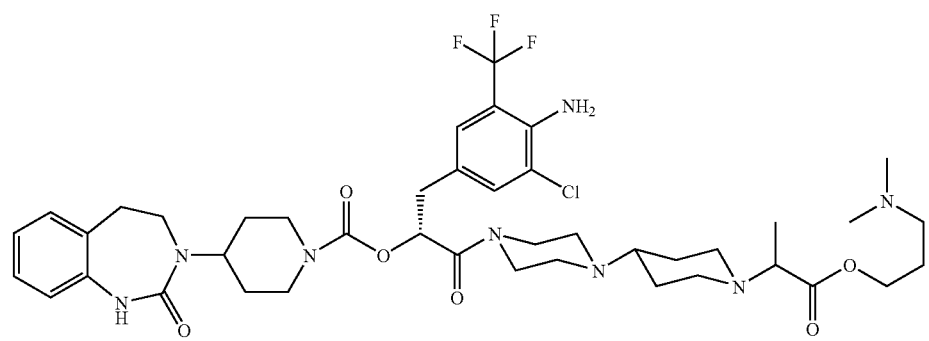 |
| (438) | 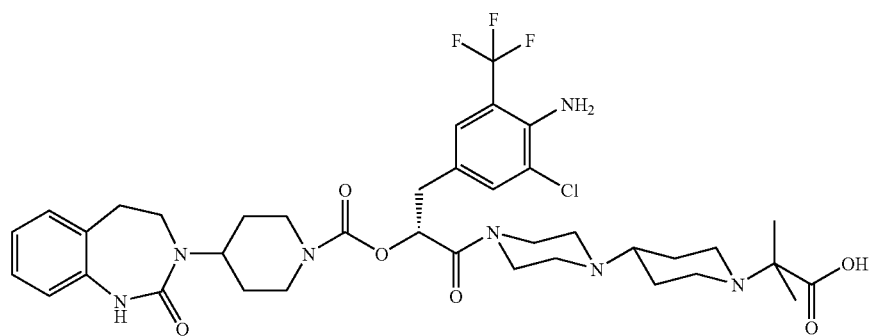 |
| (439) | 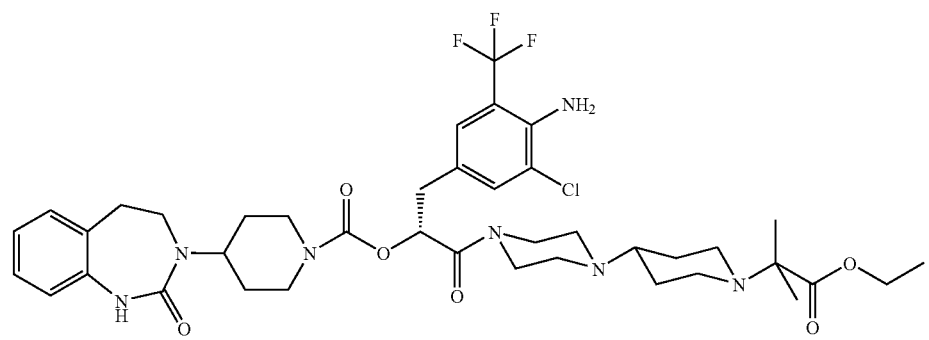 |

| No. | Structure |
|---|---|
| (440) | 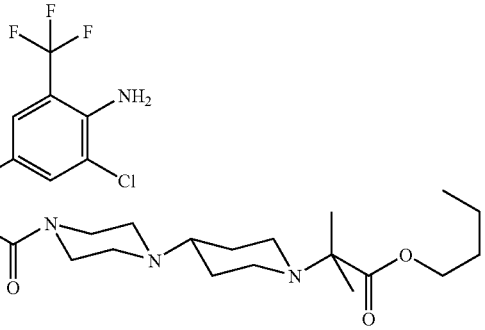 |
| (441) | 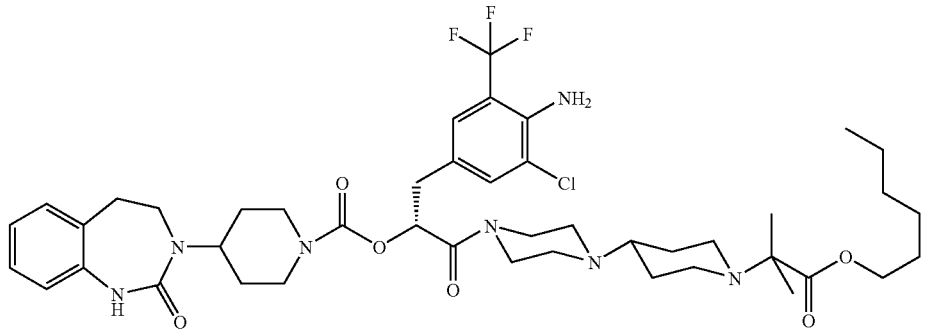 |
| (442) | 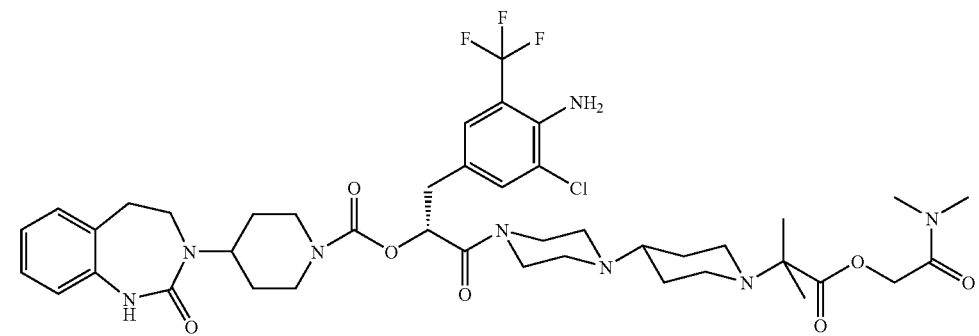 |
| (443) | 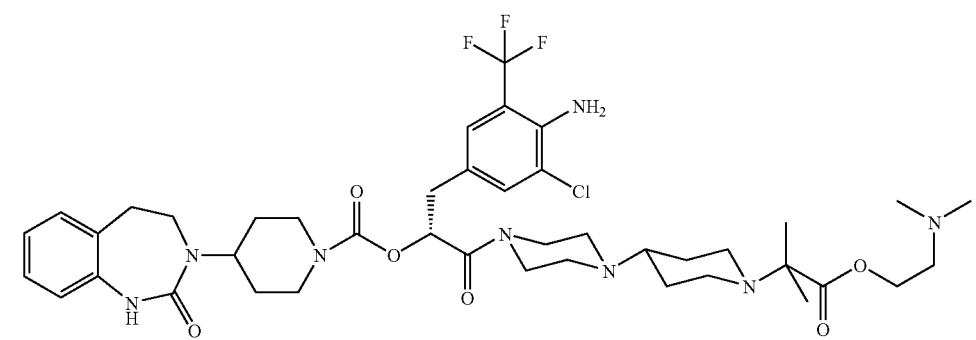 |

| No. | Structure |
|---|---|
| (444) | 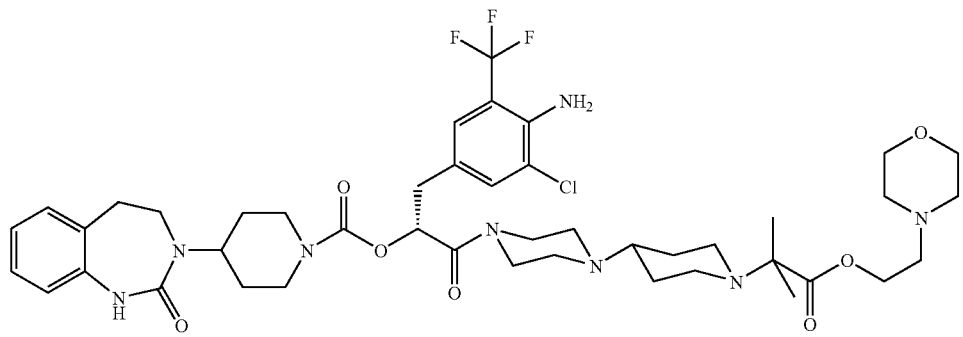 |
| (445) | 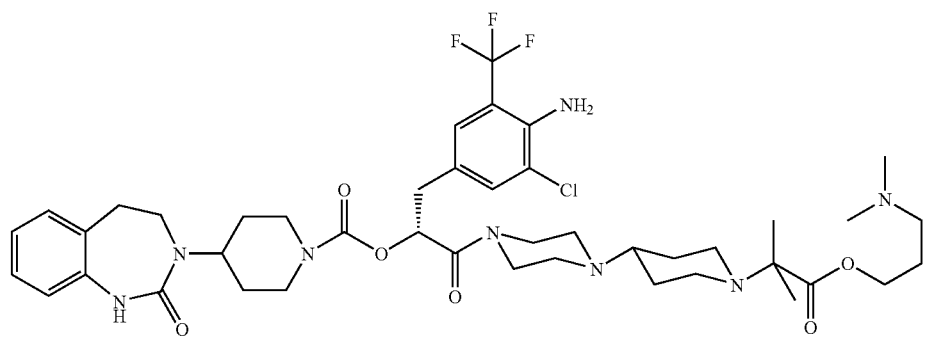 |
| (446) | 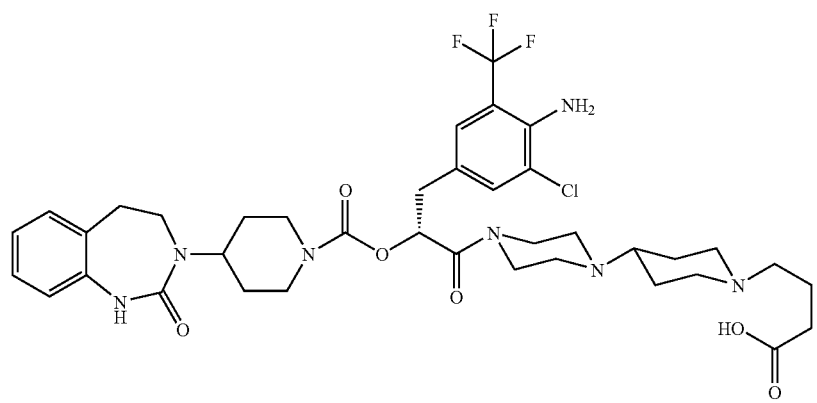 |
| (447) | 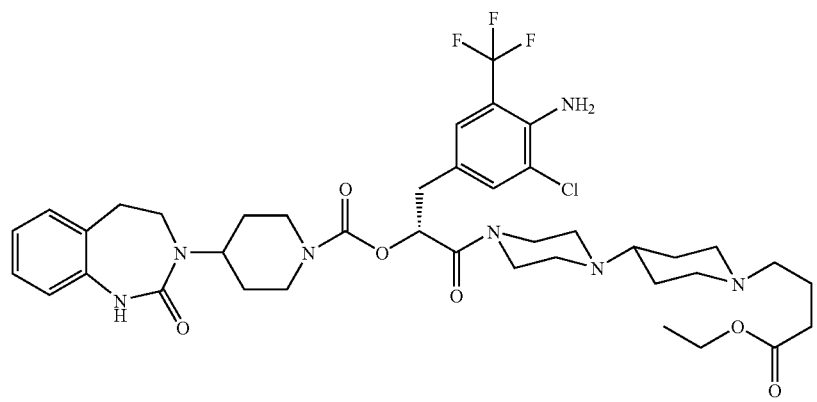 |

| No. | Structure |
|---|---|
| (448) | 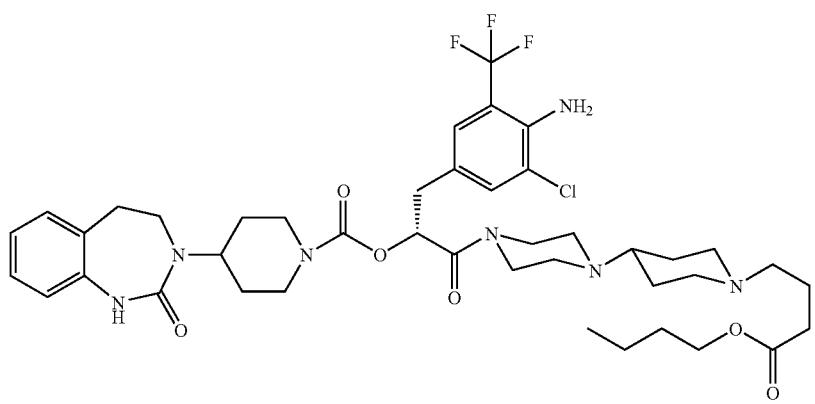 |
| (449) | 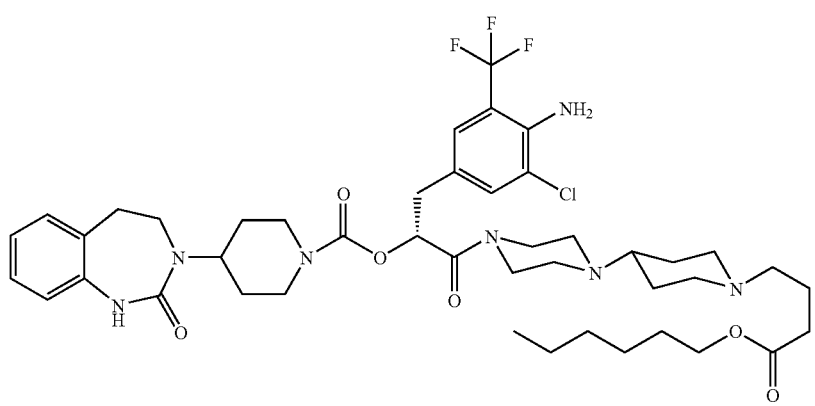 |
| (450) | 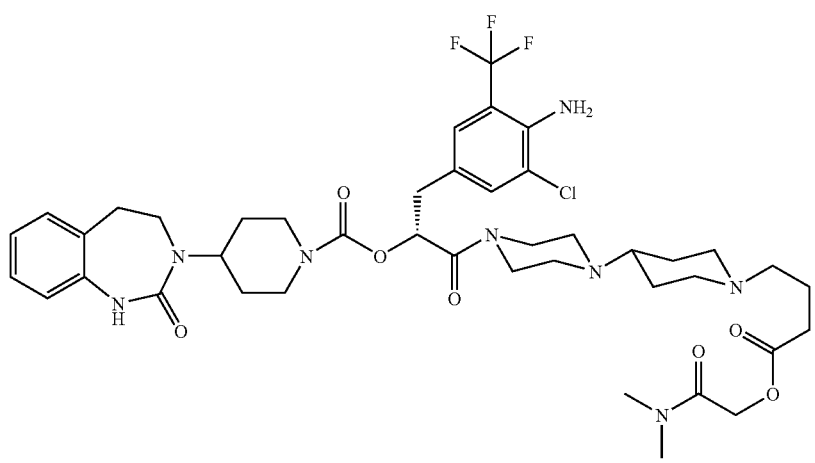 |

| No. | Structure |
|---|---|
| (451) | 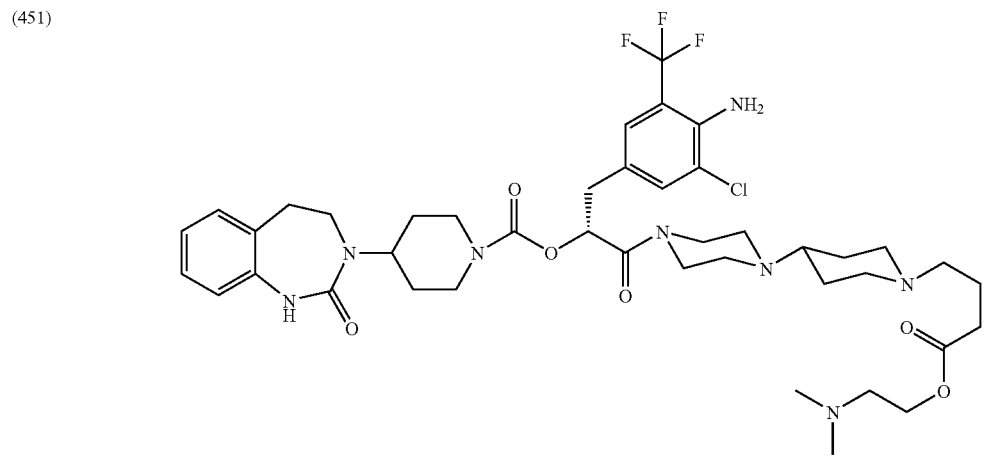 |
| (452) | 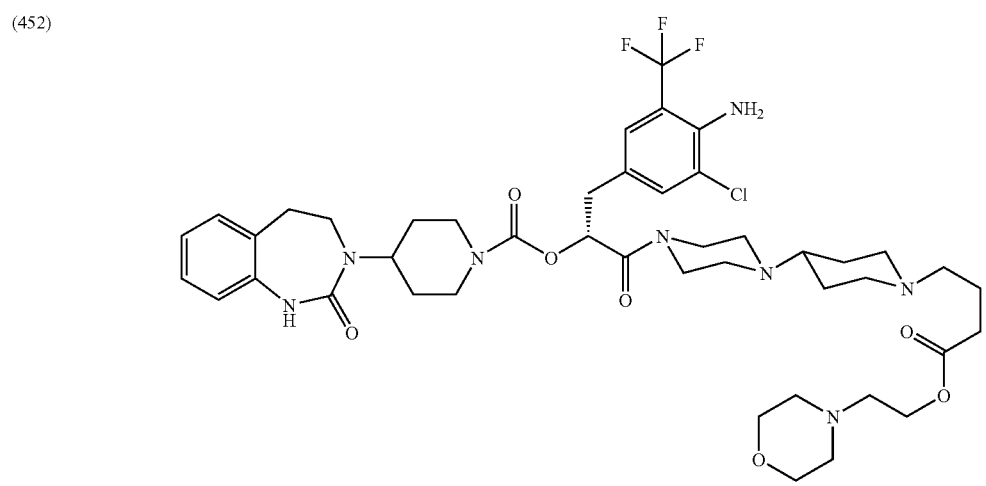 |
| (453) | 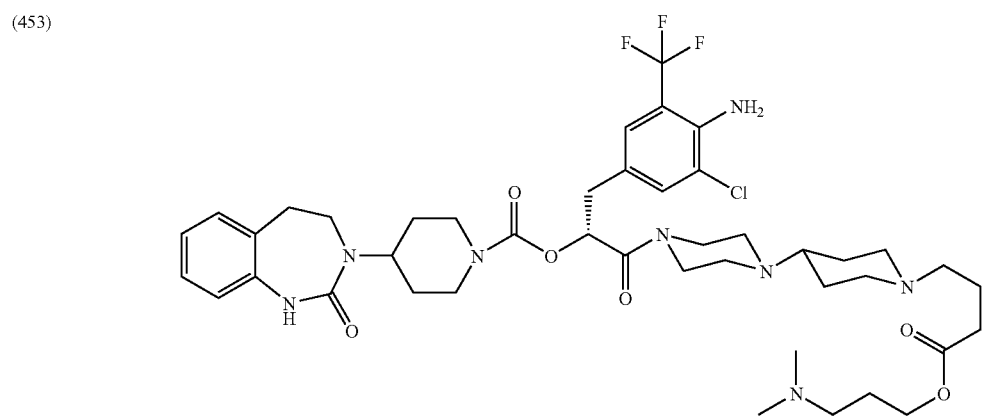 |

| No. | Structure |
|---|---|
| (454) | 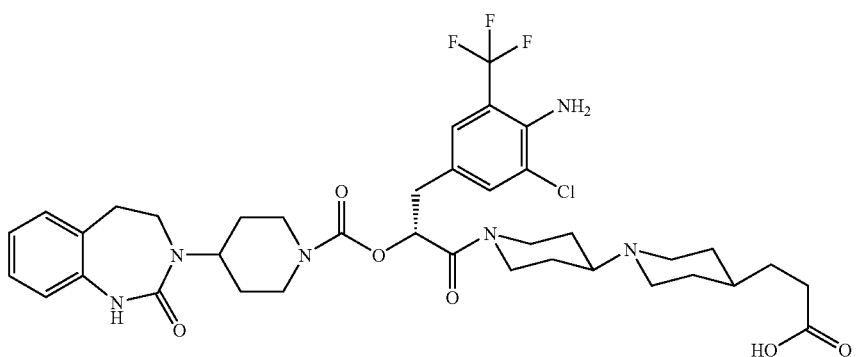 |
| (455) | 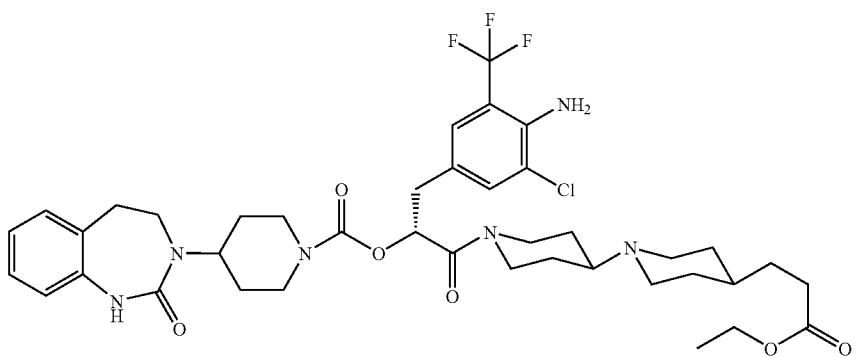 |
| (456) | 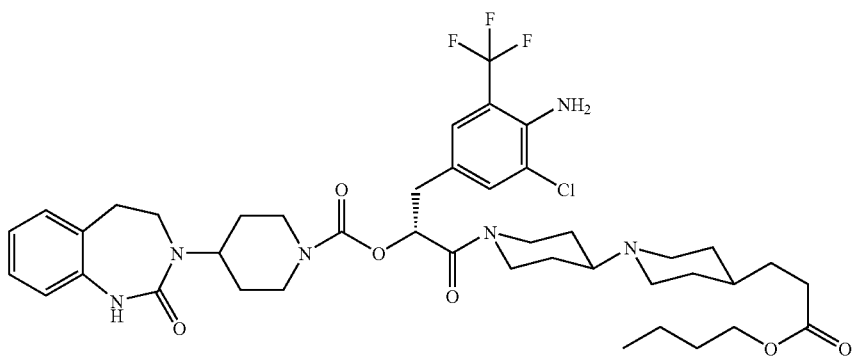 |
| (457) | 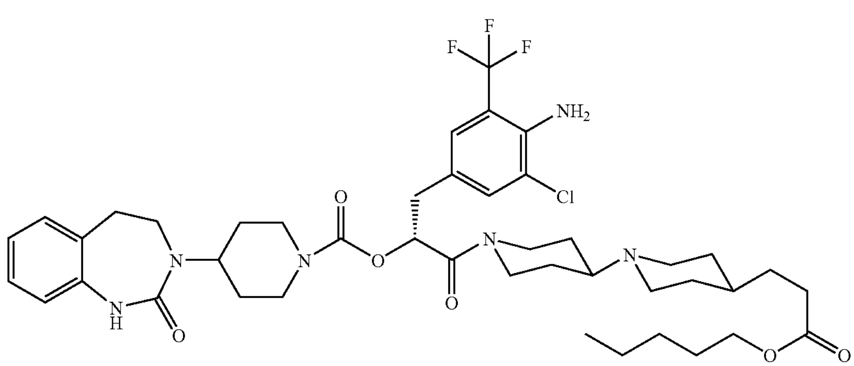 |

| No. | Structure |
|---|---|
| (458) | 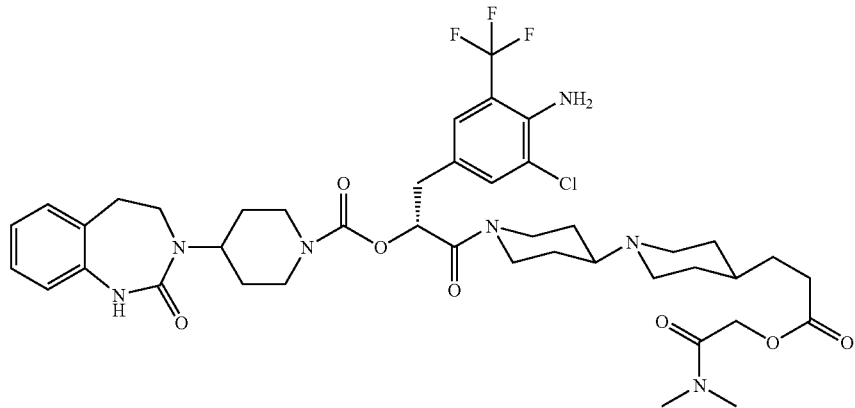 |
| (459) | 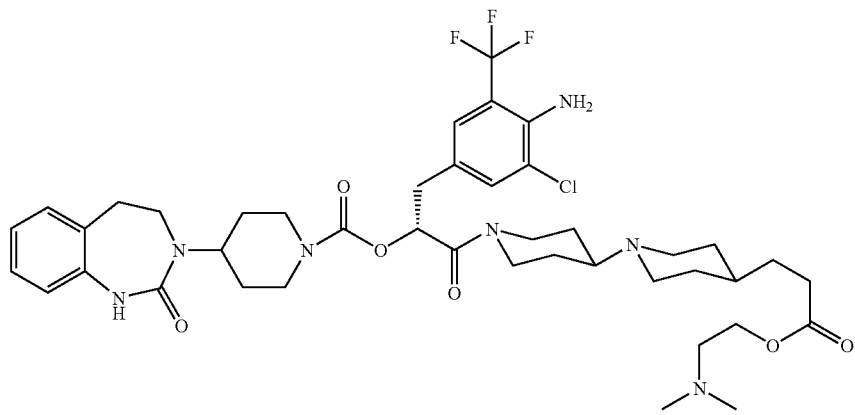 |
| (460) | 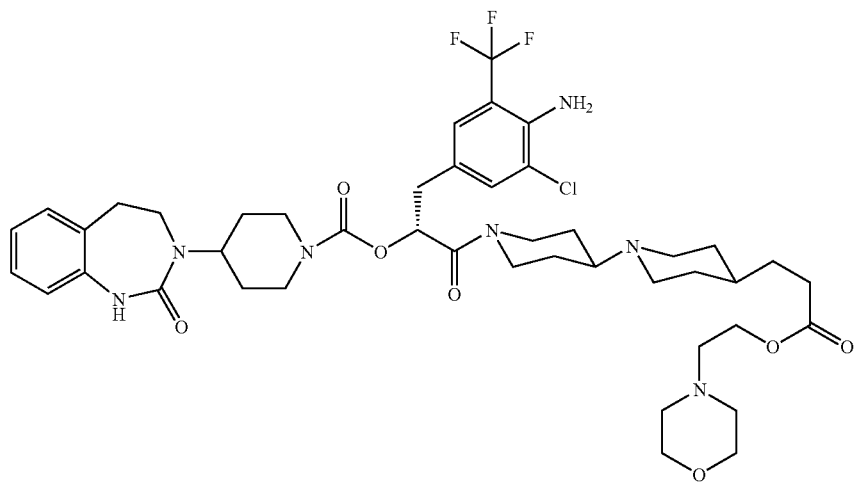 |

| No. | Structure |
|---|---|
| (461) | 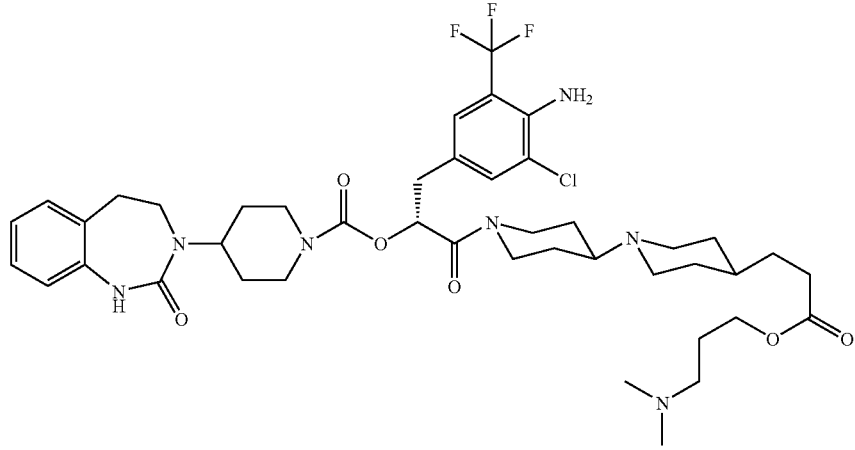 |
| (462) | 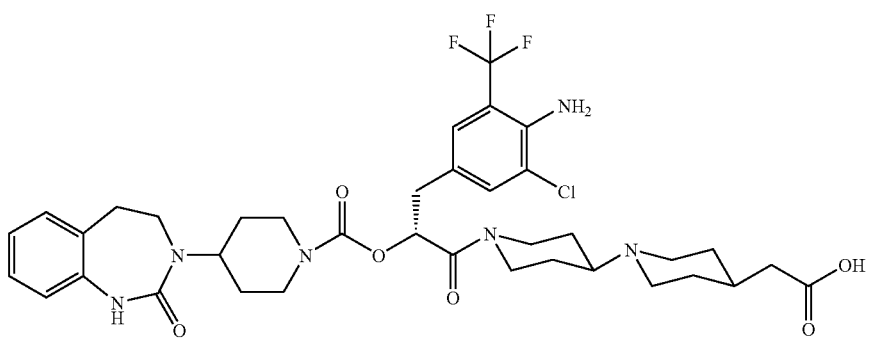 |
| (463) | 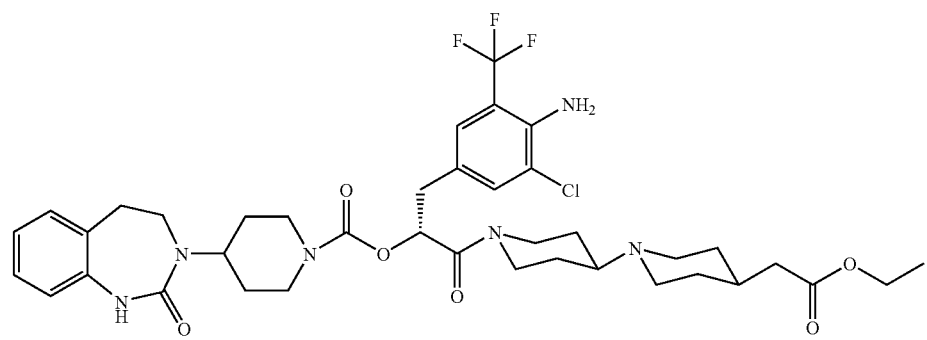 |
| (464) | 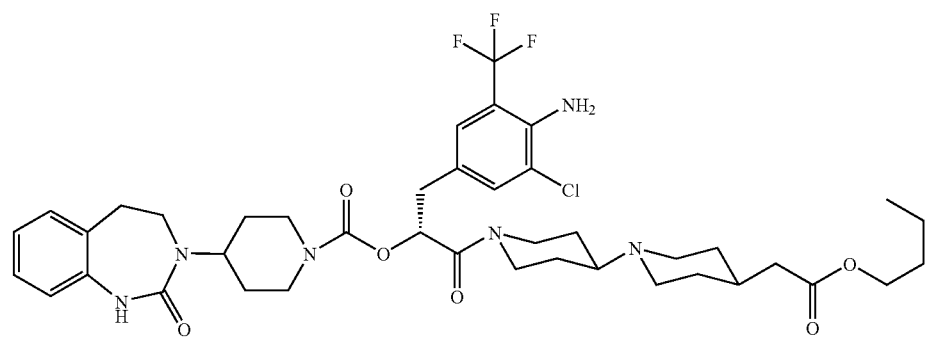 |

| No. | Structure |
|---|---|
| (465) | 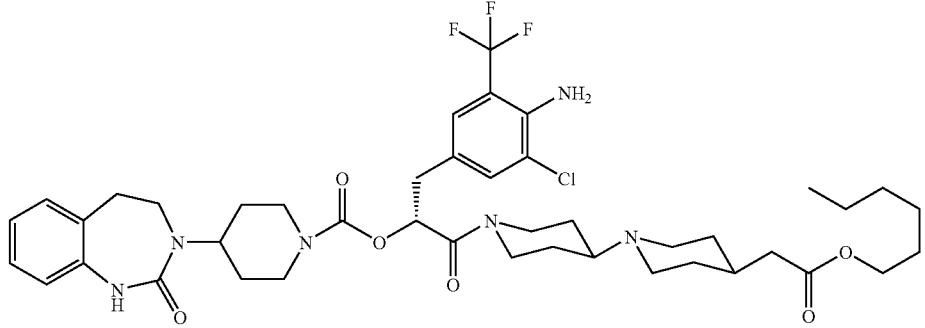 |
| (466) | 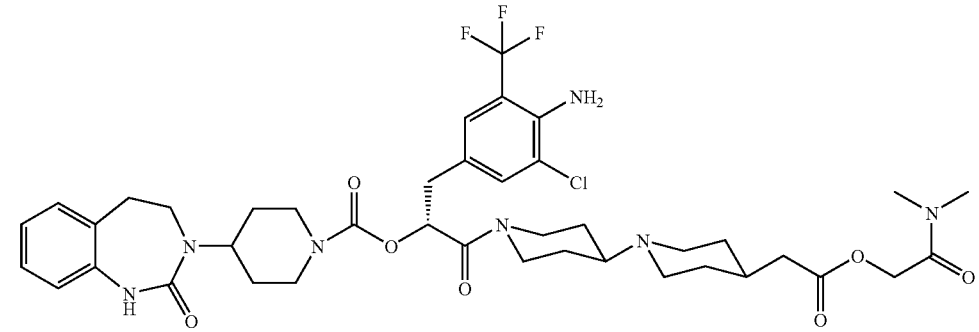 |
| (467) | 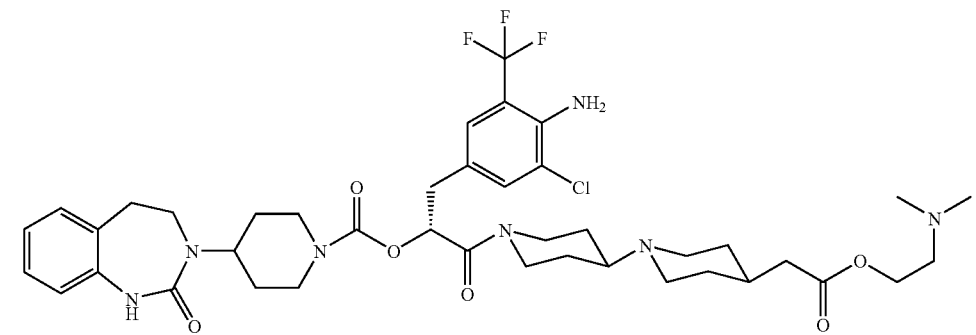 |
| (468) | 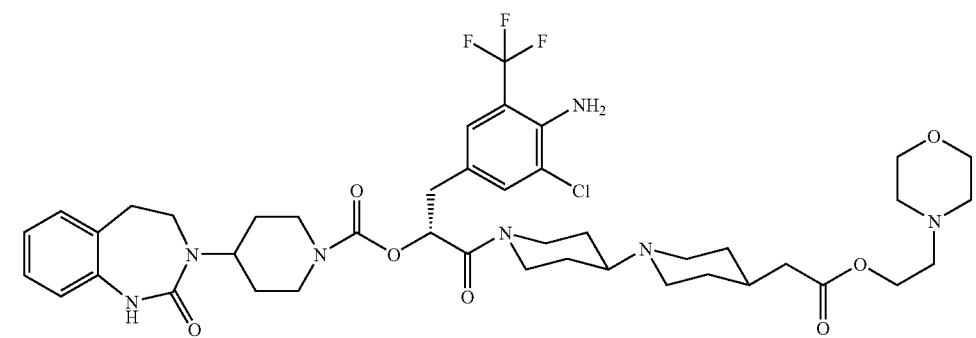 |

| No. | Structure |
|---|---|
| (469) | 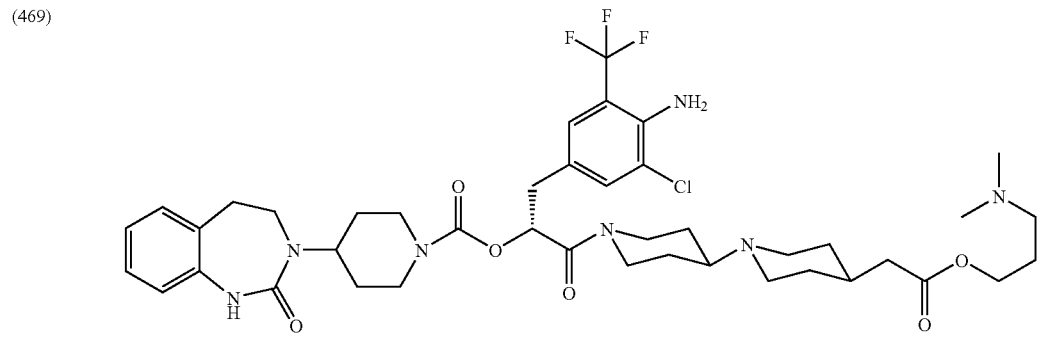 |
| (470) | 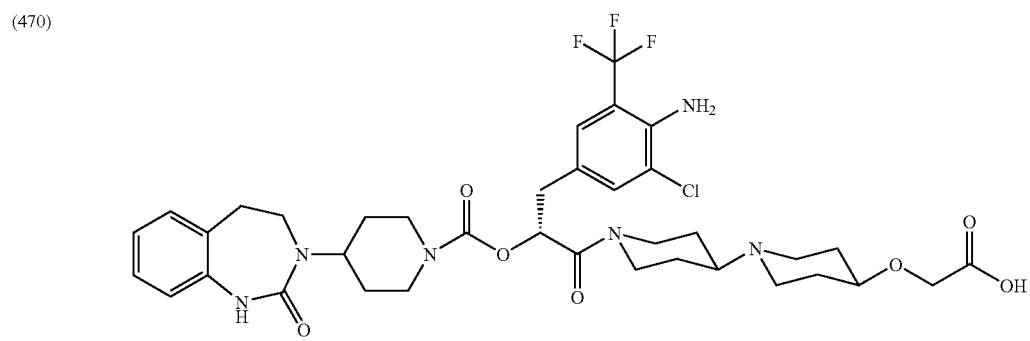 |
| (471) | 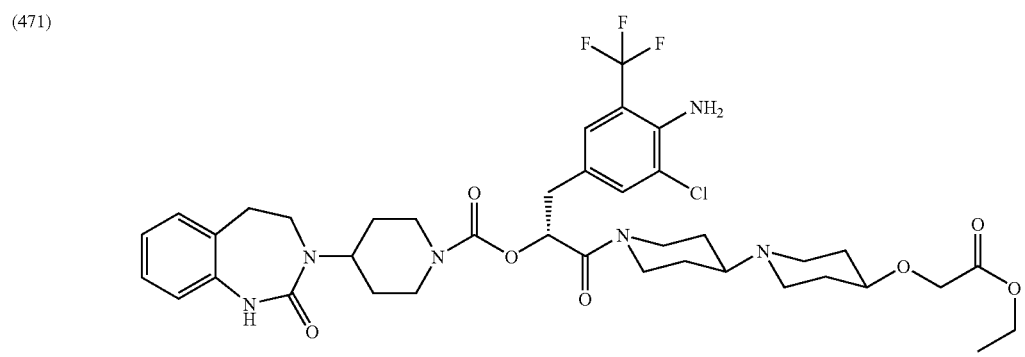 |
| (472) | 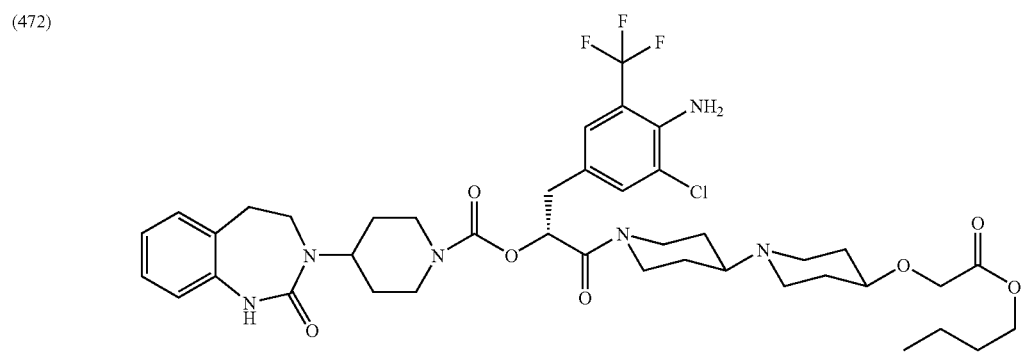 |

| No. | Structure |
|---|---|
| (473) | 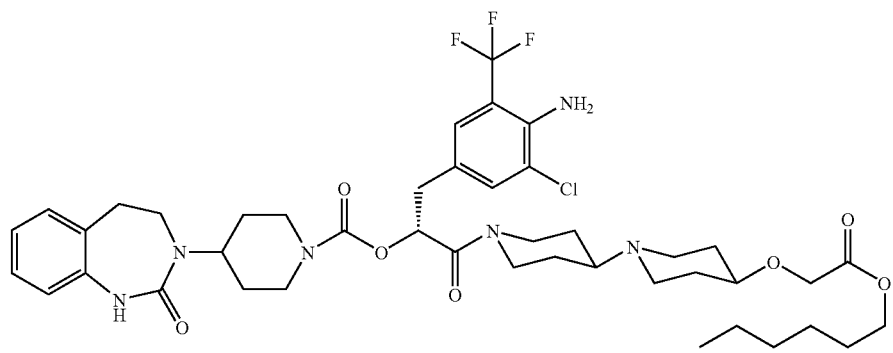 |
| (474) | 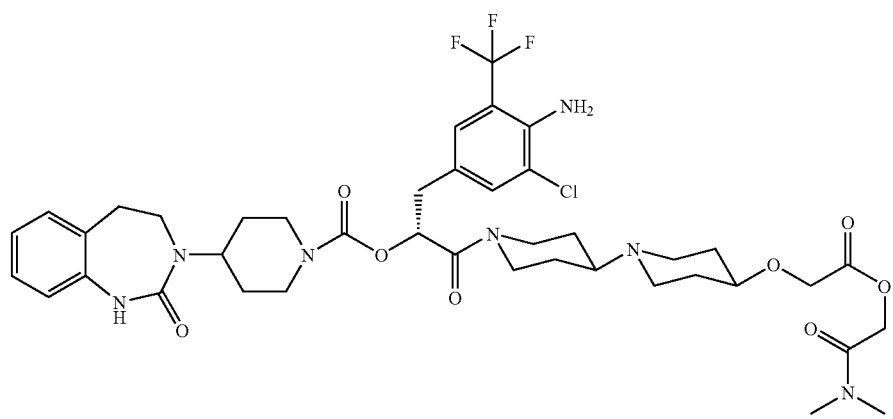 |
| (475) | 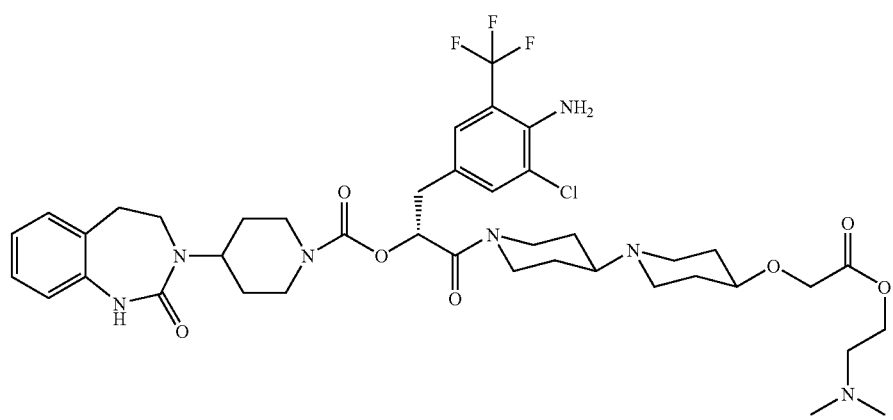 |

| No. | Structure |
|---|---|
| (476) | 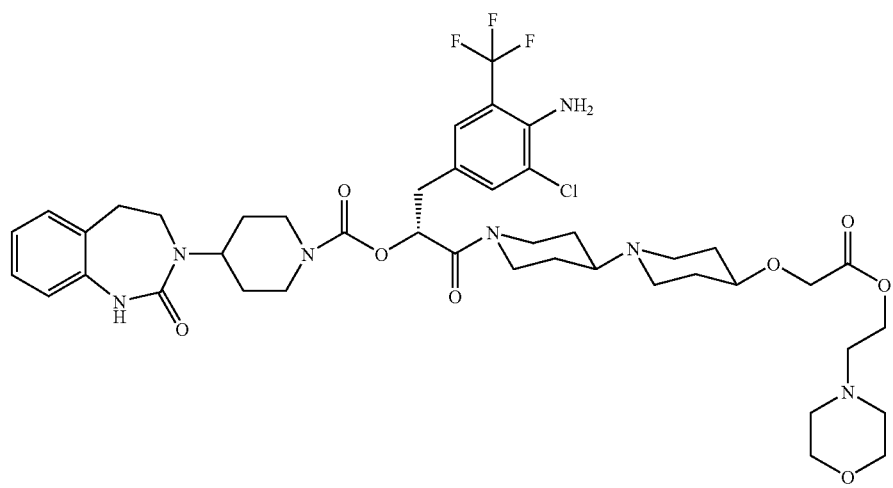 |
| (477) | 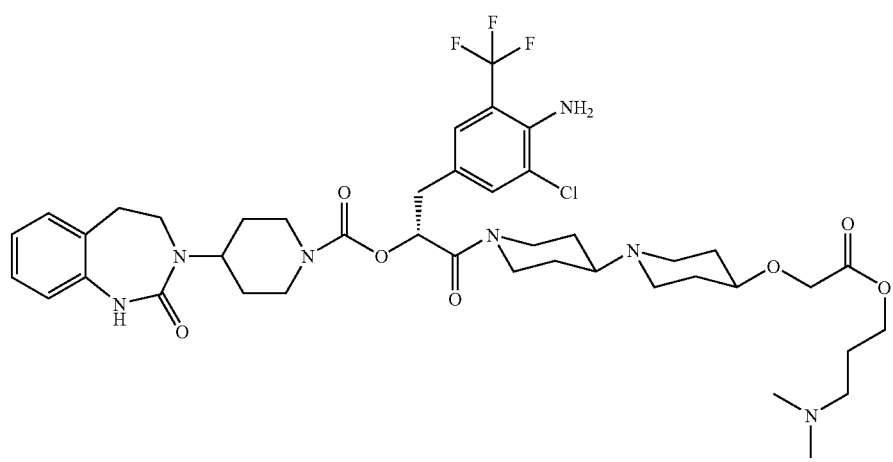 |
| (478) | 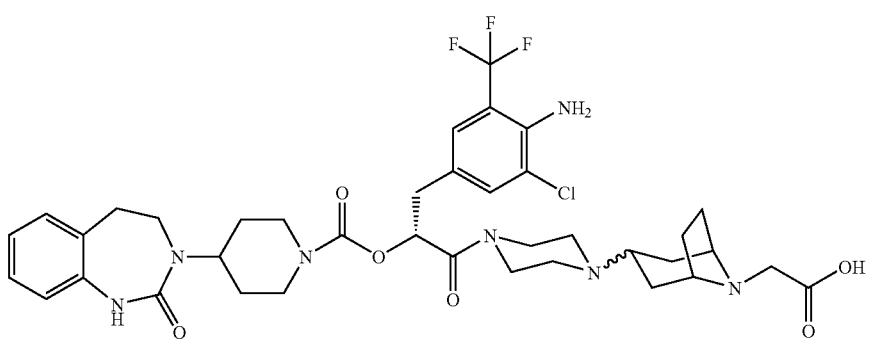 |
| (479) | 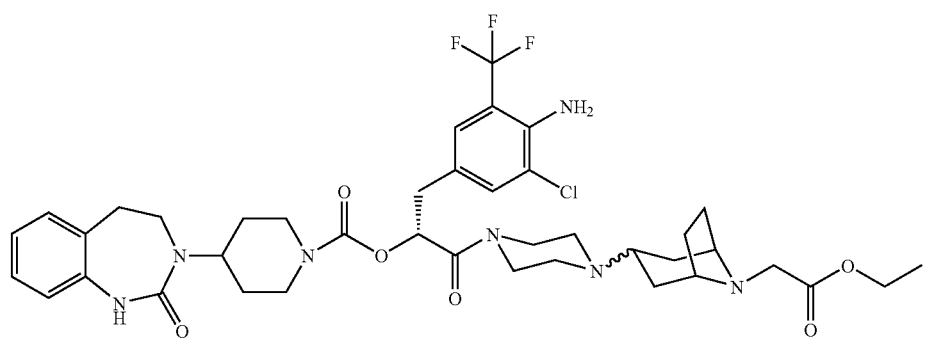 |

| No. | Structure |
|---|---|
| (480) | 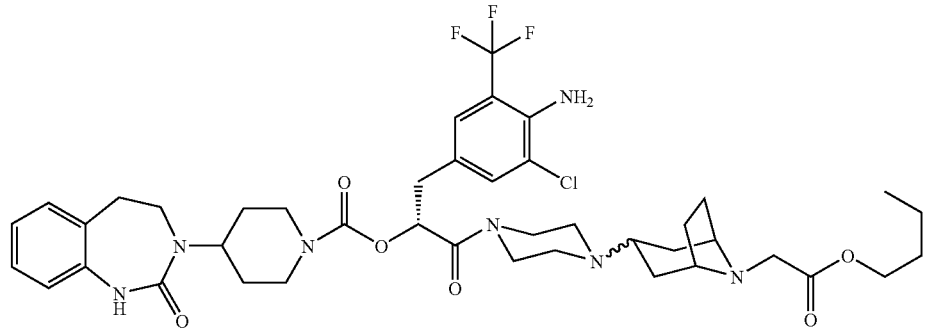 |
| (481) | 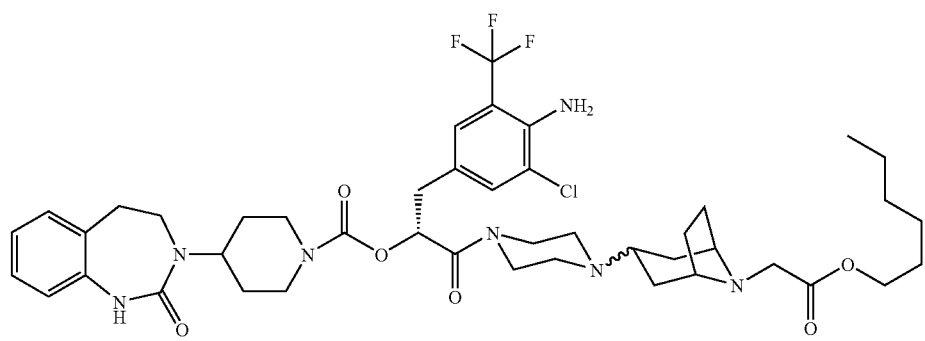 |
| (482) | 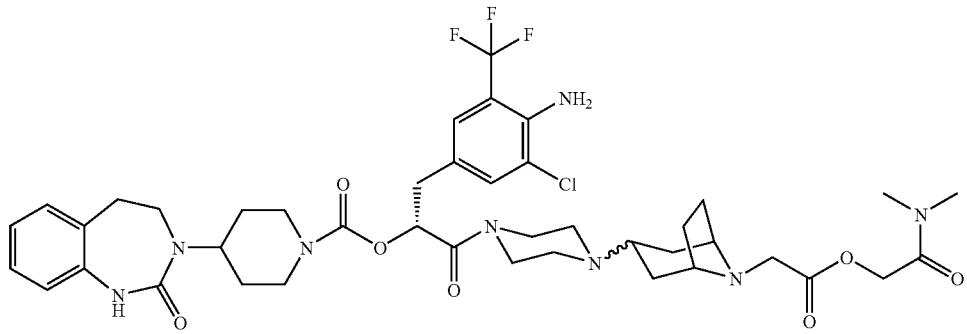 |
| (483) | 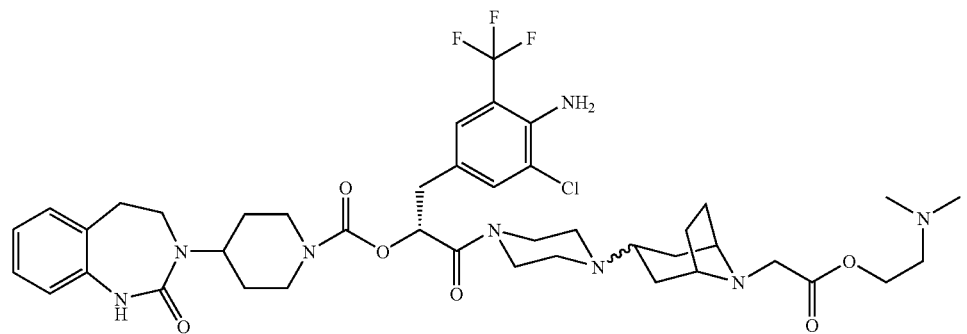 |

| No. | Structure |
|---|---|
| (484) | 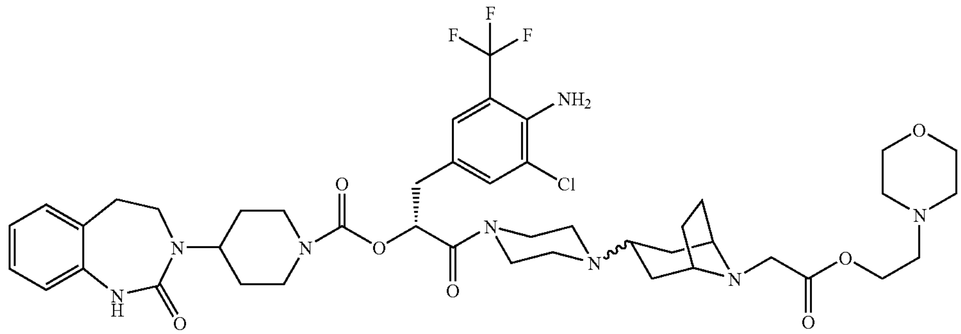 |
| (485) | 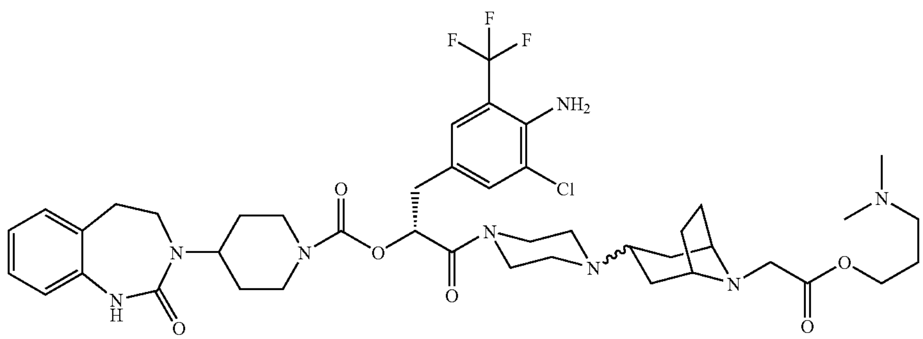 |
| (486) | 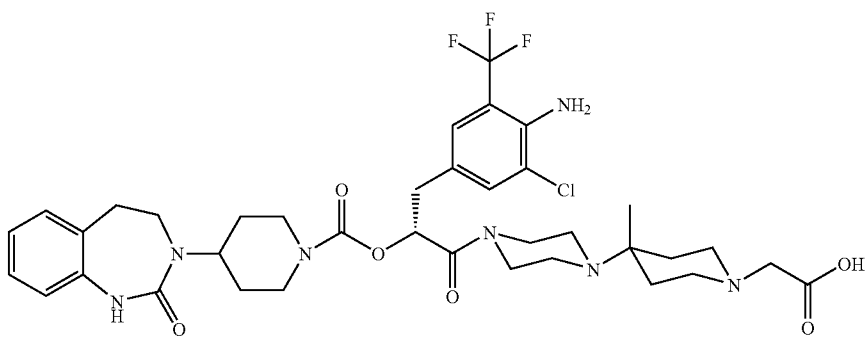 |
| (487) | 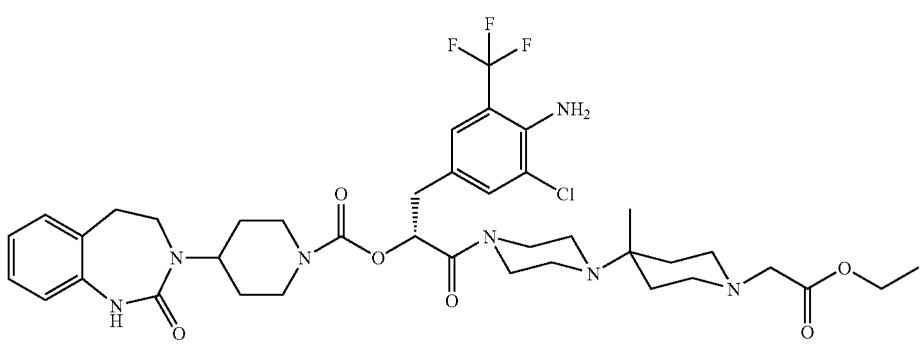 |

| No. | Structure |
|---|---|
| (488) | 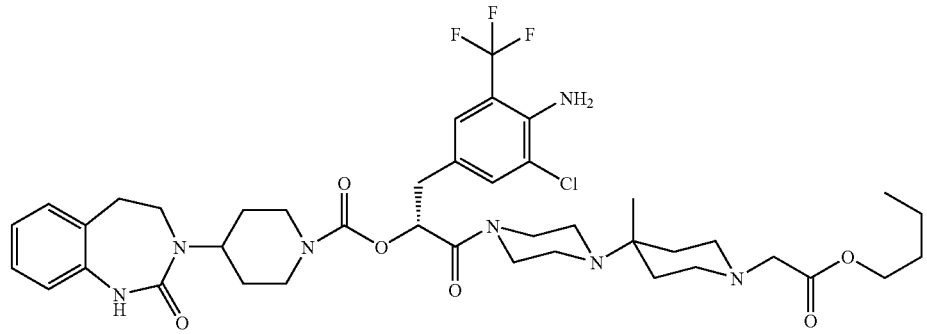 |
| (489) | 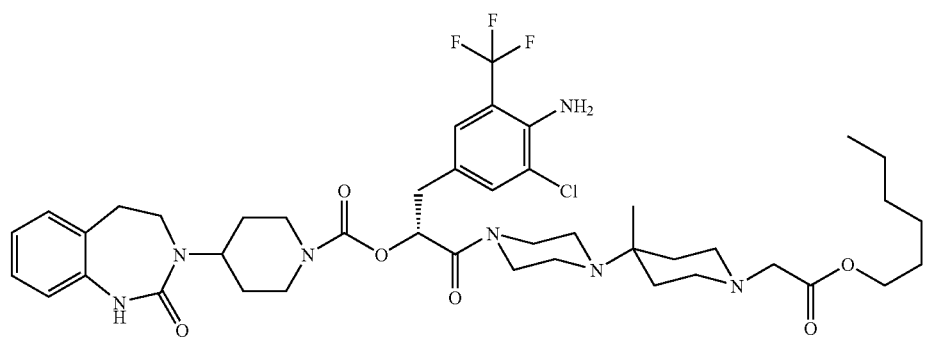 |
| (490) | 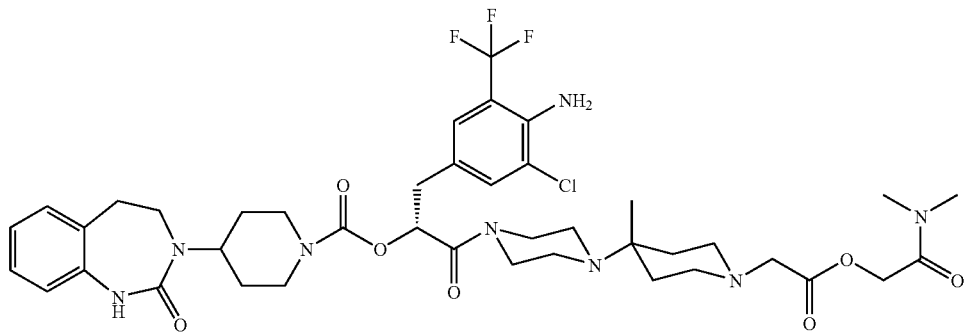 |
| (491) | 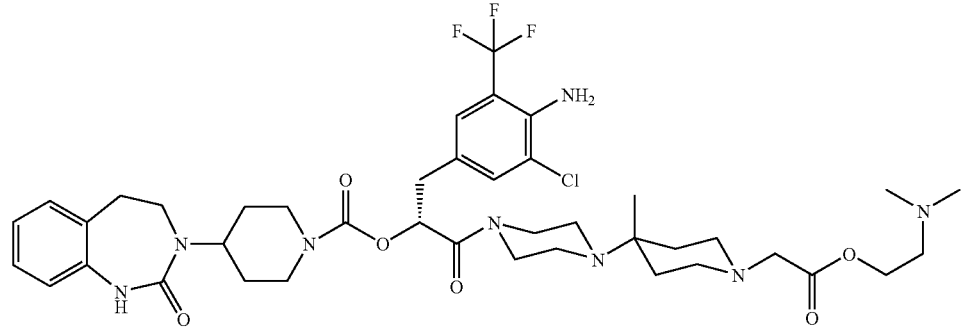 |

| No. | Structure |
|---|---|
| (492) | 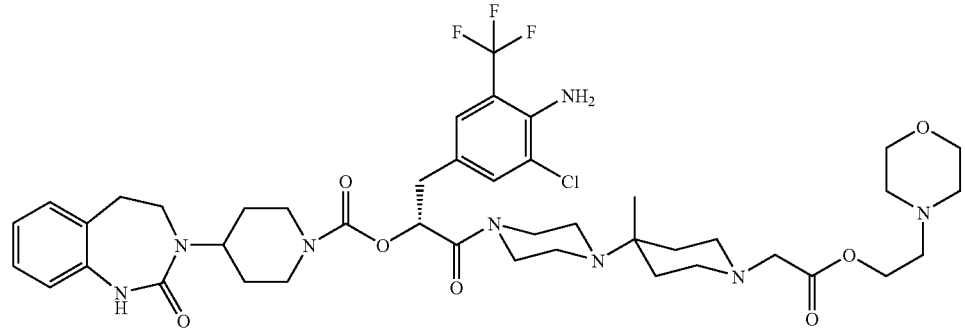 |
| (493) | 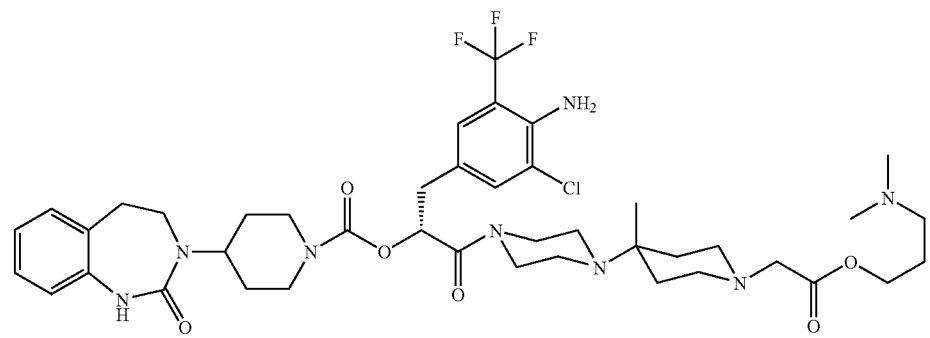 |
| (494) | 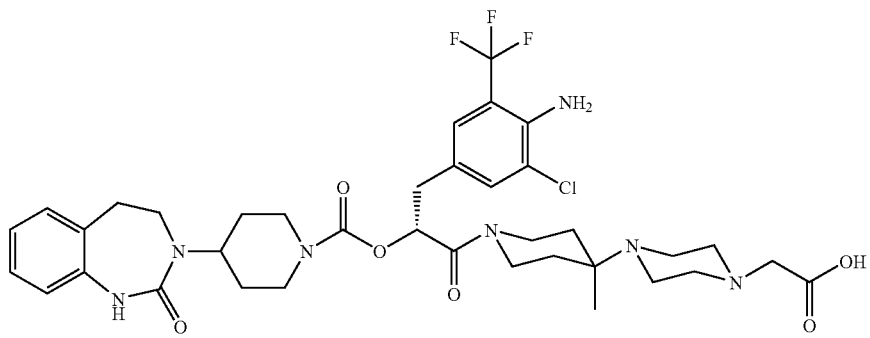 |
| (495) | 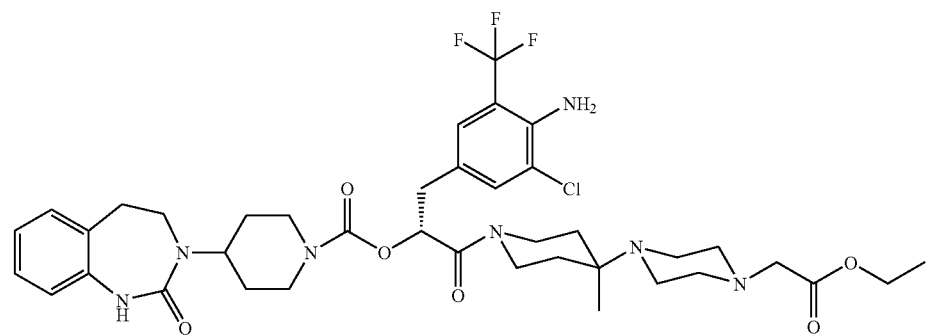 |

| No. | Structure |
|---|---|
| (496) | 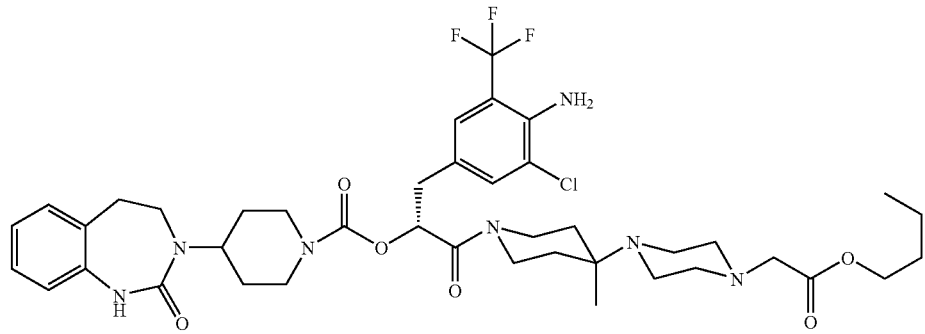 |
| (497) | 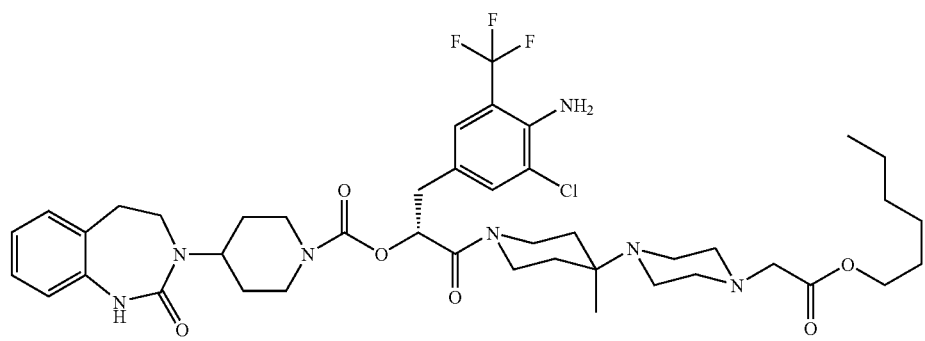 |
| (498) | 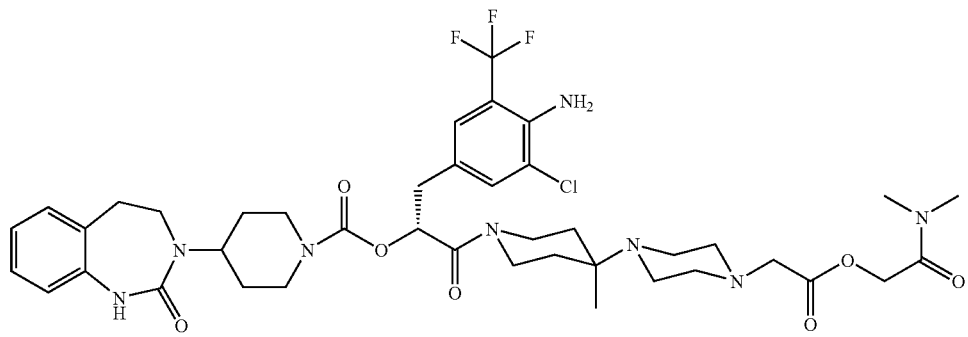 |
| (499) | 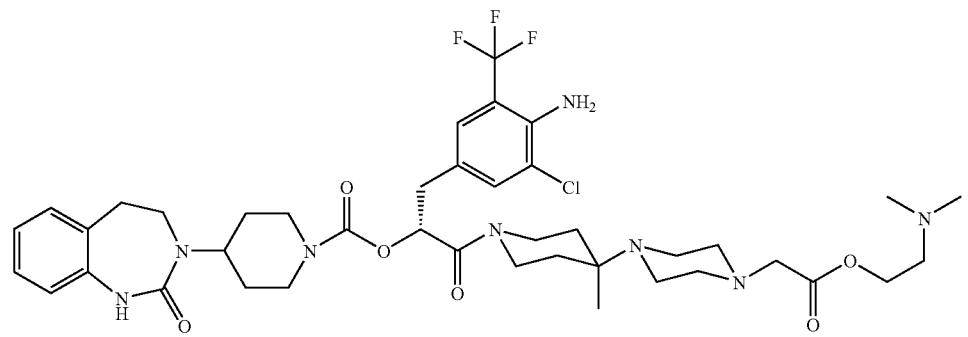 |

-continued
| No. | Structure |
|---|---|
| (500) | 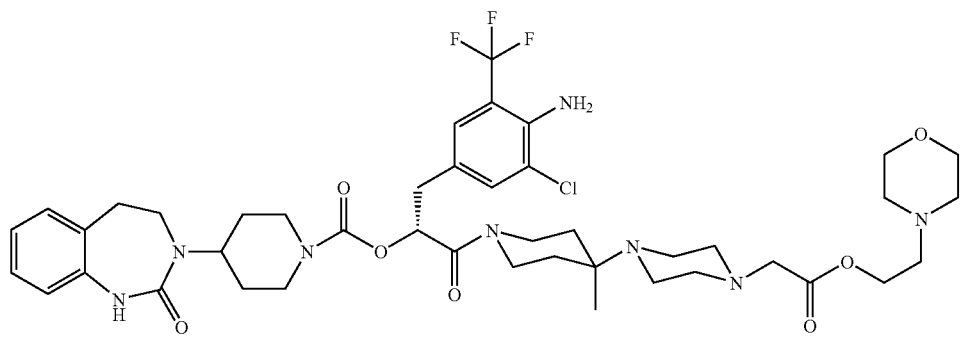 |
| (501) | 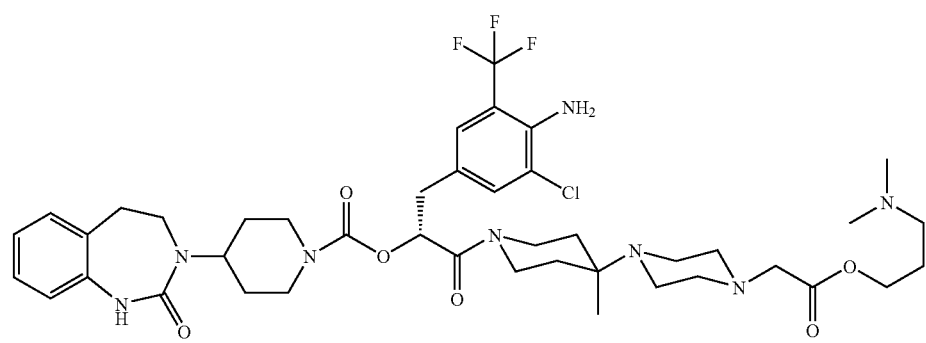 |
| (502) | 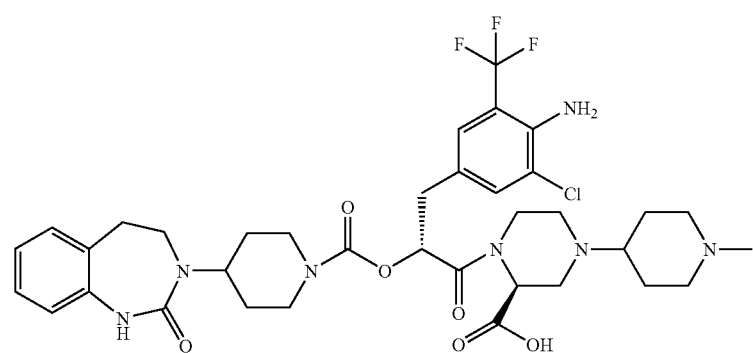 |
| (503) | 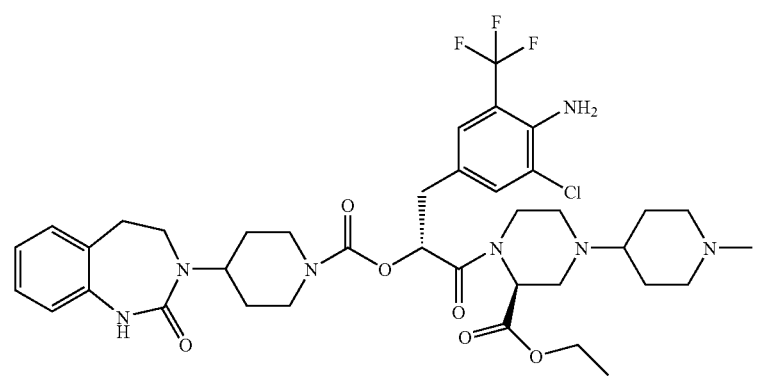 |

| No. | Structure |
|---|---|
| (504) | 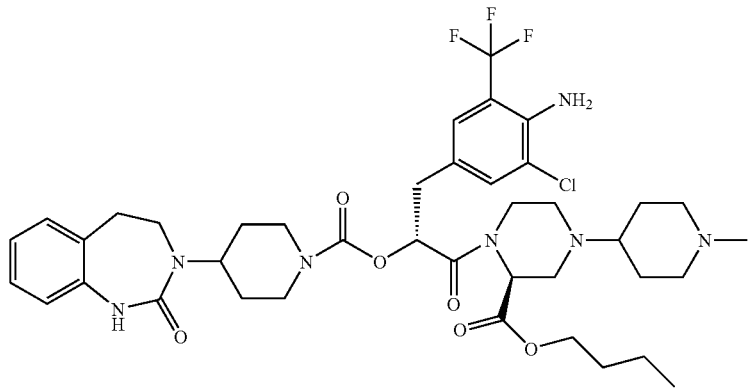 |
| (505) | 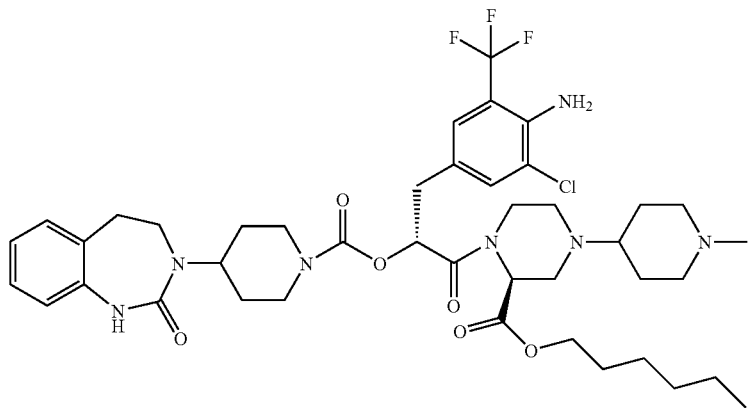 |
| (506) | 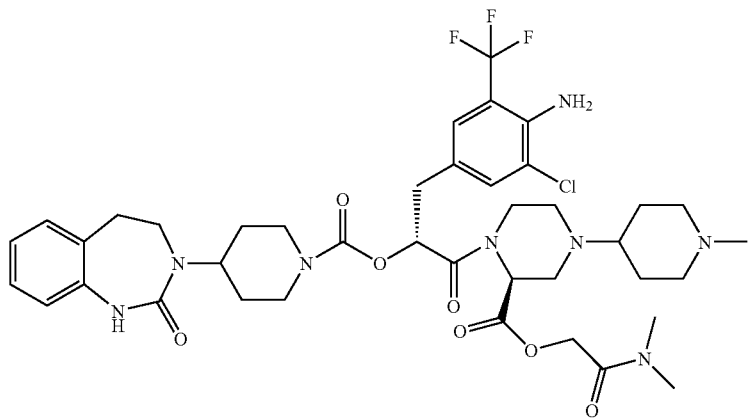 |

| No. | Structure |
|---|---|
| (507) | 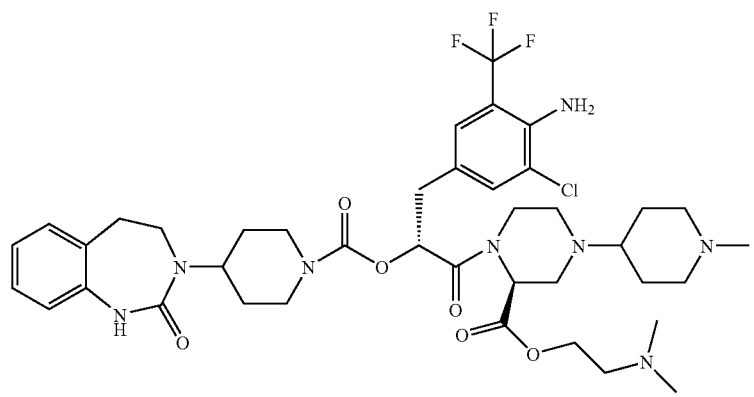 |
| (508) | 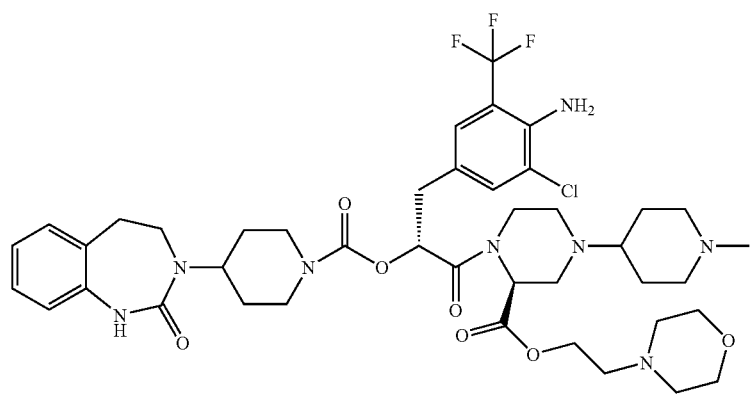 |
| (509) | 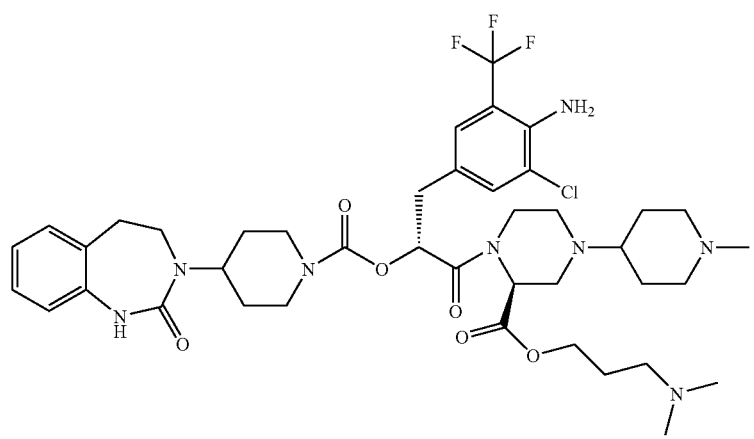 |
| (510) | 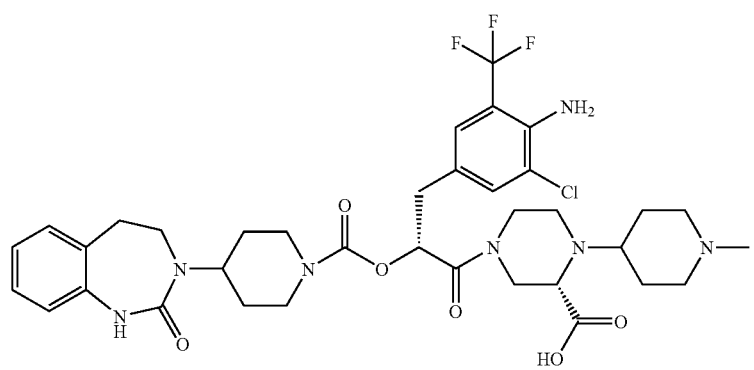 |

| No. | Structure |
|---|---|
| (511) | 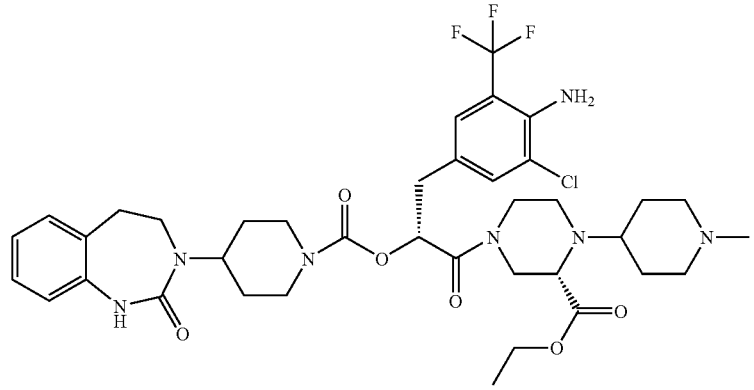 |
| (512) | 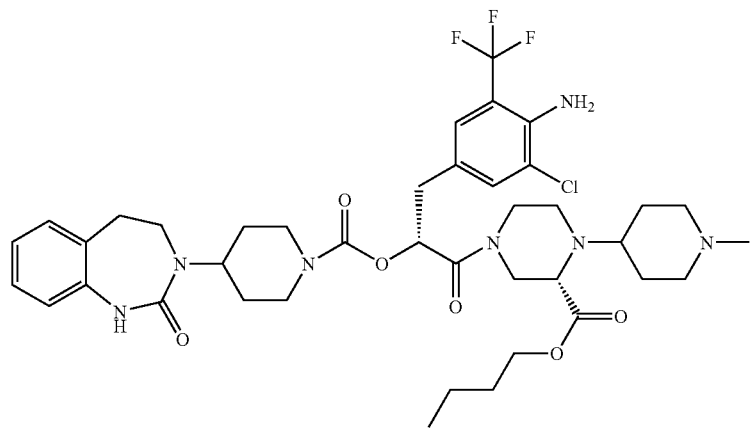 |
| (513) | 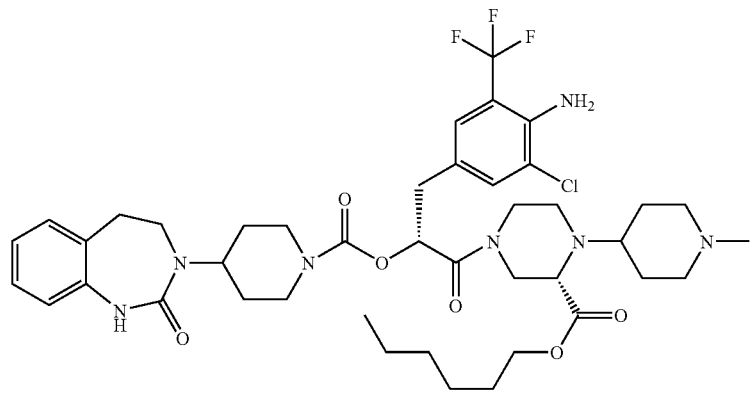 |

| No. | Structure |
|---|---|
| (514) | 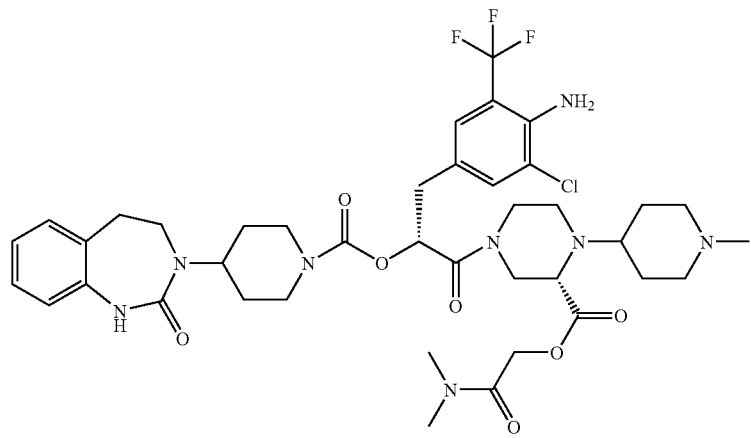 |
| (515) | 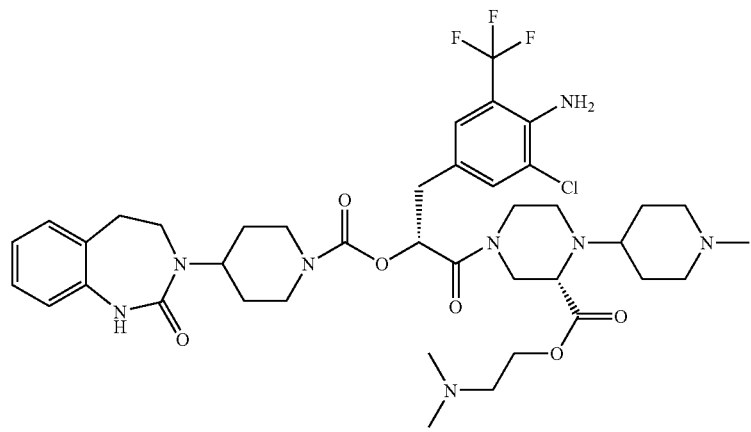 |
| (516) | 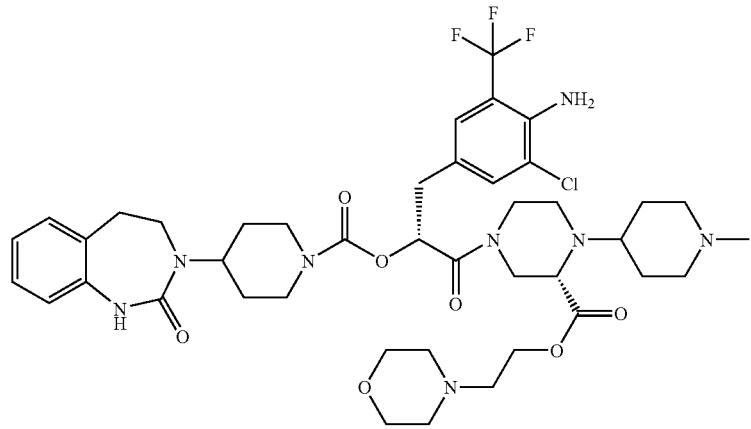 |

| No. | Structure |
|---|---|
| (517) | 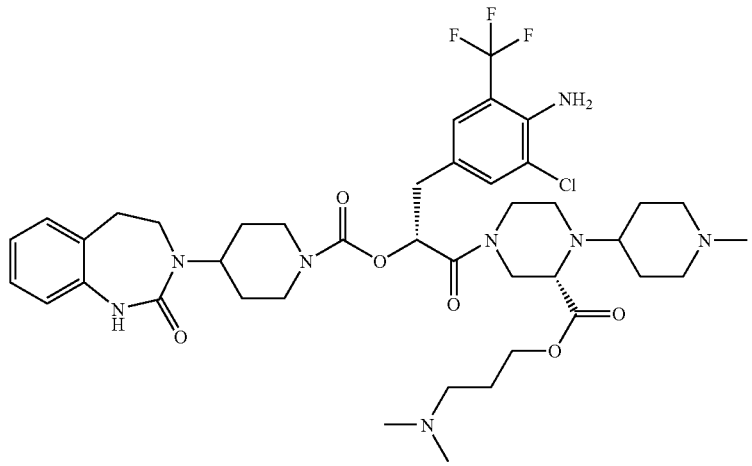 |
| (518) | 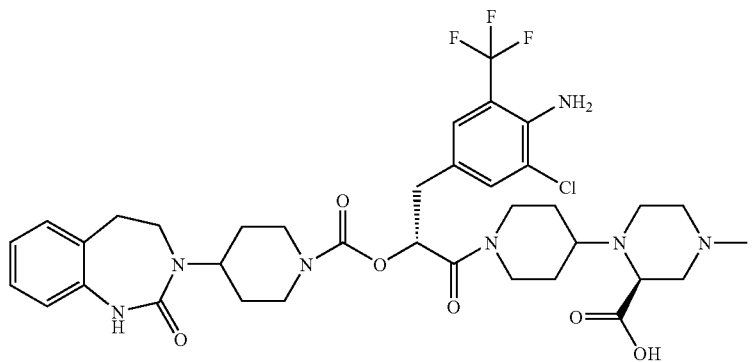 |
| (519) | 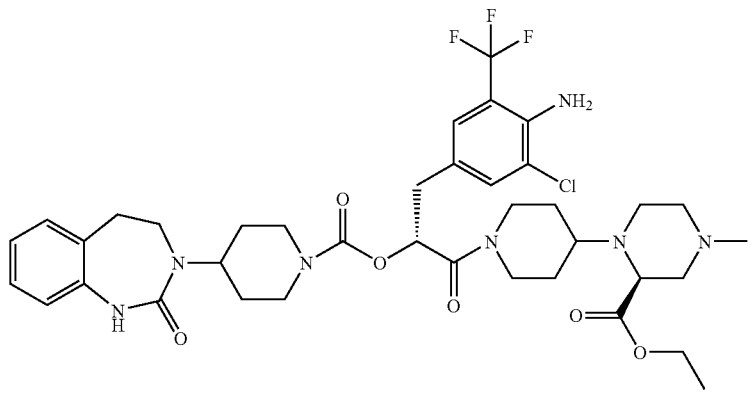 |

| No. | Structure |
|---|---|
| (520) | 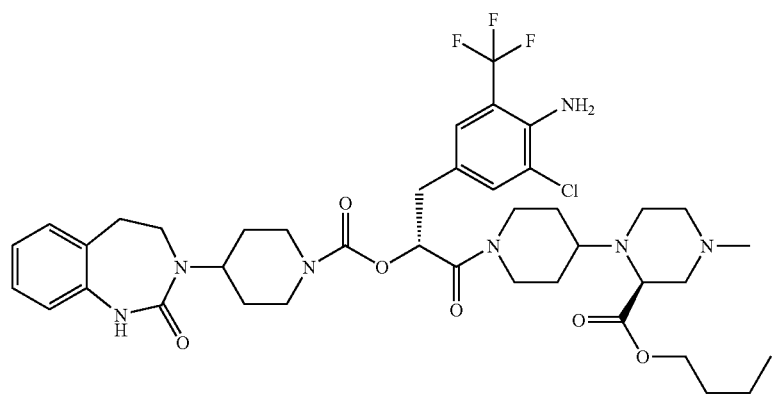 |
| (521) | 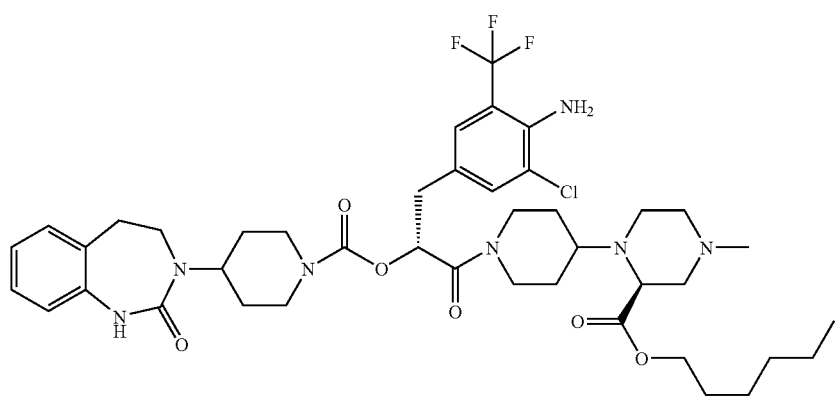 |
| (522) | 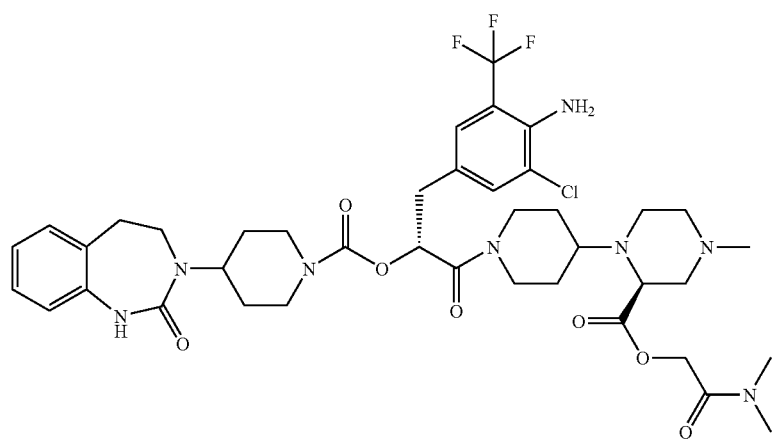 |

| No. | Structure |
|---|---|
| (523) | 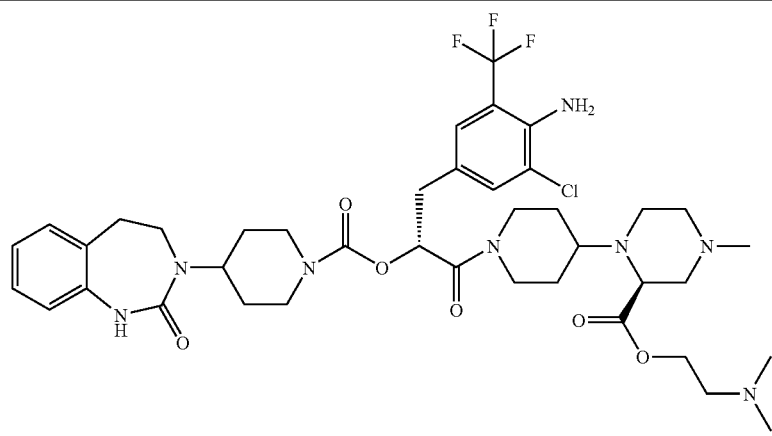 |
| (524) | 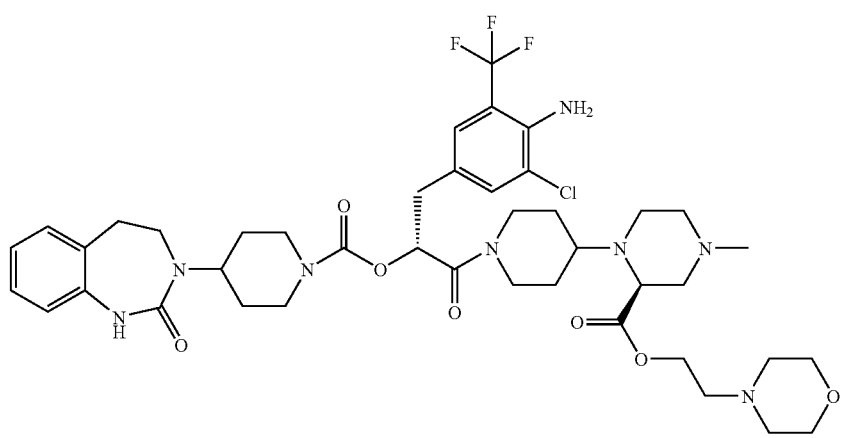 |
| (525) | 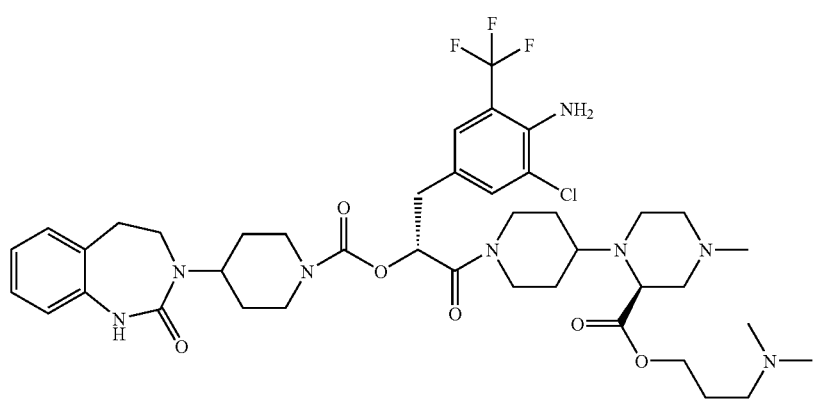 |
| (526) | 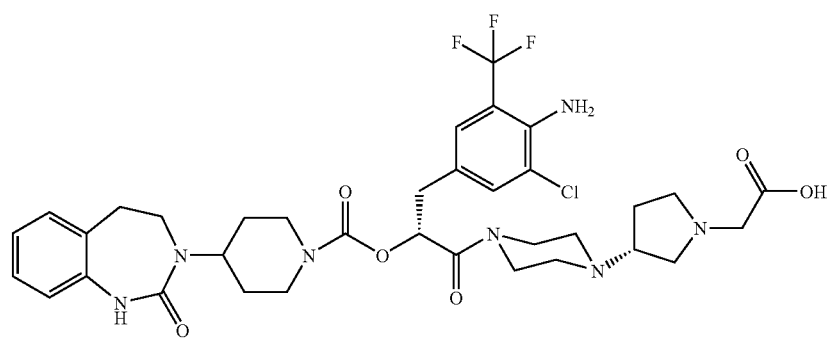 |

| No. | Structure |
|---|---|
| (527) | 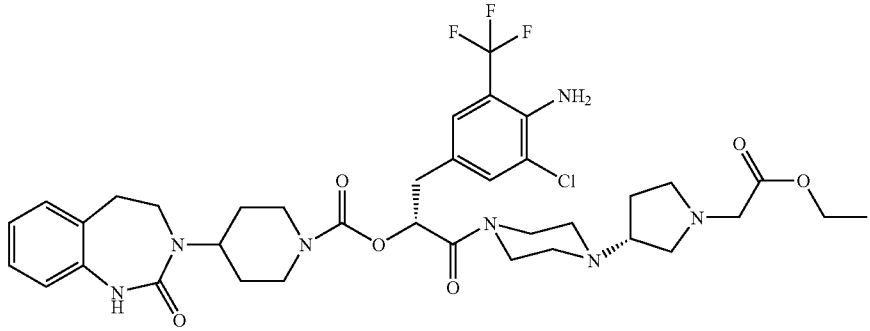 |
| (528) | 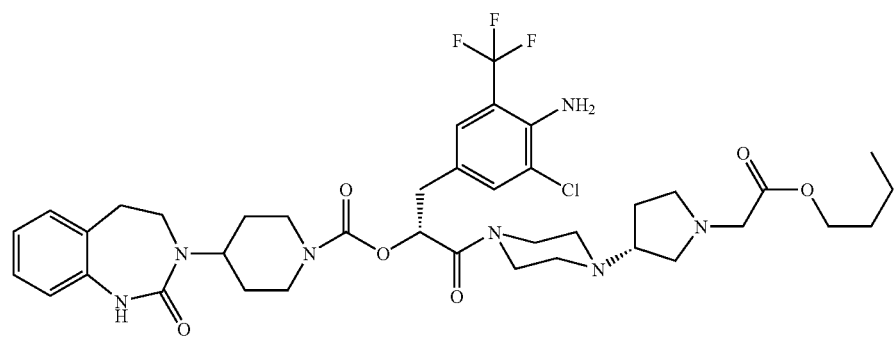 |
| (529) | 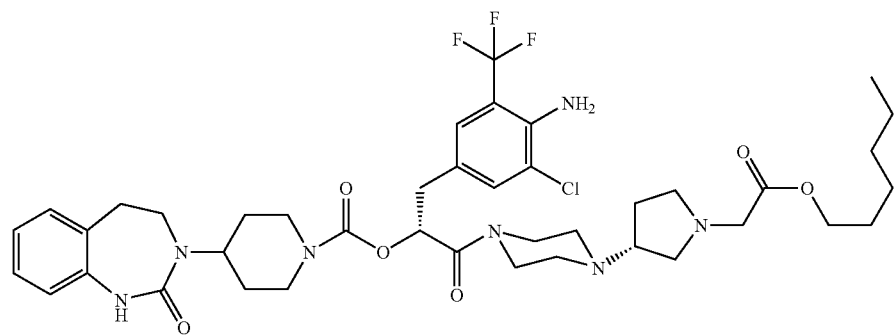 |
| (530) | 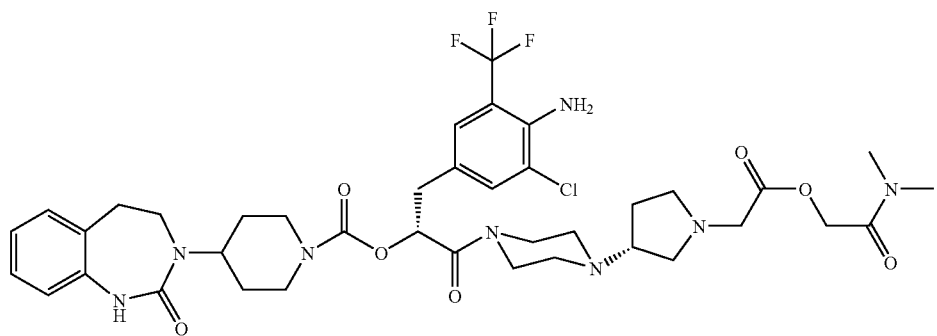 |

| No. | Structure |
|---|---|
| (531) | 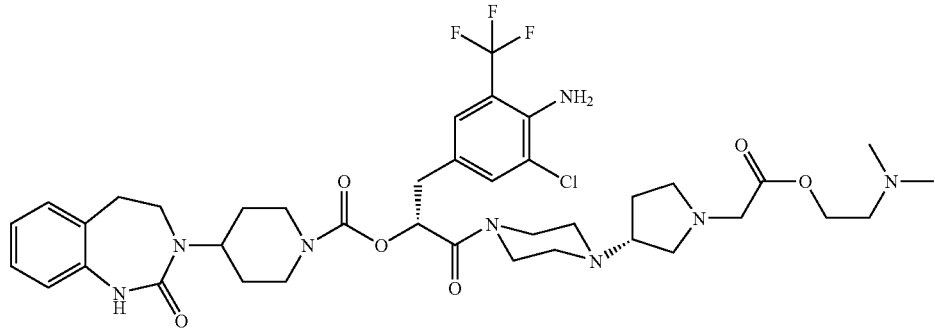 |
| (532) | 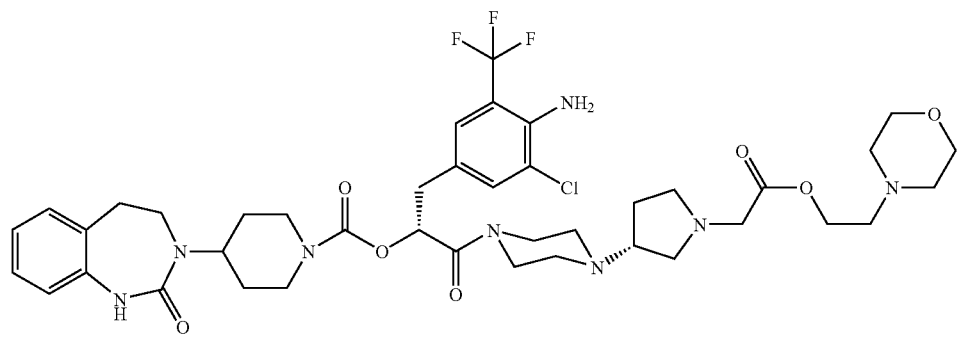 |
| (533) | 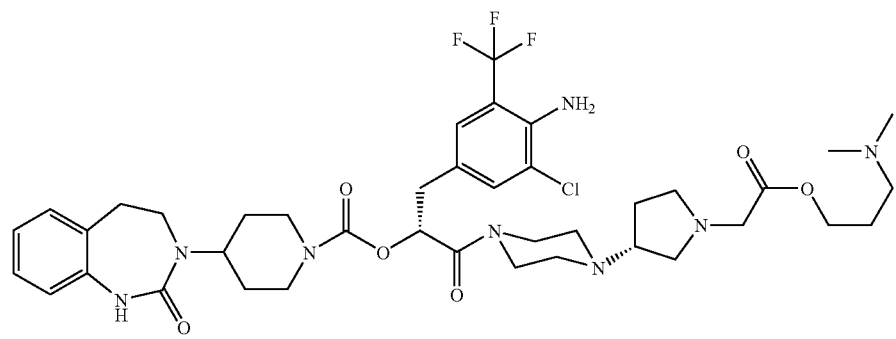 |
| (534) | 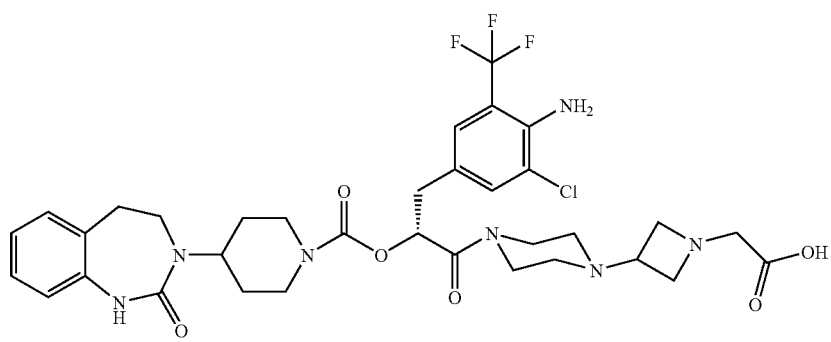 |

| No. | Structure |
|---|---|
| (535) | 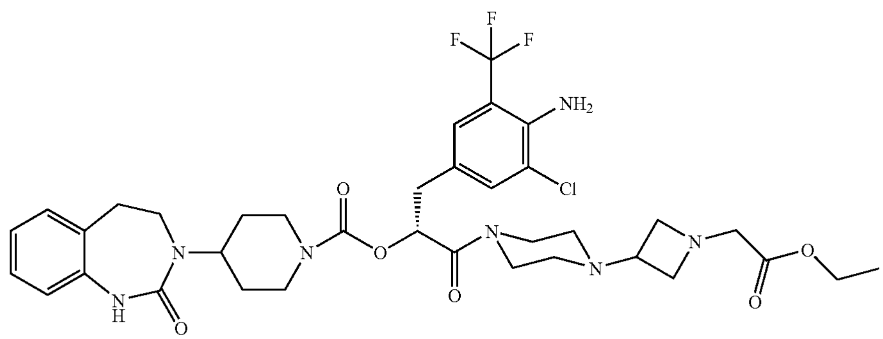 |
| (536) | 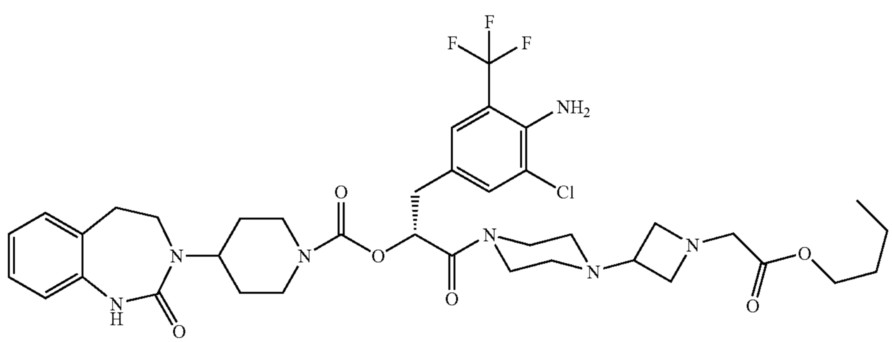 |
| (537) | 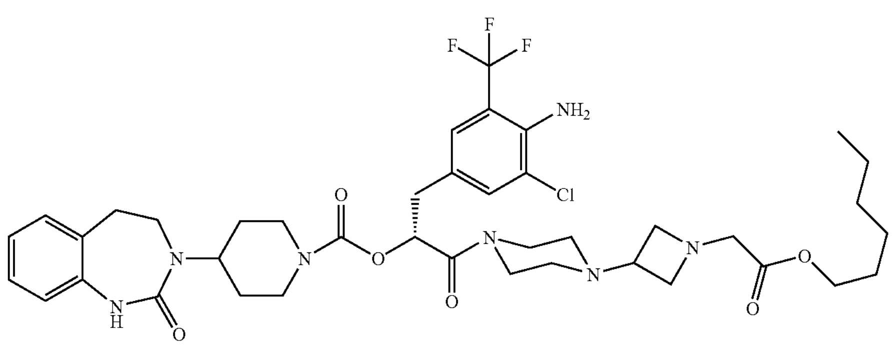 |
| (538) | 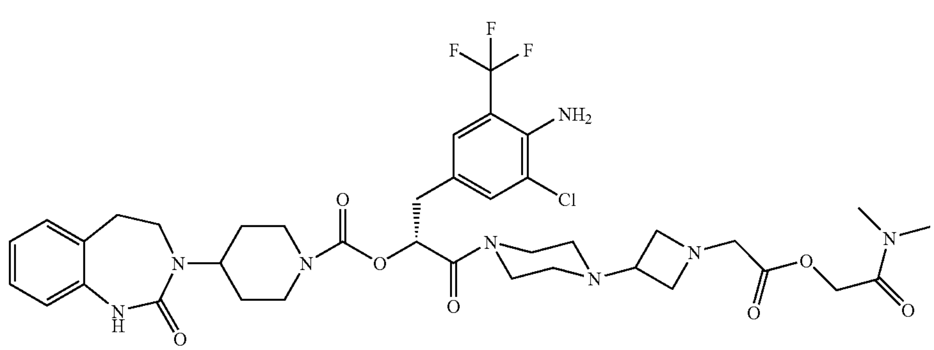 |

| No. | Structure |
|---|---|
| (539) | 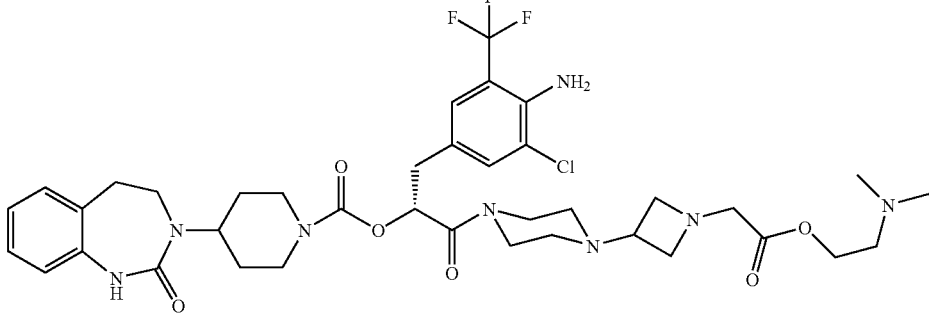 |
| (540) | 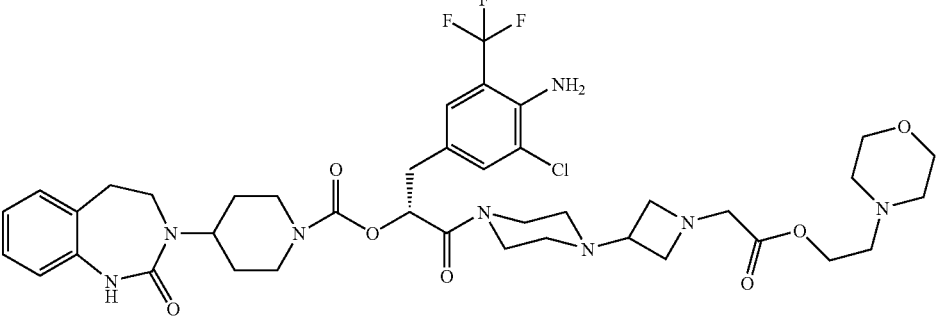 |
| (541) | 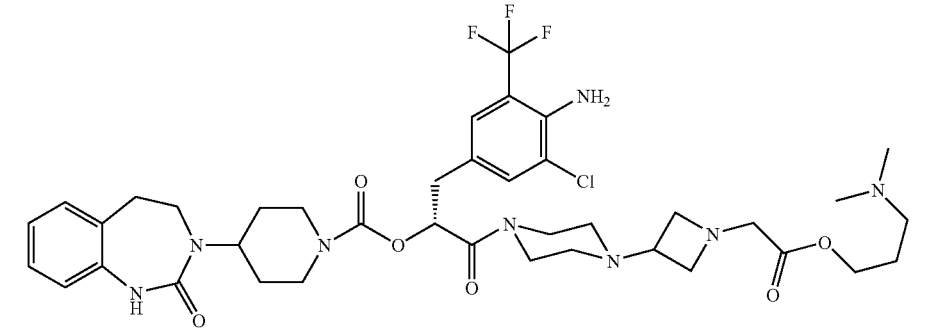 |
| (542) | 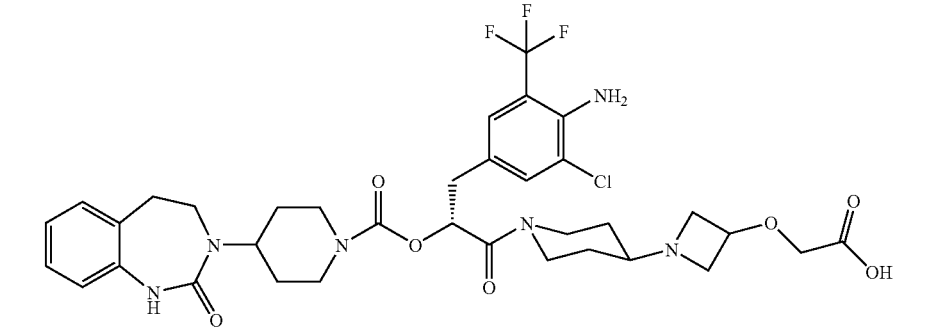 |

| No. | Structure |
|---|---|
| (543) | 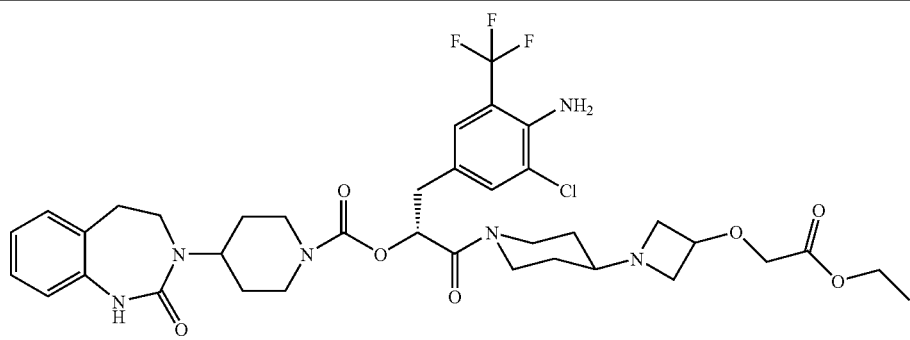 |
| (544) | 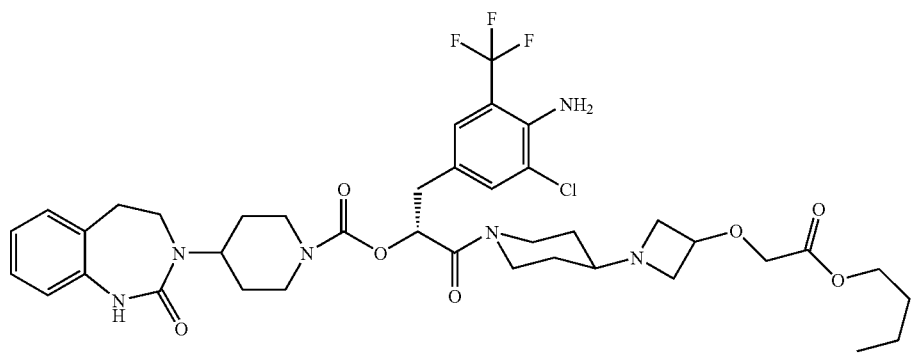 |
| (545) | 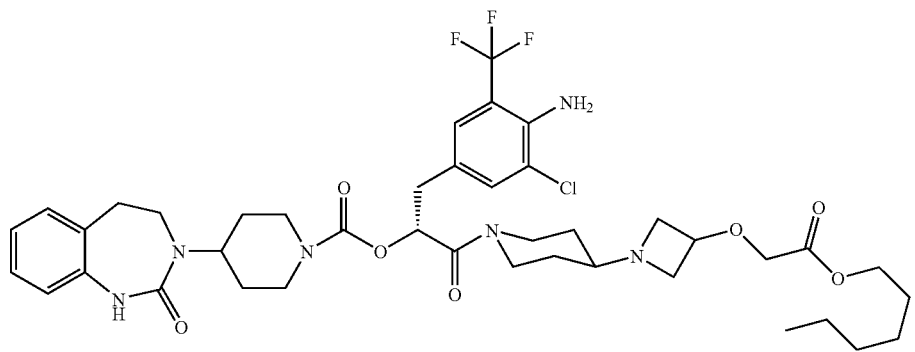 |
| (546) | 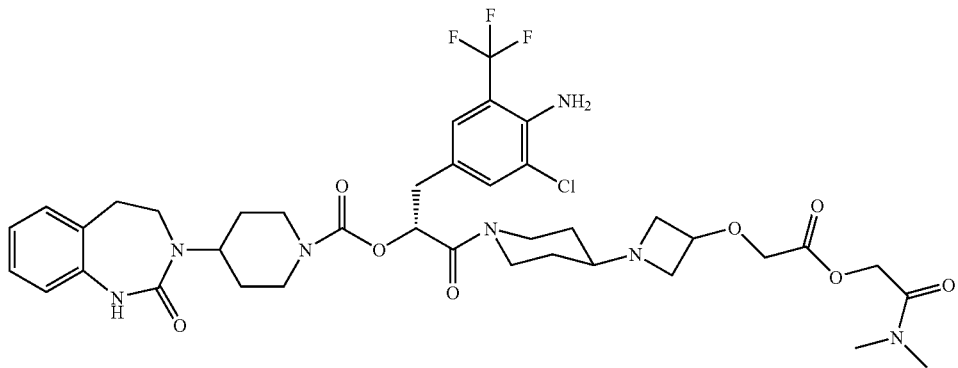 |

| No. | Structure |
|---|---|
| (547) | 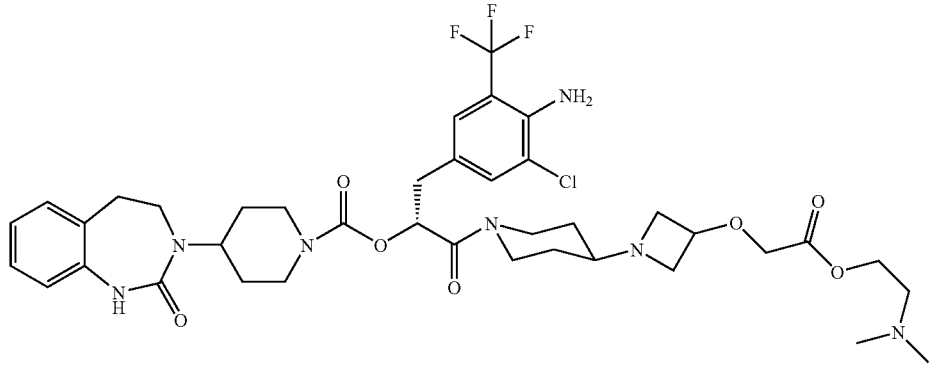 |
| (548) | 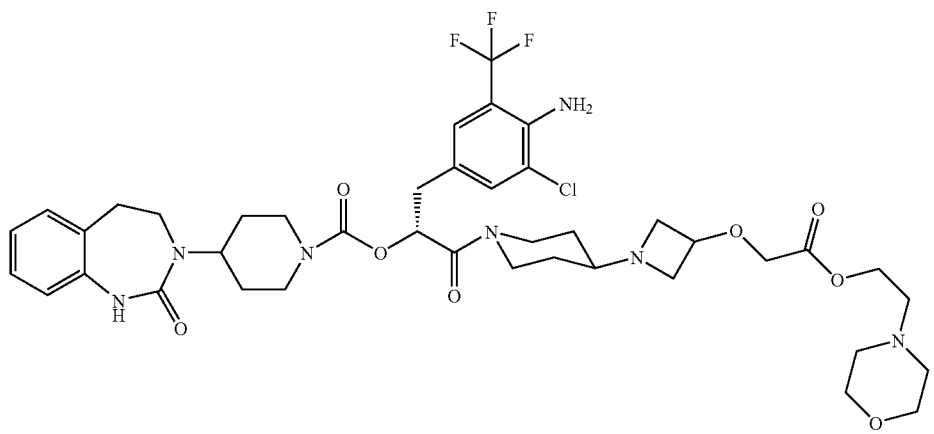 |
| (549) | 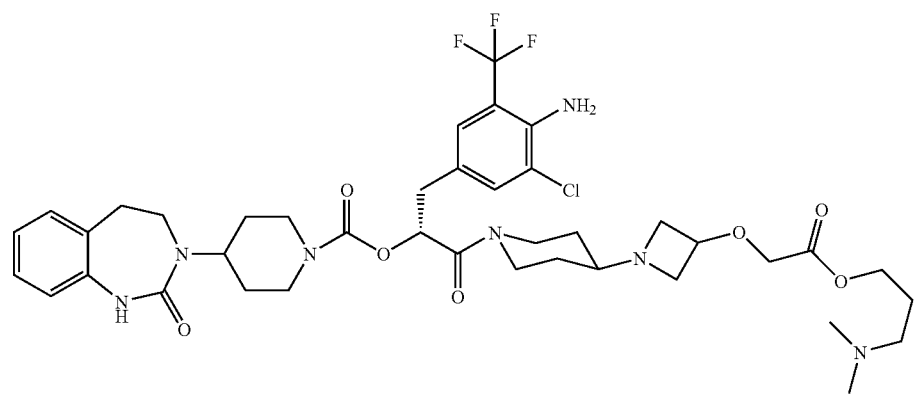 |
| (550) | 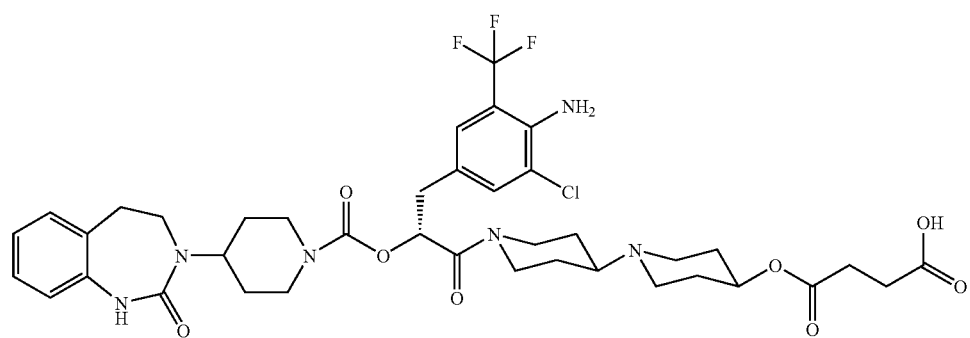 |

| No. | Structure |
|---|---|
| (551) | 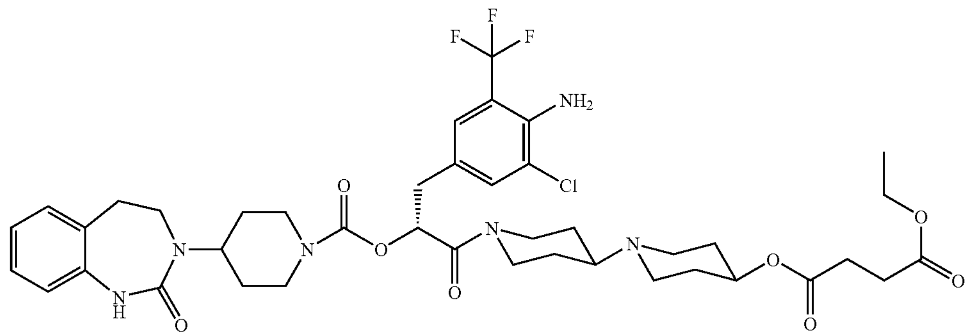 |
| (552) | 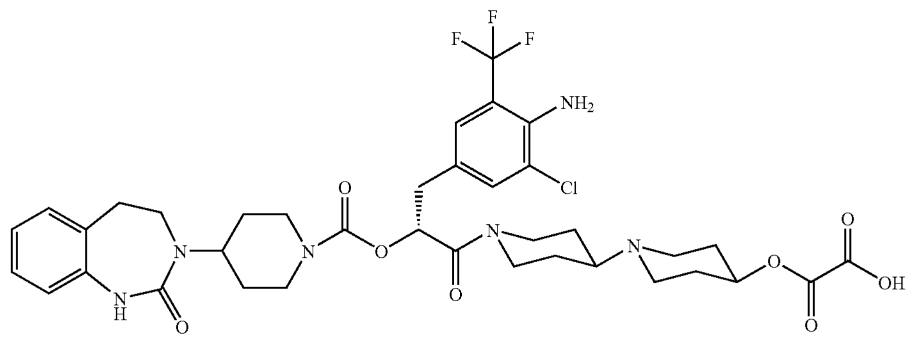 |
| (553) | 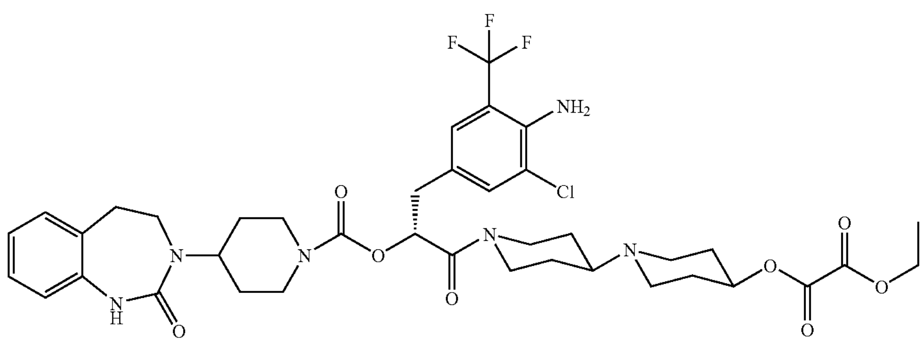 |
| (554) | 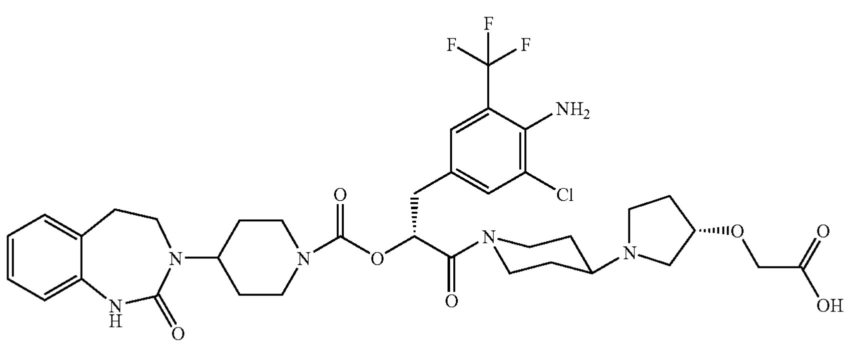 |

-continued

| No. | Structure |
|---|---|
| (555) | 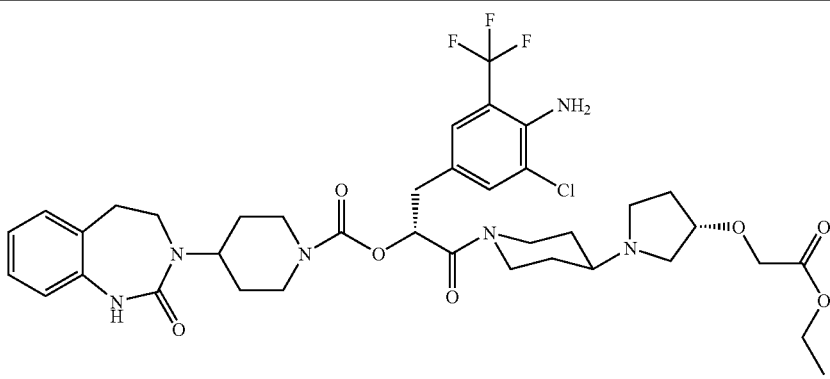 |
| (556) | 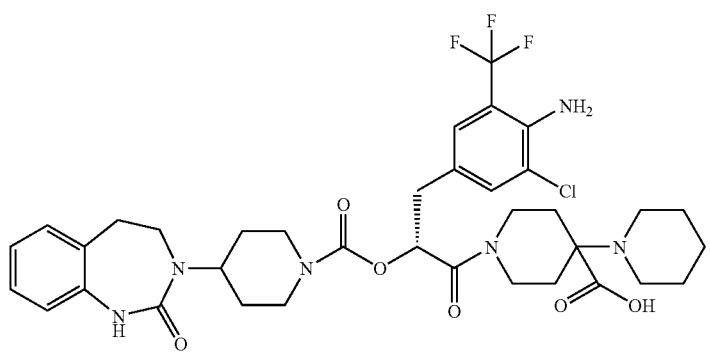 |
| (557) | 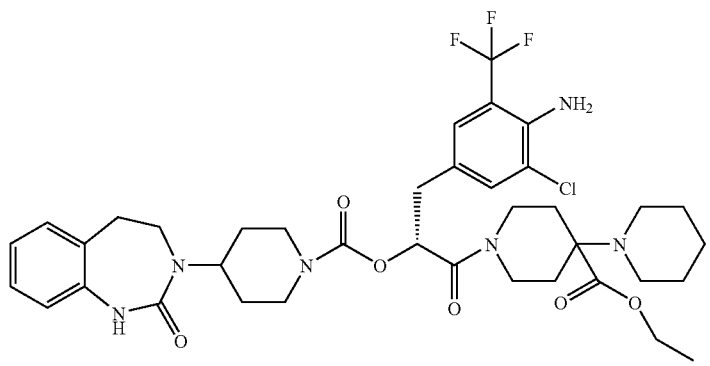 | the tautomers, the diastereomers, the enantiomers, the hydrates, the mixtures thereof and the salts thereof as well as the hydrates of the salts thereof, particularly the physiologically acceptable salts thereof with inorganic or organic acids or bases.

Terms and Definitions Used

Unless otherwise stated, all the substituents are independent of one another. If for example there are a plurality of $C_{1-6}$-alkyl groups as substituents in one group, in the case of three $C_{1-6}$-alkyl substituents, independently of one another, one may represent methyl, one n-propyl and one tert-butyl.

Within the scope of this application, in the definition of possible substituents, these may also be represented in the form of a structural formula. If present, an asterisk (*) in the structural formula of the substituent is to be understood as being the linking point to the rest of the molecule.

The subject-matter of this invention also includes the compounds according to the invention, including the salts thereof, wherein one or more hydrogen atoms, for example one, two, three, four or five hydrogen atoms, are replaced by deuterium.

By the term "$C_{1-3}$-alkyl" (including those which are part of other groups) are meant branched and unbranched alkyl groups with 1 to 3 carbon atoms, by the term "$C_{1-6}$-alkyl" are meant branched and unbranched alkyl groups with 1 to 6 carbon atoms and by the term "$C_{1-8}$-alkyl" are meant branched and unbranched alkyl groups with 1 to 8 carbon atoms. Examples include: methyl, ethyl, n-propyl, iso-propyl, n-butyl, iso-butyl, sec-butyl, tert-butyl, n-pentyl, iso-pentyl, neo-pentyl, hexyl, heptyl and octyl. The following abbreviations may optionally also be used for the above-mentioned groups: Me, Et, n-Pr, i-Pr, n-Bu, i-Bu, t-Bu, etc. Unless stated otherwise, the definitions propyl, butyl, pentyl, hexyl, heptyl or octyl include all the possible isomeric forms of the groups in question. Thus, for example, propyl includes n-propyl and iso-propyl, butyl includes iso-butyl, sec-butyl and tert-butyl etc.

By the term "$C_{1-3}$-alkylene" (including those which are part of other groups) are meant branched and unbranched alkylene groups with 1 to 3 carbon atoms and by the term "$C_{2-4}$-alkylene" are meant branched and unbranched alkylene groups with 2 to 4 carbon atoms. Examples include: methylene, ethylene, ethane-1,1-diyl, propylene, propane-2, 2-diyl, 1-methylethylene, butylene, 1-methylpropylene, 1,1-dimethylethylene, 1,2-dimethylethylene. Unless stated otherwise, the definitions propylene and butylene include all the possible isomeric forms with the same number of carbons. Thus, for example, propyl also includes 1-methylethylene and butylene includes 1-methylpropylene, 1,1-dimethylethylene, 1,2-dimethylethylene.

It should also be mentioned that within the scope of the present invention the terms "alkylene" and "alkylenyl" are used synonymously.

Compounds of general formula I may have acid groups, mainly carboxyl groups, and/or basic groups such as e.g. amino functions. Compounds of general formula I may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid, citric acid or as salts with pharmaceutically useable bases such as alkali or alkaline earth metal hydroxides, e.g. sodium hydroxide or potassium hydroxide, or carbonates, ammonia, zinc or ammonium hydroxides or organic amines such as e.g. diethylamine, triethylamine, ethanolamine, diethanolamine, triethanolamine, cyclohexylamine, dicyclohexylamine, inter alia.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

Methods of Preparation

The compounds of general formula I are prepared by methods known in principle. The following methods have proved particularly useful for preparing the compounds of general formula I according to the invention:

(a) For preparing compounds of general formula I wherein all the groups are as hereinbefore defined:

coupling a carboxylic acid of general formula V

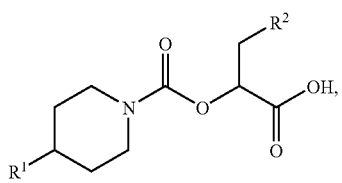

wherein $R^1$ and $R^2$ are as hereinbefore defined, with an amine of general formula VI

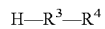

wherein $R^3$ and $R^4$ are as hereinbefore defined, the linking taking place via the nitrogen atom of $R^3$.

Before the reaction is carried out any carboxylic acid functions, primary or secondary amino functions or hydroxy functions present in the groups of the amine of formula H—$R^3$—$R^4$ may be protected by conventional protective groups and after the reaction has taken place any protective groups used may be cleaved again using methods familiar to those skilled in the art.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N-N',N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between –30° C. and +30° C., preferably –20° C. and +25° C. If necessary, N-ethyl-diisopropylamine (Hünig base) is preferably used as an additional auxiliary base.

The so-called "anhydride process" is used as a further coupling method for synthesising compounds of general formula I (cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the "mixed anhydride process" is preferred (J. R. Vaughan Jr., J. Amer. Chem. Soc. 73, 3547 (1951)), in which the mixed anhydride of the carboxylic acid of general formula V which is to be coupled and monoisobutyl carbonate is obtained, using isobutyl chlorocarbonate in the presence of bases such as 4-methylmorpholine or 4-ethylmorpholine. The preparation of this mixed anhydride and the coupling with the amines of general formula VI are carried out in a one-pot process, using the above-mentioned solvents and at temperatures between –20° C. and +25° C., preferably 0° C. and +25° C.

(b) For preparing compounds of general formula I wherein all the groups are as hereinbefore defined:

coupling a compound of general formula VII

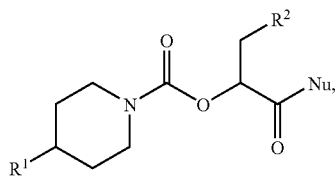

wherein $R^1$ and $R^2$ are as hereinbefore defined and Nu denotes a leaving group, for example a halogen atom, such as the chlorine, bromine or iodine atom, an alkylsulphonyloxy group with 1 to 10 carbon atoms in the alkyl moiety, a phenyl-sulphonyloxy or naphthylsulphonyloxy group optionally mono-, di- or trisubstituted by chlorine or bromine atoms, by methyl or nitro groups, wherein the substituents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxo -pyrrolidin-1-yloxy, phthalimidyloxy, 1H-benzotriazol-1-yloxy or azide group, with an amine of general formula VI

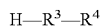

wherein all the groups are as hereinbefore defined and the link is effected via the nitrogen atom of the amine $R^3$.

Before the reaction is carried out any carboxylic acid functions, primary or secondary amino functions or hydroxy functions present in the groups of the amine of general formula VI may be protected by conventional protective groups and after the reaction has taken place any protective groups used may be cleaved again using methods familiar to those skilled in the art.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

The new compounds of general formula I according to the invention contain one or more chiral centres. If for example there are two chiral centres present, the compounds may occur in the form of two diastereomeric pairs of antipodes. The invention includes the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula I may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+) or (−)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula I is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. with dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The hydroxycarboxylic acids of general formula V needed as starting compounds may be obtained by reacting piperidines of general formula VIII

wherein $R^1$ is as hereinbefore defined, with carbonic acid derivatives of general formula IX

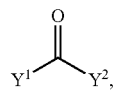

wherein $Y^1$ and $Y^2$ represent nucleofugic groups, which may be identical or different, preferably the chlorine atom, the p-nitrophenoxy or trichloromethoxy group, and with compounds of general formula X

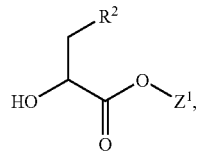

wherein $R^2$ is as hereinbefore defined and $Z^1$ denotes a protective group for a carboxy group, for example a $C_{1-6}$-alkyl or an optionally substituted benzyl group, wherein the alkyl groups may be straight-chain or branched and the benzyl group may be substituted by one or two methoxy groups.

Preferably $Z^1$ denotes the methyl, ethyl, tert-butyl or benzyl group. Before the reaction is carried out any hydroxy functions present in the group $R^2$ of a compound of formula (VI) may be protected by conventional protective groups and after the reaction is complete any protective groups used may be cleaved again using methods familiar to the skilled man.

In a first step the compounds of general formula VIII are reacted with the carbonic acid derivatives of general formula IX in a solvent, for example in dichloromethane, THF, pyridine or mixtures thereof, at a temperature between −20° C. to 50° C. in the presence of a base, for example triethylamine, pyridine or ethyldiisopropylamine. The intermediate thus formed may be purified or reacted further without purification. The reaction of these intermediates with compounds of general formula X also takes place in one of the abovementioned solvates and at the temperatures specified above, in the presence of a base, such as triethylamine or pyridine, with or without the addition of an activating reagent, such as e.g. 4-dimethylaminopyridine. To activate them the compounds of general formula X may also be deprotonated using a metal hydride, such as e.g. NaH or KH, while in this case there is no need for the base or the activating reagent to be present.

The starting compounds of formula VIII and IX are either commercially obtainable, known from the literature or may be prepared using methods known from the literature.

One way of obtaining compounds of general formula X comprises reacting aldehydes of general formula XI

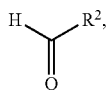

wherein $R^2$ is as hereinbefore defined, with N-acetylglycine in acetic anhydride as solvent in the presence of alkali metal acetate, preferably sodium or potassium acetate, at suitable temperatures, preferably at 80 to 130° C.

The azlactones obtained as primary product are hydrolysed without being isolated to form the compounds of general formula XII

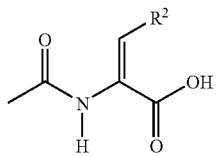

wherein $R^2$ is as hereinbefore defined. By further reaction in the presence of aqueous inorganic acids, such as sulphuric, phosphoric or hydrochloric acid, but preferably hydrochloric acid, compounds of general formula XIII are obtained

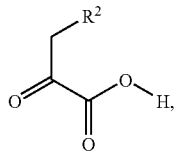

wherein $R^2$ is as hereinbefore defined.

These are then converted with suitable reducing agents into the compounds of general formula XIV

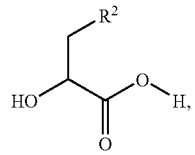

wherein $R^2$ is as hereinbefore defined.

Suitable reducing agents are alkali metal borohydrides, such as sodium or potassium borohydride. Other suitable reducing agents are chlorodialkylboranes, such as chlorodicyclohexylborane. If chiral chlorodialkylboranes, such as e.g. B -chlorodiisopinocampheylborane, are used, the compounds of general formula XIV may be isolated in enantiomerically pure form. The further reaction of compounds of general formula XIV to form compounds of general formula X is carried out in an alcoholic medium, preferably in methanol or ethanol, in the presence of a suitable acid, such as hydrochloric acid. Alternatively, the reaction may be carried out by reacting with thionyl chloride in alcoholic solvents, preferably methanol.

All the compounds of general formula I which contain primary or secondary amino, hydroxy or hydroxycarbonyl functions are preferably obtained from precursors with protective groups. Examples of protective groups for amino functions include a benzyloxycarbonyl, 2-nitrobenzyloxycarbonyl, 4-nitro-benzyloxycarbonyl, 4-methoxy-benzyloxycarbonyl, 2-chloro-benzyloxycarbonyl, 3-chloro -benzyloxycarbonyl, 4-chloro-benzyloxycarbonyl, 4-biphenylyl-α,α-dimethyl-benzyl-oxycarbonyl or 3,5-dimethoxy-α,α-dimethyl-benzyloxycarbonyl group, an alkoxycarbonyl group with a total of 1 to 5 carbon atoms in the alkyl moiety, for example the methoxycarbonyl, ethoxycarbonyl, n-propoxycarbonyl, iso-propoxycarbonyl, n-butoxycarbonyl, 1-methylpropoxycarbonyl, 2-methylpropoxy-carbonyl or tert-butyloxycarbonyl group, the allyloxycarbonyl, 2,2,2-trichloro-(1,1-dimethylethoxy)carbonyl or 9-fluorenylmethoxycarbonyl group or a formyl, acetyl or trifluoracetyl group.

Examples of protective groups for hydroxy functions include a trimethylsilyl, triethylsilyl, triisopropyl, tert-butyldimethylsilyl or tert-butyldiphenylsilyl group, a tert -butyl, benzyl, 4-methoxybenzyl or 3,4-dimethoxybenzyl group.

Examples of protective groups for hydroxycarbonyl functions include an alkyl group with a total of 1 to 5 carbon atoms, for example the methyl, ethyl, n-propyl, isopropyl, n-butyl, tert-butyl, allyl, 2,2,2-trichloroethyl, benzyl or 4-methoxybenzyl group.

The compounds of general formula I obtained may, if they contain suitable basic functions, be converted, particularly for pharmaceutical use, into their physiologically acceptable salts with inorganic or organic acids. Suitable acids include for example hydrochloric acid, hydrobromic acid, phosphoric acid, nitric acid, sulphuric acid, methanesulphonic acid, ethanesulphonic acid, benzenesulphonic acid, p-toluenesulphonic acid, acetic acid, fumaric acid, succinic acid, lactic acid, mandelic acid, malic acid, citric acid, tartaric acid or maleic acid.

Moreover, if they contain a carboxylic acid function, the new compounds of formula I may be converted into the addition salts thereof with inorganic or organic bases, particularly, for pharmaceutical use, into their physiologically acceptable addition salts. Suitable bases for this include for example sodium hydroxide, potassium hydroxide, ammonia, cyclohexylamine, dicyclohexylamine, ethanolamine, diethanolamine and triethanolamine.

The present invention relates to racemates if the compounds of general formula I have only one chiral element. However, the application also includes the individual diastereomeric pairs of antipodes or mixtures thereof which are obtained if there is more than one chiral element in the compounds of general formula I, as well as the individual optically active enantiomers of which the above-mentioned racemates are made up.

Also included in the subject matter of this invention are the compounds according to the invention, including the salts thereof, in which one or more hydrogen atoms, for example one, two, three, four or five hydrogen atoms, are replaced by deuterium.

The new compounds of general formula I and the physiologically acceptable salts thereof have valuable pharmacological properties, based on their selective CGRP-antagonistic properties. The invention further relates to pharmaceutical compositions containing these compounds, their use and the preparation thereof. The new compounds mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM MgCl$_2$, 1 mM EDTA, pH 7.40) and homogenised for 30 seconds with an Ultra-Turrax. 230 µl of the homogenised product are incubated for 180 minutes at ambient temperature with 50 pM $^{125}$I-iodotyrosyl-Calcitonin -Gene-Related Peptide (Amersham) and increasing concentrations of the test substances in a total volume of 250 µl. The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity after the presence of 1 µM human CGRP-alpha during incubation.

The concentration binding curves are analysed using computer-aided non-linear curve fitting.

The compounds mentioned hereinbefore show IC$_{50}$ values ≦10000 nM in the test described.

B. CGRP Antagonism in SK-N-MC Cells

SK-N-MC cells (1 million cells) are washed twice with 250 µl incubation buffer (Hanks' HEPES, 1 mM 3-isobutyl-1-methylxanthine,1% BSA, pH 7.4) and pre-incubated at 37° C. for 15 minutes. After the addition of CGRP (10 µl) as agonist in increasing concentrations (10$^{-11}$ to 10$^{-6}$ M), or additionally the substance in 3 to 4 different concentrations, the mixture is incubated for another 15 minutes.

Intracellular cAMP is then extracted by the addition of 20 µl of 1M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the pA$_2$ values of antagonistically acting substances are determined graphically.

The compounds according to the invention exhibit CGRP-antagonistic properties in the in vitro test model described, in a dosage range between 10$^{-12}$ and 10$^{-5}$ M.

Indications

In view of their pharmacological properties the compounds according to the invention and the salts thereof with physiologically acceptable acids are thus suitable for the acute and prophylactic treatment of headaches, particularly migraine or cluster headaches and tension headaches. Moreover, the compounds according to the invention also have a positive effect on the following diseases: non-insulin-dependent diabetes mellitus ("NIDDM"), cardiovascular diseases, morphine tolerance, diarrhea caused by *clostridium* toxin, skin diseases, particularly thermal and radiation-induced skin damage including sunburn, lichen, pruritis, pruritic toxidermies and severe itching, inflammatory diseases, e.g. inflammatory diseases of the joints (osteoarthritis, rheumatoid arthritis, neurogenic arthritis), generalised soft-tissue rheumatism (fibromyalgia), neurogenic inflammation of the oral mucosa, inflammatory lung diseases, allergic rhinitis, asthma, COPD, diseases accompanied by excessive vasodilatation and resultant reduced blood supply to the tissues, e.g. shock and sepsis, chronic pain, e.g. diabetic neuropathies, neuropathies induced by chemotherapy, HIV-induced neuropathies, postherpetic neuropathies, neuropathies induced by tissue trauma, trigeminal neuralgias, temporomandibular dysfunctions, CRPS (complex regional pain syndrome), back pain, and visceral complaints, such as e.g. irritable bowel syndrome (IBS) and inflammatory bowel syndrome. In addition, the compounds according to the invention have a general pain-relieving effect. The symptoms of menopausal hot flushes caused by vasodilatation and increased blood flow in oestrogen-deficient women and hormone-treated patients with prostate carcinoma and castrated men are favourably affected by the CGRP antagonists of the present application in a preventive and acute-therapeutic capacity, this therapeutic approach being distinguished from hormone replacement by the absence of side effects.

Preferably, the compounds according to the invention are suitable for the acute and prophylactic treatment of migraine and cluster headaches, for treating irritable bowel syndrome (IBS) and for the preventive and acute-therapeutic treatment of hot flushes in oestrogen-deficient women.

The dosage required to achieve a corresponding effect is conveniently 0.0001 to 3 mg/kg of body weight, preferably 0.01 to 1 mg/kg of body weight, when administered intravenously or subcutaneously, and 0.01 to 10 mg/kg of body weight, preferably 0.1 to 10 mg/kg of body weight when administered orally, nasally or by inhalation, 1 to 3× a day in each case.

If the treatment with CGRP antagonists and/or CGRP release inhibitors is given as a supplement to conventional hormone replacement, it is advisable to reduce the doses specified above, in which case the dosage may be from ⅕ of the lower limits mentioned above up to ¹⁄₁ of the upper limits specified.

CGRP is released by sensory nerves, e.g. the trigeminal nerve, which innervates part of the skin of the face. It has already been shown that irritation of the trigeminal ganglion in humans leads to an increase in the CGRP plasma level and causes redness of the face ([4]: P. J. Goadsby et al., Annals of Neurology, Vol. 23, No. 2, 1988, 193-196).

To demonstrate that hot flushes can be successfully treated with CGRP antagonists of general formula I, an increased release of endogenous CGRP was produced in marmosets by stimulating the trigeminal ganglion, leading to increased bloodflow through the blood vessels in the skin. The effectiveness was characterised by determining the particular dose, administered i.v., which reduces the increased blood flow through the facial skin caused by endogenous CGRP by 50%. A detailed description of the method is disclosed in European Patent EP 1 207 884 B1.

The CGRP antagonists according to the invention are also active in a model for visceral pain in rodents. In this model, hypersensitivity of the visceral system is achieved by irritating the gut by instilling chemical substances such as e.g. butyrate, trinitrobenzenesulphonic acid or acetic acid. The hypersensitivity of the gut is determined, for example, by means of the number of abdominal contractions. These occur after the expansion of a balloon introduced into the gut and are increased in a hypersensitive gut (Bourdu et al., Gastroenterology 2005, 128, 1996-2008; Diop et al., J. Phamacol. Exp. Ther. 2002, 302, 1013-1022; Plourde et al. Am. J. Physiol. 1997, 273, G191-G196).

As they reverse the hypersensitivity of the gut in the model described, the CGRP antagonists according to the invention may be used for the treatment of IBS (irritable bowel syndrome).

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Combinations

Categories of active substance which may be used in combination include e.g. antiemetics, prokinetics, neuroleptics, antidepressants, neurokinin antagonists, anticonvulsants, histamine-H1-receptor antagonists, β-blockers, α-agonists and α-antagonists, ergot alkaloids, mild analgesics, non-steroidal antiphlogistics, corticosteroids, calcium antagonists, $5\text{-HT}_{1B/1D}$-agonists or other anti-migraine agents which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, acetaminophen (paracetamol), azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib, valdecoxib, parecoxib, etoricoxib and celecoxib, as well as substances that inhibit earlier or later stages of prostaglandin synthesis or prostaglandin receptor antagonists such as e.g. EP2-receptor antagonists and IP-receptor antagonists.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, pregabalin, duloxetine, topiramate, riboflavin, montelukast, lisinopril, micardis, prochloroperazine, dexamethasone, flunarizine, dextropropoxyphene, meperidine, metoprolol, propranolol, nadolol, atenolol, clonidine, indoramin, carbamazepine, phenytoin, valproate, amitryptiline, imipramine, venlafaxine, lidocaine or diltiazem and other $5\text{-HT}_{1B/1D}$-agonists such as, for example, almotriptan, avitriptan, eletriptan, frovatriptan, naratriptan, rizatriptan, sumatriptan and zolmitriptan.

Furthermore, CGRP antagonists with vanilloid receptor antagonists, such as e.g. VR-1 antagonists, glutamate receptor antagonists, such as e.g. mGlu5 receptor antagonists, mGlu1 receptor antagonists, iGlu5 receptor antagonists, AMPA receptor antagonists, purine receptor blockers, such as e.g. P2X3 antagonists, NO-synthase inhibitors, such as e.g. iNOS inhibitors, calcium channel blockers, such as e.g. PQ-type blockers, N-type blockers, potassium channel openers, such as e.g. KCNQ channel openers, sodium channel blockers, such as e.g. PN3 channel blockers, NMDA receptor antagonists, acid-sensing ion channel antagonists, such as e.g. ASIC3 antagonists, bradykinin receptor antagonists such as e.g. B1 receptor antagonists, cannabinoid receptor agonists, such as e.g. CB2 agonists, CB1 agonists, somatostatin receptor agonists, such as e.g. sst2 receptor agonists may be added.

The dosage of these active substances is expediently ⅕ of the lowest usually recommended dose to ¹⁄₁ of the normally recommended dose, i.e. for example 20 to 100 mg of sumatriptan.

Formulations

The compounds prepared according to the invention may be administered either on their own or optionally in combination with other active substances for the treatment of migraine by intravenous, subcutaneous, intramuscular, intraarticular, intrarectal, intranasal route, by inhalation, topically, transdermally or orally, while aerosol formulations are particularly suitable for inhalation. The combinations may be administered either simultaneously or sequentially.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula I according to the preferred embodiments above.

It is particularly preferable if the compounds of formula I are administered orally, and it is also particularly preferable if they are administered once or twice a day. Suitable tablets may be obtained, for example, by mixing the active substance (s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula I are administered by inhalation, particularly preferably if they are administered once or twice a day. For this purpose, the compounds of formula I have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the compounds of formula I are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain I dissolved in the propellant gas or in dispersed form. The propellant gases which may be used to prepare the inhalation aerosols are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula I according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as, for example, sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

Experimental Section

As a rule $^1$H-NMR and mass spectra have been obtained for the compounds prepared. Unless stated otherwise, $R_f$ values are determined using ready-made TLC silica gel plates 60 F254 (E. Merck, Darmstadt, Item no. 1.05714) without chamber saturation.

The Rf values determined under the name Polygram silica gel are obtained using ready-made Polygram SIL G/UV254 TLC films (coated with 0.2 mm silica gel) made by Macherey-Nagel (Düren, Item no. 805 021).

The Rf values determined under the name Polygram Alox are obtained using ready-made Polygram Alox N/UV254 TLC films (coated with 0.2 mm aluminium oxide) made by Macherey-Nagel (Düren, Item no. 802 021).

The ratios given for the eluants relate to units by volume of the particular solvents.

The units by volume given for $NH_3$ relate to a concentrated solution of $NH_3$ in water.

Unless stated otherwise, the acid, base and salt solutions used in working up the reaction solutions are aqueous systems of the specified concentrations. Silica gel made by Millipore (MATREX™, 35-70 μm) is used for chromatographic purifications.

Aluminium oxide (Alox) made by ICN Biomedicals (Eschwege, Item no. 02090) is used for chromatographic purifications. The required activity stage (activity stage II-III) is generated before use according to the manufacturer's instructions. The HPLC data provided are measured under the parameters listed below:

Method A:

Analytical column: Merck Chromolith Speed ROD, RP18e; 4.6×50 mm; column temperature: 30° C.; flow: 1.5 mL/min; injection volume: 5 μL; detection at 254 nm

| time [min] | Percent of water by volume (with 0.1% formic acid) | Percent of acetonitrile by volume (with 0.1% formic acid) |
|---|---|---|
| 0 | 90 | 10 |
| 4.5 | 10 | 90 |
| 5 | 10 | 90 |
| 5.5 | 90 | 10 |

Method B:

Analytical column: Zorbax column (Agilent Technologies), SB (Stable Bond)—C18; 3.5 μm; 4.6×75 mm; column temperature: 30° C.; flow: 1.6 mL/min; injection volume: 5 μL; detection at 254 nm

| time [min] | Percent of water by volume (with 0.1% formic acid) | Percent of acetonitrile by volume (with 0.1% formic acid) |
|---|---|---|
| 0 | 95 | 5 |
| 4.5 | 10 | 90 |
| 5.0 | 10 | 90 |
| 5.5 | 90 | 10 |

Method C:

Analytical column: Zorbax column (Agilent Technologies), SB (Stable Bond)—C18; 3.5 μm; 4.6×75 mm; column temperature: 30° C.; flow: 0.8 mL/min; injection volume: 5 μL; detection at 254 nm

| time [min] | Percent of water by volume (with 0.1% formic acid) | Percent of acetonitrile by volume (with 0.1% formic acid) |
|---|---|---|
| 0 | 95 | 5 |
| 9 | 10 | 90 |
| 10 | 10 | 90 |
| 11 | 90 | 10 |

In preparative HPLC purifications as a rule the same gradients are used as were used to obtain the analytical HPLC data.

The products are collected under mass control, the fractions containing product are combined and freeze-dried.

In the absence of any more information regarding the configuration, it is unclear whether there are pure enantiomers involved or whether partial or even total racemisation has taken place.

The following abbreviations are used in the test descriptions:

| | |
|---|---|
| Boc | tert-butoxycarbonyl |
| Cyc | cyclohexane |
| DCM | dichloromethane |
| DIPE | diisopropylether |
| DMF | N,N-dimethylformamide |
| EtOAc | ethyl acetate |
| EtOH | ethanol |
| h | hour |
| HCl | hydrochloric acid |
| HOAc | acetic acid |
| i. vac. | in vacuo (under vacuum) |
| min | minute |
| MeOH | methanol |
| MTBE | methyl-tert-butylether |
| NaOH | sodium hydroxide |
| PE | petroleum ether |
| RT | ambient temperature |
| TBTU | 2-(1H-benzotriazol-1-yl)-1,1,3,3-tetramethyluronium tetrafluoroborate |
| TFA | trifluoroacetic acid |
| THF | tetrahydrofuran |

The preparation of starting compounds is described below:

Amine 1

Ethyl 3-[4,4']bipiperidinyl-1-yl-propionate

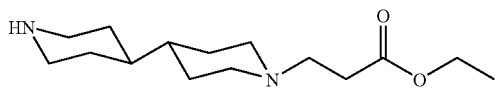

A1a) tert-butyl 1'-(2-ethoxycarbonyl-ethyl)-[4,4']bipiperidinyl-1-carboxylate 4.4 mL (40.6 mmol) ethyl acrylate were added to a solution of 10.0 g (37.3 mmol) tert-butyl[4,4']bipiperidinyl-1-carboxylate in 100 mL EtOH and the reaction mixture was refluxed for 2 h. To complete the reaction a further 1 mL (9.2 mmol) of ethyl acrylate were added, the mixture was refluxed for 1 h and left overnight at RT. The solvent was eliminated i. vac. and the crude product was further reacted without being purified.

Yield: 14.0 g (100% of theory)
ESI-MS: (M+H)$^+$=369

A1b) ethyl 3-[4,4']bipiperidinyl-1-yl-propionate 28 mL TFA were added dropwise to a solution of 14.0 g of the crude product of Example A1a in 250 mL DCM and the reaction mixture was stirred for 4 h at RT. The mixture was evaporated down i. vac., the residue was taken up in 200 mL DCM and this solution was added batchwise to a solution of 20 g Na$_2$CO$_3$ in 120 mL water. The organic phase was separated off, the aqueous phase was extracted twice more with DCM and the combined organic phases were dried over Na$_2$SO$_4$. After elimination of the desiccant and solvent the residue was dried and reacted without further purification.

Yield: 8.8 g (88% of theory)
ESI-MS: (M+H)$^+$=269

Amine 2

Ethyl 3-(4-piperazin-1-yl-piperidin-1-yl)-propionate

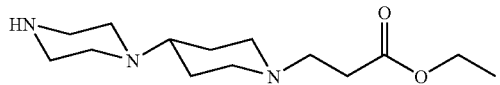

A2a) ethyl 3-[4-(4-benzyl-piperazin-1-yl)-piperidin-1-yl]-propionate 5.5 mL (50.8 mmol) ethyl acrylate were added to a solution of 11.7 g (44.9 mmol) 1-benzyl-4-piperidin-4-yl-piperazine in 120 mL dry EtOH and the reaction mixture was refluxed for 1 h and then stirred overnight at RT. The solvent was eliminated i. vac. and the residue was dried for 1 h under an oil pump vacuum. The crude product was reacted further without purification.

Yield: 16.5 g (99% of theory)
ESI-MS: (M+H)$^+$=360

A2b) ethyl 3-(4-piperazin-1-yl-piperidin-1-yl)-propionate

A suspension of 16.5 g of the crude product of Example A2a and 1.6 g of 10% Pd/C in 200 mL EtOH and was hydrogenated for 4 h at 50° C. and 50 psi hydrogen pressure. The catalyst was removed by suction filtering, the filtrate was evaporated down to about 120 mL and combined with 72 mL ethanolic HCl (1.3 M). The precipitate formed was suction filtered and dried i. vac. The product was obtained as the bis-hydrochloride salt.

Yield: 12.6 g (83% of theory)
ESI-MS: (M+H)$^+$=270

Amine 3

Ethyl 3-(4-piperidin-4-yl-piperazin-1-yl)-propionate

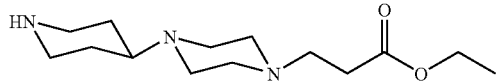

A3a) ethyl 3-[4-(1-benzyl-piperidin-4-yl)-piperazin-1-yl]-propionate 12.5 mL (73.0 mmol) ethyldiisopropylamine and 5.0 mL (46.1 mmol) ethyl acrylate were added to a solution of 11.0 g (33.2 mmol) 1-(1-benzyl-piperidin-4-yl)-piperazine (used as the bis-hydrochloride salt) in 40 mL EtOH and the reaction mixture was heated to 90° C. (bath temperature) for 3 h. After cooling, water was added, the mixture was exhaustively extracted with EtOAc and the combined organic phases were dried over Na$_2$SO$_4$. After elimination of the desiccant and solvent the residue was purified by chromatography (silica gel, DCM/EtOH/NH$_3$ 100:10:1).

Yield: 6.8 g (56% of theory)
ESI-MS: (M+H)$^+$=360
R$_f$=0.64 (silica gel, DCM/MeOH/NH$_3$ 90:9:1)

A3b) ethyl 3-(4-piperidin-4-yl-piperazin-1-yl)-propionate

A suspension of 5.13 g (14.3 mmol) ethyl 3-[4-(1-benzyl-piperidin-4-yl)-piperazin-1-yl]-propionate and 1.0 g 10% Pd/C in 100 mL EtOH was hydrogenated for 2 h at 50° C. and 50 psi hydrogen pressure. The catalyst was filtered off and the filtrate was evaporated to dryness. The oily product was reacted further without purification.

Yield: 3.6 g (93% of theory)
ESI-MS: (M+H)$^+$=270

Amine 4

Ethyl[4,4']bipiperidinyl-1-yl-oxo-acetate

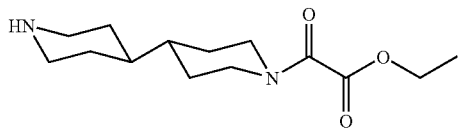

A4a) tert-butyl 1'-ethoxyoxalyl-[4,4']bipiperidinyl-1-carboxylate 1.68 mL (15.0 mmol) ethyl chloro-oxo-acetate were added dropwise to a solution of 4.0 g (14.9 mmol) tert-butyl[4,4']bipiperidinyl-1-carboxylate and 2.15 mL (15.4 mmol) triethylamine in 80 mL DCM, cooled to 0° C. After the addition had ended the cooling bath was removed and the mixture was stirred for 1 h at RT. The reaction mixture was mixed with water, the organic phase was separated off and dried over Na$_2$SO$_4$. After elimination of the desiccant and solvent the residue was taken up in EtOAc, the solution was filtered through silica gel and evaporated down i. vac.

Yield: 3.1 g (57% of theory)
ESI-MS: (M+H)$^+$=386

A4b) ethyl[4,4']bipiperidinyl-1-yl-oxo-acetate 5.0 mL TFA were added dropwise to a solution of 3.1 g (8.36 mmol) tert-butyl 1'-ethoxyoxalyl-[4,4']bipiperidinyl-1-carboxylate in 40 mL DCM and the reaction mixture was stirred for 4 h at RT. The mixture was evaporated down i. vac., the residue was taken up in 50 mL DCM and this solution was added batchwise to an ice-cold solution of 4.0 g Na$_2$CO$_3$ in 20 mL water. The organic phase was separated off, the aqueous phase was extacted twice more with DCM and the combined organic phases were dried over Na$_2$SO$_4$. After elimination of the desiccant and solvent the product was obtained as an oil, which was reacted further without purification.

Yield: 2.3 g (84% of theory)
ESI-MS: (M+H)$^+$=269

Amine 5

Ethyl4-[4,4']bipiperidinyl-1-yl-4-oxo-butyrate

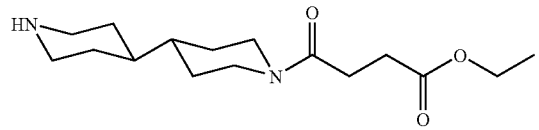

A5a) tert-butyl 1'-(3-carboxy-propionyl)-[4,4']bipiperidinyl-1-carboxylate

A solution of 4.1 g (40.7 mmol) succinic acid anhydride in 50 mL THF was added dropwise at RT to a solution of 10.0 g (37.3 mmol) tert-butyl[4,4']bipiperidinyl-1-carboxylate in 100 mL THF and the reaction mixture was stirred overnight at RT. To complete the reaction another 2.0 g (19.9 mmol) succinic acid anhydride were added, the mixture was stirred for 4 h at 50° C. and stirred overnight at RT. 200 mL of 7.5% K$_2$CO$_3$ solution was added and the aqueous phase was washed with 200 mL EtOAc. The organic phase was extracted with 200 mL 7.5% K$_2$CO$_3$ solution and the combined aqueous phases were acidified with citric acid. The mixture was extracted exhaustively with EtOAc and the combined organic phases were evaporated down i. vac.

Yield: 11.7 g (85% of theory)
ESI-MS: (M+H)$^+$=369

A5b) ethyl 4-[4,4']bipiperidinyl-1-yl-4-oxo-butyrate

A solution of 11.7 g (31.7 mmol) tert-butyl 1'-(3-carboxy-propionyl)-[4,4']bipiperidinyl-1-carboxylate in 250 mL ethanolic HCl (1.25 M) was stirred overnight at RT. The solvent was eliminated i. vac. and the product was obtained as the hydrochloride salt, which was reacted further without purification.

Yield: 4.3 g (46% of theory)
ESI-MS: (M+H)$^+$=297

Amine 6

Ethyl([1,4']bipiperidinyl-4-yl-tert-butoxycarbonyl-amino)-acetate

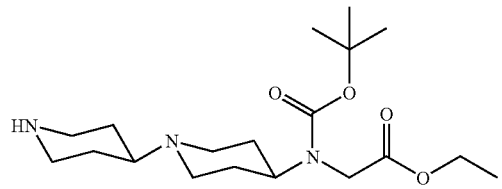

A6a) tert-butyl(1'-benzyl-[1,4']bipiperidinyl-4-yl)-carbamate

A solution of 5.0 g (25.0 mmol) tert-butyl piperidin-4-yl-carbamate and 4.46 mL (25.0 mmol) 1-benzyl-piperidin-4-one in 150 mL THF was adjusted with AcOH to a pH of 5 and then combined batchwise with 5.61 g (26.5 mmol) NaBH(OAc)$_3$ within 3 h while cooling with ice. The reaction mixture was stirred overnight at RT, then made alkaline with 500 mL 30% K$_2$CO$_3$ solution, stirred for 1 h at RT, extracted three times with 100 mL EtOAc and the combined organic phases were dried over Na$_2$SO$_4$. After elimination of the desiccant and solvent the residue was reacted further without purification.
Yield: 7.0 g (75% of theory)

A6b) 1'-benzyl-[1,4']bipiperidinyl-4-ylamine

A solution of 7.0 g (18.7 mmol) tert-butyl (1'-benzyl-[1,4']bipiperidinyl-4-yl)-carbamate and 14.3 mL (185 mmol) TFA in 80 mL DCM was refluxed overnight. The mixture was evaporated down i. vac., the residue was combined with 200 mL 30% K$_2$CO$_3$ solution and extracted three times with 100 mL EtOAc, discarding the first 100 mL of extract. The combined organic phases were dried over Na$_2$SO$_4$, filtered and evaporated down. The product was reacted further without purification.
Yield: 5.1 g (100% of theory)

A6c) ethyl(1'-benzyl-[1,4']bipiperidinyl-4-ylamino)-acetate 2.79 g (13.17 mmol) NaBH(OAc)$_3$ were added batchwise to a solution of 1.8 g (6.58 mmol) of 1'-benzyl-[1,4']bipiperidinyl-4-ylamine, 2.69 mL (13.0 mmol) ethyl oxo-acetate (used as a 50% solution in toluene) and 1 mL (17.45 mmol) of AcOH in 250 mL THF, cooled to 0° C., and the reaction mixture was stirred overnight at RT. It was evaporated down i. vac., the residue was taken up in EtOAc, the organic phase was washed with saturated K$_2$CO$_3$ solution and dried over Na$_2$SO$_4$. After elimination of the desiccant and solvent the residue was purified by HPLC. The fractions containing the product were combined, the organic solvent (acetonitrile) was eliminated i. vac., the aqueous residue was extracted exhaustively with DCM and the combined organic phases were dried over MgSO$_4$. After elimination of the desiccant and solvent the product was obtained as a yellow oil.
Yield: 1.25 g (53% of theory)
ESI-MS: (M+H)$^+$=360
R$_f$=0.35 (silica gel, DCM/MeOH/NH$_3$ 90:10:1)

A6d) ethyl[(1'-benzyl-[1,4']bipiperidinyl-4-yl)-tert-butoxycarbonyl-amino]-acetate 3.34 mL (30.0 mmol) triethylamine were added dropwise to a solution of 1.20 g (3.34 mmol) ethyl(1'-benzyl-[1,4']bipiperidinyl-4-ylamino)-acetate in 15 mL DCM and then 0.73 g (3.34 mmol) Boc-anhydride were added batchwise. The reaction mixture was stirred for 70 h at RT and then evaporated down i. vac. The residue was taken up in EtOAc, washed with 15% K$_2$CO$_3$ solution and dried over Na$_2$CO$_3$. After elimination of the desiccant and solvent the residue was reacted further without purification.
Yield: 1.3 g (85% of theory)

A6e) ethyl([1,4']bipiperidinyl-4-yl-tert-butoxycarbonyl-amino)-acetate

A suspension of 1.30 g (2.83 mmol) ethyl[(1'-benzyl-[1,4']bipiperidinyl-4-yl)-tert-butoxycarbonyl-amino]-acetate and 0.16 g 10% Pd/C in 25 mL EtOH was hydrogenated for 5 h at 50° C. and 50 psi hydrogen pressure. The catalyst was removed by suction filtering and the filtrate was evaporated to dryness. The product was obtained as a colourless oil, which was reacted further without purification.
Yield: 1.00 g (96% of theory)
ESI-MS: (M+H)$^+$=370

Amine 7

Ethyl(4-methyl-4-piperazin-1-yl-piperidin-1-yl)-acetate

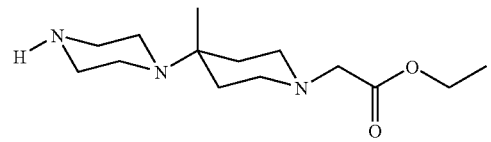

A7a) 1-benzyl-4-piperazin-1-yl-piperidine-4-carbonitrile

A mixture of 11.0 g (49.8 mmol) 1-benzyl-4-hydroxy-piperidine-4-carbonitrile and 22.0 g (255 mmol) piperazine in 200 mL MeOH was refluxed for 2 h. The precipitate was suction filtered, the filtrate was evaporated down i. vac., the residue was taken up in a little water, extracted exhaustively with DCM and the combined organic phases were dried over Na$_2$SO$_4$. After elimination of the desiccant and solvent the residue was purified by chromatography (Alox, DCM/MeOH 30:1).
Yield: 2.38 g (16% of theory)
ESI-MS: (M+H)$^+$=285
R$_f$=0.37 (Polygram-Alox, DCM/MeOH 25:1)

A7b) 1-(1-benzyl-4-methyl-piperidin-4-yl)-piperazine 15 mL methylmagnesium chloride solution (45 mmol, 3 M in THF) were added at RT to 2.37 g (7.92 mmol) 1-benzyl-4-piperazin-1-yl-piperidine-4-carbonitrile in 100 mL dry THF and the reaction mixture was stirred for 3 h. Saturated NH$_4$Cl solution was added, the mixture was stirred for another 10 min, the aqueous phase was washed with EtOAc, combined with 4 M NaOH solution until an alkaline reaction was obtained, extracted exhaustively with DCM and the combined organic phases were dried over Na$_2$SO$_4$. After elimination of the desiccant and solvent the residue was further reacted without any further purification.
Yield: 0.64 g (30% of theory)
ESI-MS: (M+H)$^+$=274

A7c) tert-butyl 4-(1-benzyl-4-methyl-piperidin-4-yl)-piperazine-1-carboxylate 1.35 g (6.00 mmol) Boc-anhydride were added to 1.63 g (5.66 mmol) 1-(1-benzyl-4-methyl-piperidin-4-yl)-piperazine in 50 mL THF and the reaction mixture was stirred for 3 h at RT. Then it was evaporated to dryness i. vac. and the residue was further reacted without any purification.
Yield: 2.10 g (100% of theory)
ESI-MS: (M+H)$^+$=374

A7d) tert-butyl 4-(4-methyl-piperidin-4-yl)-piperazine-1-carboxylate

A suspension of 2.28 g (5.62 mmol) tert-butyl 4-(1-benzyl-4-methyl-piperidin-4-yl)-piperazine-1-carboxylate and 300 mg 10% Pd/C in 50 mL MeOH was hydrogenated for 3 h at 50° C. and 3447 hPa hydrogen pressure. To complete the reaction 0.47 mL conc. HCl were added and the mixture was hydrogenated for another 3 h at 50° C. and 3447 hPa hydrogen pressure. The catalyst was filtered off, the filtrate was evaporated down i. vac., the residue was stirred with diethyl ether, suction filtered and dried.

Yield: 1.54 g (86% of theory)
ESI-MS: (M+H)$^+$=284

A7e) tert-butyl 4-(1-ethoxycarbonylmethyl-4-methyl-piperidin-4-yl)-piperazine-1-carboxylate A mixture of 1.53 g (4.78 mmol) tert-butyl 4-(4-methyl-piperidin-4-yl)-piperazine-1-carboxylate and 1.1 mL (5.55 mmol) ethyl oxo-acetate (50% in toluene) in 50 mL THF was stirred for 1 h at RT. The reaction mixture was cooled to 0° C., 1.25 g (5.90 mmol) sodium triacetoxyborohydride was added batchwise and after elimination of the cooling bath the mixture was stirred overnight at RT. It was combined with 10 mL 20% NaHCO$_3$ solution, extracted exhaustively with EtOAc and the combined organic phases were dried over Na$_2$SO$_4$. After elimination of the desiccant and solvent the residue was purified by chromatography (Alox, DCM/EtOH 100:1).

Yield: 0.47 g (27% of theory)
ESI-MS: (M+H)$^+$=370

A7f) ethyl(4-methyl-4-piperazin-1-yl-piperidin-1-yl)-acetate

At 0° C. 2 mL TFA were added to 0.46 g (1.25 mmol) tert-butyl 4-(1-ethoxycarbonylmethyl-4-methyl-piperidin-4-yl)-piperazine-1-carboxylate in 5 mL DCM and the reaction mixture was stirred for 2 h at RT. This was evaporated down i. vac. and the crude product, which was obtained as the bis-trifluoroacetate salt, was further reacted without any purification.

Yield: 0.65 g (100% of theory)
ESI-MS: (M+H)$^+$=270

Amine 8

Ethyl[4-(4-methyl-piperidin-4-yl)-piperazin-1-yl]-acetate

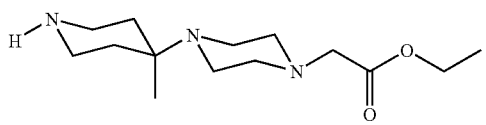

A8a) ethyl[4-(1-benzyl-4-methyl-piperidin-4-yl)-piperazin-1-yl]-acetate

Prepared analogously to Example A7e from 0.62 g (2.27 mmol) 1-(1-benzyl-4-methyl-piperidin-4-yl)-piperazine (Example A7b) and 0.55 mL (2.77 mmol) ethyl oxo-acetate (50% in toluene). The crude product was purified by chromatography (Alox, gradient PE/EtOAc 2:1 to 1:1).

Yield: 0.45 g (50% of theory)
ESI-MS: (M+H)$^+$=360
R$_f$=0.56 (Polygram-Alox, PE/EtOAc 1:1)

A8b) ethyl[4-(4-methyl-piperidin-4-yl)-piperazin-1-yl]-acetate

A suspension of 0.44 g (1.10 mmol) ethyl[4-(1-benzyl-4-methyl-piperidin-4-yl)-piperazin-1-yl]-acetate and 100 mg 10% Pd/C in 20 mL EtOH was hydrogenated for 12 h at 50° C. and 3447 hPa hydrogen pressure. The catalyst was filtered off and the filtrate was evaporated to dryness. The product was reacted further without purification.

Yield: 0.29 g (97% of theory)
ESI-MS: (M+H)$^+$=270

Amine 9

Ethyl(S)-4-methyl-1-piperidin-4-yl-piperazine-2-carboxylate

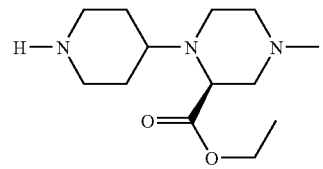

A9a) 1-benzyl-4-tert-butyl-2-ethyl(S)-piperazine-1,2,4-tricarboxylate 11.2 g (34.9 mmol) TBTU and 5.5 mL (39.6 mmol) triethylamine were added to a mixture, cooled to 0° C., of 12.2 g (32.8 mmol) 1-benzyl-4-tert-butyl(S)-piperazine-1,2,4-tricarboxylate and 30 mL EtOH in 150 mL THF, stirred for another 30 min at this temperature and then stirred for 68 h at RT. 600 mL diethyl ether were added to the reaction mixture, it was combined with 200 mL saturated NaHCO$_3$ solution, the aqueous phase was separated off, the organic phase was washed with saturated NaCl solution and dried over Na$_2$SO$_4$. After elimination of the desiccant and solvent the residue was purified by chromatography (silica gel, gradient PE/EtOAc 4:1 to 7:3).

Yield: 11.35 g (88% of theory)
ESI-MS: (M+H)$^+$=393
R$_f$=0.38 (Polygram-silica gel, PE/EtOAc 3:1)

A9b) 1-benzyl-2-ethyl(S)-piperazine-1,2-dicarboxylate 10 mL TFA were added to a mixture, cooled to 0° C., of 3.27 g (8.33 mmol) 1-benzyl-4-tert-butyl-2-ethyl(S)-piperazine-1,2,4-tricarboxylate and 30 mL DCM, the mixture was stirred for 10 min while cooling with ice and for 2 h at RT. The mixture was evaporated down i. vac. at 30° C., the residue was taken up again in EtOAc and evaporated down again i. vac. The crude product, which was obtained as the trifluoroacetate salt, was reacted further without purification.

A9c) 1-benzyl-2-ethyl(S)-4-methyl-piperazine-1,2-dicarboxylate 1.00 g (12.2 mmol) NaOAc and 10 g molecular sieve A3 were added to a mixture of 4.4 g of the crude product from A9b) and 1.2 mL (16.0 mmol) formaldehyde (37% in water) in 80 mL THF and the reaction mixture was stirred for 2 h at RT. After cooling to 0° C., 3.39 g (16.0 mmol) sodium triacetoxyborohydride was added batchwise, the mixture was stirred for 30 min at this temperature and for 68 h at RT. The insoluble components were filtered off, saturated $K_2CO_3$ solution was added to the filtrate, it was stirred for 15 min, combined with EtOAc, the organic phase was separated off and dried over $Na_2SO_4$. After elimination of the desiccant and solvent the residue was purified by chromatography (Alox, PE/EtOAc 2:1).

Yield: 2.04 g (81% of theory)
ESI-MS: $(M+H)^+=307$
$R_f=0.73$ (Polygram-Alox, PE/EtOAc 1:1)

A9d) ethyl(S)-4-methyl-piperazine-2-carboxylate

A suspension of 2.04 (6.66 mmol) 1-benzyl-2-ethyl(S)-4-methyl-piperazine-1,2-dicarboxylate and 200 mg 10% Pd/C in 100 mL EtOH was hydrogenated at 50° C. and 3447 hPa hydrogen pressure for 6 h. The catalyst was filtered off, the filtrate was evaporated to dryness i. vac. and the residue was further reacted without any purification.

Yield: 1.06 g (92% of theory)
ESI-MS: $(M+H)^+=173$

A9e) ethyl(S)-1-(1-tert-butoxycarbonyl-piperidin-4-yl)-4-methyl-piperazine-2-carboxylate A mixture of 0.90 g (5.23 mmol) ethyl(S)-4-methyl-piperazine-2-carboxylate and 1.20 g (6.02 mmol) tert-butyl 4-oxo-piperidine-1-carboxylate in 20 mL EtOH was combined with 50 µL formic acid and 3 g molecular sieve A3 and the reaction mixture was left for 66 h at RT. The molecular sieve was filtered off, the mixture was combined with 100 mg 10% Pd/C and hydrogenated at 50° C. and 3447 hPa hydrogen pressure for 4 h. The catalyst was removed by suction filtering, the filtrate was evaporated down i. vac. and the residue was purified by chromatography (silica gel, gradient DCM/EtOH 98:2 to 75:25).

Yield: 0.35 g (19% of theory)
ESI-MS: $(M+H)^+=356$
$R_f=0.5$ (Polygram-Alox, DCM/MeOH 50:1)

A9f) ethyl(S)-4-methyl-1-piperidin-4-yl-piperazine-2-carboxylate

A mixture of 0.34 g (0.96 mmol) ethyl(S)-1-(1-tert-butoxycarbonyl -piperidin-4-yl)-4-methyl-piperazine-2-carboxylate in 6 mL ethanolic HCl (1.25 M) was refluxed for 1 hour. After cooling of the reaction mixture the precipitate was suction filtered and dried. The product was obtained as the tris-hydrochloride salt.

Yield: 0.33 g (95% of theory)
ESI-MS: $(M+H)^+=256$

Amine 10

Ethyl(S)-1-(1-methyl-piperidin-4-yl)-piperazine-2-carboxylate

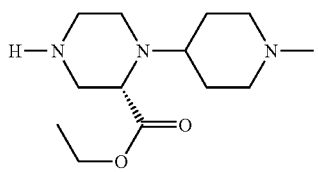

A10a) 1-tert-butyl-3-ethyl(S)-piperazine-1,3-dicarboxylate

A suspension of 4.00 g (10.2 mmol) 1-benzyl-4-tert-butyl-2-ethyl(S)-piperazine-1,2,4-tricarboxylate (Example A9a) and 200 mg 10% Pd/C in 100 mL EtOH was hydrogenated for 2 h at 50° C. and 3447 hPa hydrogen pressure. The catalyst was filtered off, the filtrate was evaporated down i. vac. and the residue was further reacted without any purification.

Yield: 2.61 g (98% of theory)
ESI-MS: $(M+H)^+=259$

A10b) 1-tert-butyl-3-ethyl(S)-4-(1-methyl-piperidin-4-yl)-piperazine-1,3-dicarboxylate A mixture of 2.65 g (10.05 mmol) 1-tert-butyl-3-ethyl(S)-piperazine-1,3-dicarboxylate and 1.36 mL (11.06 mmol) 1-methyl-piperidin-4-one in 100 mL THF was stirred for 1 h at RT. After cooling to 0° C., 3.00 g (14.16 mmol) sodium triacetoxyborohydride were added batchwise and the reaction mixture was stirred overnight at RT. To complete the reaction a further 1.00 g (4.72 mmol) sodium triacetoxyborohydride and 0.3 mL AcOH were added and the mixture was stirred for another 48 h at RT. 40 mL saturated $K_2CO_3$ solution were added, the mixture was stirred for 15 min, extracted exhaustively with EtOAc and the combined organic phases were dried over $Na_2SO_4$. After elimination of the desiccant and solvent the residue was purified by chromatography (Alox, DCM/EtOH 100:1).

Yield: 1.93 g (53% of theory)
ESI-MS: $(M+H)^+=356$

A10c) ethyl(S)-1-(1-methyl-piperidin-4-yl)-piperazine-2-carboxylate

A mixture of 1.88 (5.18 mmol) 1-tert-butyl-3-ethyl(S)-4-(1-methyl-piperidin-4-yl)-piperazine-1,3-dicarboxylate, 3 mL EtOH and 15 mL ethanolic HCl (1.25 M) was stirred overnight at RT. To complete the reaction the mixture was refluxed for 1 hour. After cooling of the reaction mixture the precipitate was suction filtered and dried. The product was obtained as the bis-hydrochloride salt.

Yield: 1.35 g (79% of theory)
ESI-MS: $(M+H)^+=256$

Amine 11

Ethyl(S)-4-(1-methyl-piperidin-4-yl)-piperazine-2-carboxylate

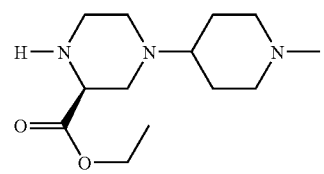

A11a) 1-benzyl-2-ethyl(S)-4-(1-methyl-piperidin-4-yl)-piperazine-1,2-dicarboxylate A mixture of 4.20 g (10.13 mmol) 1-benzyl-2-ethyl(S)-piperazine-1,2-dicarboxylate (Example A9b, used as the trifluoroacetate salt) and 1.37 mL 1-methyl-piperidin-4-one in 100 mL THF was stirred for 1 h at RT. After cooling to 0° C.

3.00 g (14.16 mmol) sodium triacetoxyborohydride were added batchwise and the reaction mixture was stirred overnight at RT. It was combined with 40 mL saturated $K_2CO_3$ solution, stirred for another 15 min, extracted exhaustively with EtOAc and the combined organic phases were dried over $Na_2SO_4$. After elimination of the desiccant and solvent the residue was purified by chromatography (Alox, DCM/EtOH 100:1).

Yield: 2.17 g (55% of theory)
ESI-MS: $(M+H)^+=390$
$R_f=0.43$ (Polygram-Alox, DCM/MeOH 50:1)

A11b) ethyl(S)-4-(1-methyl-piperidin-4-yl)-piperazine-2-carboxylate

A suspension of 2.15 g (5.52 mmol) 1-benzyl-2-ethyl(S)-4-(1-methyl-piperidin-4-yl)-piperazine-1,2-dicarboxylate and 100 mg 10% Pd/C in 50 mL EtOH was hydrogenated for 2 h at 50° C. and 3447 hPa hydrogen pressure. The catalyst was filtered off and the filtrate was evaporated to dryness. The product was reacted further without purification.

Yield: 1.35 g (96% of theory)
ESI-MS: $(M+H)^+=256$

Amine 12

Ethyl(3-piperazin-1-yl-8-aza-bicyclo[3.2.1]oct-8-yl)-acetate

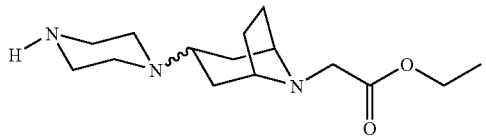

A12a) tert-butyl 3-(4-benzyloxycarbonyl-piperazin-1-yl)-8-aza -bicyclo[3.2.1]octane-8-carboxylate A mixture of 5.00 g (22.2 mmol) tert-butyl 3-oxo-8-azabicyclo[3.2.1]octan-8-carboxylate and benzyl piperazine-1-carboxylate in 60 mL THF was adjusted with AcOH to a pH of 5 and stirred for 1 h at RT. The mixture was combined batchwise with 5.64 g (26.6 mmol) sodium triacetoxyborohydride while cooling with ice and the reaction mixture was stirred overnight at RT. It was combined with 150 mL 15% $K_2CO_3$ solution, the organic phase was separated off, the aqueous phase was exhaustively extracted with EtOAc and the combined organic phases were dried over $Na_2SO_4$. After elimination of the desiccant and solvent the residue was purified by chromatography (silica gel, EtOAc). 2 isomeric products were able to be isolated:

Isomer A:
Yield: 2.10 g (22% of theory)
ESI-MS: $(M+H)^+=430$
$R_f=0.55$ (silica gel, EtOAc)
Retention time (HPLC): 3.2 min (method B)

Isomer B:
Yield: 2.20 g (23% of theory)
ESI-MS: $(M+H)^+=430$
$R_f=0.68$ (silica gel, EtOAc)

A12b) benzyl 4-(8-aza-bicyclo[3.2.1]oct-3-yl)-piperazine-1-carboxylate 6.01 mL (78.0 mmol) TFA were slowly added to a mixture of 2.10 g (4.89 mmol) tert-butyl 3-(4-benzyloxycarbonyl-piperazin-1-yl)-8-aza-bicyclo[3.2.1]octane-8-carboxylate (isomer A) in 60 mL DCM and the reaction mixture was stirred for 2 at RT. It was evaporated down i. vac., the residue was taken up in 15% $K_2CO_3$ solution, extracted exhaustively with DCM and the combined organic phases were dried over $Na_2SO_4$. After elimination of the desiccant and solvent the product was further reacted without any purification.

Yield: 1.50 g (93% of theory)
ESI-MS: $(M+H)^+=330$
$R_f=0.16$ (silica gel, DCM/Cyc/MeOH/$NH_3$ 70:15:15:2)

A12c) benzyl 4-(8-ethoxycarbonylmethyl-8-aza-bicyclo[3.2.1]oct-3-yl)-piperazine-1-carboxylate 1.29 g (9.30 mmol) $K_2CO3$ were added to 1.50 g (4.55 mmol) benzyl 4-(8-aza-bicyclo[3.2.1]oct-3-yl)-piperazine-1-carboxylate (A12b) in 10 mL DMF, then 0.56 mL (5.00 mmol) ethyl bromoacetate were slowly added dropwise and the reaction mixture was stirred for a further 4 h at RT. The insoluble components were filtered off, combined with EtOAc, the organic phase was washed twice with saturated $NaHCO_3$ solution and dried over $Na_2SO_4$. After elimination of the desiccant and solvent the residue was further reacted without any further purification.

Yield: 1.75 g (92% of theory)
ESI-MS: $(M+H)^+=416$
$R_f=0.72$ (silica gel, DCM/Cyc/MeOH/$NH_3$ 70:15:15:2)

A12d) ethyl(3-piperazin-1-yl-8-aza-bicyclo[3.2.1]oct-8-yl)-acetate

A suspension of 1.70 g (4.09 mmol) benzyl 4-(8-ethoxycarbonylmethyl-8-aza-bicyclo[3.2.1]oct-3-yl)-piperazine-1-carboxylate (A12c) and 200 mg 10% Pd/C in 30 mL EtOH was shaken for 3 h at RT and 3000 hPa hydrogen pressure. The catalyst was removed by suction filtering and the filtrate was evaporated to dryness. The product was reacted further without purification.

Yield: 1.10 g (96% of theory)
ESI-MS: $(M+H)^+=282$
$R_f=0.21$ (silica gel, DCM/MeOH/$NH_3$ 80:20:2)

Amine 13

Ethyl([1,4']bipiperidinyl-4-yloxy)-acetate

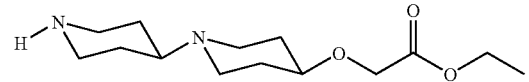

A13a) benzyl 4-tert-butoxycarbonylmethoxy-[1,4']bipiperidinyl-1'-carboxylate 2.90 g (13.27 mmol) sodium triacetoxyborohydride were added batchwise to a mixture of 2.58 g (11.06 mmol) benzyl 4-oxo-piperidine-1-carboxylate and 2.80 g (12.36 mmol) tert-butyl (piperidin-4-yloxy)-acetate in 30 mL THF and the reaction mixture was stirred overnight at RT. It was combined with 50 mL 1 M NaOH, the mixture was stirred for 1 h at RT, combined with EtOAc, the organic phase was separated off and dried over Na₂SO₄. After elimination of the desiccant and solvent the residue was purified by chromatography (Alox, DCM/MeOH 100:1).

Yield: 3.10 g (65% of theory)
ESI-MS: (M+H)⁺=433

A13b) tert-butyl([1,4']bipiperidinyl-4-yloxy)-acetate

A suspension of 3.08 g (7.12 mmol) benzyl 4-tert-butoxycarbonylmethoxy-[1,4']bipiperidinyl-1'-carboxylate and 300 mg 10% Pd/C in 60 mL MeOH was hydrogenated for 2 h at 50° C. and 3447 hPa hydrogen pressure. The catalyst was removed by suction filtering and the filtrate was evaporated to dryness. The product was reacted further without purification.

Yield: 2.15 g (99% of theory)
ESI-MS: (M+H)⁺=299

A13c) ethyl([1,4']bipiperidinyl-4-yloxy)-acetate 20 mL ethanolic HCl (1.25M) were added to 2.02 g (6.63 mmol) tert-butyl ([1,4']bipiperidinyl-4-yloxy)-acetate in 20 mL EtOH and the reaction mixture was refluxed for 3 h. After cooling to 0° C. the precipitate formed was suction filtered and dried under a high vacuum. The product, which was obtained as the bis-hydrochloride salt, was reacted further without purification.

Yield: 1.74 g (76% of theory)
ESI-MS: (M+H)⁺=271

Amine 14

Ethyl[1,4']bipiperidinyl-4-yl-acetate

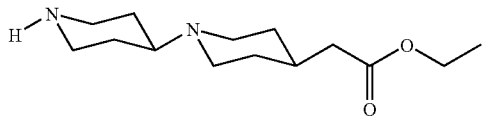

A14a) ethyl(1'-benzyl-[1,4']bipiperidinyl-4-yl)-acetate 50 mL DCM and 11.7 mL (62.5 mmol) 1-benzyl-piperidin-4-one were added to 11.8 g (56.8 mmol) ethyl piperidin-4-yl-acetate in 100 mL of THF and the reaction mixture was stirred for 2 h at RT. The mixture was combined batchwise with 13.7 g (62.5 mmol) sodium triacetoxyborohydride and stirred for another 36 h at RT. 100 mL 10% NaOH were added to the reaction mixture, this was extracted twice with 100 mL MTBE and the combined organic phases were dried over Na₂SO₄. After elimination of the desiccant and solvent the residue was purified by HPLC.

Yield: 3.27 g (17% of theory)
ESI-MS: (M+H)⁺=345
R_f=0.55 (silica gel, EtOAc/MeOH/NH₃ 90:10:1)

A14b) ethyl[1,4']bipiperidinyl-4-yl-acetate a suspension of 3.24 g (9.41 mmol) ethyl(1'-benzyl-[1,4']bipiperidinyl-4-yl)-acetate and 300 mg 10% Pd/C in 50 mL EtOH was hydrogenated at RT and 3000 hPa hydrogen pressure until the theoretical amount of hydrogen has been taken up. The catalyst was removed by suction filtering, the filtrate was evaporated to dryness, the residue was combined with 50 mL EtOH and ethanolic HCl (1.25 M). The mixture was evaporated to dryness i. vac., the residue was stirred with 100 mL DIPE/isopropanol (2:1), the precipitate was filtered off and dried at 35° C. in the circulating air dryer. The product was obtained as the bis-hydrochloride salt.

Yield: 2.90 g (94% of theory)
ESI-MS: (M+H)⁺=255
R_f=0.05 (silica gel, EtOAc/MeOH/NH₃ 70:30:3)

Amine 15

Ethyl 3-[1,4']bipiperidinyl-4-yl-propionate

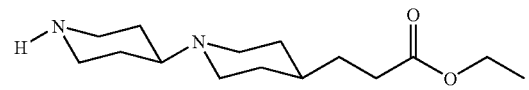

A15a) tert-butyl 4-(2-methoxycarbonyl-ethyl)-[1,4']bipiperidinyl-1'-carboxylate

Under a nitrogen atmosphere a mixture of 4.00 g (19.3 mmol) methyl 3-piperidin-4-yl-propionate and 3.85 g (19.3 mmol) tert-butyl 4-oxo-piperidine-1-carboxylate in 50 mL THF was adjusted to a pH of 5 with ACOH and the mixture was stirred for 1 h at RT. After cooling to 0C the mixture was combined batchwise with 5.15 g (24.3 mmol) sodium triacetoxyborohydride and the reaction mixture was stirred overnight at RT. Within 10 min, 90 mL of 30% K₂CO₃ solution were added, the mixture was extracted three times with EtOAc and the combined organic phases were dried over Na₂SO₄. After elimination of the desiccant and solvent the residue was further reacted without any further purification.

Yield: 5.40 g (79% of theory)
ESI-MS: (M+H)⁺=355
R_f=0.63 (silica gel, DCM/MeOH/NH₃ 80:20:2)

A15b) ethyl 3-[1,4']bipiperidinyl-4-yl-propionate 5.40 g (15.2 mmol) tert-butyl 4-(2-methoxycarbonyl-ethyl)-[1,4']bipiperidinyl-1'-carboxylate in 150 mL ethanolic HCl (1.25 M) was stirred overnight at RT. The solvent was largely removed i. vac., the precipitate formed was filtered off and dried. The product, which was obtained as the bis-hydrochloride salt, was reacted further without purification.

Yield: 2.30 g (79% of theory)
ESI-MS: (M+H)⁺=269
Retention time (HPLC): 1.2 min (method B)

Amine 16

Ethyl 4-(4-piperazin-1-yl-piperidin-1-yl)-butyrate

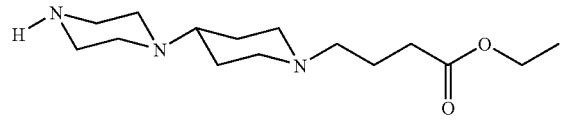

A16a) ethyl 4-[4-(4-benzyl-piperazin-1-yl)-piperidin-1-yl]-butyrate

Under a nitrogen atmosphere a mixture of 3.11 g (12.0 mmol) 1-benzyl-4-piperidin-4-yl-piperazine and 7.50 mL (12.0 mmol, 15% in water) 4-oxo-butyric acid in 70 mL THF was adjusted to a pH of 5 with ACOH and stirred for 1 h at RT. After cooling to 0° C., 5.35 g (24.0 mmol) sodium triacetoxyborohydride were added batchwise and the reaction mixture was stirred overnight at RT. Within 15 min 80 mL of 30% K$_2$CO$_3$ solution were added dropwise, the aqueous phase was washed twice with EtOAc and evaporated down by half i. vac. 1 M KHSO$_4$ solution was added, the precipitate formed was removed by suction filtering, the filtrate was washed with EtOAc and the aqueous phase was evaporated to dryness i. vac. The residue was taken up in 150 mL ethanolic HCl (1.25 M) and the reaction mixture was stirred overnight at RT. It was evaporated down i. vac., the residue was taken up in a little 15% K$_2$CO$_3$ solution, extracted exhaustively with EtOAc and the combined organic phases were dried over Na$_2$SO$_4$. After elimination of the desiccant and solvent the residue was further reacted without any further purification.

Yield: 2.90 g (65% of theory)
ESI-MS: (M+H)$^+$=374

A16b) ethyl 4-(4-piperazin-1-yl-piperidin-1-yl)-butyrate

A suspension of 2.90 g (7.76 mmol) ethyl 4-[4-(4-benzyl-piperazin-1-yl)-piperidin-1-yl]-butyrate and 300 mg 10% Pd/C in 60 mL MeOH was hydrogenated for 24 h at RT and 3447 hPa hydrogen pressure. The catalyst was removed by suction filtering, the filtrate was evaporated to dryness, the residue was taken up in DIPE and a little isopropanol and combined with 4 M HCl in 1,4-dioxane. The precipitate was suction filtered and dried. The product was obtained as the bis-hydrochloride salt.

Yield: 2.50 g (90% of theory)
ESI-MS: (M+H)$^+$=284
Retention time (HPLC): 0.7 min (method B)

Amine 17

Benzyl 4-piperazin-1-yl-piperidine-1-carboxylate

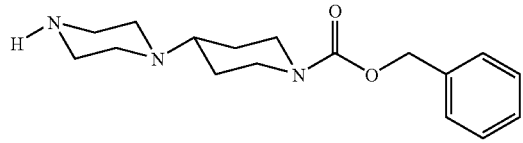

A17a) tert-butyl 4-(1-benzyloxycarbonyl-piperidin-4-yl)-piperazine-1-carboxylate A solution of 7.18 mL (48.0 mmol) benzyl chloroformate in 50 mL DCM was added dropwise to 12.3 g (45.7 mmol) tert-butyl 4-piperidin-4-yl-piperazine-1-carboxylate and 8.2 mL (50 mmol) N-ethyldiisopropylamine in 200 mL DCM while cooling with ice and the reaction mixture was stirred overnight at RT. It was washed with 200 mL of 15% K$_2$CO$_3$ solution, the organic phase was separated off and dried over Na$_2$SO$_4$. After elimination of the desiccant and solvent the residue was further reacted without any further purification.

Yield: 16.0 g (87% of theory)

A17b) benzyl 4-piperazin-1-yl-piperidine-1-carboxylate 25 mL TFA were added at RT to 16.0 g (39.7 mmol) tert-butyl 4-(1-benzyloxycarbonyl-piperidin-4-yl)-piperazine-1-carboxylate in 200 mL DCM and the reaction mixture was stirred overnight at RT. It was evaporated down i. vac., the residue was taken up in 200 mL water and 200 mL EtOAc, the aqueous phase was separated off, combined with 50 mL 15% K$_2$CO$_3$ solution, extracted twice with 200 mL EtOAc and the combined organic phases were dried over Na$_2$SO$_4$. After elimination of the desiccant and solvent the residue was reacted with any further purification.

Yield: 4.00 g (33% of theory)
ESI-MS: (M+H)$^+$=304

The preparation of the final compounds is described hereinafter:

EXAMPLE 1

Ethyl 1'-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylate

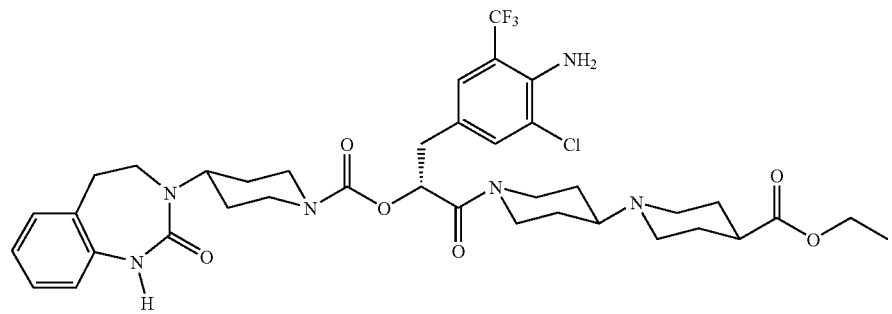

1a) (Z,E)-2-acetylamino-3-(4-amino-3-chloro-5-trifluoromethyl-phenyl)-acrylic acid 39.7 g (335 mmol) N-acetylglycine were added to a suspension of 50.0 g (224 mmol) 4-amino-3-chloro-5-trifluoromethyl-benzaldehyde and 27.5 g (335 mmol) NaOAc in 202 mL acetic anhydride and the reaction mixture was heated to 115° C. for 1 h. After cooling to 80° C. 100 mL water were added dropwise, while the temperature of the mixture was maintained at 80° C. The suspension was heated to 95° C. for a further 40 min and then added to a mixture of 250 mL toluene and 500 mL water. The suspension was stirred at RT, the precipitate was suction filtered and dried at 60° C. in the circulating air dryer.

Yield: 48.8 g (68% of theory)
ESI-MS: $(M+H)^+$=321/323 (CI)
$R_f$=0.37 (silica gel, DCM/MeOH/AcOH 90:10:1)

1b) 3-(4-amino-3-chloro-5-trifluoromethyl-phenyl)-2-oxo-propionic acid

A suspension of 97.0 g (300 mmol) (Z,E)-2-acetylamino-3-(4-amino-3-chloro-5-tri-fluoromethyl-phenyl)-acrylic acid in 900 mL 1,4-dioxane and 1050 mL 4 M HCl was heated to 100° C. for 8 h. The mixture was evaporated down to about 600 mL i. vac., cooled to RT, the substance precipitated was filtered off, washed twice with 100 mL water and dried at 50° C. The residue was taken up in 850 mL toluene, refluxed and then cooled in the ice bath. The precipitate formed was filtered, washed with PE and dried in the circulating air dryer at 50° C.

Yield: 63.0 g (74% of theory)
ESI-MS: $(M-H)^-$=280/282 (CI)
$R_f$=0.21 (silica gel, DCM/MeOH/NH$_3$ 80:20:2)

1c) (R)-3-(4-amino-3-chloro-5-trifluoromethyl-phenyl)-2-hydroxy-propionic acid A solution of 100.0 g (312 mmol) (1R)-B-chlorodiisopinocampheylborane in 150 mL THF was added dropwise to a solution of 63.0 g (224 mmol) 3-(4-amino-3-chloro-5-trifluoromethyl-phenyl)-2-oxo-propionic acid and 31.2 mL (224 mmol) triethylamine in 300 mL THF cooled to about −30° C. and the reaction mixture was kept for 1.5 h at this temperature and then heated to RT within a further hour with 80 mL 4 M NaOH were added to the reaction mixture, it was stirred for 5 min, cooled to 0° C., combined with 300 mL MTBE, stirred for another 20 min at this temperature and then the phases were separated. The organic phase was exhaustively extracted with water, the combined aqueous phases were acidified with 4 M HCl, exhaustively extracted with MTBE and the combined organic phases were dried over Na$_2$SO$_4$.

The THF/MTBE/NaOH phase was acidified with 4 M HCl, the phases were separated and the organic phase was evaporated down i. vac. The two residues were combined and reacted further without purification.

$R_f$=0.20 (silica gel, DCM/MeOH/NH$_3$ 80:20:2)

1d) methyl(R)-3-(4-amino-3-chloro-5-trifluoromethyl-phenyl)-2-hydroxy-propionate The crude product of Example 1c (62 g) was dissolved in 300 mL MeOH and 3.65 mL (50 mmol) SOCl$_2$ were slowly added dropwise to this solution. The reaction mixture was stirred for a further 3 h at RT, then evaporated down i. vac., the residue was taken up in DCM and filtered through silica gel. The solution was evaporated down i. vac. and the residue was purified by chromatography (silica gel, DCM/MeOH/NH$_3$ 80:20:2). The fractions containing the product were combined, evaporated down i. vac., the residue was combined with PE, suction filtered and dried.

Yield: 43.1 g (65% of theory over 2 steps)
ESI-MS: $(M+H)^+$=298/300 (CI)
$R_f$=0.86 (silica gel, DCM/MeOH/NH$_3$ 80:20:2)

1e) (R)-2-(4-amino-3-chloro-5-trifluoromethyl-phenyl)-1-methoxycarbonyl-ethyl 4-(2-oxo-1,2,4,5-tetrahydro-1,3-benzodiazepin-3-yl)-piperidine-1-carboxylate Under a nitrogen atmosphere a solution of 13.5 g (65.0 mmol) 4-nitrophenyl chloroformate in 40 mL THF were metered into 100 mL pyridine at 60° C. (bath temperature) within 10 min, the mixture was stirred for 10 min, then a solution of 18.0 g (60.5 mmol) methyl(R)-3-(4-amino-3-chloro-5-trifluoromethyl-phenyl)-2-hydroxy-propionate in 50 ml of pyridine was added dropwise and the reaction mixture was kept for 1.5 h at this temperature. Then 15.9 g (65.0 mmol) 3-piperidin-4-yl-1,3,4,5-tetrahydro-1,3-benzodiazepin-2-one was added batchwise. The temperature of the reaction mixture was increased to 100° C., the mixture was kept at this temperature for 6 h and then stirred overnight at RT. The mixture was evaporated down i. vac., the residue was taken up in 200 mL EtOAc, the organic phase was washed twice with 100 mL of 1 M KHSO$_4$ solution, ten times with 50 mL of 15% K$_2$CO$_3$ solution and dried over Na$_2$SO$_4$. After elimination of the desiccant and solvent the residue was reacted further without purification.

Yield: 33.1 g (96% of theory)
ESI-MS: $(M+H)^+$=569/571 (CI)
$R_f$=0.72 (silica gel, DCM/Cyc/MeOH/NH$_3$ 70:15:15:2)

1f) (R)-2-(4-amino-3-chloro-5-trifluoromethyl-phenyl)-1-carboxy-ethyl 4-(2-oxo-1,2,45-tetrahydro-1,3-benzodiazepin-3-yl)-piperidine-1-carboxylate A solution of 2.11 g (88.0 mmol) LiOH in 100 mL water was added to a solution of 33.0 g (58.0 mmol) (R)-2-(4-amino-3-chloro-5-trifluoromethyl-phenyl)-1-methoxy-carbonyl-ethyl 4-(2-oxo-1,2,4,5-tetrahydro-1,3-benzodiazepin-3-yl)-piperidine-1-carboxylate in 200 mL THF and the reaction solution was stirred for 3.5 h at RT.

THF was eliminated i. vac., the aqueous residue was washed twice with MTBE, acidified with 2 M HCl, exhaustively extracted with DCM and the combined organic phases were dried over Na$_2$SO$_4$. After elimination of the desiccant and solvent the residue was dissolved at 65° C. in 80 mL isopropanol and slowly cooled to RT overnight. The suspension was cooled in the ice bath, suction filtered, washed with a little isopropanol and DIPE and dried.

Yield: 26.2 g (81% of theory)
ESI-MS: $(M+H)^+$=555/557 (CI)
$R_f$=0.18 (silica gel, DCM/Cyc/MeOH/NH$_3$ 70:15:15:2)
Retention time (HPLC): 4.0 min (Method B)

1g) (R)-1-(4-amino-3-chloro-5-trifluoromethyl-benzyl)-2-oxo-2-(4-oxo-piperidin-1-yl)-ethyl 4-(2-oxo-1,2,4,5-tetrahydro-1,3-benzodiazepin-3-yl)-piperidine-1-carboxylate 7.40 g (23.0 mmol) TBTU and 5.84 mL (40.0 mmol) triethylamine were added to a solution of 10.0 g (18.0 mmol) (R)-2-(4-amino-3-chloro-5-trifluoromethyl-phenyl)-1-carboxy-ethyl 4-(2-oxo-1,2,4,5-tetrahydro-1,3-benzodiazepin- 3-yl)-piperidine-1-carboxylate in 50 mL DMF and stirred for 10 min at RT. 2.77 g (18.0 mmol) piperidin-4-one (used as the hydrate of the hydrochloride salt) were added to the reaction mixture and this was stirred overnight at RT. The reaction solution was poured onto 1 L of 7% $K_2CO_3$ solution, the precipitated substance was filtered off, washed with water and dried at 60° C. for 6 h. Further purification was carried out by column chromatography (silica gel, EtOAc).

Yield: 7.5 g (65% of theory)
ESI-MS: $(M+H)^+=636/638$ (Cl)
$R_f=0.25$ (silica gel, EtOAc)

1h) ethyl 1'-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylate 62.9 mg (0.4 mmol) ethyl piperidine-4-carboxylate and 11 μL (0.2 mmol) AcOH were added to a solution of 127 mg (0.2 mmol) (R)-1-(4-amino-3-chloro-5-trifluoromethyl-benzyl)-2-oxo-2-(4-oxo-piperidin-1-yl)-ethyl 4-(2-oxo-1,2,4,5-tetrahydro-1,3-benzodiazepin-3-yl)-piperidine-1-carboxylate in 2 mL THF/MeOH (2:1) and the reaction mixture was stirred for 2 h at RT. Then it was cooled to 0° C., combined with 10.6 mg (0.16 mmol) $NaBH_3CN$ after 2 h and stirred at 0° C. overnight. The solvent was allowed to evaporate, the residue was taken up in 2 mL DMF and the crude product was purified by HPLC. The fractions containing the product were combined and freeze-dried.

Yield: 68 mg (44% of theory)
ESI-MS: $(M+H)^+=777/779$ (Cl)
Retention time (HPLC): 7.0 min (Method C)

EXAMPLE 1.1

1'-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylic acid

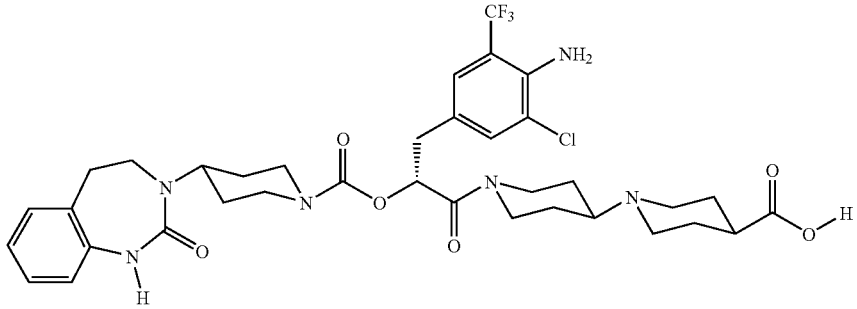

A solution of 7.2 mg (0.3 mmol) LiOH in 1 mL water was added to a solution of 140 mg (0.18 mmol) ethyl 1'-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-4-carboxylate in 1 mL THF and the reaction mixture was stirred for 3 h at RT. 1 mL HCl (1 M) was added and the crude product was purified by HPLC. The fractions containing the product were combined and freeze-dried.

Yield: 53 mg (39% of theory)
ESI-MS: $(M+H)^+=749/751$ (Cl)
Retention time (HPLC): 3.4 min (Method B)

EXAMPLE 2

(R)-1-(4-amino-3-chloro-5-trifluoromethyl-benzyl)-2-[4-(ethoxycarbonylmethyl-amino)-1,4'-bipiperidinyl-1'-yl]-2-oxo-ethyl 4-(2-oxo-1,2,4,5-tetrahydro-1,3-benzodiazepin-3-yl)-piperidine-1-carboxylate

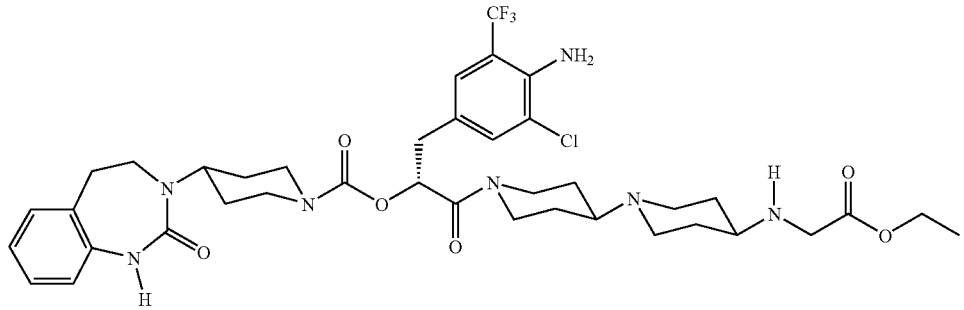

2a) (R)-1-(4-amino-3-chloro-5-trifluoromethyl-benzyl)-2-[4-(tert-butoxycarbonyl-ethoxycarbonyl-methylamino)-1,4'-bipiperidinyl-1'-yl]-2-oxo-ethyl 4-(2-oxo-1,2,45-tetrahydro-1,3-benzodiazepin-3-yl)-piperidine-1-carboxylate 128 mg (0.40 mmol) TBTU and 56 μL (0.40 mmol) triethylamine were added to a solution of 200 mg (0.36 mmol) (R)-2-(4-amino-3-chloro-5-trifluoromethyl-phenyl)-1-carboxy-ethyl 4-(2-oxo-1,2,4,5-tetrahydro-1,3-benzodiazepin- 3-yl)-piperidine-1-carboxylate in 2 mL DMF and stirred for 10 min at RT. 148 mg (0.40 mmol) ethyl ([1,4']bipiperidinyl-4-yl-tert-butoxycarbonyl-amino)-acetate (Amine A6) were added to the reaction mixture and this was stirred overnight at RT. The reaction solution was evaporated down i. vac., the residue was taken up in EtOAc, the precipitate formed was suction filtered and dried. The product was reacted further without purification.

Yield: 330 mg (100% of theory)

2b) (R)-1-(4-amino-3-chloro-5-trifluoromethyl-benzyl)-2-[4-(ethoxycarbonylmethyl-amino)-1,4'-bipiperidinyl-1'-yl]-2-oxo-ethyl 4-(2-oxo-1,2,45-tetrahydro-1,3-benzodiazepin-3-yl)-piperidine-1-carboxylate 0.5 mL TFA were added to a solution of 330 mg (0.36 mmol) (R)-1-(4-amino-3-chloro-5-trifluoromethyl-benzyl)-2-[4-(tert-butoxycarbonyl-ethoxycarbonyl-methylamino)-1,4'-bipiperidinyl-1'-yl]-2-oxo-ethyl 4-(2-oxo-1,2,4,5-tetrahydro-1,3-benzodiazepin-3-yl)-piperidine-1-carboxylate in 5 mL DCM cooled to 0° C. and the reaction mixture was stirred overnight at RT. It was evaporated down i. vac. and the residue was purified by HPLC. The fractions containing the product were combined and freeze-dried.

Yield: 263 mg (90% of theory)

ESI-MS: $(M+H)^+$=806/808 (CI)

Retention time (HPLC): 2.6 min (Method A)

EXAMPLE 2.1

(R)-1-(4-amino-3-chloro-5-trifluoromethyl-benzyl)-2-[4-(carboxymethyl-amino)-1,4'-bipiperidinyl-1'-yl]-2-oxo-ethyl 4-(2-oxo-1,2,4,5-tetrahydro-1,3-benzodiazepin-3-yl)-piperidine-1-carboxylate

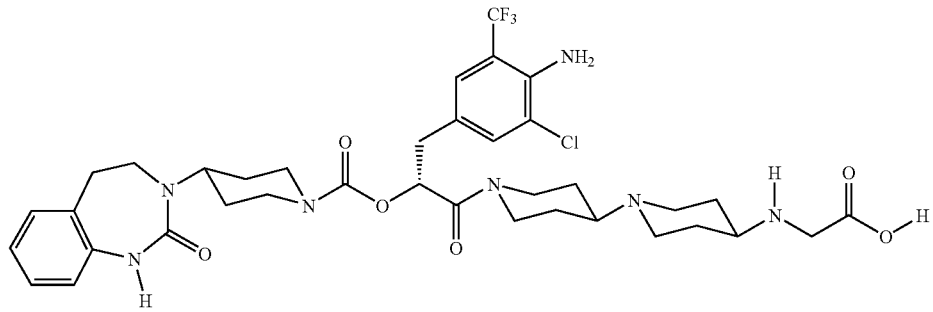

A solution of 9.4 mg (0.39 mmol) LiOH was added to a solution of 212 mg (0.26 mmol) (R)-1-(4-amino-3-chloro-5-trifluoromethyl-benzyl)-2-[4-(ethoxy-carbonylmethylamino)-1,4'-bipiperidinyl-1'-yl]-2-oxo-ethyl 4-(2-oxo-1,2,4,5-tetrahydro-1,3-benzodiazepin-3-yl)-piperidine-1-carboxylate in 9 mL THF and the reaction mixture was stirred overnight at RT. To complete the reaction 6.3 mg (0.26 mmol) LiOH were also added and the mixture was again stirred overnight at RT. The reaction mixture was purified by HPLC without further working up. The fractions containing the product were combined and freeze-dried, the product being obtained as the trifluoroacetate salt.

Yield: 130 mg (55% of theory)

ESI-MS: $(M+H)^+$=778/780 (CI)

Retention time (HPLC): 2.7 min (Method A)

EXAMPLE 3

(R)-1-(4-amino-3-chloro-5-trifluoromethyl-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate

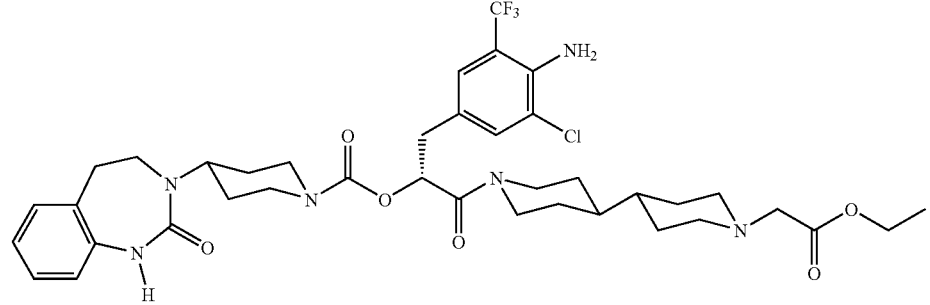

632 mg (1.97 mmol) TBTU and 0.34 mL (1.97 mmol) ethyldiisopropylamine were added to a solution of 1.0 g (1.80 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate in 10 mL THF and the mixture was stirred for 10 min at RT. 500 mg (1.97 mmol) ethyl[4,4']bipiperidinyl-1-yl-acetate were added to the0 reaction mixture and this was stirred overnight at RT. The mixture was evaporated down i. vac., the residue was taken up in DCM, the organic phase was washed with 1 M $KHSO_4$ solution and 15% $K_2CO_3$ solution and dried over $Na_2SO_4$. After elimination of the desiccant and solvent the residue was purified by HPLC. The fractions containing the product were combined, evaporated down i. vac., the residue was triturated with DIPE, suction filtered and dried.

Yield: 150 mg (11% of theory)
ESI-MS: $(M+H)^+$=791/793 (CI)
$R_f$=0.46 (silica gel, DCM/Cyc/MeOH/$NH_3$ 70:15:15:2)

EXAMPLE 3.1

(R)-1-(4-amino-3-chloro-5-trifluoromethyl-benzyl)-2-(1'-carboxymethyl-4,4'-bipiperidinyl-1-yl)-2-oxo-ethyl 4-(2-oxo-1,2,4,5-tetrahydro-1,3-benzodiazepin-3-yl)-piperidine-1-carboxylate

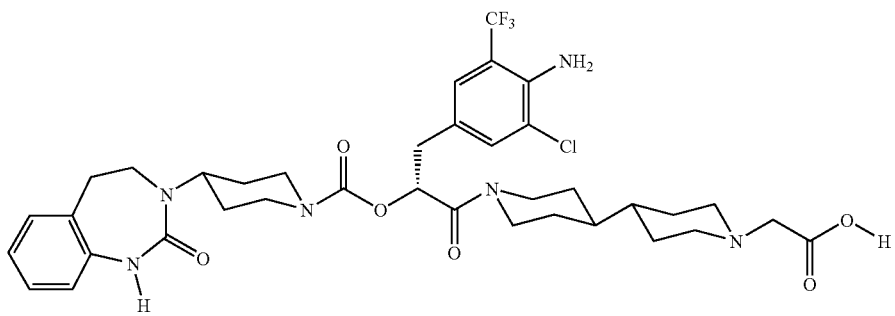

A solution of 1 mg (0.04 mmol) LiOH in 1 mL water was added to a solution of 30 mg (0.04 mmol) (R)-1-(4-amino-3-chloro-5-trifluoromethyl-benzyl)-2-(1'-ethoxy-carbonylmethyl-4,4'-bi-piperidinyl-1-yl)-2-oxo-ethyl 4-(2-oxo-1,2,4,5-tetrahydro-1,3-benzodiazepin-3-yl)-piperidine-1-carboxylate in 2 mL THF and the reaction mixture was stirred overnight at RT. The mixture was evaporated down i. vac., the residue was combined with a little water and 1 M HCl until an acidic reaction was obtained. The precipitate formed was suction filtered and dried.

Yield: 20 mg (66% of theory)
ESI-MS: $(M+H)^+$=763/765 (CI)
$R_f$=0.31 (silica gel, DCM/Cyc/MeOH/$NH_3$ 70:15:15:2)

EXAMPLE 3.2

(R)-1-(4-amino-3-chloro-5-trifluoromethyl-benzyl)-2-(1'-methoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate

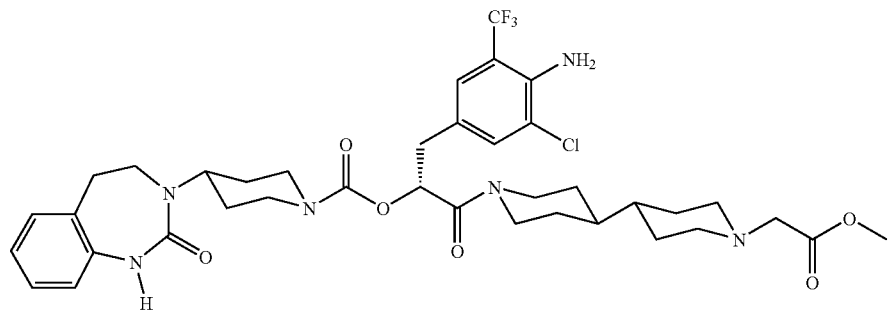

100 mg (0.31 mmol) TBTU and 0.06 mL (0.34 mmol) ethyldiisopropylamine were added to a solution of 200 mg (0.26 mmol) (R)-1-(4-amino-3-chloro -5-trifluoromethyl-benzyl)-2-(1'-carboxymethyl-4,4'-bipiperidinyl-1-yl)-2-oxo-ethyl 4-(2-oxo-1,2,4,5-tetrahydro-1,3-benzodiazepin-3-yl)-piperidine-1-carboxylate in 15 mL THF and the mixture was stirred for 10 min at RT. 1 mL (24.6 mmol) MeOH was added to the reaction mixture and this was stirred overnight at RT. It was evaporated down i. vac., the residue was taken up in 2 mL DMF and the crude product was purified by HPLC. The fractions containing the product were combined and freeze-dried.

Yield: 80 mg (39% of theory)

ESI-MS: (M+H)$^+$=777/779 (Cl)

$R_f$=0.60 (silica gel, DCM/Cyc/MeOH/NH$_3$ 70:15:15:2)

The following compounds were prepared analogously from in each case 200 mg of (R)-1-(4-amino-3-chloro-5-trifluoromethyl-benzyl)-2-(1'-carboxymethyl-4,4'-bipiperidinyl-1-yl)-2-oxo-ethyl 4-(2-oxo-1,2,4,5-tetrahydro-1,3-benzodiazepin-3-yl)-piperidine-1-carboxylate and 1 mL of the respective alcohol:

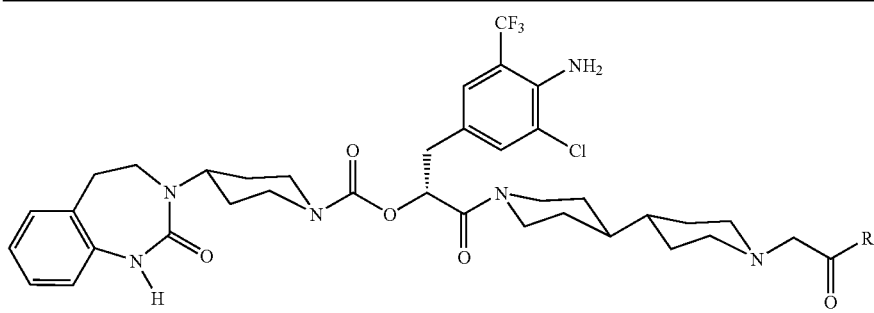

| Example | R | Yield (%) | Mass spectrum | $R_f$ (silica gel, DCM/MeOH/Cyc/NH$_3$ 70:15:15:2) |
|---|---|---|---|---|
| 3.3 | * | 33 | 805/807 [M + H]$^+$ | 0.59 |
| 3.4 | * | 30 | 819/821 [M + H]$^+$ | 0.61 |
| 3.5 | * | 47 | 821/823 [M + H]$^+$ | 0.58 |
| 3.6 | * | 39 | 875/877 [M + H]$^+$ | 0.70 |

EXAMPLE 3.7

(R)-1-(4-amino-3-chloro-5-trifluoromethyl-benzyl)-2-oxo-2-(1'-phenoxycarbonylmethyl-4,4'-bipiperidinyl-1-yl)-ethyl 4-(2-oxo-1,2,4,5-tetrahydro-1,3-benzodiazepin-3-yl)-piperidine-1-carboxylate

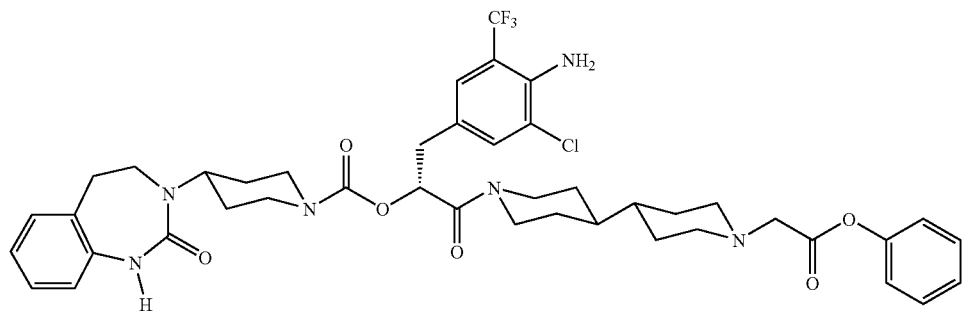

50 mg (0.16 mmol) TBTU and 37 μL (0.26 mmol) triethylamine were added to a solution of 100 mg (0.13 mmol) (R)-1-(4-amino-3-chloro-5-trifluoromethyl-benzyl)-2-(1'-carboxymethyl-4,4'-bipiperidinyl-1-yl)-2-oxo-ethyl 4-(2-oxo-1,2,4,5-tetrahydro-1,3-benzodiazepin-3-yl)-piperidine-1-carboxylate in 1.5 mL DMF and stirred for 1 h at RT. 14.8 mg (0.16 mmol) phenol were added and the reaction mixture was stirred overnight at RT. The reaction solution was filtered through a syringe filter and the crude product was purified by HPLC. The fractions containing the product were combined and freeze-dried. The residue was dissolved in DCM, evaporated down i. vac., triturated with DIPE, suction filtered and dried.

Yield: 48 mg (44% of theory)
ESI-MS: (M+H)$^+$=839/841 (Cl)
$R_f$=0.47 (silica gel, DCM/MeOH/NH$_3$ 90:10:1)
Retention time (HPLC): 3.2 min (Method B)

The following compounds were prepared analogously from in each case 100 mg (Examples 3.8 to 3.12), 120 mg (Example 3.13) or 90 mg (Examples 3.14 and 3.15) (R)-1-(4-amino-3-chloro-5-trifluoromethyl-benzyl)-2-(1'-carboxymethyl-4,4'-bipiperidinyl-1-yl)-2-oxo-ethyl 4-(2-oxo-1,2,4,5-tetrahydro-1,3-benzodiazepin-3-yl)-piperidine-1-carboxylate and the amount of the alcohol component needed in each case:

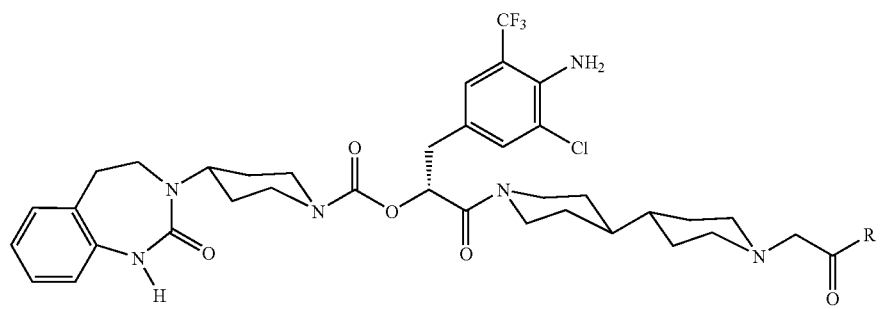

| Example | R | Yield (%) | Mass spectrum | retention time HPLC (Method) |
|---------|---|-----------|---------------|------------------------------|
| 3.8 | * | 69 | 879/881 [M + H]$^+$ | 3.1 min (B) |

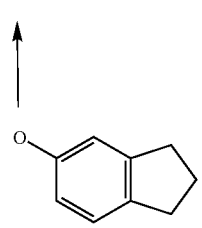

-continued
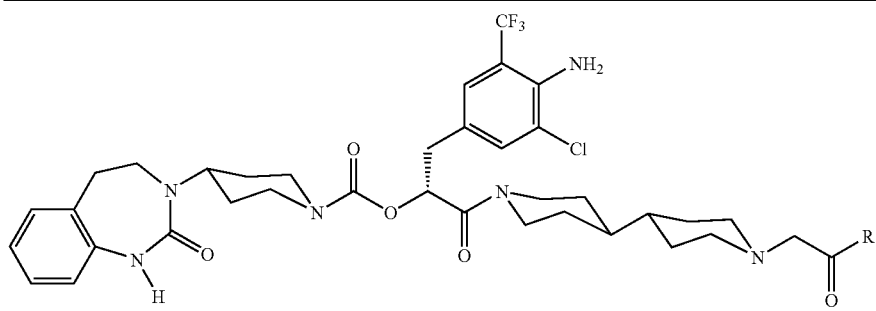
| Example | R | Yield (%) | Mass spectrum | retention time HPLC (Method) |
|---|---|---|---|---|
| 3.9 | * ↑ O—CH₂CH₂—morpholine | 57 | 876/878 [M + H]⁺ | 2.5 min (B) |
| 3.10 | * ↑ O—CH₂CH₂—N(CH₃)₂ | 59 | 834/836 [M + H]⁺ | 2.9 min (B) |
| 3.11 | * ↑ O—CH₂CH₂—(2-oxopiperidin-1-yl) | 52 | 888/890 [M + H]⁺ | 3.0 min (B) |
| 3.12 | * ↑ O—CH₂—(pyridin-4-yl) | 31 | 854/856 [M + H]⁺ | 2.4 min (B) |
| 3.13 | * ↑ O—CH₂CH₂—(2-oxopyrrolidin-1-yl) | 57 | 874/876 [M + H]⁺ | 3.0 min (B) |

-continued

| Example | R | Yield (%) | Mass spectrum | retention time HPLC (Method) |
|---|---|---|---|---|
| 3.14 | * ↑ O~~~O-N(morpholine) | 17 | 890/892 [M + H]⁺ | 3.0 min (B) |
| 3.15 | * ↑ O~~~N(CH₃)₂ | 63 | 848/850 [M + H]⁺ | 3.0 min (B) |

EXAMPLE 3.16

(R)-1-(4-amino-3-chloro-5-trifluoromethyl-benzyl)-2-[1'-(2,2-dimethylpropionyloxy-methoxycarbonyl-methyl)-4,4'-bipiperidinyl-1-yl]-2-oxo-ethyl 4-(2-oxo-1,2,4,5-tetrahydro-1,3-benzodiazepin-3-yl)-piperidine-1-carboxylate

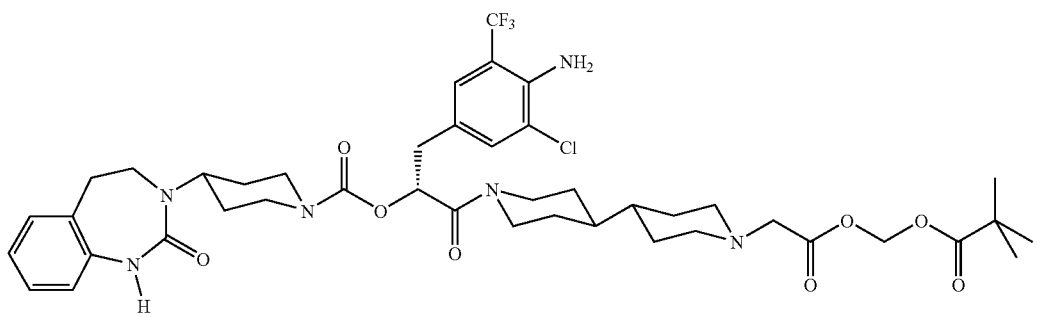

27 mg (0.20 mmol) K$_2$CO$_3$ and 28 µL (0.20 mmol) chloromethyl 2,2-dimethyl-propionate were added to a solution of 100 mg (0.13 mmol) (R)-1-(4-amino-3-chloro-5-trifluoromethyl-benzyl)-2-(1'-carboxymethyl-4,4'-bipiperidinyl-1-yl)-2-oxo-ethyl 4-(2-oxo-1,2,4,5-tetrahydro-1,3-benzodiazepin-3-yl)-piperidine-1-carboxylate in 2 mL DMF and the reaction mixture was stirred for 2 h at RT. The mixture was evaporated down i. vac., the residue was taken up in 50 mL DCM, the organic phase was washed with 20 mL water and dried over Na$_2$SO$_4$. After elimination of the desiccant and solvent the residue was purified by chromatography (silica gel, DCM/MeOH/NH$_3$ 97:3:0.3). The fractions containing the product were combined, evaporated down, the residue was triturated with a little diethyl ether/DIPE, suction filtered and dried.

Yield: 39 mg (34% of theory)

ESI-MS: (M+H)⁺=877/879 (Cl)

R$_f$=0.47 (silica gel, DCM/MeOH/NH$_3$ 90:10:1)

Retention time (HPLC): 3.3 min (Method B)

EXAMPLE 3.17

(R)-1-(4-amino-3-chloro-5-trifluoromethyl-benzyl)-
2-(1'-dimethylcarbamoylmethoxy-carbonylmethyl-4,

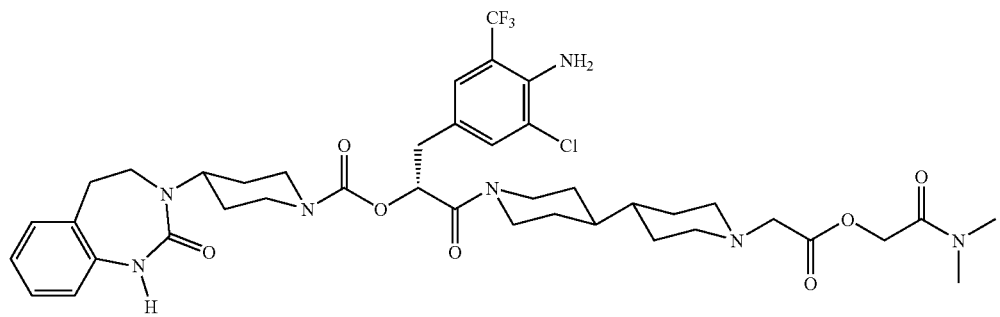

48 mg (0.15 mmol) TBTU, 21 µL (0.15 mmol) triethylamine and 15 mg (0.15 mmol) 2-hydroxy-N,N-dimethylacetamide were added to a solution of 100 mg (0.13 mmol) (R)-1-(4-amino-3-chloro-5-trifluoromethyl-benzyl)-2-(1'-carboxymethyl-4,4'-bipiperidinyl-1-yl)-2-oxo-ethyl 4-(2-oxo-1,2,4,5-tetrahydro-1,3-benzodiazepin-3-yl)-piperidine-1-carboxylate in 1 mL DMF and the reaction mixture was stirred overnight at RT. The reaction solution was filtered through a syringe filter and the crude product was purified by HPLC. The fractions containing the product were combined and evaporated down i. vac.

Yield: 23 mg (21% of theory)
ESI-MS: (M+H)$^+$=848/850 (CI)
Retention time (HPLC): 2.9 min (Method B)

EXAMPLE 4

(R)-1-(4-amino-3-chloro-5-trifluoromethyl-benzyl)-
2-[4-(1-ethoxycarbonyl methyl-piperidin-4-yl)-piperazin-1-yl]-2-oxo-ethyl 4-(2-oxo-1,2,4,5-tetrahydro-1,
3-benzodiazepin-3-yl)-piperidine-1-carboxylate

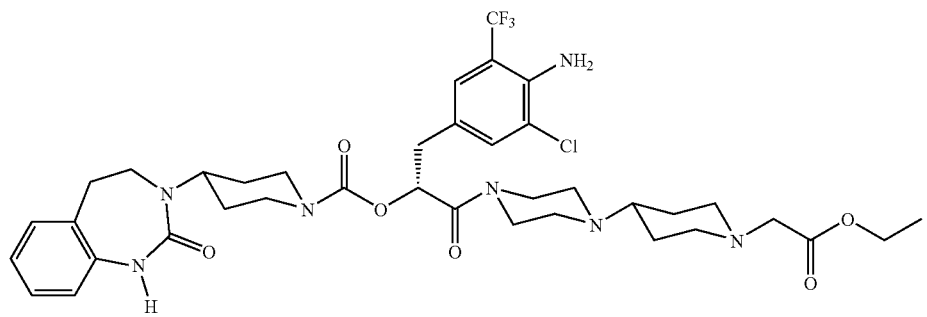

0.52 g (1.62 mmol) TBTU and 0.28 mL (1.61 mmol) ethyldiisopropylamine were added to a solution of 0.80 g (1.44 mmol) (R)-2-(4-amino-3-chloro -5-trifluoromethyl-phenyl)-1-carboxy-ethyl 4-(2-oxo-1,2,4,5-tetrahydro-1,3-benzodiazepin-3-yl)-piperidine-1-carboxylate in 30 mL THF and stirred for 10 min at RT. 0.40 g (1.57 mmol) ethyl (4-piperazin-1-yl-piperidin-1-yl) -acetate were added to the reaction mixture and this was stirred overnight at RT. 40 mL EtOAc were added, the organic phase was washed with 15% K$_2$CO$_3$ solution and dried over MgSO$_4$. After elimination of the 4'-bipiperidinyl-1-yl)-2-oxo-ethyl 4-(2-oxo-1,2,4,5-tetrahydro-1,3-benzodiazepin-3-yl)-piperidine-1-carboxylate desiccant and solvent the residue was purified by chromatography (silica gel, gradient DCM to DCM/EtOH/NH$_3$ 70:30:3).

Yield: 0.68 g (60% of theory)
ESI-MS: (M+H)$^+$=792/794 (CI)
$R_f$=0.70 (silica gel, DCM/Cyc/MeOH/NH$_3$ 70:15:15:2)

EXAMPLE 4.1

(R)-1-(4-amino-3-chloro-5-trifluoromethyl-benzyl)-2-[4-(1-carboxymethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate

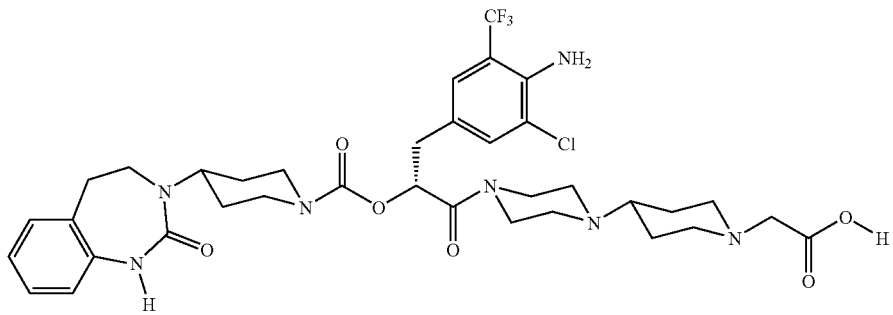

A solution of 25 mg (1.02 mmol) LiOH in 20 mL water was added to a solution of 380 mg (0.48 mmol) (R)-1-(4-amino-3-chloro-5-trifluoromethyl-benzyl)-2-[4-(1-ethoxycarbonylmethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate in 20 mL THF and the reaction mixture was stirred overnight at RT. The organic solvent was eliminated i. vac. and 20 mL water and 1.1 mL 1 M HCl were added. The mixture was evaporated down i. vac., the residue was taken up in 5 mL DMF and the crude product was purified by HPLC. The fractions containing the product were combined and freeze-dried.

Yield: 114 mg (31% of theory)
ESI-MS: $(M+H)^+ = 764/766$ (Cl)
$R_f = 0.07$ (silica gel, DCM/Cyc/MeOH/NH$_3$ 70:15:15:2)

EXAMPLE 4.2

(R)-1-(4-amino-3-chloro-5-trifluoromethyl-benzyl)-2-[4-(1-butoxycarbonylmethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate

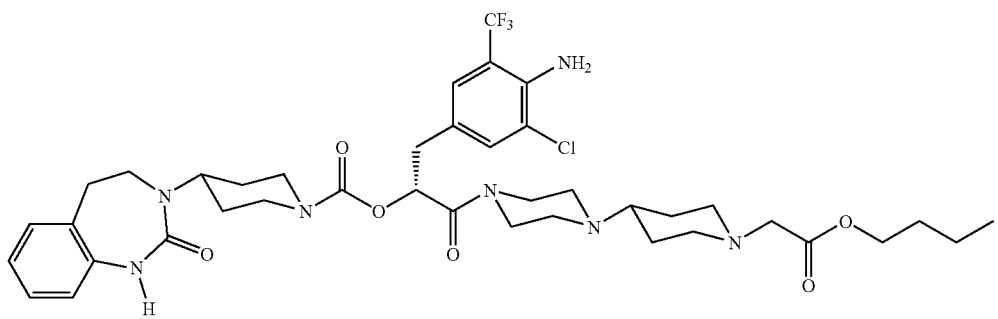

51 mg (0.16 mmol) TBTU and 29 μL (0.34 mmol) triethylamine were added to a solution of 80 mg (0.11 mmol) (R)-1-(4-amino-3-chloro-5-trifluoromethyl-benzyl)-2-[4-(1-carboxymethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate in 1.5 mL DMF and the mixture was shaken for 30 min at RT. 100 μL (1.09 mmol) 1-butanol were added to the reaction mixture and this was shaken overnight at RT. After filtration through a syringe filter the crude product was purified by HPLC. The fractions containing the product were combined and freeze-dried.

Yield: 46 mg (54% of theory)
ESI-MS: (M+H)$^+$=820/822 (CI)
$R_f$=0.67 (silica gel, DCM/Cyc/MeOH/NH$_3$ 70:15:15:2)

The following compounds were prepared analogously from in each case 80 mg (R)-1-(4-amino-3-chloro-5-trifluoromethyl-benzyl)-2-[4-(1-carboxymethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate and 100 μL of the respective alcohol component:

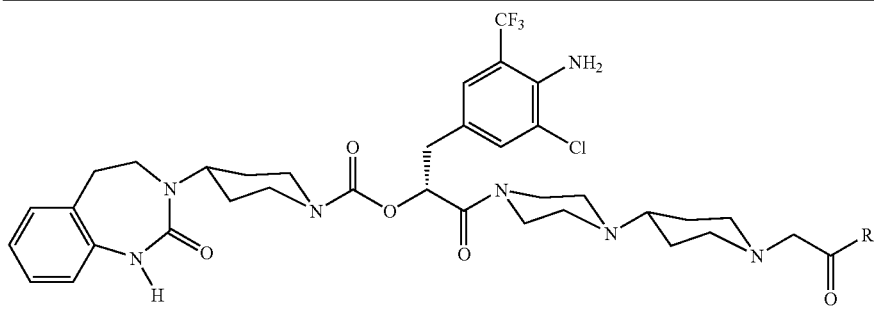

| Example | R | Yield (%) | Mass spectrum | $R_f$ (silica gel, DCM/MeOH/Cyc/NH$_3$ 70:15:15:2) |
|---|---|---|---|---|
| 4.3 | * ↑ O⁀⁀⁀ | 52 | 834/836 [M + H]$^+$ | 0.63 |
| 4.4 | * ↑ O⁀⁀⁀⁀ | 52 | 848/850 [M + H]$^+$ | 0.61 |

The following compounds were prepared analogously from in each case 80 mg (R)-1-(4-amino-3-chloro-5-trifluoromethyl-benzyl)-2-[4-(1-carboxymethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate and 1.5 equivalents (Examples 4.5 and 4.6) and 1.6 equivalents (Examples 4.7 and 4.8) of the respective alcohol component:

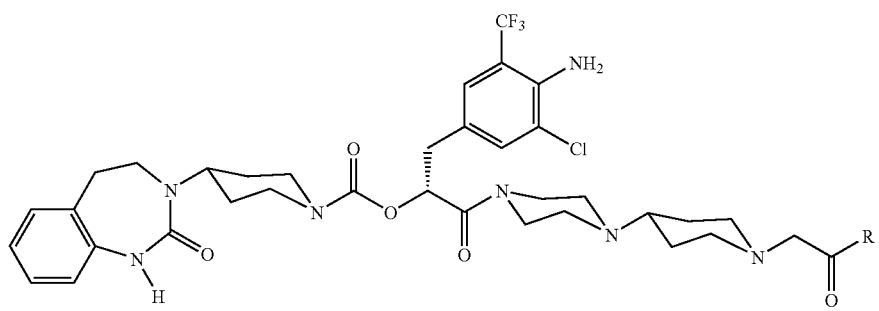
| Example | R | Yield (%) | Mass spectrum | R$_f$ (silica gel, DCM/MeOH/Cyc/NH$_3$ 70:15:15:2) |
|---|---|---|---|---|
| 4.5 | *—O-phenyl | 44 | 840/842 [M + H]$^+$ | 0.71 |
| 4.6 | *—O-CH$_2$CH$_2$-(2-oxopiperidin-1-yl) | 57 | 889/891 [M + H]$^+$ | 0.70 |
| 4.7 | *—O-(indan-5-yl) | 33 | 880/882 [M + H]$^+$ | 0.51 |
| 4.8 | *—O-CH$_2$-(pyridin-4-yl) | 49 | 855/857 [M + H]$^+$ | 0.67 |

EXAMPLE 4.9

(R)-1-(4-amino-3-chloro-5-trifluoromethyl-benzyl)-
2-{4-[1-(2-morpholin-4-yl-ethoxycarbonylmethyl)-
piperidin-4-yl]-piperazin-1-yl}-2-oxo-ethyl 4-(2-
oxo-1,2,4,5-tetrahydro-1,3-benzodiazepin-3-yl)-
piperidine-1-carboxylate

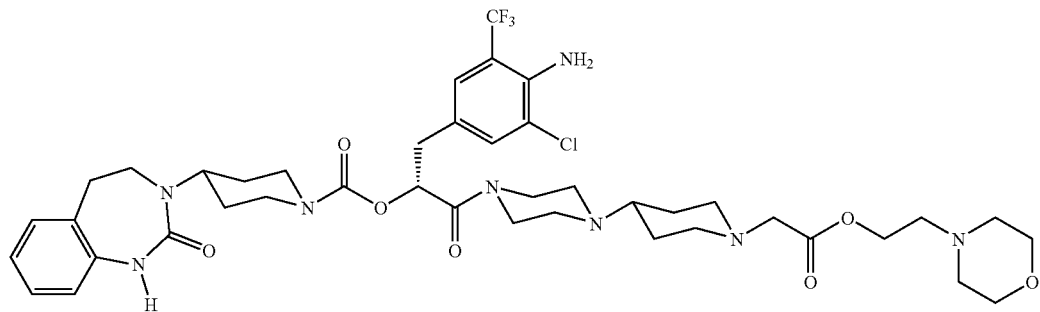

50 mg (0.16 mmol) TBTU and 37 µL (0.34 mmol) triethylamine were added to a solution of 100 mg (0.13 mmol) (R)-1-(4-amino-3-chloro-5-trifluoromethyl-benzyl)-2-[4-(1-carboxymethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate in 5 mL THF and stirred for 30 min at RT. 19 µL (0.16 mmol) 2-morpholin-4-yl-ethanol were added to the reaction mixture and the suspension was stirred for 1.5 h at RT. 3 mL of DMF were added and the mixture was stirred for another 4 h at RT. The reaction mixture was evaporated down i. vac., the residue was dissolved in 1.5 mL MeOH, filtered through a syringe filter and purified by HPLC. The fractions containing the product were evaporated down i. vac., the residue was triturated with DIPE, suction filtered and dried at 50° C. in vacuo.

Yield: 47 mg (41% of theory)
ESI-MS: (M+H)$^+$=877/879 (CI)
$R_f$=0.31 (silica gel, DCM/MeOH/NH$_3$ 90:10:1)
Retention time (HPLC): 2.7 min (Method B)

EXAMPLE 4.10

(R)-1-(4-amino-3-chloro-5-trifluoromethyl-benzyl)-
2-oxo-2-(4-{1-[2-(2-pyrrolidin-1-yl)-ethoxycarbon-
ylmethyl]-piperidin-4-yl}-piperazin-1-yl)-ethyl 4-(2-
oxo-1,2,4,5-tetrahydro-1,3-benzodiazepin-3-yl)-
piperidine-1-carboxylate

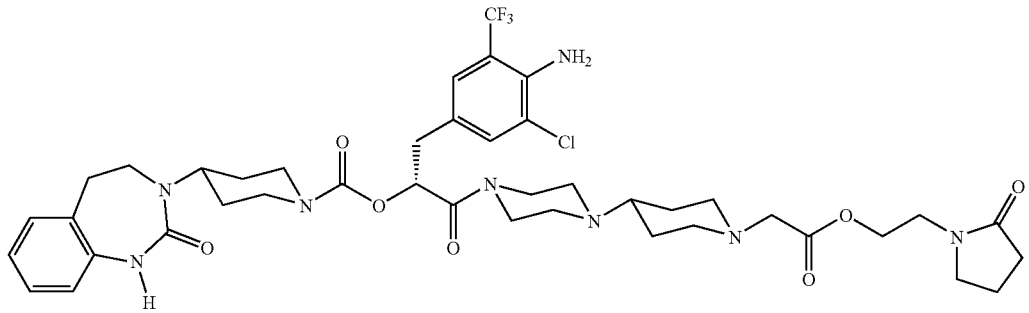

Prepared analogously to Example 4.9 from 80 mg (0.11 mmol) (R)-1-(4-amino-3-chloro-5-trifluoromethyl-benzyl)-2-[4-(1-carboxymethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate and 18 µL (0.16 mmol) 1-(2-hydroxy-ethyl)-pyrrolidin-2-one, using 1.5 mL DMF as solvent.

Yield: 39 mg (43% of theory)
ESI-MS: (M+H)$^+$=875/877 (CI)
$R_f$=0.40 (silica gel, DCM/MeOH/NH$_3$ 90:10:1)
Retention time (HPLC): 2.9 min (Method B)

EXAMPLE 4.11

(R)-1-(4-amino-3-chloro-5-trifluoromethyl-benzyl)-
2-{4-[1-(3-morpholin-4-yl-propoxycarbonyl-methyl)-piperidin-4-yl]-piperazin-1-yl}-2-oxo-ethyl
4-(2-oxo-1,2,4,5-tetrahydro-1,3-benzodiazepin-3-yl)-piperidine-1-carboxylate

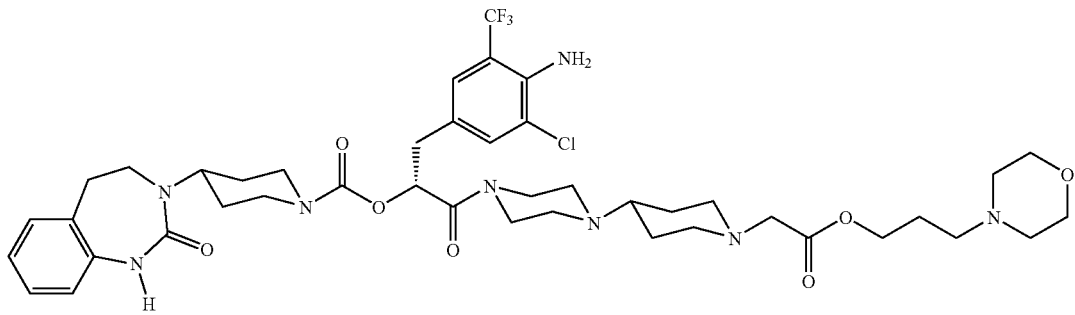

Prepared analogously to Example 4.9 from 90 mg (0.12 mmol) (R)-1-(4-amino-3-chloro-5-trifluoromethyl-benzyl)-2-[4-(1-carboxymethyl-piperidin-4-yl) -piperazin-1-yl]-2-oxo-ethyl 4-(2-oxo-1,2,4,5-tetrahydro-1,3-benzodiazepin-3-yl)-piperidine-1-carboxylate and 22 mg (0.15 mmol) 3-morpholin-4-yl-propan-1-ol, using 1.5 mL DMF as solvent. After purification by HPLC the product was taken up in DCM, the organic phase was extracted with 5% $NaHCO_3$ solution and dried over $Na_2SO_4$. After elimination of the desiccant and solvent the residue was stirred with DIPE, suction filtered and dried in the air.

Yield: 48 mg (46% of theory)
ESI-MS: $(M+H)^+$=891/893 (Cl)
$R_f$=0.17 (silica gel, DCM/MeOH/$NH_3$ 90:10:1)
Retention time (HPLC): 2.7 min (Method B)

EXAMPLE 4.12

(R)-1-(4-amino-3-chloro-5-trifluoromethyl-benzyl)-
2-{4-[1-(2,2-dimethyl-propionyloxymethoxycarbonyl-methyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate

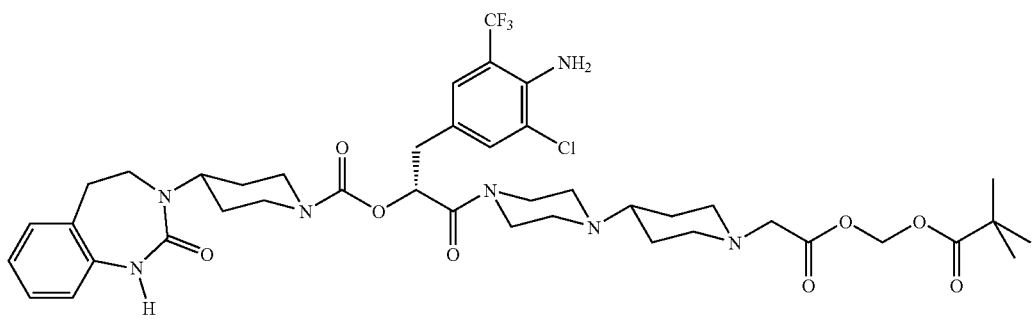

42 mg (0.30 mmol) $K_2CO_3$ and 43 μL (0.30 mmol) chloromethyl 2,2-dimethyl-propionate were added to a solution of 150 mg (0.20 mmol) (R)-1-(4-amino-3-chloro-5-trifluoromethyl-benzyl)-2-[4-(1-carboxymethyl-piperidin-4-yl) -piperazin-1-yl]-2-oxo-ethyl 4-(2-oxo-1,2,4,5-tetrahydro-1,3-benzodiazepin-3-yl)-piperidine-1-carboxylate in 5 mL DMF and the reaction mixture was stirred overnight at RT. It was evaporated down i. vac., the residue was combined with 30 mL 15% $K_2CO_3$ solution, the product precipitated was suction filtered and purified by column chromatography (silica gel, gradient DCM to DCM/MeOH/$NH_3$ 50:47:3).

Yield: 50 mg (29% of theory)
ESI-MS: $(M+H)^+$=878/880 (Cl)
$R_f$=0.63 (silica gel, DCM/Cyc/MeOH/$NH_3$ 70:15:15:2)

EXAMPLE 4.13

(R)-1-(4-amino-3-chloro-5-trifluoromethyl-benzyl)-
2-{4-[1-(1-ethoxycarbonyloxy-ethoxycarbonyl-me-
thyl)-piperidin-4-yl]-piperazin-1-yl}-2-oxo-ethyl
4-(2-oxo-1,2,4,5-tetrahydro-1,3-benzodiazepin-3-yl)-
piperidine-1-carboxylate

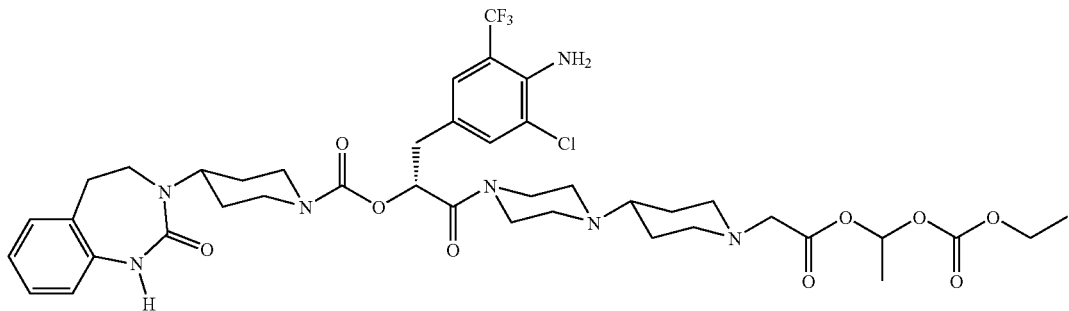

Prepared analogously to Example 4.12 from 150 mg (0.20 mmol) (R)-1-(4-amino-3-chloro-5-trifluoromethyl-benzyl)-2-[4-(1-carboxymethyl-piperidin -4-yl)-piperazin-1-yl]-2-oxo-ethyl 4-(2-oxo-1,2,4,5-tetrahydro-1,3-benzodiazepin-3-yl)-piperidine-1-carboxylate and 40 µL (0.30 mmol) 1-chloroethyl-ethylcarbonate.

Yield: 50 mg (29% of theory)
ESI-MS: $(M+H)^+=880/882$ (Cl)
$R_f=0.68$ (silica gel, DCM/Cyc/MeOH/NH$_3$ 70:15:15:2)

EXAMPLE 4.14

(R)-1-(4-amino-3-chloro-5-trifluoromethyl-benzyl)-
2-[4-(1-diethylcarbamoylmethoxy-carbonylmethyl-
piperidin-4-yl)-piperazin-1-yl]-2-oxo-ethyl 4-(2-oxo-
1,2,4,5-tetrahydro-1,3-benzodiazepin-3-yl)-
piperidine-1-carboxylate

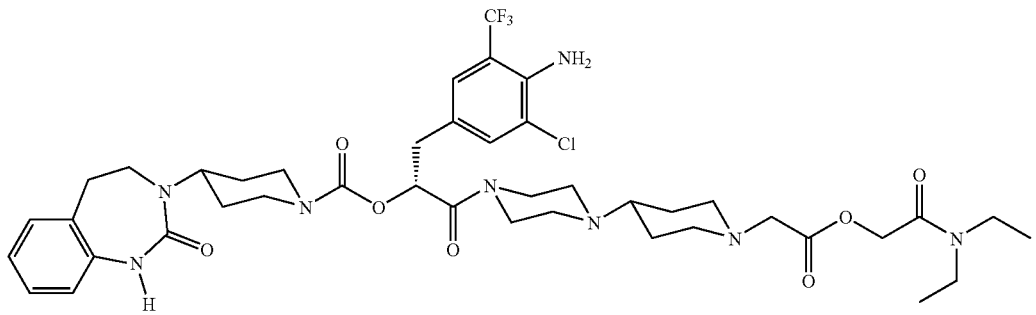

50 mg (0.16 mmol) TBTU, 25 µL (0.18 mmol) triethylamine and 30 mg (0.23 mmol) N,N-diethyl-2-hydroxy-acetamide were added to a solution of 100 mg (0.13 mmol) (R)-1-(4-amino-3-chloro-5-trifluoro-methyl-benzyl)-2-[4-(1-carboxymethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate in 1 mL DMF and the reaction mixture was stirred for 20 h at RT. The reaction solution was poured onto saturated NaHCO$_3$ solution, the precipitate formed was suction filtered and dried. The crude product was purified by HPLC. The fractions containing the product were combined and freeze-dried.

Yield: 36 mg (31% of theory)

ESI-MS: $(M+H)^+=877/879$ (Cl)

Retention time (HPLC): 3.2 min (Method B)

The following compounds were prepared analogously from in each case 100 mg (R)-1-(4-amino-3-chloro-5-trifluoromethyl-benzyl)-2-[4-(1-carboxymethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate and the corresponding amount of the respective alcohol component:

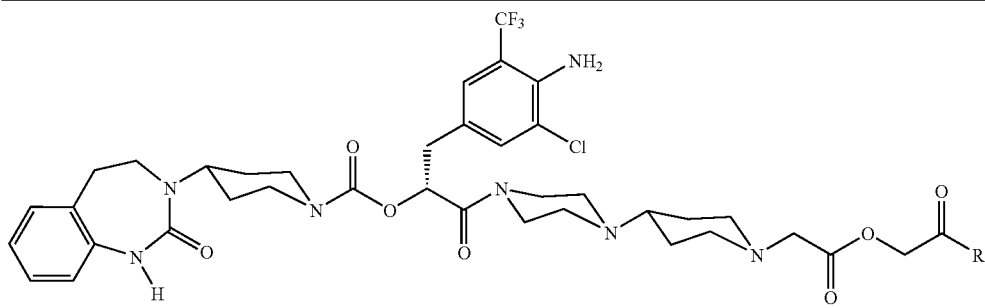

| Example | R | Yield (%) | Mass spectrum | Retention time HPLC (Method) |
|---|---|---|---|---|
| 4.15 | *–N(CH3)– | 76 | 849/851 [M + H]+ | 3.1 min (B) |
| 4.16 | *–piperidinyl | 25 | 889/891 [M + H]+ | 3.2 min (B) |

EXAMPLE 5

(R)-1-(4-amino-3-chloro-5-trifluoromethyl-benzyl)-
2-[4-(4-ethoxycarbonylmethyl-piperazin-1-yl)-pip-
eridin-1-yl]-2-oxo-ethyl 4-(2-oxo-1,2,4,5-tetrahydro-
1,3-benzodiazepin-3-yl)-piperidine-1-carboxylate

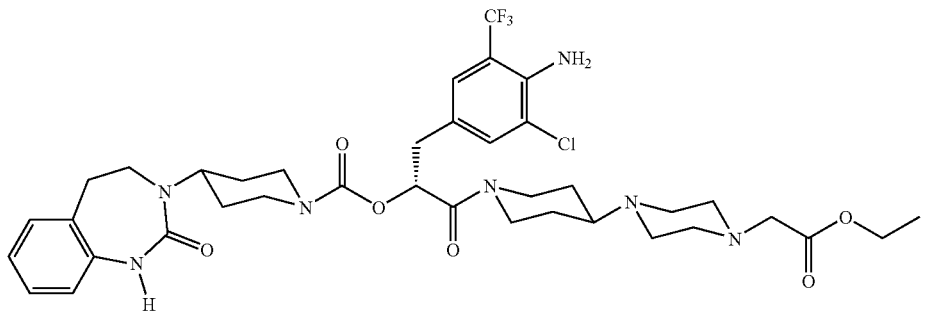

64 mg (0.20 mmol) TBTU and 28 μL (0.20 mmol) triethylamine were added to a solution of 100 mg (0.18 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate in 1 mL DMF and stirred for 10 min at RT. 51 mg (0.20 mmol) ethyl(4-piperidin-4-yl-piperazin-1-yl)-acetate were added to the reaction mixture and this was shaken overnight at RT. After filtration through a syringe filter the reaction solution was purified by HPLC without further working up. The fractions containing the product were combined and freeze-dried.

Yield: 91 mg (64% of theory)
ESI-MS: (M+H)+=792/794 (CI)
$R_f$=0.48 (silica gel, DCM/MeOH/NH3 90:10:1)

EXAMPLE 5.1

(R)-1-(4-amino-3-chloro-5-trifluoromethyl-benzyl)-
2-[4-(4-carboxymethyl-piperazin-1-yl)-piperidin-1-
yl]-2-oxo-ethyl 4-(2-oxo-1,2,4,5-tetrahydro-1,3-ben-
zodiazepin-3-yl)-piperidine-1-carboxylate

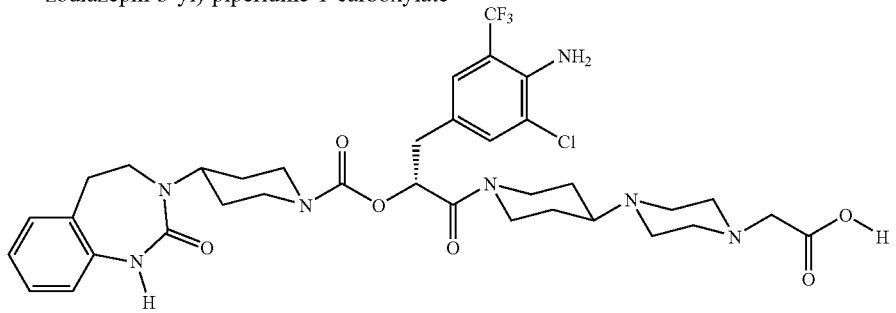

A solution of 3.6 mg (0.15 mmol) LiOH in 1 mL water was added to a solution of 70 mg (0.09 m mol) (R)-1-(4-amino-3-chloro-5-trifluoromethyl-benzyl) -2-[4-(4-ethoxy-carbonylmethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate in 10 mL THF and the reaction mixture was stirred overnight at RT. The THF was eliminated in a nitrogen stream, then a little water was added, followed by formic acid until an acidic reaction was obtained and then acetonitrile and the product was subjected to freeze-drying.

Yield: 52 mg (76% of theory)
ESI-MS: $(M-H)^-=762/764$ (Cl)
$R_f=0.14$ (silica gel, DCM/MeOH/NH$_3$ 90:10:1)

EXAMPLE 5.2

(R)-1-(4-amino-3-chloro-5-trifluoromethyl-benzyl)-
2-[4-(4-dimethylcarbamoylmethoxycarbonyl-me-
thyl-piperazin-1-yl)-piperidin-1-yl]-2-oxo-ethyl
4-(2-oxo-1,2,4,5-tetrahydro-1,3-benzodiazepin-3-yl)-
piperidine-1-carboxylate

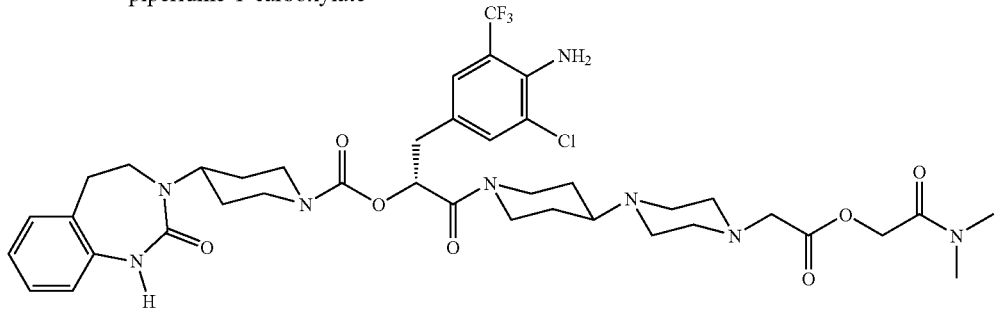

90 mg (0.28 mmol) TBTU, 39 µL (0.15 mmol) triethylamine and 29 mg (0.28 mmol) 2-hydroxy-N,N-dimethylacetamide were added to a solution of 190 mg (0.25 mmol) (R)-1-(4-amino-3-chloro-5-trifluoromethyl-benzyl)-2-[4-(4-carboxymethyl-piperazin-1-yl)-piperidin-1-yl]-2-oxo-ethyl 4-(2-oxo-1,2,4,5-tetrahydro-1,3-benzodiazepin-3-yl)-piperidine-1-carboxylate in 5 mL DMF and the reaction mixture was stirred overnight at RT. The reaction solution was filtered through a syringe filter and the crude product was purified by HPLC. The fractions containing the product were combined and freeze-dried.

Yield: 106 mg (50% of theory)
ESI-MS: $(M+H)^+=849/851$ (Cl)
Retention time (HPLC): 3.3 min (Method B)

EXAMPLE 6

(R)-1-(4-amino-3-chloro-5-trifluoromethyl-benzyl)-
2-[1'-(2-ethoxycarbonyl-ethyl)-4,4'-bipiperidinyl-1-
yl]-2-oxo-ethyl 4-(2-oxo-1,2,4,5-tetrahydro-1,3-ben-
zodiazepin-3-yl)-piperidine-1-carboxylate

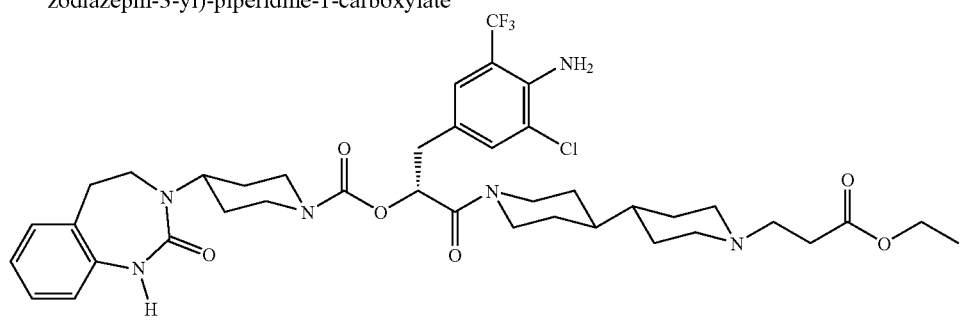

64 mg (0.20 mmol) TBTU and 28 µL (0.20 mmol) triethylamine were added to a solution of 100 mg (0.18 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate in 1 mL DMF and stirred for 10 min at RT. 54 mg (0.20 mmol) ethyl 3-[4,4']bipiperidinyl-1-yl-propionate (Amine A1) were added to the reaction mixture and this was shaken overnight at RT. After filtration through a syringe filter the reaction solution was purified by HPLC without further working up. The fractions containing the product were combined and freeze-dried.

Yield: 42 mg (29% of theory)
ESI-MS: $(M+H)^+=805/807$ (Cl)
$R_f=0.58$ (silica gel, DCM/MeOH/NH$_3$ 90:10:1)

EXAMPLE 6.1

(R)-1-(4-amino-3-chloro-5-trifluoromethyl-benzyl)-
2-[1'-(2-carboxy-ethyl)-4,4'-bipiperidinyl-1-yl]-2-
oxo-ethyl 4-(2-oxo-1,2,4,5-tetrahydro-1,3-benzodi-
azepin-3-yl)-piperidine-1-carboxylate

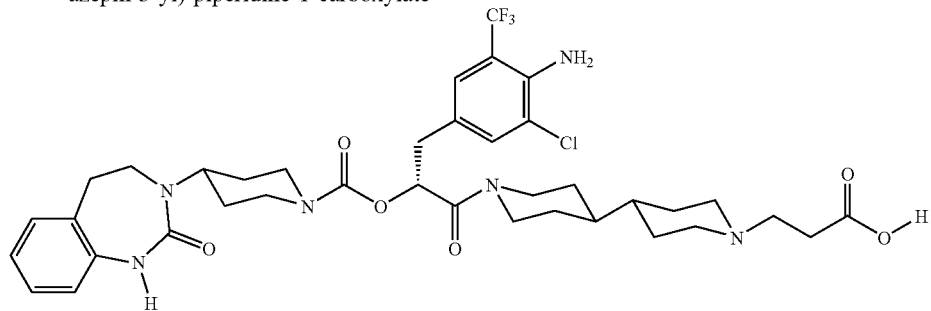

A solution of 1.4 mg (0.06 mmol) LiOH in 1 mL water was added to a solution of 30 mg (0.04 mmol) (R)-1-(4-amino-3-chloro-5-trifluoromethyl-benzyl)-2-[1'-(2-ethoxy-carbonyl-ethyl)-4,4'-bipiperidinyl-1-yl]-2-oxo-ethyl 4-(2-oxo-1,2,4,5-tetrahydro-1,3-benzodiazepin-3-yl)-piperidine-1-carboxylate in 10 mL THF and the reaction mixture was stirred overnight at RT. The THF was eliminated in a nitrogen stream, then a little water was added, followed by formic acid until an acidic reaction was obtained and then acetonitrile and the crude product was purified by HPLC. The fractions containing the product were combined and freeze-dried.

Yield: 28 mg (97% of theory)
ESI-MS: $(M+H)^+=777/779$ (Cl)
$R_f=0.15$ (silica gel, DCM/MeOH/NH$_3$ 90:10:1)

EXAMPLE 7

(R)-1-(4-amino-3-chloro-5-trifluoromethyl-benzyl)-2-{4-[1-(2-ethoxycarbonyl-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate

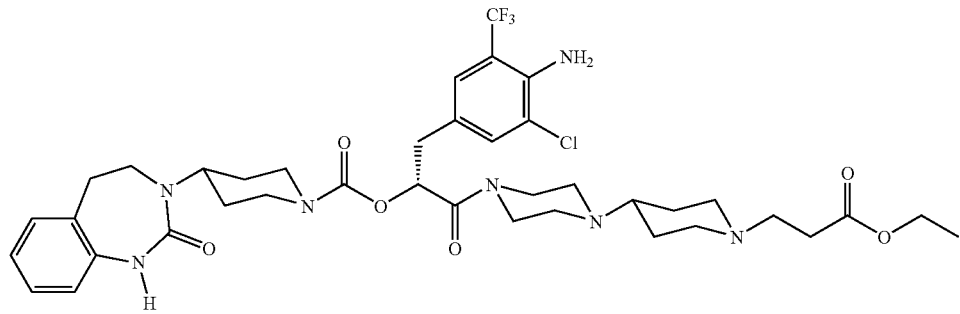

64 mg (0.20 mmol) TBTU and 111 µL (0.80 mmol) triethylamine were added to a solution of 100 mg (0.18 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate in 1 mL DMF and stirred for 10 min at RT. 122 mg (0.20 mmol) ethyl 3-(4-piperazin-1-yl-piperidin-1-yl)-propionate (Amine A2, used as the tris-trifluoroacetate salt) were added to the reaction mixture and this was shaken overnight at RT. After filtration through a syringe filter the reaction solution was purified by HPLC without further working up. The fractions containing the product were combined and freeze-dried.

Yield: 45 mg (31% of theory)
ESI-MS: $(M+H)^+ = 806/808$ (Cl)
$R_f = 0.57$ (silica gel, DCM/MeOH/NH$_3$ 90:10:1)

EXAMPLE 7.1

(R)-1-(4-amino-3-chloro-5-trifluoromethyl-benzyl)-2-{4-[1-(2-carboxy-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate

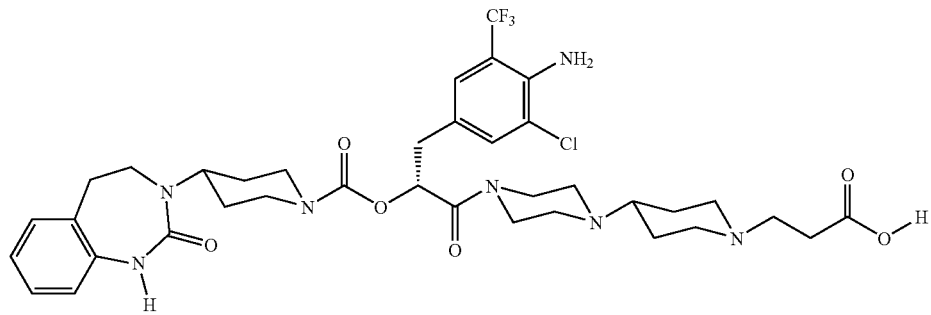

Prepared analogously to Example 6.1 from 30 mg (0.04 mmol) (R)-1-(4-amino-3-chloro-5-trifluoromethyl-benzyl)-2-{4-[1-(2-ethoxycarbonyl-ethyl) -piperidin-4-yl]-piperazin-1-yl}-2-oxo-ethyl 4-(2-oxo-1,2,4,5-tetrahydro-1,3-benzodiazepin-3-yl)-piperidine-1-carboxylate and 1.4 mg (0.06 mmol) LiOH.

Yield: 15 mg (51% of theory)
ESI-MS: $(M-H)^- = 776/778$ (Cl)
$R_f = 0.13$ (silica gel, DCM/MeOH/NH$_3$ 90:10:1)

EXAMPLE 7.2

(R)-1-(4-amino-3-chloro-5-trifluoromethyl-benzyl)-
2-(4-{1-[2-(2-dimethylamino-ethoxycarbonyl)-
ethyl]-piperidin-4-yl}-piperazin-1-yl)-2-oxo-ethyl
4-(2-oxo-1,2,4,5-tetrahydro-1,3-benzodiazepin-3-yl)-
piperidine-1-carboxylate

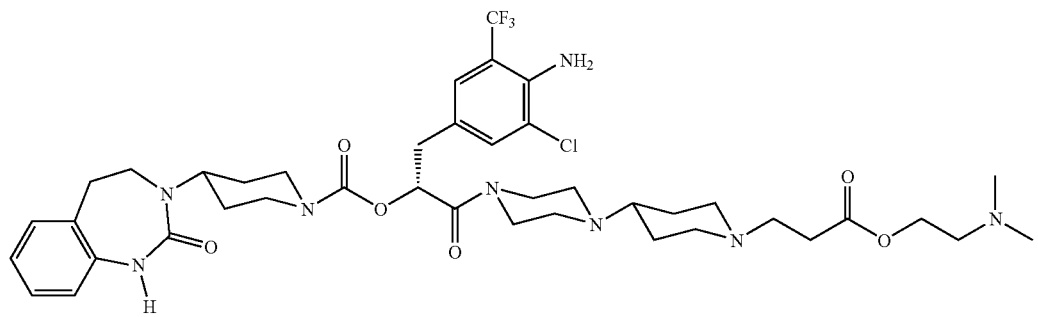

48 mg (0.15 mmol) TBTU and 21 μL (0.15 mmol) triethylamine were added to a solution of 100 mg (0.13 mmol) (R)-1-(4-amino-3-chloro-5-trifluoromethyl-benzyl)-2-{4-[1-(2-carboxy-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate in 1 mL DMF and stirred for 10 min at RT. 15 μL (0.15 mmol) 2-dimethylamino-ethanol were added to the reaction mixture and this was shaken overnight at RT. After filtration through a syringe filter the reaction solution was purified by HPLC without further working up. The fractions containing the product were combined and freeze-dried.

Yield: 22 mg (20% of theory)

ESI-MS: (M+H)$^+$=849/851 (Cl)

Retention time (HPLC): 2.8 min (Method B)

The following compounds were prepared analogously from in each case 100 mg (Examples 7.3 and 7.4) or from 95 mg (Example 7.5) (R)-1-(4-amino-3-chloro-5-trifluoromethyl-benzyl)-2-{4-[1-(2-carboxy-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate and the corresponding amount of the respective alcohol component:

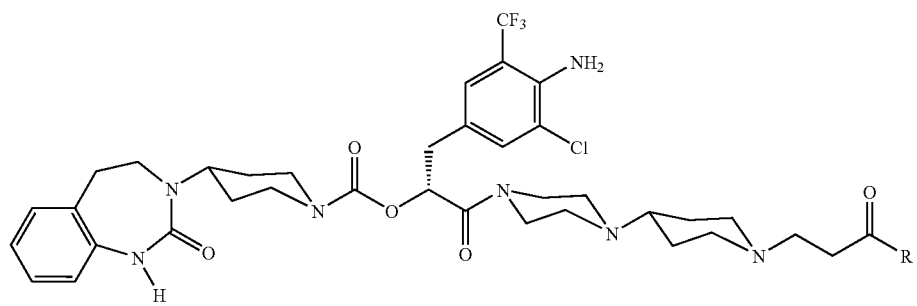

| Example | R | Yield (%) | Mass spectrum | Retention time HPLC (Method) |
|---|---|---|---|---|
| 7.3 | * | 17 | 891/893 [M + H]$^+$ | 2.1 min (B) |

-continued

| Example | R | Yield (%) | Mass spectrum | Retention time HPLC (Method) |
|---|---|---|---|---|
| 7.4 | * ↑ O~N(piperidine via CH2CH2) | 39 | 889/891 [M + H]$^+$ | 2.7 min (B) |
| 7.5 | * ↑ OCH2C(O)N(CH3)2 | 16 | 863/865 [M + H]$^+$ | 3.1 min (B) |

EXAMPLE 8

(R)-1-(4-amino-3-chloro-5-trifluoromethyl-benzyl)-2-{4-[4-(2-ethoxycarbonyl-ethyl)-piperazin-1-yl]-piperidin-1-yl}-2-oxo-ethyl 4-(2-oxo-1,2,4,5-tetrahydro-1,3-benzodiazepin-3-yl)-piperidine-1-carboxylate

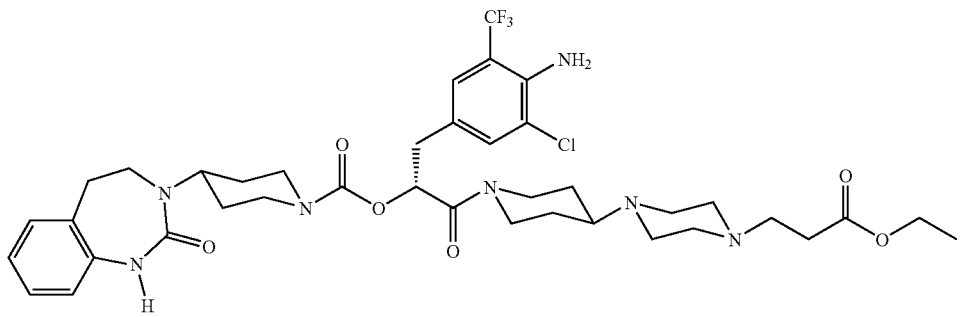

64 mg (0.20 mmol) TBTU and 28 µL (0.20 mmol) triethylamine were added to a solution of 100 mg (0.18 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate in 1 mL DMF and stirred for 10 min at RT. 54 mg (0.20 mmol) ethyl 3-(4-piperidin-4-yl-piperazin-1-yl)-propionate (Amine A3) were added to the reaction mixture and this was shaken overnight at RT. After filtration through a syringe filter the reaction solution was purified by HPLC without further working up. The fractions containing the product were combined and freeze-dried.

Yield: 77 mg (53% of theory)
ESI-MS: (M+H)$^+$=806/808 (CI)
$R_f$=0.58 (silica gel, DCM/MeOH/NH$_3$ 90:10:1)

EXAMPLE 8.1

(R)-1-(4-amino-3-chloro-5-trifluoromethyl-benzyl)-
2-{4-[4-(2-carboxy-ethyl)-piperazin-1-yl]-piperidin-
1-yl}-2-oxo-ethyl 4-(2-oxo-1,2,4,5-tetrahydro-1,3-
benzodiazepin-3-yl)-piperidine-1-carboxylate

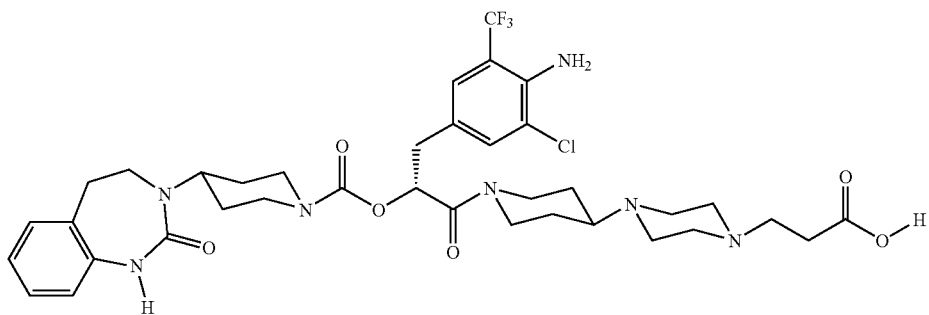

Prepared analogously to Example 6.1 from 60 mg (0.07 mmol) (R)-1-(4-amino-3-chloro-5-trifluoromethyl-benzyl)-2-{4-[4-(2-ethoxycarbonyl-ethyl) -piperazin-1-yl]-piperidin-1-yl}-2-oxo-ethyl 4-(2-oxo-1,2,4,5-tetrahydro-1,3-benzodiazepin-3-yl)-piperidine-1-carboxylate and 2.9 mg (0.12 mmol) LiOH.

Yield: 40 mg (70% of theory)
ESI-MS: $(M-H)^- = 776/778$ (Cl)
$R_f = 0.14$ (silica gel, DCM/MeOH/NH$_3$ 90:10:1)

EXAMPLE 9

(R)-1-(4-amino-3-chloro-5-trifluoromethyl-benzyl)-
2-[4-((R)-2-ethoxycarbonyl-pyrrolidin-1-yl)-piperi-
din-1-yl]-2-oxo-ethyl 4-(2-oxo-1,2,4,5-tetrahydro-1,
3-benzodiazepin-3-yl)-piperidine-1-carboxylate

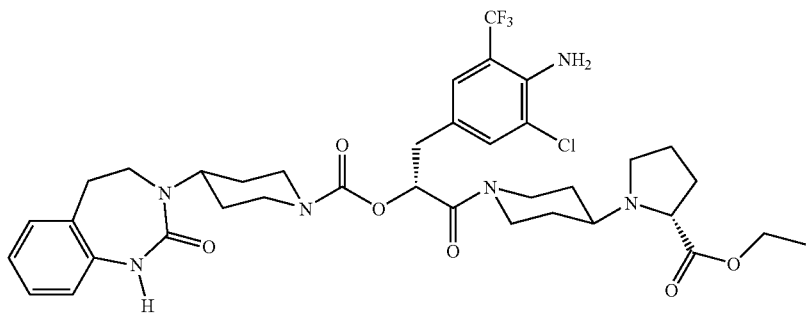

64 mg (0.20 mmol) TBTU and 28 μL (0.20 mmol) triethylamine were added to a solution of 100 mg (0.18 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate in 1 mL DMF and stirred for 10 min at RT. 45 mg (0.20 mmol) ethyl (R)-1-piperidin-4-yl-pyrrolidine-2-carboxylate were added to the reaction mixture and this was shaken overnight at RT. After filtration through a syringe filter the reaction solution was purified by HPLC without further working up. The fractions containing the product were combined and freeze-dried.

Yield: 77 mg (56% of theory)
ESI-MS: $(M+H)^+ = 763/765$ (Cl)
Retention time (HPLC): 3.4 min (Method B)

EXAMPLE 9.1

(R)-1-(4-amino-3-chloro-5-trifluoromethyl-benzyl)-
2-[4-((R)-2-carboxy-pyrrolidin-1-yl)-piperidin-1-yl]-
2-oxo-ethyl 4-(2-oxo-1,2,4,5-tetrahydro-1,3-benzo-
diazepin-3-yl)-piperidine-1-carboxylate

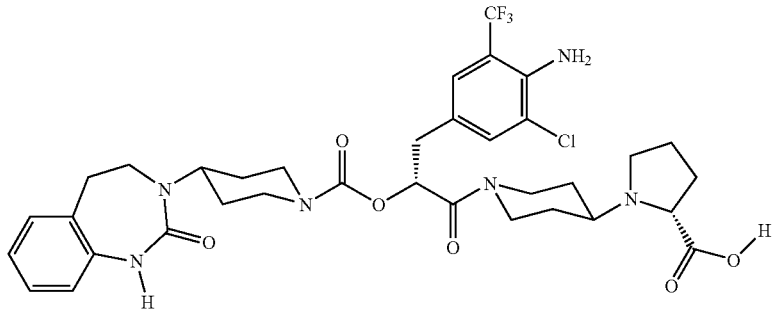

Prepared analogously to Example 6.1 from 60 mg (0.08 mmol) (R)-1-(4-amino-3-chloro-5-trifluoromethyl-benzyl)-2-[4-((R)-2-ethoxycarbonyl-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate and 2.9 mg (0.12 mmol) LiOH.

Yield: 42 mg (73% of theory)
ESI-MS: (M+H)⁺=735/737 (Cl)
Retention time (HPLC): 3.3 min (Method B)

EXAMPLE 9.2

(R)-1-(4-amino-3-chloro-5-trifluoromethyl-benzyl)-
2-[4-((R)-2-dimethylcarbamoylmethoxycarbonyl-
pyrrolidin-1-yl)-piperidin-1-yl]-2-oxo-ethyl 4-(2-
oxo-1,2,4,5-tetrahydro-1,3-benzodiazepin-3-yl)-
piperidine-1-carboxylate

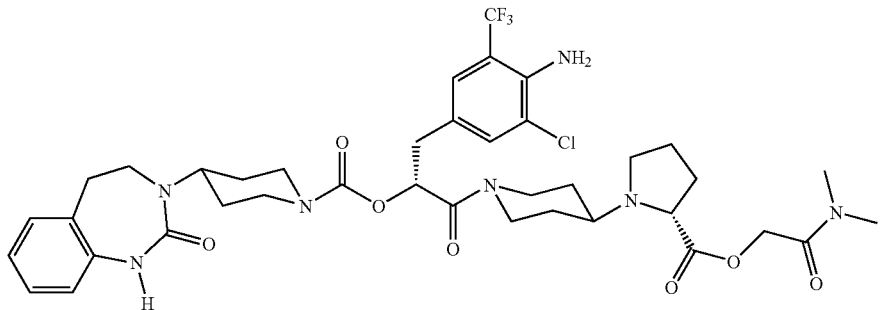

25 mg (0.08 mmol) TBTU and 11 μL (0.08 mmol) triethylamine were added to a solution of 50 mg (0.07 mmol) (R)-1-(4-amino-3-chloro-5-trifluoromethyl-benzyl)-2-[4-((R)-2-carboxy-pyrrolidin-1-yl)-piperid in-1-yl]-2-oxo-ethyl 4-(2-oxo-1,2,4,5-tetrahydro-1,3-benzodiazepin-3-yl)-piperidine-1-carboxylate in 1 mL DMF and stirred for 10 min at RT. 8.1 mg (0.08 mmol) 2-hydroxy-N,N-dimethyl-acetamide were added to the reaction mixture and this was shaken overnight at RT. After filtration through a syringe filter the reaction solution was purified by HPLC without further working up. The fractions containing the product were combined and freeze-dried.

Yield: 38 mg (68% of theory)
ESI-MS: (M+H)⁺=820/822 (Cl)
Retention time (HPLC): 2.9 min (Method A)

EXAMPLE 9.3

(R)-1-(4-amino-3-chloro-5-trifluoromethyl-benzyl)-2-{4-[(R)-2-(2-morpholin-4-yl-ethoxycarbonyl)-pyrrolidin-1-yl]-piperidin-1-yl}-2-oxo-ethyl 4-(2-oxo-1,2,4,5-tetrahydro-1,3-benzodiazepin-3-yl)-piperidine-1-carboxylate

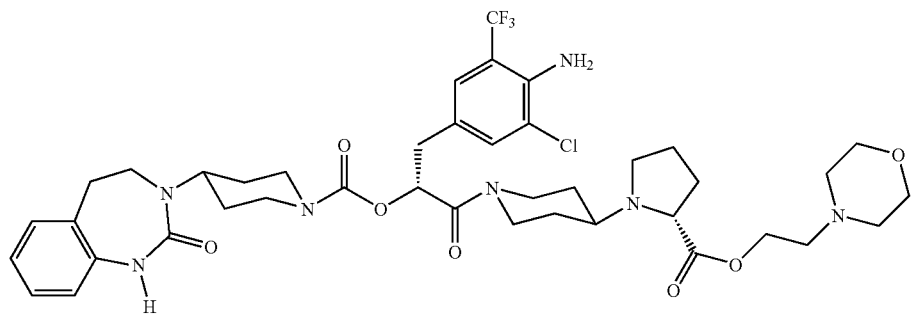

Prepared analogously to Example 9.2 from 50 mg (0.07 mmol) (R)-1-(4-amino-3-chloro-5-trifluoromethyl-benzyl)-2-[4-((R)-2-carboxy-pyrrolidin-1-yl) -piperidin-1-yl]-2-oxo-ethyl 4-(2-oxo-1,2,4,5-tetrahydro-1,3-benzodiazepin-3-yl)-piperidine-1-carboxylate and 10.3 mg (0.08 mmol) 2-morpholin-4-yl-ethanol.

Yield: 35 mg (61% of theory)
ESI-MS: $(M+H)^+$=848/850 (Cl)
Retention time (HPLC): 2.6 min (Method A)

EXAMPLE 10

(R)-1-(4-amino-3-chloro-5-trifluoromethyl-benzyl)-2-[4-((S)-2-methoxycarbonyl-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate

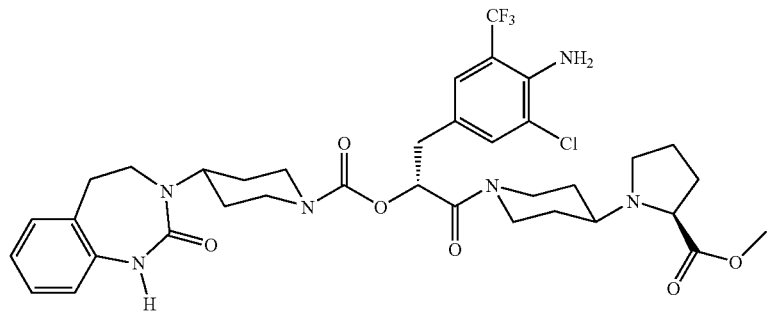

Prepared analogously to Example 9 from 100 mg (0.18 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate and 42 mg (0.20 mmol) methyl(S)-1-piperidin-4-yl-pyrrolidine-2-carboxylate.

Yield: 80 mg (59% of theory)
ESI-MS: $(M+H)^+$=749/751 (Cl)
Retention time (HPLC): 3.3 min (Method B)

EXAMPLE 10.1

(R)-1-(4-amino-3-chloro-5-trifluoromethyl-benzyl)-
2-[4-((S)-2-carboxy-pyrrolidin-1-yl)-piperidin-1-yl]-
2-oxo-ethyl 4-(2-oxo-1,2,4,5-tetrahydro-1,3-benzo-
diazepin-3-yl)-piperidine-1-carboxylate

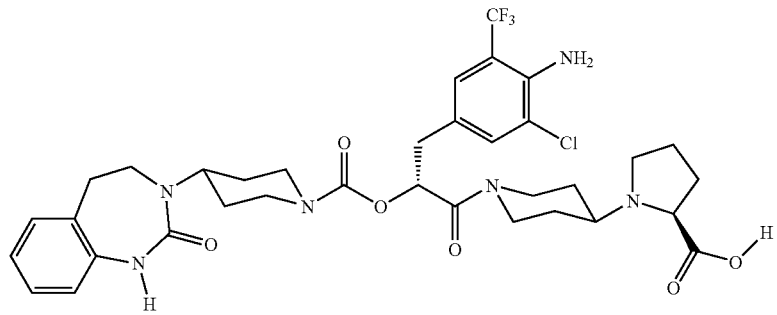

A solution of 2.9 mg (0.12 mmol) LiOH in 1 mL water was added to a solution of 60 mg (0.08 mmol) (R)-1-(4-amino-3-chloro-5-trifluoromethyl-benzyl)-2-[4-((S)-2-methoxycarbonyl-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate in 3 mL THF and the reaction mixture was stirred overnight at RT. The solvent was eliminated in the nitrogen stream, the residue was taken up in 1 mL water, formic acid was added until an acidic reaction was obtained and the mixture was exhaustively extracted with EtOAc. The combined organic extracts were dried over $Na_2SO_4$, filtered and evaporated down i. vac. The residue was taken up in a little water and acetonitrile and freeze-dried.

Yield: 51 mg (87% of theory)
ESI-MS: $(M+H)^+$=735/737 (Cl)
Retention time (HPLC): 3.3 min (Method B)

EXAMPLE 10.2

(R)-1-(4-amino-3-chloro-5-trifluoromethyl-benzyl)-
2-[4-((S)-2-dimethylcarbamoylmethoxycarbonyl-
pyrrolidin-1-yl)-piperid in-1-yl]-2-oxo-ethyl 4-(2-
oxo-1,2,4,5-tetrahydro-1,3-benzodiazepin-3-yl)-
piperidine-1-carboxylate

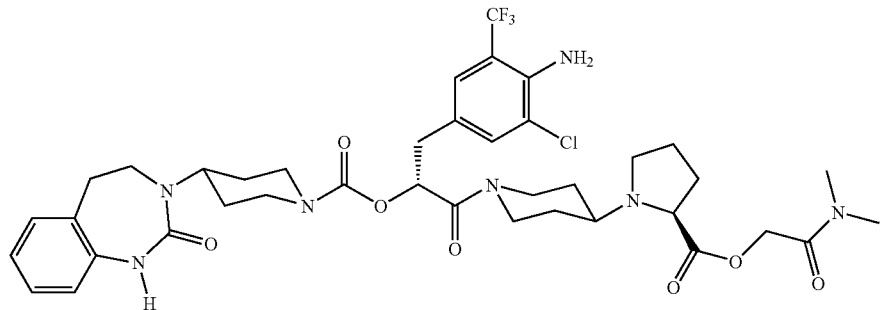

Prepared analogously to Example 9.2 from 70 mg (0.10 mmol) (R)-1-(4-amino-3-chloro-5-trifluoromethyl-benzyl)-2-[4-((S)-2-carboxy-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate and 11 mg (0.11 mmol) 2-hydroxy-N,N-dimethyl-acetamide.

Yield: 45 mg (58% of theory)
ESI-MS: $(M+H)^+$=820/822 (Cl)
Retention time (HPLC): 3.0 min (Method A)

EXAMPLE 10.3

(R)-1-(4-amino-3-chloro-5-trifluoromethyl-benzyl)-2-{4-[(S)-2-(2-morpholin-4-yl-ethoxycarbonyl)-pyrrolidin-1-yl]-piperidin-1-yl}-2-oxo-ethyl 4-(2-oxo-1,2,4,5-tetrahydro-1,3-benzodiazepin-3-yl)-piperidine-1-carboxylate

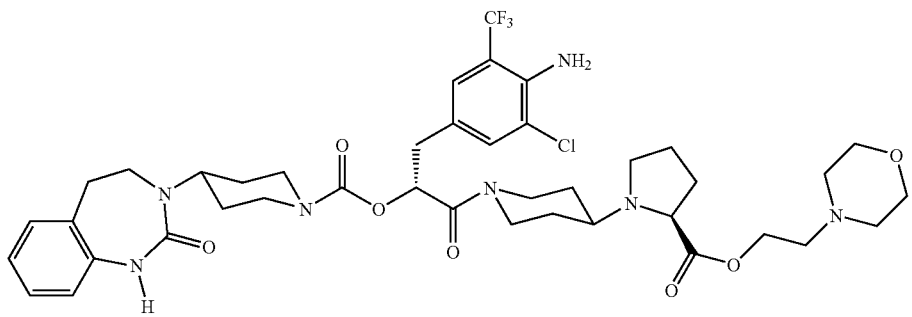

Prepared analogously to Example 9.2 from 70 mg (0.10 mmol) (R)-1-(4-amino-3-chloro-5-trifluoromethyl-benzyl)-2-[4-((S)-2-carboxy-pyrrolidin-1-yl)-piperidin-1-yl]-2-oxo-ethyl 4-(2-oxo-1,2,4,5-tetrahydro-1,3-benzodiazepin-3-yl)-piperidine-1-carboxylate and 13.2 mg (0.11 mmol) 2-morpholin-4-yl-ethanol.

Yield: 54 mg (59% of theory)
ESI-MS: $(M+H)^+=848/850$ (Cl)
Retention time (HPLC): 2.6 min (Method A)

EXAMPLE 11

Methyl(R)-1'-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-2-carboxylate

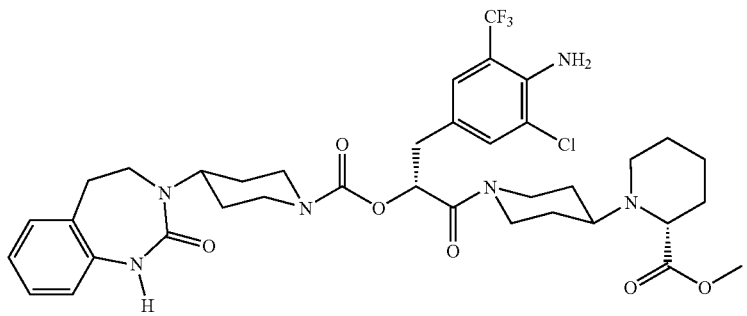

64 mg (0.20 mmol) TBTU and 56 μL (0.40 mmol) triethylamine were added to a solution of 100 mg (0.18 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate in 1 mL DMF and stirred for 10 min at RT. 57 mg (0.20 mmol) methyl (R)-[1,4']bipiperidinyl-2-carboxylate (used as the acetate salt) were added to the reaction mixture and this was shaken overnight at RT. After filtration through a syringe filter the reaction solution was purified by HPLC without further working up. The fractions containing the product were combined and freeze-dried.

Yield: 59 mg (43% of theory)
ESI-MS: $(M+H)^+=763/765$ (Cl)
$R_f=0.50$ (silica gel, DCM/MeOH/NH$_3$ 90:10:1)

EXAMPLE 11.1

(R)-1'-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-2-carboxylic acid

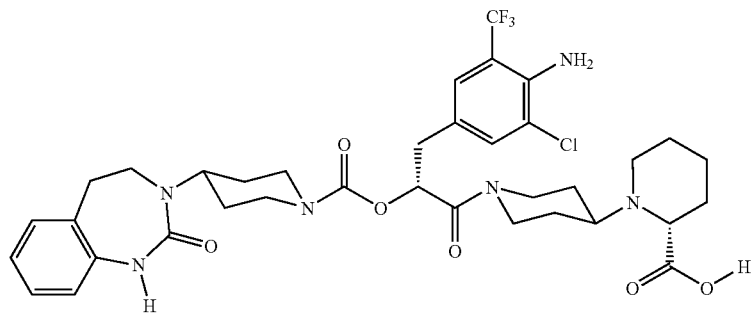

Prepared analogously to Example 6.1 from 40 mg (0.05 mmol) methyl(R)-1'-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-2-carboxylate and 1.9 mg (0.08 mmol) LiOH.

Yield: 10 mg (25% of theory)
ESI-MS: (M−H)⁻=747/749 (Cl)
$R_f$=0.27 (silica gel, DCM/MeOH/NH$_3$ 90:10:1)

EXAMPLE 12

Methyl(S)-1'-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-2-carboxylate

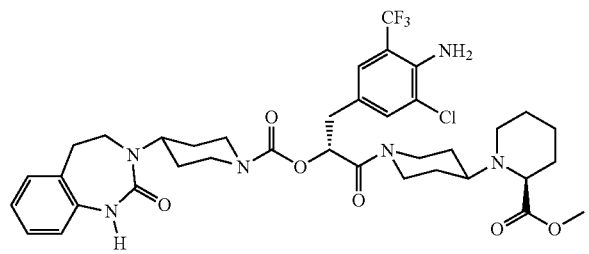

Prepared analogously to Example 11 from 100 mg (0.18 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate and 45 mg (0.20 mmol) methyl(S)-[1,4']bipiperidinyl-2-carboxylate.

Yield: 33 mg (24% of theory)
ESI-MS: (M+H)⁺=763/765 (Cl)
$R_f$=0.44 (silica gel, DCM/MeOH/NH$_3$ 90:10:1)

EXAMPLE 12.1

(S)-1'-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-2-carboxylic acid

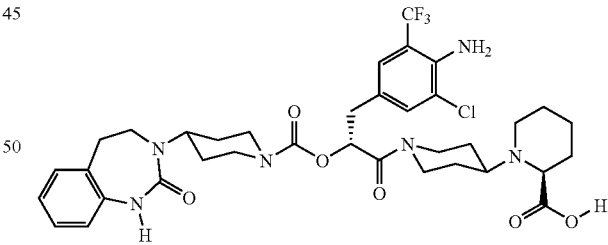

Prepared analogously to Example 6.1 from 20 mg (0.03 mmol) methyl(S)-1'-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-1,4'-bipiperidinyl-2-carboxylate and 1.2 mg (0.05 mmol) LiOH.

Yield: 3 mg (15% of theory)
ESI-MS: (M−H)⁻=747/749 (Cl)
$R_f$=0.29 (silica gel, DCM/MeOH/NH$_3$ 90:10:1)

EXAMPLE 13

(R)-1-(4-amino-3-chloro-5-trifluoromethyl-benzyl)-
2-(1'-ethoxyoxalyl-4,4'-bipiperidinyl-1-yl)-2-oxo-
ethyl 4-(2-oxo-1,2,4,5-tetrahydro-1,3-benzodiazepin-
3-yl)-piperidine-1-carboxylate

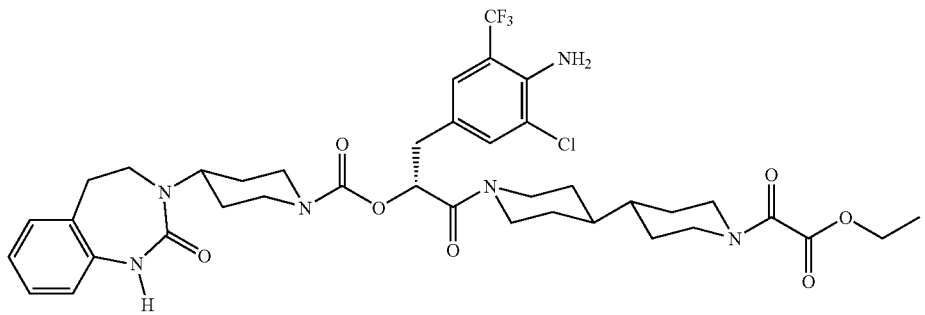

64 mg (0.20 mmol) TBTU and 70 µL (0.50 mmol) triethylamine were added to a solution of 100 mg (0.18 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate in 2 mL DMF and stirred for 10 min at RT. 54 mg (0.20 mmol) ethyl[4,4']bipiperidinyl-1-yl-oxo-acetate (Amine A4) were added to the reaction mixture and this was shaken overnight at RT. After filtration through a syringe filter the reaction solution was purified by HPLC without further working up. The fractions containing the product were combined and freeze-dried.

Yield: 88 mg (61% of theory)
ESI-MS: $(M+H)^+$=805/807 (Cl)
Retention time (HPLC): 4.5 min (Method B)

EXAMPLE 13.1

(R)-1-(4-amino-3-chloro-5-trifluoromethyl-benzyl)-
2-(1'-oxalyl-4,4'-bipiperidinyl-1-yl)-2-oxo-ethyl
4-(2-oxo-1,2,4,5-tetrahydro-1,3-benzodiazepin-3-yl)-
piperidine-1-carboxylate

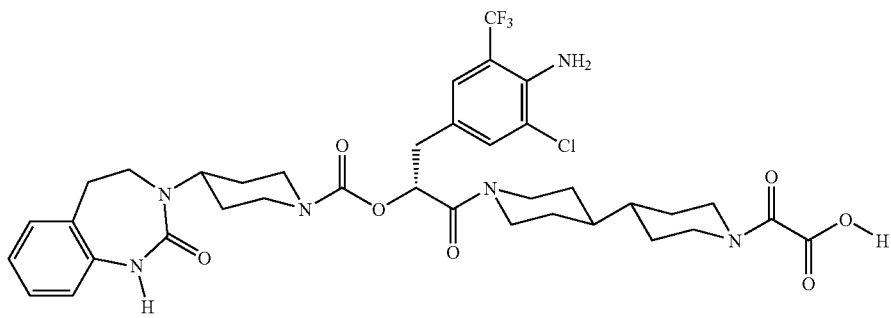

Prepared analogously to Example 6.1 from 40 mg (0.05 mmol) (R)-1-(4-amino-3-chloro-5-trifluoromethyl-benzyl)-2-(1'-ethoxyoxalyl-4,4'-bipiperidinyl-1-yl)-2-oxo-ethyl 4-(2-oxo-1,2,4,5-tetrahydro-1,3-benzodiazepin-3-yl)-piperidine-1-carboxylate and 3.6 mg (0.15 mmol) LiOH.

Yield: 26 mg (67% of theory)
ESI-MS: $(M+H)^+$=777/779 (Cl)
Retention time (HPLC): 5.0 min (Method C)

EXAMPLE 13.2

(R)-1-(4-amino-3-chloro-5-trifluoromethyl-benzyl)-2-(1'-dimethylcarbamoyl-methoxyoxalyl-4,4'-bipiperidinyl-1-yl)-2-oxo-ethyl 4-(2-oxo-1,2,4,5-tetrahydro-1,3-benzodiazepin-3-yl)-piperidine-1-carboxylate

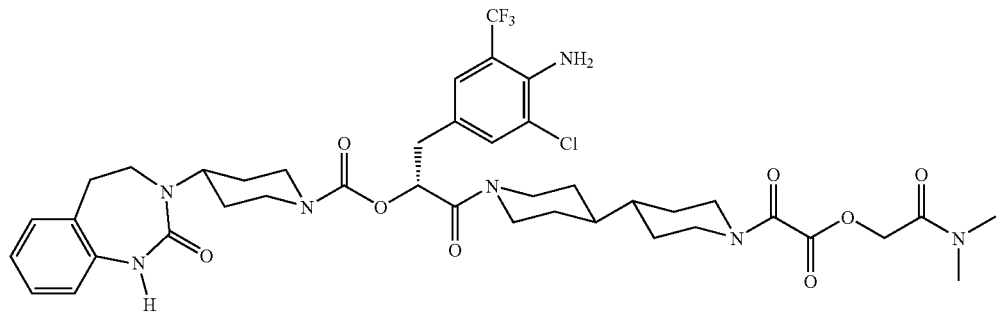

Prepared analogously to Example 7.2 from 100 mg (0.13 mmol) (R)-1-(4-amino-3-chloro-5-trifluoromethyl-benzyl)-2-(1'-oxalyl-4,4'-bipiperidinyl-1-yl)-2-oxo-ethyl 4-(2-oxo-1,2,4,5-tetrahydro-1,3-benzodiazepin-3-yl)-piperidine-1-carboxylate and 15 mg (0.15 mmol) 2-hydroxy-N,N-dimethyl-acetamide.

Yield: 70 mg (63% of theory)
ESI-MS: $(M+H)^+=862/864$ (Cl)
Retention time (HPLC): 4.1 min (Method B)

EXAMPLE 13.3

(R)-1-(4-amino-3-chloro-5-trifluoromethyl-benzyl)-2-[1'-(2-morpholin-4-yl-ethoxyoxalyl)-4,4'-bipiperidinyl-1-yl]-2-oxo-ethyl 4-(2-oxo-1,2,4,5-tetrahydro-1,3-benzodiazepin-3-yl)-piperidine-1-carboxylate

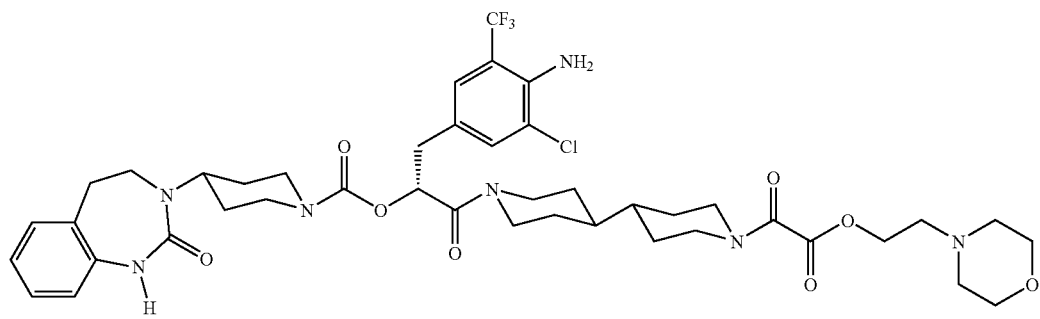

Prepared analogously to Example 9.2 from 100 mg (0.13 mmol) (R)-1-(4-amino-3-chloro-5-trifluoromethyl-benzyl)-2-(1'-oxalyl-4,4'-bipiperidinyl-1-yl)-2-oxo-ethyl 4-(2-oxo-1,2,4,5-tetrahydro-1,3-benzodiazepin-3-yl)-piperidine-1-carboxylate and 18 µL (0.15 mmol) 2-morpholin-4-yl-ethanol.

Yield: 69 mg (60% of theory)
ESI-MS: $(M+H)^+=890/892$ (Cl)
Retention time (HPLC): 3.6 min (Method B)

EXAMPLE 14

(R)-1-(4-amino-3-chloro-5-trifluoromethyl-benzyl)-2-[1'-(3-ethoxycarbonyl-propionyl)-4,4'-bipiperidinyl-1-yl]-2-oxo-ethyl 4-(2-oxo-1,2,4,5-tetrahydro-1,3-benzodiazepin-3-yl)-piperidine-1-carboxylate

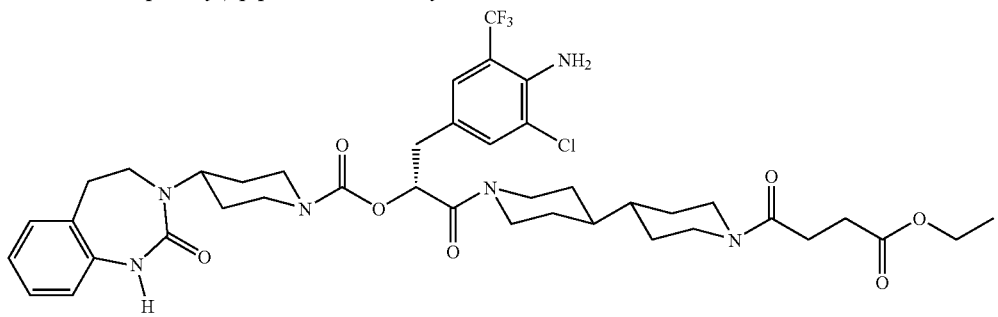

64 mg (0.20 mmol) TBTU and 28 μL (0.50 mmol) triethylamine were added to a solution of 100 mg (0.18 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate in 1 mL DMF and stirred for 10 min at RT. 59 mg (0.20 mmol) ethyl 4-[4,4']bipiperidinyl-1-yl-4-oxo-butyrate (Amine A5) were added to the reaction mixture and this was shaken overnight at RT. After filtration through a syringe filter the reaction solution was purified by HPLC without further working up. The fractions containing the product were combined and freeze-dried.

Yield: 61 mg (41% of theory)
ESI-MS: (M+H)$^+$=833/835 (Cl)
$R_f$=0.61 (silica gel, DCM/MeOH/NH$_3$ 90:10:1)

EXAMPLE 14.1

(R)-1-(4-amino-3-chloro-5-trifluoromethyl-benzyl)-2-[1'-(3-carboxy-propionyl)-4,4'-bipiperidinyl-1-yl]-2-oxo-ethyl 4-(2-oxo-1,2,4,5-tetrahydro-1,3-benzodiazepin-3-yl)-piperidine-1-carboxylate

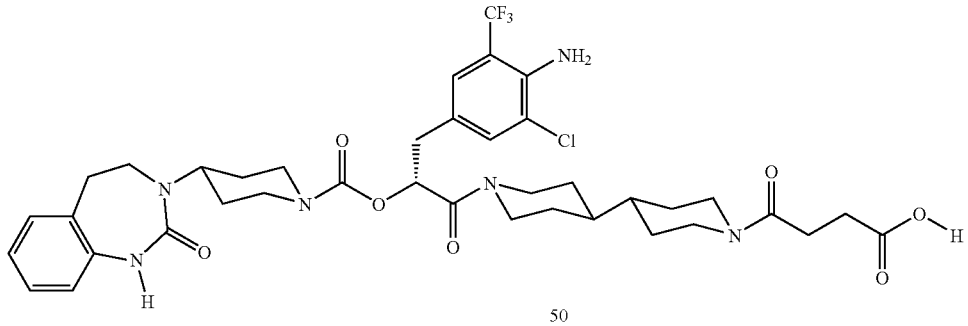

A solution of 1.9 mg (0.08 mmol) LiOH in 1 mL water was added to a solution of 40 mg (0.05 mmol) (R)-1-(4-amino-3-chloro-5-trifluoromethyl-benzyl)-2-[1'-(3-ethoxy-carbonyl-propionyl)-4,4'-bipiperidinyl-1-yl]-2-oxo-ethyl 4-(2-oxo-1,2,4,5-tetrahydro-1,3-benzodiazepin-3-yl)-piperidine-1-carboxylate in 10 mL THF and the reaction mixture was stirred overnight at RT. The solvent was eliminated in a nitrogen stream, the residue was taken up in 1 mL water, combined with formic acid until an acidic reaction was obtained and mixed with 1 mL acetonitrile and freeze-dried. The residue was taken up in 1 mL DMF and purified by HPLC. The fractions containing the product were combined and freeze-dried.

Yield: 19 mg (39% of theory)
ESI-MS: (M+H)$^+$=805/807 (Cl)
$R_f$=0.16 (silica gel, DCM/MeOH/NH$_3$ 90:10:1)

EXAMPLE 14.2

(R)-1-(4-amino-3-chloro-5-trifluoromethyl-benzyl)-2-{1'-[3-(2-morpholin-4-yl-ethoxycarbonyl)-propionyl]-4,4'-bipiperidinyl-1-yl}-2-oxo-ethyl 4-(2-oxo-1,2,4,5-tetrahydro-1,3-benzodiazepin-3-yl)-piperidine-1-carboxylate

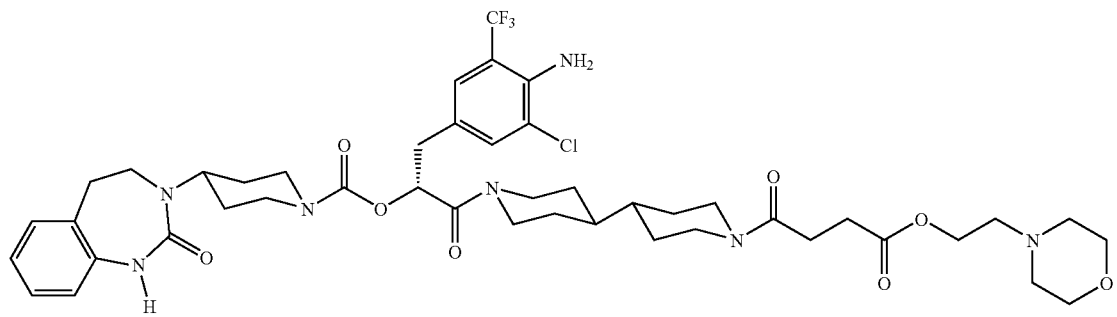

Prepared analogously to Example 9.2 from 100 mg (0.12 mmol) (R)-1-(4-amino-3-chloro-5-trifluoromethyl-benzyl)-2-[1'-(3-carboxy-propionyl)-4,4'-bipiperidinyl-1-yl]-2-oxo-ethyl 4-(2-oxo-1,2,4,5-tetrahydro-1,3-benzodiazepin-3-yl)-piperidine-1-carboxylate and 17 μL (0.14 mmol) 2-morpholin-4-yl-ethanol.

Yield: 16 mg (14% of theory)
ESI-MS: (M+H)$^{2+}$=459/460 (Cl)
Retention time (HPLC): 3.7 min (Method B)

EXAMPLE 15

(R)-1-(4-amino-3-chloro-5-trifluoromethyl-benzyl)-2-(1'-ethoxycarbonyl methyl-4,4'-bipiperidinyl-1-yl)-2-oxo-ethyl 4-(7-methoxy-2-oxo-1,2,4,5-tetrahydro-1,3-benzodiazepin-3-yl)-piperidine-1-carboxylate phenyl)-2-hydroxy-propionate in 15 mL pyridine was added dropwise and the reaction mixture was stirred for 2 h at RT. Then 1.77 g (6.42 mmol) 7-methoxy-3-piperidin-4-yl-1,3,4,5-tetrahydro-1,3-benzodiazepin-2-one was added batchwise. The suspension was stirred for 72 h at RT and then evaporated down i. vac. The residue was combined with 200 mL EtOAc, washed with 200 mL 15% K$_2$CO$_3$ solution, the organic phase was separated off and evaporated down i. vac. The residue was purified by chromatography (silica gel, gradient DCM to MeOH/NH$_3$ 95:5).

Yield: 1.80 g (46% of theory)
ESI-MS: (M+H)$^+$=613/615 (Cl)
R$_f$=0.50 (silica gel, DCM/MeOH 9:1)

15b) (R)-2-(4-amino-3-chloro-5-trifluoromethyl-phenyl)-1-carboxy-ethyl 4-(7-methoxy-2-oxo-1,2,4,5-tetrahydro-1,3-benzodiazepin-3-yl)-piperidine-1-carboxylate A solution of 0.11 g (4.50 mmol) LiOH in 50 mL water was added to a solution of 1.80 g (2.94 mmol) (R)-2-(4-amino-3-chloro-5-trifluoromethyl-phenyl)-1-ethoxycarbonyl-ethyl 4-(7-methoxy-2-oxo-1,2,4,5-tetrahydro-1,3-benzodiazepin-

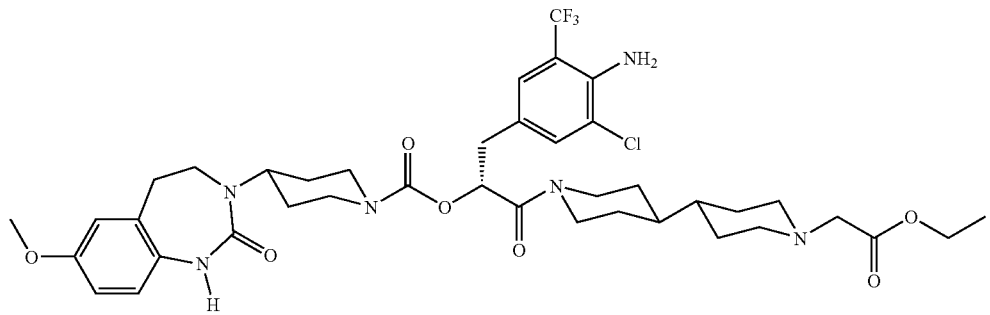

15a) (R)-2-(4-amino-3-chloro-5-trifluoromethyl-phenyl)-1-ethoxycarbonyl-ethyl 4-(7-methoxy-2-oxo-1,2,4,5-tetrahydro-1,3-benzodiazepin-3-yl)-piperidine-1-carboxylate 1.29 g (6.42 mmol) 4-nitrophenyl chloroformate were added to a solution of 0.79 g (6.42 mmol) DMAP in 50 mL pyridine and stirred for 1 h at RT. A solution of 2.00 g (6.42 mmol) ethyl(R)-3-(4-amino-3-chloro-5-trifluoromethyl- 3-yl)-piperidine-1-carboxylate in 50 mL THF and the reaction mixture was stirred for 3 h at RT. The THF was eliminated i. vac., diluted with 100 mL water and acidified with 1 M HCl. The substance precipitated was suction filtered, washed with 50 mL water and dried in the vacuum drying cupboard at 65° C.

Yield: 1.60 g (93% of theory)
ESI-MS: (M+H)$^+$=585/587 (Cl)

15c) (R)-1-(4-amino-3-chloro-5-trifluoromethyl-benzyl)-2-(1'-ethoxycarbonylmethyl-4,4'-bipiperidinyl-1-yl)-2-oxo-ethyl 4-(7-methoxy-2-oxo-1,2,4,5-tetrahydro-1,3-benzodiazepin-3-yl)-piperidine-1-carboxylate Prepared analogously to Example 9 from 100 mg (0.17 mmol) (R)-2-(4-amino-3-chloro-5-trifluoromethyl-phenyl)-1-carboxy-ethyl 4-(7-methoxy-2-oxo-1,2,4,5-tetrahydro-1,3-benzodiazepin-3-yl)-piperidine-1-carboxylate and 48 mg (0.19 mmol) ethyl[4,4']bipiperidinyl-1-yl-acetate.

Yield: 58 mg (41% of theory)
ESI-MS: (M+H)$^+$=821/823 (Cl)
Retention time (HPLC): 3.0 min (Method B)

EXAMPLE 15.1

(R)-1-(4-amino-3-chloro-5-trifluoromethyl-benzyl)-2-(1'-carboxymethyl-4,4'-bipiperidinyl-1-yl)-2-oxo-ethyl 4-(7-methoxy-2-oxo-1,2,4,5-tetrahydro-1,3-benzodiazepin-3-yl)-piperidine-1-carboxylate

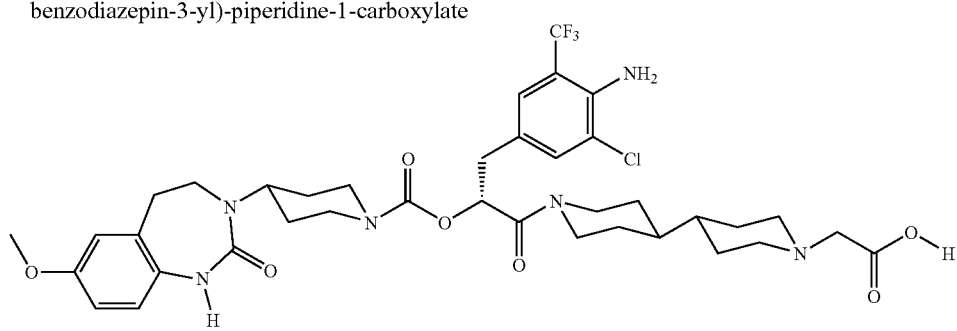

A solution of 1 mg (0.04 mmol) LiOH in 1 mL water was added to a solution of 20 mg (0.02 mmol) (R)-1-(4-amino-3-chloro-5-trifluoromethyl-benzyl)-2-(1'-ethoxycarbonylmethyl-4,4'-bipiperidinyl-1-yl)-2-oxo-ethyl 4-(7-methoxy-2-oxo-1,2,4,5-tetrahydro-1,3-benzodiazepin-3-yl)-piperidine-1-carboxylate in 1 mL THF and the reaction mixture was stirred overnight at RT. To complete the reaction a solution of 1 mg LiOH in 1 mL water was again added and the mixture was stirred for another 3 h at RT. The solvents were eliminated in a nitrogen stream, the residue was taken up in a mixture of acetonitrile and water and the product was subjected to freeze-drying.

Yield: 14 mg (72% of theory)
ESI-MS: (M+H)$^+$=793/795 (Cl)
Retention time (HPLC): 2.6 min (Method B)

EXAMPLE 15.2

(R)-1-(4-amino-3-chloro-5-trifluoromethyl-benzyl)-2-[1'-(2-morpholin-4-yl-ethoxycarbonyl-methyl)-4,4'-bipiperidinyl-1-yl]-2-oxo-ethyl 4-(7-methoxy-2-oxo-1,2,4,5-tetrahydro-1,3-benzodiazepin-3-yl)-piperidine-1-carboxylate

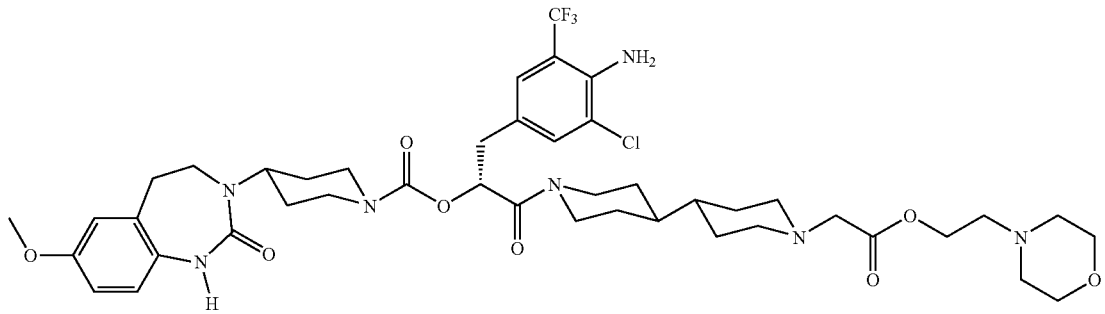

113 mg (0.35 mmol) TBTU, 84 μL (0.60 mmol) triethylamine and 39 mg (0.30 mmol) 2-morpholin-4-yl-ethanol were added to a solution of 230 mg (0.29 mmol) (R)-1-(4-amino-3-chloro-5-trifluoromethyl-benzyl)-2-(1'-carboxymethyl-4,4'-bipiperidinyl-1-yl)-2-oxo-ethyl 4-(7-methoxy-2-oxo-1,2,4,5-tetrahydro-1,3-benzodiazepin-3-yl)-piperidine-1-carboxylate in 5 mL DMF and the reaction mixture was stirred overnight at RT. The reaction solution was poured onto a saturated NaHCO$_3$ solution, the product precipitated was suction filtered and dried at 40° C. The crude product was dissolved in 25 mL dry isopropanol and precipitated with 0.5 M HCl in isopropanol as the salt. The precipitate was filtered off, washed with 5 mL isopropanol and 30 mL DIPE and dried overnight in the vacuum drying cupboard at 30° C.

Yield: 90 mg (34% of theory)
ESI-MS: (M+H)$^+$=906/908 (Cl)
Retention time (HPLC): 3.1 min (Method B)

EXAMPLE 16

(R)-1-(4-amino-3-chloro-5-trifluoromethyl-benzyl)-2-[4-(4-ethoxycarbonylmethyl-piperazin-1-yl)-piperidin-1-yl]-2-oxo-ethyl 4-(7-methoxy-2-oxo-1,2,4,5-tetrahydro-1,3-benzodiazepin-3-yl)-piperidine-1-carboxylate

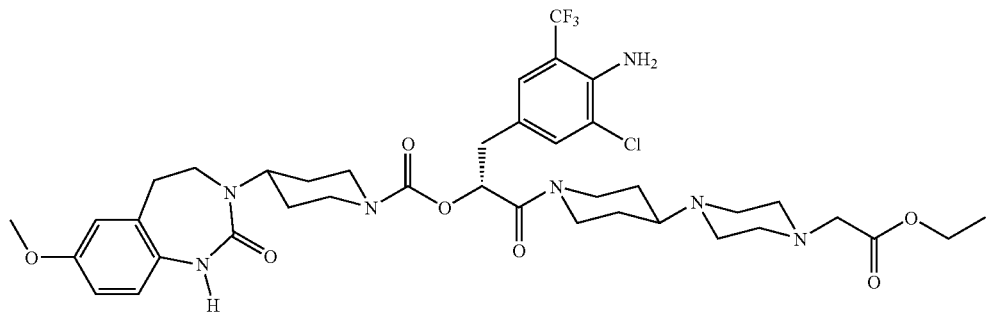

Prepared analogously to Example 9 from 100 mg (0.17 mmol) (R)-2-(4-amino-3-chloro-5-trifluoromethyl-phenyl)-1-carboxy-ethyl 4-(7-methoxy-2-oxo-1,2,4,5-tetrahydro-1,3-benzodiazepin-3-yl)-piperidine-1-carboxylate and 49 mg (0.19 mmol) ethyl(4-piperidin-4-yl-piperazin-1-yl)-acetate.

Yield: 62 mg (44% of theory)
ESI-MS: (M+H)$^+$=822/824 (Cl)
Retention time (HPLC): 2.9 min (Method B)

EXAMPLE 16.1

(R)-1-(4-amino-3-chloro-5-trifluoromethyl-benzyl)-2-[4-(4-carboxymethyl-piperazin-1-yl)-piperidin-1-yl]-2-oxo-ethyl 4-(7-methoxy-2-oxo-1,2,4,5-tetrahydro-1,3-benzodiazepin-3-yl)-piperidine-1-carboxylate

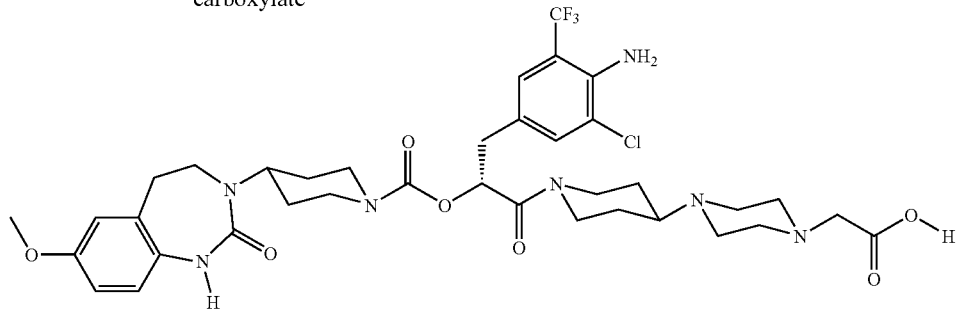

Prepared analogously to Example 15.1 from 20 mg (0.02 mmol) (R)-1-(4-amino-3-chloro-5-trifluoromethyl-benzyl)-2-[4-(4-ethoxycarbonylmethyl-piperazin-1-yl)-piperidin-1-yl]-2-oxo-ethyl 4-(7-methoxy-2-oxo-1,2,4,5-tetrahydro-1,3-benzodiazepin-3-yl)-piperidine-1-carboxylate and 2 mg (0.08 mmol) LiOH.

Yield: 19 mg (99% of theory)
ESI-MS: (M+H)$^+$=794/796 (Cl)
Retention time (HPLC): 2.6 min (Method B)

EXAMPLE 17

(R)-1-(4-amino-3-chloro-5-methyl-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate

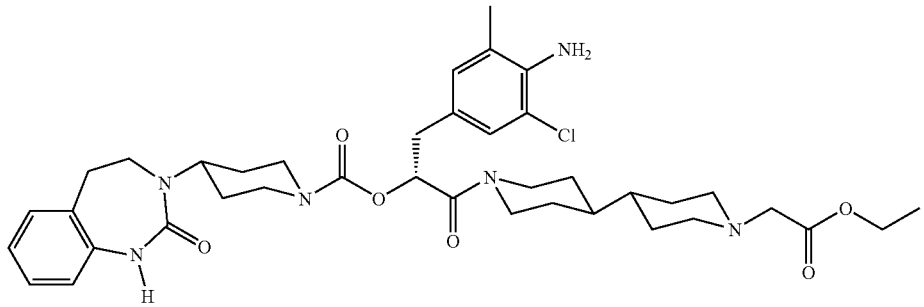

17a) methyl(Z,E)-2-acetylamino-3-(4-amino-3-chloro-5-methyl-phenyl)-acrylate Under a nitrogen atmosphere 15.4 g (49.1 mmol) tri-o-tolyl-phosphane and 11.0 g (49.0 mmol) Pd(OAc)$_2$ were added to a mixture of 72.8 g (330 mmol) 4-bromo-2-chloro-6-methyl-phenylamine and 58.0 g (397 mmol) methyl 2-acetylamino-acrylate in 970 mL triethylamine and 1.2 L acetonitrile and the reaction mixture was stirred for 18 h at 80° C. After cooling the reaction solution was filtered, evaporated down i. vac., the residue was stirred with 350 mL water and 350 mL EtOAc. The solvents were decanted off, the residue was again stirred with 300 mL EtOAc, suction filtered, washed with a little EtOAc and MTBE and dried at 60° C.

Yield: 40.6 g (44% of theory)
ESI-MS: (M+H)$^+$=283/285 (CI)
$R_f$=0.47 (silica gel, DCM/Cyc/MeOH/NH$_3$ 70:15:15:2)

17b) 3-(4-amino-3-chloro-5-methyl-phenyl)-2-oxo-propionic acid

Under a nitrogen atmosphere a solution of 28.0 g (99.0 mmol) methyl(Z,E)-2-acetylamino-3-(4-amino-3-chloro-5-methyl-phenyl)-acrylate in 250 mL 1,4-dioxane and 125 mL HCl (4 M) was stirred for 6 h at 80° C. The solvents were eliminated i. vac., the residue was triturated with isopropanol and DIPE, the precipitate was removed by suction filtering and dried at 60° C. The product was obtained as the hydrochloride salt, which was reacted further without purification.

Yield: 26.0 g (99% of theory)
ESI-MS: (M−H)$^−$=226/228 (CI)
$R_f$=0.15 (silica gel, DCM/Cyc/MeOH/NH$_3$ 70:15:15:2)

17c) methyl(R)-3-(4-amino-3-chloro-5-methyl-phenyl)-2-hydroxy-propionate

Under a nitrogen atmosphere a solution of 27.0 g (84.2 mmol) (1R)-B -chlorodiisopinocampheylborane in 75 mL THF was added dropwise within 15 min to a solution of 13.0 g (49.2 mmol) 3-(4-amino-3-chloro-5-methyl -phenyl)-2-oxo-propionic acid and 17.0 mL (122.3 mmol) triethylamine in 175 mL THF cooled to about −30° C. After the addition had ended the cooling bath was removed and the reaction mixture was stirred overnight at RT. 150 mL 1 M NaOH were added dropwise to the reaction mixture while cooling with ice. 200 mL of EtOAc were added, the mixture was stirred for another 15 min, the aqueous phase was separated off and the organic phase was washed twice with 50 mL of 1 M NaOH, once with 40 mL water and acidified with 4 M HCl. The organic phase was separated off, dried over MgSO$_4$ and evaporated down i. vac. The residue was combined with 250 mL methanolic HCl (1.25 M) and stirred overnight at RT. The reaction mixture was evaporated down i. vac., the residue was dissolved in a little PE and EtOAc, placed on silica gel and eluted with PE/EtOAc (2:1). The fractions containing the product were combined and evaporated down.

Yield: 6.0 g (50% of theory)
ESI-MS: (M+H)$^+$=244/246 (CI)
$R_f$=0.74 (silica gel, DCM/Cyc/MeOH/NH$_3$ 70:15:15:2)

17d) (R)-2-(4-amino-3-chloro-5-methyl-phenyl)-1-carboxy -ethyl 4-(2-oxo-1,2,4,5-tetrahydro-1,3-benzodiazepin-3-yl)-piperidine-1-carboxylate Prepared analogously to Example 1e from 6.0 g (24.6 mmol) methyl(R)-3-(4-amino-3-chloro-5-methyl-phenyl)-2-hydroxy-propionate and 6.1 g (24.9 mmol) 3-piperidin-4-yl-1,3,4,5-tetrahydro-1,3-benzodiazepin-2-one.

The crude methyl ester product was dissolved in 100 mL THF and combined with a solution of 1.0 g (40.9 mmol) LiOH in 50 mL water. The reaction mixture was stirred for 15 h at RT, diluted with water and the organic solvent was eliminated i. vac. The aqueous phase was washed with 60 mL EtOAc, acidified with 21 mL of 4 M HCl and stirred for 15 min at RT. The mixture was extracted three times with 150 mL of DCM and the combined organic phases were dried over MgSO$_4$. After elimination of the desiccant and solvent the residue was purified by chromatography (silica gel, gradient DCM to DCM/MeOH/NH$_3$ 70:27:3).

Yield: 0.88 g (7% of theory)
ESI-MS: (M+H)$^+$=501/503 (CI)
$R_f$=0.17 (silica gel, DCM/Cyc/MeOH/NH$_3$ 70:15:15:2)

17e) (R)-1-(4-amino-3-chloro-5-methyl-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate Prepared analogously to Example 5 from 100 mg (0.20 mmol) (R)-2-(4-amino-3-chloro-5-methyl-phenyl)-1-carboxy-ethyl 4-(2-oxo-1,2,4,5-tetrahydro-1,3-benzodiazepin-3-yl)-piperidine-1-carboxylate and 56 mg (0.22 mmol) ethyl [4,4']bipiperidinyl-1-yl-acetate Yield: 19 mg (13% of theory)
ESI-MS: (M+H)$^+$=737/739 (CI)
$R_f$=0.72 (silica gel, DCM/Cyc/MeOH/NH$_3$ 70:15:15:2)

EXAMPLE 17.1

(R)-1-(4-amino-3-chloro-5-methyl-benzyl)-2-(1'-carboxymethyl-4,4'-bipiperidinyl-1-yl)-2-oxo-ethyl 4-(2-oxo-1,2,4,5-tetrahydro-1,3-benzodiazepin-3-yl)-piperidine-1-carboxylate

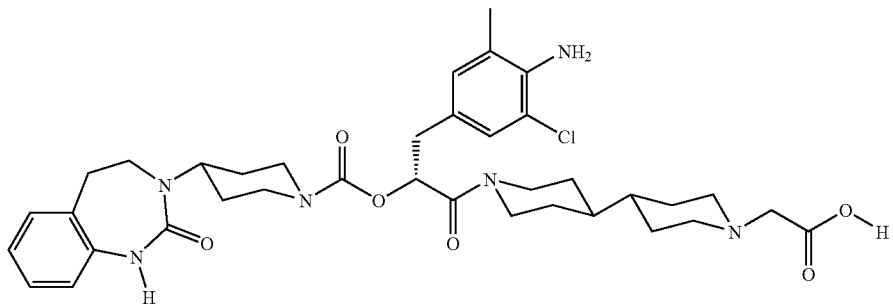

A solution of 7.0 mg (0.29 mmol) LiOH in 5 mL water was added to a solution of 80 mg (0.11 mmol) (R)-1-(4-amino-3-chloro-5-methyl-benzyl)-2-(1'-ethoxycarbonyl-methyl-4,4'-bipiperidinyl-1-yl)-2-oxo-ethyl 4-(2-oxo-1,2,4,5-tetrahydro-1,3-benzodiazepin-3-yl)-piperidine-1-carboxylate in 10 mL THF and the reaction mixture was stirred overnight at RT. The THF was eliminated i. vac., the aqueous residue was combined with 0.35 mL of 1 M HCl and evaporated down i. vac. The residue was purified by HPLC. The fractions containing the product were combined and freeze-dried.

Yield: 8 mg (10% of theory)
ESI-MS: (M+H)$^+$=709/711 (Cl)
$R_f$=0.21 (silica gel, DCM/Cyc/MeOH/NH$_3$ 70:15:15:2)

EXAMPLE 18

(R)-1-(3-chloro-4-hydroxy-5-methyl-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate

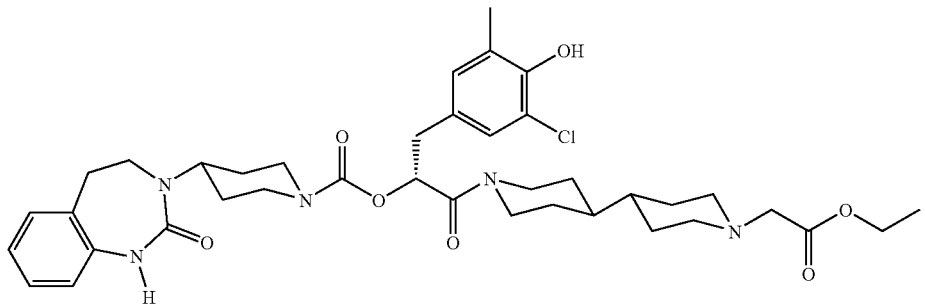

18a)
2-benzyloxy-5-bromo-1-chloro-3-methyl-benzene 7.0 mL (57.7 mmol) benzyl bromide were added to a suspension of 10.2 g (46.1 mmol) 4-bromo-2-chloro-6-methyl-phenol and 30.0 g (217 mmol) K$_2$CO$_3$ in 130 mL DMF and the reaction mixture was stirred overnight at RT. The insoluble constituents were filtered off, the filtrate was evaporated down i. vac., combined with water and extracted exhaustively with EtOAc. The combined organic phases were dried over Na$_2$SO$_4$, filtered and evaporated down. The product was reacted further without purification.

Yield: 14.0 g (98% of theory)
$R_f$=0.91 (silica gel, DCM/Cyc/MeOH/NH$_3$ 70:15:15:2)

18b) methyl(Z,E)-2-acetylamino-3-(4-benzyloxy-3-chloro-5-methyl-phenyl)-acrylate Under a nitrogen atmosphere 4.4 g (14.0 mmol) tri-o-tolyl-phosphane and 3.2 g (14.3 mmol) Pd(OAc)$_2$ were added to a mixture of 28.0 g (89.9 mmol) of 2-benzyl-oxy-5-bromo-1-chloro-3-methyl-benzene and 15.0 g (103 mmol) methyl 2-acetylamino-acrylate in 260 mL of triethylamine and 400 mL acetonitrile and the reaction mixture was stirred for 18 h at 80° C. After cooling the reaction solution was evaporated down i. vac., the residue was stirred with 100 mL water, 50 mL EtOAc and 50 mL PE and filtered to remove the insoluble components. The residue was taken up in DCM/MeOH (5:1), combined with activated charcoal, filtered and evaporated down i. vac. The crude product was reacted further without purification.

Yield: 12.5 g (37% of theory)
ESI-MS: (M+H)$^+$=374/376 (Cl)
$R_f$=0.67 (silica gel, DCM/Cyc/MeOH/NH$_3$ 70:15:15:2)

18c) 3-(4-benzyloxy-3-chloro-5-methyl-phenyl)-2-oxo-propionic acid 75 mL 4 M HCl were added to a solution of 18.4 g (49.2 mmol) methyl(Z,E)-2-acetylamino-3-(4-benzyloxy-3-chloro-5-methylphenyl)-acrylate in 150 mL 1,4-dioxane and the reaction mixture was refluxed overnight. The 1,4-dioxane was eliminated i. vac., the precipitated product was filtered off, dissolved again in DIPE and dried over MgSO$_4$. After elimination of the desiccant and solvent the residue was reacted further without purification.

Yield: 15.5 g (99% of theory)
ESI-MS: (M–H)$^-$=317/319 (CI)
R$_f$=0.20 (silica gel, DCM/Cyc/MeOH/NH$_3$ 70:15:15:2)

18d) methyl(R)-3-(4-benzyloxy-3-chloro-5-methyl-phenyl)-2-hydroxy-propionate

Under a nitrogen atmosphere a solution of 27.6 g (86.0 mmol) (1R)-B -chlorodiisopinocampheylborane in 100 mL THF was added dropwise within 15 min to a solution of 15.5 g (48.6 mmol) 3-(4-benzyloxy-3-chloro-5-methyl-phenyl)-2-oxo-propionic acid and 9.2 mL (66.2 mmol) triethylamine in 200 mL THF cooled to about –30° C. After the addition had ended the cooling bath was remover and the reaction mixture was stirred overnight at RT. 240 mL of 1 M NaOH were added dropwise to the reaction mixture while cooling with ice. 400 mL EtOAc were added, the mixture was stirred for 15 min, the aqueous phase was separated off and the organic phase was washed twice with 100 mL of 1 M NaOH and once with 100 mL water. The combined aqueous phases were acidified with semi-concentrated HCl, extracted twice with 150 mL of EtOAc and the combined organic phases were dried over MgSO$_4$. After elimination of the desiccant and solvent the oily residue was combined with 150 mL methanolic HCl (1.25 M) and the reaction mixture was stirred overnight at RT. It was evaporated down i. vac., the residue was combined with 70 mL of 15% K$_2$CO$_3$ solution and extracted twice with 50 mL of EtOAc. The combined organic phases were dried over MgSO$_4$, filtered and evaporated down i. vac. The product was reacted further without purification.

Yield: 7.0 g (43% of theory)
ESI-MS: (M+NH$_4$)$^+$=352/354 (CI)
R$_f$=0.87 (silica gel, DCM/Cyc/MeOH/NH$_3$ 70:15:15:2)

18e) (R)-2-(4-benzyloxy-3-chloro-5-methyl-phenyl)-1-carboxy-ethyl 4-(2-oxo-1,2,45-tetrahydro-1,3-benzodiazepin-3-yl)-piperidine-1-carboxylate Prepared analogously to Example 1e from 7.0 g (20.9 mmol) methyl(R)-3-(4-benzyloxy-3-chloro-5-methyl-phenyl)-2-hydroxy-propionate and 5.2 g (21.2 mmol) 3-piperidin-4-yl-1,3,4,5-tetrahydro-1,3-benzodiazepin-2-one. The crude methyl ester product was dissolved in 150 mL of THF and combined with a solution of 0.5 g (20.7 mmol) of LiOH in 50 mL water. The reaction mixture was stirred overnight at RT, diluted with water and the organic solvent was eliminated i. vac. The aqueous phase was washed twice with 60 mL EtOAc, acidified with 21 mL of 4 M HCl and the oil thus formed was exhaustively extracted with EtOAc. The combined organic phases were dried over MgSO$_4$, filtered and the solvent was evaporated down i. vac. The residue was triturated with DIPE and suction filtered.

Yield: 3.3 g (26% of theory)
ESI-MS: (M+H)$^+$=592/594 (CI)
R$_f$=0.35 (silica gel, DCM/Cyc/MeOH/NH$_3$ 70:15:15:2)

18f) (R)-1-carboxy-2-(3-chloro-4-hydroxy-5-methyl -phenyl)-ethyl 4-(2-oxo-1,2,45-tetrahydro-1,3-benzodiazepin-3-yl)-piperidine-1-carboxylate A suspension of 2.75 g (4.65 mmol) (R)-2-(4-benzyloxy-3-chloro -5-methyl-phenyl)-1-carboxy-ethyl 4-(2-oxo-1,2,4, 5-tetrahydro-1,3-benzodiazepin-3-yl)-piperidine-1-carboxylate and 1.0 g rhodium on aluminium oxide in 150 mL MeOH was hydrogenated for 18 h at 40° C. and 50 psi hydrogen pressure. To complete the reaction another 0.5 g rhodium on aluminium oxide were added and the mixture was hydrogenated for a further 6 h. The catalyst was removed by suction filtering and the filtrate was evaporated down i. vac. The residue, which was contaminated with about 50% of the corresponding methyl ester, was dissolved in 25 mL THF and combined with a solution of 250 mg (10.23 mmol) LiOH in 15 mL water and the reaction mixture was stirred for 3 h at RT. The THF was eliminated i. vac., water and 10.5 mL of 1 M HCl were added, the product precipitated was suction filtered, then this was washed with a little water and dried at 60° C.

Yield: 2.1 g (90% of theory)
ESI-MS: (M+H)$^+$=502/504 (CI)
R$_f$=0.12 (silica gel, DCM/Cyc/MeOH/NH$_3$ 70:15:15:2)

18g) (R)-1-(3-chloro-4-hydroxy-5-methyl-benzyl)-2-(1'-ethoxycarbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate Prepared analogously to Example 5 from 100 mg (0.20 mmol) (R)-1-carboxy-2-(3-chloro-4-hydroxy-5-methyl-phenyl)-ethyl and 51 mg (0.20 mmol) ethyl [4,4']bipiperidinyl-1-yl-acetate Yield: 14 mg (9% of theory)
ESI-MS: (M+H)$^+$=738/740 (CI)
Retention time (HPLC): 3.2 min (Method B)

EXAMPLE 18.1

(R)-2-(1'-carboxymethyl-4,4'-bipiperidinyl-1-yl)-1-(3-chloro-4-hydroxy-5-methyl-benzyl)-2-oxo-ethyl 4-(2-oxo-1,2,4,5-tetrahydro-1,3-benzodiazepin-3-yl)-piperidine-1-carboxylate

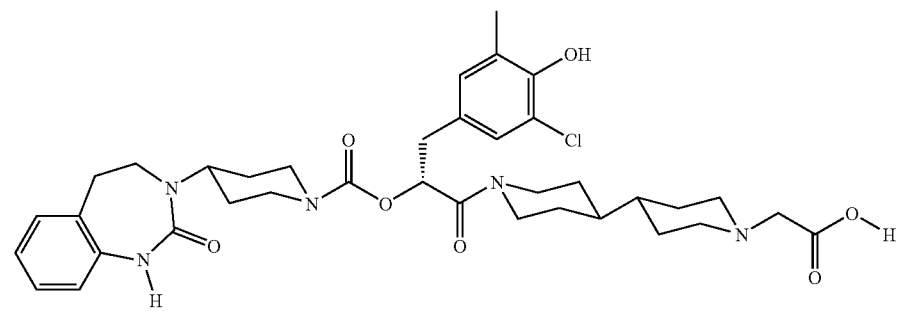

A solution of 2.0 mg (0.08 mmol) LiOH in 1 mL water was added to a solution of 38 mg (0.05 mmol) (R)-1-(3-chloro-4-hydroxy-5-methyl-benzyl)-2-(1'-ethoxy-carbonylmethyl-4,4'-bipiperidinyl-1-yl)-2-oxo-ethyl 4-(2-oxo-1,2,4,5-tetrahydro-1,3-benzodiazepin-3-yl)-piperidine-1-carboxylate in 1 mL THF and the reaction mixture was shaken for 3 h at RT. The reaction solution was acidified with 1 M HCl and purified by HPLC. The fractions containing the product were combined and freeze-dried.

Yield: 30 mg (82% of theory)
ESI-MS: $(M+H)^+=710/712$ (Cl)
$R_f=0.20$ (silica gel, DCM/Cyc/MeOH/NH$_3$ 70:15:15:2)

EXAMPLE 19

(R)-1-(4-amino-3-chloro-5-trifluoromethyl-benzyl)-2-[4-(1-ethoxycarbonylmethyl-4-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate

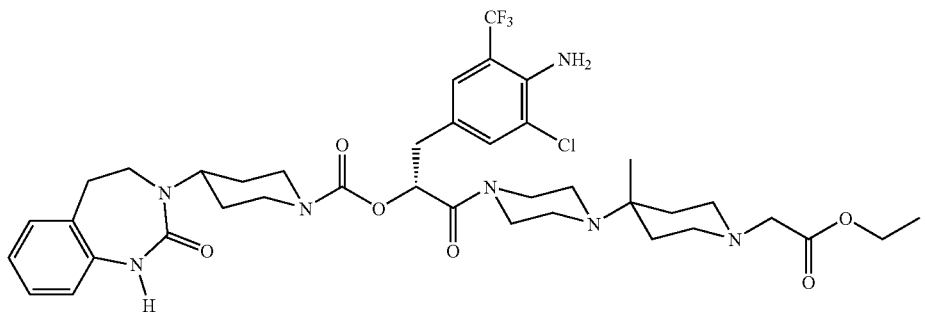

0.25 mL (1.18 mmol) triethylamine were added to a mixture of 250 mg (0.45 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate (Example 1f), 250 mg (0.50 mmol) ethyl(4-methyl-4-piperazin-1-yl-piperidin-1-yl)-acetate (Example A7f) and 160 mg (0.50 mmol) TBTU in 2 mL DMF and the reaction mixture was stirred for 4 h at RT. It was evaporated down i. vac. and the residue was purified by HPLC; the fractions containing the product were combined and lyophilised.

Yield: 225 mg (62% of theory)
ESI-MS: $(M+H)^+=806/808$ (Cl)
Retention time (HPLC): 3.2 min (method B)

EXAMPLE 19.1

(R)-1-(4-amino-3-chloro-5-trifluoromethyl-benzyl)-2-[4-(1-carboxymethyl-4-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate

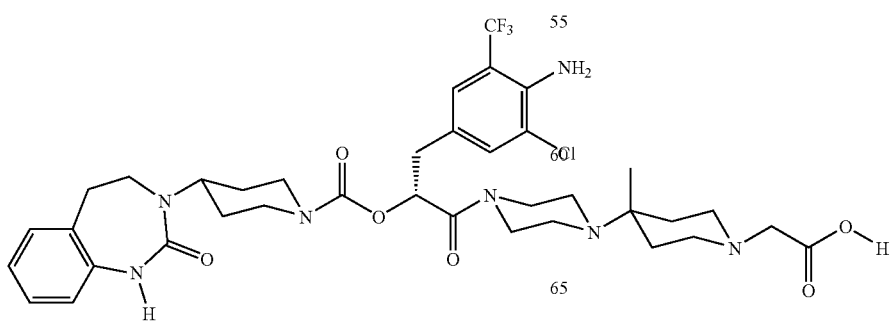

A solution of 10.0 mg (0.42 mmol) LiOH in 5 mL water was added to 100 mg (0.12 mmol) (R)-1-(4-amino-3-chloro-5-trifluoromethyl-benzyl)-2-[4-(1-ethoxy-carbonyl-methyl-4-methyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate in 10 mL THF and the reaction mixture was stirred for 3 h at RT. 0.42 mL (0.42 mmol) 1 M HCl were added and the mixture was evaporated down i. vac. The residue was taken up in a little DCM/MeOH (1:1), filtered through a little silica gel and eluted with DCM/MeOH (1:1). The filtrate was evaporated down i. vac. and dried under a high vacuum.

Yield: 95 mg (98% of theory)
ESI-MS: (M+H)$^+$=778/780 (CI)
Retention time (HPLC): 2.9 min (method B)

EXAMPLE 20

(R)-1-(4-amino-3-chloro-5-trifluoromethyl-benzyl)-2-[4-(4-ethoxycarbonylmethyl-piperazin-1-yl)-4-methyl-piperidin-1-yl]-2-oxo-ethyl 4-(2-oxo-1,2,4,5-tetrahydro-1,3-benzodiazepin-3-yl)-piperidine-1-carboxylate

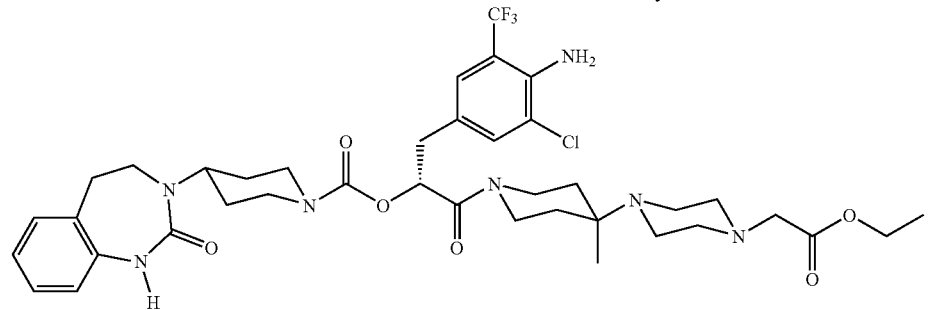

0.10 mL (0.72 mmol) triethylamine were added to a mixture of 250 mg (0.45 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate (Example 1f), 140 mg (0.49 mmol) ethyl[4-(4-methyl-piperidin-4-yl)-piperazin-1-yl]-acetate (Example A8b) and 160 mg (0.50 mmol) TBTU in 2 mL DMF and the reaction mixture was stirred for 18 h at RT. It was evaporated down i. vac. and the residue was purified by chromatography (Alox, gradient DCM/MeOH 40:1 nach 30:1). The fractions containing the product were combined, evaporated down i. vac. and purified by HPLC; the fractions containing the product were combined and lyophilised.

Yield: 178 mg (49% of theory)
ESI-MS: (M+H)$^+$=806/808 (CI)
Retention time (HPLC): 3.8 min (method B)

EXAMPLE 20.1

(R)-1-(4-amino-3-chloro-5-trifluoromethyl-benzyl)-2-[4-(4-carboxymethyl-piperazin-1-yl)-4-methyl-piperidin-1-yl]-2-oxo-ethyl 4-(2-oxo-1,2,4,5-tetrahydro-1,3-benzodiazepin-3-yl)-piperidine-1-carboxylate

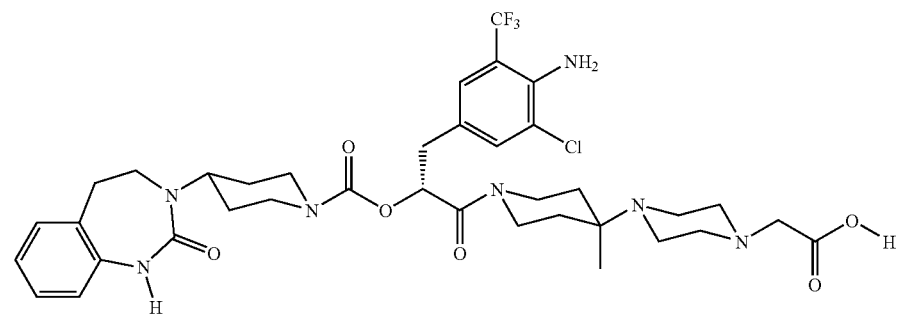

Prepared analogously to Example 19.1 from 100 mg (0.12 mmol) (R)-1-(4-amino-3-chloro-5-trifluoromethyl-benzyl)-2-[4-(4-ethoxycarbonylmethyl-piperazin-1-yl)-4-methyl-piperidin-1-yl]-2-oxo-ethyl 4-(2-oxo-1,2,4,5-tetrahydro-1,3-benzodiazepin-3-yl)-piperidine-1-carboxylate and 10.0 mg (0.42 mmol) LiOH.

Yield: 42 mg (44% of theory)
ESI-MS: (M+H)⁺=778/780 (Cl)
Retention time (HPLC): 3.3 min (method B)

EXAMPLE 21

Ethyl(S)-1-(1-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-piperidin-4-yl)-4-methyl-piperazine-2-carboxylate

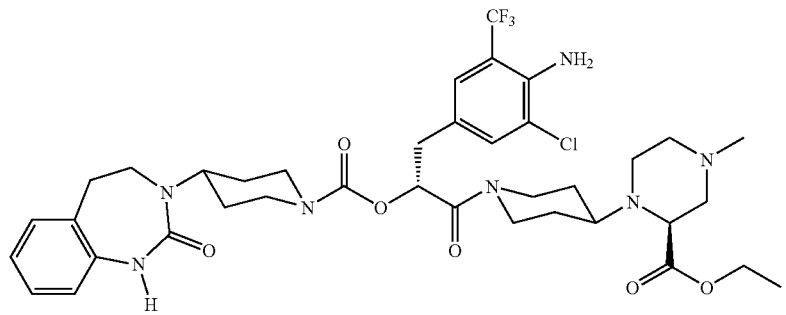

0.40 mL (2.88 mmol) triethylamine were added to a mixture of 260 mg (0.46 mmol) (R)-2-(4-amino-3-chloro-5-trifluoromethyl-phenyl)-1l-carboxy-ethyl 4-(2-oxo-1,2,4,5-tetrahydro-1,3-benzodiazepin-3-yl)-piperidine-1-carboxylate (Example 1f), 210 mg (0.58 mmol) ethyl(S)-4-methyl-1-piperidin-4-yl-piperazine-2-carboxylate (Example A9f) and 170 mg (0.53 mmol) TBTU in 2.4 mL DMF and the reaction mixture was stirred for 18 h at RT. The reaction mixture was purified by HPLC without any further working up; the fractions containing the product were combined and lyophilised.

Yield: 227 mg (61% of theory)
ESI-MS: (M+H)⁺=792/794 (Cl)
Retention time (HPLC): 3.4 min (method B)

EXAMPLE 21.1

(S)-1-(1-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-piperidin-4-yl)-4-methyl-piperazine-2-carboxylic acid

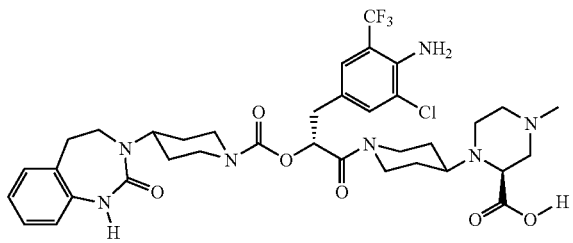

0.5 mL (1.00 mmol) 2 M LiOH solution were added to 80.0 mg (0.10 mmol) ethyl (S)-1-(1-{(R)-3-(4-amino-3-chloro-5-trifluoromethyl -phenyl)-2-[4-(2-oxo-1,2,4,5-tetrahydro-1,3-benzodiazepin-3-yl)-piperidine-1-carbonyloxy]-propionyl}-piperidin-4-yl)-4-methyl-piperazine-2-carboxylate in 1 mL THF and the reaction mixture was stirred for 20 h at RT. This was purified by HPLC without working up; the fractions containing the product were combined and lyophilised.

Yield: 50 mg (65% of theory)

ESI-MS: (M+H)⁺=764/766 (Cl)

Retention time (HPLC): 3.0 min (method B)

EXAMPLE 22

Ethyl(S)-4-{(R)-3-(4-amino-3-chloro-5-trifluoromethyl -phenyl)-2-[4-(2-oxo-1,2,4,5-tetrahydro-1,3-benzodiazepin-3-yl)-piperidine-1-carbonyloxy]-propionyl}-1-(1-methyl-piperidin-4-yl)-piperazine-2-carboxylate

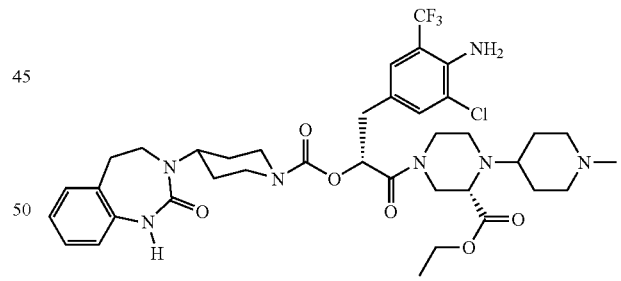

0.25 mL (2.88 mmol) triethylamine were added to a mixture of 200 mg (0.36 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate (Example 1f), 150 mg (0.58 mmol) ethyl(S)-1-(1-methyl-piperidin-4-yl)-piperazine-2-carboxylate (Example A10c) and 140 mg (0.44 mmol) TBTU in 2.0 mL DMF and the reaction mixture was stirred for 5 h at RT. This was purified by HPLC without any further working up; the fractions containing the product were combined and lyophilised.

Yield: 84 mg (29% of theory)
ESI-MS: (M+H)⁺=792/794 (Cl)
Retention time (HPLC): 3.5 min (method B)

EXAMPLE 22.1

(S)-4-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-1-(1-methyl-piperidin-4-yl)-piperazine-2-carboxylic acid

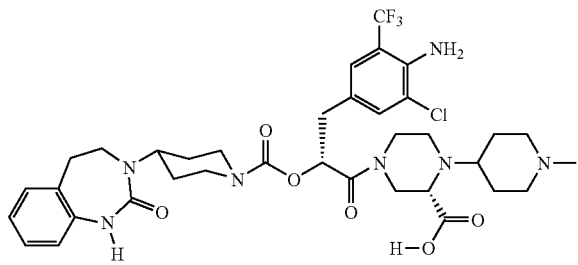

0.26 mL (0.13 mmol) 0.5 M LiOH solution were added to 50.0 mg (0.06 mmol) ethyl(S)-4-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-1-(1-methyl-piperidin-4-yl)-piperazine-2-carboxylate in 0.8 mL THF and the reaction mixture was stirred overnight at RT. To complete the reaction another 50 μL (0.1 mmol) 0.5 M LiOH solution were added, it was stirred for another 4 h at RT and then the reaction mixture was purified by HPLC without working up; the fractions containing the product were combined and lyophilised.

Yield: 22 mg (46% of theory)
ESI-MS: (M+H)$^+$=764/766 (Cl)
Retention time (HPLC): 2.9 min (method B)

EXAMPLE 23

Ethyl(S)-1-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-4-(1-methyl-piperidin-4-yl)-piperazine-2-carboxylate

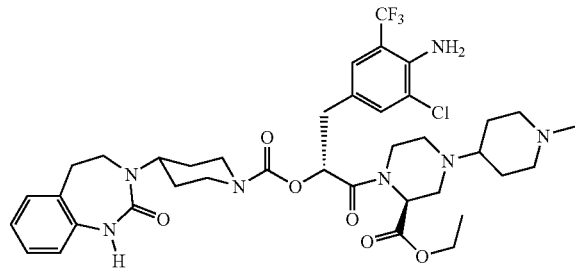

0.30 mL (2.16 mmol) triethylamine were added to a mixture of 700 mg (1.26 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate (Example 1f), 430 mg (1.41 mmol) ethyl(S)-4-(1-methyl-piperidin-4-yl)-piperazine-2-carboxylate (Example A11b) and 450 mg (1.40 mmol) TBTU in 7 mL DMF and the reaction mixture was stirred for 18 h at RT. It was evaporated down i. vac., the residue was stirred with saturated NaHCO$_3$ solution, extracted exhaustively with EtOAc and the combined organic phases were dried over Na$_2$SO$_4$. After elimination of the desiccant and solvent the residue was purified by HPLC; the fractions containing the product were combined and lyophilised.

Yield: 670 mg (67% of theory)
ESI-MS: (M+H)$^+$=792/794 (Cl)
Retention time (HPLC): 3.4 min (method B)

EXAMPLE 23.1

(S)-1-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-4-(1-methyl-piperidin-4-yl)-piperazine-2-carboxylic acid

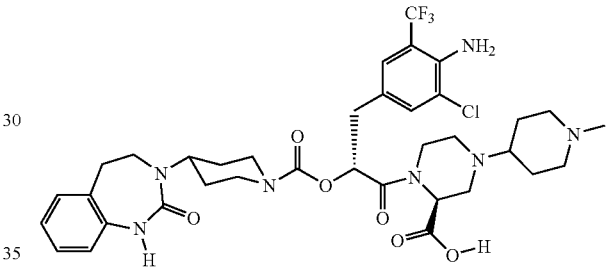

Prepared analogously to Example 22.1 from 80.0 mg (0.10 mmol) ethyl(S)-1-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-4-(1-methyl-piperidin-4-yl)-piperazine-2-carboxylate and 0.46 mL (0.23 mmol) 0.5 M LiOH solution.

Yield: 53 mg (69% of theory)
ESI-MS: (M+H)$^+$=764/766 (Cl)
Retention time (HPLC): 2.9 min (method B)

EXAMPLE 24

(R)-1-(4-amino-3-chloro-5-trifluoromethyl-benzyl)-2-[4-(8-ethoxycarbonyl methyl-8-aza-bicyclo[3.2.1]oct-3-yl)-piperazin-1-yl]-2-oxo-ethyl 4-(2-oxo-1,2,4,5-tetrahydro-1,3-benzodiazepin-3-yl)-piperidine-1-carboxylate

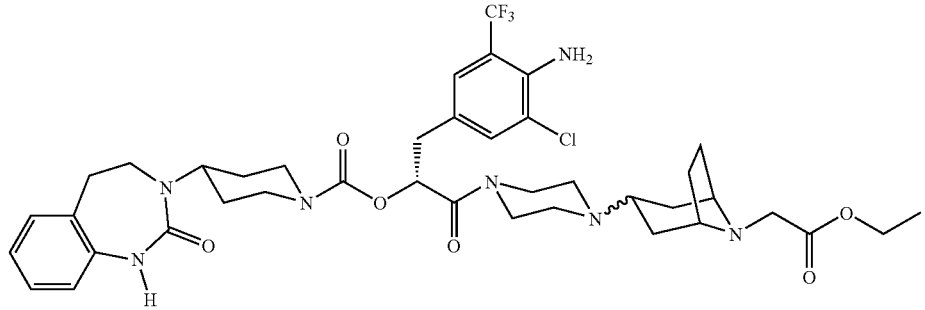

113 mg (0.40 mmol) ethyl(3-piperazin-1-yl-8-aza-bicyclo[3.2.1]oct-8-yl)-acetate (Example A12d) were added to a mixture of 200 mg (0.45 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate (Example 1f), 128 mg (0.40 mmol) TBTU and 56 μL (0.40 mmol) triethylamine in 2 mL DMF and the reaction mixture was stirred for 2 h at RT. This was purified by HPLC without any further working up; the fractions containing the product were combined and evaporated down i. vac.

Yield: 156 mg (53% of theory)
ESI-MS: (M+H)$^+$=818/820 (Cl)
Retention time (HPLC): 3.1 min (method B)

EXAMPLE 24.1

(R)-1-(4-amino-3-chloro-5-trifluoromethyl-benzyl)-2-[4-(8-carboxymethyl-8-aza-bicyclo[3.2.1]oct-3-yl)-piperazin-1-yl]-2-oxo-ethyl 4-(2-oxo-1,2,4,5-tetrahydro-1,3-benzodiazepin-3-yl)-piperidine-1-carboxylate

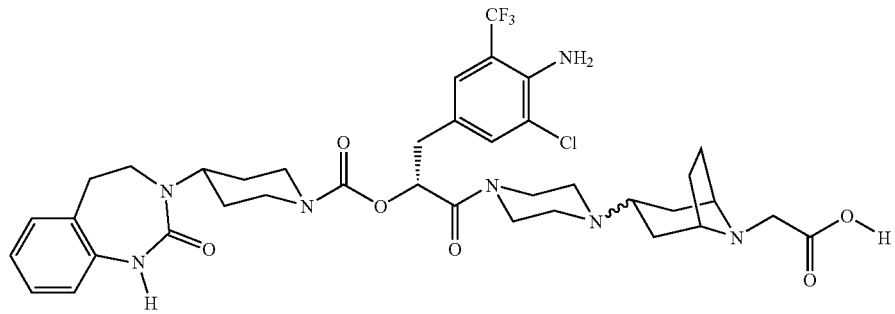

A solution of 1.92 mg (0.08 mmol) LiOH in 1 mL water was added to 40.0 mg (0.05 mmol) (R)-1-(4-amino-3-chloro-5-trifluoromethyl-benzyl)-2-[4-(8-ethoxycarbonyl-methyl-8-aza-bicyclo[3.2.1]oct-3-yl)-piperazin-1-yl]-2-oxo-ethyl 4-(2-oxo-1,2,4,5-tetrahydro-1,3-benzodiazepin-3-yl)-piperidine-1-carboxylate in 1 mL THF and the reaction mixture was shaken overnight at RT. The solvents were eliminated in a nitrogen stream and the residue was purified by HPLC; the fractions containing the product were combined and lyophilised.

Yield: 13 mg (34% of theory)
ESI-MS: (M+H)$^+$=790/792 (Cl)
Retention time (HPLC): 2.7 min (method B)

EXAMPLE 25

(R)-1-(4-amino-3-chloro-5-trifluoromethyl-benzyl)-2-(4-ethoxycarbonylmethoxy-1,4'-bipiperidinyl-1'-yl)-2-oxo-ethyl 4-(2-oxo-1,2,4,5-tetrahydro-1,3-benzodiazepin-3-yl)-piperidine-1-carboxylate

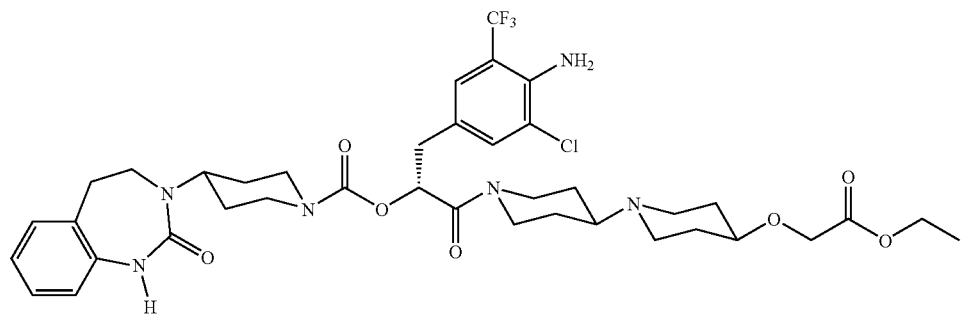

0.30 mL (2.16 mmol) triethylamine were added to a mixture of 300 mg (0.54 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate (Example 1f), 220 mg (0.64 mmol) ethyl([1,4']bipiperidinyl-4-yloxy)-acetate (Example A13c) and 200 mg (0.62 mmol) TBTU in 3 mL DMF and the reaction mixture was stirred for 4 h at RT. Ice and saturated NaHCO₃ solution were added and the precipitate was filtered off. This was taken up in DCM and a little EtOH and dried over Na₂SO₄. After elimination of the desiccant and solvent the residue was purified by HPLC; the fractions containing the product were combined and lyophilised.

Yield: 170 mg (39% of theory)
ESI-MS: (M+H)⁺=807/809 (Cl)
Retention time (HPLC): 3.7 min (method B)

EXAMPLE 25.1

(R)-1-(4-amino-3-chloro-5-trifluoromethyl-benzyl)-2-(4-carboxymethoxy-1,4'-bipiperidinyl-1'-yl)-2-oxo-ethyl 4-(2-oxo-1,2,4,5-tetrahydro-1,3-benzodiazepin-3-yl)-piperidine-1-carboxylate

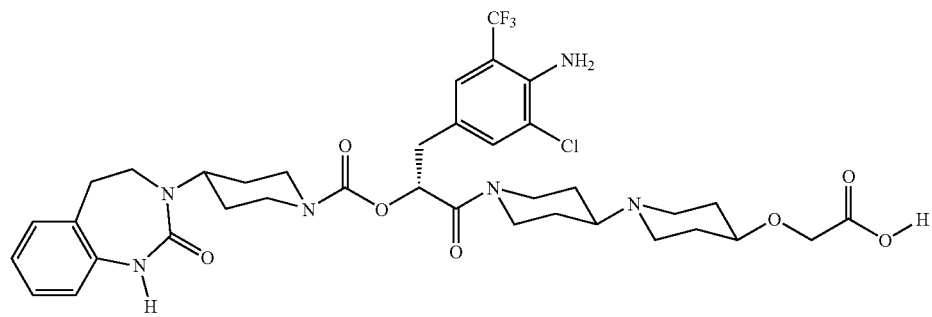

A solution of 8.00 mg (0.33 mmol) LiOH in 2.5 mL water was added to 100 mg (0.12 mmol) (R)-1-(4-amino-3-chloro-5-trifluoromethyl-benzyl)-2-(4-ethoxycarbonyl-methoxy-1,4'-bipiperidinyl-1'-yl)-2-oxo-ethyl 4-(2-oxo-1,2,4,5-tetrahydro-1,3-benzodiazepin-3-yl)-piperidine-1-carboxylate in 8 mL THF and the reaction mixture was stirred for 3 h at RT. 0.34 mL (0.34 mmol) 1 M HCl was added and the mixture was evaporated down i. vac. The residue was taken up in DCM/MeOH, filtered through a little silica gel and eluted with DCM/MeOH (7:3). It was evaporated down i. vac. and the residue was dried under a high vacuum.

Yield: 61 mg (63% of theory)
ESI-MS: (M+H)⁺=779/781 (Cl)
Retention time (HPLC): 3.2 min (method B)

EXAMPLE 26

(R)-1-(4-amino-3-chloro-5-trifluoromethyl-benzyl)-2-(4-ethoxycarbonylmethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate

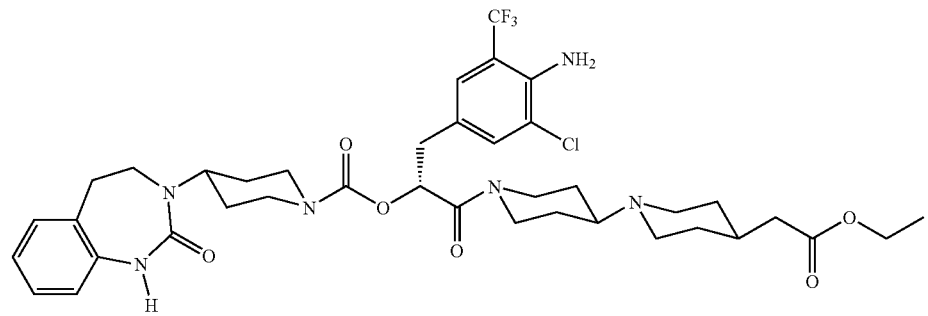

200 µL (1.43 mmol) triethylamine and 414 mg (1.29 mmol) TBTU were added to 650 mg (1.17 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate (Example 1f) in 30 mL of THF and 5 mL of DMF and the reaction mixture was stirred for 30 min at RT. Then 422 mg (1.29 mmol) ethyl[1,4']bipiperidinyl-4-yl-acetate (A14b) and 330 μL (2.38 mmol) triethylamine in 10 mL DCM were added and the mixture was stirred for a further 18 h at RT. 50 mL of semisaturated NaHCO$_3$ solution were added, the mixture was extracted twice with 50 mL EtOAc, the combined organic phases were washed with 50 mL saturated NaCl solution and dried over Na$_2$SO$_4$. After elimination of the desiccant and solvent the residue was purified by chromatography (silica gel, EtOAc/MeOH/NH$_3$ 95:5:0.5). The fractions containing the product were combined, evaporated down i. vac., the residue was triturated with DIPE, suction filtered and dried.

Yield: 646 mg (70% of theory)
ESI-MS: (M+H)$^+$=791/793 (Cl)
R$_f$=0.33 (silica gel, EtOAc/MeOH/NH$_3$ 90:10:1)

EXAMPLE 26.1

(R)-1-(4-amino-3-chloro-5-trifluoromethyl-benzyl)-2-(4-carboxymethyl-1,4'-bipiperidinyl-1'-yl)-2-oxo-ethyl 4-(2-oxo-1,2,4,5-tetrahydro-1,3-benzodiazepin-3-yl)-piperidine-1-carboxylate

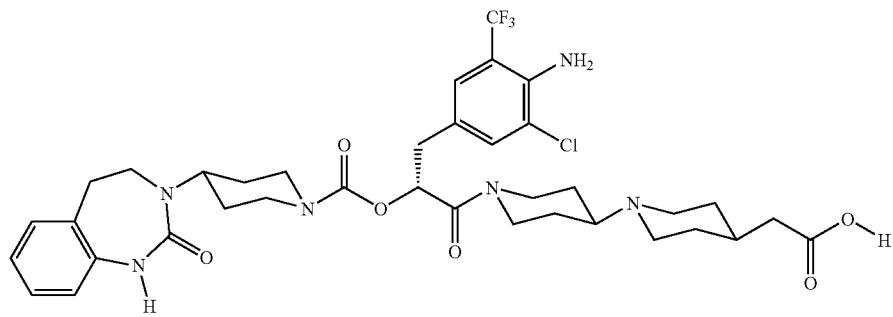

A solution of 5.00 mg (0.21 mmol) LiOH in 3 mL water was added to 100 mg (0.13 mmol) (R)-1-(4-amino-3-chloro-5-trifluoromethyl-benzyl)-2-(4-ethoxycarbonyl-methyl-1,4'-bipiperidinyl-1'-yl)-2-oxo-ethyl 4-(2-oxo-1,2,4,5-tetrahydro-1,3-benzodiazepin-3-yl)-piperidine-1-carboxylate in 10 mL THF and the reaction mixture was stirred for 2 days at RT. The mixture was evaporated to dryness i. vac., the residue was taken up in 1 mL DMF and purified by HPLC; the fractions containing the product were combined and lyophilised.

Yield: 22 mg (22% of theory)
ESI-MS: (M+H)$^+$=763/765 (Cl)
Retention time (HPLC): 3.2 min (method B)

EXAMPLE 27

(R)-1-(4-amino-3-chloro-5-trifluoromethyl-benzyl)-2-[4-(2-ethoxycarbonyl-ethyl)-1,4'-bipiperidinyl-1'-yl]-2-oxo-ethyl 4-(2-oxo-1,2,4,5-tetrahydro-1,3-benzodiazepin-3-yl)-piperidine-1-carboxylate

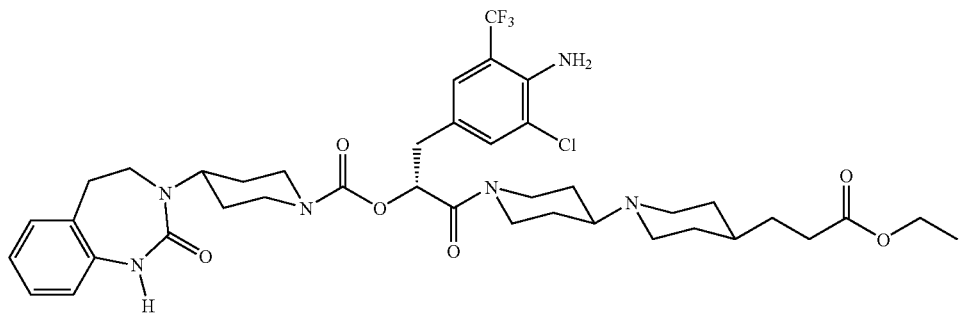

Prepared analogously to Example 24 from 500 mg (0.90 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate (Example 1f) and 341 mg (1.00 mmol) ethyl 3-[1,4']bipiperidinyl-4-yl-propionate (Example A15b).

Yield: 340 mg (47% of theory)
ESI-MS: (M+H)⁺=805/807 (Cl)
Retention time (HPLC): 3.6 min (method B)

EXAMPLE 27.1

(R)-1-(4-amino-3-chloro-5-trifluoromethyl-benzyl)-2-[4-(2-carboxy-ethyl)-1,4'-bipiperidinyl-1'-yl]-2-oxo-ethyl 4-(2-oxo-1,2,4,5-tetrahydro-1,3-benzodiazepin-3-yl)-piperidine-1-carboxylate

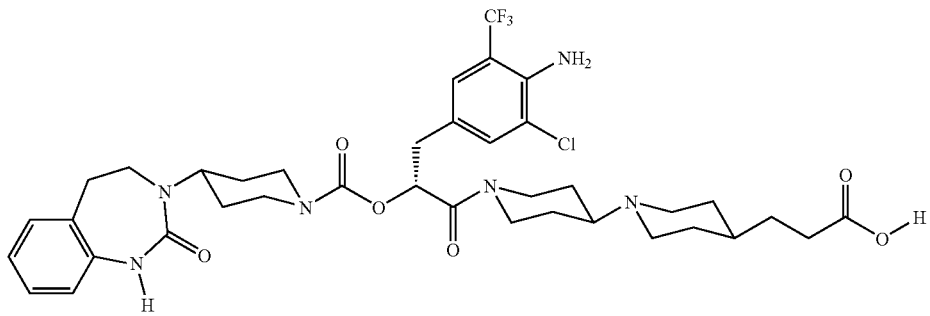

A solution of 2.40 mg (0.10 mmol) LiOH in 1 mL water was added to 50 mg (0.06 mmol) (R)-1-(4-amino-3-chloro-5-trifluoromethyl-benzyl)-2-[4-(2-ethoxycarbonyl-ethyl)-1,4'-bipiperidinyl-1'-yl]-2-oxo-ethyl 4-(2-oxo-1,2,4,5-tetrahydro-1,3-benzodiazepin-3-yl)-piperidine-1-carboxylate in 3 mL THF and the reaction mixture was stirred for 4 h at RT. THF was eliminated in a nitrogen stream, the residue was taken up in a little water and purified by HPLC; the fractions containing the product were combined and lyophilised.

Yield: 38 mg (79% of theory)
ESI-MS: (M+H)⁺=777/779 (Cl)
Retention time (HPLC): 3.4 min (method B)

EXAMPLE 28

(R)-1-(4-amino-3-chloro-5-trifluoromethyl-benzyl)-2-{4-[1-(3-ethoxycarbonyl-propyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate triethylamine in 10 mL DMF and the reaction mixture was stirred for 2 h at RT. This was purified by HPLC without any further working up; the fractions containing the product were combined, evaporated down i. vac., the residue was stirred with saturated NaHCO₃ solution, filtered and dried.

Yield: 165 mg (22% of theory)
ESI-MS: (M+H)⁺=820/822 (Cl)
Retention time (HPLC): 3.1 min (method B)

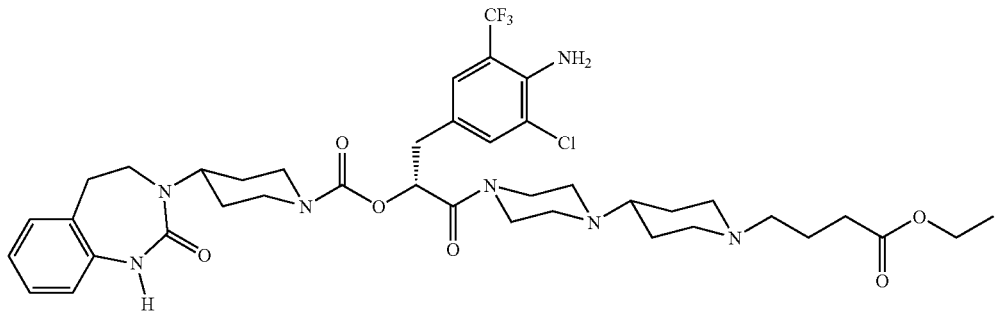

283 mg (1.00 mmol) ethyl 4-(4-piperazin-1-yl-piperidin-1-yl)-butyrate (Example A16b) were added to a mixture of 500 mg (0.90 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate (Example 1f), 321 mg (1.00 mmol) TBTU and 0.14 mL (1.00 mmol)

EXAMPLE 28.1

(R)-1-(4-amino-3-chloro-5-trifluoromethyl-benzyl)-2-{4-[1-(3-carboxy-propyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate

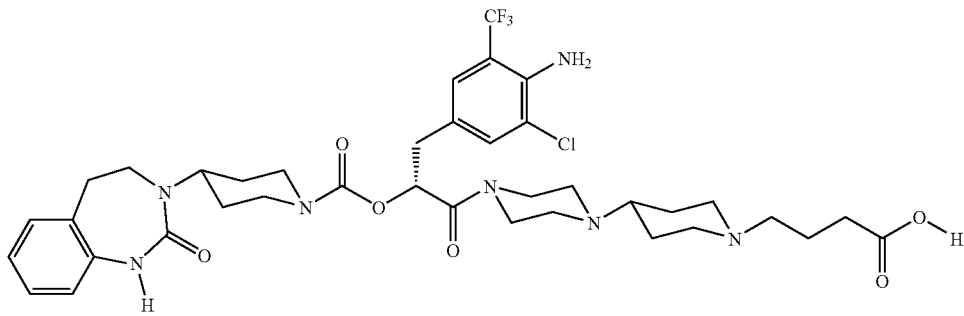

Prepared analogously to Example 27.1 from 50 mg (0.06 mmol) (R)-1-(4-amino-3-chloro-5-trifluoromethyl-benzyl)-2-{4-[1-(3-ethoxycarbonyl-propyl) -piperidin-4-yl]-piperazin-1-yl}-2-oxo-ethyl 4-(2-oxo-1,2,4,5-tetrahydro-1,3-benzodiazepin-3-yl)-piperidine-1-carboxylate and 2.40 mg (0.10 mmol) LiOH.

Yield: 29 mg (60% of theory)
ESI-MS: $(M+H)^+=792/794$ (CI)
Retention time (HPLC): 3.0 min (method B)

EXAMPLE 29

(R)-1-(4-amino-3-chloro-5-trifluoromethyl-benzyl)-2-{4-[1-(1-ethoxycarbonyl-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate 4-piperazin-1-yl -piperidine-1-carboxylate (Example A17b), 643 mg (2.00 mmol) TBTU and 0.35 mL (2.50 mmol) triethylamine in 10 mL DMF was stirred overnight at RT. This was combined with 150 mL of 15% $K_2CO_3$ solution, the precipitate was removed by suction filtering, washed with 30 mL water and the crude product was dried at 40° C. in the drying cupboard.

Yield: 1.50 g (99% of theory)
ESI-MS: $(M+H)^+=840/842$ (CI)
Retention time (HPLC): 3.7 min (method B)

A suspension of 750 mg (0.89 mmol) of the above product and 600 mg Raney nickel in 50 mL MeOH was hydrogenated for 30 h at RT and 3447 hPa. The catalyst was removed by suction filtering, evaporated down i. vac. and the residue was purified by HPLC. The fractions containing the product were combined, evaporated down i. vac., the residue was made alkaline with 15% $K_2CO_3$ solution, extracted with 100 mL EtOAc, the organic phase was separated off and dried over $Na_2SO_4$. After elimination of the desiccant and solvent the residue was triturated with 30 mL DIPE, suction filtered and dried.

Yield: 280 mg (44% of theory)
ESI-MS: $(M+H)^+=706/708$ (CI)
Retention time (HPLC): 2.8 min (method B)

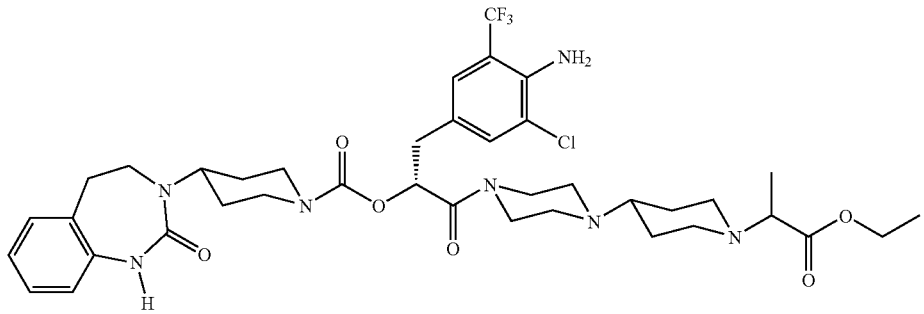

29a) (R)-1-(4-amino-3-chloro-5-trifluoromethyl-benzyl)-2-oxo-2-(4-piperidin-4-yl-piperazin-1-yl)-ethyl 4-(2-oxo-1,2,4,5-tetrahydro-1,3-benzodiazepin-3-yl)-piperidine-1-carboxylate A mixture of 1.00 g (1.80 mmol) (R)-2-(4-amino-3-chloro-5-trifluoromethyl-phenyl)-1-carboxy-ethyl 4-(2-oxo-1,2,4,5-tetrahydro-1,3-benzodiazepin-3-yl)-piperidine-1-carboxylate (Example 1f), 546 mg (1.80 mmol) benzyl 29b) (R)-1-(4-amino-3-chloro-5-trifluoromethyl-benzyl)-2-{4-[1-(1-ethoxycarbonyl-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate A mixture of 140 mg (0.20 mmol) (R)-1-(4-amino-3-chloro-5-trifluoromethyl-benzyl)-2-oxo-2-(4-piperidin-4-yl-piperazin-1-yl)-ethyl 4-(2-oxo-1,2,4,5-tetrahydro-1,3- benzodiazepin-3-yl)-piperidine-1-carboxylate, 60.8 mg (0.44 mmol) $K_2CO_3$ and 29 μL (0.22 mmol) ethyl 2-bromopropionate in 1.8 mL DMF was shaken for 2 h at 50° C. The reaction mixture was purified by HPLC without working up; the fractions containing the product were combined and lyophilised.

Yield: 111 mg (69% of theory)
ESI-MS: $(M+H)^+$=806/808 (Cl)
Retention time (HPLC): 3.1 min (method B)

EXAMPLE 29.1

(R)-1-(4-amino-3-chloro-5-trifluoromethyl-benzyl)-2-{4-[1-(1-carboxy-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate A mixture of 140 mg (0.20 mmol) (R)-1-(4-amino-3-chloro-5-trifluoromethyl-benzyl)-2-oxo-2-(4-piperidin-4-yl-piperazin-1-yl)-ethyl 4-(2-oxo -1,2,4,5-tetrahydro-1,3-benzodiazepin-3-yl)-piperidine-1-carboxylate (Example 29a), 60.8 mg (0.44 mmol) $K_2CO_3$ and 45 μL (0.30 mmol) ethyl 2-bromo-2-methyl-propionate in 1.8 mL DMF was shaken at 50° C. for 12 h and then for 48 h at RT. The precipitate was filtered off and the filtrate was purified by HPLC without working up; the fractions containing the product were combined, evaporated down i. vac., the residue was made alkaline with saturated $NaHCO_3$ solution, the precipitate was suction filtered, washed with 20 mL water and dried at 40° C.

Yield: 85 mg (52% of theory)
ESI-MS: $(M+H)^+$=820/822 (Cl)
Retention time (HPLC): 3.0 min (method B)

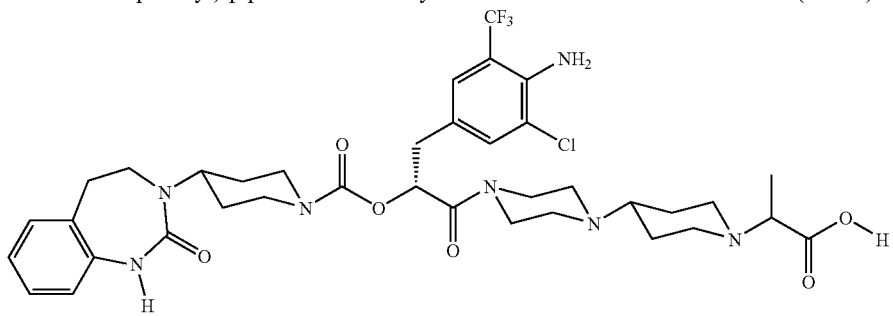

A solution of 2.4 mg (0.10 mmol) LiOH in 0.8 mL water was added to 50 mg (0.06 mmol) (R)-1-(4-amino-3-chloro-5-trifluoromethyl-benzyl)-2-{4-[1-(1-ethoxycarbonyl-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate in 1 mL THF and the reaction mixture was shaken for 2 h at RT and for 4 h at 50° C. It was then purified by HPLC without working up; the fractions containing the product were combined and lyophilised.

Yield: 42 mg (87% of theory)
ESI-MS: $(M+H)^+$=778/780 (Cl)
Retention time (HPLC): 3.0 min (method B)

EXAMPLE 30

(R)-1-(4-amino-3-chloro-5-trifluoromethyl-benzyl)-2-{4-[1-(1-ethoxycarbonyl-1-methyl-ethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate

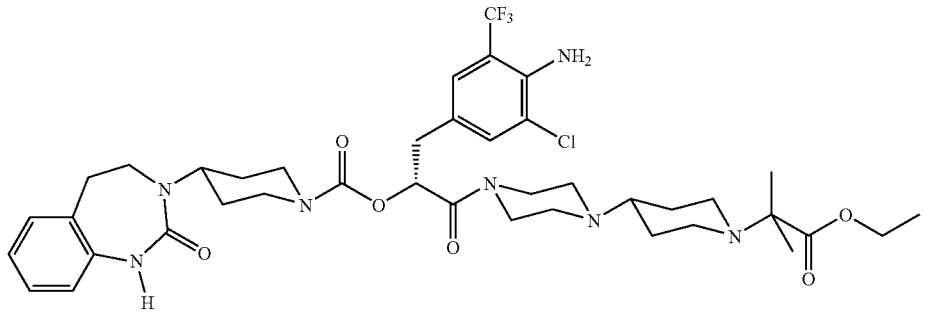

EXAMPLE 31

Ethyl 1'-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-4-methyl-1,4'-bipiperidinyl-4-carboxylate

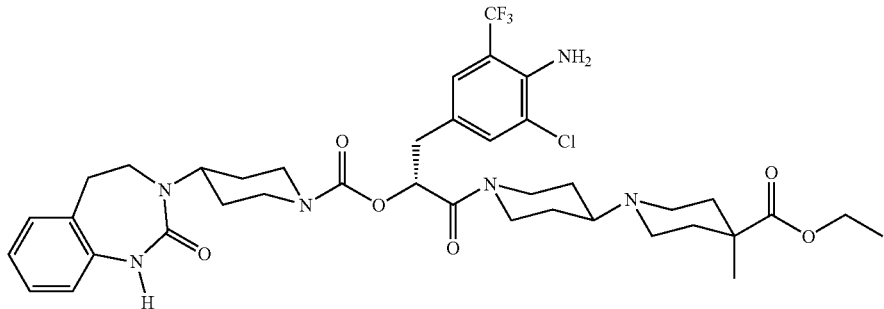

A mixture of 127 mg (0.20 mmol) (R)-1-(4-amino-3-chloro-5-trifluoromethyl-benzyl)-2-oxo-2-(4-oxo-piperidin-1-yl)-ethyl 4-(2-oxo-1,2,4,5-tetrahydro-1,3-benzodiazepin-3-yl)-piperidine-1-carboxylate (Example 1g), 68.5 mg (0.40 mmol) ethyl 4-methyl-piperidine-4-carboxylate and 11 µL (0.2 mmol) ACOH in 2 mL DCM was stirred for 2 h at RT, cooled to 0° C., stirred for 2 h, then mixed with 57.7 mg (0.26 mmol) sodium triacetoxyborohydride and stirred overnight at 0° C. The reaction mixture was purified by HPLC without working up; the fractions containing the product were combined and lyophilised.

Yield: 85 mg (54% of theory)
ESI-MS: (M+H)⁺=791/793 (Cl)
Retention time (HPLC): 7.7 min (method C)

The following compounds were prepared analogously from in each case 127 mg (R)-1-(4-amino-3-chloro-5-trifluoromethyl-benzyl)-2-oxo-2-(4-oxo-piperidin-1-yl)-ethyl 4-(2-oxo-1,2,4,5-tetrahydro-1,3-benzodiazepin-3-yl)-piperidine-1-carboxylate (Example 1g) and the amount of amine component required in each case:

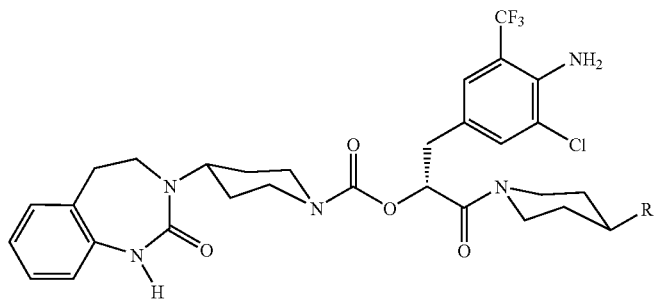

| Example | R | Yield (%) | Mass spectrum | Retention time HPLC (method) |
|---|---|---|---|---|
| 31.1 | *←—N⟩—CO₂Et (3S-pyrrolidine ethyl ester) | 23 | 763/765 [M + H]⁺ | 7.2 min (C) |
| 31.2 | *←—N⟩—CO₂Et (3R-pyrrolidine ethyl ester) | 74 | 763/765 [M + H]⁺ | 7.1 min (C) |

-continued

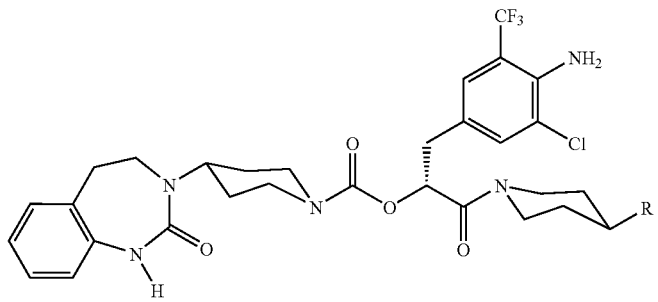

| Example | R | Yield (%) | Mass spectrum | Retention time HPLC (method) |
|---|---|---|---|---|
| 31.3 | *←—[piperidine-3-carboxylic acid ethyl ester]* | 75 | 777/779 [M + H]⁺ | 7.3 min (C) |
| 31.4 | *←—[piperidine-3-carboxylic acid ethyl ester]* | 72 | 777/779 [M + H]⁺ | 7.3 min (C) |

EXAMPLE 32

1'-{(R)-3-(4-amino-3-chloro-5-trifluoromethyl-phenyl)-2-[4-(2-oxo-1,2,4,5-tetrahydro-1,3-benzodiazepin-3-yl)-piperidine-1-carbonyloxy]-propionyl}-4-methyl -1,4'-bipiperidinyl-4-carboxylic acid

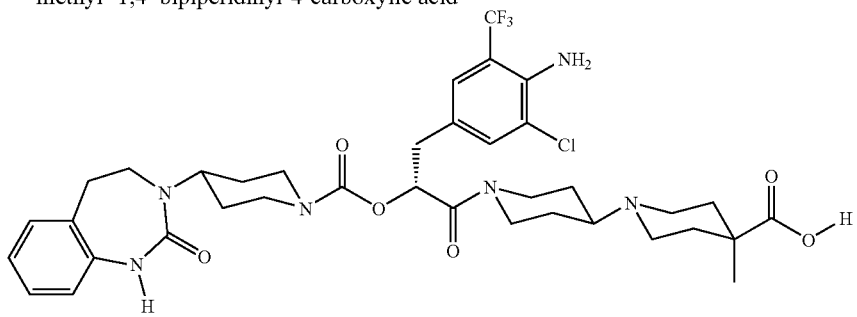

A solution of 2.00 mg (0.08 mmol) LiOH in 1 mL water was added to 40 mg (0.05 m mol) ethyl 1'-{(R)-3-(4-amino-3-chloro-5-trifluoromethyl -phenyl)-2-[4-(2-oxo-1,2,4,5-tetrahydro-1,3-benzodiazepin-3-yl)-piperidine-1-carbonyloxy]-propionyl}-4-methyl-1,4'-bipiperidinyl-4-carboxylate in 0.8 mL THF and the reaction mixture was stirred for 1 h at RT and for 8 h at 50° C. This was purified by HPLC without working up; the fractions containing the product were combined and lyophilised.

Yield: 18 mg (47% of theory)

ESI-MS: (M+H)⁺=763/765 (Cl)

Retention time (HPLC): 3.5 min (method B)

The following compounds were prepared analogously from in each case 40 mg of the corresponding ethyl ester, the hydrolysis requiring only 1 h at RT:

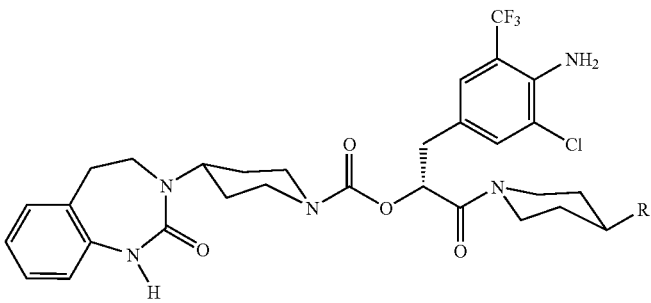

| Example | R | Yield (%) | Mass spectrum | Retention time HPLC (method) |
|---|---|---|---|---|
| 32.1 | *←N⟩–COOH (pyrrolidine-3-carboxylic acid) | 93 | 735/737 [M + H]+ | 3.3 min (B) |
| 32.2 | *←N⟩–COOH (pyrrolidine-3-carboxylic acid, opposite stereo) | 73 | 735/737 [M + H]+ | 3.3 min (B) |
| 32.3 | *←N⟩–COOH (piperidine-3-carboxylic acid) | 73 | 749/751 [M + H]+ | 3.3 min (B) |
| 32.4 | *←N⟩–COOH (piperidine-3-carboxylic acid, opposite stereo) | 80 | 749/751 [M + H]+ | 3.5 min (B) |

EXAMPLE 33

(R)-1-(4-amino-3-chloro-5-trifluoromethyl-benzyl)-2-{4-[1-(5-methyl-2-oxo-1,3-dioxol-4-ylmethoxy-carbonylmethyl)-piperidin-4-yl]-piperazin-1-yl}-2-oxo-ethyl 4-(2-oxo-1,2,4,5-tetrahydro-1,3-benzodiazepin-3-yl)-piperidine-1-carboxylate

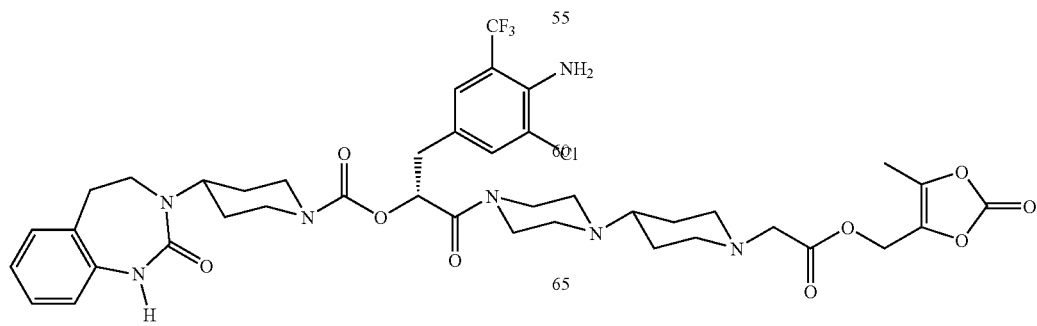

A mixture of 185 mg (0.24 mmol) (R)-1-(4-amino-3-chloro-5-trifluoromethyl-benzyl)-2-[4-(1-carboxymethyl-piperidin-4-yl)-piperazin-1-yl]-2-oxo-ethyl 4-(2-oxo-1,2,4,5-tetrahydro-1,3-benzodiazepin-3-yl)-piperidine-1-carboxylate (Example 4.1), 25 mg (0.25 mmol) KHCO₃ and 50 mg (0.26 mmol) 4-bromomethyl-5-methyl-1,3-dioxol-2-one in 1 mL DMF was shaken overnight at RT. The reaction mixture was filtered through a syringe filter and purified by HPLC; the fractions containing the product were combined and lyophilised.

Yield: 14 mg (7% of theory)
ESI-MS: (M+H)⁺=876/878 (Cl)
R$_f$=0.54 (silica gel, DCM/Cyc/MeOH/NH₃ 70:15:15:2)

EXAMPLE 33.1

(R)-1-(4-amino-3-chloro-5-trifluoromethyl-benzyl)-2-[1'-(5-methyl-2-oxo-1,3-dioxol-4-ylmethoxycarbonylmethyl)-4,4'-bipiperidinyl-1-yl]-2-oxo-ethyl 4-(2-oxo-1,2,4,5-tetrahydro-1,3-benzodiazepin-3-yl)-piperidine-1-carboxylate

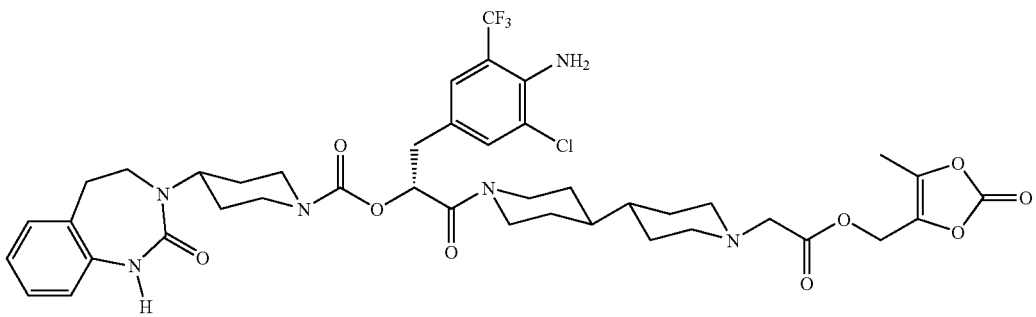

Prepared analogously to Example 33 from 150 mg (0.20 mmol) (R)-1-(4-amino-3-chloro-5-trifluoromethyl-benzyl)-2-(1'-carboxymethyl-4,4'-bipiperidinyl-1-yl)-2-oxo-ethyl 4-(2-oxo-1,2,4,5-tetrahydro-1,3-benzodiazepin-3-yl)-piperidine-1-carboxylate (Example 3.1) and 50 mg (0.26 mmol) 4-bromomethyl-5-methyl-1,3-dioxol-2-one.

Yield: 8 mg (5% of theory)
ESI-MS: (M+H)⁺=875/877 (Cl)
R$_f$=0.74 (silica gel, DCM/Cyc/MeOH/NH₃ 70:15:15:2)

EXAMPLE 34

(R)-1-(4-amino-3-chloro-5-trifluoromethyl-benzyl)-2-(4-{1-[2-(2-methoxy-ethox)-ethoxycarbonylmethyl]-piperidin-4-yl}-piperazin-1-yl)-2-oxo-ethyl 4-(2-oxo-1,2,4,5-tetrahydro-1,3-benzodiazepin-3-yl)-piperidine-1-carboxylate

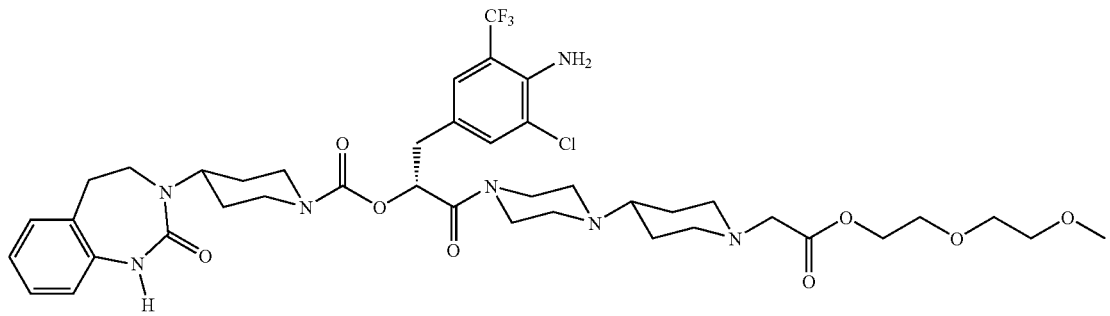

13 μL (0.11 mmol) 2-(2-methoxy-ethoxy)-ethanol were added to a mixture of 75 mg (0.10 mmol) of (R)-1-(4-amino-3-chloro-5-trifluoromethyl -benzyl)-2-[4-(1-carboxymethyl-piperidin-4-yl)-piperazin-1-yl]-2-oxo-ethyl 4-(2-oxo-1,2,4,5-tetrahydro-1,3-benzodiazepin-3-yl)-piperidine-1- carboxylate (Example 4.1), 35 mg (0.11 mmol) TBTU and 28 µL (0.20 mmol) triethylamine in 1 mL DMF and the reaction mixture was stirred for 1 h at RT. This was purified by HPLC without working up; the fractions containing the product were combined and lyophilised.

Yield: 22 mg (26% of theory)
ESI-MS: $(M+H)^+ = 866/868$ (Cl)
Retention time (HPLC): 3.2 min (method B)

EXAMPLE 35

(R)-1-(4-amino-3-chloro-5-trifluoromethyl-benzyl)-2-[1'-(2-morpholin-4-yl-ethoxycarbonylmethyl)-4,4'-bipiperidinyl-1-yl]-2-oxo-ethyl 4-(7-methoxy-2-oxo-1,2,4,5-tetrahydro-1,3-benzodiazepin-3-yl)-piperidine-1-carboxylate

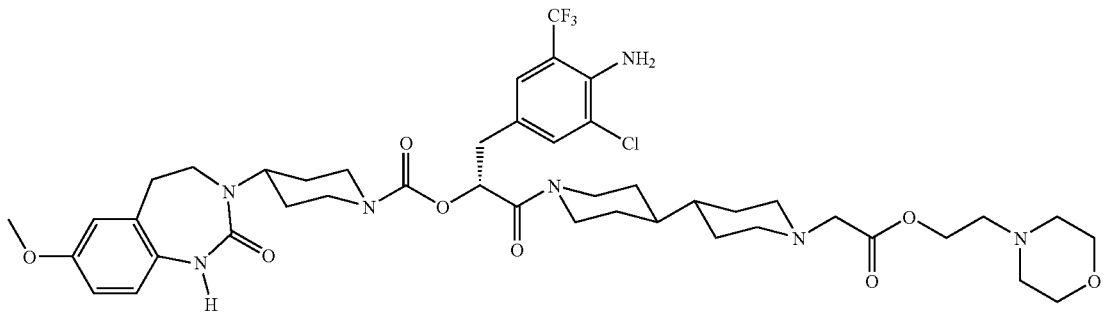

A mixture of 230 mg (0.29 mmol) (R)-1-(4-amino-3-chloro-5-trifluoromethyl-benzyl)-2-(1'-carboxymethyl-4,4'-bipiperidinyl-1-yl)-2-oxo-ethyl 4-(7-methoxy-2-oxo-1,2,4,5-tetrahydro-1,3-benzodiazepin-3-yl)-piperidine-1-carboxylate (Example 15.1), 113 mg (0.35 mmol) TBTU, 84 µL (0.60 mmol) triethylamine and 39.3 mg (0.30 mmol) 2-morpholin-4-yl-ethanol in 5 mL DMF was stirred overnight at RT. The reaction mixture was poured onto saturated NaHCO$_3$ solution, the product precipitated was suction filtered and dried at 40° C. This was dissolved in 25 mL of isopropanol and precipitated as the hydrochloride salt by the addition of 0.5 M HCl in isopropanol. This was suction filtered, washed with 5 mL isopropanol and 30 mL DIPE and dried at 30° C. in the vacuum drying cupboard.

Yield: 90 mg (34% of theory)
ESI-MS: $(M+H)^+ = 906/908$ (Cl)
Retention time (HPLC): 3.1 min (method B)

The Examples that follow describe the preparation of pharmaceutical formulations which contain as active substance any desired compound of general formula I:

EXAMPLE I

Capsules for Powder Inhalation Containing 1 mg of Active Ingredient
Composition:
1 capsule for powder inhalation contains:

| active ingredient | 1.0 mg |
| lactose | 20.0 mg |
| hard gelatine capsules | 50.0 mg |
| | 71.0 mg |

Method of Preparation:
The active ingredient is ground to the particle size required for inhaled substances. The ground active ingredient is homogeneously mixed with the lactose. The mixture is transferred into hard gelatine capsules.

EXAMPLE II

Inhalable Solution for Respimat® Containing 1 mg of Active Ingredient
Composition:
1 puff contains:

| active ingredient | 1.0 mg |
| benzalkonium chloride | 0.002 mg |

-continued

| disodium edetate | 0.0075 mg |
| purified water ad | 15.0 µl |

Method of Preparation:
The active ingredient and benzalkonium chloride are dissolved in water and transferred into Respimat® cartridges.

EXAMPLE III

Inhalable Solution for Nebulisers Containing 1 mg of Active Ingredient
Composition:
1 vial contains:

| active ingredient | 0.1 g |
| sodium chloride | 0.18 g |
| benzalkonium chloride | 0.002 g |
| purified water ad | 20.0 ml |

Method of Preparation:
The active ingredient, sodium chloride and benzalkonium chloride are dissolved in water.

EXAMPLE IV

Propellant Gas-Operated Metering Aerosol Containing 1 mg of Active Ingredient
Composition:
1 puff contains:

| active ingredient | 1.0 mg |
| lecithin | 0.1% |
| propellant gas ad | 50.0 µl |

Method of Preparation:

The micronised active ingredient is homogeneously suspended in the mixture of lecithin and propellant gas. The suspension is transferred into a pressurised container with a metering valve.

EXAMPLE V

Nasal Spray Containing 1 mg of Active Ingredient
Composition:

| | |
|---|---|
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

EXAMPLE VI

Injectable Solution Containing 5 mg of Active Substance Per 5 ml
Composition:

| | |
|---|---|
| active substance | 5 mg |
| glucose | 250 mg |
| human serum albumin | 10 mg |
| glycofurol | 250 mg |
| water for injections ad | 5 ml |

Preparation:

Glycofurol and glucose are dissolved in water for injections (WfI); human serum albumin is added; active ingredient is dissolved with heating; made up to specified volume with WfI; transferred into ampoules under nitrogen gas.

EXAMPLE VII

Injectable Solution Containing 100 mg of Active Substance Per 20 ml
Composition:

| | |
|---|---|
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (WfI); human serum albumin is added; active ingredient is dissolved with heating; made up to specified volume with WfI; transferred into ampoules.

EXAMPLE VIII

Lyophilisate Containing 10 mg of Active Substance
Composition:

| | |
|---|---|
| Active substance | 10 mg |
| Mannitol | 300 mg |
| human serum albumin | 20 mg |
| water for injections ad | 2 ml |

Preparation:

Mannitol is dissolved in water for injections (WfI); human serum albumin is added; active ingredient is dissolved with heating; made up to specified volume with WfI; transferred into vials; freeze-dried.

Solvent for Lyophilisate:

| | |
|---|---|
| Polysorbate 80 = Tween 80 | 20 mg |
| mannitol | 200 mg |
| water for injections ad | 10 ml |

Preparation:

Polysorbate 80 and mannitol are dissolved in water for injections (WfI); transferred into ampoules.

EXAMPLE IX

Tablets containing 20 mg of active substance
Composition:

| | |
|---|---|
| active substance | 20 mg |
| lactose | 120 mg |
| corn starch | 40 mg |
| magnesium stearate | 2 mg |
| Povidone K 25 | 18 mg |

Preparation:

Active substance, lactose and corn starch are homogeneously mixed; granulated with an aqueous solution of Povidone; mixed with magnesium stearate; compressed in a tablet press; weight of tablet 200 mg.

EXAMPLE X

Capsules Containing 20 mg Active Substance
Composition:

| | |
|---|---|
| active substance | 20 mg |
| corn starch | 80 mg |
| highly dispersed silica | 5 mg |
| magnesium stearate | 2.5 mg |

Preparation:

Active substance, corn starch and silica are homogeneously mixed; mixed with magnesium stearate; the mixture is packed into size for 3 hard gelatine capsules in a capsule filling machine.

EXAMPLE XI

Suppositories Containing 50 mg of Active Substance
Composition:

| active substance | 50 mg |
|---|---|
| hard fat (Adeps solidus) q.s. ad | 1700 mg |

Preparation:

Hard fat is melted at about 38° C.; ground active substance is homogeneously dispersed in the molten hard fat; after cooling to about 35° C. it is poured into chilled moulds.

EXAMPLE XII

Injectable Solution Containing 10 mg of Active Substance Per 1 ml
Composition:

| active substance | 10 mg |
|---|---|
| mannitol | 50 mg |
| human serum albumin | 10 mg |
| water for injections ad | 1 ml |

Preparation:

Mannitol is dissolved in water for injections (WfI); human serum albumin is added; active ingredient is dissolved with heating; made up to specified volume with WfI; transferred into ampoules under nitrogen gas.

What is claimed is:

1. A compound of the formula I

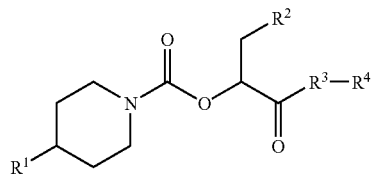

wherein $R^1$ denotes a group of the formula

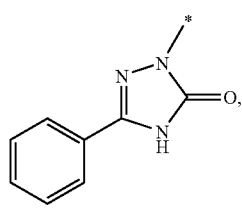

wherein $R^{1.1}$ denotes H or $H_3C$—O, $R^2$ denotes a group selected from

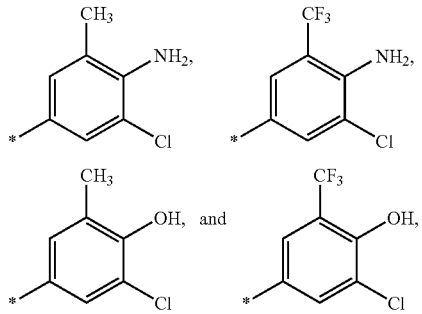

$R^3$ denotes a group of general formula II

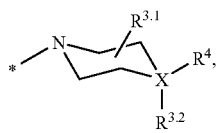

wherein

X denotes N or C, $R^{3.1}$ denotes H, $C_{1-3}$-alkyl or $R^{3.1.1}$—O—C(O), $R^{3.1.1}$ denotes H, $C_{1-6}$-alkyl, $H_2N$—$C_{2-4}$-alkylene, $(C_{1-3}$-alkyl)-NH—$C_{2-4}$-alkylene, $(C_{1-3}$-alkyl)$_2$N—$C_{2-4}$-alkylene, $H_2N$—C(O)—$C_{1-3}$-alkylene, $(C_{1-3}$-alkyl)-NH—C(O)—$C_{1-3}$-alkylene, $(C_{1-3}$-alkyl)$_2$N—C(O)—$C_{1-3}$-alkylene or $R^{3.1.1.1}$—$C_{2-4}$-alkylene, $R^{3.1.1.1}$ denotes a group selected from

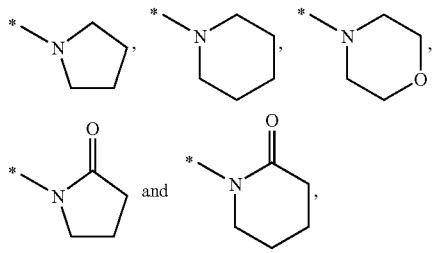

$R^{3.2}$ denotes a pair of free electrons, if X=N, or $R^{3.2}$ denotes H, $C_{1-3}$-alkyl or $R^{3.2.1}$—O—C(O), if X=C, $R^{3.2.1}$ denotes H, $C_{1-6}$-alkyl, $H_2N$—$C_{2-4}$-alkylene, $(C_{1-3}$-alkyl)-NH—$C_{2-4}$-alkylene, $(C_{1-3}$-alkyl)$_2$N—$C_{2-4}$-alkylene, $H_2N$—C(O)—$C_{1-3}$-alkylene, $(C_{1-3}$-alkyl)-NH—C(O)—$C_{1-3}$-alkylene, $(C_{1-3}$-alkyl)$_2$N—C(O)—$C_{1-3}$-alkylene or $R^{3.2.1.1}$—$C_{2-4}$-alkylene, $R^{3.2.1.1}$ denotes a group selected from

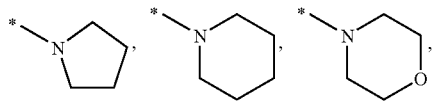

-continued

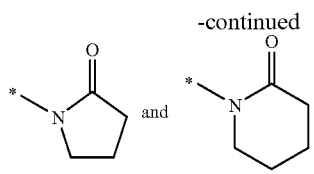

$R^4$ denotes a group of general formulae III

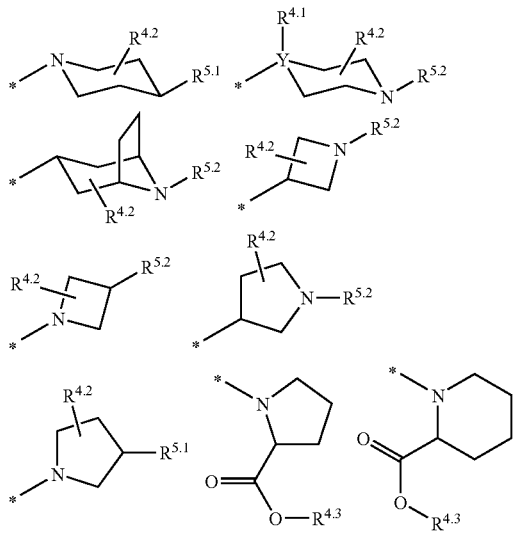

wherein
Y denotes C and
$R^{4.1}$ denotes H or $C_{1-3}$-alkyl, or
Y denotes N and
$R^{4.1}$ denotes a pair of free electrons,
with the proviso that X and Y do not simultaneously represent N,
$R^{4.2}$ denotes H, $C_{1-3}$-alkyl or $R^{4.2.1}$—O—C(O),
$R^{4.2.1}$ denotes H, $C_{1-6}$-alkyl, $H_2N$—$C_{2-4}$-alkylene, $(C_{1-3}$-alkyl)-NH—$C_{2-4}$-alkylene, $(C_{1-3}$-alkyl)$_2$N—$C_{2-4}$-alkylene, $H_2N$—C(O)—$C_{1-3}$-alkylene, $(C_{1-3}$-alkyl)-NH—C(O)—$C_{1-3}$-alkylene, $(C_{1-3}$-alkyl)$_2$N—C(O)—$C_{1-3}$-alkylene or $R^{4.2.1.1}$—$C_{2-4}$-alkylene,
$R^{4.2.1.1}$ denotes a group selected from

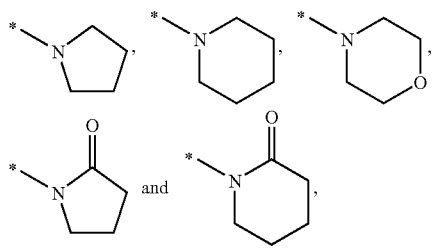

and
$R^{4.3}$ denotes H, $C_{1-6}$-alkyl, $H_2N$—$C_{2-4}$-alkylene, $(C_{1-3}$-alkyl)-NH—$C_{2-4}$-alkylene, $(C_{1-3}$-alkyl)$_2$N—$C_{2-4}$-alkylene, $H_2N$—C(O)—$C_{1-3}$-alkylene, $(C_{1-3}$-alkyl)-NH—C(O)—$C_{1-3}$-alkylene, $(C_{1-3}$-alkyl)$_2$N—C(O)—$C_{1-3}$-alkylene or $R^{4.3.1}$—$C_{2-4}$-alkylene- and $R^{4.3.1}$ denotes a group selected from

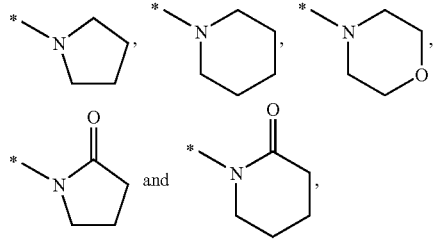

$R^{5.1}$ denotes H, $C_{1-3}$-alkyl, $R^{5.1.1}$—O—C(O), $R^{5.1.1}$—O—C(O)—$C_{1-3}$-alkylene-NH, $R^{5.1.1}$—O—C(O)—$C_{1-3}$-alkylene-N($C_{1-3}$-alkyl), $R^{5.1.1}$—O—C(O)—$C_{1-3}$-alkylene-O, $R^{5.1.1}$—O—C(O)—$C_{1-3}$-alkylene, $R^{5.1.1}$—O—C(O)—C(O), $R^{5.1.1}$—O—C(O)—C(O)—O, $R^{5.1.1}$—O—C(O)—$C_{1-3}$-alkylene-C(O) or $R^{5.1.1}$—O—C(O)—$C_{1-3}$-alkylene-C(O)—O, $R^{5.1.1}$ denotes H, $C_{1-8}$-alkyl, phenyl, indanyl, pyridyl-$C_{1-3}$-alkylene, HO—$C_{2-4}$-alkylene, $C_{1-6}$-alkyl-O—$C_{2-4}$-alkylene, $H_2N$—$C_{2-4}$-alkylene, $(C_{1-6}$-alkyl)-NH—$C_{2-4}$-alkylene, $(C_{1-6}$-alkyl)$_2$N—$C_{2-4}$-alkylene, $H_2N$—C(O)—$C_{1-3}$-alkylene, $(C_{1-6}$-alkyl)-NH—C(O)—$C_{1-3}$-alkylene, $(C_{1-6}$-alkyl)$_2$N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.1.1.1}$—C(O)—$C_{1-3}$-alkylene or $R^{5.1.1,2}$—$C_{2-4}$-alkylene, $R^{5.1.1.1}$ denotes a group selected from

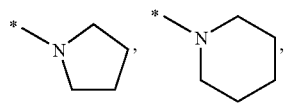

$R^{5.1.1.2}$ denotes a group selected from

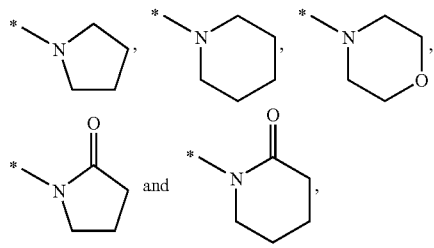

$R^{5.2}$ denotes H, $C_{1-3}$-alkyl, $R^{5.2.1}$—O—C(O)—$C_{1-3}$-alkylene-NH, $R^{5.2.1}$—O—C(O)—$C_{1-3}$-alkylene-O, $R^{5.2.1}$—O—C(O)—$C_{1-3}$-alkylene, $R^{5.2.1}$—O—C(O)—C(O) or $R^{5.2.1}$—O—C(O)—$C_{1-3}$-alkylene-C(O), $R^{5.2.1}$ denotes H, $C_{1-8}$-alkyl, phenyl, indanyl, pyridyl-$C_{1-3}$-alkylene, HO—$C_{2-4}$-alkylene, $C_{1-6}$-alkyl-O—$C_{2-4}$-alkylene, $C_{1-6}$-alkyl-O—$C_{2-4}$-alkylene-O—$C_{2-4}$-alkylene, $H_2N$—$C_{2-4}$-alkylene, $(C_{1-6}$-alkyl)-NH—$C_{2-4}$-alkylene, $(C_{1-6}$-alkyl)$_2$N—$C_{2-4}$-alkylene, $H_2N$—C(O)—$C_{1-3}$-alkylene, $(C_{1-6}$-alkyl)-NH—C(O)—$C_{1-3}$-alkylene, $(C_{1-6}$-alkyl)$_2$N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.2.1.1}$—C(O)—$C_{1-3}$-alkylene or $R^{5.2.1,2}$—$C_{2-4}$-alkylene, $R^{5.2.1.1}$ denotes a group selected from

$R^{5.2.1.2}$ denotes a group selected from

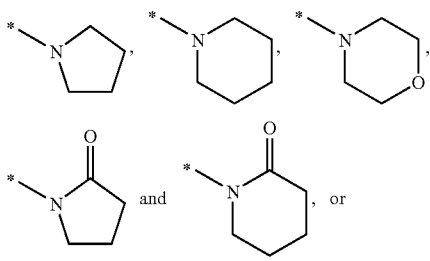

$R^{5.2.1}$ denotes a group of formula

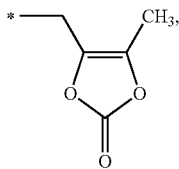

with the proviso that at least one of the groups $R^{3.1}$, $R^{3.2}$, $R^{4.2}$, $R^{5.1}$ or $R^{5.2}$ denotes a group other than H or $C_{1-3}$-alkyl, or a tautomer or salt thereof.

2. A compound of the formula I according to claim 1, wherein $R^1$ denotes a group of the formula

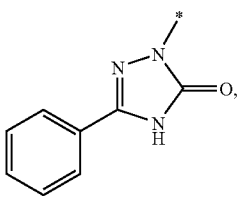

wherein $R^{1.1}$ denotes H or $H_3C$—O, $R^2$ denotes a group selected from

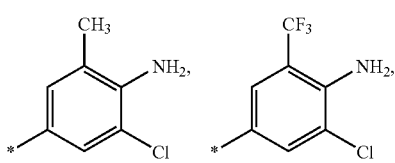

-continued

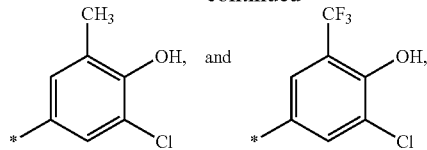

$R^3$ denotes a group of general formula II

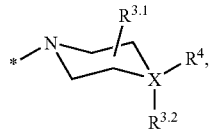

wherein

X denotes N or C, $R^{3.1}$ denotes H, $C_{1-3}$-alkyl or $R^{3.1.1}$—(O)C, $R^{3.1.1}$ denotes HO, $C_{1-6}$-alkyl-O, $R^{3.2}$ denotes a pair of free electrons, if X=N, or $R^{3.2}$ denotes H or $C_{1-3}$-alkyl, if X=C, $R^4$ denotes a group of general formulae III

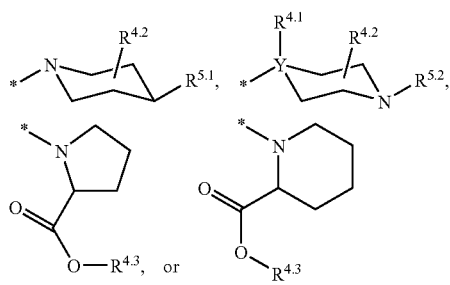

wherein

Y denotes C and $R^{4.1}$ denotes H or $C_{1-3}$-alkyl, or

Y denotes N and $R^{4.1}$ denotes a pair of free electrons, with the proviso that X and Y do not simultaneously represent N, $R^{4.2}$ denotes H, $C_{1-3}$-alkyl or $R^{4.2.1}$—(O)C, $R^{4.2.1}$ denotes HO, $C_{1-6}$-alkyl-O, and $R^{4.3}$ denotes H, $C_{1-6}$-alkyl, $H_2N$—$C_{2-4}$-alkylene, $(C_{1-3}$-alkyl)-NH—$C_{2-4}$-alkylene, $(C_{1-3}$-alkyl)$_2$N—$C_{2-4}$-alkylene, $H_2N$—C(O)—$C_{1-3}$-alkylene, $(C_{1-3}$-alkyl)-NH—C(O)—$C_{1-3}$-alkylene, $(C_{1-3}$-alkyl)$_2$N—C(O)—$C_{1-3}$-alkylene or $R^{4.3.1}$—$C_{2-4}$-alkylene, $R^{4.3.1}$ denotes a group selected from

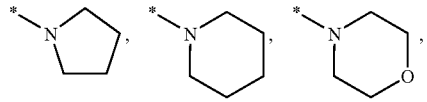

-continued

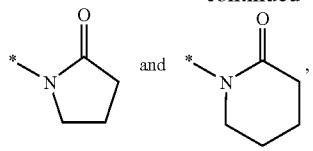 and , $R^{5.1}$ denotes $R^{5.1.1}$—O—C(O), $R^{5.1.1}$—O—C(O)—$C_{1-3}$-alkylene-NH, $R^{5.1.1}$—O—C(O)—$C_{1-3}$-alkylene-O, $R^{5.1.1}$—O—C(O)—$C_{1-3}$-alkylene, $R^{5.1.1}$—O—C(O)—C(O) or $R^{5.1.1}$—O—C(O)—$C_{1-3}$-alkylene-C(O), $R^{5.1.1}$ denotes H, $C_{1-8}$-alkyl, phenyl, indanyl, pyridyl-$C_{1-3}$-alkylene, HO—$C_{2-4}$-alkylene, $C_{1-6}$-alkyl-O—$C_{2-4}$-alkylene, $H_2N$—$C_{2-4}$-alkylene, $(C_{1-6}$-alkyl)-NH—$C_{2-4}$-alkylene, $(C_{1-6}$-alkyl)$_2$N—$C_{2-4}$-alkylene, $H_2N$—C(O)—$C_{1-3}$-alkylene, $(C_{1-6}$-alkyl)-NH—C(O)—$C_{1-3}$-alkylene, $(C_{1-6}$-alkyl)$_2$N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.1.1.1}$—C(O)—$C_{1-3}$-alkylene or $R^{5.1.1,2}$-$C_{2-4}$-alkylene, $R^{5.1.1.1}$ denotes a group selected from

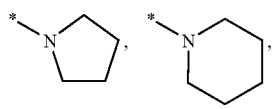

$R^{5.1.1.2}$ denotes a group selected from

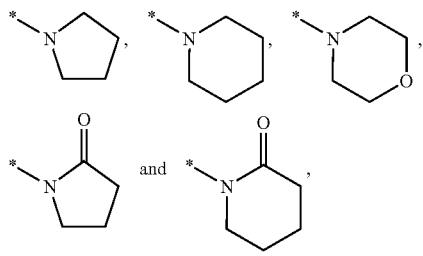

$R^{5.2}$ denotes $R^{5.2.1}$—O—C(O)—$C_{1-3}$-alkylene-NH, $R^{5.2.1}$—O—C(O)—$C_{1-3}$-alkylene-O, $R^{5.2.1}$—O—C(O)—$C_{1-3}$-alkylene, $R^{5.2.1}$—O—C(O)—C(O) or $R^{5.2.1}$—O—C(O)—$C_{1-3}$-alkylene-C(O), $R^{5.2.1}$ denotes H, $C_{1-8}$-alkyl, phenyl, indanyl, pyridyl-$C_{1-3}$-alkylene, HO—$C_{2-4}$-alkylene, $C_{1-6}$-alkyl-O—$C_{2-4}$-alkylene, $H_2N$—$C_{2-4}$-alkylene, $(C_{1-6}$-alkyl)-NH—$C_{2-4}$-alkylene, $(C_{1-6}$-alkyl)$_2$N—$C_{2-4}$-alkylene, $H_2N$—C(O)—$C_{1-3}$-alkylene, $(C_{1-6}$-alkyl)-NH—C(O)—$C_{1-3}$-alkylene, $(C_{1-6}$-alkyl)$_2$N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.2.1.1}$—C(O)—$C_{1-3}$-alkylene or $R^{5.2.1,2}$-$C_{2-4}$-alkylene, $R^{5.2.1.1}$ denotes a group selected from

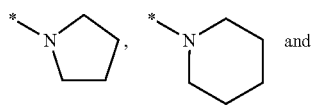

$R^{5.2.1.2}$ denotes a group selected from

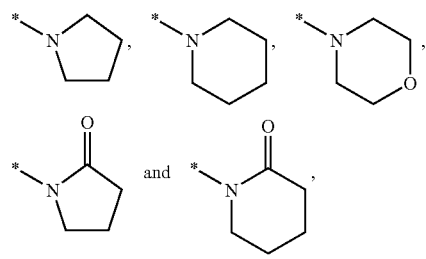

or a tautomer or salt thereof.

3. A compound of the formula I according to claim 1, wherein $R^1$ denotes a group of the formula

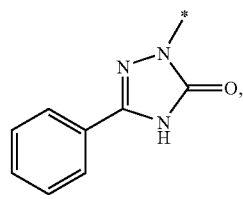

wherein
  $R^{1.1}$ denotes H or $H_3C$—O, $R^2$ denotes a group selected from

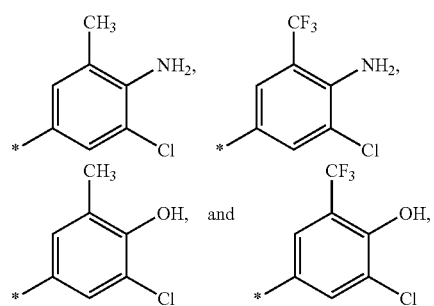

$R^3$-$R^4$ together denote a group of general formulae IV

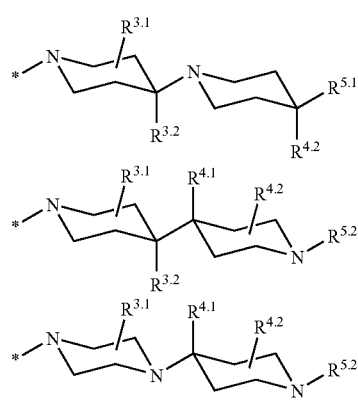

-continued

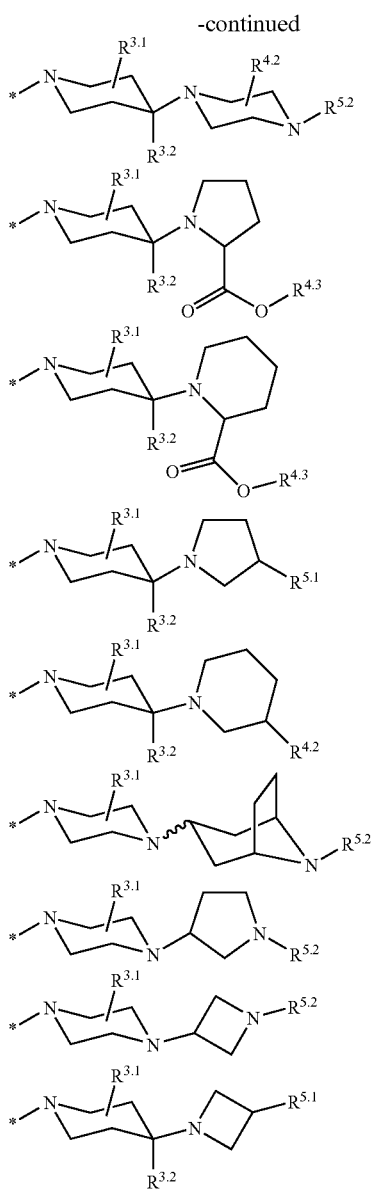

wherein
R^{3.1} denotes H, H₃C or R^{3.1.1}—O—C(O),
R^{3.1.1} denotes H, $C_{1-6}$-alkyl, $(C_{1-3}$-alkyl$)_2$N—$C_{2-4}$-alkylene, $(C_{1-3}$-alkyl$)_2$N—C(O)—$C_{1-3}$-alkylene or R^{3.1.1.1}—$C_{2-4}$-alkylene,
R^{3.1.1.1} denotes a group selected from

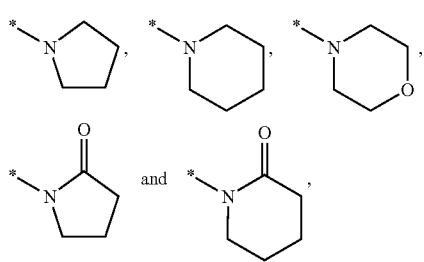

R^{3.2} denotes H, $C_{1-3}$-alkyl or R^{3.2.1}—O—C(O),
R^{3.2.1} denotes H, $C_{1-6}$-alkyl, $(C_{1-3}$-alkyl$)_2$N—$C_{2-4}$-alkylene, $(C_{1-3}$-alkyl$)_2$N—C(O)—$C_{1-3}$-alkylene or R^{3.2.1.1}—$C_{2-4}$-alkylene,
R^{3.2.1.1} denotes a group selected from

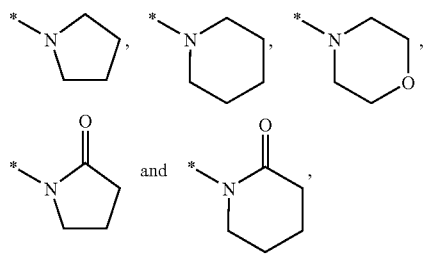

R^{4.1} denotes H or $C_{1-3}$-alkyl,
R^{4.2} denotes H, $C_{1-3}$-alkyl or R^{4.2.1}—O—C(O),
R^{4.2.1} denotes H, $C_{1-6}$-alkyl, $(C_{1-3}$-alkyl$)_2$N—$C_{2-4}$-alkylene, $(C_{1-3}$-alkyl$)_2$N—C(O)—$C_{1-3}$-alkylene or R^{4.2.1.1}—$C_{2-4}$-alkylene,
R^{4.2.1.1} denotes a group selected from

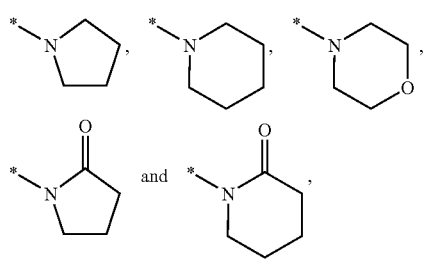

R^{4.3} denotes H, $C_{1-6}$-alkyl, $H_2$N—$C_{2-4}$-alkylene, $(C_{1-3}$-alkyl$)$-NH—$C_{2-4}$-alkylene, $(C_{1-3}$-alkyl$)_2$N—$C_{2-4}$-alkylene, $H_2$N—C(O)—$C_{1-3}$-alkylene, $(C_{1-3}$-alkyl$)$-NH—C(O)—$C_{1-3}$-alkylene, $(C_{1-3}$-alkyl$)_2$N—C(O)—$C_{1-3}$-alkylene or R^{4.3.1}—$C_{2-4}$-alkylene, and
R^{4.3.1} denotes a group selected from

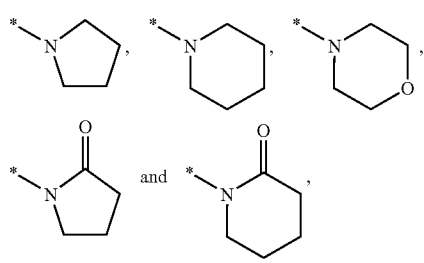

R^{5.1} denotes H, H₃C, R^{5.1.1}—O—C(O), R^{5.1.1}—O—C(O)—$C_{1-3}$-alkylene-NH, R^{5.1.1}—O—C(O)—$C_{1-3}$-alkylene-N($C_{1-3}$-alkyl), R^{5.1.1}—O—C(O)—$C_{1-3}$-alkylene-O, R^{5.1.1}—O—C(O)—$C_{1-3}$-alkylene, R^{5.1.1}—O—C(O)—C(O), R^{5.1.1}—O—C(O)—C(O)—O, R^{5.1.1}—O—C(O)—$C_{1-3}$-alkylene-C(O) or R^{5.1.1}—O—C(O)—$C_{1-3}$-alkylene-C(O)—O,
R^{5.1.1} denotes H, $C_{1-8}$-alkyl, phenyl, indanyl, pyridyl-CH₂, HO—$C_{2-4}$-alkylene, $C_{1-6}$-alkyl-O—$C_{2-4}$-alkylene, $H_2$N—$C_{2-4}$-alkylene, $(C_{1-6}$-alkyl$)$-NH—$C_{2-4}$-alkylene, $(C_{1-6}$-alkyl$)_2$N—$C_{2-4}$-alkylene, $H_2$N—C (O)—C$_{1-3}$-alkylene, (C$_{1-6}$-alkyl)-NH—C(O)—C$_{1-3}$-alkylene, (C$_{1-6}$-alkyl)$_2$N—C(O)—C$_{1-3}$-alkylene, C$_{1-6}$-alkyl-C(O)—O—C$_{1-3}$-alkylene, C$_{1-6}$-alkyl-O—C(O)—O—C$_{1-3}$-alkylene, R$^{5.1.1.1}$—C(O)—C$_{1-3}$-alkylene or R$^{5.1.1.2}$-C$_{2-4}$-alkylene, R$^{5.1.1.1}$ denotes a group selected from

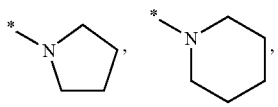

R$^{5.1.1.2}$ denotes a group selected from

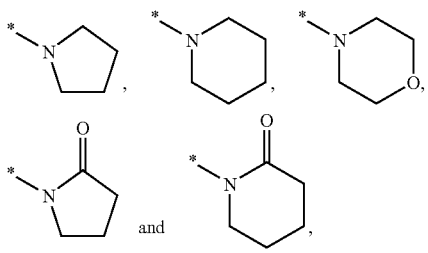

R$^{5.2}$ denotes H, H$_3$C, R$^{5.2.1}$—O—C(O)—C$_{1-3}$-alkylene-NH, R$^{5.2.1}$—O—C(O)—C$_{1-3}$-alkylene-O, R$^{5.2.1}$—O—C(O)—C$_{1-3}$-alkylene, R$^{5.2.1}$—O—C(O)—C(O) or R$^{5.2.1}$—O—C(O)—C$_{1-3}$-alkylene-C(O), R$^{5.2.1}$ denotes H, C$_{1-8}$-alkyl, phenyl, indanyl, pyridyl-CH$_2$, HO—C$_{2-4}$-alkylene, C$_{1-6}$-alkyl-O—C$_{2-4}$-alkylene, C$_{1-6}$-alkyl-O—C$_{2-4}$-alkylene-O—C$_{2-4}$-alkylene, H$_2$N—C$_{2-4}$-alkylene, (C$_{1-6}$-alkyl)-NH—C$_{2-4}$-alkylene, (C$_{1-6}$-alkyl)$_2$N—C$_{2-4}$-alkylene, H$_2$N—C(O)—C$_{1-3}$-alkylene, (C$_{1-6}$-alkyl)-NH—C(O)—C$_{1-3}$-alkylene, (C$_{1-6}$-alkyl)$_2$N—C(O)—C$_{1-3}$-alkylene, C$_{1-6}$-alkyl-C(O)—O—C$_{1-3}$-alkylene, C$_{1-6}$-alkyl-O—C(O)—O—C$_{1-3}$-alkylene, R$^{5.2.1.1}$—C(O)—C$_{1-3}$-alkylene or R$^{5.2.1.2}$-C$_{2-4}$-alkylene, R$^{5.2.1.1}$ denotes a group selected from

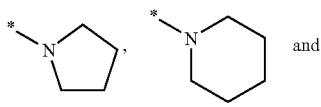

R$^{5.2.1.2}$ denotes a group selected from

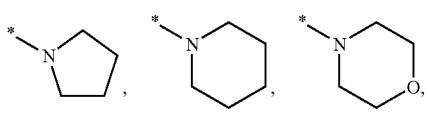

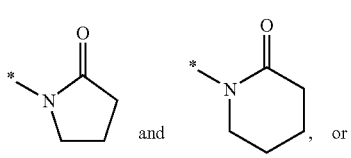

R$^{5.2.1}$ denotes a group of formula

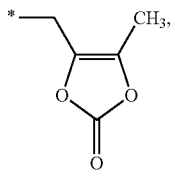

with the proviso that at least one of the groups R$^{3.1}$, R$^{3.2}$, R$^{4.2}$, R$^{5.1}$ or R$^{5.2}$ denotes a group other than H or C$_{1-3}$-alkyl, or a tautomer or salt thereof.

4. A compound of the formula I according to claim 1, wherein

R$^1$ denotes a group of the formula

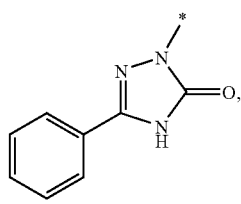

wherein

R$^{1.1}$ denotes H or H$_3$C—O,

R$^2$ denotes a group selected from

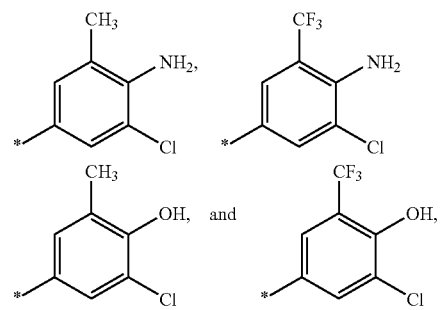

R$^3$-R$^4$ together denote a group of general formulae IV

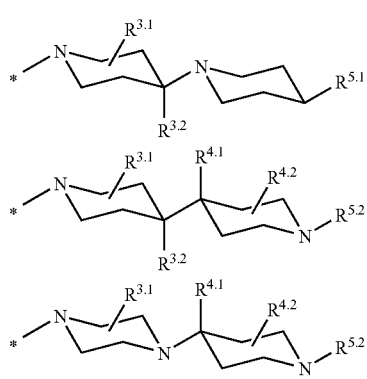

-continued

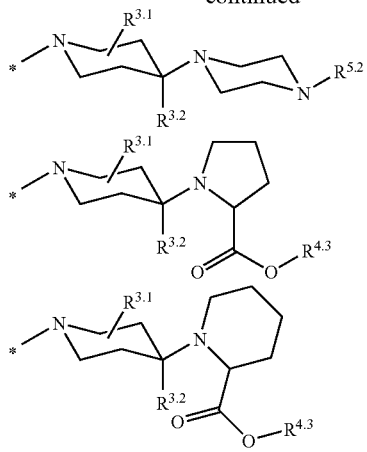

wherein
$R^{3.1}$ denotes H,
$R^{3.2}$ denotes H or $C_{1-3}$-alkyl,
$R^{4.1}$ denotes H or $C_{1-3}$-alkyl,
$R^{4.2}$ denotes H,
$R^{4.3}$ denotes H, $C_{1-6}$-alkyl, $H_2N$—$C_{2-4}$-alkylene, $(C_{1-3}$-alkyl)-NH—$C_{2-4}$-alkylene, $(C_{1-3}$-alkyl)$_2$N—$C_{2-4}$-alkylene, $H_2N$—C(O)—$C_{1-3}$-alkylene, $(C_{1-3}$-alkyl)-NH—C(O)—$C_{1-3}$-alkylene, $(C_{1-3}$-alkyl)$_2$N—C(O)—$C_{1-3}$-alkylene or $R^{4.3.1}$—$C_{2-4}$-alkylene,
$R^{4.3.1}$ denotes a group selected from

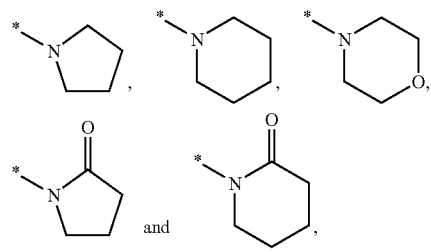

$R^{5.1}$ denotes $R^{5.1.1}$—O—C(O), $R^{5.1.1}$—O—C(O)—$C_{1-3}$-alkylene-NH, $R^{5.1.1}$—O—C(O)—$C_{1-3}$-alkylene-O, $R^{5.1.1}$—O—C(O)—$C_{1-3}$-alkylene, $R^{5.1.1}$—O—C(O)—C(O) or $R^{5.1.1}$—O—C(O)—$C_{1-3}$-alkylene-C(O),
$R^{5.1.1}$ denotes H, $C_{1-8}$-alkyl, phenyl, indanyl, pyridyl-$C_{1-3}$-alkylene, HO—$C_{2-4}$-alkylene, $C_{1-6}$-alkyl-O—$C_{2-4}$-alkylene, $H_2N$—$C_{2-4}$-alkylene, $(C_{1-6}$-alkyl)-NH—$C_{2-4}$-alkylene, $(C_{1-6}$-alkyl)$_2$N—$C_{2-4}$-alkylene, $H_2N$—C(O)—$C_{1-3}$-alkylene, $(C_{1-6}$-alkyl)-NH—C(O)—$C_{1-3}$-alkylene, $(C_{1-6}$-alkyl)$_2$N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.1.1.1}$—C(O)—$C_{1-3}$-alkylene or $R^{5.1.1.2}$—$C_{2-4}$-alkylene,
$R^{5.1.1.1}$ denotes a group selected from

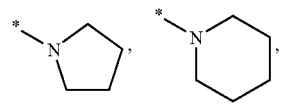

$R^{5.1.1.2}$ denotes a group selected from

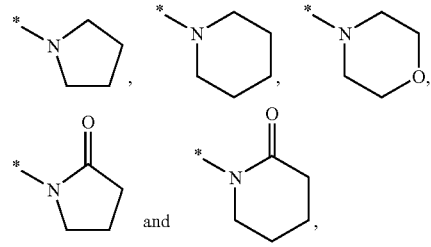

$R^{5.2}$ denotes $R^{5.2.1}$—O—C(O)—$C_{1-3}$-alkylene-NH, $R^{5.2.1}$—O—C(O)—$C_{1-3}$-alkylene-O, $R^{5.2.1}$—O—C(O)—$C_{1-3}$-alkylene, $R^{5.2.1}$—O—C(O)—C(O) or $R^{5.2.1}$—O—C(O)—$C_{1-3}$-alkylene-C(O),
$R^{5.2.1}$ denotes H, $C_{1-8}$-alkyl, phenyl, indanyl, pyridyl-$C_{1-3}$-alkylene, HO—$C_{2-4}$-alkylene, $C_{1-6}$-alkyl-O—$C_{2-4}$-alkylene, $H_2N$—$C_{2-4}$-alkylene, $(C_{1-6}$-alkyl)-NH—$C_{2-4}$-alkylene, $(C_{1-6}$-alkyl)$_2$N—$C_{2-4}$-alkylene, $H_2N$—C(O)—$C_{1-3}$-alkylene, $(C_{1-6}$-alkyl)-NH—C(O)—$C_{1-3}$-alkylene, $(C_{1-6}$-alkyl)$_2$N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.2.1.1}$—C(O)—$C_{1-3}$-alkylene or $R^{5.2.1.2}$—$C_{2-4}$-alkylene,
$R^{5.2.1.1}$ denotes a group selected from

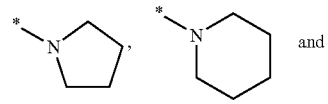

$R^{5.2.1.2}$ denotes a group selected from

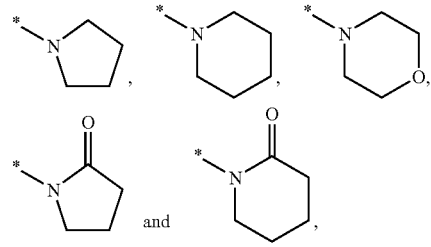

or a tautomer or salt thereof.

5. A compound of the formula I according to claim 1, wherein
$R^1$ denotes a group of the formula

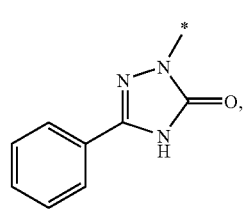

wherein
$R^{1.1}$ denotes H or $H_3C$—O, $R^2$ denotes a group selected from

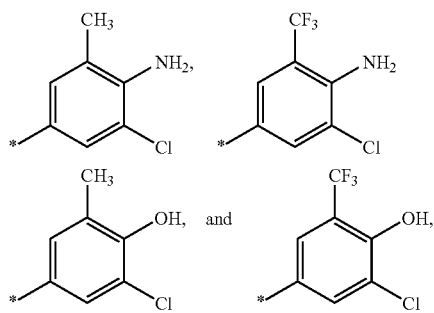

$R^3$-$R^4$ together denote a group of general formulae IV

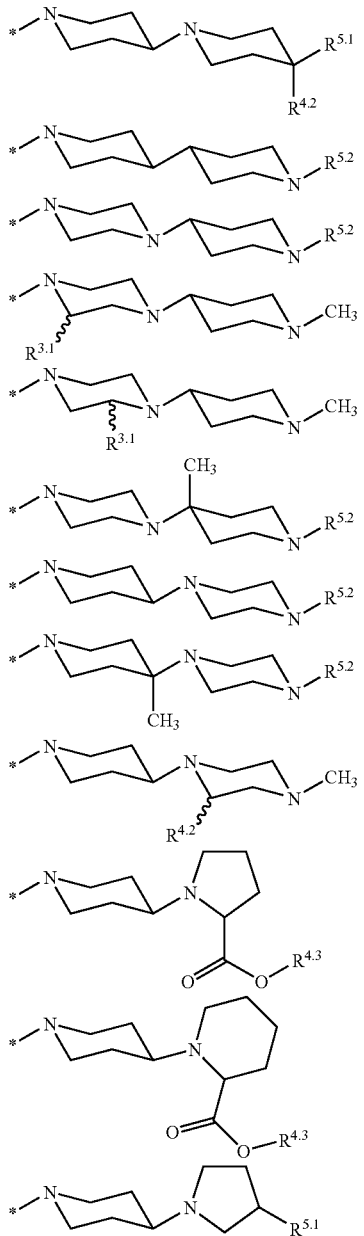

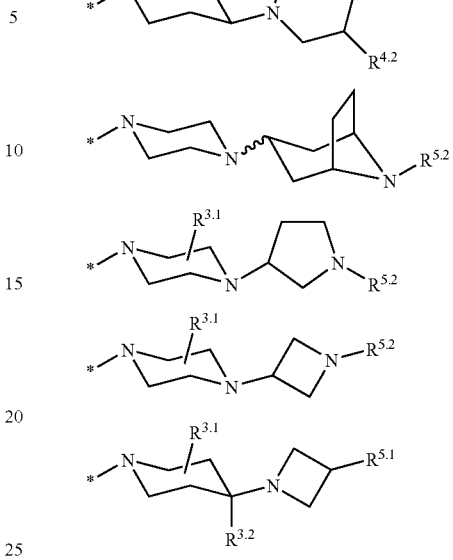

wherein $R^{3.1}$ denotes H or $R^{3.1.1}$—O—C(O), $R^{3.1.1}$ denotes H, $C_{1-6}$-alkyl, $(C_{1-3}$-alkyl$)_2$N—$C_{2-4}$-alkylene, $(C_{1-3}$-alkyl$)_2$N—C(O)—$C_{1-3}$-alkylene or $R^{3.1.1.1}$—$C_{2-4}$-alkylene, $R^{3.1.1.1}$ denotes a group

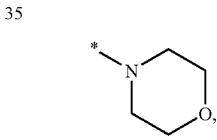

$R^{3.2}$ denotes H, $H_3C$ or $R^{3.2.1}$—O—C(O), $R^{3.2.1}$ denotes H, $C_{1-6}$-alkyl, $(C_{1-3}$-alkyl$)_2$N—$C_{2-4}$-alkylene, $(C_{1-3}$-alkyl$)_2$N—C(O)—$C_{1-3}$-alkylene or $R^{3.2.1.1}$—$C_{2-4}$-alkylene, $R^{3.2.1.1}$ denotes a group

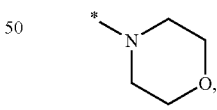

$R^{4.2}$ denotes H or $H_3C$, $R^{4.3}$ denotes H, $C_{1-6}$-alkyl, $(C_{1-3}$-alkyl$)_2$N—$C_{2-4}$-alkylene, $(C_{1-3}$-alkyl$)_2$N—C(O)—$C_{1-3}$-alkylene or $R^{4.3.1}$—$C_{2-4}$-alkylene, and $R^{4.3.1}$ denotes a group selected from

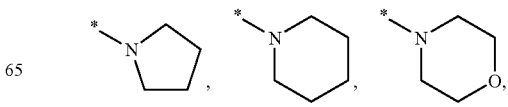

-continued

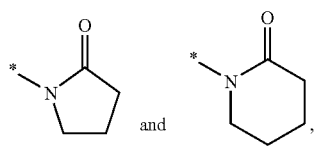 and ,

R$^{5.1}$ denotes H, H$_3$C, R$^{5.1.1}$—O—C(O), R$^{5.1.1}$—O—C(O)—C$_{1-3}$-alkylene-NH, R$^{5.1.1}$—O—C(O)—C$_{1-3}$-alkylene-N(C$_{1-3}$-alkyl), R$^{5.1.1}$—O—C(O)—C$_{1-3}$-alkylene-O, R$^{5.1.1}$—O—C(O)—C$_{1-3}$-alkylene, R$^{5.1.1}$—O—C(O)—C(O), R$^{5.1.1}$—O—C(O)—C(O)—O—R$^{5.1.1}$—O—C(O)—C$_{1-3}$-alkylene-C(O) or R$^{5.1.1}$—O—C(O)—C$_{1-3}$-alkylene-C(O)—O, R$^{5.1.1}$ denotes H, C$_{1-8}$-alkyl, phenyl, indanyl, pyridyl-methyl, HO—C$_{2-4}$-alkylene, C$_{1-6}$-alkyl-O—C$_{2-4}$-alkylene, H$_2$N—C$_{2-4}$-alkylene, (C$_{1-6}$-alkyl)-NH—C$_{2-4}$-alkylene, (C$_{1-6}$-alkyl)$_2$N—C$_{2-4}$-alkylene, H$_2$N—C(O)—C$_{1-3}$-alkylene, (C$_{1-6}$-alkyl)-NH—C(O)—C$_{1-3}$-alkylene, (C$_{1-6}$-alkyl)$_2$N—C(O)—C$_{1-3}$-alkylene, C$_{1-6}$-alkyl-C(O)—O—C$_{1-3}$-alkylene, C$_{1-6}$-alkyl-O—C(O)—O—C$_{1-3}$-alkylene, R$^{5.1.1.1}$—C(O)—C$_{1-3}$-alkylene or R$^{5.1.1,2}$-C$_{2-4}$-alkylene, R$^{5.1.1.1}$ denotes a group selected from

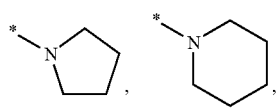 , ,

R$^{5.1.1.2}$ denotes a group selected from

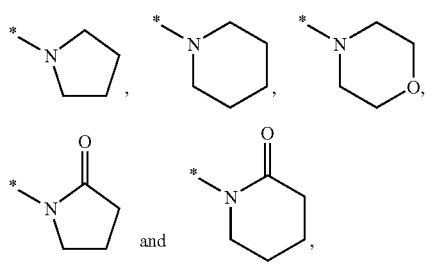 , , ,
and ,

R$^{5.2}$ denotes H, H$_3$C, R$^{5.2.1}$—O—C(O)—C$_{1-3}$-alkylene, R$^{5.2.1}$—O—C(O)—C(O) or R$^{5.2.1}$—O—C(O)—C$_{1-3}$-alkylene-C(O), R$^{5.2.1}$ denotes H, C$_{1-8}$-alkyl, phenyl, indanyl, pyridyl-methyl, HO—C$_{2-4}$-alkylene, C$_{1-6}$-alkyl-O—C$_{2-4}$-alkylene, C$_{1-6}$-alkyl-O—C$_{2-4}$-alkylene-O—C$_{2-4}$-alkylene, H$_2$N—C$_{2-4}$-alkylene, (C$_{1-6}$-alkyl)-NH—C$_{2-4}$-alkylene, (C$_{1-6}$-alkyl)$_2$N—C$_{2-4}$-alkylene, H$_2$N—C(O)—C$_{1-3}$-alkylene, (C$_{1-6}$-alkyl)-NH—C(O)—C$_{1-3}$-alkylene, (C$_{1-6}$-alkyl)$_2$N—C(O)—C$_{1-3}$-alkylene, C$_{1-6}$-alkyl-C(O)—O—C$_{1-3}$-alkylene, C$_{1-6}$-alkyl-O—C(O)—O—C$_{1-3}$-alkylene, R$^{5.2.1.1}$—C(O)—C$_{1-3}$-alkylene or R$^{5.2.1,2}$-C$_{2-4}$-alkylene, R$^{5.2.1.1}$ denotes a group selected from

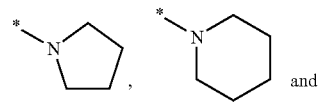 , and

R$^{5.2.1.2}$ denotes a group selected from

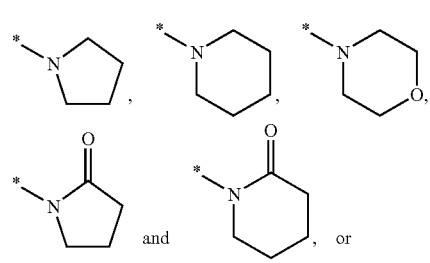 , , ,
and , or

R$^{5.2.1}$ denotes a group of formula

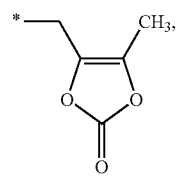

with the proviso that at least one of the groups R$^{3.1}$, R$^{3.2}$, R$^{4.2}$, R$^{5.1}$ or R$^{5.2}$ denotes a group other than H, H$_3$C or C$_{1-3}$-alkyl,
or a tautomer or salt thereof.

6. A compound of the formula I according to claim 1, wherein
R$^1$ denotes a group of the formula

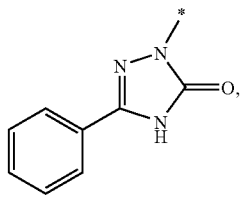

wherein
R$^{1.1}$ denotes H or H$_3$C—O,
R$^2$ denotes a group selected from

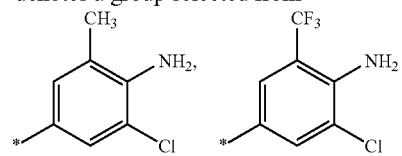

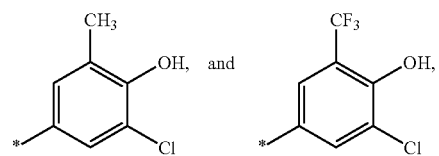

$R^3$-$R^4$ together denote a group of general formulae IV

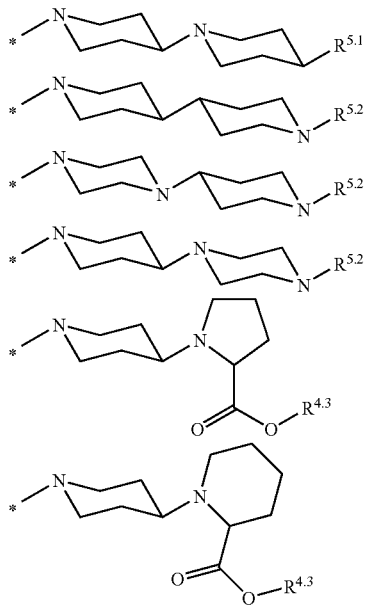

wherein
$R^{4.3}$ denotes H, $C_{1-6}$-alkyl, $(C_{1-3}$-alkyl$)_2$N—$C_{2-4}$-alkylene, $(C_{1-3}$-alkyl$)_2$N—C(O)—$C_{1-3}$-alkylene or $R^{4.3.1}$—$C_{2-4}$-alkylene,
$R^{4.3.1}$ denotes a group selected from

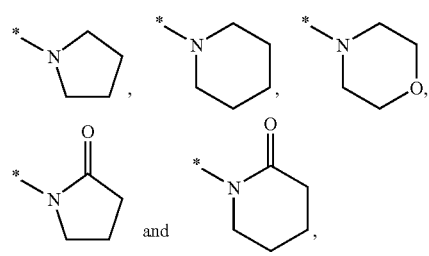

$R^{5.1}$ denotes $R^{5.1.1}$—O—C(O), $R^{5.1.1}$—O—C(O)—$C_{1-3}$-alkylenl-NH, $R^{5.1.1}$—O—C(O)—$C_{1-3}$-alkylene-O, $R^{5.1.1}$—O—C(O)—$C_{1-3}$-alkylene, $R^{5.1.1}$—O—C(O)—C(O) or $R^{5.1.1}$—O—C(O)—$C_{1-3}$-alkylene-C(O),
$R^{5.1.1}$ denotes H, $C_{1-8}$-alkyl, phenyl, indanyl, pyridyl-$CH_2$, HO—$C_{2-4}$-alkylene, $C_{1-6}$-alkyl-O—$C_{2-4}$-alkylene, $H_2N$—$C_{2-4}$-alkylene, $(C_{1-6}$-alkyl)-NH—$C_{2-4}$-alkylene, $(C_{1-6}$-alkyl$)_2$N—$C_{2-4}$-alkylene, $H_2N$—C(O)—$C_{1-3}$-alkylene, $(C_{1-6}$-alkyl)-NH—C(O)—$C_{1-3}$-alkylene, $(C_{1-6}$-alkyl$)_2$N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.1.1.1}$—C(O)—$C_{1-3}$-alkylene or $R^{5.1.1,2}$-$C_{2-4}$-alkylene,
$R^{5.1.1.1}$ denotes a group selected from

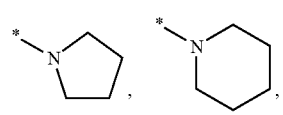

$R^{5.1.1.2}$ denotes a group selected from

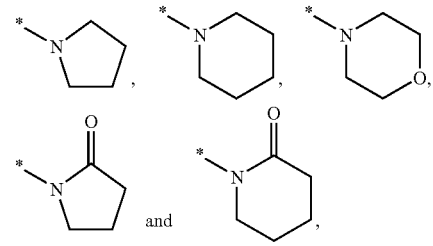

$R^{5.2}$ denotes $R^{5.2.1}$—O—C(O)—$C_{1-3}$-alkylene, $R^{5.2.1}$—O—C(O)—C(O) or $R^{5.2.1}$—O—C(O)—$C_{1-3}$-alkylene-C(O),
$R^{5.2.1}$ denotes H, $C_{1-8}$-alkyl, phenyl, indanyl, pyridyl-$CH_2$, HO—$C_{2-4}$-alkylene, $C_{1-6}$-alkyl-O—$C_{2-4}$-alkylene, $H_2N$—$C_{2-4}$-alkylene, $(C_{1-6}$-alkyl)-NH—$C_{2-4}$-alkylene, $(C_{1-6}$-alkyl$)_2$N—$C_{2-4}$-alkylene, $H_2N$—C(O)—$C_{1-3}$-alkylene, $(C_{1-6}$-alkyl)-NH—C(O)—$C_{1-3}$-alkylene, $(C_{1-6}$-alkyl$)_2$N—C(O)—$C_{1-3}$-alkylene, $C_{1-6}$-alkyl-C(O)—O—$C_{1-3}$-alkylene, $C_{1-6}$-alkyl-O—C(O)—O—$C_{1-3}$-alkylene, $R^{5.2.1.1}$—C(O)—$C_{1-3}$-alkylene or $R^{5.2.1,2}$-$C_{2-4}$-alkylene,
$R^{5.2.1.1}$ denotes a group selected from

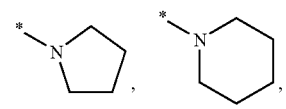

$R^{5.2.1.2}$ denotes a group selected from

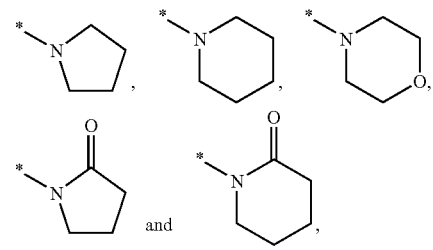

or a tautomer or salt thereof.

7. A compound of the formula I according to claim 1, wherein
$R^1$ denotes a group of the formula

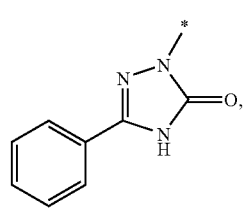

wherein
$R^{1.1}$ denotes H or $H_3C$—O,

517
$R^2$ denotes a group selected from
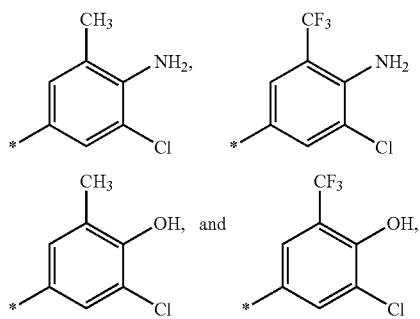
$R^3$-$R^4$ together denote a group of formulae IV
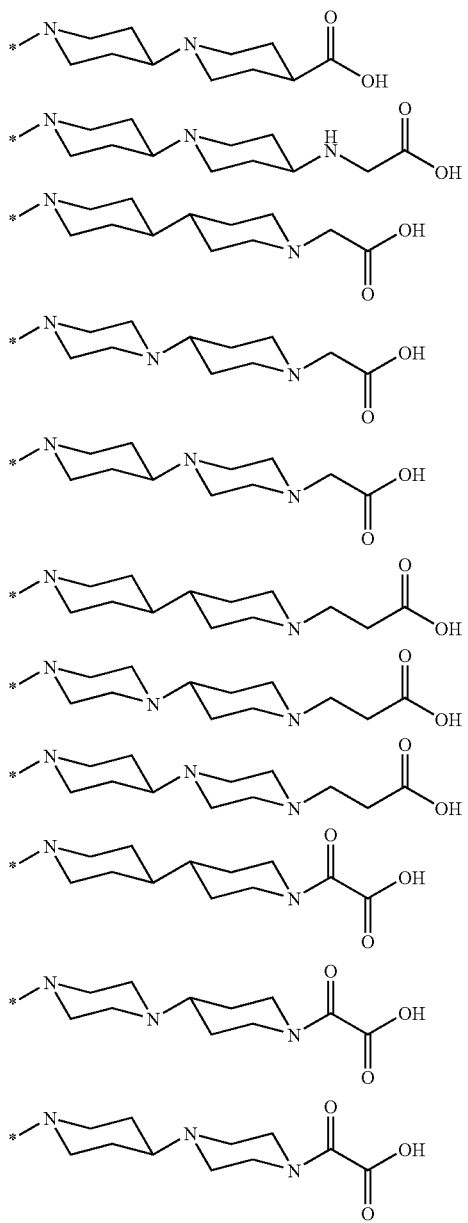
518
-continued
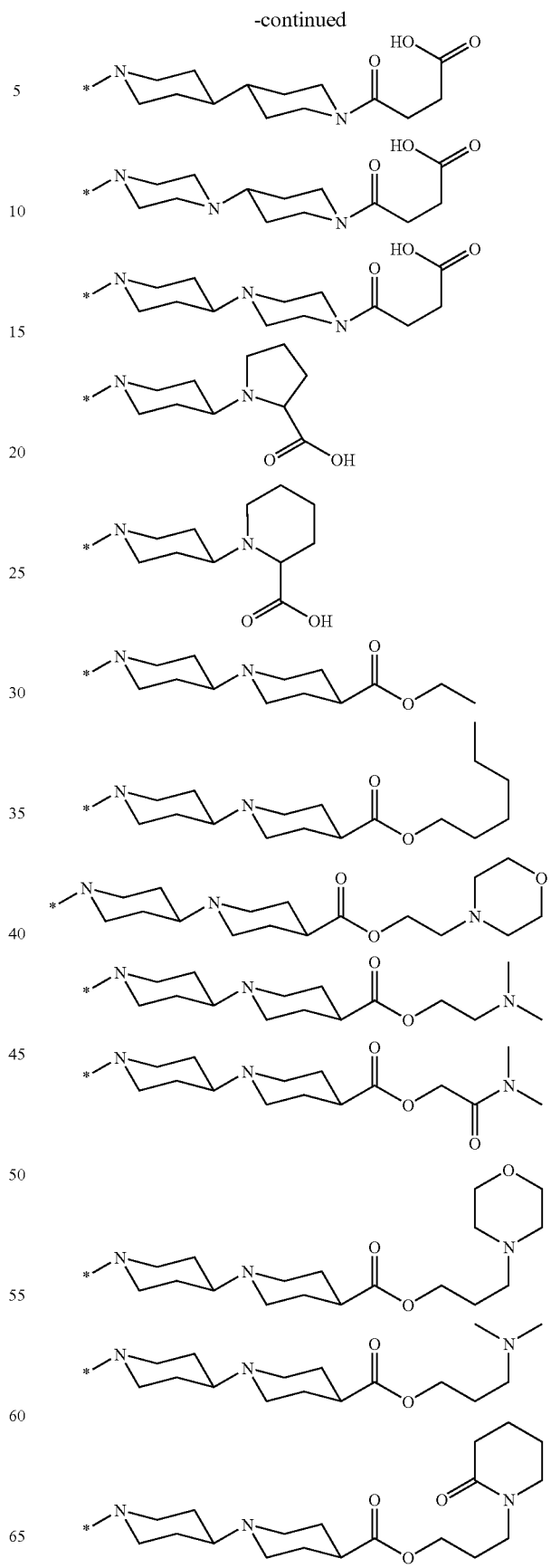

519
-continued
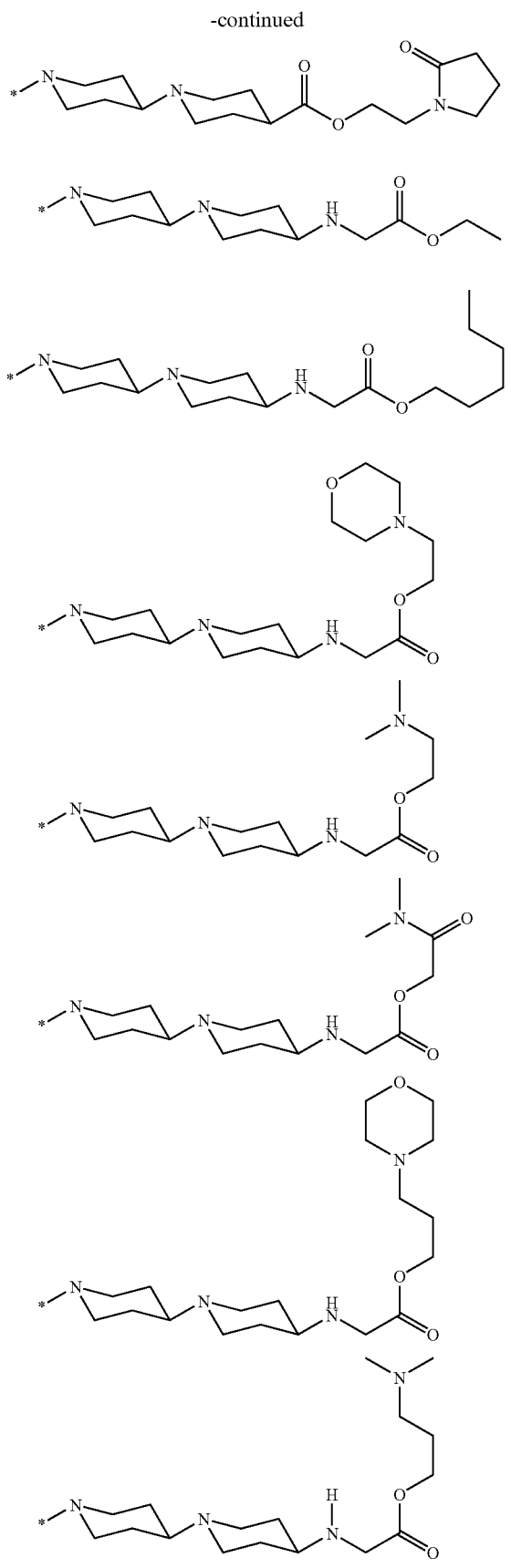
520
-continued
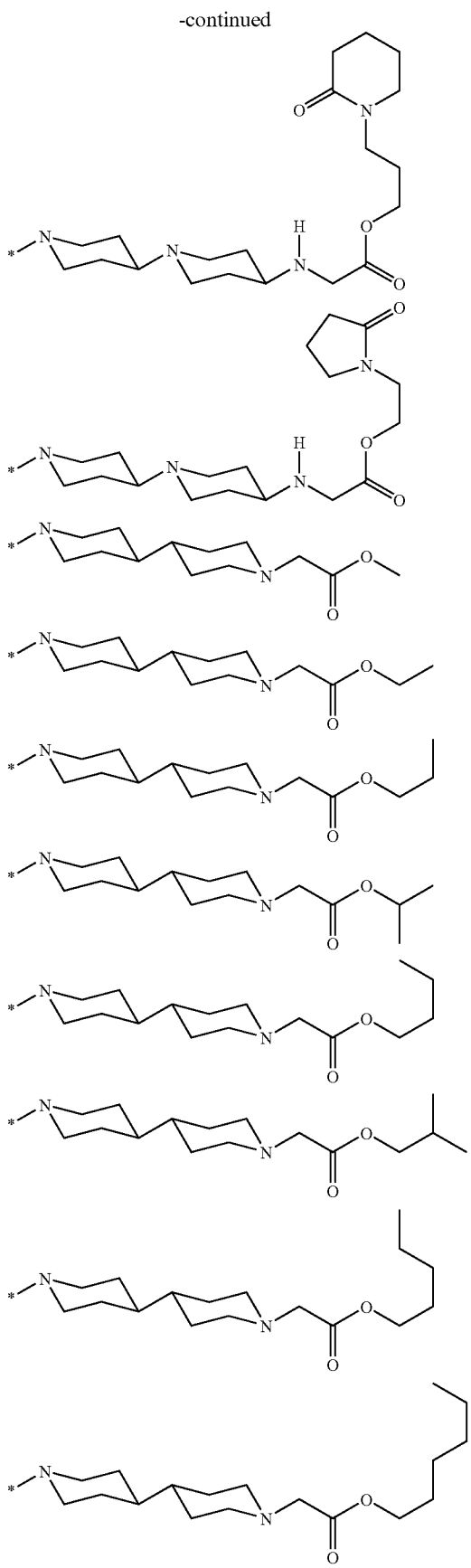

521
-continued
522
-continued
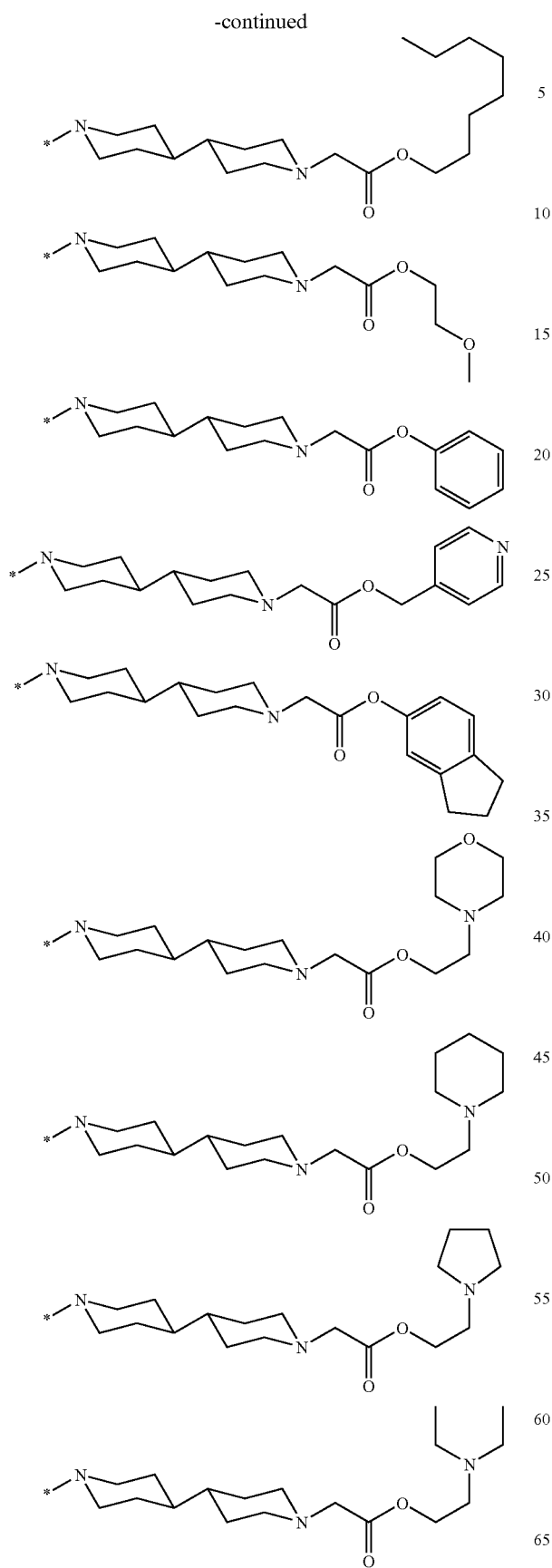
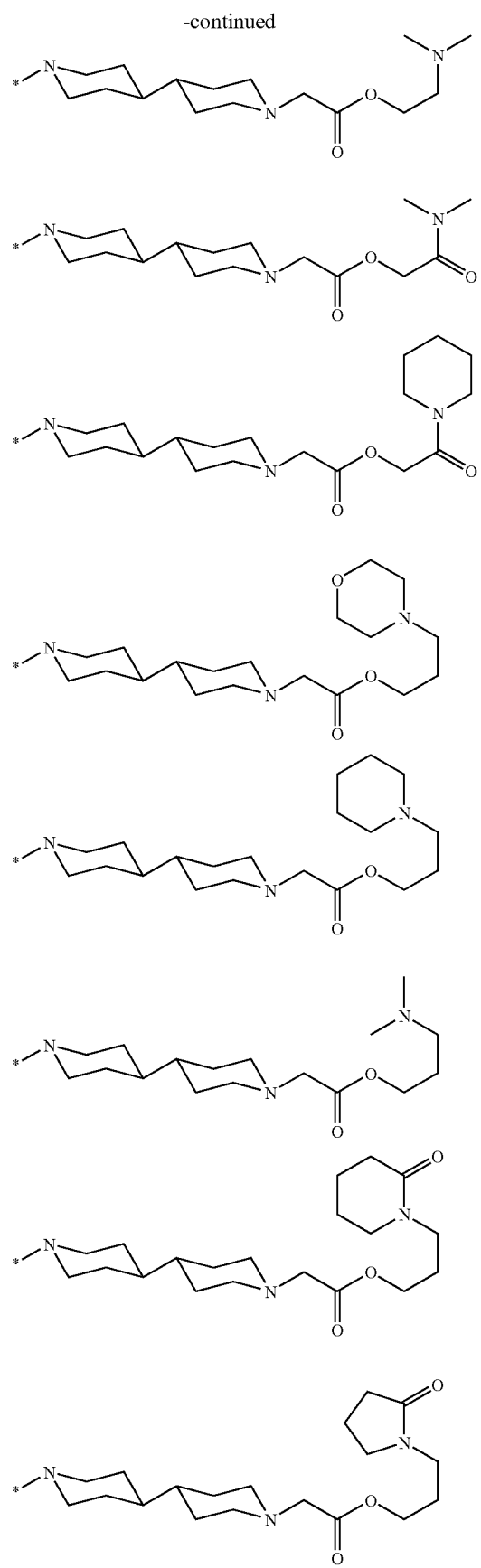

523
-continued
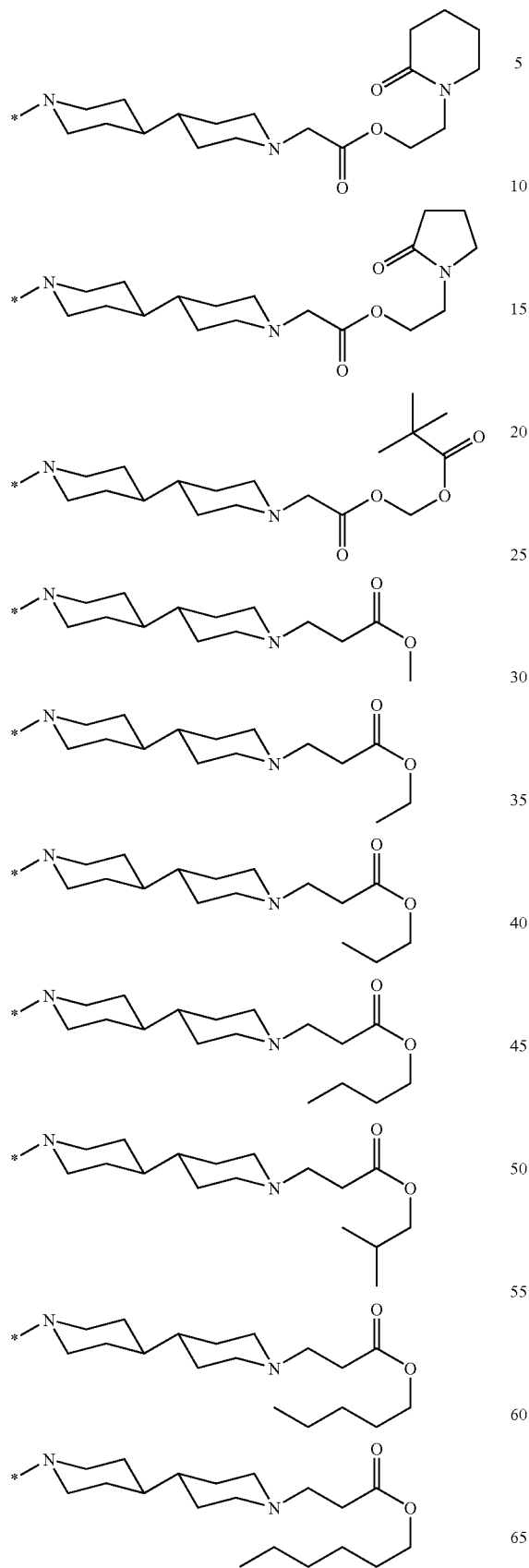
524
-continued
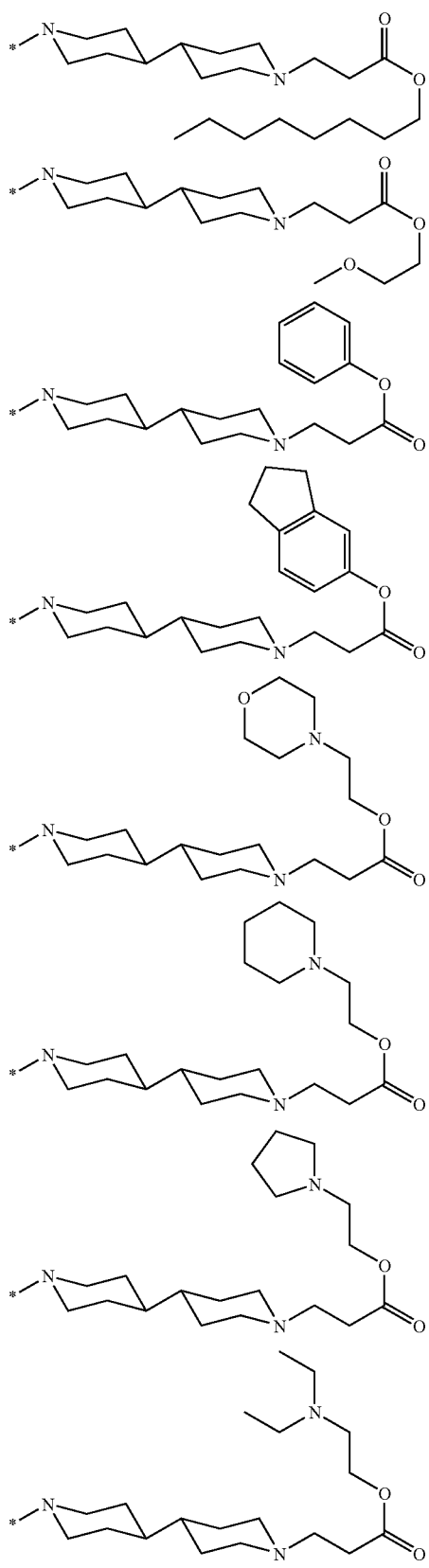

525 526
-continued
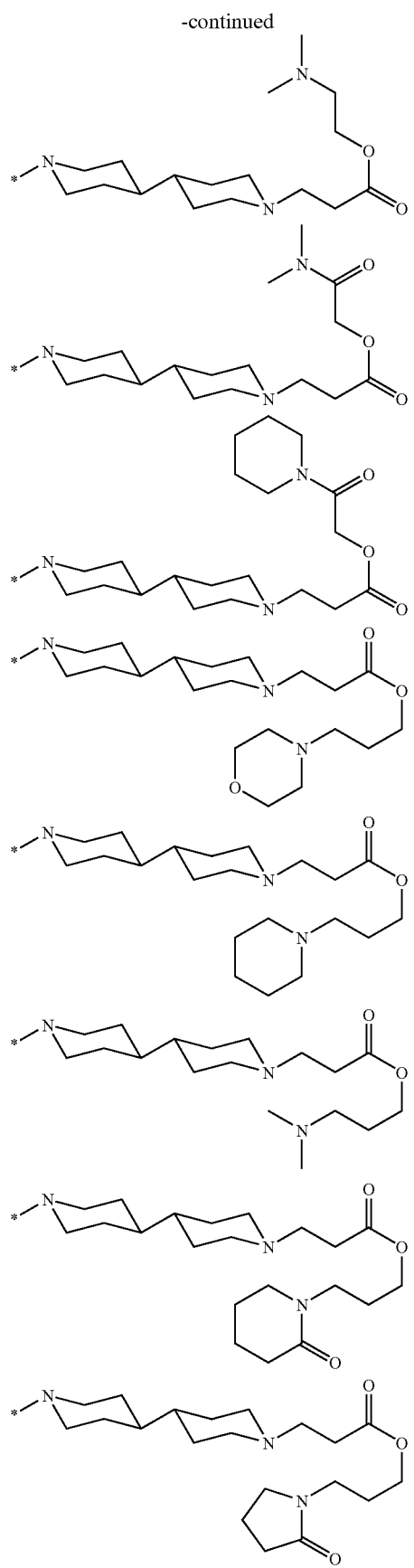
-continued
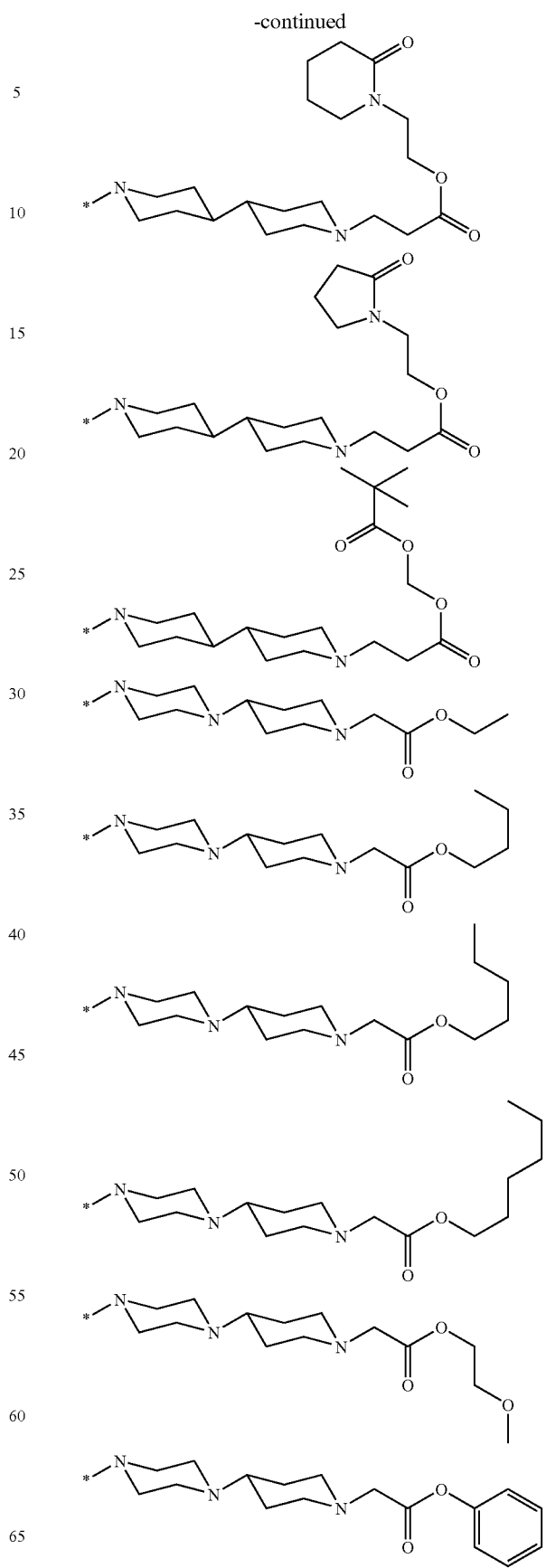

527
-continued
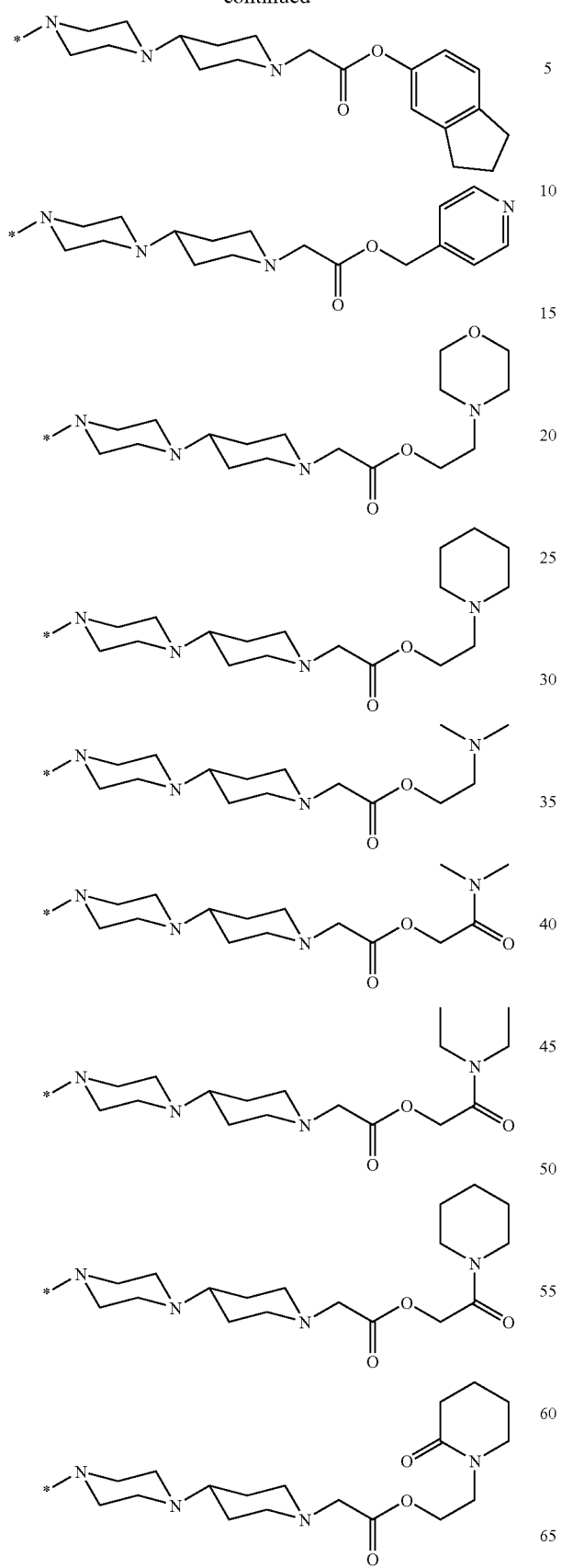
528
-continued
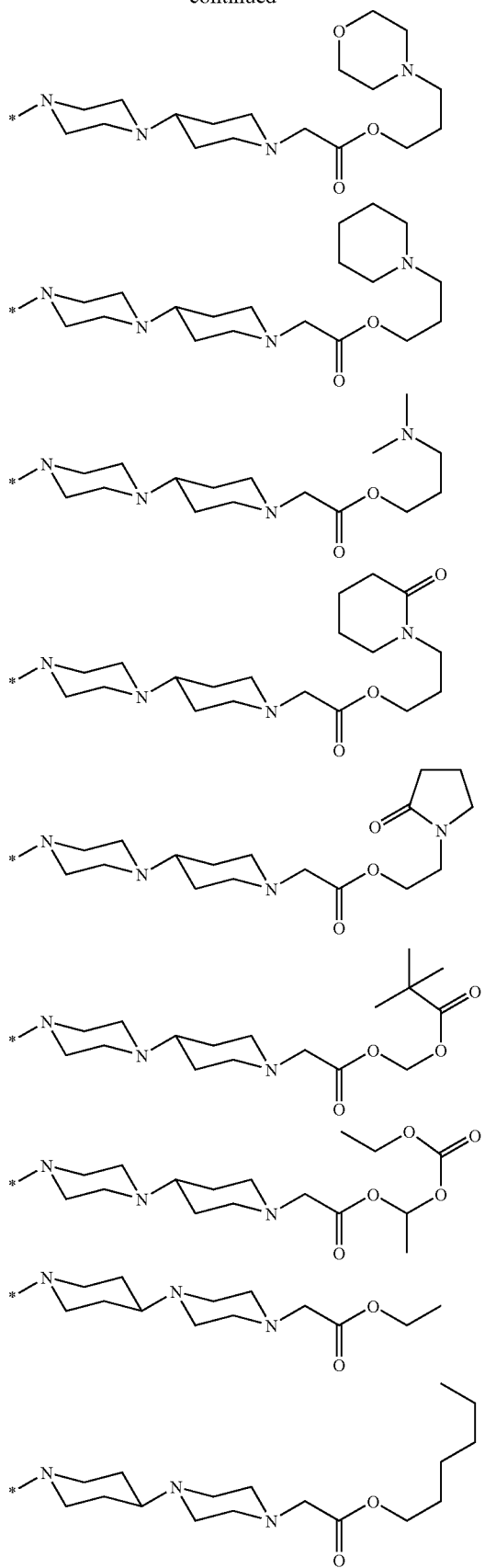

529
-continued
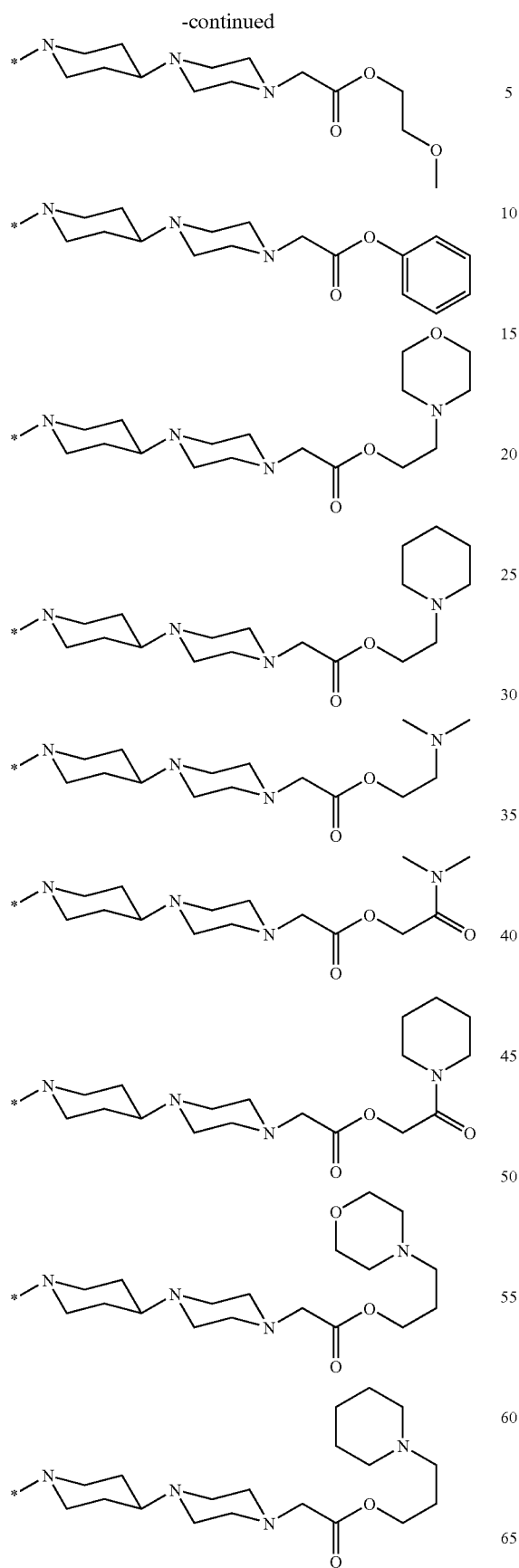
530
-continued
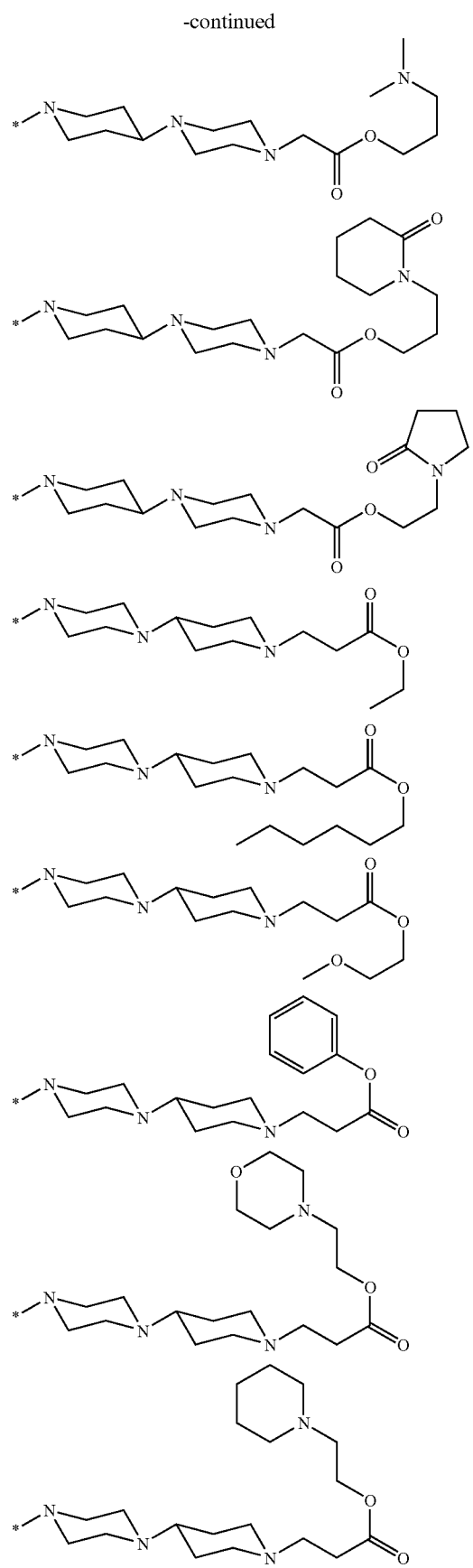

531
-continued
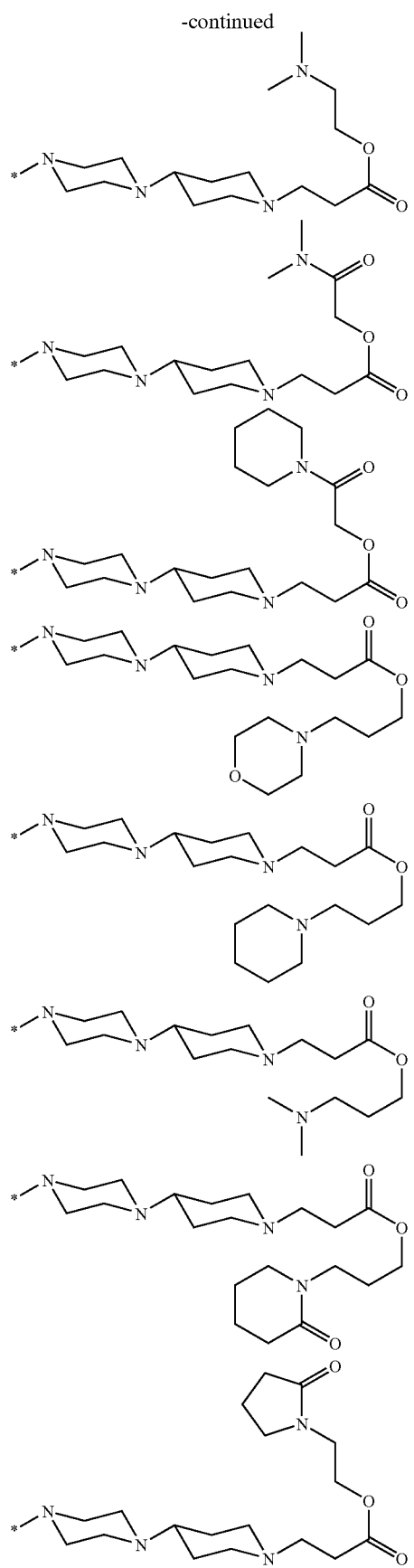
532
-continued
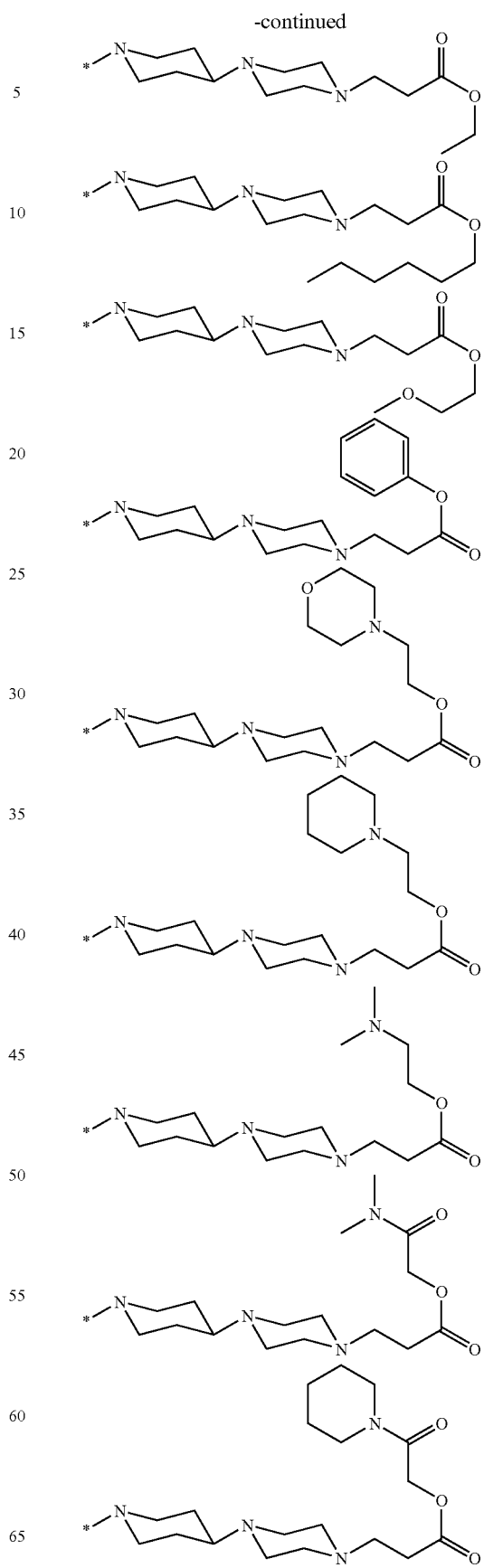

533
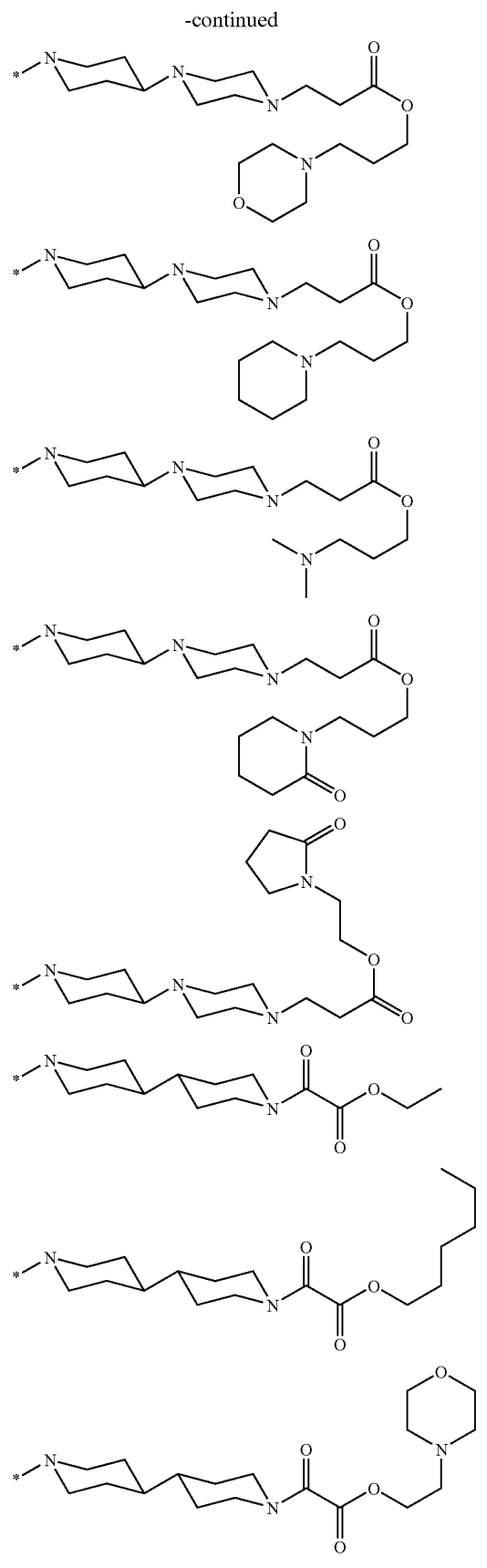
534
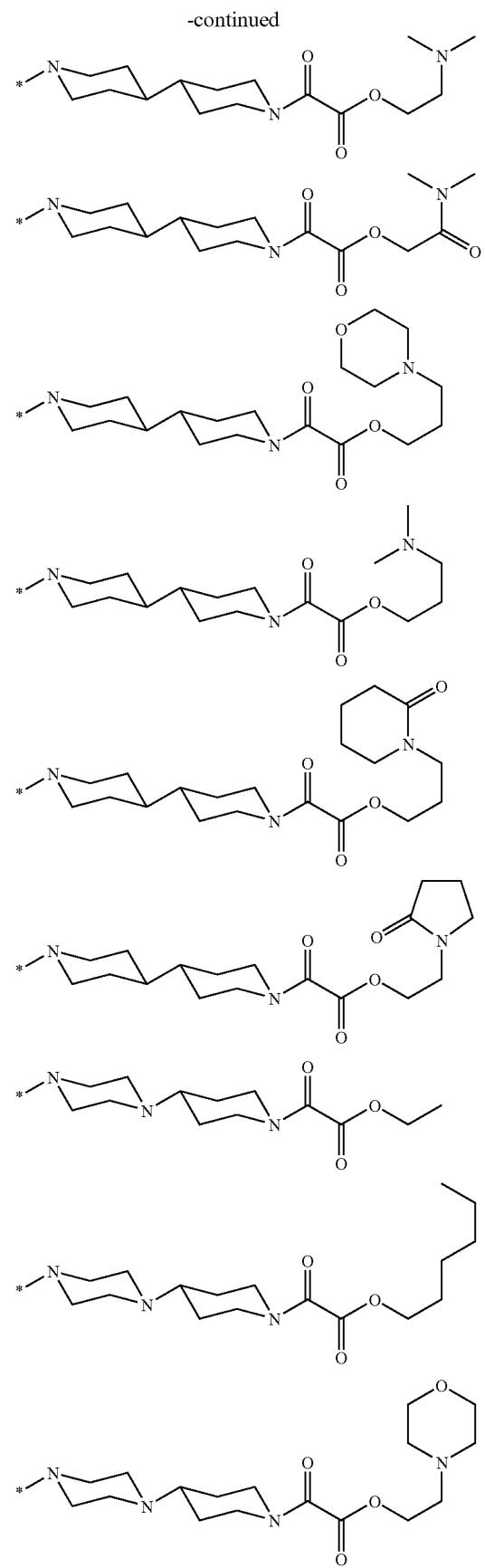

535
-continued
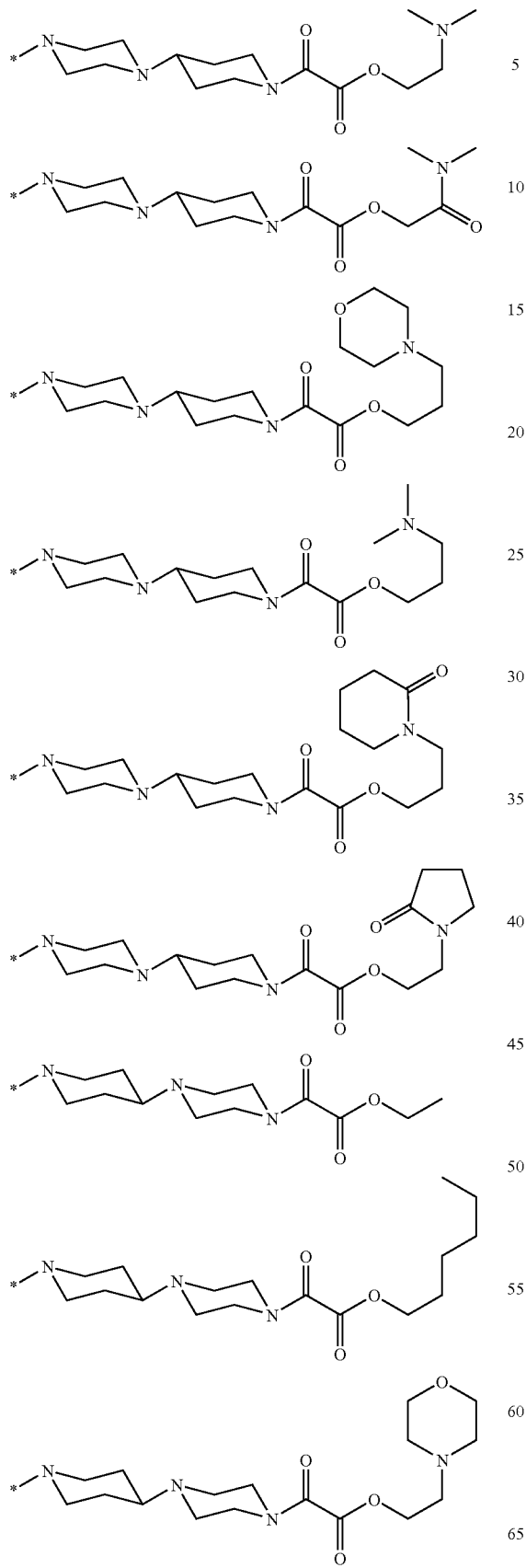
536
-continued
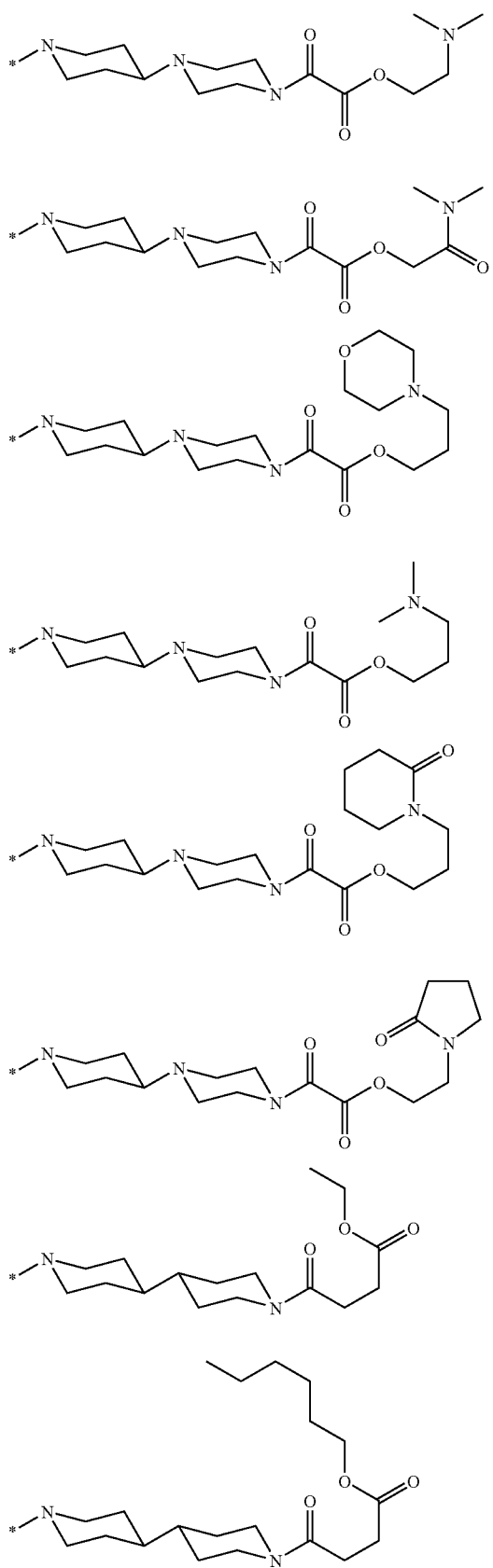

537
-continued
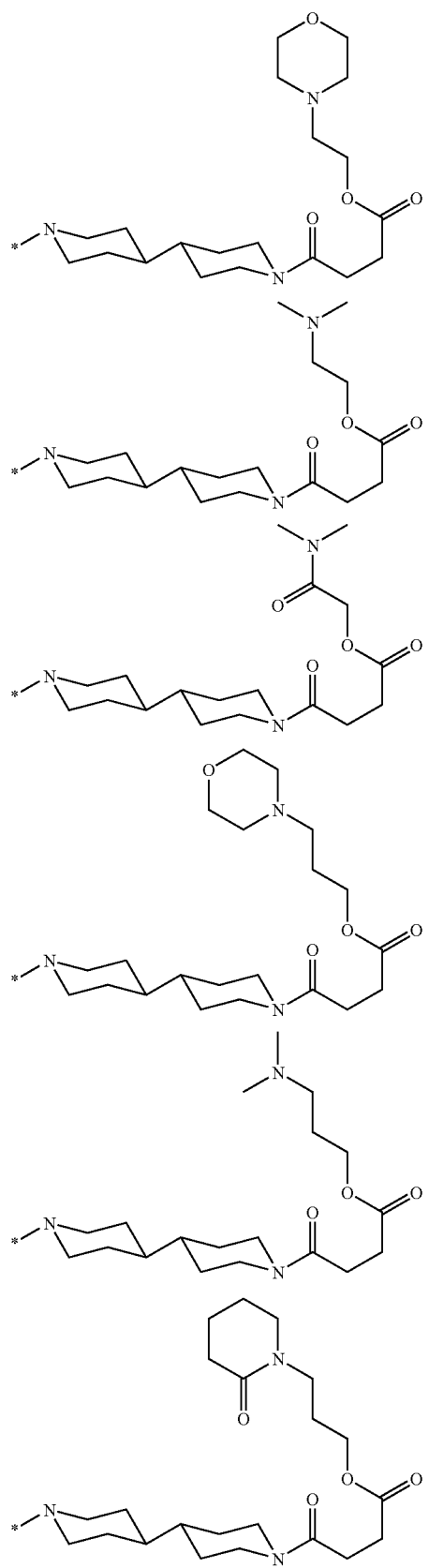
538
-continued
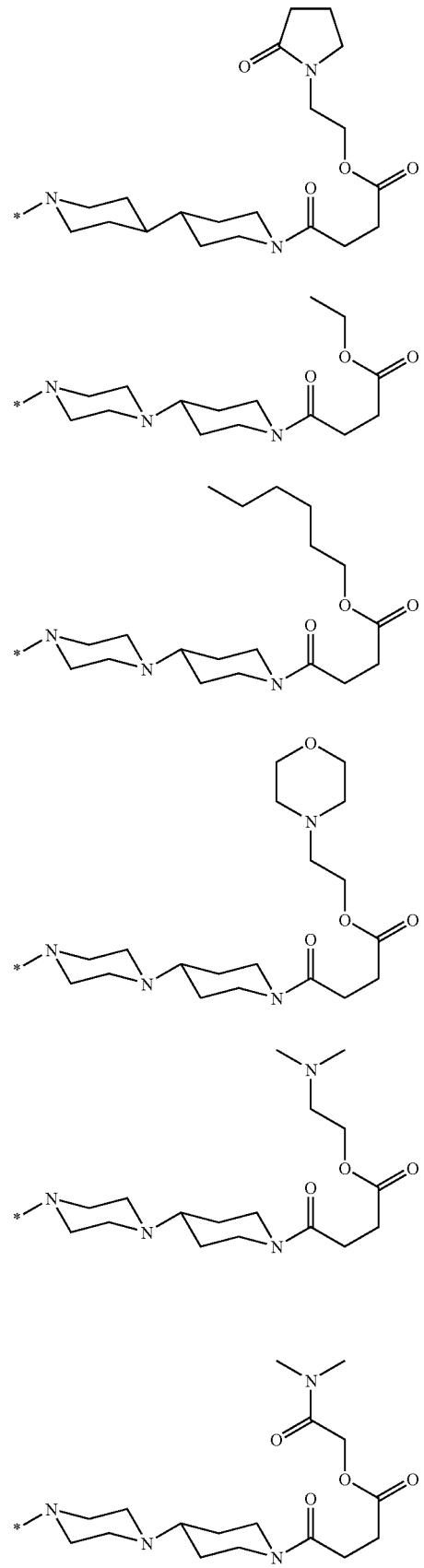

539
-continued
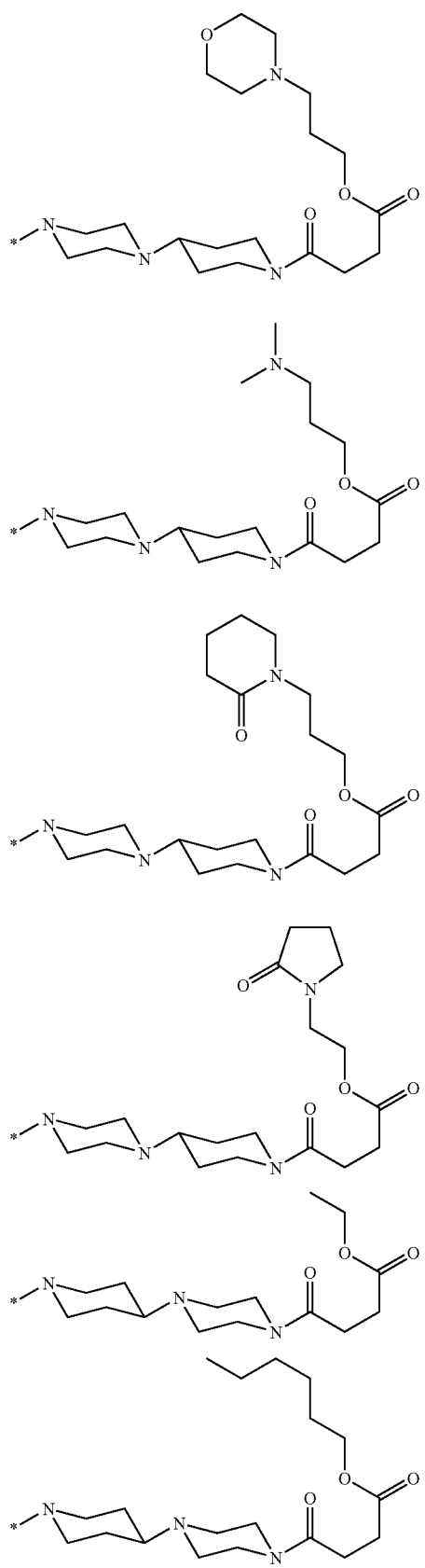
540
-continued
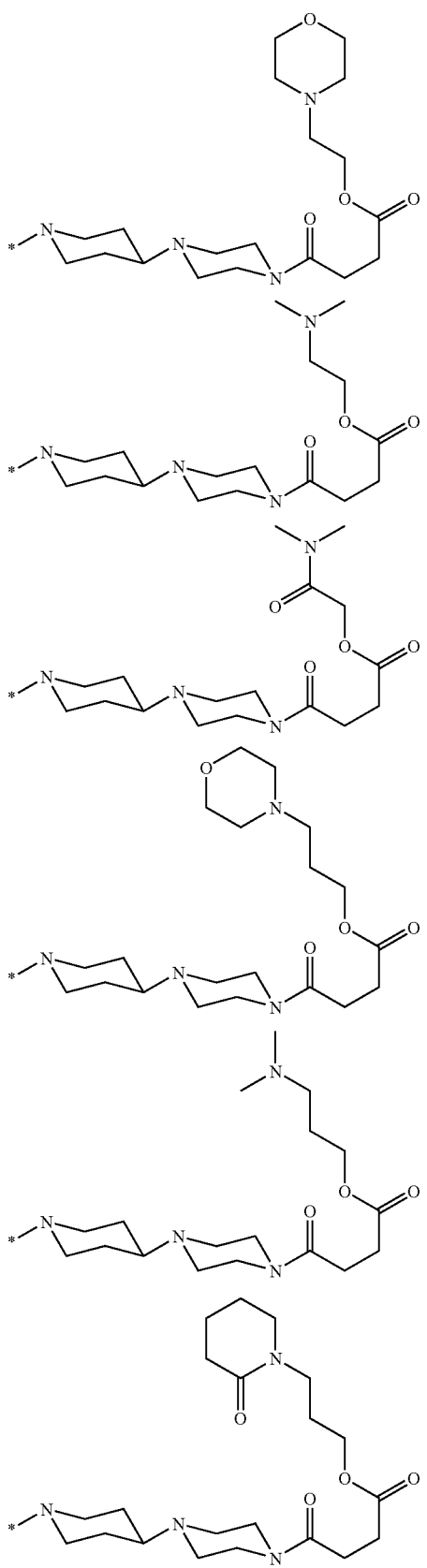

-continued
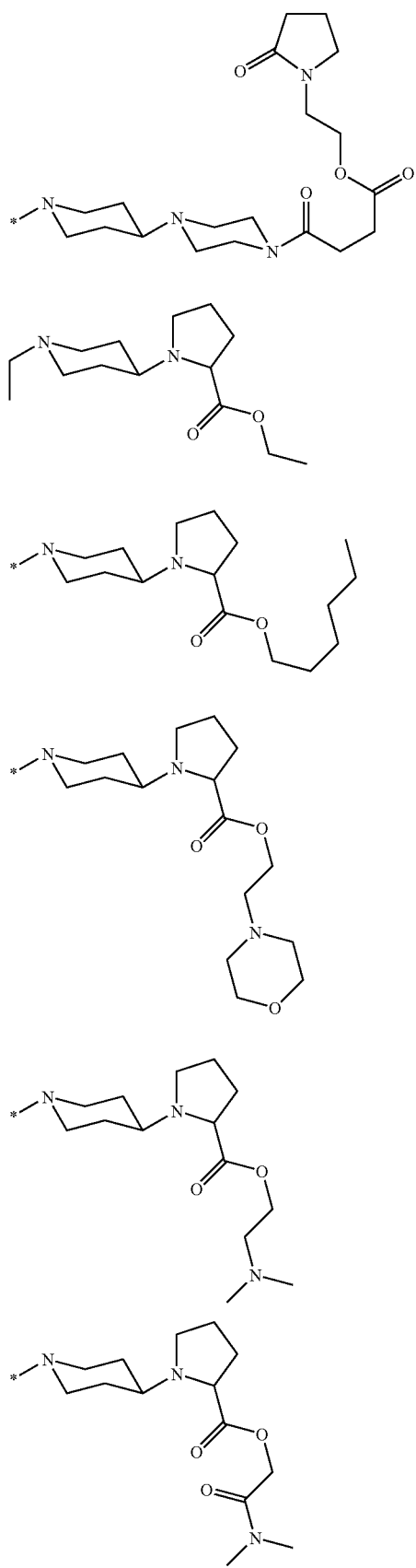
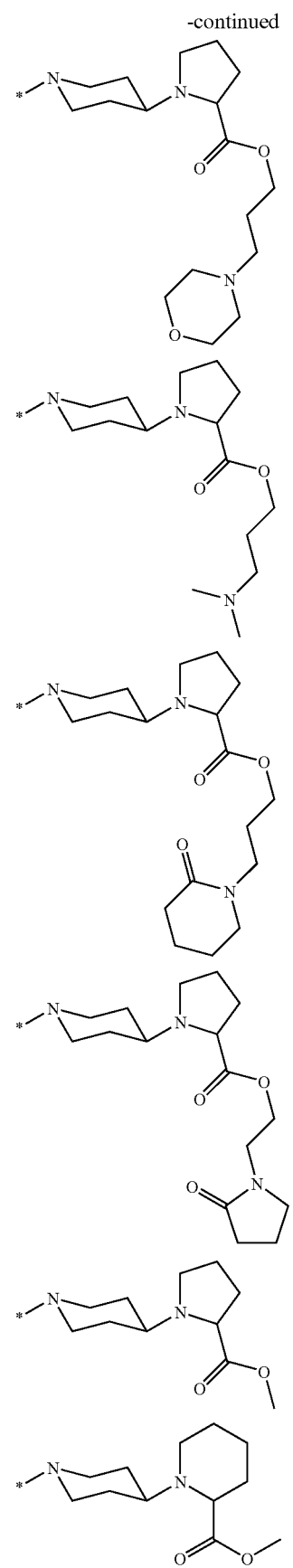

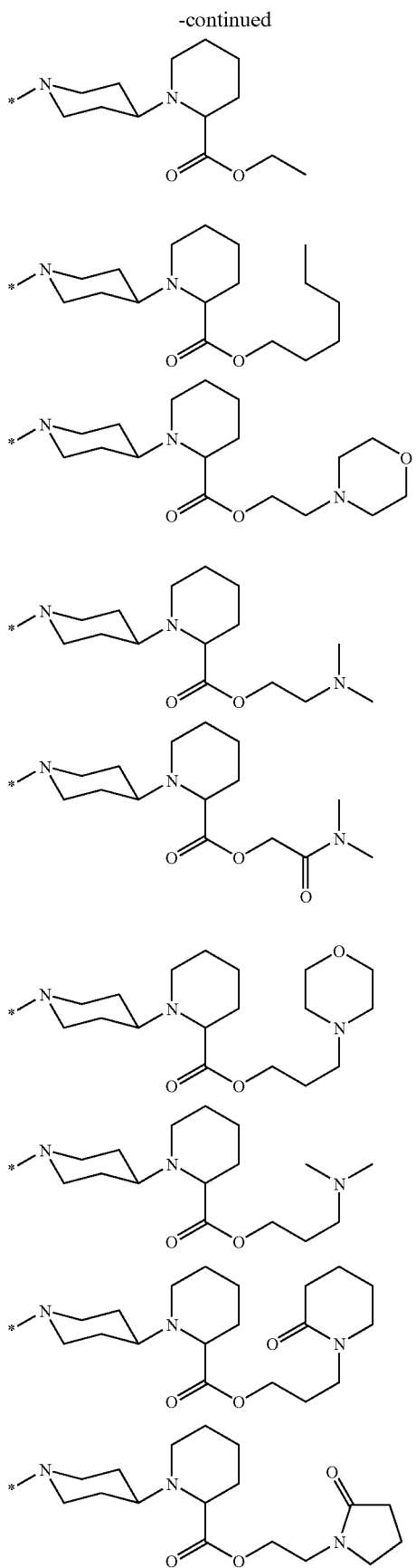
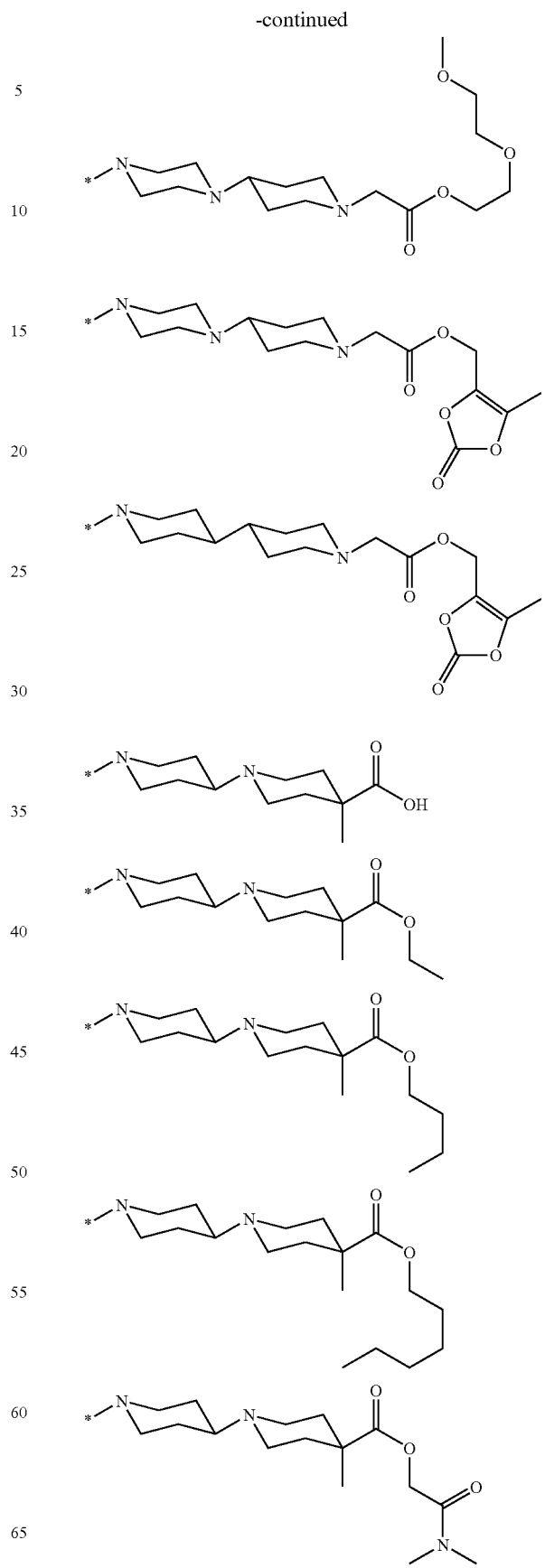

545
-continued
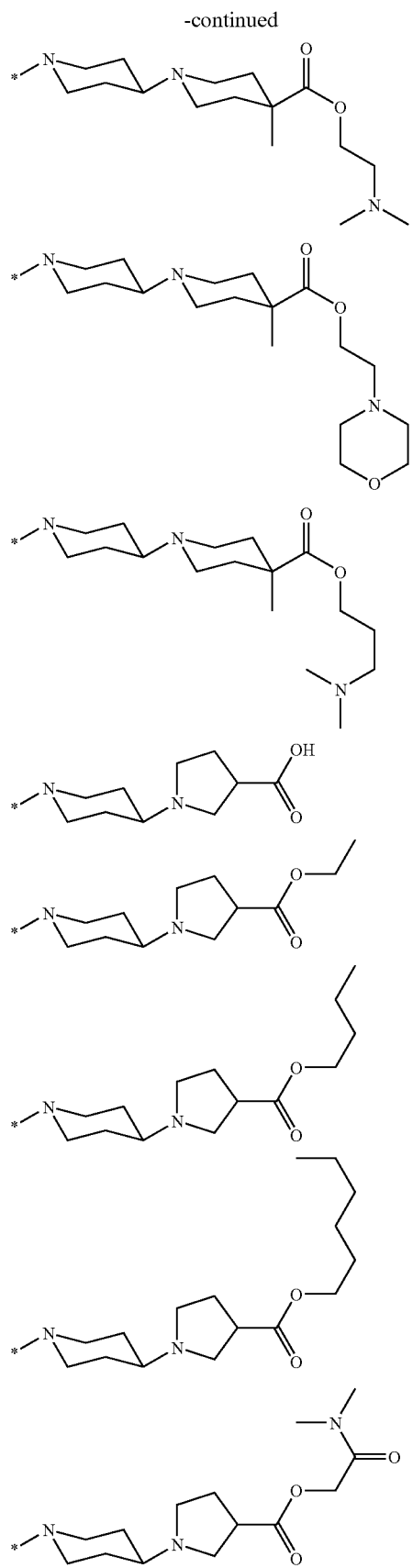
546
-continued
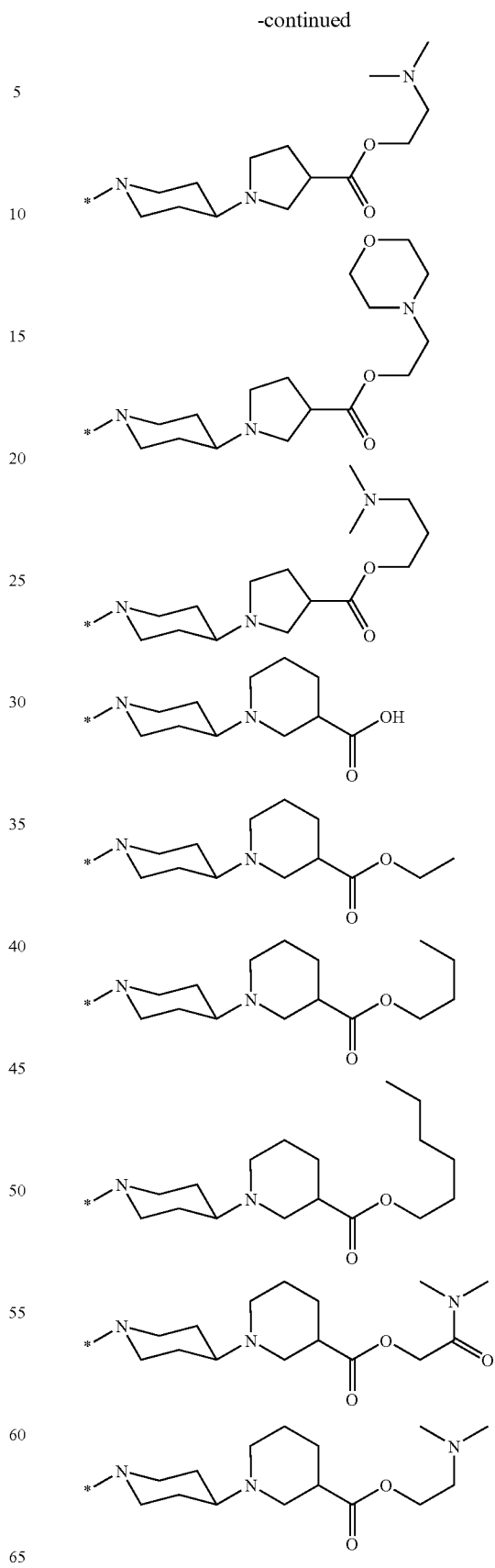

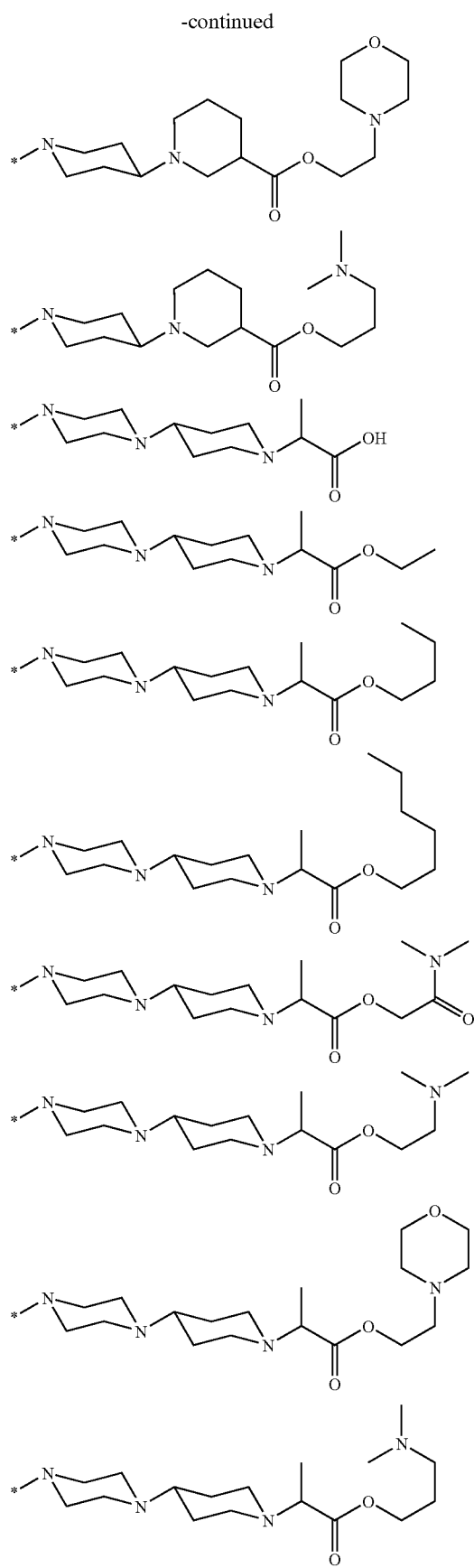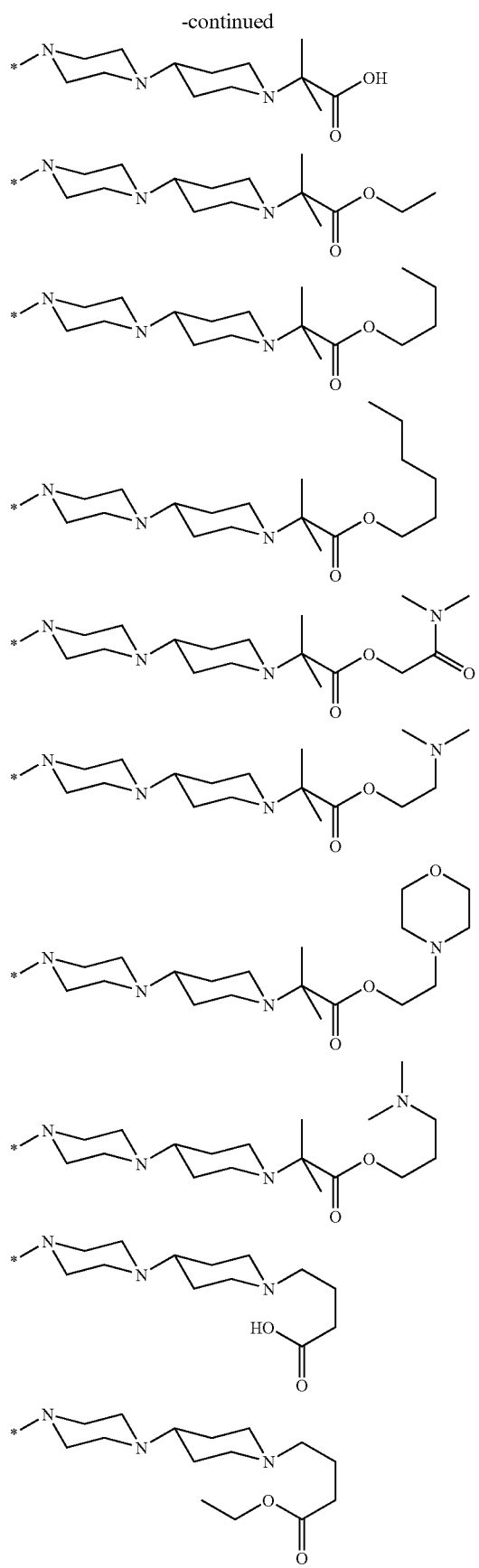

549
-continued
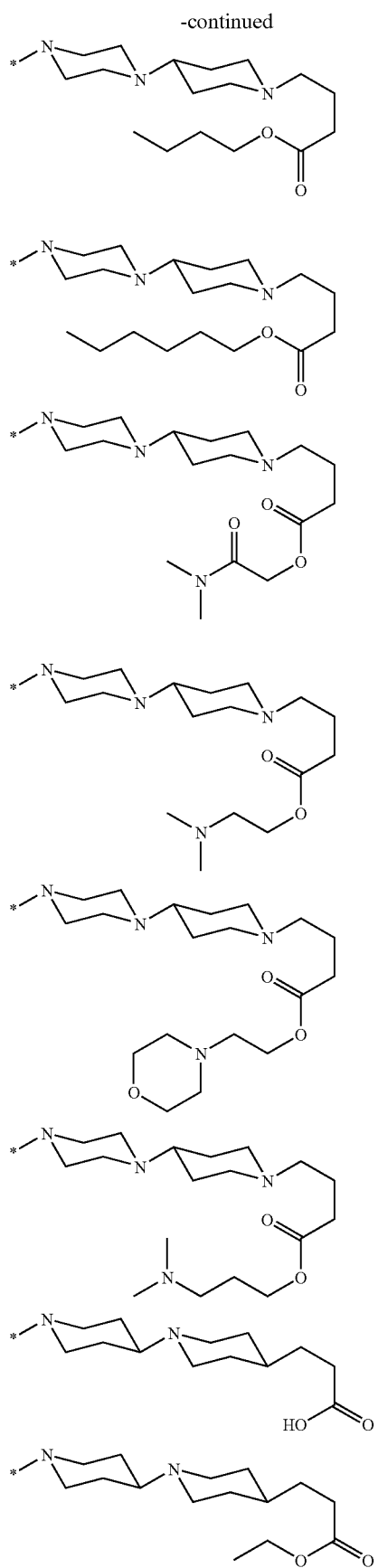
550
-continued
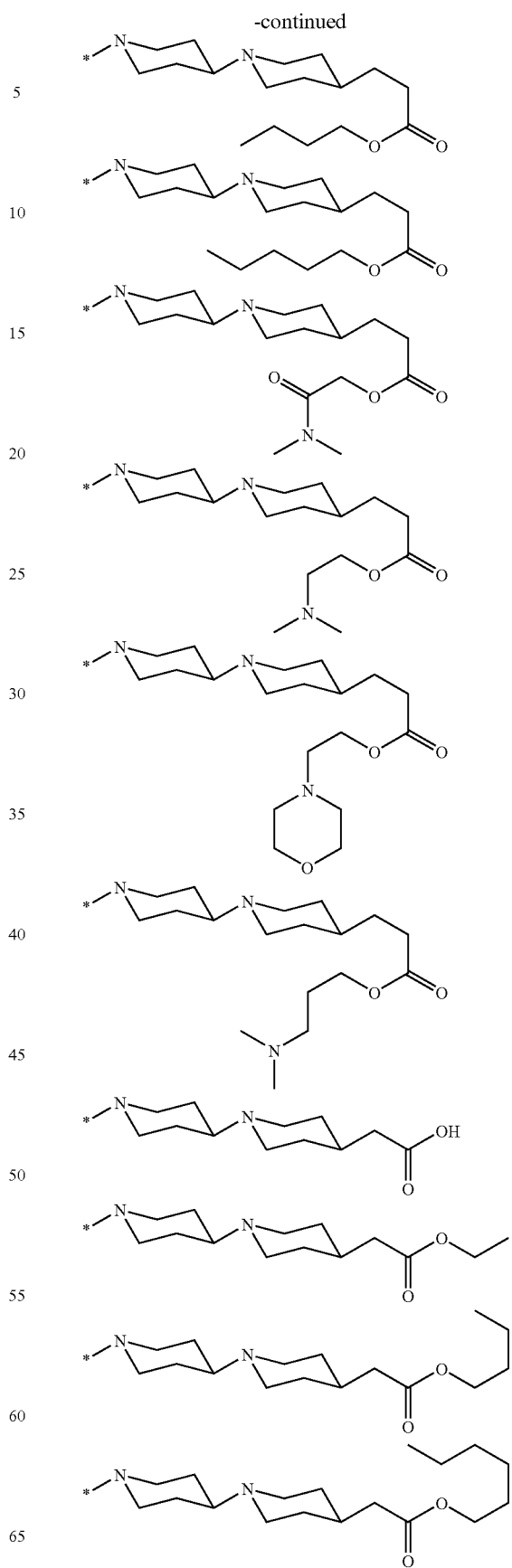

551
-continued
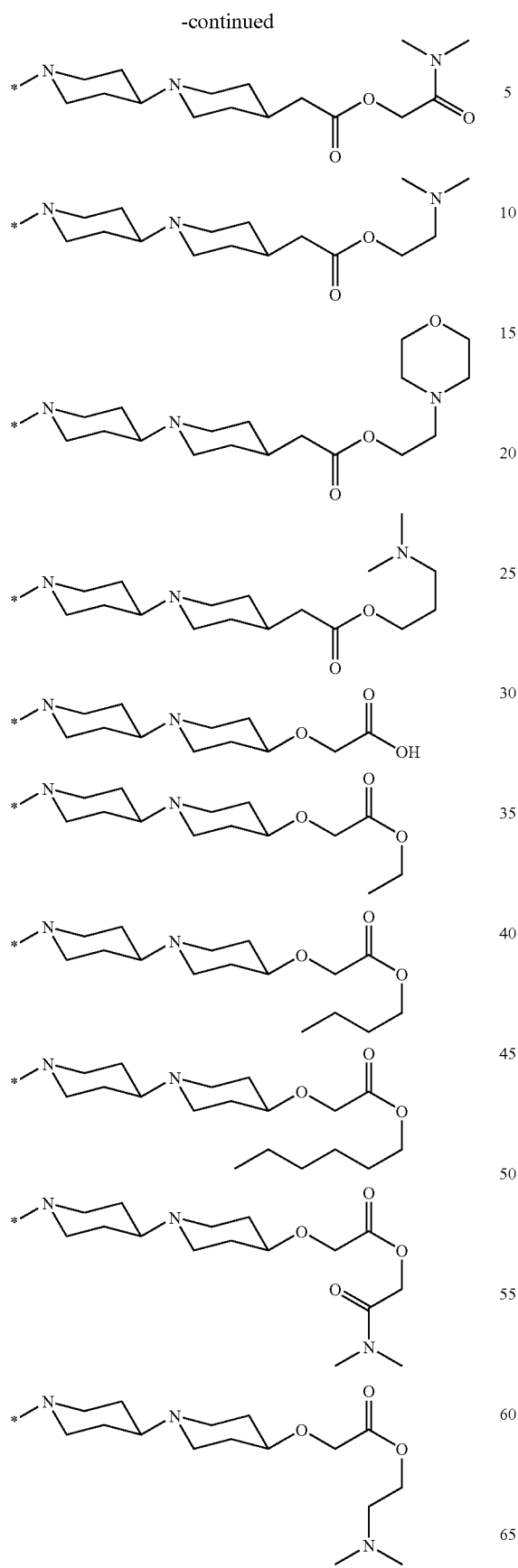
552
-continued
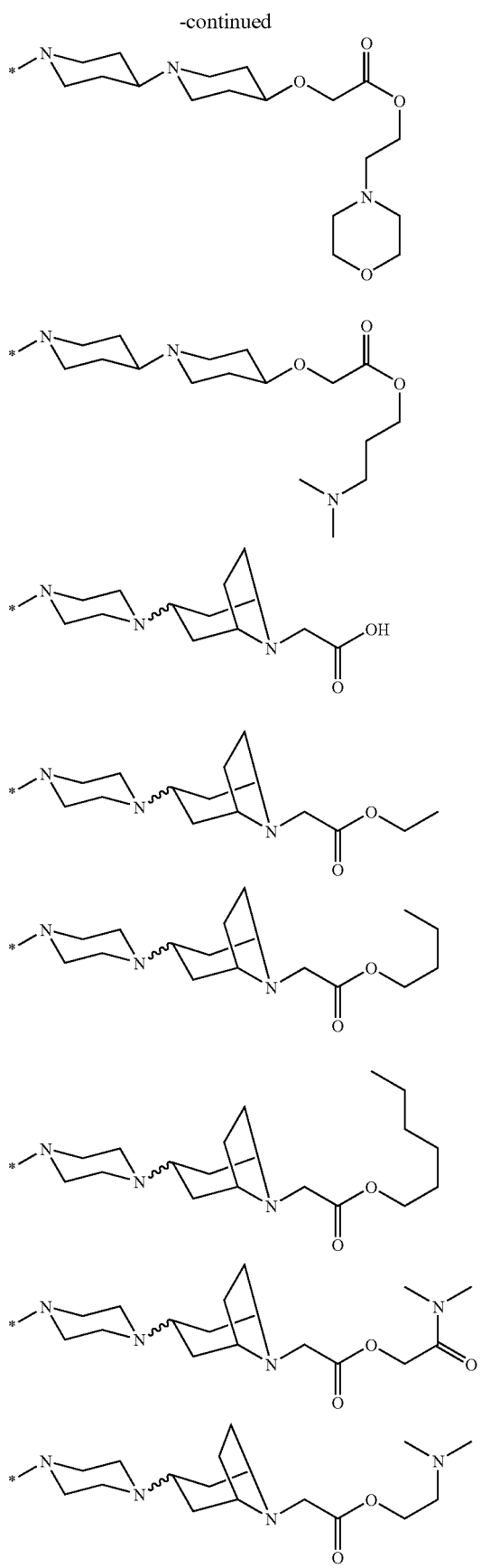

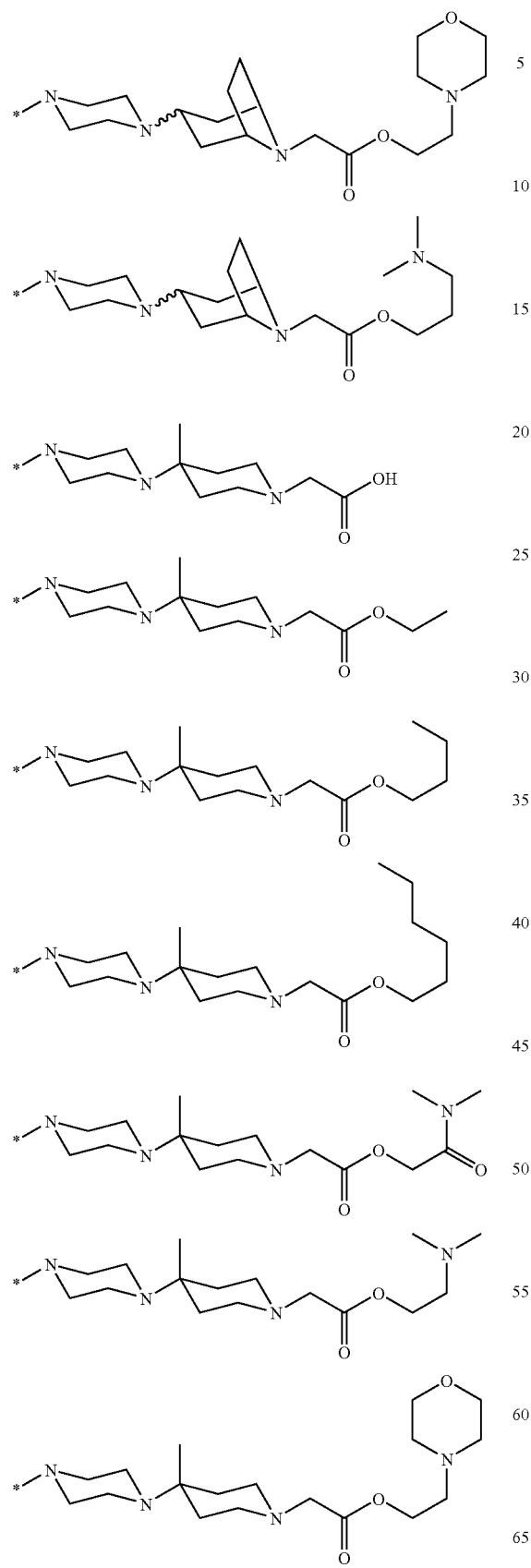
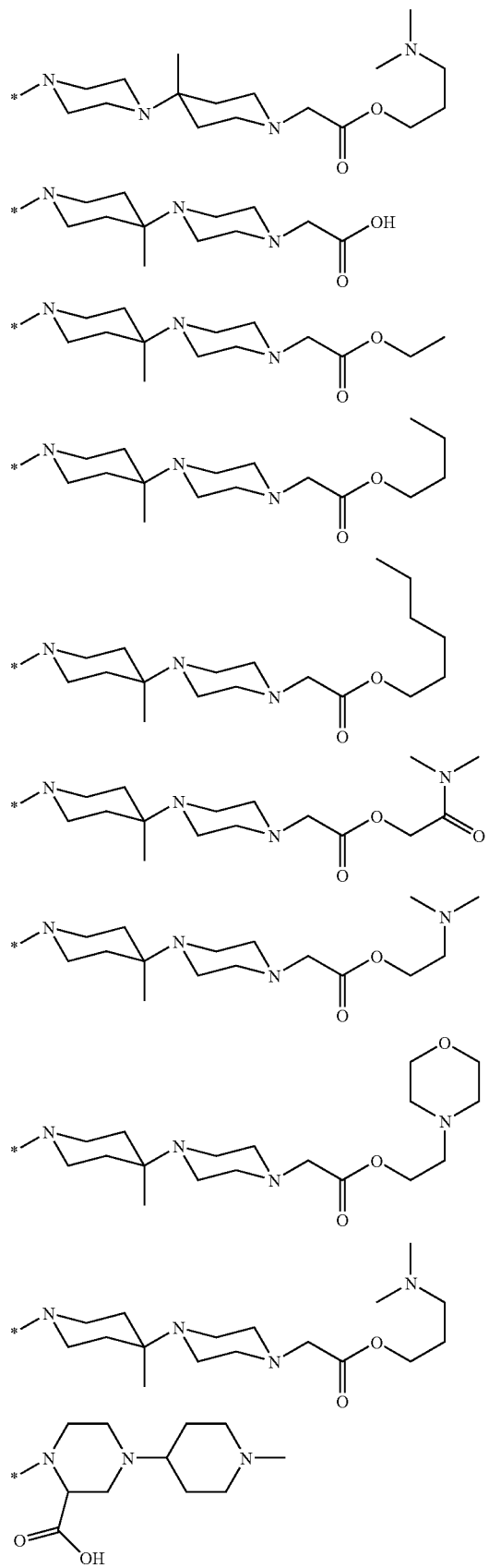

555
-continued
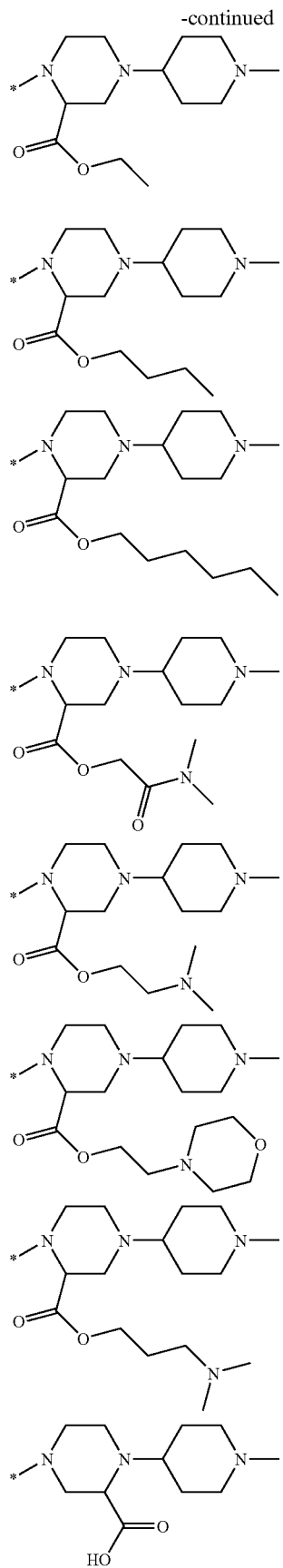
556
-continued
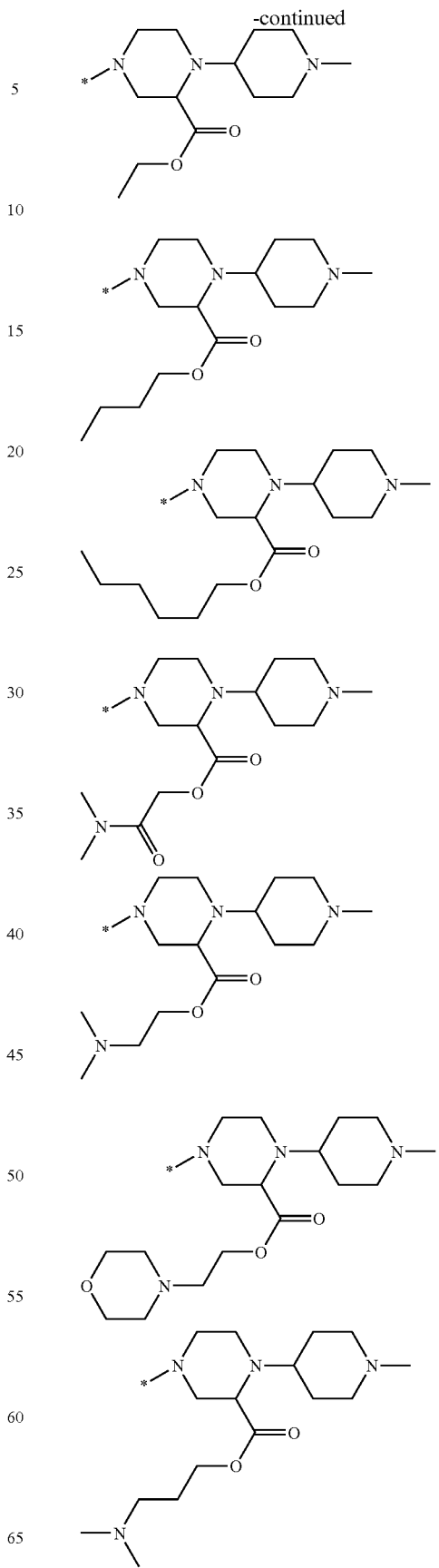

557
-continued
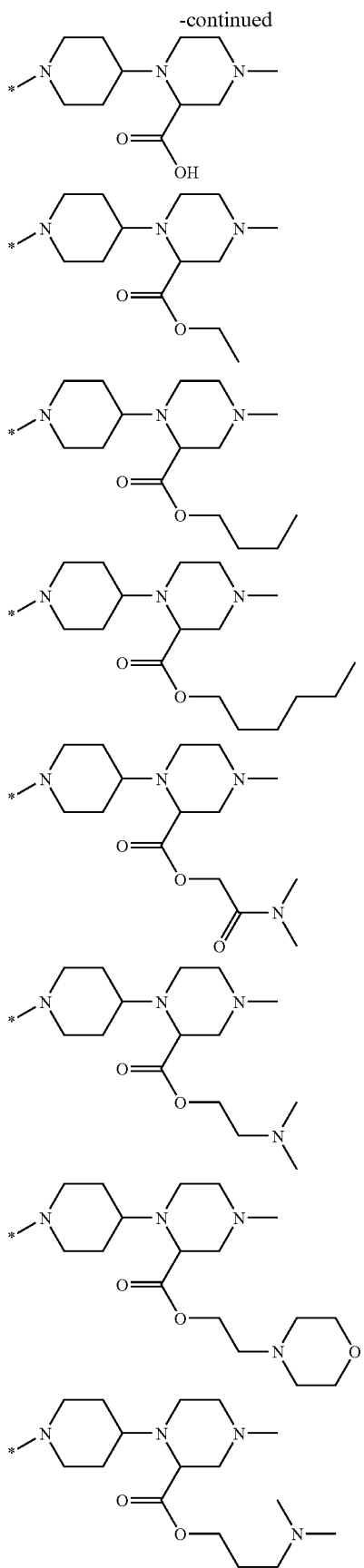
558
-continued
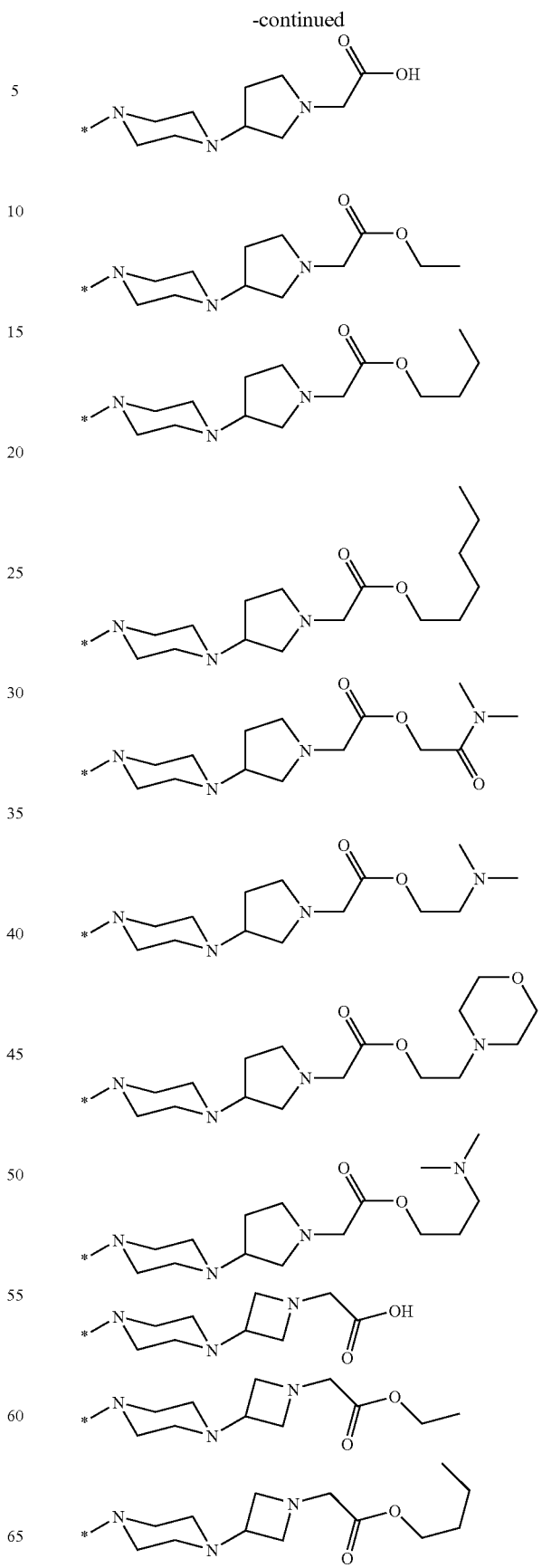

-continued
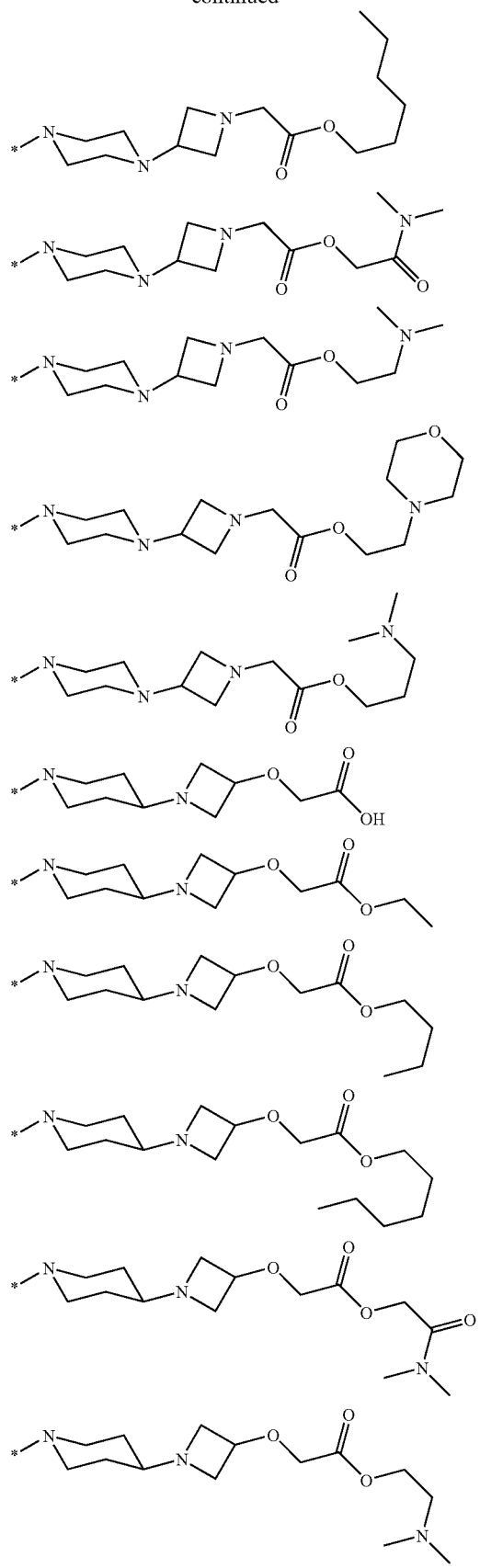
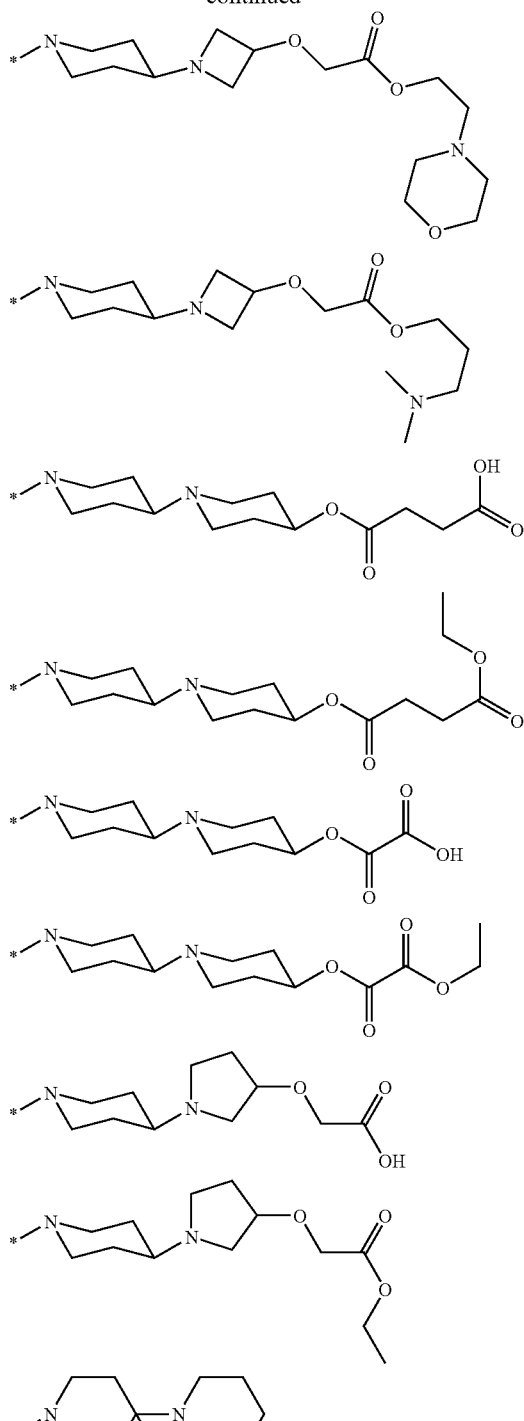
or a tautomer or salt thereof.

8. A compound of the formula I according to claim 1, selected from the group consisting of:
| No. | Structure |
|---|---|
| (30) | 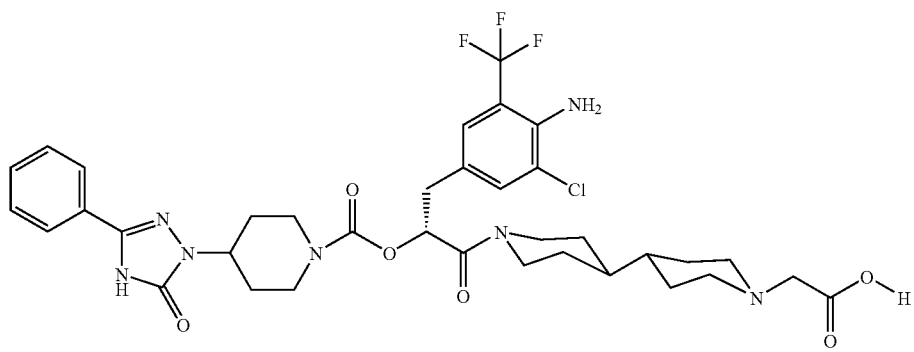 |
| (31) | 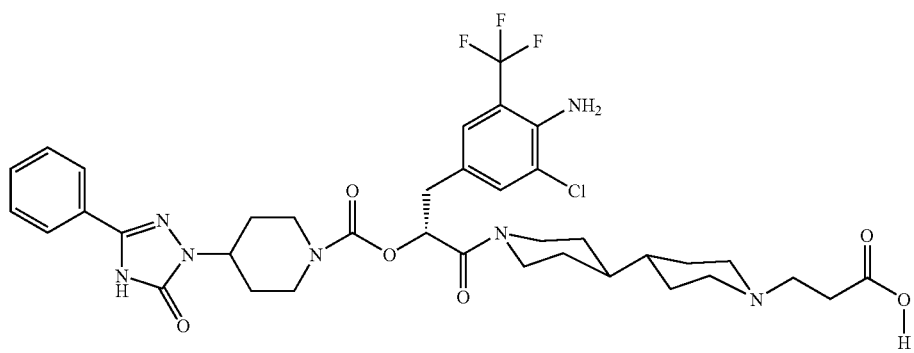 |
| (350) | 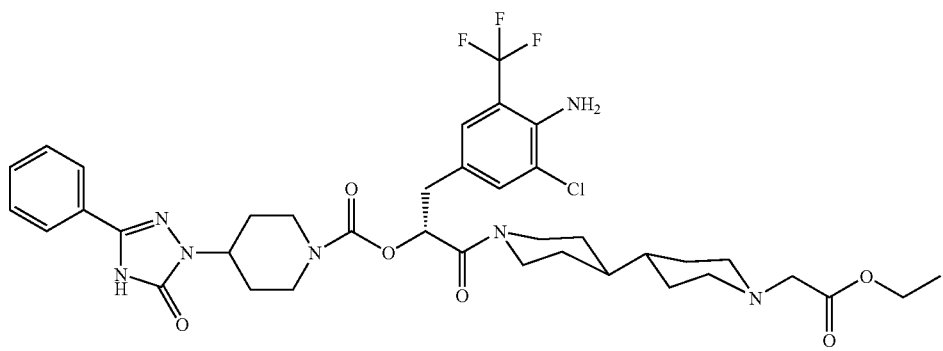 |
| (351) | 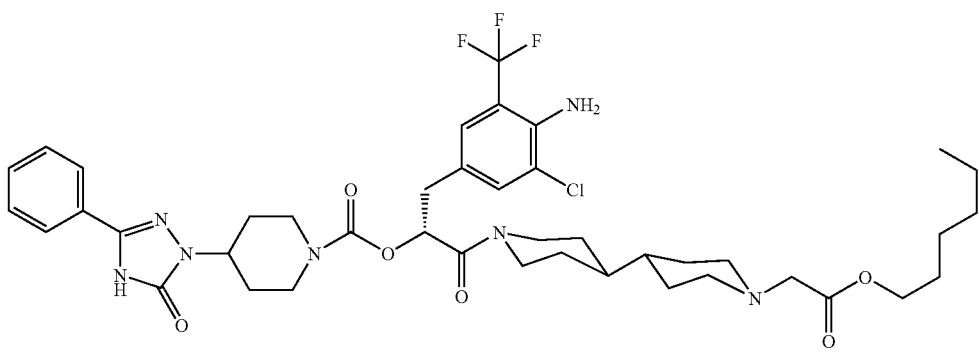 |

| No. | Structure |
|---|---|
| (352) | 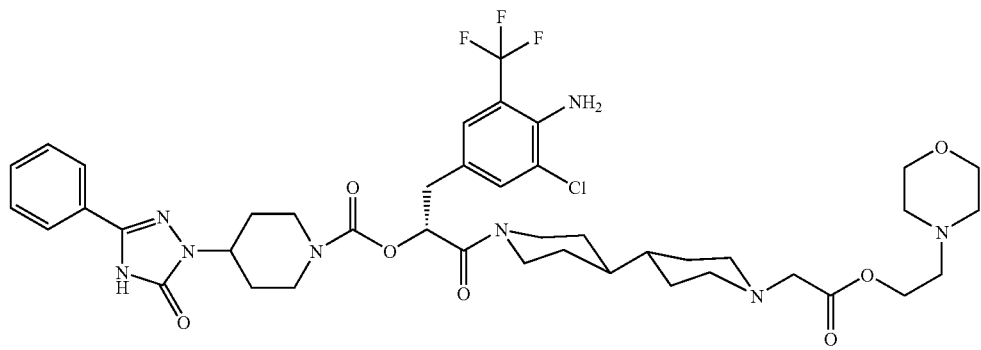 |
| (353) | 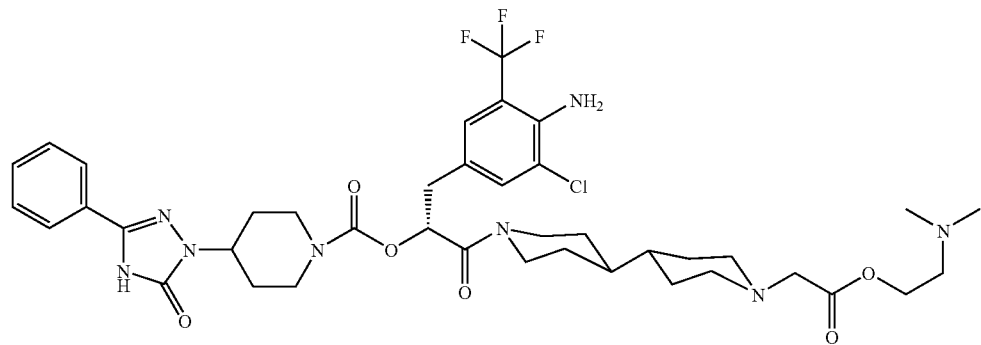 |
| (354) | 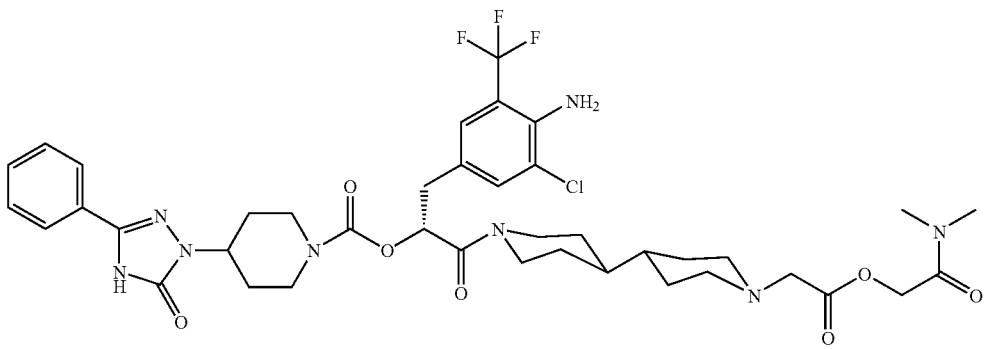 |
| (355) | 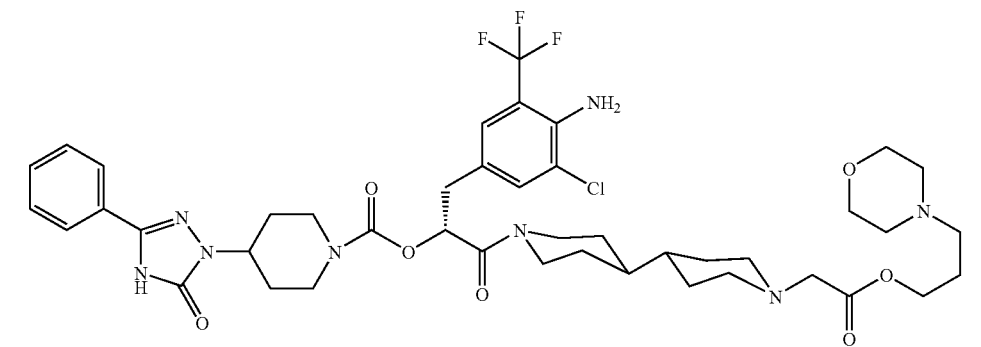 |

-continued
| No. | Structure |
|---|---|
| (356) | 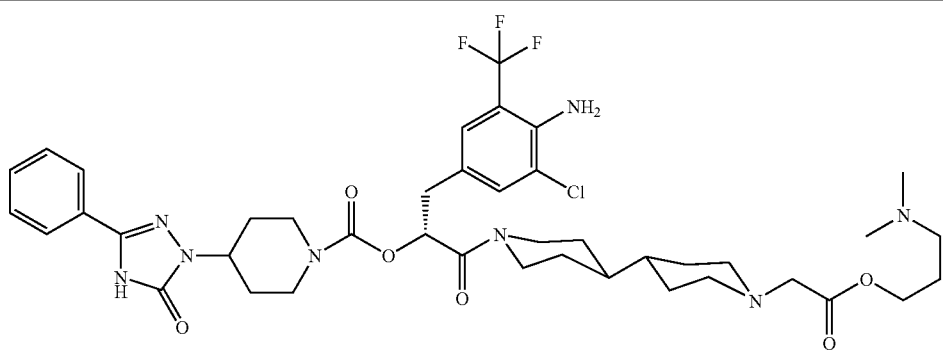 |
| (357) | 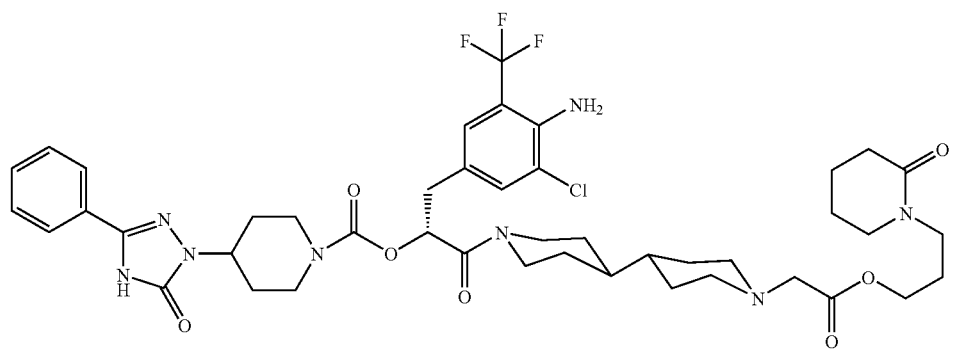 |
| (358) | 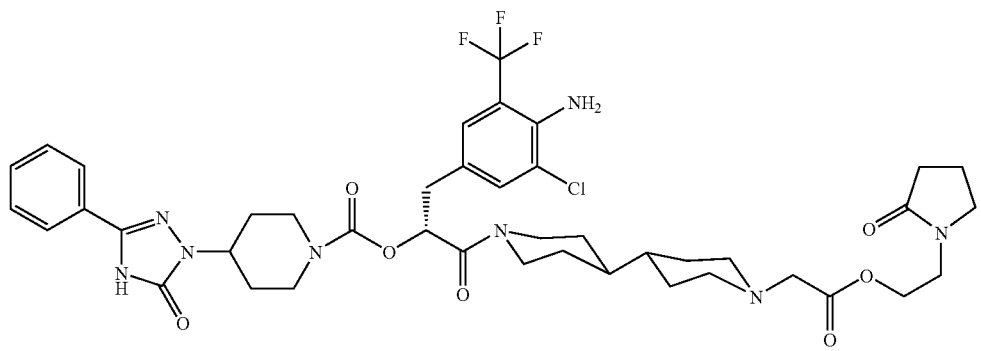 |
| (359) | 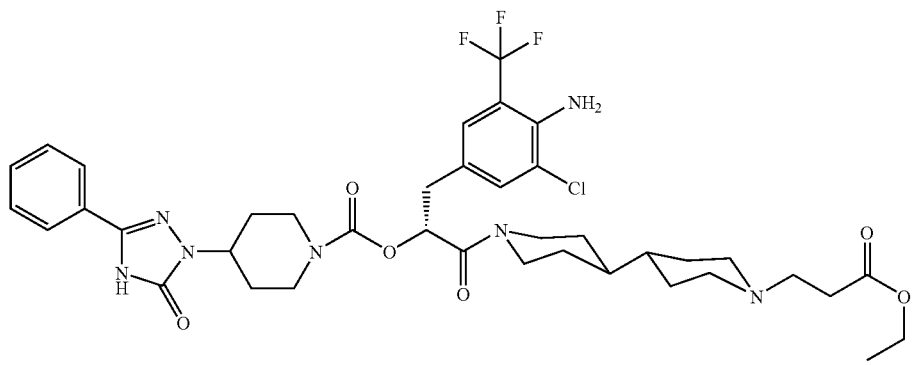 |

| No. | Structure |
|---|---|
| (360) | 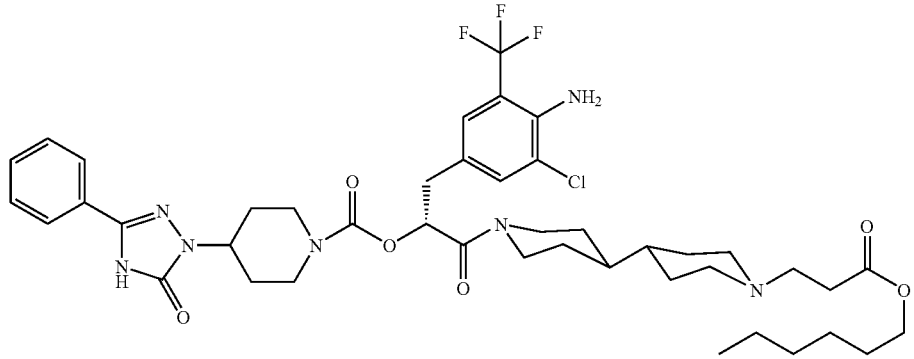 |
| (361) | 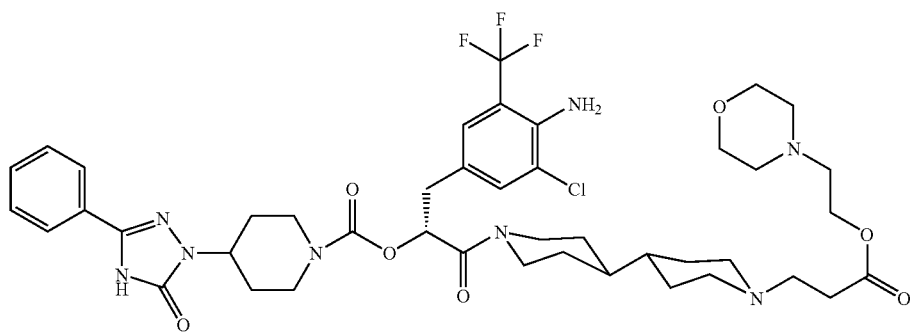 |
| (362) | 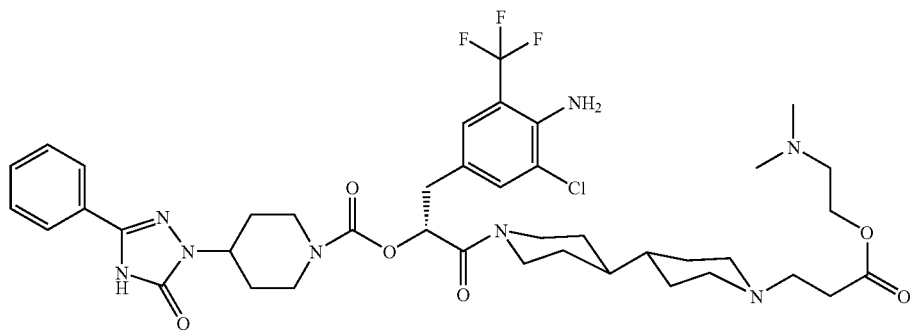 |
| (363) | 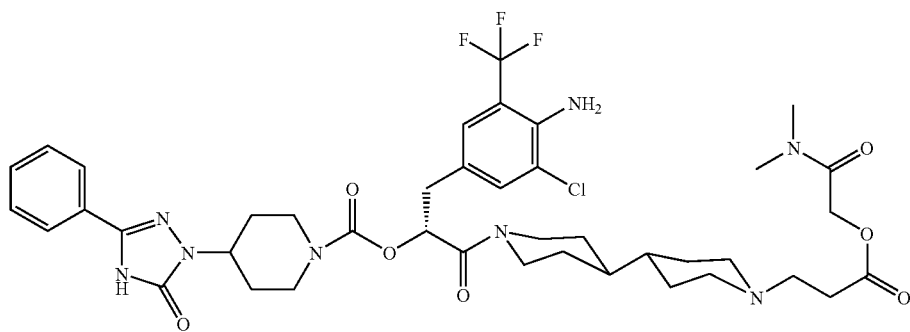 |

| No. | Structure |
|---|---|
| (364) | 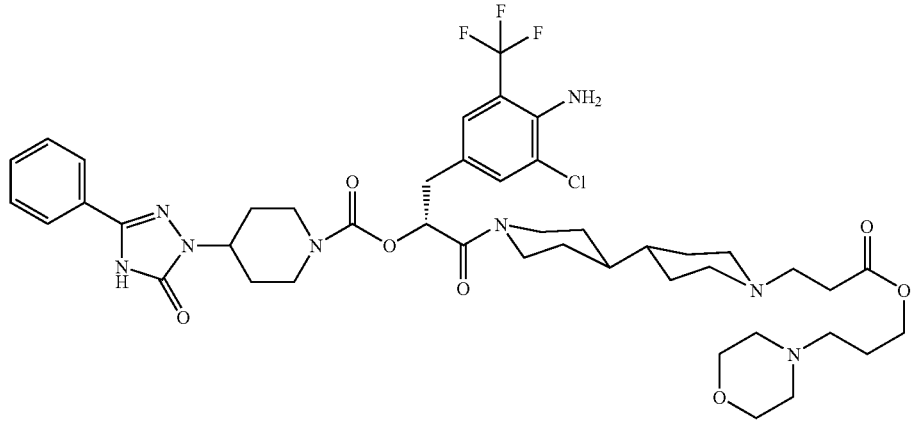 |
| (365) | 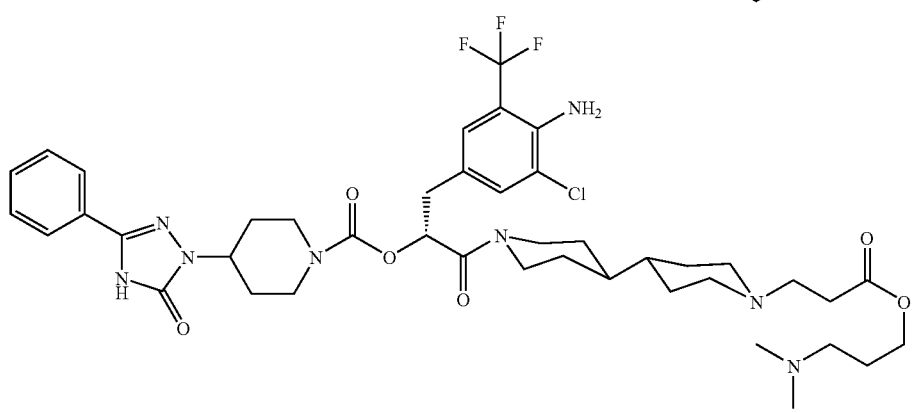 |
| (366) | 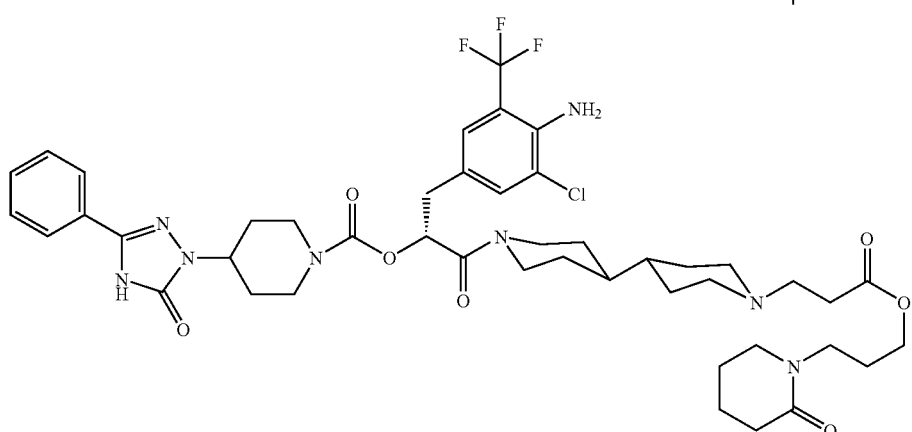 |
| (367) | 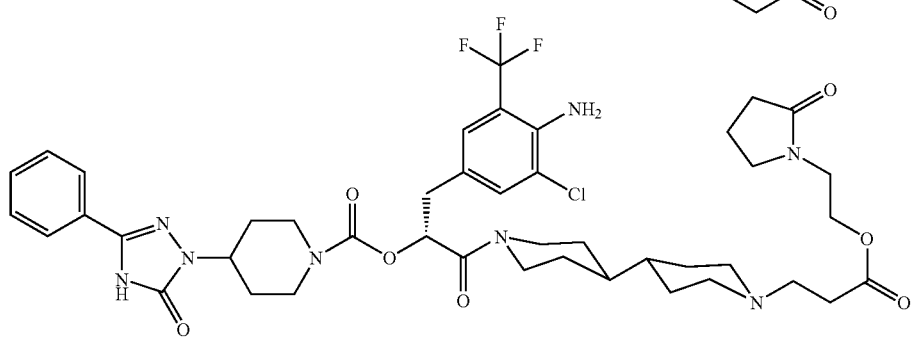 |
or a tautomer or salt thereof.

9. A physiologically acceptable salt of a compound according to claim 1, 2, 3, 4, 5, 6, 7, or 8.

10. A pharmaceutical composition, containing a compound according to claim 1, 2, 3, 4, 5, 6, 7, or 8, or a pharmaceutically acceptable salt thereof, together with one or more inert carriers and/or diluents.

11. A method for treating a condition selected from the group consisting of migraine, cluster headaches and tension headaches, which method comprises administering a therapeutically effective amount of a compound according to claim 1, 2, 3, 4, 5, 6, 7, or 8, or a pharmaceutically acceptable salt thereof.

12. A method for treating non-insulin-dependent diabetes mellitus (NIDDM), which method comprises administering a therapeutically effective amount of a compound according to claim 1, 2, 3, 4, 5, 6, 7, or 8, or a pharmaceutically acceptable salt thereof.

13. A method for treating a condition selected from the group consisting of migraine, cluster headaches and tension headaches, which method comprises administering a therapeutically effective amount of a compound according to claim 1, 2, 3, 4, 5, 6, 7, or 8, or a pharmaceutically acceptable salt thereof.

14. A method for treating irritable bowel syndrome (IBS), which method comprises administering a therapeutically effective amount of a compound according to claim 1, 2, 3, 4, 5, 6, 7, or 8, or a pharmaceutically acceptable salt thereof.

15. A method for treating hot flushes in an oestrogen-deficient woman, which method comprises administering a therapeutically effective amount of a compound according to claim 1, 2, 3, 4, 5, 6, 7, or 8, or a pharmaceutically acceptable salt thereof.

* * * * *